US010023862B2

(12) United States Patent
Bettencourt et al.

(10) Patent No.: US 10,023,862 B2
(45) Date of Patent: Jul. 17, 2018

(54) ORGANIC COMPOSITIONS TO TREAT BETA-CATENIN-RELATED DISEASES

(71) Applicants: Dieter Huesken, Basel (CH); Brian Bettencourt, Cambridge, MA (US); David Bumcrot, Cambridge, MA (US); Satyanarayana Kuchimanchi, Cambridge, MA (US); Stuart Milstein, Cambridge, MA (US); Michael Schlabach, Jr., Cambridge, MA (US); Frank P. Stegmeier, Cambridge, MA (US); Markus Warmuth, Cambridge, MA (US); Jan Weiler, Cambridge, MA (US); NOVARTIS AG, Basel (CH)

(72) Inventors: Brian Richard Bettencourt, Cambridge, MA (US); David Anton Bumcrot, Cambridge, MA (US); Dieter Huesken, Freiburg i. Br. (DE); Satyanarayana Kuchimanchi, Cambridge, MA (US); Stuart Milstein, Cambridge, MA (US); Michael Ray Schlabach, Jr., Cambridge, MA (US); Frank Peter Stegmeier, Acton, MA (US); Markus Warmuth, Natick, MA (US); Jan Weiler, Cambridge, MA (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 0 days.

(21) Appl. No.: 14/371,131

(22) PCT Filed: Jan. 8, 2013

(86) PCT No.: PCT/IB2013/050159
§ 371 (c)(1),
(2) Date: Jul. 8, 2014

(87) PCT Pub. No.: WO2013/105022
PCT Pub. Date: Jul. 18, 2013

(65) Prior Publication Data
US 2015/0291954 A1 Oct. 15, 2015

Related U.S. Application Data

(60) Provisional application No. 61/584,530, filed on Jan. 9, 2012, provisional application No. 61/598,530, filed on Feb. 14, 2012.

(51) Int. Cl.
A61P 35/00 (2006.01)
A61P 17/02 (2006.01)
C12N 15/113 (2010.01)
A61K 31/713 (2006.01)

(52) U.S. Cl.
CPC .......... C12N 15/113 (2013.01); A61K 31/713 (2013.01); C12N 2310/14 (2013.01); C12N 2310/321 (2013.01); C12N 2310/344 (2013.01)

(58) Field of Classification Search
USPC ........... 435/6.1, 91.1, 91.31, 455, 458, 6.11; 514/44; 536/23.1, 24.5
See application file for complete search history.

(56) References Cited

U.S. PATENT DOCUMENTS

| 2,779,780 | A | 1/1957 | Middleton |
| 4,169,846 | A | 10/1979 | Inagaki et al. |
| 4,261,989 | A | 4/1981 | Sasaki et al. |
| 4,439,196 | A | 3/1984 | Higuchi |
| 4,447,224 | A | 5/1984 | DeCant, Jr. et al. |
| 4,447,233 | A | 5/1984 | Mayfield |
| 4,475,196 | A | 10/1984 | La Zor |
| 4,486,194 | A | 12/1984 | Ferrara |
| 4,487,603 | A | 12/1984 | Harris |
| 4,522,811 | A | 6/1985 | Eppstein et al. |
| 4,596,556 | A | 6/1986 | Morrow et al. |
| 4,790,824 | A | 12/1988 | Morrow et al. |
| 4,941,880 | A | 7/1990 | Burns |
| 5,030,453 | A | 7/1991 | Lenk et al. |
| 5,032,401 | A | 7/1991 | Jamas et al. |

(Continued)

FOREIGN PATENT DOCUMENTS

| CA | 2359180 A1 | 8/2000 |
| CA | 2677068 | 3/2011 |

(Continued)

OTHER PUBLICATIONS

Alignment Data re: SEQ ID No. 6121.*
Sequence alignments.*
Original sequences from U.S. Appl. No. 13/937,412 and U.S. Appl. No. 14/371,131.*
Agrawal et al, Molecular Med. Today, vol. 6, pp. 72-81. A. Branch, Trends in (Year: 2000).*
Chirila et al, Biomaterials, vol. 23, pp. 321-342. (Year: 2002).*
Peracchi et al, Rev. Med. Virol., 14, pp. 47-64. (Year: 2004).*
A. Branch, Trends in Biochem. Sci., 23, 45-50. (Year: 1998).*
S. Crooke, Antisense Res. & Application, Chapter 1, pp. 1-50, (1998, ed. by S. Crooke, Springer-Verlag). (Year: 1998).*
Behrens et al. 1993 J. Cell Biol. 120: 757-766.
Behrens et al. 1996 Nature 382: 638-642.
Bernstein et al. 2001 Nature 409:363-366.

(Continued)

Primary Examiner — Jane Zara
(74) Attorney, Agent, or Firm — Robert Michael Teigen

(57) ABSTRACT

The present disclosure relates to RNAi agents useful in methods of treating Beta-Catenin-related diseases such as adenomatous polyposis of the colon, colorectal cancer, basal cell carcinoma, breast cancer, kidney cancer, Wilms tumors, medulloblastoma, ovarian cancer, adrenocortical tumors, gastric cancer, liver cancer, melanoma, pancreatic cancers, prostate cancer, renal cancer, ectopic teeth and taste papillae, skin cancer, pilomatrixoma, anaplastic thyroid carcinoma, and uterine carcinosarcoma, oligodontia, osteoporosis, ageing, degenerative diseases, bedsores, chronic wounds and impaired wound healing, and similar and related diseases, using a therapeutically effective amount of a RNAi agent to Beta-Catenin.

9 Claims, 1 Drawing Sheet

(56) References Cited

U.S. PATENT DOCUMENTS

| | | | |
|---|---|---|---|
| 5,064,413 A | 11/1991 | McKinnon et al. | |
| 5,266,573 A | 11/1993 | Elf | |
| 5,312,335 A | 5/1994 | McKinnon et al. | |
| 5,374,548 A | 12/1994 | Caras | |
| 5,383,851 A | 1/1995 | McKinnon, Jr. et al. | |
| 5,399,163 A | 3/1995 | Peterson et al. | |
| 5,399,331 A | 3/1995 | Loughrey et al. | |
| 5,416,016 A | 5/1995 | Low et al. | |
| 5,607,677 A | 3/1997 | Jamas et al. | |
| 5,621,002 A | 4/1997 | Bosslet et al. | |
| 5,962,016 A | 10/1999 | Willis | |
| 6,506,559 B1 | 1/2003 | Fire et al. | |
| 6,680,068 B2 | 1/2004 | Campbell et al. | |
| 6,780,996 B2 | 8/2004 | Boschelli et al. | |
| 8,084,600 B2 | 12/2011 | Natt et al. | |
| 8,097,716 B2 | 1/2012 | Weiler et al. | |
| 8,518,907 B2 * | 8/2013 | Brown | C12N 15/113 514/44 A |
| 8,815,825 B2 * | 8/2014 | Brown et al. | 514/44 A |
| 8,835,623 B2 * | 9/2014 | Brown | C12N 15/113 536/24.5 |
| 2002/0137210 A1 | 9/2002 | Churikov | |
| 2003/0012812 A1 | 1/2003 | Tormo et al. | |
| 2003/0177507 A1 | 9/2003 | Hoener et al. | |
| 2003/0182672 A1 | 9/2003 | Graham et al. | |
| 2004/0038921 A1 | 2/2004 | Kreutzer et al. | |
| 2004/0064842 A1 | 4/2004 | Graham et al. | |
| 2004/0204377 A1 | 10/2004 | Rana | |
| 2004/0208921 A1 | 10/2004 | Ho et al. | |
| 2005/0255487 A1 | 11/2005 | Khvorova et al. | |
| 2005/0281781 A1 | 12/2005 | Ostroff | |
| 2006/0193870 A1 | 8/2006 | King et al. | |
| 2006/0240093 A1 | 10/2006 | MacLachlan et al. | |
| 2007/0039072 A1 | 2/2007 | Khvorova et al. | |
| 2007/0042381 A1 | 2/2007 | Bentwich et al. | |
| 2007/0111230 A1 | 5/2007 | Pompejus et al. | |
| 2007/0135372 A1 | 6/2007 | MacLachlan et al. | |
| 2007/0207974 A1 | 9/2007 | Khvorova et al. | |
| 2007/0275914 A1 | 11/2007 | Manoharan et al. | |
| 2008/0113351 A1 | 5/2008 | Naito et al. | |
| 2010/0105134 A1 | 4/2010 | Quay et al. | |
| 2011/0152353 A1 | 6/2011 | Koizumi et al. | |

FOREIGN PATENT DOCUMENTS

| | | |
|---|---|---|
| WO | 2000035436 A2 | 6/2000 |
| WO | 2000044914 A1 | 8/2000 |
| WO | 2000063364 A2 | 10/2000 |
| WO | 2001002369 A2 | 1/2001 |
| WO | 2001004313 A1 | 1/2001 |
| WO | 2001075164 A2 | 10/2001 |
| WO | 2001092513 A1 | 12/2001 |
| WO | 2002006213 A2 | 1/2002 |
| WO | 2002010192 A2 | 2/2002 |
| WO | 2002044321 A2 | 6/2002 |
| WO | 2002066470 A1 | 8/2002 |
| WO | 2002100435 A1 | 12/2002 |
| WO | 2003015757 A1 | 2/2003 |
| WO | 2003064383 A2 | 8/2003 |
| WO | 2003064625 A2 | 8/2003 |
| WO | 2003064626 A2 | 8/2003 |
| WO | 2003075836 A2 | 9/2003 |
| WO | 2003076424 A1 | 9/2003 |
| WO | 2003077914 A1 | 9/2003 |
| WO | 2004002453 A1 | 1/2004 |
| WO | 2004029213 A2 | 4/2004 |
| WO | 2004091515 A2 | 10/2004 |
| WO | 2005021749 A1 | 3/2005 |
| WO | 2005028443 A2 | 3/2005 |
| WO | 2006/031977 | 3/2006 |
| WO | 2006028958 A2 | 3/2006 |
| WO | 2006031977 A2 | 3/2006 |
| WO | 2006086772 A2 | 8/2006 |
| WO | 2006122806 A2 | 11/2006 |
| WO | 2007014011 A2 | 2/2007 |
| WO | 2007128477 A2 | 11/2007 |
| WO | WO2008/109460 | 8/2008 |
| WO | 2008109460 A2 | 9/2008 |
| WO | 2008132234 A2 | 11/2008 |
| WO | 2008/156702 | 12/2008 |
| WO | 2008147824 A2 | 12/2008 |
| WO | 2008156702 A2 | 12/2008 |
| WO | 2009036082 A2 | 3/2009 |
| WO | 2009055730 A1 | 4/2009 |
| WO | 2009082817 A1 | 7/2009 |
| WO | 2009155386 A1 | 12/2009 |
| WO | 2010/146055 | 12/2010 |
| WO | 2010146055 A1 | 12/2010 |
| WO | 2011044671 A1 | 4/2011 |
| WO | 2011073326 A2 | 6/2011 |
| WO | 2001068836 A2 | 9/2011 |
| WO | 2012006243 A2 | 1/2012 |
| WO | WO2012/006243 | 1/2012 |

OTHER PUBLICATIONS

Briscoe et al. (1995) The American Physiological Society; 268(3); L374-L380.
Burgin et al. 1996 Biochemistry 35: 14090-14097.
Caplen et al. 2001 Proc. Natl. Acad. Sci. (USA), 98: 9742-9747.
Chan et al. 1999 Nature Genet. 21: 410-413.
Chenn et al. 2003 Cer. Cortex 13: 599-606.
Chiu and Rana 2003 RNA 9: 1034-1048.
Clements et al. 2002 Cancer Res. 62: 3503-6.
Clevers 2006 Cell 127: 469-480.
Delektorskaya et al. 2008. Bull. Exp. Biol. Med. 146: 616-619.
Devroe et al. 2002. BMC Biotechnol. 2:15, pp. 1-5.
Donze and Picard, 2002, 30(10): e46.
Duxbury et al., J. Surgical Research, 2004, 117: 339-344.
Elbashir et al. 2001 Genes Dev. 15: 188-200.
Elbashir et al. 2001 EMBO J. 20: 6877-6888.
Elbashir et al. 2001 Nature 411: 494-498.
Farhood, et al., Biochimica et Biophysica Acta, 1235, (1995), 289-295.
Fuchs 2009 Cell 137: 811-819.
Fukuchi et al. 1998 Cancer Res. 58: 3526-3528.
Funayama et al. 1995 J. Cell Biol. 128: 959-968.
Garcia-Rostan et al. 1999 Cancer Res. 59: 1811-1815.
Gautier et al. 1987 Nucleic Acids. Res. 15: 6625-6641.
Ha et al. 2002 Acta Derm. Venereol. 82: 428-431.
Hamaguchi et al. 1993 EMBO J. 12:307-314.
Harborth et al. 2003 Anti-sense & Nucleic Acid Drug Development 13: 83-105.
He et al. 1998 Science 281: 1509-1512.
He et al. 2004 Develop. 131: 1663-1677.
Helene 1991 Anticancer Drug Des. 6(6) : 569-84.
Helene et al. 1992 Ann. N.Y. Acad. Sci. 660: 27-36.
Hu-Lieskovan et al. 2005 Cancer Res. 65: 8984-8992.
Huang et al. 2008. Curr. Opin. Cell Biol. 20: 119-125.
Hutvagner et al. 2001 Science 293: 834-838.
Inoue et al. 1987 Nucleic Acids Res. 15: 6131-6148.
Inoue et al. 1987 FEBS Lett. 215: 327-330.
Iwao et al. 1998 Cancer Res. 58: 1021-1026.
Kawanishi et al. 1995 Mol. Cell. Biol. 15: 1175-1181.
Keinanen, K; Laukkanen, M.L. (1994) FEBS Lett. 346: 123-126.
Khramtsov et al. 2010 Am. J. Pathol. 176: 2911-2920.
Killion, J.J.; Fidler, I.J. (1994) Immunomethods 4: 273-279.
Kraus et al. 1994. Genomics 23: 272-274.
Kraynack et al. 2006 RNA 12:163-176.
Li et al. 2002 Gene 283: 255-62.
Li et al. 2005 World J. Gastroent. 11: 2117-23.
Liu et al. 2010 J. Dental Res. 89: 318-330.
Logan et al. 2004 Ann. Rev. Cell. Dev. Biol. 20: 781-810.
Lovell et al. 2011 Nature Mater. 10: 324-32.
Maher 1992, Bioassays 14(12) : 807-15.
Martinez et al. 2002 Cell, 110, 563-574.
Matsuyoshi et al. 1992 J. Cell Biol. 118: 703-714.
McCaffrey et al., Nature, 2002, 418(6893):38-39.
McDonald et al. 2009 Dev. Cell 17: 9-26.

(56) References Cited

OTHER PUBLICATIONS

Miller, et al., Biochemistry, 1998, 37(37): 12875-83.
Miyaki et al. 1999 Cancer Res. 59: 4506-4509.
Miyoshi et al. 1998 Cancer Res. 58: 2524-2527.
Moon et al. 2002 science 296: 1644-1646.
Moon et al. 2004 Nat. Rev. Genet. 5: 689-699.
Munemitsu et al. 1995 Proc. Natl. Acad. Sci. USA 92:3046-3050.
Munemitsu et al. 1996 Mol. Cell. Biol. 16: 4088-4094.
Nelson et al. 2004 Science 303: 1483-1487.
Noda et al. 1009 Br. J. Cancer 100: 1647-1658.
Niyakanen et al. 2001 Cell 107:309-321.
Ovcharenko, D.; "Efficient delivery of siRNAs to human primary cells: Electroporation Vs. Chemical Transfection", Ambion ; pp. 1-4.
Owais, M. et al. (1995) Antimicrob. Agents Chemother. 39: 180-184.
Palacios et al. 1998 Cancer Res. 58: 1344-1347.
Parrish et al. 2000 Molecular Cell 6: 1077-1087.
Bloeman, P.G., et al. (1995) FEBS Lett. 357: 140-144.
POLAKISS 2007. Curr. Opin. Genet. Dev. 17: 45-51.
Rubinfeld et al. 1997 Science 275: 1790-1792.
Saegusa et al. 2009 Am. J. Pathol. 174: 2107-2115.
Saldanha et al. 2004; Br. J. Dermatol. 151: 157-64.
Schiffelers et al. 2004 Nucl. Acids Res. 32: el49, pp. 1-10.
Schreier et al. (1994) J. Biol. Chem. 269: 9090-9098.
Sharp et al. 2001 Genes Dev. 15:485-490.
Sioud 2005 J. Mol. Biol. 348:1079-1090.
Sioud and Sorensen, Biochem Biophys Res Commun. 2003, 312(4):1220-1225.
Sommers et al. 1994 Cancer Res. 54: 3544-3552.
Song et al.,2003 Nature Medicine, vol. 9, No. 3, 347-351.
Song et al. 2005 Nat Biotech. 23: 709-717.
Soutschek et al. 2004 Nature 432: 173-178.
Stojadinovic et al. Am. J. Pathol. 167: 59-69.
Thompson et al. 2007 Hepatology 45: 1298-305.
Umezawa et al., (1988) Biochem. Biophys. Res. Commun. 153: 1038-1044.
Usman et al. 1994 Nucleic Acids Symp. Ser. 31: 163-164.
Ranade, V.V. (1989) J. Clin. Pharmacol. 29: 685-694.
Voeller et al. 1998 Cancer Res. 2520-2523.
Wang et al. 2008 Cancer Epidemiol. Biomarkers Prev. 17: 2101-8.
Xia et al. 2002 Nat. Biotechnol. 20, 1006-1010.
Yost et al. 1996 Genes Dev. 10: 1443-1454.
Zurawel et al. 1998 Cancer Res. 58: 896-899.
Henschel et al. 2004 DeQor: a web-based tool for the design and quality control of siRNAs. Nucleic Acids Research 32 (Web Server Issue): W113-W120.
Usman, N., and Cedergren, R. 1992; 17(9):334-339.
Examination Report for corresponding Australian Application AU2013208720.
Examination Report 2 for corresponding Australian Application AU2013208720.
Office Action for corresponding Chinese Application CN201380013297.9.
Written Opinion for corresponding International Application WO2013105022.
Third Office Action for corresponding Chinese Application No. 201380013297.9 dated Mar. 20, 2017.
Office Action for corresponding Japanese Application No. 2014-551706 dated Nov. 8, 2016.
Communication for corresponding European Patent Application No. 13704633.0 dated Sep. 14, 2016.
Office Action for corresponding European Application No. 13704633.0 dated Jan. 29, 2018.
Office Action for corresponding European Application No. 13704633.0 dated Mar. 23, 2017.
Second Office Action for corresponding Chinese Patent Application No. 201380013297.9 dated Jul. 5, 2016.

* cited by examiner

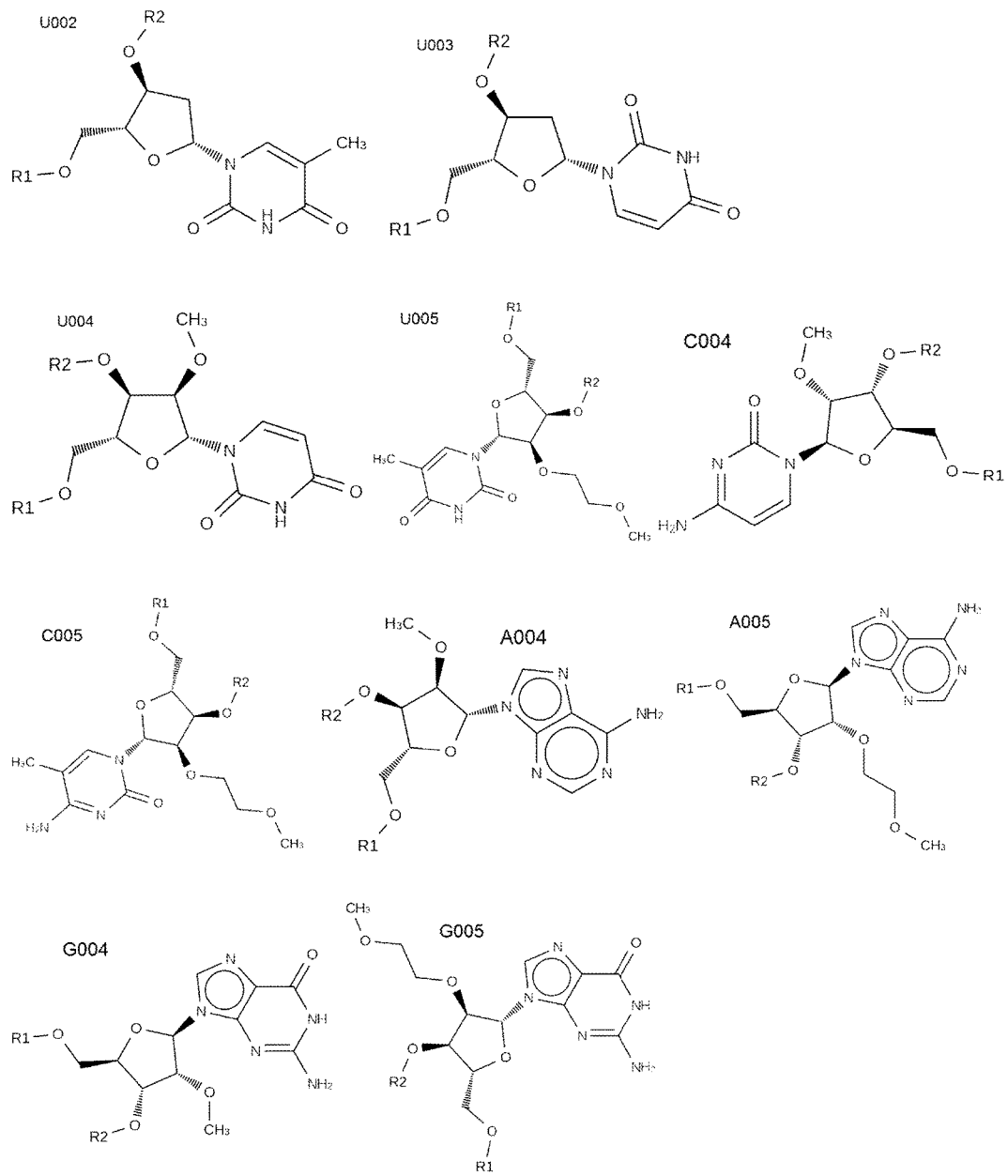

ies. Indeed, APC deletion or Beta-catenin activation in stem cells is essential for intestinal neoplasia. Fuchs 2009 Cell 137: 811-819.

ORGANIC COMPOSITIONS TO TREAT BETA-CATENIN-RELATED DISEASES

This application is a U.S. National Phase filing of International Application No. PCT/IB2013/050159 filed 8 Jan. 2013, which claims priority to U.S. Application No. 61/584,530 filed 9 Jan. 2012 and 61/598,530 filed 14 Feb. 2012, the contents of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Apr. 10, 2013, is named PAT054417-WO-PCT_SL.txt and is 1,553,980 bytes in size.

BACKGROUND OF THE INVENTION

Signaling by the Wnt family of secreted glycolipoproteins is one of the fundamental mechanisms that direct cell proliferation, cell polarity, and cell fate determination during embryonic development and tissue homeostasis. As a result, mutations in the Wnt pathway are often linked to human birth defects, cancer, and other diseases. A critical Wnt pathway is the canonical Wnt signaling pathway.

The transcriptional co-activator Beta-Catenin is the molecular node in this pathway. In the absence of Wnt, cytoplasmic Beta-catenin protein is constantly degraded by the action of the Axin complex, which is composed of the scaffolding protein Axin, the tumor suppressor adenomatous polyposis coli gene product (APC), casein kinase 1 (CK1), and glycogen synthase kinase 3 (GSK3). CK1 and GSK3 sequentially phosphorylate the amino terminal region of Beta-catenin, resulting in Beta-catenin recognition by Beta-Trcp, an E3 ubiquitin ligase subunit, and subsequent Beta-catenin ubiquitination and proteasomal degradation.

This continual elimination of Beta-catenin prevents Beta-catenin from reaching the nucleus, and Wnt target genes are thereby repressed by the DNA-bound T cell factor/lymphoid enhancer factor (TCF/LEF) family of proteins. The Wnt/Beta-catenin pathway is activated when a Wnt ligand binds to the seven-pass transmembrane Frizzled (Fz or Fzd) receptor and its coreceptor, low-density lipoprotein receptor-related protein 6 (LRP6), or its close relative LRP5. The formation of a likely Wnt-Fz-LRP6 complex, together with the recruitment of the scaffolding protein Dishevelled (Dvl), results in LRP6 phosphorylation and activation and the recruitment of the Axin complex to the receptors. These events lead to inhibition of Axin-mediated Beta-catenin phosphorylation and thereby to the stabilization of Beta-catenin, which accumulates, travels to the nucleus to form complexes with TCF/LEF and activates Wnt target gene expression.

Given the critical roles of Wnt/Beta-catenin signaling in development and homeostasis, it is no surprise that mutations of the Wnt pathway components are associated with many disorders and diseases. McDonald et al. 2009 Dev. Cell 17: 9-26. Association of deregulated Wnt/Beta-catenin signaling with cancer has been well documented, particularly with colorectal cancer. Polakis 2007. Curr. Opin. Genet. Dev. 17: 45-51. Constitutively activated Beta-catenin signaling, due to APC deficiency or Beta-catenin mutations that prevent its degradation, leads to excessive stem cell renewal/proliferation that predisposes cells to tumorigenesis. Indeed, APC deletion or Beta-catenin activation in stem cells is essential for intestinal neoplasia. Fuchs 2009 Cell 137: 811-819.

Mutations in Beta-Catenin, alterations of levels and cellular compartmentalization of Beta-Catenin, and other aberrations of the Wnt/Beta-Catenin pathway are thus involved directly or indirectly with many diseases. In some Beta-Catenin-related cancers, Beta-Catenin is required for tumor growth but is not amplified, over-expressed or mis-localized.

There exists the need for treatments related to Beta-Catenin-related diseases.

BRIEF SUMMARY OF THE INVENTION

The present disclosure provides RNAi (RNA interference) agents to Beta-Catenin, for inhibition of the target gene Beta-Catenin, which are useful in the treatment of Beta-Catenin-related diseases, such as adenomatous polyposis of the colon, colorectal cancer, basal cell carcinoma, breast cancer, kidney cancer, Wilms tumors, medulloblastoma, ovarian cancer, adrenocortical tumors, gastric cancer, liver cancer, melanoma, pancreatic cancers, prostate cancer, renal cancer, ectopic teeth and taste papillae, skin cancer, pilomatrixoma, anaplastic thyroid carcinoma, and uterine carcinosarcoma, oligodontia, osteoporosis, ageing, degenerative diseases, bedsores, chronic wounds and impaired wound healing, and similar and related diseases. The present disclosure also encompasses a method of treating a human subject having a pathological state mediated at least in part by Beta-Catenin expression, the method comprising the step of administering to the subject a therapeutically effect amount of a RNAi agent to Beta-Catenin.

The present disclosure provides specific RNAi agents and methods that are useful in reducing Beta-Catenin levels in a subject, e.g., a mammal, such as a human. The present disclosure specifically provides double-stranded RNAi agents comprising at least 15 or more contiguous nucleotides of Beta-Catenin. In particular, the present disclosure provides agents comprising a sense strand and an anti-sense strand, wherein the sense strand and/or the anti-sense strand comprise sequences of 15 or more contiguous nucleotides differing by 0, 1, 2 or 3 from those of the RNAi agents provided, e.g., in Table 1 or elsewhere herein, and modified and unmodified variants thereof. Unmodified sequences are sometimes referred to as "generic". The present disclosure also provides agents comprising a sense strand and an anti-sense strand, wherein the sense strand and/or the anti-sense strand comprise sequences of 19 or more contiguous nucleotides differing by 0, 1, 2 or 3 from those of the RNAi agents provided, e.g., in Table 1 or elsewhere herein, and modified and unmodified variants thereof. The sense strand and anti-sense strand can be contiguous, or covalently bound, e.g., via a loop or linker. The RNAi agents particularly can in one embodiment comprise less than about 30 nucleotides per strand, e.g., such as 17 to 23 nucleotides, 18 to 22 nucleotides, 17 to 23 nucleotides, and/or 19 to 21 nucleotides, and/or 19 to 30 nucleotides, and/or such as those provided, e.g., in Tables 1, 2, 3, 4, 5, 6, 7, 8 and/or 9 or elsewhere herein.

The double-stranded RNAi agents can have 0, 1 or 2 blunt ends, and/or overhangs of 1, 2, 3 or 4 nucleotides (i.e., 1 to 4 nt) from one or both 3' and/or 5' ends. The double-stranded RNAi agents can also optionally comprise one or two 3' caps and/or one or more modified nucleotides. Modified variants of sequences as provided herein include those that are otherwise identical but contain substitutions of a naturally-occurring nucleotide for a corresponding modified nucleotide.

Further, the RNAi agent can either contain only naturally-occurring ribonucleotide subunits, or one or more modifications to the sugar, phosphate or base of one or more of the replacement nucleotide subunits, whether they comprise ribonucleotide subunits or deoxyribonucleotide subunits. In one embodiment, modified variants of the disclosed RNAi agents have a thymidine (as RNA, or, preferably, DNA) replacing a uridine. In one embodiment, modified variants of the disclosed RNAi agents include RNAi agents with the same sequence (e.g., the same sequence of bases), but with one or more modifications to one or more of the sugar, phosphate or base of one or more of the nucleotide subunits. In one embodiment, the modifications improve efficacy, stability (e.g., against nucleases in blood serum and/or intestinal fluid), and/or reduce immunogenicity of the RNAi agent. One aspect of the present disclosure relates to a double-stranded oligonucleotide comprising at least one non-natural nucleobase. In certain embodiments, the non-natural nucleobase is difluorotolyl, nitroindolyl, nitropyrrolyl, or nitroimidazolyl. In a particular embodiment, the non-natural nucleobase is difluorotolyl. In certain embodiments, only one of the two oligonucleotide strands contains a non-natural nucleobase. In certain embodiments, both of the oligonucleotide strands contain a non-natural nucleobase.

The RNAi agent(s) can optionally be attached to a ligand selected to improve one or more characteristics, e.g., stability, distribution and/or cellular uptake of the agent, e.g. cholesterol or a derivative thereof. The RNAi agent(s) can be isolated or part of a pharmaceutical composition used for the methods described herein. The pharmaceutical compositions can optionally comprise two or more RNAi agents, each one directed to the same or a different segment the Beta-Catenin mRNA. Optionally, the pharmaceutical compositions can further comprise or be used in conjunction with any known treatment for any Beta-Catenin-related disease.

The present disclosure further provides methods for reducing the level of Beta-Catenin mRNA in a cell, particularly in the case of a disease characterized by over-expression or hyper-activity of Beta-Catenin. Such methods comprise the step of administering one or more of the RNAi agents of the present disclosure to a cell, as further described below. The present methods utilize the cellular mechanisms involved in RNA interference to selectively degrade the target RNA in a cell and are comprised of the step of contacting a cell with one of the RNAi agents of the present disclosure. The present disclosure also encompasses a method of treating a human subject having a pathological state mediated at least in part by Beta-Catenin expression, over-expression, hyper-activity or improper cellular compartmentalization, the method comprising the step of administering to the subject a therapeutically effect amount of a RNAi agent to Beta-Catenin. Additional methods involve a pathological state wherein disease progression (e.g., tumor growth) requires Beta-Catenin, although Beta-Catenin is not amplified, over-expressed or mis-localized. Such methods can be performed directly on a cell or can be performed on a mammalian subject by administering to a cell or a subject one or more of the RNAi agents/pharmaceutical compositions of the present disclosure. Reduction of target Beta-Catenin RNA in a cell results in a reduction in the amount of encoded Beta-Catenin protein produced. In an organism, this can result in restoration of balance in the Wnt/Beta-Catenin pathway, and/or prevention of Beta-Catenin accumulation, and/or restoration of proper cell compartmentalization of Beta-Catenin, and/or a reduction in Beta-Catenin activity and/or expression, and/or prevention of Beta-Catenin-mediated activation of Wnt-related genes such as the proto-oncogene c-myc, and/or amelioration, treatment and/or prevention of a Beta-Catenin-related disease. In some Beta-Catenin-related cancers, Beta-Catenin is required for tumor growth but is not amplified, over-expressed or mis-localized. A reduction in Beta-Catenin expression, level or activity should thus limit tumor growth.

The methods and compositions of the present disclosure, e.g., the methods and Beta-Catenin RNAi agent compositions, can be used with any dosage and/or formulation described herein, as well as with any route of administration described herein.

The details of one or more embodiments of the present disclosure are set forth in the accompanying drawings and the description below. Elements of the various embodiments (e.g., sequences, modifications, endcaps, combinations of RNAi agents, ligands, additional treatments or methods which can be used, etc.) which are not mutually-exclusive can be combined with each other. Combinations which are mutually exclusive include, for example, the fact that a RNAi agent comprising two strands cannot by definition have both two blunt ends and two overhangs. Furthermore, any RNAi agent sequence can be combined with any set of modifications or endcaps disclosed herein, provided the elements of the combination are not mutually exclusive. Any combination of modifications, 5' end caps, and/or 3' end caps can be used with any RNAi agent sequence disclosed herein. Any RNAi agent can be combined with any other RNAi agent or other treatment composition or method. Other features, objects, and advantages of the present disclosure will be apparent from this description, the drawings, and from the claims.

BRIEF DESCRIPTION OF THE FIGURES

FIG. 1 illustrates various modified nucleotides: U002, U003, U004, U005, C004, C005, A004, A005, G005, and G004, which can be used in the RNAi agents disclosed herein. U002 indicates a 2'-deoxy-thymidine which is DNA. U003 indicates 2'-deoxy uridine. U004 indicates a nucleotide with a U base with a 2'-O-methyl modification. U005 indicates a U base with a 2'-O-methoxyethyl (MOE) modification. C004 indicates a C base with a 2'-O-methyl modification. C005 indicates a C base with 2'-O-methoxyethyl modification. A004 indicates an A base with a 2'-O-methyl modification. A005 indicates an A base with 2'-O-methoxyethyl modification. G005 indicates a G base with a 2'O-methyl modification. G004 indicates a G base with a 2'O-methyl modification. Polynucleotide sequences written with the symbols U002, U003, U004, etc. are sometimes prefaced by "X" (indicating the start of the sequence), and sometimes have a "p" between the bases, indicating the phosphodiester bond between nucleosides.

DETAILED DESCRIPTION OF THE INVENTION

The present disclosure encompasses RNAi agents to Beta-Catenin, for inhibition of the target gene Beta-Catenin, which are useful in treatment of Beta-Catenin-related diseases (e.g., diseases associated with mutations in and/or altered expression, compartmentalization, level and/or activity of Beta-Catenin, and/or diseases treatable by modulating the expression, level and/or activity of Beta-Catenin), such as adenomatous polyposis of the colon, colorectal cancer, basal cell carcinoma, breast cancer, kidney cancer, Wilms tumors, medulloblastoma, ovarian cancer, adrenocortical tumors, gastric cancer, liver cancer, melanoma, pancreatic cancers, prostate cancer, renal cancer, ectopic teeth and taste papillae, skin cancer, pilomatrixoma, anaplastic thyroid carcinoma, and uterine carcinosarcoma, oligodontia, osteoporosis, ageing, degenerative diseases, bedsores, chronic wounds and impaired wound healing, and similar and related diseases. In some Beta-Catenin-related cancers, Beta-Catenin is required for tumor growth but is not amplified, over-expressed or mis-localized. A reduction in Beta-Catenin expression, level or activity should thus limit tumor growth. The present disclosure also encompasses a method of treating a human subject having a pathological state mediated at least in part by Beta-Catenin expression, the method comprising the step of administering to the subject a therapeutically effect amount of a RNAi agent to Beta-Catenin.

Various Embodiments of the Present Disclosure Include

RNAi Agent Comprising an Anti-Sense Strand of a RNAi Agent Described Herein.

In one embodiment, the present disclosure relates to a composition comprising a RNAi agent comprising a sense strand and an antisense strand, wherein the antisense strand comprises at least 15 contiguous nucleotides differing by 0, 1, 2, or 3 nucleotides from the antisense strand of a RNAi agent specific to Beta-Catenin (or any set of overlapping RNAi agents specific to Beta-Catenin) provided, e.g., in Tables 1, 2, 3, 4, 5, 6, 7, 8 and/or 9. In another embodiment, the present disclosure relates to a composition comprising a RNAi agent comprising a sense and an anti-sense strand, wherein the sense strand comprises at least 15 contiguous nucleotides differing by 0, 1, 2, or 3 nucleotides from the sense strand of a RNAi agent from any sequence provided herein. In another embodiment, the present disclosure relates to a composition comprising a RNAi agent comprising a first strand and a second strand, wherein the first strand comprises at least 15 contiguous nucleotides differing by 0, 1, 2, or 3 nucleotides from the sequence of the first strand, and the second strand comprises at least 15 contiguous nucleotides differing by 0, 1, 2, or 3 nucleotides from the sequence of the second strand of any RNAi agent provided herein. In another embodiment, the present disclosure relates to a composition comprising a RNAi agent comprising a first strand and a second strand, wherein the sequence of the first strand comprises the sequence of the first strand of any RNAi agent provided herein. In another embodiment, the present disclosure relates to a composition comprising a RNAi agent comprising a first strand and a second strand, wherein the sequence of the first strand is the sequence of the first strand of any RNAi agent provided herein. In another embodiment, the present disclosure relates to a composition comprising a RNAi agent comprising a first strand and a second strand, wherein the sequences of the first and/or second strands comprise the sequences of the first and/or second strand of any RNAi agent provided herein. In another embodiment, the present disclosure relates to a composition comprising a RNAi agent comprising a first strand and a second strand, wherein the sequences of the first and/or second strand are the sequences of the first and/or second strand of any RNAi agent provided herein. In these various embodiments, the RNAi agent is for inhibition of the target gene Beta-Catenin.

Particular duplexes include the unmodified and example modified sequences listed in Table 1. In addition to the described example modifications, other modified variants can be made using the nucleotide sequences provided.

TABLE 1

SEQ ID NOs. for RNAi Agents to Beta-Catenin
Provided in Table 1 are the nickname of various Beta-Catenin RNAi duplexes; the unmodified sense and anti-sense sequences and SEQ ID NOs; an example modified sense and antisense sequence and SEQ ID NOs; and the position of the RNAi agent within the Beta-Catenin gene.

| | UNMODIFIED SEQUENCE | | EXAMPLE MODIFIED SEQUENCE | | |
|---|---|---|---|---|---|
| DUPLEX | Sense SEQ ID NO: | Anti-sense SEQ ID NO: | Sense SEQ ID NO: | Anti-sense SEQ NO: | Position |
| AD-18892 | 4771 | 5430 | 1 | 6497 | 2500 |
| AD-18893 | 4772 | 5431 | 2 | 661 | 1659 |
| AD-18894 | 4773 | 5432 | 3 | 662 | 3038 |
| AD-18895 | 4774 | 5433 | 4 | 663 | 2096 |
| AD-18896 | 4775 | 5434 | 5 | 664 | 265 |
| AD-18897 | 4776 | 5435 | 6 | 665 | 1797 |
| AD-18898 | 4777 | 5436 | 7 | 666 | 2587 |
| AD-18899 | 4778 | 5437 | 8 | 667 | 1541 |
| AD-18900 | 4779 | 5438 | 9 | 668 | 2391 |
| AD-18901 | 4780 | 5439 | 10 | 669 | 954 |
| AD-18902 | 4781 | 5440 | 11 | 670 | 2908 |
| AD-18903 | 4782 | 5441 | 12 | 671 | 3104 |
| AD-18904 | 4783 | 5442 | 13 | 672 | 1665 |
| AD-18905 | 4784 | 5443 | 14 | 673 | 2594 |
| AD-18906 | 4785 | 5444 | 15 | 674 | 3147 |
| AD-18907 | 4786 | 5445 | 16 | 675 | 2592 |
| AD-18908 | 4787 | 5446 | 17 | 676 | 2507 |
| AD-18909 | 4788 | 5447 | 18 | 677 | 2325 |
| AD-18910 | 4789 | 5448 | 19 | 678 | 2326 |
| AD-18911 | 4790 | 5449 | 20 | 679 | 577 |
| AD-18912 | 4791 | 5450 | 21 | 680 | 2116 |
| AD-18913 | 4792 | 5451 | 22 | 681 | 2708 |
| AD-18914 | 4793 | 5452 | 23 | 682 | 2912 |
| AD-18915 | 4794 | 5453 | 24 | 683 | 2704 |
| AD-18916 | 4795 | 5454 | 25 | 684 | 3146 |
| AD-18917 | 4796 | 5455 | 26 | 685 | 1542 |
| AD-18918 | 4797 | 5456 | 27 | 686 | 621 |
| AD-18919 | 4798 | 5457 | 28 | 687 | 2505 |
| AD-18920 | 4799 | 5458 | 29 | 688 | 2590 |
| AD-18921 | 4800 | 5459 | 30 | 689 | 3099 |
| AD-18922 | 4801 | 5460 | 31 | 690 | 2591 |
| AD-18923 | 4802 | 5461 | 32 | 691 | 2112 |
| AD-18925 | 4803 | 5462 | 33 | 692 | 366 |
| AD-18926 | 4804 | 5463 | 34 | 693 | 2479 |
| AD-18927 | 4805 | 5464 | 35 | 694 | 1502 |
| AD-18928 | 4806 | 5465 | 36 | 695 | 2073 |
| AD-18929 | 4807 | 5466 | 37 | 696 | 2702 |
| AD-18930 | 4808 | 5467 | 38 | 697 | 1774 |
| AD-18931 | 4809 | 5468 | 39 | 698 | 708 |
| AD-18932 | 4810 | 5469 | 40 | 699 | 1667 |
| AD-18933 | 4811 | 5470 | 41 | 700 | 2629 |
| AD-18934 | 4812 | 5471 | 42 | 701 | 2114 |
| AD-18935 | 4813 | 5472 | 43 | 702 | 2706 |
| AD-18936 | 4814 | 5473 | 44 | 703 | 2899 |
| AD-18937 | 4815 | 5474 | 45 | 704 | 1639 |
| AD-18938 | 4816 | 5475 | 46 | 705 | 1638 |
| AD-18939 | 4817 | 5476 | 47 | 706 | 2906 |
| AD-18940 | 4818 | 5477 | 48 | 707 | 3145 |
| AD-18941 | 4819 | 5478 | 49 | 708 | 2390 |
| AD-18942 | 4820 | 5479 | 50 | 709 | 2707 |
| AD-18943 | 4821 | 5480 | 51 | 710 | 1668 |
| AD-18944 | 4822 | 5481 | 52 | 711 | 2506 |
| AD-18945 | 4823 | 5482 | 53 | 712 | 1286 |
| AD-18946 | 4824 | 5483 | 54 | 713 | 1660 |
| AD-18947 | 4825 | 5484 | 55 | 714 | 2328 |
| AD-18948 | 4826 | 5485 | 56 | 715 | 1776 |
| AD-18949 | 4827 | 5486 | 57 | 716 | 619 |
| AD-18950 | 4828 | 5487 | 58 | 717 | 807 |
| AD-18951 | 4829 | 5488 | 59 | 718 | 2417 |
| AD-18952 | 4830 | 5489 | 60 | 719 | 3165 |
| AD-18953 | 4831 | 5490 | 61 | 720 | 266 |

TABLE 1-continued

SEQ ID NOs. for RNAi Agents to Beta-Catenin
Provided in Table 1 are the nickname of various Beta-Catenin RNAi
duplexes; the unmodified sense and anti-sense sequences and SEQ ID NOs;
an example modified sense and antisense sequence and SEQ ID NOs;
and the position of the RNAi agent within the Beta-Catenin gene.

| | UNMODIFIED SEQUENCE | | EXAMPLE MODIFIED SEQUENCE | | |
|---|---|---|---|---|---|
| DUPLEX | Sense SEQ ID NO: | Anti-sense SEQ ID NO: | Sense SEQ ID NO: | Anti-sense SEQ ID NO: | Position |
| AD-18954 | 4832 | 5491 | 62 | 721 | 618 |
| AD-18955 | 4833 | 5492 | 63 | 722 | 2113 |
| AD-18956 | 4834 | 5493 | 64 | 723 | 3040 |
| AD-18957 | 4835 | 5494 | 65 | 724 | 3166 |
| AD-18958 | 4836 | 5495 | 66 | 725 | 3041 |
| AD-18959 | 4837 | 5496 | 67 | 726 | 582 |
| AD-18960 | 4838 | 5497 | 68 | 727 | 3220 |
| AD-18961 | 4839 | 5498 | 69 | 728 | 2125 |
| AD-18962 | 4840 | 5499 | 70 | 729 | 2101 |
| AD-18963 | 4841 | 5500 | 71 | 730 | 1773 |
| AD-18964 | 4842 | 5501 | 72 | 731 | 2588 |
| AD-18965 | 4843 | 5502 | 73 | 732 | 2598 |
| AD-18966 | 4844 | 5503 | 74 | 733 | 2907 |
| AD-18967 | 4845 | 5504 | 75 | 734 | 2508 |
| AD-18968 | 4846 | 5505 | 76 | 735 | 3102 |
| AD-18969 | 4847 | 5506 | 77 | 736 | 3042 |
| AD-18970 | 4848 | 5507 | 78 | 737 | 2499 |
| AD-18971 | 4849 | 5508 | 79 | 738 | 2124 |
| AD-18972 | 4850 | 5509 | 80 | 739 | 3105 |
| AD-18973 | 4851 | 5510 | 81 | 740 | 2119 |
| AD-18974 | 4852 | 5511 | 82 | 741 | 641 |
| AD-18975 | 4853 | 5512 | 83 | 742 | 2584 |
| AD-18976 | 4854 | 5513 | 84 | 743 | 2105 |
| AD-18977 | 4855 | 5514 | 85 | 744 | 1069 |
| AD-18978 | 4856 | 5515 | 86 | 745 | 2330 |
| AD-18979 | 4857 | 5516 | 87 | 746 | 2388 |
| AD-18980 | 4858 | 5517 | 88 | 747 | 3224 |
| AD-18981 | 4859 | 5518 | 89 | 748 | 3098 |
| AD-18982 | 4860 | 5519 | 90 | 749 | 2049 |
| AD-18983 | 4861 | 5520 | 91 | 750 | 1796 |
| AD-18984 | 4862 | 5521 | 92 | 751 | 2127 |
| AD-18985 | 4863 | 5522 | 93 | 752 | 3029 |
| AD-18986 | 4864 | 5523 | 94 | 753 | 2596 |
| AD-18987 | 4865 | 5524 | 95 | 754 | 3221 |
| AD-18988 | 4866 | 5525 | 96 | 755 | 3159 |
| AD-18989 | 4867 | 5526 | 97 | 756 | 2583 |
| AD-18990 | 4868 | 5527 | 98 | 757 | 1655 |
| AD-18991 | 4869 | 5528 | 99 | 758 | 874 |
| AD-18992 | 4870 | 5529 | 100 | 759 | 3028 |
| AD-18993 | 4871 | 5530 | 101 | 760 | 3037 |
| AD-18994 | 4872 | 5531 | 102 | 761 | 1504 |
| AD-18995 | 4873 | 5532 | 103 | 762 | 3095 |
| AD-18996 | 4874 | 5533 | 104 | 763 | 2703 |
| AD-18997 | 4875 | 5534 | 105 | 764 | 3154 |
| AD-18998 | 4876 | 5535 | 106 | 765 | 3094 |
| AD-18999 | 4877 | 5536 | 107 | 766 | 2599 |
| AD-19000 | 4878 | 5537 | 108 | 767 | 643 |
| AD-19001 | 4879 | 5538 | 109 | 768 | 2389 |
| AD-19002 | 4880 | 5539 | 110 | 769 | 1669 |
| AD-19003 | 4881 | 5540 | 111 | 770 | 2106 |
| AD-19004 | 4882 | 5541 | 112 | 771 | 3170 |
| AD-19005 | 4883 | 5542 | 113 | 772 | 3103 |
| AD-19006 | 4884 | 5543 | 114 | 773 | 642 |
| AD-19007 | 4885 | 5544 | 115 | 774 | 3230 |
| AD-19008 | 4886 | 5545 | 116 | 775 | 3222 |
| AD-19009 | 4887 | 5546 | 117 | 776 | 2905 |
| AD-19010 | 4888 | 5547 | 118 | 777 | 2904 |
| AD-19011 | 4889 | 5548 | 119 | 778 | 579 |
| AD-19012 | 4890 | 5549 | 120 | 779 | 3171 |
| AD-19042 | 4891 | 5550 | 121 | 780 | 2504 |
| AD-19043 | 4892 | 5551 | 122 | 781 | 3039 |
| AD-19044 | 4893 | 5552 | 123 | 782 | 3034 |
| AD-19045 | 4894 | 5553 | 124 | 783 | 1505 |
| AD-19046 | 4895 | 5554 | 125 | 784 | 1288 |
| AD-19047 | 4896 | 5555 | 126 | 785 | 2123 |
| AD-19048 | 4897 | 5556 | 127 | 786 | 620 |
| AD-19049 | 4898 | 5557 | 128 | 787 | 3164 |
| AD-19050 | 4899 | 5558 | 129 | 788 | 3101 |
| AD-19051 | 4900 | 5559 | 130 | 789 | 2329 |
| AD-19052 | 4901 | 5560 | 131 | 790 | 2115 |
| AD-19053 | 4902 | 5561 | 132 | 791 | 2627 |
| AD-19054 | 4903 | 5562 | 133 | 792 | 2902 |
| AD-19055 | 4904 | 5563 | 134 | 793 | 262 |
| AD-19056 | 4905 | 5564 | 135 | 794 | 1406 |
| AD-19057 | 4906 | 5565 | 136 | 795 | 2497 |
| AD-19058 | 4907 | 5566 | 137 | 796 | 3043 |
| AD-19059 | 4908 | 5567 | 138 | 797 | 2589 |
| AD-19060 | 4909 | 5568 | 139 | 798 | 2586 |
| AD-19061 | 4910 | 5569 | 140 | 799 | 1658 |
| AD-19062 | 4911 | 5570 | 141 | 800 | 2050 |
| AD-19063 | 4912 | 5571 | 142 | 801 | 2385 |
| AD-19064 | 4913 | 5572 | 143 | 802 | 1637 |
| AD-19065 | 4914 | 5573 | 144 | 803 | 707 |
| AD-19066 | 4915 | 5574 | 145 | 804 | 2597 |
| AD-19067 | 4916 | 5575 | 146 | 805 | 3161 |
| AD-19068 | 4917 | 5576 | 147 | 806 | 875 |
| AD-19069 | 4918 | 5577 | 148 | 807 | 3044 |
| AD-19070 | 4919 | 5578 | 149 | 808 | 617 |
| AD-19071 | 4920 | 5579 | 150 | 809 | 2498 |
| AD-19072 | 4921 | 5580 | 151 | 810 | 367 |
| AD-19073 | 4922 | 5581 | 152 | 811 | 2545 |
| AD-19074 | 4923 | 5582 | 153 | 812 | 1544 |
| AD-19075 | 4924 | 5583 | 154 | 813 | 3148 |
| AD-19076 | 4925 | 5584 | 155 | 814 | 2909 |
| AD-19077 | 4926 | 5585 | 156 | 815 | 2509 |
| AD-19078 | 4927 | 5586 | 157 | 816 | 1775 |
| AD-19079 | 4928 | 5587 | 158 | 817 | 1407 |
| AD-19080 | 4929 | 5588 | 159 | 818 | 2327 |
| AD-19081 | 4930 | 5589 | 160 | 819 | 3031 |
| AD-19082 | 4931 | 5590 | 161 | 820 | 1661 |
| AD-19083 | 4932 | 5591 | 162 | 821 | 3162 |
| AD-19738 | 4933 | 5592 | 163 | 822 | 1906 |
| AD-19739 | 4934 | 5593 | 164 | 823 | 825 |
| AD-19740 | 4935 | 5594 | 165 | 824 | 1838 |
| AD-19741 | 4936 | 5595 | 166 | 825 | 1714 |
| AD-19742 | 4937 | 5596 | 167 | 826 | 1859 |
| AD-19743 | 4938 | 5597 | 168 | 827 | 324 |
| AD-19744 | 4939 | 5598 | 169 | 828 | 535 |
| AD-19745 | 4940 | 5599 | 170 | 829 | 822 |
| AD-19746 | 4941 | 5600 | 171 | 830 | 826 |
| AD-19747 | 4942 | 5601 | 172 | 831 | 851 |
| AD-19748 | 4943 | 5602 | 173 | 832 | 1313 |
| AD-19749 | 4944 | 5603 | 174 | 833 | 1860 |
| AD-19750 | 4945 | 5604 | 175 | 834 | 2016 |
| AD-19751 | 4946 | 5605 | 176 | 835 | 1868 |
| AD-19752 | 4947 | 5606 | 177 | 836 | 1869 |
| AD-19753 | 4948 | 5607 | 178 | 837 | 1876 |
| AD-19754 | 4949 | 5608 | 179 | 838 | 1908 |
| AD-19755 | 4950 | 5609 | 180 | 839 | 2192 |
| AD-19756 | 4951 | 5610 | 181 | 840 | 520 |
| AD-19757 | 4952 | 5611 | 182 | 841 | 524 |
| AD-19758 | 4953 | 5612 | 183 | 842 | 623 |
| AD-19759 | 4954 | 5613 | 184 | 843 | 916 |
| AD-19760 | 4955 | 5614 | 185 | 844 | 1153 |
| AD-19761 | 4956 | 5615 | 186 | 845 | 1677 |
| AD-19762 | 4957 | 5616 | 187 | 846 | 1864 |
| AD-19763 | 4958 | 5617 | 188 | 847 | 246 |
| AD-19765 | 4959 | 5618 | 189 | 848 | 637 |
| AD-19766 | 4960 | 5619 | 190 | 849 | 823 |
| AD-19767 | 4961 | 5620 | 191 | 850 | 1028 |
| AD-19768 | 4962 | 5621 | 192 | 851 | 1314 |
| AD-20124 | 4963 | 5622 | 193 | 852 | 2012 |
| AD-25889 | 4964 | 5623 | 194 | 853 | 2632 |
| AD-25890 | 4965 | 5624 | 195 | 854 | 2637 |

TABLE 1-continued

SEQ ID NOs. for RNAi Agents to Beta-Catenin
Provided in Table 1 are the nickname of various Beta-Catenin RNAi
duplexes; the unmodified sense and anti-sense sequences and SEQ ID NOs;
an example modified sense and antisense sequence and SEQ ID NOs;
and the position of the RNAi agent within the Beta-Catenin gene.

| | UNMODIFIED SEQUENCE | | EXAMPLE MODIFIED SEQUENCE | | |
|---|---|---|---|---|---|
| DUPLEX | Sense SEQ ID NO: | Anti-sense SEQ ID NO: | Sense SEQ ID NO: | Anti-sense SEQ ID NO: | Position |
| AD-25891 | 4966 | 5625 | 196 | 855 | 2648 |
| AD-25892 | 4967 | 5626 | 197 | 856 | 2649 |
| AD-25893 | 4968 | 5627 | 198 | 857 | 2663 |
| AD-25894 | 4969 | 5628 | 199 | 858 | 2664 |
| AD-25895 | 4970 | 5629 | 200 | 859 | 2694 |
| AD-25896 | 4971 | 5630 | 201 | 860 | 2695 |
| AD-25897 | 4972 | 5631 | 202 | 861 | 2697 |
| AD-25898 | 4973 | 5632 | 203 | 862 | 2698 |
| AD-25899 | 4974 | 5633 | 204 | 863 | 2699 |
| AD-25900 | 4975 | 5634 | 205 | 864 | 2751 |
| AD-25901 | 4976 | 5635 | 206 | 865 | 2752 |
| AD-25902 | 4977 | 5636 | 207 | 866 | 2753 |
| AD-25903 | 4978 | 5637 | 208 | 867 | 2832 |
| AD-25904 | 4979 | 5638 | 209 | 868 | 2833 |
| AD-25905 | 4980 | 5639 | 210 | 869 | 2837 |
| AD-25906 | 4981 | 5640 | 211 | 870 | 2843 |
| AD-25907 | 4982 | 5641 | 212 | 871 | 2844 |
| AD-25908 | 4983 | 5642 | 213 | 872 | 2845 |
| AD-25909 | 4984 | 5643 | 214 | 873 | 2846 |
| AD-25910 | 4885 | 5644 | 215 | 874 | 2859 |
| AD-25911 | 4986 | 5645 | 216 | 875 | 2913 |
| AD-25912 | 4987 | 5646 | 217 | 876 | 2914 |
| AD-25913 | 4988 | 5647 | 218 | 877 | 2938 |
| AD-25914 | 4989 | 5648 | 219 | 878 | 2940 |
| AD-25915 | 4990 | 5649 | 220 | 879 | 2941 |
| AD-25916 | 4991 | 5650 | 221 | 880 | 2942 |
| AD-25917 | 4992 | 5651 | 222 | 881 | 2991 |
| AD-25918 | 4993 | 5652 | 223 | 882 | 2992 |
| AD-25919 | 4994 | 5653 | 224 | 883 | 2997 |
| AD-25920 | 4995 | 5654 | 225 | 884 | 2998 |
| AD-25921 | 4996 | 5655 | 226 | 885 | 3077 |
| AD-25922 | 4997 | 5656 | 227 | 886 | 3078 |
| AD-25923 | 4998 | 5657 | 228 | 887 | 3080 |
| AD-25924 | 4999 | 5658 | 229 | 888 | 3083 |
| AD-25925 | 5000 | 5659 | 230 | 889 | 3110 |
| AD-25926 | 5001 | 5660 | 231 | 890 | 3111 |
| AD-25927 | 5002 | 5661 | 232 | 891 | 3112 |
| AD-25928 | 5003 | 5662 | 233 | 892 | 3123 |
| AD-25929 | 5004 | 5663 | 234 | 893 | 3124 |
| AD-25930 | 5005 | 5664 | 235 | 894 | 3125 |
| AD-25931 | 5006 | 5665 | 236 | 895 | 3132 |
| AD-25932 | 5007 | 5666 | 237 | 896 | 3133 |
| AD-25933 | 5008 | 5667 | 238 | 897 | 3135 |
| AD-25934 | 5009 | 5668 | 239 | 898 | 3168 |
| AD-25935 | 5010 | 5669 | 240 | 899 | 3169 |
| AD-25936 | 5011 | 5670 | 241 | 900 | 3172 |
| AD-25937 | 5012 | 5671 | 242 | 901 | 3192 |
| AD-25938 | 5013 | 5672 | 243 | 902 | 2665 |
| AD-25939 | 5014 | 5673 | 244 | 903 | 2682 |
| AD-25940 | 5015 | 5674 | 245 | 904 | 2683 |
| AD-25941 | 5016 | 5675 | 246 | 905 | 2684 |
| AD-25942 | 5017 | 5676 | 247 | 906 | 2685 |
| AD-25943 | 5018 | 5677 | 248 | 907 | 2686 |
| AD-25944 | 5019 | 5678 | 249 | 908 | 2687 |
| AD-25945 | 5020 | 5679 | 250 | 909 | 2696 |
| AD-25946 | 5021 | 5680 | 251 | 910 | 2709 |
| AD-25947 | 5022 | 5681 | 252 | 911 | 2710 |
| AD-25948 | 5023 | 5682 | 253 | 912 | 2711 |
| AD-25949 | 5024 | 5683 | 254 | 913 | 2712 |
| AD-25950 | 5025 | 5684 | 255 | 914 | 2713 |
| AD-25951 | 5026 | 5685 | 256 | 915 | 2714 |
| AD-25952 | 5027 | 5686 | 257 | 916 | 2834 |
| AD-25953 | 5028 | 5687 | 258 | 917 | 2835 |
| AD-25954 | 5029 | 5688 | 259 | 918 | 2836 |
| AD-25955 | 5030 | 5689 | 260 | 919 | 2842 |
| AD-25956 | 5031 | 5690 | 261 | 920 | 2847 |
| AD-25957 | 5032 | 5691 | 262 | 921 | 2848 |
| AD-25958 | 5033 | 5692 | 263 | 922 | 2871 |
| AD-25959 | 5034 | 5693 | 264 | 923 | 2993 |
| AD-25960 | 5035 | 5694 | 265 | 924 | 2996 |
| AD-25961 | 5036 | 5695 | 266 | 925 | 3079 |
| AD-25962 | 5037 | 5696 | 267 | 926 | 3084 |
| AD-25963 | 5038 | 5697 | 268 | 927 | 3092 |
| AD-25964 | 5039 | 5698 | 269 | 928 | 3109 |
| AD-26017 | 5040 | 5699 | 270 | 929 | 3152 |
| AD-26018 | 5041 | 5700 | 271 | 930 | 3170 |
| AD-26019 | 5042 | 5701 | 272 | 931 | 3171 |
| AD-26020 | 5043 | 5702 | 273 | 932 | 3198 |
| AD-26021 | 5044 | 5703 | 274 | 933 | 3199 |
| AD-26022 | 5045 | 5704 | 275 | 934 | 207 |
| AD-26023 | 5046 | 5705 | 276 | 935 | 208 |
| AD-26024 | 5047 | 5706 | 277 | 936 | 215 |
| AD-26025 | 5048 | 5707 | 278 | 937 | 216 |
| AD-26026 | 5049 | 5708 | 279 | 938 | 217 |
| AD-26027 | 5050 | 5709 | 280 | 939 | 221 |
| AD-26028 | 5051 | 5710 | 281 | 940 | 222 |
| AD-26029 | 5052 | 5711 | 282 | 941 | 225 |
| AD-26030 | 5053 | 5712 | 283 | 942 | 230 |
| AD-26031 | 5054 | 5713 | 284 | 943 | 231 |
| AD-26032 | 5055 | 5714 | 285 | 944 | 232 |
| AD-26033 | 5056 | 5715 | 286 | 945 | 235 |
| AD-26034 | 5057 | 5716 | 287 | 946 | 236 |
| AD-26035 | 5058 | 5717 | 288 | 947 | 251 |
| AD-26036 | 5059 | 5718 | 289 | 948 | 252 |
| AD-26037 | 5060 | 5719 | 290 | 949 | 257 |
| AD-26038 | 5061 | 5720 | 291 | 950 | 262 |
| AD-26039 | 5062 | 5721 | 292 | 951 | 268 |
| AD-26040 | 5063 | 5722 | 293 | 952 | 269 |
| AD-26041 | 5064 | 5723 | 294 | 953 | 270 |
| AD-26042 | 5065 | 5724 | 295 | 954 | 273 |
| AD-26043 | 5066 | 5725 | 296 | 955 | 285 |
| AD-26044 | 5067 | 5726 | 297 | 956 | 291 |
| AD-26045 | 5068 | 5727 | 298 | 957 | 295 |
| AD-26046 | 5069 | 5728 | 299 | 958 | 305 |
| AD-26047 | 5070 | 5729 | 300 | 959 | 307 |
| AD-26048 | 5071 | 5730 | 301 | 960 | 111 |
| AD-26049 | 5072 | 5731 | 302 | 961 | 316 |
| AD-26050 | 5073 | 5732 | 303 | 962 | 317 |
| AD-26051 | 5074 | 5733 | 304 | 963 | 331 |
| AD-26052 | 5075 | 5734 | 305 | 964 | 338 |
| AD-26053 | 5076 | 5735 | 306 | 965 | 339 |
| AD-26054 | 5077 | 5736 | 307 | 966 | 353 |
| AD-26055 | 5078 | 5737 | 308 | 967 | 354 |
| AD-26056 | 5079 | 5738 | 309 | 968 | 358 |
| AD-26057 | 5080 | 5739 | 310 | 969 | 1216 |
| AD-26058 | 5081 | 5740 | 311 | 970 | 383 |
| AD-26059 | 5082 | 5741 | 312 | 971 | 397 |
| AD-26060 | 5083 | 5742 | 313 | 972 | 402 |
| AD-26061 | 5084 | 5743 | 314 | 973 | 412 |
| AD-26062 | 5085 | 5744 | 315 | 974 | 418 |
| AD-26063 | 5086 | 5745 | 316 | 975 | 424 |
| AD-26064 | 5087 | 5746 | 317 | 976 | 441 |
| AD-26065 | 5088 | 5747 | 318 | 977 | 442 |
| AD-26066 | 5089 | 5748 | 319 | 978 | 451 |
| AD-26067 | 5090 | 5749 | 320 | 979 | 458 |
| AD-26068 | 5091 | 5750 | 321 | 980 | 1232 |
| AD-26069 | 5092 | 5751 | 322 | 981 | 1233 |
| AD-26070 | 5093 | 5752 | 323 | 982 | 460 |
| AD-26071 | 5094 | 5753 | 324 | 983 | 461 |
| AD-26072 | 5095 | 5754 | 325 | 984 | 471 |
| AD-26073 | 5096 | 5755 | 326 | 985 | 478 |
| AD-26074 | 5097 | 5756 | 327 | 986 | 481 |
| AD-26075 | 5098 | 5757 | 328 | 987 | 487 |
| AD-26076 | 5099 | 5758 | 329 | 988 | 493 |

TABLE 1-continued

SEQ ID NOs. for RNAi Agents to Beta-Catenin
Provided in Table 1 are the nickname of various Beta-Catenin RNAi duplexes; the unmodified sense and anti-sense sequences and SEQ ID NOs; an example modified sense and antisense sequence and SEQ ID NOs; and the position of the RNAi agent within the Beta-Catenin gene.

| DUPLEX | UNMODIFIED SEQUENCE Sense SEQ ID NO: | UNMODIFIED SEQUENCE Anti-sense SEQ ID NO: | EXAMPLE MODIFIED SEQUENCE Sense SEQ ID NO: | EXAMPLE MODIFIED SEQUENCE Anti-sense SEQ NO: | Position |
|---|---|---|---|---|---|
| AD-26077 | 5100 | 5759 | 330 | 989 | 507 |
| AD-26078 | 5101 | 5760 | 331 | 990 | 512 |
| AD-26079 | 5102 | 5761 | 332 | 991 | 532 |
| AD-26080 | 5103 | 5762 | 333 | 992 | 542 |
| AD-26081 | 5104 | 5763 | 334 | 993 | 543 |
| AD-26082 | 5105 | 5764 | 335 | 994 | 546 |
| AD-26083 | 5106 | 5765 | 336 | 995 | 558 |
| AD-26084 | 5107 | 5766 | 337 | 996 | 559 |
| AD-26085 | 5108 | 5767 | 338 | 997 | 562 |
| AD-26086 | 5109 | 5768 | 339 | 998 | 576 |
| AD-26087 | 5110 | 5769 | 340 | 999 | 581 |
| AD-26088 | 5111 | 5770 | 341 | 1000 | 584 |
| AD-26089 | 5112 | 5771 | 342 | 1001 | 591 |
| AD-26090 | 5113 | 5772 | 343 | 1002 | 595 |
| AD-26091 | 5114 | 5773 | 344 | 1003 | 604 |
| AD-26092 | 5115 | 5774 | 345 | 1004 | 611 |
| AD-26093 | 5116 | 5775 | 346 | 1005 | 612 |
| AD-26094 | 5117 | 5776 | 347 | 1006 | 613 |
| AD-26095 | 5118 | 5777 | 348 | 1007 | 623 |
| AD-26096 | 5119 | 5778 | 349 | 1008 | 635 |
| AD-26097 | 5120 | 5779 | 350 | 1009 | 642 |
| AD-26098 | 5121 | 5780 | 351 | 1010 | 648 |
| AD-26099 | 5122 | 5781 | 352 | 1011 | 649 |
| AD-26100 | 5123 | 5782 | 353 | 1012 | 652 |
| AD-26101 | 5124 | 5783 | 354 | 1013 | 658 |
| AD-26102 | 5125 | 5784 | 355 | 1014 | 662 |
| AD-26103 | 5126 | 5785 | 356 | 1015 | 666 |
| AD-26104 | 5127 | 5786 | 357 | 1016 | 669 |
| AD-26105 | 5128 | 5787 | 358 | 1017 | 670 |
| AD-26106 | 5129 | 5788 | 359 | 1018 | 672 |
| AD-26107 | 5130 | 5789 | 360 | 1019 | 682 |
| AD-26108 | 5131 | 5790 | 361 | 1020 | 685 |
| AD-26109 | 5132 | 5791 | 362 | 1021 | 691 |
| AD-26110 | 5133 | 5792 | 363 | 1022 | 707 |
| AD-26111 | 5134 | 5793 | 364 | 1023 | 708 |
| AD-26112 | 5135 | 5794 | 365 | 1024 | 715 |
| AD-26123 | 5136 | 5795 | 366 | 1025 | 722 |
| AD-26124 | 5137 | 5796 | 367 | 1026 | 723 |
| AD-26125 | 5138 | 5797 | 368 | 1027 | 724 |
| AD-26126 | 5139 | 5798 | 369 | 1028 | 730 |
| AD-26127 | 5140 | 5799 | 370 | 1029 | 731 |
| AD-26128 | 5141 | 5800 | 371 | 1030 | 732 |
| AD-26129 | 5142 | 5801 | 372 | 1031 | 733 |
| AD-26130 | 5143 | 5802 | 373 | 1032 | 755 |
| AD-26131 | 5144 | 5803 | 374 | 1033 | 756 |
| AD-26132 | 5145 | 5804 | 375 | 1034 | 757 |
| AD-26133 | 5146 | 5805 | 376 | 1035 | 758 |
| AD-26134 | 5147 | 5806 | 377 | 1036 | 1548 |
| AD-26135 | 5148 | 5807 | 378 | 1037 | 1551 |
| AD-26136 | 5149 | 5808 | 379 | 1038 | 759 |
| AD-26137 | 5150 | 5809 | 380 | 1039 | 778 |
| AD-26138 | 5151 | 5810 | 381 | 1040 | 785 |
| AD-26139 | 5152 | 5811 | 382 | 1041 | 788 |
| AD-26140 | 5153 | 5812 | 383 | 1042 | 789 |
| AD-26141 | 5154 | 5813 | 384 | 1043 | 1624 |
| AD-26142 | 5155 | 5814 | 385 | 1044 | 790 |
| AD-26143 | 5156 | 5815 | 386 | 1045 | 791 |
| AD-26144 | 5157 | 5816 | 387 | 1046 | 812 |
| AD-26145 | 5158 | 5817 | 388 | 1047 | 813 |
| AD-26146 | 5159 | 5818 | 389 | 1048 | 816 |
| AD-26147 | 5160 | 5819 | 390 | 1049 | 821 |
| AD-26148 | 5161 | 5820 | 391 | 1050 | 831 |
| AD-26149 | 5162 | 5821 | 392 | 1051 | 842 |
| AD-26150 | 5163 | 5822 | 393 | 1052 | 843 |
| AD-26151 | 5164 | 5823 | 394 | 1053 | 851 |
| AD-26152 | 5165 | 5824 | 395 | 1054 | 855 |
| AD-26153 | 5166 | 5825 | 396 | 1055 | 861 |
| AD-26154 | 5167 | 5826 | 397 | 1056 | 862 |
| AD-26155 | 5168 | 5827 | 398 | 1057 | 866 |
| AD-26156 | 5169 | 5828 | 399 | 1058 | 871 |
| AD-26157 | 5170 | 5829 | 400 | 1059 | 874 |
| AD-26158 | 5171 | 5830 | 401 | 1060 | 877 |
| AD-26159 | 5172 | 5831 | 402 | 1061 | 887 |
| AD-26160 | 5173 | 5832 | 403 | 1062 | 903 |
| AD-26161 | 5174 | 5833 | 404 | 1063 | 907 |
| AD-26162 | 5175 | 5834 | 405 | 1064 | 909 |
| AD-26163 | 5176 | 5835 | 406 | 1065 | 913 |
| AD-26164 | 5177 | 5836 | 407 | 1066 | 914 |
| AD-26165 | 5178 | 5837 | 408 | 1067 | 919 |
| AD-26166 | 5179 | 5838 | 409 | 1068 | 960 |
| AD-26167 | 5180 | 5839 | 410 | 1069 | 975 |
| AD-26168 | 5181 | 5840 | 411 | 1070 | 976 |
| AD-26169 | 5182 | 5841 | 412 | 1071 | 977 |
| AD-26170 | 5183 | 5842 | 413 | 1072 | 978 |
| AD-26171 | 5184 | 5843 | 414 | 1073 | 982 |
| AD-26172 | 5185 | 5844 | 415 | 1074 | 986 |
| AD-26173 | 5186 | 5845 | 416 | 1075 | 997 |
| AD-26174 | 5187 | 5846 | 417 | 1076 | 998 |
| AD-26175 | 5188 | 5847 | 418 | 1077 | 1848 |
| AD-26176 | 5189 | 5848 | 419 | 1078 | 1849 |
| AD-26177 | 5190 | 5849 | 420 | 1079 | 1005 |
| AD-26178 | 5191 | 5850 | 421 | 1080 | 1008 |
| AD-26179 | 5192 | 5851 | 422 | 1081 | 1009 |
| AD-26180 | 5193 | 5852 | 423 | 1082 | 1010 |
| AD-26181 | 5194 | 5853 | 424 | 1083 | 1011 |
| AD-26182 | 5195 | 5854 | 425 | 1084 | 1012 |
| AD-26183 | 5196 | 5855 | 426 | 1085 | 1018 |
| AD-26184 | 5197 | 5856 | 427 | 1086 | 1927 |
| AD-26185 | 5198 | 5857 | 428 | 1087 | 1019 |
| AD-26186 | 5199 | 5858 | 6495 | 1088 | 1022 |
| AD-26187 | 5200 | 5859 | 6496 | 1089 | 1032 |
| AD-26188 | 5201 | 5860 | 431 | 1090 | 1036 |
| AD-26189 | 5202 | 5861 | 432 | 1091 | 1037 |
| AD-26190 | 5203 | 5862 | 433 | 1092 | 1038 |
| AD-26191 | 5204 | 5863 | 434 | 1093 | 1039 |
| AD-26192 | 5205 | 5864 | 435 | 1094 | 1040 |
| AD-26193 | 5206 | 5865 | 436 | 1095 | 1041 |
| AD-26194 | 5207 | 5866 | 437 | 1096 | 1042 |
| AD-26195 | 5208 | 5867 | 438 | 1097 | 1048 |
| AD-26196 | 5209 | 5868 | 439 | 1098 | 1051 |
| AD-26197 | 5210 | 5869 | 440 | 1099 | 1058 |
| AD-26198 | 5211 | 5870 | 441 | 1100 | 1059 |
| AD-26199 | 5212 | 5871 | 442 | 1101 | 1061 |
| AD-26200 | 5213 | 5872 | 443 | 1102 | 1062 |
| AD-26201 | 5214 | 5873 | 444 | 1103 | 1073 |
| AD-26202 | 5215 | 5874 | 445 | 1104 | 1075 |
| AD-26203 | 5216 | 5875 | 446 | 1105 | 1110 |
| AD-26204 | 5217 | 5876 | 447 | 1106 | 206 |
| AD-26205 | 5218 | 5877 | 448 | 1107 | 1113 |
| AD-26206 | 5219 | 5878 | 449 | 1108 | 1114 |
| AD-26207 | 5220 | 5879 | 450 | 1109 | 1115 |
| AD-26208 | 5221 | 5880 | 451 | 1110 | 1118 |
| AD-26209 | 5222 | 5881 | 452 | 1111 | 1119 |
| AD-26210 | 5223 | 5882 | 453 | 1112 | 1139 |
| AD-26211 | 5224 | 5883 | 454 | 1113 | 1153 |
| AD-26212 | 5225 | 5884 | 455 | 1114 | 1185 |
| AD-26213 | 5226 | 5885 | 456 | 1115 | 1220 |
| AD-26214 | 5227 | 5886 | 457 | 1116 | 1221 |
| AD-26215 | 5228 | 5887 | 458 | 1117 | 1222 |
| AD-26216 | 5229 | 5888 | 459 | 1118 | 1225 |
| AD-26217 | 5230 | 5889 | 460 | 1119 | 1226 |
| AD-26218 | 5231 | 5890 | 461 | 1120 | 1227 |
| AD-26651 | 5232 | 5891 | 462 | 1121 | 1228 |
| AD-26652 | 5233 | 5892 | 463 | 1122 | 1229 |

TABLE 1-continued

SEQ ID NOs. for RNAi Agents to Beta-Catenin
Provided in Table 1 are the nickname of various Beta-Catenin RNAi
duplexes; the unmodified sense and anti-sense sequences and SEQ ID NOs;
an example modified sense and antisense sequence and SEQ ID NOs;
and the position of the RNAi agent within the Beta-Catenin gene.

| DUPLEX | UNMODIFIED SEQUENCE | | EXAMPLE MODIFIED SEQUENCE | | Position |
|---|---|---|---|---|---|
| | Sense SEQ ID NO: | Anti-sense SEQ ID NO: | Sense SEQ ID NO: | Anti-sense SEQ ID NO: | |
| AD-26653 | 5234 | 5893 | 464 | 1123 | 1230 |
| AD-26654 | 5235 | 5894 | 465 | 1124 | 1231 |
| AD-26655 | 5236 | 5895 | 466 | 1125 | 1242 |
| AD-26656 | 5237 | 5896 | 467 | 1126 | 1243 |
| AD-26657 | 5238 | 5897 | 468 | 1127 | 1244 |
| AD-26658 | 5239 | 5898 | 469 | 1128 | 1247 |
| AD-26659 | 5240 | 5899 | 470 | 1129 | 1271 |
| AD-26660 | 5241 | 5900 | 471 | 1130 | 1284 |
| AD-26661 | 5242 | 5901 | 472 | 1131 | 1291 |
| AD-26662 | 5243 | 5902 | 473 | 1132 | 1292 |
| AD-26663 | 5244 | 5903 | 474 | 1133 | 1337 |
| AD-26664 | 5245 | 5904 | 475 | 1134 | 1338 |
| AD-26665 | 5246 | 5905 | 476 | 1135 | 1346 |
| AD-26666 | 5247 | 5906 | 477 | 1136 | 1347 |
| AD-26667 | 5248 | 5907 | 478 | 1137 | 1366 |
| AD-26668 | 5249 | 5908 | 479 | 1138 | 1370 |
| AD-26669 | 5250 | 5909 | 480 | 1139 | 1375 |
| AD-26670 | 5251 | 5910 | 481 | 1140 | 1381 |
| AD-26671 | 5252 | 5911 | 482 | 1141 | 1384 |
| AD-26672 | 5253 | 5912 | 483 | 1142 | 1396 |
| AD-26673 | 5254 | 5913 | 484 | 1143 | 1397 |
| AD-26674 | 5255 | 5914 | 485 | 1144 | 1410 |
| AD-26675 | 5256 | 5915 | 486 | 1145 | 1411 |
| AD-26676 | 5257 | 5916 | 487 | 1146 | 1414 |
| AD-26677 | 5258 | 5917 | 488 | 1147 | 2371 |
| AD-26678 | 5259 | 5918 | 489 | 1148 | 1415 |
| AD-26679 | 5260 | 5919 | 490 | 1149 | 1420 |
| AD-26680 | 5261 | 5920 | 491 | 1150 | 1427 |
| AD-26681 | 5262 | 5921 | 492 | 1151 | 1430 |
| AD-26682 | 5263 | 5922 | 493 | 1152 | 1432 |
| AD-26683 | 5264 | 5923 | 494 | 1153 | 1438 |
| AD-26684 | 5265 | 5924 | 495 | 1154 | 1447 |
| AD-26685 | 5266 | 5925 | 496 | 1155 | 1456 |
| AD-26686 | 5267 | 5926 | 497 | 1156 | 1465 |
| AD-26687 | 5268 | 5927 | 498 | 1157 | 1468 |
| AD-26688 | 5269 | 5928 | 499 | 1158 | 1474 |
| AD-26689 | 5270 | 5929 | 500 | 1159 | 1481 |
| AD-26690 | 5271 | 5930 | 501 | 1160 | 1486 |
| AD-26691 | 5272 | 5931 | 502 | 1161 | 1489 |
| AD-26692 | 5273 | 5932 | 503 | 1162 | 1490 |
| AD-26693 | 5274 | 5933 | 504 | 1163 | 2441 |
| AD-26694 | 5275 | 5934 | 505 | 1164 | 1491 |
| AD-26695 | 5276 | 5935 | 506 | 1165 | 1493 |
| AD-26696 | 5277 | 5936 | 507 | 1166 | 1494 |
| AD-26697 | 5278 | 5937 | 508 | 1167 | 1517 |
| AD-26698 | 5279 | 5938 | 509 | 1168 | 1518 |
| AD-26699 | 5280 | 5939 | 510 | 1169 | 1519 |
| AD-26700 | 5281 | 5940 | 511 | 1170 | 1522 |
| AD-26701 | 5282 | 5941 | 512 | 1171 | 1523 |
| AD-26702 | 5283 | 5942 | 513 | 1172 | 1526 |
| AD-26703 | 5284 | 5943 | 514 | 1173 | 1527 |
| AD-26704 | 5285 | 5944 | 515 | 1174 | 1539 |
| AD-26705 | 5286 | 5945 | 516 | 1175 | 1540 |
| AD-26706 | 5287 | 5946 | 517 | 1176 | 1545 |
| AD-26707 | 5288 | 5947 | 518 | 1177 | 1546 |
| AD-26708 | 5289 | 5948 | 519 | 1178 | 1547 |
| AD-26709 | 5290 | 5949 | 520 | 1179 | 1580 |
| AD-26710 | 5291 | 5950 | 521 | 1180 | 1581 |
| AD-26711 | 5292 | 5951 | 522 | 1181 | 1591 |
| AD-26712 | 5293 | 5952 | 523 | 1182 | 1598 |
| AD-26713 | 5294 | 5953 | 524 | 1183 | 1606 |
| AD-26714 | 5295 | 5954 | 525 | 1184 | 1629 |
| AD-26715 | 5296 | 5955 | 526 | 1185 | 1644 |
| AD-26716 | 5297 | 5956 | 527 | 1186 | 1654 |
| AD-26717 | 5298 | 5957 | 528 | 1187 | 1678 |
| AD-26718 | 5299 | 5958 | 529 | 1188 | 1681 |
| AD-26719 | 5300 | 5959 | 530 | 1189 | 1689 |
| AD-26720 | 5301 | 5960 | 531 | 1190 | 1699 |
| AD-26721 | 5302 | 5961 | 532 | 1191 | 1705 |
| AD-26722 | 5303 | 5962 | 533 | 1192 | 1711 |
| AD-26723 | 5304 | 5963 | 534 | 1193 | 1716 |
| AD-26724 | 5305 | 5964 | 535 | 1194 | 1717 |
| AD-26725 | 5306 | 5965 | 536 | 1195 | 1723 |
| AD-26726 | 5307 | 5966 | 537 | 1196 | 1729 |
| AD-26727 | 5308 | 5967 | 538 | 1197 | 1735 |
| AD-26728 | 5309 | 5968 | 539 | 1198 | 1736 |
| AD-26729 | 5310 | 5969 | 540 | 1199 | 1737 |
| AD-26730 | 5311 | 5970 | 541 | 1200 | 1743 |
| AD-26731 | 5312 | 5971 | 542 | 1201 | 1744 |
| AD-26732 | 5313 | 5972 | 543 | 1202 | 1754 |
| AD-26733 | 5314 | 5973 | 544 | 1203 | 1770 |
| AD-26734 | 5315 | 5974 | 545 | 1204 | 1771 |
| AD-26735 | 5316 | 5975 | 546 | 1205 | 1772 |
| AD-26736 | 5317 | 5976 | 547 | 1206 | 1778 |
| AD-26737 | 5318 | 5977 | 548 | 1207 | 1783 |
| AD-26738 | 5319 | 5978 | 549 | 1208 | 1787 |
| AD-26739 | 5320 | 5979 | 550 | 1209 | 1792 |
| AD-26740 | 5321 | 5980 | 551 | 1210 | 1798 |
| AD-26741 | 5322 | 5981 | 552 | 1211 | 1861 |
| AD-26742 | 5323 | 5982 | 553 | 1212 | 1866 |
| AD-26743 | 5324 | 5983 | 554 | 1213 | 1870 |
| AD-26744 | 5325 | 5984 | 555 | 1214 | 1873 |
| AD-26745 | 5326 | 5985 | 556 | 1215 | 1882 |
| AD-26746 | 5327 | 5986 | 557 | 1216 | 1888 |
| AD-26747 | 5328 | 5987 | 558 | 1217 | 1889 |
| AD-26748 | 5329 | 5988 | 559 | 1218 | 1928 |
| AD-26749 | 5330 | 5989 | 560 | 1219 | 1929 |
| AD-26750 | 5331 | 5990 | 561 | 1220 | 1930 |
| AD-26751 | 5332 | 5991 | 562 | 1221 | 1955 |
| AD-26752 | 5333 | 5992 | 563 | 1222 | 1956 |
| AD-26753 | 5334 | 5993 | 564 | 1223 | 1999 |
| AD-26754 | 5335 | 5994 | 565 | 1224 | 2002 |
| AD-26755 | 5336 | 5995 | 566 | 1225 | 2007 |
| AD-26756 | 5337 | 5996 | 567 | 1226 | 2013 |
| AD-26757 | 5338 | 5997 | 568 | 1227 | 2014 |
| AD-26758 | 5339 | 5998 | 569 | 1228 | 2038 |
| AD-26759 | 5340 | 5999 | 570 | 1229 | 2042 |
| AD-26760 | 5341 | 6000 | 571 | 1230 | 2046 |
| AD-26761 | 5342 | 6001 | 572 | 1231 | 2047 |
| AD-26762 | 5343 | 6002 | 573 | 1232 | 2059 |
| AD-26763 | 5344 | 6003 | 574 | 1233 | 2060 |
| AD-26764 | 5345 | 6004 | 575 | 1234 | 2061 |
| AD-26765 | 5346 | 6005 | 576 | 1235 | 2062 |
| AD-26766 | 5347 | 6006 | 577 | 1236 | 2063 |
| AD-26767 | 5348 | 6007 | 578 | 1237 | 2070 |
| AD-26768 | 5349 | 6008 | 579 | 1238 | 2071 |
| AD-26769 | 5350 | 6009 | 580 | 1239 | 2076 |
| AD-26770 | 5351 | 6010 | 581 | 1240 | 2079 |
| AD-26771 | 5352 | 6011 | 582 | 1241 | 2083 |
| AD-26772 | 5353 | 6012 | 583 | 1242 | 2110 |
| AD-26773 | 5354 | 6013 | 584 | 1243 | 2128 |
| AD-26774 | 5355 | 6014 | 585 | 1244 | 2178 |
| AD-26775 | 5356 | 6015 | 586 | 1245 | 2179 |
| AD-26776 | 5357 | 6016 | 587 | 1246 | 2182 |
| AD-26777 | 5358 | 6017 | 588 | 1247 | 2189 |
| AD-26778 | 5359 | 6018 | 589 | 1248 | 2193 |
| AD-26779 | 5360 | 6019 | 590 | 1249 | 2194 |
| AD-26780 | 5361 | 6020 | 591 | 1250 | 2197 |
| AD-26781 | 5362 | 6021 | 592 | 1251 | 2234 |
| AD-26782 | 5363 | 6022 | 593 | 1252 | 2235 |
| AD-26783 | 5364 | 6023 | 594 | 1253 | 2254 |
| AD-26784 | 5365 | 6024 | 595 | 1254 | 2257 |
| AD-26785 | 5366 | 6025 | 596 | 1255 | 2262 |
| AD-26786 | 5367 | 6026 | 597 | 1256 | 2265 |

TABLE 1-continued

SEQ ID NOs. for RNAi Agents to Beta-Catenin
Provided in Table 1 are the nickname of various Beta-Catenin RNAi
duplexes; the unmodified sense and anti-sense sequences and SEQ ID NOs;
an example modified sense and antisense sequence and SEQ ID NOs;
and the position of the RNAi agent within the Beta-Catenin gene.

| DUPLEX | UNMODIFIED SEQUENCE | | EXAMPLE MODIFIED SEQUENCE | | Position |
|---|---|---|---|---|---|
| | Sense SEQ ID NO: | Anti-sense SEQ ID NO: | Sense SEQ ID NO: | Anti-sense SEQ ID NO: | |
| AD-26787 | 5368 | 6027 | 598 | 1257 | 2272 |
| AD-26788 | 5369 | 6028 | 599 | 1258 | 2278 |
| AD-26789 | 5370 | 6029 | 600 | 1259 | 2298 |
| AD-26790 | 5371 | 6030 | 601 | 1260 | 2303 |
| AD-26791 | 5372 | 6031 | 602 | 1261 | 2365 |
| AD-26792 | 5373 | 6032 | 603 | 1262 | 2375 |
| AD-26793 | 5374 | 6033 | 604 | 1263 | 2376 |
| AD-26794 | 5375 | 6034 | 605 | 1264 | 2386 |
| AD-26795 | 5376 | 6035 | 606 | 1265 | 2393 |
| AD-26796 | 5377 | 6036 | 607 | 1266 | 2397 |
| AD-26797 | 5378 | 6037 | 608 | 1267 | 2398 |
| AD-26798 | 5379 | 6038 | 609 | 1268 | 2402 |
| AD-26799 | 5380 | 6039 | 610 | 1269 | 2406 |
| AD-26800 | 5381 | 6040 | 611 | 1270 | 2407 |
| AD-26801 | 5382 | 6041 | 612 | 1271 | 2420 |
| AD-26802 | 5383 | 6042 | 613 | 1272 | 2421 |
| AD-26803 | 5384 | 6043 | 614 | 1273 | 2422 |
| AD-26804 | 5385 | 6044 | 615 | 1274 | 2431 |
| AD-26805 | 5386 | 6045 | 616 | 1275 | 2436 |
| AD-26806 | 5387 | 6046 | 617 | 1276 | 2451 |
| AD-26807 | 5388 | 6047 | 618 | 1277 | 2454 |
| AD-26808 | 5389 | 6048 | 619 | 1278 | 675 |
| AD-26809 | 5390 | 6049 | 620 | 1279 | 676 |
| AD-26810 | 5391 | 6050 | 621 | 1280 | 679 |
| AD-26811 | 5392 | 6051 | 622 | 1281 | 2458 |
| AD-26812 | 5393 | 6052 | 623 | 1282 | 2461 |
| AD-26813 | 5394 | 6053 | 624 | 1283 | 2466 |
| AD-26814 | 5395 | 6054 | 625 | 1284 | 2493 |
| AD-26815 | 5396 | 6055 | 626 | 1285 | 2494 |
| AD-26816 | 5397 | 6056 | 627 | 1286 | 2503 |
| AD-26817 | 5398 | 6057 | 628 | 1287 | 2515 |
| AD-26818 | 5399 | 6058 | 629 | 1288 | 2542 |
| AD-26819 | 5400 | 6059 | 630 | 1289 | 2580 |
| AD-26820 | 5401 | 6060 | 631 | 1290 | 2581 |
| AD-26821 | 5402 | 6061 | 632 | 1291 | 2595 |
| AD-26822 | 5403 | 6062 | 633 | 1292 | 2601 |
| AD-26823 | 5404 | 6063 | 634 | 1293 | 2605 |
| AD-26824 | 5405 | 6064 | 635 | 1294 | 2606 |
| AD-26825 | 5406 | 6065 | 636 | 1295 | 2607 |
| AD-26826 | 5407 | 6066 | 637 | 1296 | 878 |
| AD-26900 | 5408 | 6067 | 638 | 1297 | 2745 |
| AD-26901 | 5409 | 6068 | 639 | 1298 | 2872 |
| AD-26902 | 5410 | 6069 | 640 | 1299 | 2915 |
| AD-26903 | 5411 | 6070 | 641 | 1300 | 2916 |
| AD-26904 | 5412 | 6071 | 642 | 1301 | 2918 |
| AD-26905 | 5413 | 6072 | 643 | 1302 | 2919 |
| AD-26906 | 5414 | 6073 | 644 | 1303 | 2939 |
| AD-26907 | 5415 | 6074 | 645 | 1304 | 2978 |
| AD-26908 | 5416 | 6075 | 646 | 1305 | 2979 |
| AD-26909 | 5417 | 6076 | 647 | 1306 | 2980 |
| AD-26910 | 5418 | 6077 | 648 | 1307 | 2981 |
| AD-26911 | 5419 | 6078 | 649 | 1308 | 2983 |
| AD-26912 | 5420 | 6079 | 650 | 1309 | 2984 |
| AD-26913 | 5421 | 6080 | 651 | 1310 | 2986 |
| AD-26914 | 5422 | 6081 | 652 | 1311 | 3081 |
| AD-26915 | 5423 | 6082 | 653 | 1312 | 3082 |
| AD-26916 | 5424 | 6083 | 654 | 1313 | 2917 |
| AD-26917 | 5425 | 6084 | 655 | 1314 | 2994 |
| AD-26918 | 5426 | 6085 | 656 | 1315 | 2995 |
| AD-26919 | 5427 | 6086 | 657 | 1316 | 3134 |
| AD-26920 | 5428 | 6087 | 658 | 1317 | 1535 |
| AD-26921 | 5429 | 6088 | 659 | 1318 | 1801 |
| SET1 1245 | 6090 | 6111 | 6193 | 6361 | 1227 |
| SET1 1245 | 6090 | 6111 | 6214 | 6382 | 1227 |
| SET1 1245 | 6090 | 6111 | 6151 | 6319 | 1227 |
| SET1 1245 | 6090 | 6111 | 6172 | 6340 | 1227 |
| SET1 1249 | 6091 | 6112 | 6199 | 6367 | 1231 |
| SET1 1249 | 6091 | 6112 | 6220 | 6388 | 1231 |
| SET1 1249 | 6091 | 6112 | 6157 | 6325 | 1231 |
| SET1 1249 | 6091 | 6112 | 6178 | 6346 | 1231 |
| SET1 1250 | 6092 | 6113 | 6200 | 6368 | 1232 |
| SET1 1250 | 6092 | 6113 | 6221 | 6389 | 1232 |
| SET1 1250 | 6092 | 6113 | 6158 | 6326 | 1232 |
| SET1 1250 | 6092 | 6113 | 6179 | 6347 | 1232 |
| SET1 1450 | 6093 | 6114 | 6195 | 6363 | 1432 |
| SET1 1450 | 6093 | 6114 | 6216 | 6384 | 1432 |
| SET1 1450 | 6093 | 6114 | 6153 | 6321 | 1432 |
| SET1 1450 | 6093 | 6114 | 6174 | 6342 | 1432 |
| SET1 1545 | 6094 | 6115 | 6202 | 6370 | 1527 |
| SET1 1545 | 6094 | 6115 | 6223 | 6391 | 1527 |
| SET1 1545 | 6094 | 6115 | 6160 | 6328 | 1527 |
| SET1 1545 | 6094 | 6115 | 6181 | 6349 | 1527 |
| SET1 1755 | 6095 | 6116 | 6203 | 6371 | 1737 |
| SET1 1755 | 6095 | 6116 | 6224 | 6392 | 1737 |
| SET1 1755 | 6095 | 6116 | 6161 | 6329 | 1737 |
| SET1 1755 | 6095 | 6116 | 6182 | 6350 | 1737 |
| SET1 1814 | 6096 | 6117 | 6192 | 6360 | 1796 |
| SET1 1814 | 6096 | 6117 | 6213 | 6381 | 1796 |
| SET1 1814 | 6096 | 6117 | 6150 | 6318 | 1796 |
| SET1 1814 | 6096 | 6117 | 6171 | 6339 | 1796 |
| SET1 1816 | 6097 | 6118 | 6187 | 6355 | 1798 |
| SET1 1816 | 6097 | 6118 | 6208 | 6376 | 1798 |
| SET1 1816 | 6097 | 6118 | 6145 | 6313 | 1798 |
| SET1 1816 | 6097 | 6118 | 6166 | 6334 | 1798 |
| SET1 1974 | 6098 | 6119 | 6188 | 6356 | 1956 |
| SET1 1974 | 6098 | 6119 | 6209 | 6377 | 1956 |
| SET1 1974 | 6098 | 6119 | 6146 | 6314 | 1956 |
| SET1 1974 | 6098 | 6119 | 6167 | 6335 | 1956 |
| SET1 2202 | 6099 | 6120 | 6201 | 6369 | 2184 |
| SET1 2202 | 6099 | 6120 | 6222 | 6390 | 2184 |
| SET1 2202 | 6099 | 6120 | 6159 | 6327 | 2184 |
| SET1 2202 | 6099 | 6120 | 6180 | 6348 | 2184 |
| SET1 2425 | 6100 | 6121 | 6189 | 6357 | 2407 |
| SET1 2425 | 6100 | 6121 | 6210 | 6378 | 2407 |
| SET1 2425 | 6100 | 6121 | 6147 | 6315 | 2407 |
| SET1 2425 | 6100 | 6121 | 6168 | 6336 | 2407 |
| SET1 254 | 6101 | 6122 | 6183 | 6351 | 236 |
| SET1 254 | 6101 | 6122 | 6204 | 6372 | 236 |
| SET1 254 | 6101 | 6122 | 6141 | 6309 | 236 |
| SET1 254 | 6101 | 6122 | 6162 | 6330 | 236 |
| SET1 3146 | 6102 | 6123 | 6190 | 6358 | 3128 |
| SET1 3146 | 6102 | 6123 | 6211 | 6379 | 3128 |
| SET1 3146 | 6102 | 6123 | 6148 | 6316 | 3128 |
| SET1 3146 | 6102 | 6123 | 6169 | 6337 | 3128 |
| SET1 3169 | 6103 | 6124 | 6196 | 6364 | 3151 |
| SET1 3169 | 6103 | 6124 | 6217 | 6385 | 3151 |
| SET1 3169 | 6103 | 6124 | 6154 | 6322 | 3151 |
| SET1 3169 | 6103 | 6124 | 6175 | 6343 | 3151 |
| SET1 3196 | 6104 | 6125 | 6194 | 6362 | 3178 |
| SET1 3196 | 6104 | 6125 | 6215 | 6383 | 3178 |
| SET1 3196 | 6104 | 6125 | 6152 | 6320 | 3178 |
| SET1 3196 | 6104 | 6125 | 6173 | 6341 | 3178 |
| SET1 3477 | 6105 | 6126 | 6197 | 6365 | 3459 |
| SET1 3477 | 6105 | 6126 | 6218 | 6386 | 3459 |
| SET1 3477 | 6105 | 6126 | 6155 | 6323 | 3459 |
| SET1 3477 | 6105 | 6126 | 6176 | 6344 | 3459 |
| SET1 703 | 6106 | 6127 | 6184 | 6352 | 685 |
| SET1 703 | 6106 | 6127 | 6205 | 6373 | 685 |
| SET1 703 | 6106 | 6127 | 6142 | 6310 | 685 |
| SET1 703 | 6106 | 6127 | 6163 | 6331 | 685 |
| SET1 709 | 6107 | 6128 | 6185 | 6353 | 691 |
| SET1 709 | 6107 | 6128 | 6206 | 6374 | 691 |
| SET1 709 | 6107 | 6128 | 6143 | 6311 | 691 |
| SET1 709 | 6107 | 6128 | 6164 | 6332 | 691 |

TABLE 1-continued

SEQ ID NOs. for RNAi Agents to Beta-Catenin
Provided in Table 1 are the nickname of various Beta-Catenin RNAi duplexes; the unmodified sense and anti-sense sequences and SEQ ID NOs; an example modified sense and antisense sequence and SEQ ID NOs; and the position of the RNAi agent within the Beta-Catenin gene.

| DUPLEX | UNMODIFIED SEQUENCE | | EXAMPLE MODIFIED SEQUENCE | | Position |
|---|---|---|---|---|---|
| | Sense SEQ ID NO: | Anti-sense SEQ ID NO: | Sense SEQ ID NO: | Anti-sense SEQ ID NO: | |
| SET1 865 | 6108 | 6129 | 6198 | 6366 | 847 |
| SET1 865 | 6108 | 6129 | 6219 | 6387 | 847 |
| SET1 865 | 6108 | 6129 | 6156 | 6324 | 847 |
| SET1 865 | 6108 | 6129 | 6177 | 6345 | 847 |
| SET1 889 | 6109 | 6130 | 6191 | 6359 | 871 |
| SET1 889 | 6109 | 6130 | 6212 | 6380 | 871 |
| SET1 889 | 6109 | 6130 | 6149 | 6317 | 871 |
| SET1 889 | 6109 | 6130 | 6170 | 6338 | 871 |
| SET1 895 | 6110 | 6131 | 6186 | 6354 | 877 |
| SET1 895 | 6110 | 6131 | 6207 | 6375 | 877 |
| SET1 895 | 6110 | 6131 | 6144 | 6312 | 877 |
| SET1 895 | 6110 | 6131 | 6165 | 6333 | 877 |
| SET1 1245 | 6090 | 6111 | 6235 | 6403 | 1227 |
| SET1 1245 | 6090 | 6111 | 6256 | 6424 | 1227 |
| SET1 1245 | 6090 | 6111 | 6277 | 6445 | 1227 |
| SET1 1245 | 6090 | 6111 | 6298 | 6466 | 1227 |
| SET1 1249 | 6091 | 6112 | 6241 | 6409 | 1231 |
| SET1 1249 | 6091 | 6112 | 6262 | 6430 | 1231 |
| SET1 1249 | 6091 | 6112 | 6283 | 6451 | 1231 |
| SET1 1249 | 6091 | 6112 | 6304 | 6472 | 1231 |
| SET1 1250 | 6092 | 6113 | 6242 | 6410 | 1232 |
| SET1 1250 | 6092 | 6113 | 6263 | 6431 | 1232 |
| SET1 1250 | 6092 | 6113 | 6284 | 6452 | 1232 |
| SET1 1250 | 6092 | 6113 | 6305 | 6473 | 1232 |
| SET1 1450 | 6093 | 6114 | 6237 | 6405 | 1432 |
| SET1 1450 | 6093 | 6114 | 6258 | 6426 | 1432 |
| SET1 1450 | 6093 | 6114 | 6279 | 6447 | 1432 |
| SET1 1450 | 6093 | 6114 | 6300 | 6468 | 1432 |
| SET1 1545 | 6094 | 6115 | 6244 | 6412 | 1527 |
| SET1 1545 | 6094 | 6115 | 6265 | 6433 | 1527 |
| SET1 1545 | 6094 | 6115 | 6286 | 6454 | 1527 |
| SET1 1545 | 6094 | 6115 | 6307 | 6475 | 1527 |
| SET1 1755 | 6095 | 6116 | 6245 | 6413 | 1737 |
| SET1 1755 | 6095 | 6116 | 6266 | 6434 | 1737 |
| SET1 1755 | 6095 | 6116 | 6287 | 6455 | 1737 |
| SET1 1755 | 6095 | 6116 | 6308 | 6476 | 1737 |
| SET1 1814 | 6096 | 6117 | 6234 | 6402 | 1796 |
| SET1 1814 | 6096 | 6117 | 6255 | 6423 | 1796 |
| SET1 1814 | 6096 | 6117 | 6276 | 6444 | 1796 |
| SET1 1814 | 6096 | 6117 | 6297 | 6465 | 1796 |
| SET1 1816 | 6097 | 6118 | 6229 | 6397 | 1798 |
| SET1 1816 | 6097 | 6118 | 6250 | 6418 | 1798 |
| SET1 1816 | 6097 | 6118 | 6271 | 6439 | 1798 |
| SET1 1816 | 6097 | 6118 | 6292 | 6460 | 1798 |
| SET1 1974 | 6098 | 6119 | 6230 | 6398 | 1956 |
| SET1 1974 | 6098 | 6119 | 6251 | 6419 | 1956 |
| SET1 1974 | 6098 | 6119 | 6272 | 6440 | 1956 |
| SET1 1974 | 6098 | 6119 | 6293 | 6461 | 1956 |
| SET1 2202 | 6099 | 6120 | 6243 | 6411 | 2184 |
| SET1 2202 | 6099 | 6120 | 6264 | 6432 | 2184 |
| SET1 2202 | 6099 | 6120 | 6285 | 6453 | 2184 |
| SET1 2202 | 6099 | 6120 | 6306 | 6474 | 2184 |
| SET1 2425 | 6100 | 6121 | 6231 | 6399 | 2407 |
| SET1 2425 | 6100 | 6121 | 6252 | 6420 | 2407 |
| SET1 2425 | 6100 | 6121 | 6273 | 6441 | 2407 |
| SET1 2425 | 6100 | 6121 | 6294 | 6462 | 2407 |
| SET1 254 | 6101 | 6122 | 6225 | 6393 | 236 |
| SET1 254 | 6101 | 6122 | 6246 | 6414 | 236 |
| SET1 254 | 6101 | 6122 | 6267 | 6435 | 236 |
| SET1 254 | 6101 | 6122 | 6288 | 6456 | 236 |
| SET1 3146 | 6102 | 6123 | 6232 | 6400 | 3128 |
| SET1 3146 | 6102 | 6123 | 6253 | 6421 | 3128 |
| SET1 3146 | 6102 | 6123 | 6274 | 6442 | 3128 |
| SET1 3146 | 6102 | 6123 | 6295 | 6463 | 3128 |
| SET1 3169 | 6103 | 6124 | 6238 | 6406 | 3151 |
| SET1 3169 | 6103 | 6124 | 6259 | 6427 | 3151 |
| SET1 3169 | 6103 | 6124 | 6280 | 6448 | 3151 |
| SET1 3169 | 6103 | 6124 | 6301 | 6469 | 3151 |
| SET1 3196 | 6104 | 6125 | 6236 | 6404 | 3178 |
| SET1 3196 | 6104 | 6125 | 6257 | 6425 | 3178 |
| SET1 3196 | 6104 | 6125 | 6278 | 6446 | 3178 |
| SET1 3196 | 6104 | 6125 | 6299 | 6467 | 3178 |
| SET1 3477 | 6105 | 6126 | 6239 | 6407 | 3459 |
| SET1 3477 | 6105 | 6126 | 6260 | 6428 | 3459 |
| SET1 3477 | 6105 | 6126 | 6281 | 6449 | 3459 |
| SET1 3477 | 6105 | 6126 | 6302 | 6470 | 3459 |
| SET1 703 | 6106 | 6127 | 6226 | 6394 | 685 |
| SET1 703 | 6106 | 6127 | 6247 | 6415 | 685 |
| SET1 703 | 6106 | 6127 | 6268 | 6436 | 685 |
| SET1 703 | 6106 | 6127 | 6289 | 6457 | 685 |
| SET1 709 | 6107 | 6128 | 6227 | 6395 | 691 |
| SET1 709 | 6107 | 6128 | 6248 | 6416 | 691 |
| SET1 709 | 6107 | 6128 | 6269 | 6437 | 691 |
| SET1 709 | 6107 | 6128 | 6290 | 6458 | 691 |
| SET1 865 | 6108 | 6129 | 6240 | 6408 | 847 |
| SET1 865 | 6108 | 6129 | 6261 | 6429 | 847 |
| SET1 865 | 6108 | 6129 | 6282 | 6450 | 847 |
| SET1 865 | 6108 | 6129 | 6303 | 6471 | 847 |
| SET1 889 | 6109 | 6130 | 6233 | 6401 | 871 |
| SET1 889 | 6109 | 6130 | 6254 | 6422 | 871 |
| SET1 889 | 6109 | 6130 | 6275 | 6443 | 871 |
| SET1 889 | 6109 | 6130 | 6296 | 6464 | 871 |
| SET1 895 | 6110 | 6131 | 6228 | 6396 | 877 |
| SET1 895 | 6110 | 6131 | 6249 | 6417 | 877 |
| SET1 895 | 6110 | 6131 | 6270 | 6438 | 877 |
| SET1 895 | 6110 | 6131 | 6291 | 6459 | 877 |

Various Embodiments of the Present Disclosure

Various RNAi agents to Beta-Catenin are disclosed in Tables 1, 2, 3, 4, 5, 6, 7, 8 and/or 9.

Tables 1, 2 and 3 provide the sequence, SEQ ID NOs and positions of various RNAi agents to Beta-Catenin, including both unmodified sequences and example modified sequences. The sequences in Table 2 are not modified.

Table 3 provides the sequences and SEQ ID NOs for example modified sequences of the sense and anti-sense strands of various RNAi agents to Beta-Catenin. The present disclosure also encompasses unmodified versions of these sequences, and different versions comprising other modifications or patterns of modification (but the same sequence of bases).

In the sequences in Table 3, lower-case letters (e.g., c, u) indicate modified nucleotides while upper case letters (e.g., C, U, A, G) indicate unmodified nucleotides. In Table 3, example modified versions of each of the sequences are shown. However, the present disclosure encompasses unmodified versions of these sequences and other versions which comprise additional or alternative modifications. Thus, for example, AD-18892 can optionally have the unmodified (or "generic") sequence UGGUGCUGAC-UAUCCAGUU (SEQ ID NO: 429) in the sense strand and AACUGGAUAGUCAGCACCA (SEQ ID NO: 430) in the anti-sense strand. The present disclosure also encompasses alternative modified versions of the duplex comprising UGGUGCUGACUAUCCAGUU (SEQ ID NO: 429) in the sense strand and AACUGGAUAGUCAGCACCA (SEQ ID NO: 430) in the anti-sense strand.

In the sequences in Tables 1, 2, 3, 4, 5, 6, 7 and 8, the modified and unmodified sequences can optionally comprise the sequence "dTdT", "dTsdT" or "UU" at the 3' end. Thus, for example, AD-18892 can optionally have the modified sequence uGGuGcuGAcuAuccAGuudTdT (SEQ ID NO: 6136) or uGGuGcuGAcuAuccAGuudTsdT (SEQ ID NO: 6137) in the sense strand; and AACUGGAuAGUcAGcACcAdTdT (SEQ ID NO: 6138) or AACUGGAuAGUcAGcACcAdTsdT (SEQ ID NO: 6139) in the anti-sense strand. As noted in Table 3, below, dT is 2'-deoxy-thymidine-5'-phosphate and sdT is 2'-deoxy Thymidine 5'-phosphorothioate. In the disclosed sequences, terminal dinucleotide "UU" is 2'-OMe-U 2'-OMe-U, and neither the terminal TT nor the terminal UU are in the inverted/reverse orientation. In various embodiments UU as standard RNA can also be used.

The terminal dithymidine (or TT or dTdT or sdTsdT or UU or the like) is not part of the Beta-Catenin target sequence, but is a modified variant of the dithymidine dinucleotide commonly placed as an overhang to protect the ends of siRNAs from nucleases (see, for example, Elbashir et al. 2001 Nature 411: 494-498; Elbashir et al. 2001 EMBO J. 20: 6877-6888; and Kraynack et al. 2006 RNA 12:163-176). A terminal dinucleotide is known from these references to enhance nuclease resistance but not contribute to target recognition. On any modified or unmodified sequence, a 3' end cap, as is known in the art, can be used instead of a terminal dinucleotide to stabilize the end from nuclease degradation provided that the 3' end cap is able to both stabilize the RNAi agent (e.g., against nucleases) and not interfere excessively with siRNA activity.

Table 4 provides sets of overlapping RNAi agents to Beta-Catenin.

Activity levels of various Beta-Catenin RNAi agents are provided in Tables 5 to 9.

RNAi Agent Comprising an Anti-Sense Strand of a RNAi Agent Described Herein

In one particular specific embodiment, the present disclosure relates to a composition comprising a RNAi agent for inhibition of the target gene Beta-Catenin comprising an anti-sense strand, wherein the anti-sense strand comprises at least 15 contiguous nucleotides differing by 0, 1, 2, or 3 nucleotides from the anti-sense strand of a RNAi agent to Beta-Catenin selected from those anti-sense strands in the specific duplexes provided herein and as listed, e.g., in Tables 1, 2, 3, 4, 5, 6, 7, 8 and/or 9.

In one embodiment, the composition comprises a RNAi agent for inhibition of the target gene Beta-Catenin comprising a sense and an anti-sense strand, wherein the sequence of the sense strand and the sequence of the anti-sense strand are the sequences of the sense and anti-sense strand, respectively, of any RNAi agent provided herein. In one embodiment, the composition comprises a RNAi agent for inhibition of the target gene Beta-Catenin comprising a sense and an anti-sense strand, wherein the sequence of the antisense strand is the sequence of antisense strand of any RNAi agent provided herein. In one embodiment, the composition comprises a RNAi agent for inhibition of the target gene Beta-Catenin comprising a sense and an anti-sense strand, wherein the sequence of the sense strand and the sequence of the anti-sense strand are the sequences of the sense and anti-sense strand, respectively, of any RNAi agent provided herein, further comprising an additional about 6 to 20 nucleotides on one or both strands (e.g., about 6, 7, 8, 9, 10, 11, 12, 13, 14, 15, 16, 17, 18, 19 or 20 nt). In one embodiment, the composition comprises a RNAi agent for inhibition of the target gene Beta-Catenin comprising a sense and an anti-sense strand, wherein the sequence of the anti-sense strand is the sequence of the anti-sense strand of any RNAi agent provided herein, further comprising an additional about 6 to 20 nucleotides on one or both strands (e.g., about 6, 7, 8, 9, 10, 11, 12, 13, 14, 15, 16, 17, 18, 19 or 20 nt). In these various embodiments, the RNAi agent is for inhibition of the target gene Beta-Catenin.

Various specific embodiments of these embodiments are described below.

In one embodiment, the composition further comprises a second RNAi agent to Beta-Catenin. In various embodiments, the second RNAi agent is physically separate from the first, or the two are physically connected (e.g., covalently linked or otherwise conjugated), or combined within the same pharmaceutical composition.

In one embodiment, the antisense strand is about 30 or fewer nt in length.

In one embodiment, the sense strand and the antisense strand form a duplex region of about 15 to about 30 nucleotide pairs in length.

In one embodiment, the antisense strand is about 15 to about 36 nt in length, about 17 to about 30 nt in length, about 17 to 23 nt in length, about 19 to about 49 nt in length, or about 19 to about 23 nt in length. In one embodiment, the antisense strand has at least the length selected from about 15 nt, about 16 nt, about 17 nt, about 18 nt, about 19 nt, about 20 nt, about 21 nt, about 22 nt, about 23 nt, about 24 nt, about 25 nt, about 26 nt, about 27 nt, about 28 nt, about 29 nt and about 30 nt.

In one embodiment, the RNAi agent comprises a modification that causes the RNAi agent to have increased stability in a biological sample or environment, e.g., blood serum or intestinal lavage fluid.

In one embodiment, the RNAi agent comprises at least one sugar backbone modification (e.g., phosphorothioate linkage) and/or at least one 2'-modified nucleotide. In one embodiment, all the pyrimidines are 2' O-methyl-modified nucleotides.

In one embodiment, the RNAi agent comprises: at least one 5'-uridine-adenine-3' (5'-ua-3') dinucleotide, wherein the uridine is a 2'-modified nucleotide; and/or at least one 5'-uridine-guanine-3' (5'-ug-3') dinucleotide, wherein the 5'-uridine is a 2'-modified nucleotide; and/or at least one 5'-cytidine-adenine-3' (5'-ca-3') dinucleotide, wherein the 5'-cytidine is a 2'-modified nucleotide; and/or at least one 5'-uridine-uridine-3' (5'-uu-3') dinucleotide, wherein the 5'-uridine is a 2'-modified nucleotide.

In one embodiment, the RNAi agent comprises a 2'-modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA). In one embodiment, all the pyrimidines are 2' O-methyl-modified nucleotides.

In one embodiment, the RNAi agent comprises a blunt end.

In one embodiment, the RNAi agent comprises an overhang having 1 to 4 unpaired nucleotides.

In one embodiment, the RNAi agent comprises an overhang at the 3'-end of the antisense strand of the RNAi agent.

In one embodiment, the RNAi agent is ligated to one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

In one embodiment, the RNAi agent is capable of inhibiting expression of the Beta-Catenin gene by at least about 60% at a concentration of 10 nM in HeLa cells in vitro.

In one embodiment, the RNAi agent is capable of inhibiting expression of the Beta-Catenin gene by at least about 70% at a concentration of 10 nM in HeLa cells in vitro.

In one embodiment, the RNAi agent is capable of inhibiting expression of the Beta-Catenin gene by at least about 80% at a concentration of 10 nM in HeLa cells in vitro.

In one embodiment, the RNAi agent is capable of inhibiting expression of the Beta-Catenin gene by at least about 90% at a concentration of 10 nM in HeLa cells in vitro.

In one embodiment, the RNAi has an EC50 of no more than about 0.1 nM.

In one embodiment, the RNAi has an EC50 of no more than about 0.01 nM.

In one embodiment, the RNAi has an EC50 of no more than about 0.001 nM.

A RNAi Agent Comprising a First and a Second Strand

In one particular specific embodiment, the present disclosure relates to a composition comprising a RNAi agent for inhibition of the target gene Beta-Catenin comprising a first strand and a second strand, wherein the first strand and second strand comprise at least 15 contiguous nucleotides, each differing by 0, 1, 2, or 3 nucleotides from the first and second strand, respectively, of a RNAi agent to Beta-Catenin selected from the specific duplexes provided herein and listed, e.g., in Tables 1, 2, 3, 4, 5, 6, 7, 8 and/or 9. In these various embodiments, the RNAi agent is for inhibition of the target gene Beta-Catenin.

Various specific embodiments of this embodiment are described below.

In one embodiment, the composition further comprises a second RNAi agent to Beta-Catenin. In various embodiments, the second RNAi agent is physically separate from the first, or the two are physically connected (e.g., covalently linked or otherwise conjugated), or combined within the same pharmaceutical composition.

In one embodiment, the antisense strand is about 30 or fewer nt in length.

In one embodiment, the sense strand and the antisense strand form a duplex region of about 15 to about 30 nt pairs in length.

In one embodiment, the antisense strand is about 15 to about 36 nt in length, including about 17 to about 23 nt in length, and including about 19 to about 23 nt in length. In one embodiment, the antisense strand has at least the length selected from about 15 nt, about 16 nt, about 17 nt, about 18 nt, about 19 nt, about 20 nt, about 21 nt, about 22 nt, about 23 nt, about 24 nt, about 25 nt, about 26 nt, about 27 nt, about 28 nt, about 29 nt and about 30 nt.

In one embodiment, the RNAi agent comprises a modification that causes the RNAi agent to have increased stability in a biological sample or environment, e.g., blood serum or intestinal lavage fluid.

In one embodiment, the RNAi agent comprises at least one sugar backbone modification (e.g., phosphorothioate linkage) and/or at least one 2'-modified nucleotide. In one embodiment, all the pyrimidines are 2' O-methyl-modified nucleotides.

In one embodiment, the RNAi agent comprises: at least one 5'-uridine-adenine-3' (5'-ua-3') dinucleotide, wherein the uridine is a 2'-modified nucleotide; and/or at least one 5'-uridine-guanine-3' (5'-ug-3') dinucleotide, wherein the 5'-uridine is a 2'-modified nucleotide; and/or at least one 5'-cytidine-adenine-3' (5'-ca-3') dinucleotide, wherein the 5'-cytidine is a 2'-modified nucleotide; and/or at least one 5'-uridine-uridine-3' (5'-uu-3') dinucleotide, wherein the 5'-uridine is a 2'-modified nucleotide.

In one embodiment, the RNAi agent comprises a 2'-modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA).

In one embodiment, the RNAi agent comprises a blunt end.

In one embodiment, the RNAi agent comprises an overhang having 1 to 4 unpaired nucleotides.

In one embodiment, the RNAi agent comprises an overhang at the 3'-end of the antisense strand of the RNAi agent.

In one embodiment, the RNAi agent is ligated to one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

In one embodiment, the RNAi agent is capable of inhibiting expression of the Beta-Catenin gene by at least about 60% at a concentration of 10 nM in HeLa cells in vitro.

In one embodiment, the RNAi agent is capable of inhibiting expression of the Beta-Catenin gene by at least about 70% at a concentration of 10 nM in HeLa cells in vitro.

In one embodiment, the RNAi agent is capable of inhibiting expression of the Beta-Catenin gene by at least about 80% at a concentration of 10 nM in HeLa cells in vitro.

In one embodiment, the RNAi agent is capable of inhibiting expression of the Beta-Catenin gene by at least about 90% at a concentration of 10 nM in HeLa cells in vitro.

In one embodiment, the RNAi has an EC50 of no more than about 0.1 nM.

In one embodiment, the RNAi has an EC50 of no more than about 0.01 nM.

In one embodiment, the RNAi has an EC50 of no more than about 0.001 nM.

A Method of Treatment Using a RNAi Agent Described Herein

In one particular specific embodiment, the present disclosure relates to a method of treating a Beta-Catenin-related disease in an individual, comprising the step of administering to the individual a therapeutically effective amount of a composition comprising any one or more of the RNAi agents disclosed herein. In one embodiment of this method, the RNAi agent comprises at least an antisense strand, wherein the antisense strand comprises at least 15 contiguous nucleotides differing by 0, 1, 2, or 3 nucleotides from the antisense strand of a RNAi agent to Beta-Catenin selected from the specific duplexes provided herein and as listed, e.g., in Tables 1, 2, 3, 4, 5, 6, 7, 8 and/or 9. In one embodiment, the RNAi agent comprises a sense and an anti-sense strand, wherein the sense strand comprises at least 15 contiguous nucleotides differing by 0, 1, 2, or 3 nucleotides from the sense strand of a RNAi agent to Beta-Catenin selected from the specific duplexes provided herein and as listed, e.g., in Tables 1, 2, 3, 4, 5, 6, 7, 8 and/or 9. In one embodiment, the RNAi agent comprises a first and a second strand, wherein the first strand comprises at least 15 contiguous nucleotides differing by 0, 1, 2, or 3 nucleotides from the first strand of a RNAi agent to Beta-Catenin selected from the specific duplexes provided herein and as listed, e.g., in Tables 1, 2, 3, 4, 5, 6, 7, 8 and/or 9. In one embodiment, the RNAi agent comprises a first and a second strand, wherein the sequence of the first strand comprises the sequence of the first strand of a RNAi agent to Beta-Catenin selected from the specific duplexes provided herein and as listed, e.g., in Tables 1, 2, 3, 4, 5, 6, 7, 8 and/or 9. In one embodiment, the RNAi agent comprises a first and a second strand, wherein the sequence of the first strand is the sequence of the first strand of a RNAi agent to Beta-Catenin selected from the specific duplexes provided herein and as listed, e.g., in Tables 1, 2, 3, 4, 5, 6, 7, 8 and/or 9. In these various embodiments, the RNAi agent is for the inhibition of the target gene Beta-Catenin.

Various particular specific embodiments of these embodiments are described below.

In one embodiment, the Beta-Catenin-related disease is adenomatous polyposis of the colon, colorectal cancer, basal cell carcinoma, breast cancer, kidney cancer, Wilms tumors, medulloblastoma, ovarian cancer, adrenocortical tumors, gastric cancer, liver cancer, melanoma, pancreatic cancers, prostate cancer, renal cancer, ectopic teeth and taste papillae, skin cancer, pilomatrixoma, anaplastic thyroid carcinoma, and uterine carcinosarcoma, oligodontia, osteoporosis, ageing, degenerative diseases, bedsores, chronic wounds and/or impaired wound healing, and/or similar and related diseases.

In one embodiment, the Beta-Catenin-related disease is cancer.

In one embodiment, the method further comprises the administration of an additional treatment. In one embodiment, the additional treatment is a therapeutically effective amount of a composition.

In one embodiment, the additional treatment is a method (or procedure).

In one embodiment, the additional treatment and the RNAi agent can be administered in any order, or can be administered simultaneously.

In one embodiment, the method further comprises the step of administering an additional treatment for adenomatous polyposis of the colon, colorectal cancer, basal cell carcinoma, breast cancer, kidney cancer, Wilms tumors, medulloblastoma, ovarian cancer, adrenocortical tumors, gastric cancer, liver cancer, melanoma, pancreatic cancers, prostate cancer, renal cancer, ectopic teeth and taste papillae, skin cancer, pilomatrixoma, anaplastic thyroid carcinoma, and uterine carcinosarcoma, oligodontia, osteoporosis, ageing, degenerative diseases, bedsores, chronic wounds and/or impaired wound healing, and/or similar and related diseases.

In one embodiment, the composition comprises a second RNAi agent to Beta-Catenin. In various embodiments, the second RNAi agent is physically separate from the first, or the two are physically connected (e.g., covalently linked or otherwise conjugated), or combined within the same pharmaceutical composition.

In one embodiment, the method further comprises the step of administering an additional RNAi agent which comprises at least 15 contiguous nucleotides differing by 0, 1, 2, or 3 nucleotides from the antisense strand of a RNAi agent to Beta-Catenin selected from the specific duplexes provided herein and as listed, e.g., in Tables 1, 2, 3, 4, 5, 6, 7, 8 and/or 9.

Inhibiting the Expression of Beta-Catenin, Using a RNAi Agent

In one particular specific embodiment, the present disclosure relates to a method of inhibiting the expression of the Beta-Catenin gene in an individual, comprising the step of administering to the individual a therapeutically effective amount of a composition comprising any one or more of the RNAi agents of the present disclosure. In one embodiment, the RNAi agent comprises at least an anti-sense strand, and/or comprises a sense and an anti-sense strand, wherein the anti-sense strand comprises at least 15 contiguous nucleotides differing by 0, 1, 2, or 3 nucleotides from the anti-sense strand of a RNAi agent to Beta-Catenin selected from those specific duplex provided herein and as listed, e.g., in Tables 1, 2, 3, 4, 5, 6, 7, 8 and/or 9. In one embodiment, the RNAi agent comprises a sense and an anti-sense strand, wherein the anti-sense strand comprises at least 15 contiguous nucleotides differing by 0, 1, 2, or 3 nucleotides from the anti-sense strand of a RNAi agent to Beta-Catenin selected from those specific duplex provided herein and as listed, e.g., in Tables 1, 2, 3, 4, 5, 6, 7, 8 and/or 9. In one embodiment, the RNAi agent comprises a first and a second strand, wherein the sequence of the first strand comprises sequence of the first strand of a RNAi agent to Beta-Catenin selected from those specific duplex provided herein and as listed, e.g., in Tables 1, 2, 3, 4, 5, 6, 7, 8 and/or 9. In one embodiment, the RNAi agent comprises a first and a second strand, wherein the sequence of the first strand is sequence of the first strand of a RNAi agent to Beta-Catenin selected from those specific duplex provided herein and as listed, e.g., in Tables 1, 2, 3, 4, 5, 6, 7, 8 and/or 9.

Various embodiments of this aspect of these embodiments are described below.

In one embodiment, the individual is afflicted with or susceptible to a Beta-Catenin-related disease.

In one embodiment, the Beta-Catenin-related disease is adenomatous polyposis of the colon, colorectal cancer, basal cell carcinoma, breast cancer, kidney cancer, Wilms tumors, medulloblastoma, ovarian cancer, adrenocortical tumors, gastric cancer, liver cancer, melanoma, pancreatic cancers, prostate cancer, renal cancer, ectopic teeth and taste papillae, skin cancer, pilomatrixoma, anaplastic thyroid carcinoma, and uterine carcinosarcoma, oligodontia, osteoporosis, ageing, degenerative diseases, bedsores, chronic wounds and/or impaired wound healing, and/or similar and related diseases.

In one embodiment, the Beta-Catenin-related disease is cancer.

In one embodiment, the method further comprises the administration of an additional treatment. In one embodiment, the additional treatment is a therapeutically effective amount of a composition.

In one embodiment, the additional treatment is a method (or procedure).

In one embodiment, the additional treatment and the RNAi agent can be administered in any order or can be administered simultaneously.

In one embodiment, the method further comprises the step of administering an additional treatment for adenomatous polyposis of the colon, colorectal cancer, basal cell carcinoma, breast cancer, kidney cancer, Wilms tumors, medulloblastoma, ovarian cancer, adrenocortical tumors, gastric cancer, liver cancer, melanoma, pancreatic cancers, prostate cancer, renal cancer, ectopic teeth and taste papillae, skin cancer, pilomatrixoma, anaplastic thyroid carcinoma, and uterine carcinosarcoma, oligodontia, osteoporosis, ageing, degenerative diseases, bedsores, chronic wounds and/or impaired wound healing, and/or similar and related diseases.

In one embodiment, the composition comprises a second RNAi agent to Beta-Catenin. In various embodiments, the second RNAi agent is physically separate from the first, or the two are physically connected (e.g., covalently linked or otherwise conjugated), or combined within the same pharmaceutical composition.

In one embodiment, the method further comprises the step of administering an additional RNAi agent which comprises at least 15 contiguous nucleotides differing by 0, 1, 2, or 3 nucleotides from the antisense strand of a RNAi agent to Beta-Catenin selected from the specific duplexes provided herein and as listed, e.g., in Tables 1, 2, 3, 4, 5, 6, 7, 8 and/or 9.

Pharmaceutical Formulations of a RNAi Agent to Beta-Catenin

In one particular specific embodiment, the present disclosure relates to a composition comprising any one or more of the RNAi agents of the present disclosure. In one embodiment, the RNAi agent comprises at least an anti-sense strand, and/or comprises a sense and an anti-sense strand, wherein the anti-sense strand comprises at least 15 contiguous nucleotides differing by 0, 1, 2, or 3 nucleotides from the anti-sense strand of a RNAi agent to Beta-Catenin selected from those specific duplex provided herein and as listed, e.g., in Tables 1, 2, 3, 4, 5, 6, 7, 8 and/or 9, wherein the composition is in a pharmaceutically effective formulation. In one embodiment, the RNAi agent comprises a first and a second strand, wherein the sequence of the first strand comprises at least 15 contiguous nucleotides differing by 0, 1, 2, or 3 nucleotides from the sequence of the first strand of a RNAi agent to Beta-Catenin selected from those specific duplex provided herein and as listed, e.g., in Tables 1, 2, 3, 4, 5, 6, 7, 8 and/or 9, wherein the composition is in a pharmaceutically effective formulation. In one embodiment, the RNAi agent comprises a first and a second strand, wherein the sequence of the first strand comprises the sequence of the first strand of a RNAi agent to Beta-Catenin selected from those specific duplex provided herein and as listed, e.g., in Tables 1, 2, 3, 4, 5, 6, 7, 8 and/or 9, wherein the composition is in a pharmaceutically effective formulation. In one embodiment, the RNAi agent comprises a first and a second strand, wherein the sequence of the first strand is the sequence of the first strand of a RNAi agent to Beta-Catenin selected from those specific duplex provided herein and as listed, e.g., in Tables 1, 2, 3, 4, 5, 6, 7, 8 and/or 9, wherein the composition is in a pharmaceutically effective formulation.

In one embodiment, the present disclosure pertains to the use of a RNAi agent in the manufacture of a medicament for treatment of a Beta-Catenin-related disease, wherein the RNAi agent is any RNAi disclosed herein. In one embodiment, the RNAi agent comprises a sense strand and an antisense strand, wherein the antisense strand comprises at least 15 contiguous nucleotides differing by 0, 1, 2, or 3 nucleotides from the antisense strand of a RNAi agent to Beta-Catenin selected from those specific duplex provided herein and as listed, e.g., in Tables 1, 2, 3, 4, 5, 6, 7, 8 and/or 9. In one embodiment, the RNAi agent comprises at least an anti-sense strand, and/or comprises a sense and an anti-sense strand, wherein the anti-sense strand comprises at least 15 contiguous nucleotides differing by 0, 1, 2, or 3 nucleotides from the anti-sense strand of a RNAi agent to Beta-Catenin selected from those specific duplex provided herein and as listed, e.g., in Tables 1, 2, 3, 4, 5, 6, 7, 8 and/or 9, wherein the composition is in a pharmaceutically effective formulation. In one embodiment, the RNAi agent comprises a first and a second strand, wherein the sequence of the first strand comprises at least 15 contiguous nucleotides differing by 0, 1, 2, or 3 nucleotides from the sequence of the first strand of a RNAi agent to Beta-Catenin selected from those specific duplex provided herein and as listed, e.g., in Tables 1, 2, 3, 4, 5, 6, 7, 8 and/or 9, wherein the composition is in a pharmaceutically effective formulation. In one embodiment, the RNAi agent comprises a first and a second strand, wherein the sequence of the first strand comprises the sequence of the first strand of a RNAi agent to Beta-Catenin selected from those specific duplex provided herein and as listed, e.g., in Tables 1, 2, 3, 4, 5, 6, 7, 8 and/or 9, wherein the composition is in a pharmaceutically effective formulation. In one embodiment, the RNAi agent comprises a first and a second strand, wherein the sequence of the first strand is the sequence of the first strand of a RNAi agent to Beta-Catenin selected from those specific duplex provided herein and as listed, e.g., in Tables 1, 2, 3, 4, 5, 6, 7, 8 and/or 9, wherein the composition is in a pharmaceutically effective formulation.

Specific Embodiments of RNAi Agents to Beta-Catenin Comprising Mismatches from the Disclosed Sequences Various specific embodiments of a RNAi agent to Beta-Catenin are disclosed herein. The present disclosure encompasses the example modified sequences provided in Tables 1, 2, 3, 4, 5, 6, 7, 8 and/or 9, and the corresponding unmodified sequences and other modified sequences (e.g., modified and unmodified variants). Specific embodiments of the present disclosure include RNAi agents which comprise sequences differing by 0, 1, 2, or 3 nt (nucleotides) or by [basepair(s)] (e.g., with 0, 1, 2 or 3 mismatches) from any of the RNAi agents listed in Table 1, and modified and unmodified variants thereof. As described in additional detail below, a mismatch is defined herein as a difference between the base sequence (e.g., A instead of G) or length when two sequences are maximally aligned and compared. In addition, as described in more detail below, an "unmodified variant" is a variant in which the base sequence is identical, but none of the bases are modified; this includes, for example, the corresponding portion of the wild-type Beta-Catenin mRNA or gene. A "modified variant" contains one or more modifications (or one or more fewer or different modifications) to a nucleotide, sugar, phosphate or backbone, and/or addition of one or more moieties; but without a change, substitution, addition, or deletion to the base sequence. A particular sequence and its modified or unmodified variants have 0 mismatches among them.

In one particular embodiment, the present disclosure comprises a RNAi agent comprising a anti-sense strand comprising at least 15 contiguous nucleotides differing by 0, 1, 2, or 3 nt from the sequence of the anti-sense strand of: any of the RNAi agents listed in Tables 1, 2, 3, 4, 5, 6, 7, 8 and/or 9, and modified and unmodified variants thereof.

In another particular embodiment, the RNAi agent comprises a sense strand comprising at least 15 contiguous nucleotides differing by 0, 1, 2, or 3 nt from the sense strand of any of the RNAi agents listed in Tables 1, 2, 3, 4, 5, 6, 7, 8 and/or 9, and modified and unmodified variants thereof.

Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

OTHER EMBODIMENTS

Various particular specific embodiments of this disclosure are described below.

In one embodiment, the disclosure pertains to a composition according to any of the disclosed embodiments, for use in a method of treating a Beta-Catenin-related disease in an individual, the method comprising the step of administering to the individual a therapeutically effective amount of a composition according to the disclosure.

Various particular specific embodiments of this embodiment are described below.

In one embodiment, the disclosure pertains to the composition according to any of the above embodiments, for use in a method of inhibiting the expression of Beta-Catenin in an individual, the method comprising the step of administering to the individual a therapeutically effective amount of a composition according to any of the disclosed embodiments.

One embodiment of the disclosure is the use of a composition according to any of the above embodiments, in the manufacture of a medicament for treatment of an Beta-Catenin-related disease.

In one embodiment, the Beta-Catenin-related disease is selected from cancer, viral disease or autoimmune disease.

In one embodiment, the disclosure pertains to the composition of any of the above embodiments, for use in the treatment of an Beta-Catenin-related disease.

In one embodiment, the Beta-Catenin-related disease is selected from cancer, viral disease or autoimmune disease.

In one embodiment, the disclosure relates to a method of inhibiting the expression of Beta-Catenin in an cell, comprising the step of introducing into the cell a composition comprising an RNAi agent comprising an antisense strand, wherein the antisense strand comprises at least 15 contiguous nucleotides differing by 0, 1, 2, or 3 nucleotides from the antisense strand of an RNAi agent to Beta-Catenin selected from the Beta-Catenin siRNAs disclosed herein.

In one embodiment, the disclosure relates to a method of inhibiting the expression of Beta-Catenin in an cell, comprising the step of introducing into the cell a composition comprising an RNAi agent comprising a sense strand and an antisense strand, wherein the antisense strand comprises at least 15 contiguous nucleotides differing by 0, 1, 2, or 3 nucleotides from the antisense strand, and the sense strand comprises at least 15 contiguous nucleotides differing by 0, 1, 2, or 3 nucleotides from the sense strand of an RNAi agent to Beta-Catenin selected from the Beta-Catenin siRNAs disclosed herein.

Beta-Catenin

By "Beta-Catenin" is meant the gene, mRNA, and/or protein, or any nucleic acid encoding the protein, also designated cadherin-associated protein beta 1; CTNNB1; CTNNB; CTNNB; CTNB1; FLJ25606; OMIM: 116806; MGI: 88276 HomoloGene: 1434; OTTHUMP00000209288; DKFZp686D02253; HGNC: 2514; Entrez Gene: 1499; Ensembl: ENSG00000168036; UniProtKB: P35222; GC03P040551; GC03P041054; or GC03P041201. See: Kraus et al. 1994. Genomics 23: 272-4.

Beta-Catenin is involved in the regulation of cell adhesion and in signal transduction through the Wnt pathway. It is part of a complex of proteins that constitute adherens junctions (AJs). AJs are necessary for the creation and maintenance of epithelial cell layers and regulate cell growth and adhesion between cells. Beta-Catenin also anchors the actin cytoskeleton and may be responsible for transmitting the contact inhibition signal that causes cells to stop dividing once the epithelial sheet is complete.

When Beta-Catenin was sequenced, it was found to be a member of the armadillo family of proteins. These proteins have multiple copies of the so-called armadillo repeat domain, which is specialized for protein-protein binding. When Beta-Catenin is not associated with cadherins and alpha-catenin, it can interact with other proteins such as ICAT and APC.

Beta-Catenin is also involved in the Wnt pathway. When Wnt is not present, GSK-3 (a kinase) constitutively phosphorylates the Beta-Catenin protein. Beta-Catenin is associated with axin (scaffolding protein) complexed with GSK-3 and APC (adenomatosis polyposis coli). The creation of this complex increases the phosphorylation of Beta-Catenin by facilitating the activity of GSK-3. When Beta-Catenin is phosphorylated, it is degraded and thus does not significantly accumulate in the cell. When Wnt binds to frizzled (Fz), its receptor, dishevelled (Dsh), is recruited to the membrane. GSK-3 is inhibited by the activation of Dsh by Fz. Because of this, Beta-Catenin is permitted to accumulate in the cytosol and can be translocated to the nucleus, where it performs several functions. It can act in conjunction with TCF/LEF transcription factors to activate target genes involved in different processes, including proliferation, survival and matrix remodeling.

Beta-Catenin interacts with many other proteins, including: cadherins, transcription factors, axin, galectin-3, beta-galactoside-binding protein, GSK-3, protein kinase A, Androgen receptor, APC, AXIN1, CBY1, CDH1, CDH2, CDH3, CDK5R1, CHUK, CTNNA1, CTNND1, EGFR, FHL2, HER2/neu, HNF4A, IKK2, LEF1, MAGI1, MUC1, NF5A1, PCAF, PHF17, Plakoglobin, PTPN14, PTPRF, PRPRK, PSEN1, RuvB-like 1, SMAD7, SLC913R1, SMARCA4, USP9X, and VE-cadherin.

Beta-Catenin is associated with several diseases. Beta-Catenin itself can act as an oncogene. In adenomatous polyposis of the colon, the APC gene, whose product binds Beta-Catenin, is mutated. As described in more detail below, mutations in, over-expression of, and/or abnormal cellular compartmentalization (e.g., aberrant accumulation in the cytoplasm and/or nucleus) of Beta-Catenin are associated with various diseases, including: adenomatous polyposis of the colon, colorectal cancer, basal cell carcinoma, pilomatrixoma, medulloblastoma, ovarian cancer, adrenocortical tumors, gastric cancer, liver cancer, melanoma, prostate cancer, renal cancer, ectopic teeth and taste papillae, skin cancer, anaplastic thyroid carcinoma, and uterine carcinosarcoma. See: Thompson et al. 2007 Hepatology 45: 1298-305; Wang et al. 2008 Cancer Epidemiol. Biomarkers Prev. 17: 2101-8; Saldanha et al. Br. J. Dermatol. 151: 157-64.

Nuclear and cytosolic accumulation (e.g., improper cellular compartmentalization) is enriched in basal-like breast cancer and are associated with poor outcome. Beta-Catenin accumulation is more often observed in basal-like in situ carcinomas than in other sub-types, suggesting that activation of this pathway might be an early event in basal-like tumor development. Khramtsov et al. 2010 Am. J. Pathol. 176: 2911-2920.

Sequences and Structure of Beta-Catenin

Three human transcript variants encoding the same protein have been found for this gene: NP_001091679.1; NP_001091680.1; and NP_001895.1. The amino acid and nucleotide sequences of human Beta-Catenin are provided in LOCUS NM_001098209 (ACCESSION NM_001098209 XM_001133660 XM_001133664 XM_001133673 XM_001133675; VERSION NM_001098209.1 GI:148233337); LOCUS NM_001098210 (ACCESSION NM_001098210; VERSION NM_001098210.1 GI:148227671); and LOCUS NM_001904 (ACCESSION NM_001904 XM_942045 XM_945648 XM_945650 XM_945651 XM_945652 XM_945653 XM_945654 XM_945655 XM_945657; VERSION NM_001904.3 GI:148228165).

The mouse (*Mus musculus*) sequence of Beta-Catenin is available as Q02248 (CTNB1_MOUSE); MGI:88276; NP_031640.1 GI:6671684; NM_007614.3. The rat (*Rattus norvegicus*) sequence is available as Q9WU82 (CTNB1_RAT); Li et al. 2002 Gene 283: 255-62.

A RNAi agent specific to Beta-Catenin can be designed such that the sequence thereof completely matches that of the mRNA corresponding to the human Beta-Catenin gene and the homologous gene from a test animal. Thus, the exact same RNAi agent can be used in both test animals (e.g., rat, mouse, cynomolgus monkey, etc.) and humans. The sequences for the various Beta-Catenin genes have been determined in many species, including humans, mice and rats (as described above).

The Beta-Catenin sequence in cynomolgus monkey (*Macaca fascicularis*, or "cyno") has been determined.

The alignment of the cyno and human (NM_001098210.1) Beta-Catenin mRNA sequences is shown below.

```
Human  AGGATACAGCGGCTTCTGCGCGACTTATAAGAGCTCCTTGTGCGGCGCCATTTTAAGCCT   60
Cyno   --------------------------------------------CGCCATTTTAAGCCT   15
                                                   ***************

Human  CTCGGTCTGTGGCAGCAGCGTTGGCCCGGCCCCGGGAGCGGAGAGCGAGGGGAGGCGGAG  120
Cyno   CTTGGTCTGTGGCAGCCGTGTTGGCCCGGCCCCGAGAGCGGAGAGCGAGGGGAGGCGGAG   75
       **  ************ * ***************** *********************

Human  ACGGAGGAAGGTCTGAGGAGCAGCTTCAGTCCCCGCCGAGCCGCCACCGCAGGTCGAGGA  180
Cyno   ACGGAGGAAGGTCCGAGGAGCAGCTTCAGTCCTCGCCGAGCCGCCACCGCAGGTCGAGGA  135
       ************* ****************** ***************************

Human  CGGTCGGACTCCCGCGGCGGGAGGAGCCTGTTCCCCTGAGGGTATTTGAAGTATACCATA  240
Cyno   CGGTCGGACTCCCGCGACGGGAGGAGCCTGTTCCCCTGAGGGTATTTGAAGTATACCATA  195
       **************** *******************************************

Human  CAACTGTTTTGAAAATCCAGCGTGGACAATGGCTACTCAAGCTGATTTGATGGAGTTGGA  300
Cyno   CAACTGTTTTGAAAATCCAGCGTGGACAATGGCTACTCAAGCTGATTTGATGGAGTTGGA  255
       ************************************************************

Human  CATGGCCATGGAACCAGACAGAAAAGCGGCTGTTAGTCACTGGCAGCAACAGTCTTACCT  360
Cyno   CATGGCCATGGAACCAGACAGAAAAGCGGCTGTTAGTCACTGGCAGCAACAGTCTTACCT  315
       ************************************************************

Human  GGACTCTGGAATCCATTCTGGTGCCACTACCACAGCTCCTTCTCTGAGTGGTAAAGGCAA  420
Cyno   GGACTCTGGAATCCATTCTGGTGCCACTACCACAGCTCCTTCTCTGAGTGGTAAAGGCAA  375
       ************************************************************

Human  TCCTGAGGAAGAGGATGTGGATACCTCCCAAGTCCTGTATGAGTGGGAACAGGGATTTTC  480
Cyno   TCCTGAGGAAGAGGATGTGGATACCTCCCAAGTCCTGTATGAGTGGGAACAGGGATTTTC  435
       ************************************************************

Human  TCAGTCCTTCACTCAAGAACAAGTAGCTGATATTGATGGACAGTATGCAATGACTCGAGC  540
Cyno   TCAGTCCTTCACTCAAGAACAAGTAGCTGATATTGATGGACAGTATGCAATGACTCGAGC  495
       ************************************************************

Human  TCAGAGGGTACGAGCTGCTATGTTCCCTGAGACATTAGATGAGGGCATGCAGATCCCATC  600
Cyno   TCAGAGGGTACGAGCTGCTATGTTCCCTGAGACATTAGATGAGGGCATGCAGATCCCATC  555
       ************************************************************

Human  TACACAGTTTGATGCTGCTCATCCCACTAATGTCCAGCGTTTGGCTGAACCATCACAGAT  660
Cyno   TACACAGTTTGATGCTGCTCATCCCACTAATGTCCAGCGTTTGGCTGAACCATCACAGAT  615
       ************************************************************

Human  GCTGAAACATGCAGTTGTAAACTTGATTAACTATCAAGATGATGCAGAACTTGCCACACG  720
Cyno   GCTGAAACATGCAGTTGTAAACTTGATTAACTATCAAGATGATGCAGAACTTGCCACACG  675
       ************************************************************

Human  TGCAATCCCTGAACTGACAAAACTGCTAAATGACGAGGACCAGGTGGTGGTTAATAAGGC  780
Cyno   TGCAATCCCTGAACTGACAAAACTGCTAAATGATGAGGACCAGGTGGTGGTTAATAAGGC  735
       ********************************* **************************

Human  TGCAGTTATGGTCCATCAGCTTTCTAAAAAGGAAGCTTCCAGACACGCTATCATGCGTTC  840
Cyno   TGCAGTTATGGTCCATCAGCTTTCTAAAAAGGAAGCTTCCAGACACGCTATCATGCGTTC  795
       ************************************************************

Human  TCCTCAGATGGTGTCTGCTATTGTACGTACCATGCAGAATACAAATGATGTAGAAACAGC  900
Cyno   TCCTCAGATGGTGTCTGCTATTGTACGTACCATGCAGAATACAAATGATGTAGAAACAGC  855
       ************************************************************
```

```
                                                  -continued
Human    TCGTTGTACCGCTGGGACCTTGCATAACCTTTCCCATCATCGTGAGGGCTTACTGGCCAT       960
Cyno     TCGTTGTACCGCTGGGACCTTGCATAACCTTTCCCATCATCGGGAGGGCTTGTTGGCCAT       915
         ****************************************  *******  *******

Human    CTTTAAGTCTGGAGGCATTCCTGCCCTGGTGAAAATGCTTGGTTCACCAGTGGATTCTGT      1020
Cyno     CTTTAAGTCTGGAGGCATTCCTGCCCTGGTGAAAATGCTTGGTTCACCAGTGGATTCTGT       975
         ************************************************************

Human    GTTGTTTTATGCCATTACAACTCTCCACAACCTTTTATTACATCAAGAAGGAGCTAAAAT      1080
Cyno     GTTGTTTTATGCCATTACAACTCTCCACAACCTTTTATTACATCAAGAAGGAGCTAAAAT      1035
         ************************************************************

Human    GGCAGTGCGTTTAGCTGGTGGGCTGCAGAAAATGGTTGCCTTGCTCAACAAAACAAATGT      1140
Cyno     GGCAGTGCGTTTAGCTGGCGGGCTACAGAAAATGGTTGCCTTGCTCAACAAAACAAACGT      1095
         ****************** ***** ******************************** **

Human    TAAATTCTTGGCTATTACGACAGACTGCCTTCAAATTTTAGCTTATGGCAACCAAGAAAG      1200
Cyno     TAAATTCTTGGCTATTACGACAGACTGCCTTCAGATTTTAGCATATGGCAACCAAGAAAG      1155
         ********************************* ******** *****************

Human    CAAGCTCATCATACTGGCTAGTGGTGGACCCCAAGCTTTAGTAAATATAATGAGGACCTA      1260
Cyno     CAAGCTGATCATACTGGCTAGTGGTGGACCCCAAGCTTTAGTAAATATAATGAGGACCTA      1215
         ****** *****************************************************

Human    TACTTACGAAAAACTACTGTGGACCACAAGCAGAGTGCTGAAGGTGCTATCTGTCTGCTC      1320
Cyno     TACTTATGAGAAACTACTGTGGACCACAAGCAGAGTGCTGAAGGTGCTATCCGTCTGCTC      1275
         ****** ** ***************************************** ********

Human    TAGTAATAAGCCGGCTATTGTAGAAGCTGGTGAATGCAAGCTTTAGGACTTCACCTGAC      1380
Cyno     TAGTAATAAGCCAGCTATTGTAGAAGCTGGTGAATGCAAGCTTTAGGACTTCACCTGAC      1335
         ************ ***********************************************

Human    AGATCCAAGTCAACGTCTTGTTCAGAACTGTCTTTGGACTCTCAGGAATCTTTCAGATGC      1440
Cyno     AGATCCAAGTCAACGTCTTGTTCAGAACTGTCTTTGGACTCTCAGGAATCTTTCAGATGC      1395
         ************************************************************

Human    TGCAACTAAACAGGAAGGGATGGAAGGTCTCCTTGGGACTCTTGTTCAGCTTCTGGGTTC      1500
Cyno     TGCAACTAAACAGGAAGGGATGGAAGGTCTCCTTGGGACTCTTGTTCAGCTTCTGGGTTC      1455
         ************************************************************

Human    AGATGATATAAATGTGGTCACCTGTGCAGCTGGAATTCTTTCTAACCTCACTTGCAATAA      1560
Cyno     AGATGATATAAATGTGGTCACCTGTGCAGCTGGAATTCTTTCTAACCTCACTTGCAATAA      1515
         ************************************************************

Human    TTATAAGAACAAGATGATGGTCTGCCAAGTGGGTGGTATAGAGGCTCTTGTGCGTACTGT      1620
Cyno     TTATAAGAATAAGATGATGGTCTGCCAAGTGGGTGGTATAGAGGCTCTTGTGCGTACTGT      1575
         ********* **************************************************

Human    CCTTCGGGCTGGTGACAGGGAAGACATCACTGAGCCTGCCATCTGTGCTCTTCGTCATCT      1680
Cyno     CCTTCGGGCTGGTGACAGGGAAGACATCACTGAGCCTGCCATCTGTGCTCTTCGTCATCT      1635
         ************************************************************

Human    GACCAGCCGACACCAAGAAGCAGAGATGGCCCAGAATGCAGTTCGCCTTCACTATGGACT      1740
Cyno     GACCAGCCGACACCAAGAAGCAGAGATGGCCCAGAATGCAGTTCGCCTTCACTATGGACT      1695
         ************************************************************

Human    ACCAGTTGTGGTTAAGCTCTTACACCCACCATCCCACTGGCCTCTGATAAAGGCTACTGT      1800
Cyno     ACCAGTTGTGGTTAAGCTCTTACACCCACCATCCCACTGGCCTCTGATAAAGGCTACTGT      1755
         ************************************************************

Human    TGGATTGATTCGAAATCTTGCCCTTTGTCCCGCAAATCATGCACCTTTGCGTGAGCAGGG      1860
Cyno     TGGATTGATTCGAAATCTTGCCCTTTGTCCAGCAAATCATGCACCTTTGCGTGAGCAGGG      1815
         ****************************** *****************************

Human    TGCCATTCCACGACTAGTTCAGTTGCTTGTTCGTGCACATCAGGATACCCAGCGCCGTAC      1920
Cyno     TGCCATTCCACGACTAGTTCAGTTGCTTGTTCGTGCACATCAGGATACCCAGCGCCGTAC      1875
         ************************************************************

Human    GTCCATGGGTGGGACACAGCAGCAATTTGTGGAGGGGGTCCGCATGGAAGAAATAGTTGA      1980
Cyno     GTCCATGGGTGGGACACAGCAGCAATTTGTGGAGGGGGTCCGCATGGAAGAAATAGTTGA      1935
         ************************************************************

Human    AGGTTGTACCGGAGCCCTTCACATCCTAGCTCGGGATGTTCACAACCGAATTGTTATCAG      2040
Cyno     AGGTTGTACTGGAGCCCTTCACATCCTAGCTCGGGATGTTCACAACCGAATTGTAATCAG      1995
         ********* ******************************************** *****

Human    AGGACTAAATACCATTCCATTGTTTGTGCAGCTGCTTTATTCTCCCATTGAAAACATCCA      2100
Cyno     AGGACTAAATACCATTCCATTGTTTGTGCAGCTGCTTTATTCTCCCATTGAAAACATCCA      2055
         ************************************************************
```

```
Human  AAGAGTAGCTGCAGGGGTCCTCTGTGAACTTGCTCAGGACAAGGAAGCTGCAGAAGCTAT    2160
Cyno   AAGAGTAGCTGCAGGGGTCCTCTGTGAACTTGCTCAGGACAAGGAAGCTGCAGAAGCGAT    2115
       *********************************************************  **

Human  TGAAGCTGAGGGAGCCACAGCTCCTCTGACAGAGTTACTTCACTCTAGGAATGAAGGTGT    2220
Cyno   TGAAGCTGAGGGAGCCACAGCTCCTCTGACAGAGTTACTTCACTCTAGGAATGAAGGTGT    2175
       ************************************************************

Human  GGCGACATATGCAGCTGCTGTTTTGTTCCGAATGTCTGAGGACAAGCCACAAGATTACAA    2280
Cyno   GGCGACGTATGCAGCTGCTGTTTTGTTCCGAATGTCTGAGGACAAGCCACAAGATTACAA    2235
       ******  ****************************************************

Human  GAAACGGCTTTCAGTTGAGCTGACCAGCTCTCTCTTCAGAACAGAGCCAATGGCTTGGAA    2340
Cyno   GAAACGGCTTTCAGTTGAGCTGACCAGCTCTCTCTTCAGAACGGAGCCAATGGCTTGGAA    2295
       ****************************************** *****************

Human  TGAGACTGCTGATCTTGGACTTGATATTGGTGCCCAGGGAGAACCCCTTGGATATCGCCA    2400
Cyno   TGAGACTGCGGATCTTGGACTTGATATTGGTGCCCAGGGAGAACCCCTTGGATATCGCCA    2355
       ********* **************************************************

Human  GGATGATCCTAGCTATCGTTCTTTTCACTCTGGTGGATATGGCCAGGATGCCTTGGGTAT    2460
Cyno   GGATGATCCTAGCTATCGTTCTTTTCACTCTGGTGGATATGGCCAGGATGCCTTGGGTAT    2415
       ************************************************************

Human  GGACCCCATGATGGAACATGAGATGGGTGGCCACCACCCTGGTGCTGACTATCCAGTTGA    2520
Cyno   GGACCCCATGATGGAACATGAGATGGGTGGCCACCACCCTGGTGCTGACTATCCAGTTGA    2475
       ************************************************************

Human  TGGGCTGCCAGATCTGGGGCATGCCCAGGACCTCATGGATGGGCTGCCTCCAGGTGACAG    2580
Cyno   TGGGCTGCCAGATCTGGGACATGCCCAGGACCTCATGGATGGGCTGCCTCCAGGTGATAG    2535
       ******************  ************************************  *

Human  CAATCAGCTGGCCTGGTTTGATACTGACCTGTAAATCATCCTTTAG---------------    2626
Cyno   CAATCAGCTGGCCTGGTTTGATACTGACCTGTAAATCATCCTTTAGCTGTATTGTCTGAA    2595
       *************************************************

Human   ------------------------------------------------------------
Cyno   CTTGCATTGTGATTGGCCTGTAGAGTTGCTGAGAGGGCTCGAGGGGTGGGCTGGTATCTC    2655

Human   ------------------------------------------------------------
Cyno   AGAAAGTGCCTGACACACTAACCAAGCTGAGTTTCCTATGGGAACAATTGAAGTAAACTT    2715

Human   ------------------------GAGTAACAATACAAATGGATTTGGGAGTGACTCA    2661
Cyno   TTTGTTCTGGTCCTTTTTGGTCGAGGAGTAACAATACAAATGGATTTTGGGAGTGACTCA    2775
                               ******************************* ******

Human  AGAAGTGAAGAATGCACAAGAATGGATCACAAGATGGAATTTATCAAACCCTAGCCTTGC    2721
Cyno   AGAAGTGAAGAATGCACAAGAATGGATCACAAGATGGAATTTATCAAACCCTAGCCTTGC    2835
       ************************************************************

Human  TTGTTAAATTTTTTTTTTTTTTTTTTTAAGAATATCTGTAATGGTACTGACTTTGCTTGC    2781
Cyno   TTGTTAAATTTTTTTTTTTTTTTTTTTAAGAATATCTGTAATGGTACTGACTTTGCTTGC    2895
       ************************************************************

Human  TTTGAAGTAGCTCTTTTTTTTTTTTTTTTTTTTTGCAGTAACTGTTTTTTAAGTCT       2841
Cyno   TTTGAAGTAGCTCTTTTTTTTTTTTTTTTTTTTTTGCAGTAACTGTTTTTTAAGTCT      2955
       **********************************  ************************

Human  CTCGTAGTGTTAAGTTATAGTGAATACTGCTACAGCAATTTCTAATTTTTAAGAATTGAG    2901
Cyno   CTCGTAGTGTTAAGTTATAGTGAATACTGCTACAGCAATTTCTAATTTTTAAGAATTGAG    3015
       ************************************************************

Human  TAATGGTGTAGAACACTAATTCATAATCACTCTAATTAATTGTAATCTGAATAAAGTGTA    2961
Cyno   TAATGGTGTAGAACACTAATTCATAATCACTCTAAT-AATTGTAATCTGAATAAAGTGTA    3074
       *********************************** ************************

Human  ACAATTGTGTAGCCTTTTTGTATAAAATAGACAAATAGAAAATGGTCCAATTAGTTTCCT    3021
Cyno   ACA-TTGTGTAGCCTTTTTGTATAAAATAGACAAATAGAAAATGGTCCAATTAGTTTCCT    3133
       *** ********************************************************

Human  TTTTAATATGCTTAAAATAAGCAGGTGGATCTATTTCATGTTTTTGATCAAAAACT--AT    3079
Cyno   TTTTAATATGCTTAAAATAAGCAGGTGGATCTATTTCATGTTTTTGATCAAAAACTTTAT    3193
       ********************************************************  **

Human  TTGGGATATGTATGGGTAGGGTAAATCAGTAAGAGGTGTTATTTGGAACCTTGTTTTGGA    3139
Cyno   TTGGGATATGTATGGGTAGGGTAAATCAGTAAGAGGTGTTATTTGGAACCTTGTTTTGGA    3253
       ************************************************************
```

```
Human  CAGTTTACCAGTTGCCTTTTATCCCAAAGTTGTTGTAACCTGCTGTGATACGATGCTTCA    3199
Cyno   CAGTTTACCAGTTGCCTTTTATCCCAAAGTTGTTGTAACCTGCTGTGATACAATGCTTCA    3313
       *********************************************** ********

Human  AGAGAAAATGCGGTTATAAAAAATGGTTCAGAATTAAACTTTTAATTCATTCGATTG       3256
Cyno   AGAGAAAATGCGGTTATAAAAAATGGTTCAGAA------------------------       3346
       *********************************

Human  (SEQ ID NO: 4112)
Cyno   (SEQ ID NO: 4113)

The start (ATG) and stop (TGA) of the cyno and human sequences are in bold,
underlined. Nucleotides matching between the human and cyno sequences are
marked with an asterisk (*). Whether or not a given sequence (e.g., a
first or second strand of a siRNA or duplex) matches the sense or anti-
sense strand of the Beta-Catenin sequence can be readily determined by
comparison of the sequences above (SEQ ID NOs: 4112 and 4113).
```

Additional Embodiments of a RNAi Agent to Beta-Catenin

The present disclosure encompasses various embodiments of RNAi agents to Beta-Catenin.

In one embodiment, the Beta-Catenin RNAi agent of the present disclosure comprises a sequence which is identical in the human, rat and cyno Beta-Catenin mRNAs. This sequence identity facilitates animal testing prior to human testing. In another embodiment, the Beta-Catenin RNAi agent comprises a sequence which is identical in the human, mouse and cyno Beta-Catenin mRNAs. In another embodiment, the Beta-Catenin RNAi agent comprises a sequence which is identical in the human and mouse Beta-Catenin mRNAs. In another embodiment, the Beta-Catenin RNAi agent comprises a sequence which is identical in the human and rat cyno Beta-Catenin mRNAs. In another embodiment, the Beta-Catenin RNAi agent comprises a sequence which is identical in the human, mouse and rat Beta-Catenin mRNAs. In another embodiment, the Beta-Catenin RNAi agent comprises a sequence which is identical in the human, rat and cyno Beta-Catenin mRNAs.

In one embodiment, the Beta-Catenin RNAi agent comprises a sequence which does not match that of any other mRNA. In one embodiment, the Beta-Catenin RNAi agent comprises a sequence which differs from all other known non-Beta-Catenin mRNAs by at least 0, 1, 2 or 3 nucleotides. In various embodiments, the Beta-Catenin RNAi agent does knock-down any other gene by more than 5, 10, 15, 20, 25, 30, or 40%. The ability of the Beta-Catenin RNAi agent to knock down other genes can be tested in vitro, or by using arrays of various genes.

Various mutations in Beta-Catenin are known; many of these are involved in Beta-Catenin-related diseases. These include mutations of the residues at 33, 37, 41 and 45, but disease-associated mutations have also been found at positions 8, 11, 13, 21, 24, 25, 28, 29, 32, 34, 39, 47, 48 and 55. In various embodiments of the present disclosure, RNAi agents can be devised to preferentially target the mutated (rather than wildtype) form of Beta-Catenin.

In other embodiments, the RNAi agents of the present disclosure bind to the 5' or 3' UTR [untranslated region(s)].

The efficacy of a RNAi agent in reducing the level of Beta-Catenin can be measured directly, e.g., measuring the levels of Beta-Catenin mRNA abundance or levels or cellular distribution of the protein itself. For example, the accumulation of Beta-Catenin in the cytoplasm and/or nucleus is associated with various disease states. After administration of a RNAi agent, cells and tissues can be tested for the accumulation of Beta-Catenin in the cytoplasm and nucleus. Alternatively, the efficacy of the RNAi can be measured indirectly by measuring the level of any one or more of the known activities of Beta-Catenin. For example, localization of Beta-Catenin to the nucleus can lead to transcription of various genes, including c-myc. After administration of a RNAi agent to Beta-Catenin, the expression of c-myc or other genes activated by Beta-Catenin can be measured.

In one embodiment, the Beta-Catenin RNAi agent of the present disclosure is administered to a patient in need thereof (e.g., a patient suffering from, suspected of having, or predisposed for, adenomatous polyposis of the colon, colorectal cancer, basal cell carcinoma, breast cancer, kidney cancer, Wilms tumors, medulloblastoma, ovarian cancer, adrenocortical tumors, gastric cancer, liver cancer, melanoma, pancreatic cancers, prostate cancer, renal cancer, ectopic teeth and taste papillae, skin cancer, pilomatrixoma, anaplastic thyroid carcinoma, and uterine carcinosarcoma, oligodontia, osteoporosis, ageing, degenerative diseases, bedsores, chronic wounds and impaired wound healing, and similar and related diseases).

The patient can also be administered more than one RNAi agent specific to Beta-Catenin. In one embodiment, the Beta-Catenin RNAi agent(s) of the present disclosure can optionally be administered along with one or more additional pharmaceutical agent appropriate for that disease. In one embodiment, the Beta-Catenin RNAi agent(s) of the present disclosure can be optionally administered along with any other appropriate additional treatment, wherein the additional treatment can be a composition or a method.

Various disease states are associated with mutations in Beta-Catenin (such as those listed above), which result in over-expression, hyper-activity and/or improper cellular compartmentalization of Beta-Catenin. Mutations in components other than Beta-Catenin can also activate the Wnt signaling pathway. For example, APC (adenomatous polyposis coli) normally controls Beta-Catenin activity. APC normally builds a complex with glycogen synthase kinase 3-beta (GSK-3beta) and axin. This complex binds Beta-Catenin in the cytoplasm. With the help of casein kinase (CK1), which carries out an initial phosphyrlation of Beta-Catenin, GSK-3beta is able to phosphorylate Beta-Catenin a second time. This targets Beta-Catenin for ubiquitination and degradation by cellular proteosomes and prevents translocation of Beta-Catenin to the nucleus. APC mutations thus can result in constitutive activation of the Wnt signaling pathway. RNAi agents to Beta-Catenin can thuse be administered to patients with disease strates associated not only with mutations in Beta-Catenin but also in related mutations in other components (such as APC) of the Wnt signaling pathway.

In the case of adenomatous polyposis of the colon, colorectal cancer, basal cell carcinoma, breast cancer, kidney cancer, Wilms tumors, medulloblastoma, ovarian cancer, adrenocortical tumors, gastric cancer, liver cancer, melanoma, pancreatic cancers, prostate cancer, renal cancer, ectopic teeth and taste papillae, skin cancer, pilomatrixoma, anaplastic thyroid carcinoma, and uterine carcinosarcoma, oligodontia, osteoporosis, ageing, degenerative diseases, bedsores, chronic wounds and impaired wound healing, and similar and related diseases, the RNAi agent(s) and additional disease treatment(s) can be administered in any order, simultaneously or sequentially, or in one or multiple doses over time.

In the treatment of these Beta-Catenin-related diseases, the RNAi agent(s) and additional disease treatment(s) can be administered in any order, simultaneously or sequentially, or in multiple doses over time. Administration of the RNAi agent and the additional treatment can be, for example, simultaneous, concurrent, separate or sequential.

Simultaneous administration may, e.g., take place in the form of one fixed combination with two or more active ingredients, or by simultaneously administering two or more active ingredients that are formulated independently. Sequential use (administration) preferably means administration of one (or more) components of a combination at one time point, other components at a different time point, that is, in a chronically staggered manner, preferably such that the combination shows more efficiency than the single compounds administered independently (especially showing synergism). Separate use (administration) preferably means administration of the components of the combination independently of each other at different time points, preferably meaning that the components (a) and (b) are administered such that no overlap of significant measurable blood levels of both compounds are present in an overlapping manner (at the same time).

Also combinations of two or more of sequential, separate and simultaneous administration are possible, preferably such that the combination component-drugs show a joint therapeutic effect that exceeds the effect found when the combination component-drugs are used independently at time intervals so large that no mutual effect on their therapeutic efficiency can be found, a synergistic effect being especially preferred.

The term "delay of progression" as used herein means administration of the combination to patients being in a pre-stage or in an early phase, of the first manifestation or a relapse of the disease to be treated, in which patients, e.g., a pre-form of the corresponding disease is diagnosed or which patients are in a condition, e.g., during a medical treatment or a condition resulting from an accident, under which it is likely that a corresponding disease will develop.

"Jointly therapeutically active" or "joint therapeutic effect" means that the compounds may be given separately (in a chronically staggered manner, especially a sequence-specific manner) in such time intervals that they preferably, in the warm-blooded animal, especially human, to be treated, still show a (preferably synergistic) interaction (joint therapeutic effect). Whether this is the case, can inter alia be determined by following the blood levels, showing that both compounds are present in the blood of the human to be treated at least during certain time intervals.

Additional Definitions

For convenience, the meaning of certain terms and phrases used in the specification, examples, and appended claims, are provided below. If there is an apparent discrepancy between the usage of a term in other parts of this specification and its definition provided in this document, the definition in this document shall prevail.

As used throughout this disclosure, articles such as "a" and "an" refer to one or more than one (at least one) of the grammatical object of the article.

RNAi Agents to Beta-Catenin

In one embodiment, the present disclosure pertains to a Beta-Catenin RNAi agent or other anti-sense nucleic acid complementary to a mRNA encoding the Beta-Catenin gene (or portion thereof), or a recombinant expression vector encoding encoding at least one strand of the siRNA (RNAi agent) or a composition comprising the antisense nucleic acid that can function as an RNAi agent as defined below.

As used herein, an "anti-sense" nucleic acid comprises a nucleotide sequence complementary to a "sense" nucleic acid encoding the Beta-Catenin protein (e.g., complementary to the coding strand of a double-stranded DNA, complementary to an mRNA or complementary to the coding strand of a Beta-Catenin gene).

As used herein, the term "RNAi agent to Beta-Catenin," "RNAi agent specific to Beta-Catenin," "iRNA agent to Beta-Catenin," "siRNA to Beta-Catenin", "Beta-Catenin siRNA" and the like refer to a siRNA (short inhibitory RNA), siRNA (short or small hairpin RNA), iRNA (interference RNA) agent, RNAi (RNA interference) agent, dsRNA (double-stranded RNA), microRNA, and the like, and refer to a composition which specifically targets, is specific to, and/or binds to a mRNA corresponding to the Beta-Catenin gene. As used herein, the term "antisense nucleic acid" or "composition comprising an anti-sense nucleic acid" and the like is broadly meant to encompass any composition comprising at least one nucleic acid strand which is anti-sense to its target; this includes, but is not limited to, any siRNA, shRNA, iRHA, dsRNA, microRNA, antisense oligonucleotide, and any other composition comprising an anti-sense nucleic acid.

As used herein, the terms "iRNA" and "RNAi" refers to an agent that contains RNA (or a derivative thereof), and which mediates the targeted cleavage of another RNA transcript via an RNA-induced silencing complex (RISC) pathway. In one embodiment, the RNAi agent is an oligonucleotide composition that activates the RISC complex/pathway. In another embodiment, the RNAi agent comprises an anti-sense strand sequence (anti-sense oligonucleotide). RNAi agents include, for example, siRNAs, dsRNAs and shRNAs. The RNAi agents can be wholly RNA, or can comprise a backbone or individual nucleotides which are not RNA, such as LNA, GNA, TNA, boranophosphate RNA, FANA, etc. Individual nucleotides can be replaced by DNA (e.g., the terminal UU, TT, or the like) or individual nucleotides at the 5' end or internally. However, in no case does the disclosure contemplate the RNAi agent comprising two strands which are completely DNA (e.g., a double-stranded DNA).

In one embodiment, the RNAi comprises a single strand. This single-stranded RNAi agent oligonucleotide or polynucleotide can comprise the sense or antisense strand, as described by Sioud 2005 J. Mol. Biol. 348:1079-1090, and references therein. Thus the disclosure encompasses RNAi agents with a single strand comprising either the sense or antisense strand of an RNAi agent described herein.

The RNAi agent(s) of the present disclosure target (e.g., bind to, anneal to, etc.) the Beta-Catenin mRNA. The use of the RNAi agent specific to Beta-Catenin results in a decrease of Beta-Catenin activity, level and/or expression, e.g., a "knock-down" or "knock-out" of the target gene or target sequence. Particularly, in one embodiment, in the case of a disease state characterized by over-expression or hyper-activity of Beta-Catenin, administration of a RNAi agent to Beta-Catenin knocks down the Beta-Catenin target enough to restore a normal level of Beta-Catenin activity.

In one embodiment, the RNAi comprises a single strand (such as an shRNA, as described herein). In other embodiments, the RNAi agent comprises a single strand because the sense and anti-sense strands are contiguous, connected by a loop, or otherwise linked.

In various embodiments, one or both strands are nicked.

In one embodiment, a single-stranded RNAi agent oligonucleotide or polynucleotide can comprise the sense and/or antisense strand. See, e.g., Sioud 2005 J. Mol. Biol. 348: 1079-1090, and references cited therein. Thus the present disclosure encompasses RNAi agents with a single strand comprising either the sense or antisense strand of a RNAi agent described herein.

RNAi agents that are particularly useful for this disclosure include those which can bind specifically to a region of the Beta-Catenin mRNA, and have one or more of the following qualities: binding in the coding segment of Beta-Catenin; binding at or near the junction of the 5' untranslated region and the start of the coding segment; binding at or near the translational start site of the mRNA; binding in the third exon of the Beta-Catenin gene; binding at or near junctions of exons and introns; little or no binding to the mRNAs of other genes (little or no "off-target effects"); binding to the Beta-Catenin mRNA in or near a region or regions that is not double-stranded or a stem region, e.g., in a loop or single-stranded portion; eliciting little or no immunogenicity; binding in a segment of the Beta-Catenin mRNA sequence which is conserved among various animal species (including human, mouse, rat, cynomolgus monkey, etc.), as the presence of a conserved sequence facilitates testing using various laboratory animals; binding to double-stranded region(s) of the mRNA; binding to an AT-rich region (e.g., at least about 50, 51, 52, 53, 54, 55, 56, 57, 58, 59, or 60% AT-rich); and/or lacking particular sequences known or suspected to decrease siRNA activity, e.g., the presence of a GG sequence at the 5' end, which may decrease separation of the double-stranded portion of the RNAi agent. In various embodiments, the RNAi agent specific to Beta-Catenin can be a double-stranded RNA having any one or more of these qualities.

The term "double-stranded RNA" or "dsRNA," as used herein, refers to a RNAi agent comprising a first and a second strand; e.g., a composition that includes an RNA molecule or complex of molecules having a hybridized duplex region (i.e., a region where the nucleotide bases from the first strand and the second strand are paired) that comprises two anti-parallel and substantially complementary nucleic acid strands, which will be referred to as having "sense" and "anti-sense" orientations with respect to a target RNA. The anti-sense strand, with respect to the mRNA target, is also called the "guide" strand, and the sense strand is also called the "passenger" strand. The passenger strand can include at least one or more of the following: one or more extra nucleotides (e.g., a bulge or 1 nt loop) compared to the other strand, a nick, a gap, etc., compared to the other strand. In various embodiments, the RNAi agent comprises a first strand and a second strand. In various embodiments, the first strand is the sense strand and the second strand is the anti-sense strand. In other embodiments, the first strand is the anti-sense strand and the second strand is the sense strand.

The duplex region can be of any length that permits specific degradation of a desired target RNA through a RISC pathway, but will typically range from 9 to 36 base pairs ("bp") in length, e.g., 15-30 base pairs in length. Considering a duplex between 9 and 36 base pairs, the duplex can be any length in this range, for example, 9, 10, 11, 12, 13, 14, 15, 16, 17, 18, 19, 20, 21, 22, 23, 24, 25, 26, 27, 28, 29, 30, 31, 32, 33, 34, 35, or 36 base pairs (bp) and any sub-range therebetween, including, but not limited to 15-30 base pairs, 15-26 base pairs, 15-23 base pairs, 15-22 base pairs, 15-21 base pairs, 15-20 base pairs, 15-19 base pairs, 15-18 base pairs, 15-17 base pairs, 18-30 base pairs, 18-26 base pairs, 18-23 base pairs, 18-22 base pairs, 18-21 base pairs, 18-20 base pairs, 19-30 base pairs, 19-26 base pairs, 19-23 base pairs, 19-22 base pairs, 19-21 base pairs, 19-20 base pairs, 19 base pairs, 20-30 base pairs, 20-26 base pairs, 20-25 base pairs, 20-24 base pairs, 20-23 base pairs, 20-22 base pairs, 20-21 base pairs, 20 basepairs, 21-30 base pairs, 21-26 base pairs, 21-25 base pairs, 21-24 base pairs, 21-23 base pairs, 21-22 base pairs, 21 base pairs, 22 base pairs, or 23 base pairs. dsRNAs generated in the cell by processing with Dicer and similar enzymes are generally in the range of 19-22 base pairs in length. One strand of the duplex region of a dsRNA comprises a sequence that is substantially complementary to a region of a target RNA. The two strands forming the duplex structure can be from a single RNA molecule having at least one self-complementary duplex region, or can be formed from two or more separate RNA molecules that hybridize to form the duplex. Where the duplex region is formed from two strands of a single molecule, the molecule can have a duplex region separated by a single-stranded chain of nucleotides (herein referred to as a "hairpin loop", e.g., such as found in a shRNA construct) between the 3'-end of one strand and the 5'-end of the respective other strand forming the duplex structure. The hairpin loop can comprise at least one unpaired nucleotide; in some embodiments the hairpin loop can comprise at least 3, at least 4, at least 5, at least 6, at least 7, at least 8, at least 9, at least 10, at least 20, at least 23 or more unpaired nucleotides. Where the two substantially complementary strands of a dsRNA are comprised by separate RNA molecules, those molecules need not, but can be covalently connected. Where the two strands are connected covalently by a hairpin loop, the construct is generally referred to herein and in the art as a "shRNA." Where the two strands are connected covalently by means other than a hairpin loop, the connecting structure is referred to as a "linker."

The terms "RNAi agent" and "siRNA" are also used herein to refer to a dsRNA as described above, useful for RNA interference.

In various embodiments of the present disclosure, the composition pertains to RNAi agents to Beta-Catenin comprising a sense strand comprising at least 15 contiguous nt with 0, 1, 2 or 3 mismatches from the sense strand, and/or an anti-sense strand comprising at least 15 contiguous nt with 0, 1, 2, or 3 mismatches from the anti-sense strand of any RNAi agent disclosed herein, particularly in Tables 1, 2, 3, 4, 5, 6, 7, 8 and/or 9, and modified and unmodified variants thereof.

RNAi Agents to Beta-Catenin Comprising Mismatches from the Disclosed Sequences

Various specific embodiments of a RNAi agent to Beta-Catenin are disclosed herein; example sequences are provided in Tables 1, 2 and 3. Specific embodiments of the present disclosure include RNAi agents which comprise sequences differing by 0, 1, 2, or 3 nt (nucleotides) or by [basepair(s)] (e.g., with 0, 1, 2 or 3 mismatches) from any of the RNAi agents listed in Tables 1, 2, 3, 4, 5, 6, 7, 8 and/or 9, and modified and unmodified variants thereof.

A mismatch is defined herein as a difference between the base sequence or length when two sequences are maximally aligned and compared. A mismatch is defined as a position wherein the base of one sequence does not match the base of the other sequence. Thus, a mismatch is counted, for example, if a position in one sequence has a particular base (e.g., A), and the corresponding position on the other sequence has a different base (e.g., G). Substitution of A, for example, with T, C, G or U would constitute a mismatch. Substitution of G with T, A, C or U would also constitute a mismatch. Substitution of C with T, G, A or U would also constitute a mismatch. Substitution of U with A, C or G would constitute a mismatch. Note, however, that on a given strand, a U can be replaced by T (either as RNA or, preferably, DNA, e.g., 2'-deoxy-thymidine); the replacement of a U with a T is not a mismatch, as either U or A can pair with A on the opposite strand. The RNAi agent can thus comprise some DNA bases, e.g., T, or a terminal TT or UU.

A mismatch is also counted, e.g., if a position in one sequence has a base (e.g., A), and the corresponding position on the other sequence has no base (e.g., that position is an abasic nucleotide, which comprises a phosphate-sugar backbone but no base). A single-stranded nick in either sequence (or in the sense or anti-sense strand) is not counted as mismatch. Thus, as a non-limiting example, no mismatch would be counted if one sequence comprises the sequence AG, but the other sequence comprises the sequence AG with a single-stranded nick between the A and the G. If one sequence comprises a C, and the other sequence comprises a modified C (e.g., 2'-modification) at the same position, no mismatch would be counted.

In addition, no mismatches are counted if modifications are made to the sugar, phosphate, or backbone of the RNAi agent without modifying the base. Thus, a sequence of UGGUGCUGACUAUCCAGUU (SEQ ID NO: 429) as an RNA and the same sequence as a PNA (peptide nucleic acid) have 0 mismatches from each other.

It is also noted that the sequences of the RNAi agents in Tables 1, 2, 3, 4, 5, 6, 7, 8 and/or 9 include sequences which comprise modifications, as detailed in Table 3. For example, one modified variant of the RNAi agent AD-18892 comprises strands of the sequences uGGuGcuGAcuAuccA-GuudTdT (SEQ ID NO: 6132) and AACUGGAuAGUcA-GcACcAdTdT (SEQ ID NO: 660). It is noted that dTdT (2'-deoxy-thymidine-5'-phosphate and 2'-deoxy-thymidine-5'-phosphate), or in some cases, TT or UU, is added as a cap or extension to both 3'-ends, but this cap or extension is not included in the calculation of the total number of mismatches. In addition, the sequence uGGuGcuGAcuAuccA-Guu (SEQ ID NO: 1) comprises modifications from the corresponding portion of the Beta-Catenin gene, or UGGUGCUGACUAUCCAGUU (SEQ ID NO: 4771). In this case, lowercase "c" represents 2'-O-methylcytidine-5'-phosphate, and lowercase "u" represents 2'-O-methyluridine-5'-phosphate. Uppercase "A", "C", "G" and "U" represent the un-modified adenosine-5'-phosphate, cytidine-5'-phosphate, guanosine-5'-phosphate, and uridine-5'-phosphate, respectively. The substitution of modified c for unmodified C does not count as a mismatch in numbering the 0, 1, 2, or 3 mismatches between sequences. This is true of all sequences in Tables 1, 2, 3, 4, 5, 6, 7, 8 and/or 9. Thus, an equal number of mismatches would be calculated (a) between a test sequence and a modified sequence (e.g., that of AD-18892 or any other sequence in Tables 1, 2, 3, 4, 5, 6, 7, 8 and/or 9), and (b) between the same test sequence and the corresponding unmodified sequence from the Beta-Catenin gene (e.g., the portion of the Beta-Catenin gene corresponding to AD-18892 or any other sequence in Table 1), and (c) between a modified sequence and a differently modified sequence which have the same base sequence.

In one particular embodiment, the present disclosure comprises a RNAi agent comprising a anti-sense strand comprising at least 15 or 19 contiguous nucleotides differing by 0, 1, 2, or 3 nt from the sequence of the anti-sense strand of: any of the RNAi agents listed in Tables 1, 2, 3, 4, 5, 6, 7, 8 and/or 9, and modified and unmodified variants thereof.

It is noted that the present disclosure pertains to "modified and unmodified variants" of the disclosed sequences.

An "unmodified variant" (also known as a "generic") of a particular sequence is the corresponding portion of Beta-Catenin without any modifications. For example, a modified variant (or "generic") of AD-18892 comprises a strand of the sequence uGGuGcuGAcuAuccAGuudTdT (SEQ ID NO: 6132); the corresponding "unmodified variant" is the corresponding portion of the wild-type Beta-Catenin sequence without modifications or terminal dTdT, namely, UGGUGCUGACUAUCCAGUU (SEQ ID NO: 6140), as described above. The "unmodified variants" of the sequences of Tables 1, 2, 3, 4, 5, 6, 7, 8 and/or 9 have the identical sequence, without base modifications or terminal dTdT. A given sequence and an "unmodified variant" of it differ by 0 nt (and have no mismatches).

A "modified variant" of a particular sequence comprises one or more (or one or more fewer) modifications to the backbone, sugar, phosphate or base, but do not have any base substitutions (e.g., G for C, or A for G); thus a given sequence and a modified variant thereof differ by 0 nt (and have no mismatches). A modified variant of the sequence of uGGuGcuGAcuAuccAGuu (SEQ ID NO: 1) is, as a non-limiting example, UGGuGcuGAcUAuccAGuu (SEQ ID NO: 6089). As another example, a given sequence [e.g., uGGuGcuGAcuAuccAGuu (SEQ ID NO: 1)] as a RNA and the same sequence as a PNA are modified variants of each other and differ by 0 nt (and have no mismatches). Similarly, the same sequence (with no base substitutions) as a locked nucleic acid (LNA), Morpholino, threose nucleic acid (TNA), or glycol nucleic acid (GNA) or FANA would be a modified variant which has 0 mismatches.

As detailed below, substituting a single nucleotide at a given position with a modified version of the same nucleotide would produce a modified variant (with 0 mismatches).

In another particular embodiment, the RNAi agent comprises a sense strand comprising at least 15 contiguous nucleotides differing by 0, 1, 2, or 3 nt from the sense strand of any of the RNAi agents listed in Tables 1, 2, 3, 4, 5, 6, 7, 8 and/or 9, and modified and unmodified variants thereof.

RNAi agents to Beta-Catenin of the present disclosure can be used in RNA interference.

Modifications of RNAi Agent Sequences

The present disclosure encompasses both unmodified sequences and example modified sequences, such as those disclosed in Tables 1, 2 and 3.

The present disclosure further encompasses any other modification of a disclosed sequence (e.g., a modified variant).

For example, the disclosure encompasses a RNAi agent with a substitution of a single nucleotide at a given position with a modified version of the same nucleotide. Thus a nucleotide (A, G, C or U) can be replaced by the corresponding 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, or 2,6-diaminopurine.

Additional modified variants include the addition of any other moiety (e.g., a radiolabel or other tag or conjugate) to the RNAi agent; provided that the base sequence is identical, the addition of other moieties produces a "modified variant" (with no mismatches).

Various sets of modifications can be used. These include the following formats, which are used in various screens disclosed herein.
A22 a All UA as 2'-OMe-U A and all CA as 2'-OMe-C A
S26 a All U as 2'-OMe-U and all C as 2'-OMe-C
All 3' overhangs as 2'-OMe-U 2'-OMe-U
A25S27
A25 a wt RNA
S27 a wt RNA
All 3' overhangs as 2'-OMe-U 2'-OMe-U
A48S26
A48 a All UA as 2'-OMe-U A and all CA as 2'-OMe-C A, first 5'-N is DNA
S26 a All U as 2'-OMe-U and all C as 2'-OMe-C
All 3' overhangs as 2'-OMe-U 2'-OMe-U
A51S26
A51 a All U as 2'-OMe-U and all C as 2'-OMe-C, except pos. 1, 2 and 14
S26 a All U as 2'-OMe-U and all C as 2'-OMe-C
All 3' overhangs as 2'-OMe-U 2'-OMe-U
A52S36
A52 a 2'-OMe-N at pos. 3, 7, 10 and 13, 2'-MOE-N at pos. 18 and 19
S36 a 2'-OMe-N at pos. 4, 8, 12 and 15, 2'-MOE-N at pos. 1, 2, 18 and 19
All 3' overhangs as 2'-OMe-U 2'-OMe-U
A53S37
A53 a 2'-MOE-N at pos. 3, 7, 10, 13, 18 and 19
S37 a 2'-MOE-N at pos. 1, 2, 4, 8, 12, 15, 18 and 19
All 3' overhangs as 2'-OMe-U 2'-OMe-U
A54S36
A54 a 2'-OMe-N at pos. 3, 7, 10 and 13, 2'-MOE-N at pos. 18 and 19, DNA at pos. 1
S36 a 2'-OMe-N at pos. 4, 8, 12 and 15, 2'-MOE-N at pos. 1, 2, 18 and 19
All 3' overhangs as 2'-OMe-U 2'-OMe-U
A55S36
A55 a 2'-OMe-N at pos. 3, 7, 10 and 13, 2'-MOE-N at pos. 18 and 19,
2'-F-N at pos. 1
S36 a 2'-OMe-N at pos. 4, 8, 12 and 15, 2'-MOE-N at pos. 1, 2, 18 and 19
All 3' overhangs as 2'-OMe-U 2'-OMe-U In addition to these modifications and patterns (e.g, formats) for modifications, other modifications or sets of modifications of the sequences provided can be generated using common knowledge of nucleic acid modification.

RNA Interference

RNA interference (RNAi) is a post-transcriptional, targeted gene-silencing technique that uses double-stranded RNA (dsRNA) to degrade messenger RNA (mRNA) containing the same sequence as the dsRNA. The process of RNAi occurs when ribonuclease III (Dicer) cleaves the longer dsRNA into shorter fragments called siRNAs. siRNAs (small interfering RNAs) produced by Dicer are typically about 21 to 23 nucleotides long and comprise about 19 base pair duplexes (though artificial siRNAs or RNAi agents can be shorter, and/or blunt-ended, and/or comprises one or more endcaps). The smaller RNA segments then mediate the degradation of the target mRNA. Dicer has also been implicated in the excision of 21- and 22-nucleotide small temporal RNAs (stRNAs) from precursor RNA of conserved structure that are implicated in translational control. Hutvagner et al. 2001 Science 293: 834. The RNAi response also features an endonuclease complex, commonly referred to as an RNA-induced silencing complex (RISC), which mediates cleavage of single-stranded mRNA complementary to the anti-sense strand of the RNAi agent. Cleavage of the target RNA takes place in the middle of the region complementary to the anti-sense strand of the siRNA duplex.

In one aspect, an RNA interference agent includes a single-stranded RNA that interacts with a target RNA sequence to direct the cleavage of the target RNA. Without wishing to be bound by theory, long double-stranded RNA introduced into plants and invertebrate cells is broken down into siRNA by a Type III endonuclease known as Dicer. Sharp et al. 2001 Genes Dev. 15:485. Dicer, a ribonuclease-III-like enzyme, processes the dsRNA into 19-23 base pair short interfering RNAs with characteristic two base 3' overhangs. Bernstein et al. 2001 Nature 409:363. The siRNAs are then incorporated into an RNA-induced silencing complex (RISC) where one or more helicases unwind the siRNA duplex, enabling one of the now-unpaired siRNA strands to act as a "guide" strand to guide target recognition. Nykanen et al. 2001 Cell 107:309. Upon binding of the anti-sense guide strand to the appropriate target mRNA, one or more endonucleases within the RISC cleaves the target to induce silencing. Elbashir et al. 2001 Genes Dev. 15:188. Thus, in one aspect the present disclosure relates to a single-stranded RNA that promotes the formation of a RISC complex to effect silencing of the target gene.

RNA interference has also been studied in a variety of systems. Work in *Drosophila* embryonic lysates (Elbashir et al. 2001 EMBO J. 20: 6877 and Tuschl et al. International PCT Publication No. WO 01/75164) has revealed certain requirements for siRNA length, structure, chemical composition, and sequence that are essential to mediate efficient RNAi activity in a variety of systems, including especially mammals. These studies have shown that 21-nucleotide siRNA duplexes are most active when containing 3'-terminal dinucleotide overhangs. Substitution of the 3'-terminal siRNA overhang nucleotides with 2'-deoxy nucleotides (2'-H) was tolerated. In addition, a 5'-phosphate on the target-complementary strand of a siRNA duplex is usually required for siRNA activity. Most importantly for therapeutic uses, siRNA duplexes shorter than 50 bp or so do not activate the interferon response in mammalian cells. See, e.g., Tuschl et al., WO 01/752164.

Others have reported on various RNAi and gene-silencing systems. For example, Churikov et al. International PCT Publication No. WO 01/42443 describe certain methods for modifying genetic characteristics of an organism using certain dsRNAs. Reed et al. International PCT Publication No. WO 01/68836 describe certain methods for gene silencing in plants. Honer et al. International PCT Publication No. WO 01/70944 describe certain methods of drug screening using transgenic nematodes as Parkinson's Disease models using certain dsRNAs. Arndt et al. International PCT Publication No. WO 01/92513 describe certain methods for mediating gene suppression by using factors that enhance RNAi. Tuschl et al. International PCT Publication No. WO 02/44321 describe certain synthetic siRNA constructs. Pachuk et al. International PCT Publication No. WO 00/63364, and Satishchandran et al. International PCT Publication No. WO 01/04313 describe certain methods and compositions for inhibiting the function of certain polynucleotide sequences using certain long (over 250 bp), vector expressed dsRNAs. Kreutzer et al. International PCT Publications Nos. WO 02/055692, WO 02/055693, and EP 1144623 B1 describes certain methods for inhibiting gene expression using dsRNA. Graham et al. International PCT Publications Nos. WO 99/49029 and WO 01/70949, and AU 4037501 describe certain vector expressed siRNA molecules. Fire et al. U.S. Pat. No. 6,506,559 describe certain methods for inhibiting gene expression in vitro using certain long dsRNA (299 bp-1033 bp) constructs that mediate RNAi. Martinez et al. 2002 Cell, 110, 563-574 describe certain single-stranded siRNA constructs, including certain 5'-phosphorylated single-stranded siRNAs that mediate RNA interference in HeLa cells. Harborth et al. 2003 Anti-sense & Nucleic Acid Drug Development 13: 83-105 describe certain chemically and structurally modified siRNA molecules. Chiu and Rana 2003 RNA 9: 1034-1048 describe certain chemically and structurally modified siRNA molecules. Woolf et al. International PCT Publication Nos. WO 03/064626 and WO 03/064625 describe certain chemically modified dsRNA constructs.

Kits for RNAi synthesis are commercially available, e.g., from New England Biolabs and Ambion.

The RNAi agent(s) of the present disclosure target (e.g., bind to, anneal to, etc.) the Beta-Catenin mRNA. The use of the RNAi agent to Beta-Catenin results in a decrease of Beta-Catenin activity, level and/or expression, e.g., a "knock-down" or "knock-out" of the target gene or target sequence. Particularly, in one embodiment, in the case of a disease state characterized by over-expression or hyperactivity or improper cellular compartmentalization of Beta-Catenin, administration of a RNAi agent to Beta-Catenin knocks down the Beta-Catenin target enough to restore a normal level of Beta-Catenin activity.

A suitable RNAi agent can be selected by any process known in the art or conceivable by one of ordinary skill in the art. For example, the selection criteria can include one or more of the following steps: initial analysis of the Beta-Catenin gene sequence and design of RNAi agents; this design can take into consideration sequence similarity across species (human, cynomolgus, mouse, etc.) and dissimilarity to other (non-Beta-Catenin) genes; screening of RNAi agents in vitro (e.g., at 10 nM in HeLa cells); determination of EC50 in HeLa cells; determination of viability of cells treated with RNAi agents, including insensitive cells which do not require Beta-Catenin for survival (e.g., NCI-H28 or RKO), or sensitive cells, which do require Beta-Catenin for survival (e.g., LoVo, DLD-1, LS411N, or SW403); testing with human PBMC (peripheral blood mononuclear cells), e.g., to test levels of TNF-alpha to estimate immunogenicity, wherein immunostimulatory sequences are less desired; testing in human whole blood assay, wherein fresh human blood is treated with an RNAi agent and cytokine/chemokine levels are determined [e.g., TNF-alpha (tumor necrosis factor-alpha) and/or MCP1 (monocyte chemotactic protein 1)], wherein Immunostimulatory sequences are less desired; determination of gene knockdown in vivo using Hep3B subcutaneous tumors in test animals; Beta-Catenin target gene modulation analysis, e.g., using a pharmacodynamic (PD) marker, for example, other components of the Wnt/Beta-Catenin pathway, wherein Beta-Catenin knockdown leads to a dose-dependent reduction of abundance of those components; and optimization of specific modifications of the RNAi agents.

The dsRNA molecules (RNAi agents) described herein are thus useful in RNA interference of the Beta-Catenin gene.

Features of a RNAi Agent: Sense Strand, Anti-Sense Strand and (Optional) Overhangs In various embodiments, the RNAi agents comprise a first strand and a second strand, e.g., a sense strand and an anti-sense strand. Optionally, one or both ends of the duplex contain unpaired nucleotides referred to herein as "overhangs".

The term "anti-sense strand" refers to the strand of a RNAi agent which includes a region that is substantially complementary to a target sequence. As used herein, the term "region of complementarity" refers to the region on the anti-sense strand that is substantially complementary to a sequence, for example a target sequence, as defined herein. Where the region of complementarity is not fully complementary to the target sequence, the mismatches may be in the internal or terminal regions of the molecule. Generally, the most tolerated mismatches are in the terminal regions, e.g., within 5, 4, 3, or 2 nucleotides of the 5' and/or 3' terminus.

The term "sense strand," as used herein, refers to the strand of a RNAi agent that includes a region that is substantially complementary to a region of the anti-sense strand as that term is defined herein.

The sequence of a gene may vary from individual to individual, especially at wobble positions within the coding segment, or in the untranslated region; individuals may also differ from each other in coding sequence, resulting in additional differences in mRNA. The sequence of the sense and anti-sense strands of the RNAi agent can thus be designed to correspond to that of an individual patient, if and where needed. RNAi agents can also be modified in sequence to reduce immunogenicity, binding to undesired mRNAs (e.g., "off-target effects") or to increase stability in the blood. These sequence variants are independent of chemical modification of the bases or 5' or 3' or other end-caps of the RNAi agents. In the case of Beta-Catenin, three human transcripts have been published: NP_001091679.1; NP_001091680.1; and NP_001895.1. Variants between these can be used to design RNAi agents to Beta-Catenin.

The RNAi agents can comprise overhang(s), blunt end(s) and/or endcap(s). The RNAi agents can have overhangs of 0, 1, or 2 overhangs; in the case of 0 nt overhangs, they are blunt-ended. A RNAi agent can have 0, 1 or 2 blunt ends. In a "blunt-ended RNAi agent" both strands terminate in a base-pair; thus a blunt-ended molecule lacks either 3' or 5' single-stranded nucleotide overhangs.

As used herein, the term "overhang" or "nucleotide overhang" refer to at least one unpaired nucleotide that protrudes from end of at least one of the two strands of the duplex structure of a RNAi agent. For example, when a 3'-end of one strand of a dsRNA extends beyond the 5'-end of the other strand, or vice versa, there is an overhang. A dsRNA can comprise an overhang of at least one nucleotide; alternatively the overhang can comprise at least two nucleotides, at least three nucleotides, at least four nucleotides, at least five nucleotides or more. An overhang can comprise or consist of a nucleotide/nucleoside analog, including a deoxynucleotide/nucleoside. The overhang(s) may be on the sense strand, the anti-sense strand or any combination thereof. Furthermore, the nucleotide(s) of an overhang can be present on the 5' end, 3' end or both ends of either an anti-sense or sense strand of a dsRNA.

The RNAi agent can also optionally comprise a cap. The term "Cap" and the like include a chemical moiety attached to the end of a double-stranded nucleotide duplex, but is used herein to exclude a chemical moiety that is a nucleotide or nucleoside. A "3' Cap" is attached at the 3' end of a nucleotide or oligonucleotide and protects the molecule, e.g., from nucleases, such as those in blood serum or intestinal fluid. A useful 3' cap will increase stability (e.g., reduce degradation, for example, by nucleases) and also still allow RNAi activity. Various 3' end caps are as disclosed in, for example, WO 2005/021749 and WO 2007/128477; and U.S. Pat. Nos. 8,084,600 and 8,097,716. A "5' cap" is attached at the 5' end of a nucleotide or oligonucleotide. A cap should not interfere (or unduly interfere) with RNAi activity.

The present disclosure thus contemplates a RNAi agent specific to Beta-Catenin comprising an anti-sense strand. In a more specific embodiment, the present disclosure contemplates a RNAi agent specific to Beta-Catenin comprising a first and a second strand, e.g., a sense strand and an anti-sense strand (which may optionally be contiguous or connected via a linker or loop), or an anti-sense strand and a sense strand (which may optionally be contiguous or connected via a linker or loop), which together comprise a double-stranded or complementary region, and can also optionally comprise one or two overhangs, and/or one or two caps, and/or modifications of the sugar, phosphate or base, and/or additional moieties. The RNAi agent is used to induce RNA interference of the Beta-Catenin gene.

Target and Complementary Sequences

The RNAi agents of the present disclosure target (e.g., specifically bind to, anneal to, etc.) the mRNA encoding the gene Beta-Catenin. The use of the RNAi agent specific to Beta-Catenin results in a decrease of Beta-Catenin activity, level and/or expression and/or cellular distribution/compartmentalization, e.g., a "knock-down" or "knock-out" of the target gene or target sequence. Particularly in one embodiment, in the case of a disease state characterized by over-expression or hyper-activity of Beta-Catenin, administration of a RNAi agent to Beta-Catenin knocks down the Beta-Catenin gene enough to restore a normal level, abundance or cellular distribution of Beta-Catenin activity.

As used herein, "target sequence" or "target gene" refer to a contiguous portion of the nucleotide sequence of an mRNA molecule formed during the transcription of a gene, e.g., a Beta-Catenin gene, including mRNA that is a product of RNA processing of a primary transcription product. The target portion of the sequence will be at least long enough to serve as a substrate for iRNA-directed cleavage at or near that portion. For example, the target sequence will generally be from 9-36 nucleotides (nt) in length, e.g., 15-30 nucleotides in length, including all sub-ranges therebetween. As non-limiting examples, the target sequence can be from 15-30 nucleotides, 15-26 nucleotides, 15-23 nucleotides, 15-22 nucleotides, 15-21 nucleotides, 15-20 nucleotides, 15-19 nucleotides, 15-18 nucleotides, 15-17 nucleotides, 18-30 nucleotides, 18-26 nucleotides, 18-23 nucleotides, 18-22 nucleotides, 18-21 nucleotides, 18-20 nucleotides, 19-30 nucleotides, 19-26 nucleotides, 19-23 nucleotides, 19-22 nucleotides, 19-21 nucleotides, 19-20 nucleotides, 19 nucleotides, 20-30 nucleotides, 20-26 nucleotides, 20-25 nucleotides, 20-24 nucleotides, 20-23 nucleotides, 20-22 nucleotides, 20-21 nucleotides, 20 nucleotides, 21-30 nucleotides, 21-26 nucleotides, 21-25 nucleotides, 21-24 nucleotides, 21-23 nucleotides, or 21-22 nucleotides, 21 nucleotides, 22 nucleotides, or 23 nucleotides. The sense and anti-sense strands of the RNAi comprise a sequence complementary to that of the target nucleic acid, Beta-Catenin.

As used herein, the term "strand comprising a sequence" refers to an oligonucleotide comprising a chain of nucleotides that is described by the sequence referred to using the standard nucleotide nomenclature.

As used herein, and unless otherwise indicated, the term "complementary" refers to the ability of an oligonucleotide or polynucleotide comprising a first nucleotide sequence to hybridize and form a duplex structure under certain conditions with an oligonucleotide or polynucleotide comprising a second nucleotide sequence. Such conditions can, for example, be stringent, e.g., 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

Complementary sequences within a RNAi agent, e.g., within a dsRNA as described herein, include base-paired oligonucleotides or polynucleotides comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they may form one or more, but generally not more than 5, 4, 3 or 2 mismatched base pairs upon hybridization for a duplex up to 30 base pairs, while retaining the ability to hybridize under the conditions most relevant to their ultimate application, e g, inhibition of gene expression via a RISC pathway. However, where two oligonucleotides are designed to form, upon hybridization, one or more single-stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein. The term "overhang" describes an unpaired nucleotide at the 3' or 5' end of a double-stranded nucleotide duplex, as described above. In one embodiment, the overhang is 1 to 4 nt long and is on the 3' end.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but are not limited to, G:U Wobble or Hoogstein base pairing.

The terms "complementary," "fully complementary" and "substantially complementary" herein may furthermore be used with respect to the base matching between the sense strand and the anti-sense strand of a dsRNA, or between the anti-sense strand of a RNAi agent and a target sequence, as will be understood from the context of their use. The RNAi agent of the present disclosure can comprise a sequence which is complementary to the sequence of a target sequence (DNA) which is disclosed herein. For example, if the target sequence disclosed is DNA, the RNAi agent can comprise a strand which is complementary to it (anti-parallel and having a sequence of bases which hydrogen bonds to the sequence of the target) and which is, for example, RNA, or RNA with a small number of DNA substitutions, or an alternative backbone such as FANA, PNA, GNA, TNA, boranophosphate or LNA, or RNA with a small number of substitutions which are FANA, PNA, GNA, TNA, boranophosphate or LNA, etc.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding Beta-Catenin). For example, a polynucleotide is complementary to at least a part of a Beta-Catenin mRNA if the sequence is substantially complementary to a non-interrupted portion of an mRNA encoding Beta-Catenin.

Thus, the RNAi agent of the present disclosure is complimentary or substantially complimentary to a target sequence in the mRNA corresponding to the target gene Beta-Catenin and is double-stranded, comprising a sense and an anti-sense strand (which can be contiguous, linked via a loop, or otherwise joined), where the double-stranded region an be 9 to 36 bp long (particularly for example, 19 to 22 or 19 to 23 bp long), and can furthermore optionally comprise a 3' or 5' overhang, and the RNAi agent can furthermore comprise a 3' cap. The RNAi agent mediates RNA interference, down-regulating or inhibiting the level, expression and/or activity of Beta-Catenin, and/or establishing or re-establishing an approximately normal level of Beta-Catenin and/or Beta-Catenin activity, or other biological function related to Beta-Catenin.

Double-Stranded RNA

The term "double-stranded RNA" or "dsRNA," as used herein, refers to an RNAi agent comprising a first and a second strand; e.g., a composition that includes an RNA molecule or complex of molecules having a hybridized duplex region that comprises two anti-parallel and substantially complementary nucleic acid strands, which will be referred to as having "sense" and "antisense" orientations with respect to a target RNA. The antisense strand, with respect to the mRNA target, is also called the "guide" strand, and the sense strand is also called the "passenger" strand. The passenger strand can include at least one or more of the following: one or more extra nucleotides (e.g., a bulge or 1 nt loop) compared to the other strand, a nick, a gap, etc., compared to the other strand. In various embodiments, the first strand is the sense strand and the second strand is the anti-sense strand. In other embodiments, the first strand is the anti-sense strand, and the second strand is the sense strand.

The duplex region can be of any length that permits specific degradation of a desired target RNA through a RISC pathway, but will typically range from 9 to 36 base pairs ("bp") in length, e.g., 15-30 base pairs in length. Considering a duplex between 9 and 36 base pairs, the duplex can be any length in this range, for example, 9, 10, 11, 12, 13, 14, 15, 16, 17, 18, 19, 20, 21, 22, 23, 24, 25, 26, 27, 28, 29, 30, 31, 32, 33, 34, 35, or 36 bp and any sub-range therebetween, including, but not limited to 15-30 base pairs, 15-26 bp, 15-23 bp, 15-22 bp, 15-21 bp, 15-20 bp, 15-19 bp, 15-18 bp, 15-17 bp, 18-30 bp, 18-26 bp, 18-23 bp, 18-22 bp, 18-21 bp, 18-20 bp, 19-30 bp, 19-26 bp, 19-23 bp, 19-22 bp, 19-21 bp, 19-20 bp, 19 bp, 20-30 bp, 20-26 bp, 20-25 bp, 20-24 bp, 20-23 bp, 20-22 bp, 20-21 bp, 20 bp, 21-30 bp, 21-26 bp, 21-25 bp, 21-24 bp, 21-23 bp, 21-22 bp, 21 bp, 22 bp, or 23 bp. The dsRNAs generated in the cell by processing with Dicer and similar enzymes are generally in the range of about 19 to about 22 base pairs in length. One strand of the duplex region of a dsRNA comprises a sequence that is substantially complementary to a region of a target RNA. The two strands forming the duplex structure can be from a single RNA molecule having at least one self-complementary duplex region, or can be formed from two or more separate RNA molecules that hybridize to form the duplex. Where the duplex region is formed from two self-complementary regions of a single molecule, the molecule can have a duplex region separated by a single stranded chain of nucleotides (herein referred to as a "hairpin loop", e.g., such as found in an shRNA construct) between the 3'-end of one strand and the 5'-end of the respective other strand forming the duplex structure. The hairpin loop can comprise at least one unpaired nucleotide; in some embodiments the hairpin loop can comprise at least 3, at least 4, at least 5, at least 6, at least 7, at least 8, at least 9, at least 10, at least 20, at least 23 or more unpaired nucleotides. Where the two substantially complementary strands of a dsRNA are comprised by separate RNA molecules, those molecules need not, but can be covalently connected. Where the two strands are connected covalently by a hairpin loop, the construct is generally referred to herein and in the art as a "shRNA". Where the two strands are connected covalently by means other than a hairpin loop, the connecting structure is referred to as a "linker." The term "siRNA" is also used herein to refer to a dsRNA as described above.

RNAi Agents Lowering or Normalizing Beta-Catenin Level, Expression, Cellular Distribution, and/or Activity Example RNAi agents for targeting Beta-Catenin include those which bind to a mRNA corresponding to the Beta-Catenin gene provided herein. Example RNAi agents to Beta-Catenin are provided in Tables 1, 2, 3, 4, 5, 6, 7, 8 and/or 9.

Any method known in the art can be use to measure changes in Beta-Catenin activity, level, cellular distribution (e.g., localization to the membrane but not the cytoplasm or nucleus) and/or expression induced by a Beta-Catenin RNAi agent. Measurements can be performed at multiple timepoints, prior to, during and after administration of the RNAi agent, to determine the effect of the RNAi agent.

The RNAi agents of the present disclosure silence, inhibit the expression of, down-regulate the expression of, and/or suppress the expression of the Beta-Catenin gene, such that an approximately normal level of Beta-Catenin activity, expression and/or level and/or distribution in various cellular compartments is achieved.

In addition, in various embodiments, depending on the disease condition and biological context, it is acceptable to use the RNAi agents of the present disclosure to establish a level of Beta-Catenin expression, activity and/or level which is below the normal level, or above the normal level.

Types of RNAi Agents and Modification Thereof

The use of RNAi agents or compositions comprising an anti-sense nucleic acid to down-modulate the expression of a particular protein in a cell is well known in the art. A RNAi agent comprises a sequence complementary to, and is capable of hydrogen binding to, the coding strand of another nucleic acid (e.g., an mRNA). Thus, in various embodiments, the RNAi agents of the present disclosure encompass any RNAi agents which target (e.g., are complementary to, capable of specific hydrogen binding to, etc.) any sequences presented herein, e.g., in Tables 1, 2, 3, 4, 5, 6, 7, 8 and/or 9.

Anti-sense sequences complementary to an mRNA can be complementary to the coding region, the 5' or 3' untranslated region of the mRNA, and/or a region bridging the coding and untranslated regions, and/or portions thereof. Furthermore, a RNAi agent can be complementary to a regulatory region of the gene encoding the mRNA, for instance a transcription or translation initiation sequence or regulatory element. Particularly, a RNAi agent or any portion thereof can be complementary to a region preceding or spanning the initiation codon on the coding strand or in the 3' untranslated region of an mRNA.

RNAi agent molecules can be designed according to the rules of Watson and Crick base pairing. The RNAi agent can be complementary to the entire coding region of Beta-Catenin mRNA, but more particularly is an oligonucleotide which is anti-sense to only a portion of the coding or non-coding region of Beta-Catenin mRNA. For example, the anti-sense oligonucleotide can be complementary to the region surrounding the translation start site of Beta-Catenin mRNA. An anti-sense oligonucleotide can be, for example, about 5, 10, 15, 19, 20, 21, 22, 23, 24, 25, 30, 35, 40, 45 or 50 nucleotides in length.

RNAi agent may have modifications internally, and/or at one or both ends. The modifications at the ends can help stabilize the RNAi agent, protecting it from degradation by nucleases in the blood.

The RNAi agents can also optionally be designed to anneal to known or predicted exposed and/or single-stranded regions of the mRNA (e.g., loops).

A RNAi agent can be constructed using chemical synthesis and enzymatic ligation reactions using procedures known in the art. For example, a RNAi agent can be chemically synthesized using naturally-occurring nucleotides or variously modified nucleotides designed to decrease off-target effects, and/or increase the biological stability of the molecules or to increase the physical stability of the duplex formed between the anti-sense and sense nucleic acids, e.g., phosphorothioate derivatives and acridine substituted nucleotides can be used.

"G," "C," "A," "T" and "U" each generally stand for a nucleotide that contains guanine, cytosine, adenine, thymidine and uracil as a base, respectively. However, the term "ribonucleotide" or "nucleotide" can also refer to a modified nucleotide or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of dsRNA featured in the present disclosure by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the present disclosure.

The skilled artisan will recognize that the term "RNA molecule" or "ribonucleic acid molecule" encompasses not only RNA molecules as expressed or found in nature (i.e., are naturally occurring), but also non-naturally-occurring analogs and derivatives of RNA comprising one or more ribonucleotide/ribonucleoside analogs or derivatives as described herein or as known in the art. Strictly speaking, a "ribonucleoside" includes a nucleoside base and a ribose sugar, and a "ribonucleotide" is a ribonucleoside with one, two or three phosphate moieties. However, the terms "ribonucleoside" and "ribonucleotide" can be considered to be equivalent as used herein. The RNA can be modified in the nucleobase structure or in the ribose-phosphate backbone structure, e.g., as described herein below. However, the molecules comprising ribonucleoside analogs or derivatives must retain the ability to form a duplex. As non-limiting examples, an RNA molecule can also include at least one modified ribonucleoside, including but not limited to a 2'-O-methyl modified nucleotide, a nucleoside comprising a 5' phosphorothioate group, a terminal nucleoside linked to a cholesteryl derivative or dodecanoic acid bisdecylamide group, a locked nucleoside, an abasic nucleoside, a 2'-deoxy-2'-fluoro modified nucleoside, a 2'-amino-modified nucleoside, 2'-alkyl-modified nucleoside, morpholino nucleoside, an unlocked ribonucleotide (e.g., an acyclic nucleotide monomer, as described in WO 2008/147824), a phosphoramidate or a non-natural base comprising nucleoside, or any combination thereof. Alternatively, an RNA molecule can comprise at least two modified ribonucleosides, at least 3, at least 4, at least 5, at least 6, at least 7, at least 8, at least 9, at least 10, at least 15, at least 20 or more, up to the entire length of the dsRNA molecule. The modifications need not be the same for each of such a plurality of modified ribonucleosides in an RNA molecule. In one embodiment, modified RNAs contemplated for use in methods and compositions described herein are peptide nucleic acids (PNAs) that have the ability to form the required duplex structure and that permit or mediate the specific degradation of a target RNA via a RISC pathway. In some cases, a RNA molecule can include a terminal dinucleotide (e.g., TT) which is DNA, and/or a small number of internal (e.g., base-pairing) DNA bases (e.g., fewer than the number of RNA bases), for example, a T substituting a U.

Examples of modified nucleotides which can be used to generate the RNAi agent include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

A "modified variant" of a sequence disclosed herein includes any variant comprising the same sequence, but with a modification in the base, sugar, phosphate or backbone (but not a base substitution, e.g., A for G, or C for U). Thus, a modified variant can comprise any modified nucleotide described above (e.g., 5-fluorouracil, 5-bromouracil, 5-chlorouracil, 5-iodouracil, hypoxanthine, xantine, 4-acetylcytosine, 5-(carboxyhydroxylmethyl) uracil, etc.). When a base is replaced by a corresponding modified base (e.g., A for modified A), these modified nucleotides do not constitute a mismatch or base difference. Thus a given sequence with a U at a particular position and a modified variant comprising a 5-fluorouracil, 5-bromouracil, 5-chlorouracil, or 5-iodouracil at the same sequence would differ by 0 nt (or have no mismatches); however, a given sequence with a C at a particular position and a different sequence with a 5-fluorouracil (wherein the two sequences are otherwise identical) would differ by 1 nt (1 mismatch).

In one embodiment, the present disclosure encompasses any modified variant of any RNAi agent disclosed herein. The modified variant contains the same sequence, but can be modified to contain modifications in the phosphate, sugar, base, nucleotide, etc. For example, the modified variant can contain one or more of the modified nucleotides listed herein, for example a C replaced by a 2'-modified C (such sequences would differ by 0 mismatches).

In one aspect, a modified ribonucleoside includes a deoxyribonucleoside. In such an instance, a RNAi agent can comprise one or more deoxynucleosides, including, for example, a deoxynucleoside overhang(s), or one or more deoxynucleosides within the double-stranded portion of a dsRNA. However, it is self-evident that under no circumstances is a double-stranded DNA molecule encompassed by the term "RNAi agent."

Replacing the 3'-terminal nucleotide overhanging segments of a 21-mer RNAi agent duplex having two-nucleotide 3'-overhangs with deoxyribonucleotides does not have an adverse effect on RNAi activity. Replacing up to four nucleotides on each end of the RNAi agent with deoxyribonucleotides has been well tolerated, whereas complete substitution with deoxyribonucleotides results in no RNAi activity. International PCT Publication No. WO 00/44914, and Beach et al. International PCT Publication No. WO 01/68836 preliminarily suggest that siRNA may include modifications to either the phosphate-sugar backbone or the nucleoside to include at least one of a nitrogen or sulfur heteroatom. Kreutzer et al. Canadian Patent Application No. 2,359,180, also describe certain chemical modifications for use in dsRNA constructs in order to counteract activation of double-stranded RNA-dependent protein kinase PKR, specifically 2'-amino or 2'-O-methyl nucleotides, and nucleotides containing a 2'-O or 4'-C methylene bridge. Additional 3'-terminal nucleotide overhangs include dT (deoxythimidine), 2'-O,4'-C-ethylene thymidine (eT), and 2-hydroxyethyl phosphate (hp).

Parrish et al. 2000 Molecular Cell 6: 1077-1087 tested certain chemical modifications targeting the unc-22 gene in *C. elegans* using long (>25 nt) siRNA transcripts. The authors describe the introduction of thiophosphate residues into these siRNA transcripts by incorporating thiophosphate nucleotide analogs with T7 and T3 RNA polymerase and observed that RNAs with two phosphorothioate modified bases also had substantial decreases in effectiveness as RNAi. Further, Parrish et al. reported that phosphorothioate modification of more than two residues greatly destabilized the RNAs in vitro such that interference activities could not be assayed. Id. at 1081. The authors also tested certain modifications at the 2'-position of the nucleotide sugar in the long siRNA transcripts and found that substituting deoxynucleotides for ribonucleotides produced a substantial decrease in interference activity, especially in the case of Uridine to Thymidine and/or Cytidine to deoxy-Cytidine substitutions. Id. In addition, the authors tested certain base modifications, including substituting, in sense and anti-sense strands of the siRNA, 4-thiouracil, 5-bromouracil, 5-iodouracil, and 3-(aminoallyl) uracil for uracil, and inosine for guanosine. Whereas 4-thiouracil and 5-bromouracil substitution appeared to be tolerated, Parrish reported that inosine produced a substantial decrease in interference activity when incorporated in either strand. Parrish also reported that incorporation of 5-iodouracil and 3-(aminoallyl) uracil in the anti-sense strand resulted in a substantial decrease in RNAi activity as well.

Those skilled in the art will appreciate that it is possible to synthesize and modify the siRNA as desired, using any conventional method known in the art (see Henschel et al. 2004 DEQOR: a web-based tool for the design and quality control of siRNAs. Nucleic Acids Research 32 (Web Server Issue): W113-W120). Further, it will be apparent to those skilled in the art that there are a variety of regulatory sequences (for example, constitutive or inducible promoters, tissue-specific promoters or functional fragments thereof, etc.) which are useful for the anti-sense oligonucleotide, siRNA, or shRNA expression construct/vector.

There are several examples in the art describing sugar, base, phosphate and backbone modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-flouro, 2'-O-methyl, 2'-O-allyl, 2'-H, nucleotide base modifications (for a review see Usman and Cedergren 1992 TIBS. 17: 34; Usman et al. 1994 Nucleic Acids Symp. Ser. 31: 163; Burgin et al. 1996 Biochemistry 35: 14090). Sugar modification of nucleic acid molecules are extensively described in the art.

Additional modifications and conjugations of RNAi agents have been described. Soutschek et al. 2004 Nature 432: 173-178 presented conjugation of cholesterol to the 3'-end of the sense strand of a RNAi agent by means of a pyrrolidine linker, thereby generating a covalent and irreversible conjugate. Chemical modifications (including conjugation with other molecules) of siRNA may also be made to improve the in vivo pharmacokinetic retention time and efficiency.

In various embodiments of the present disclosure, the RNAi agent to Beta-Catenin comprises at least one 5'-uridine-adenine-3' (5'-ua-3') dinucleotide, wherein the uridine is a 2'-modified nucleotide; at least one 5'-uridine-guanine-3' (5'-ug-3') dinucleotide, wherein the 5'-uridine is a 2'-modified nucleotide; at least one 5'-cytidine-adenine-3' (5'-ca-3') dinucleotide, wherein the 5'-cytidine is a 2'-modified nucleotide; and/or at least one 5'-uridine-uridine-3' (5'-uu-3') dinucleotide, wherein the 5'-uridine is a 2'-modified nucleotide.

In various embodiments of the present disclosure, the RNAi agent comprises a 2'-modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA).

In another embodiment, the RNAi comprises a gap or missing base. For example, the phosphate-sugar backbone may be present, but the base missing.

In another embodiment, the RNAi agent has a single-stranded nick (e.g., a break or missing bond in the backbone). In various embodiments, a single-stranded nick can be in either the sense or anti-sense strand, or both.

This nick can be, for example, in the sense strand, producing a small internally segmented interfering RNA, or sisiRNA, which may have less off-target effects than the corresponding RNAi agent without a nick.

The anti-sense nucleic acid or RNAi agent can also have an alternative backbone such as locked nucleic acid (LNA), Morpholino, peptidic nucleic acid (PNA), threose nucleic acid (TNA), or glycol nucleic acid (GNA), FANA, boranophosphate RNA, or be primarily RNA with a few nucleotides which are substituted by DNA, LNA, PNA, TNA, GNA, FANA, boranophosphate, or the like, and/or it can be labeled (e.g., radiolabeled or otherwise tagged).

One or both strands can comprise an alternative backbone

In yet another embodiment, the RNAi agent employed by the methods of the present disclosure can include an α-anomeric nucleic acid molecule. An α-anomeric nucleic acid molecule forms specific double-stranded hybrids with complementary RNA in which, contrary to the usual (3-units, the strands run parallel to each other. Gaultier et al. 1987 Nucleic Acids. Res. 15: 6625-6641. The RNAi agent can also comprise a 2'-o-methylribonucleotide (Inoue et al. 1987 Nucleic Acids Res. 15: 6131-6148) or a chimeric RNA-DNA analogue (Inoue et al. 1987 FEBS Lett. 215: 327-330).

Alternatively, gene expression can be inhibited by targeting nucleotide sequences complementary to the regulatory region of Beta-Catenin (e.g., the promoter and/or enhancers) to form triple helical structures that prevent transcription of the Beta-Catenin gene. See generally, Helene 1991 Anticancer Drug Des. 6(6): 569-84; Helene et al. 1992 Ann N.Y. Acad. Sci. 660: 27-36; and Maher 1992, Bioassays 14(12): 807-15.

Production of RNAi Agents

The RNAi agent can be produced biologically within a cell using an expression vector into which a nucleic acid has been subcloned in an anti-sense orientation (i.e., RNA transcribed from the inserted nucleic acid will be in an anti-sense orientation to a target nucleic acid of interest). The RNAi agent can also be produced biologically using an expression vector into which a nucleic acid has been subcloned as an shRNA construct (eg., RNA transcribed from the inserted nucleic acid will have a first region in an anti-sense orientation to a target nucleic acid of interest, a second region that comprises a loop or hinge, and a third region in a sense orientation to the target nucleic acid of interest, wherein the first and third regions of the transcript preferably hydribize to each other, thereby forming a stem-and-loop structure.

Methods of producing RNAi agents are well-known in the art and available to persons of ordinary skill in the art.

Kits for synthesis of RNAi are commercially available from, e.g., New England Biolabs and Ambion.

Delivery of RNAi Agents

RNAi agents of the present disclosure can be delivered or introduced (e.g., to a cell in vitro, to a test animal, or to a human) by any means known in the art.

The RNAi agents of the present disclosure are typically administered to a subject or generated in situ such that they hybridize with cellular mRNA and/or genomic DNA encoding Beta-Catenin, and inhibit expression by inhibiting transcription and/or translation. An example of a route of administration of RNAi agents includes direct injection at a tissue site. Alternatively, RNAi agents can be modified to target selected cells and then administered systemically. For example, for systemic administration, anti-sense molecules can be modified such that they specifically bind to receptors or antigens expressed on a selected cell surface, e.g., by linking the anti-sense nucleic acid molecules to peptides or antibodies which bind to cell surface receptors or antigens. The anti-sense nucleic acid molecules can also be delivered to cells using vectors well known in the art and described in, for example, US20070111230. To achieve sufficient intracellular concentrations of the anti-sense molecules, vector constructs in which the anti-sense nucleic acid molecule is placed under the control of a strong pol II or pol III promoter are preferred.

"Introducing into a cell," when referring to a RNAi agent, means facilitating or effecting uptake or absorption into the cell, as is understood by those skilled in the art. Absorption or uptake of a RNAi agent can occur through unaided diffusive or active cellular processes, or by auxiliary agents or devices. The meaning of this term is not limited to cells in vitro; a RNAi agent may also be "introduced into a cell," wherein the cell is part of a living organism. In such an instance, introduction into the cell will include the delivery to the organism. For example, for in vivo delivery, a RNAi agent can be injected into a tissue site or administered systemically. In vivo delivery can also be by a beta-glucan delivery system, such as those described in U.S. Pat. Nos. 5,032,401 and 5,607,677, and U.S. Publication No. 2005/0281781. In vitro introduction into a cell includes methods known in the art such as electroporation and lipofection. Further approaches are described herein below or known in the art.

Delivery of RNAi agent to tissue is a problem both because the material must reach the target organ and must also enter the cytoplasm of target cells. RNA cannot penetrate cellular membranes, so systemic delivery of naked RNAi agent is unlikely to be successful. RNA is quickly degraded by RNAse activity in serum. For these reasons, other mechanisms to deliver RNAi agent to target cells has been devised. Methods known in the art include but are not limited to: viral delivery (retrovirus, adenovirus, lentivirus, baculovirus, AAV); liposomes (Lipofectamine, cationic DOTAP, neutral DOPC) or nanoparticles (cationic polymer, PEI), bacterial delivery (tkRNAi), electroporation, and also chemical modification (LNA) of siRNA to improve stability. Xia et al. 2002 Nat. Biotechnol. 20 and Devroe et al. 2002. BMC Biotechnol. 2 1: 15, disclose incorporation of siRNA into a viral vector. Porphysomes can also be used to deliver RNAi agents. Lovell et al. 2001 Nature Mater. 10: 324-32; and WO 2011/044671. Other systems for delivery of RNAi agents are contemplated and the RNAi agents of the present disclosure can be delivered by various methods yet to be found and/or approved by the FDA or other regulatory authorities. RNAi agents of the present disclosure can delivered in a suitable pharmaceutical composition. Several of these are described in greater detail, below.

Pharmaceutical Compositions of RNAi Agents

As used here, a "pharmaceutical composition" comprises a pharmaceutically effective amount of one or more Beta-Catenin RNAi agent, a pharmaceutically acceptable carrier, and, optionally, an additional disease treatment which works synergistically with the RNAi agent. The additional disease treatment can be additional RNAi agent(s) to Beta-Catenin, and/or additional RNAi agent(s) to another gene. As used herein, "pharmacologically effective amount," "therapeutically effective amount" or simply "effective amount" refers to that amount of a RNAi agent effective to produce the intended pharmacological, therapeutic or preventive result. For example, if a given clinical treatment is considered effective when there is at least a 10% reduction in a measurable parameter associated with a disease or disorder, a therapeutically effective amount of a drug for the treatment of that disease or disorder is the amount necessary to effect at least a 10% reduction in that parameter. In this embodiment, a therapeutically effective amount of a RNAi agent targeting Beta-Catenin can reduce Beta-Catenin protein levels by at least 10%. In additional embodiments, a given clinical treatment is considered effective where there is at least a 15, 20, 25, 30, 35, 40, 45, 50, 55, 60, 65, 70, 75, 80, 85, 90, or 95% reduction in a measurable parameter associated with a disease or disorder, and the therapeutically effective amount of a drug for the treatment of that disease or disorder is the amount necessary to effect at least a 15, 20, 25, 30, 35, 40, 45, 50, 55, 60, 65, 70, 75, 80, 85, 90, or 95% reduction, respectively, in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. Agents included in drug formulations are described further herein.

The pharmaceutical compositions comprising a Beta-Catenin RNAi agent can be in solid form, for example, powders, granules, tablets, pills, gelcaps, gelatin capsules, liposomes, suppositories, chewable forms, or patches. The pharmaceutical compositions comprising a Beta-Catenin RNAi agent can also be presented in liquid form, for example, solutions, emulsions, suspensions, elixirs, or syrups. Appropriate liquid supports can be, for example, water, organic solvents such as polyol, such as glycerol or glycols, including propylene glycol and polyethylene glycol, or ethanol, Cremophor EL, or mixtures thereof, in varying proportions, in water. The compositions can comprise nano-sized amorphous or crystalline granules coated with albumin or a surfactant.

Appropriate supports can include, for example, antibacterial and antifungal agents, buffering agents, calcium phosphate, cellulose, methyl cellulose, chlorobutanol, cocoa butter, colorings, dextrin, emulsifiers, enteric coatings, flavorings, gelatin, isotonic agents, lecithin, magnesium stearate, perfuming agents, polyalcohols such as mannitol, injectable organic esters such as ethyl oleate, paraben, phenol sorbic acid, polyethylene glycol, polyvinylpyrrolidine, phosphate buffered saline (PBS), preserving agents, propylene glycol, sodium carboxymethylcellulose, sodium chloride, sorbitol, various sugars (including, but not limited to, sucrose, fructose, galactose, lactose and trehalose), starch, suppository wax, talc, vegetable oils, such as olive oil and corn oil, vitamins, wax, and/or wetting agents. For Beta-Catenin RNAi agents, a preferred support comprises dextran and water, e.g. 5% dextrose in water (D5W).

The biologically inert portion of the pharmaceutical composition can optionally be erodible, allowing timed release of the RNAi agent.

The pharmaceutical composition can comprise additional components which aid in delivery, stability, efficacy, or reduction of immunogenicity.

Additional Components of a Pharmaceutical Composition Comprising a RNAi Agent to Beta-Catenin Additional components of a pharmaceutical composition comprising a RNAi Agent to Beta-Catenin can be added to aid in delivery, stability, efficacy, or reduction of immunogenicity.

Liposomes have been used previously for drug delivery (e.g., delivery of a chemotherapeutic). Liposomes (e.g., cationic liposomes) are described in PCT publications WO02/100435A1, WO03/015757A1, and WO04029213A2; U.S. Pat. Nos. 5,962,016; 5,030,453; and 6,680,068; and U.S. Patent Application 2004/0208921. A process of making liposomes is also described in WO04/002453A1. Furthermore, neutral lipids have been incorporated into cationic liposomes (e.g., Farhood et al. 1995).

Cationic liposomes have been used to deliver RNAi agent to various cell types (Sioud and Sorensen 2003; U.S. Patent Application 2004/0204377; Duxbury et al., 2004; Donze and Picard, 2002).

Use of neutral liposomes disclosed in Miller et al. 1998, and U.S. Patent Application 2003/0012812.

As used herein, the term "SNALP" refers to a stable nucleic acid-lipid particle. A SNALP represents a vesicle of lipids coating a reduced aqueous interior comprising a nucleic acid such as an iRNA or a plasmid from which an iRNA is transcribed. SNALPs are described, e.g., in U.S. Patent Application Publication Nos. 20060240093, 20070135372, and in International Application No. WO 2009082817.

Chemical transfection using lipid-based, amine-based and polymer-based techniques, is disclosed in products from Ambion Inc., Austin, Tex.; and Novagen, EMD Biosciences, Inc, an Affiliate of Merck KGaA, Darmstadt, Germany); Ovcharenko D (2003) "Efficient delivery of siRNAs to human primary cells." Ambion TechNotes 10 (5): 15-16). Additionally, Song et al. (Nat Med. published online (Fete 1 0, 2003) doi: 10.1038/nm828) and others [Caplen et al. 2001 Proc. Natl. Acad. Sci. (USA), 98: 9742-9747; and McCaffrey et al. Nature 414: 34-39] disclose that liver cells can be efficiently transfected by injection of the siRNA into a mammal's circulatory system.

A variety of molecules have been used for cell-specific RNAi agent delivery. For example, the nucleic acid-condensing property of protamine has been combined with specific antibodies to deliver siRNAs. Song et al. 2005 Nat Biotech. 23: 709-717. The self-assembly PEGylated polycation polyethylenimine (PEI) has also been used to condense and protect siRNAs. Schiffelers et al. 2004 Nucl. Acids Res. 32: e149, 141-1 10.

The siRNA-containing nanoparticles were then successfully delivered to integrin-overexpressing tumor neovasculature. Hu-Lieskovan et al. 2005 Cancer Res. 65: 8984-8992.

The RNAi agents of the present disclosure can be delivered via, for example, Lipid nanoparticles (LNP); neutral liposomes (NL); polymer nanoparticles; double-stranded RNA binding motifs (dsRBMs); or via modification of the RNAi agent (e.g., covalent attachment to the dsRNA).

Lipid nanoparticles (LNP) are self-assembling cationic lipid based systems. These can comprise, for example, a neutral lipid (the liposome base); a cationic lipid (for siRNA loading); cholesterol (for stabilizing the liposomes); and PEG-lipid (for stabilizing the formulation, charge shielding and extended circulation in the bloodstream).

The cationic lipid can comprise, for example, a headgroup, a linker, a tail and a cholesterol tail. The LNP can have, for example, good tumor delivery, extended circulation in the blood, small particles (e.g., less than 100 nm), and stability in the tumor microenvironment (which has low pH and is hypoxic).

Neutral liposomes (NL) are non-cationic lipid based particles.

Polymer nanoparticles are self-assembling polymer-based particles.

Double-stranded RNA binding motifs (dsRBMs) are self-assembling RNA binding proteins, which will need modifications.

In various embodiments of the present disclosure, the RNAi agent to Beta-Catenin is ligated to one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized litho-cholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and transferrin.

The RNAi agents of the present disclosure can be prepared in a pharmaceutical composition comprising various components appropriate for the particular method of administration of the RNAi agent.

Administration of a Pharmaceutical Composition Comprising a RNAi Agent

The pharmaceutical composition comprising a Beta-Catenin can be administered by buccal, inhalation (including insufflation and deep inhalation), nasal, oral, parenteral, implant, injection or infusion via epidural, intra-arterial, intra-articular, intra-capsular, intra-cardiac, intra-cerebroventricular, intracranial, intradermal, intramuscular, intra-orbital, ocular, intraperitoneal, intra-spinal, intrasternal, intrathecal, intravenous, subarachnoid, sub-capsular, subcutaneous, sub-cuticular, transendothelial, transtracheal, transvascular, rectal, sublingual, topical, and/or vaginal routes. This may be by injection, infusion, dermal patch, or any other method known in the art. The formulation can be powdered, nebulized, aerosolized, granulized or otherwise appropriately prepared for delivery. The administration, if liquid, may be slow or via bolus, though, under some circumstances known in the art, bolus injections may lead to loss of material through the kidneys.

The pharmaceutical compositions comprising a Beta-Catenin RNAi agent can be administered with medical devices known in the art. For example, in a particular embodiment, a RNAi agent can be administered with a needle-less hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present disclosure include: U.S. Pat. No. 4,487,603, which discloses an implantable micro-infusion pump for dispensing medication at a controlled rate; U.S. Pat. No. 4,486,194, which discloses a therapeutic device for administering medications through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the pharmaceutical compositions comprising a RNAi agent can be formulated to ensure proper distribution in vivo. Administration of a RNAi agent to Beta-Catenin can be systemic (whole-body) or, particularly, targeted to tissues or organs that express (or over-express or demonstrate a hyper-activity of) Beta-Catenin. Methods for targeting these particular tissues or organs are described herein, and/or are known in the art. For example, they can be formulated in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29: 685).

Example targeting moieties include folate or biotin (see, e.g., U.S. Pat. No. 5,416,016 to Low et al.); mannosides (Umezawa et al., (1988) Biochem. Biophys. Res. Commun. 153: 1038); antibodies (P. G. Bloeman et al. (1995) FEBS Lett. 357: 140; M. Owais et al. (1995) Antimicrob. Agents Chemother. 39: 180); surfactant protein A receptor (Briscoe et al. (1995) Am. J. Physiol. 1233: 134), different species of which may comprise the formulations of the present disclosures, as well as components of the invented molecules; p120 (Schreier et al. (1994) J. Biol. Chem. 269: 9090); see also K. Keinanen; M. L. Laukkanen (1994) FEBS Lett. 346: 123; J. J. Killion; I. J. Fidler (1994) Immunomethods 4: 273.

The present disclosure thus encompasses pharmaceutical compositions comprising one or more RNAi agents to Beta-Catenin, which can optionally comprise various modifications and/or additional components, for use in treatment of Beta-Catenin-related diseases.

Measuring the Effect of a RNAi Agent on Beta-Catenin Activity, Level, Expression or Compartmentalization Any method known in the art can be used to measure changes in Beta-Catenin activity, level, cellular distribution, and/or expression induced or altered by Beta-Catenin RNAi agent. Measurements can be performed at multiple timepoints, prior to, during and after administration of the RNAi agent, to determine the effect of the RNAi agent.

The terms "silence," "inhibit the expression of," "downregulate the expression of," "suppress the expression of," and the like, in so far as they refer to a Beta-Catenin gene, herein refer to the at least partial suppression of the expression of a Beta-Catenin gene, as manifested by a reduction of the amount of Beta-Catenin mRNA which may be isolated from or detected in a first cell or group of cells in which a Beta-Catenin gene is transcribed and which has or have been treated such that the expression of a Beta-Catenin gene is inhibited, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \cdot 100\% \qquad \text{Equation 1}$$

Alternatively, the degree of inhibition may be given in terms of a reduction of a parameter that is functionally linked to Beta-Catenin gene expression, e.g., the amount of protein encoded by a Beta-Catenin gene, etc. In principle, Beta-Catenin gene silencing may be determined in any cell expressing Beta-Catenin, either constitutively or by genomic engineering, and by any appropriate assay. However, when a reference or control is needed in order to determine whether a given RNAi agent inhibits the expression of the Beta-Catenin gene by a certain degree and therefore is encompassed by the instant disclosure, the assays provided in the Examples below shall serve as such reference.

For example, in certain instances, expression of a Beta-Catenin gene is suppressed by at least about 10%, 15%, 20%, 25%, 30%, 35%, 40%, 45%, or 50% by administration of a RNAi agent featured in the present disclosure. In some embodiments, a Beta-Catenin gene is suppressed by at least about 60%, 70%, or 80% by administration of a RNAi agent featured in the present disclosure. In some embodiments, a Beta-Catenin gene is suppressed by at least about 85%, 90%, or 95% or more by administration of a RNAi agent, as described herein.

The ability of a RNAi agent to suppress Beta-Catenin can be first tested in vitro (e.g., using test cells such as HeLa cells).

RNAi agents which can suppress Beta-Catenin in vitro can then be tested for immunostimulation using, for example, a PBMC (peripheral blood mononuclear cell) assay. RNAi agents can also be tested in animal tests. Test and control animals include those which over-express or under-express Beta-Catenin, as described in, for example, Chenn et al. 2003 Cer. Cortex 13: 599-606. RNAi agents which suppress or alter the level, activity and/or expression of Beta-Catenin can be used in medicaments to treat various Beta-Catenin-related diseases.

By "lower" in the context of Beta-Catenin or a symptom of a Beta-Catenin-related disease is meant a statistically significant decrease in such level. The decrease can be, for example, at least 10%, at least 20%, at least 30%, at least 40%, at least 50%, at least 60%, at least 70%, at least 80%, at least 90%, at least 95%, or more. If, for a particular disease, or for an individual suffering from a particular disease, the levels or expression of Beta-Catenin are elevated, treatment with a Beta-Catenin RNAi agent of the present disclosure can particularly reduce the level or expression of Beta-Catenin to a level considered in the literature as within the range of normal for an individual without such disorder.

The level or expression of Beta-Catenin can be measured by evaluation of mRNA (e.g., via Northern blots or PCR), or protein (e.g., Western blots). The effect of a RNAi agent on Beta-Catenin expression can be determined by measuring Beta-Catenin gene transcription rates (e.g., via Northern blots; or reverse transcriptase polymerase chain reaction or real-time polymerase chain reaction). Direct measurements can be made of levels of Beta-Catenin (which is expressed by the cell surface), e.g. by Western blots of tissues in which Beta-Catenin is expressed. The presence of Beta-Catenin in various cellular compartments (membrane, cytoplasm, and nucleus) can also be determined.

As used herein, "down-regulates" refers to any statistically significant decrease in a biological activity and/or expression of Beta-Catenin, including full blocking of the activity (i.e., complete inhibition) and/or expression. For example, "down-regulation" can refer to a decrease of at least about 10, 20, 30, 40, 50, 60, 70, 80, 90 or 100% in Beta-Catenin level, activity and/or expression.

As used herein, the term "inhibit" or "inhibiting" Beta-Catenin refers to any statistically significant decrease in biological level, activity and/or expression of Beta-Catenin, including full blocking of the activity and/or expression. For example, "inhibition" can refer to a decrease of at least about 10, 20, 30, 40, 50, 60, 70, 80, 90 or 100% in Beta-Catenin level, activity and/or expression. As used herein, the term "inhibit" similarly refers to a significant decrease in level, activity and/or expression, while referring to any other biological agent or composition.

By "level", it is meant that the Beta-Catenin RNAi agent can alter the level of Beta-Catenin, e.g., the level of Beta-Catenin mRNA or the level of Beta-Catenin protein, or the level of activity of Beta-Catenin.

Some diseases, such as adenomatous polyposis of the colon, colorectal cancer, basal cell carcinoma, breast cancer, kidney cancer, Wilms tumors, medulloblastoma, ovarian cancer, adrenocortical tumors, gastric cancer, liver cancer, melanoma, pancreatic cancers, prostate cancer, renal cancer, ectopic teeth and taste papillae, skin cancer, pilomatrixoma, anaplastic thyroid carcinoma, and uterine carcinosarcoma, oligodontia, osteoporosis, ageing, degenerative diseases, bedsores, chronic wounds and impaired wound healing, and similar and related diseases, are characterized by excessive and/or mutated Beta-Catenin activity, and/or unusual Beta-Catenin distribution within the cell. Thus, in various embodiments, administration of a RNAi agent to Beta-Catenin particularly establishes or re-establishes a normal or approximately normal level of Beta-Catenin activity, expression, distribution, and/or level.

By "normal" or "approximately normal" in terms of level, expression and/or activity, is meant at least: about 50%, about 60%, about 70%, about 80%, about 90%, and/or about 100%; and/or no more than: about 100%, about 120%, about 130%, about 140%, or about 150% of the level, expression or activity of Beta-Catenin in a healthy cellular compartment, cell, tissue, or organ. In one embodiment, administration of the appropriate amount of the appropriate Beta-Catenin RNAi agent restores Beta-Catenin level, activity and/or expression levels to about 50% to about 150%, more particularly about 60% to about 140%, more particularly to about 70% to about 130%, more particularly to about 80% to about 120%, more particularly to about 90% to about 110%, and most particularly to about 100% of that of a healthy cell, tissue or organ. Administration of a Beta-Catenin RNAi to a patient with a Beta-Catenin-related disease thus particularly restores the level, activity, and/or expression of Beta-Catenin to an approximately normal level, as determined by direct measurements of Beta-Catenin mRNA or protein levels, or indirect determinations, such as analyses of histological samples or levels of tissue samples. The RNAi agents of the present disclosure can also achieve a normal or approximately normal level of distribution of Beta-Catenin within the cell (e.g., in the membrane but not in the cytoplasm or nucleus).

In some Beta-Catenin-related cancers, Beta-Catenin is required for tumor growth but is not amplified, over-expressed or mis-localized. A reduction in Beta-Catenin expression, level or activity should thus limit tumor growth. The disclosure thus encompasses methods wherein Beta-Catenin expression, level or activity is reduced to an expression, level or activity which is lower than normal.

In addition, in various embodiments, depending on the disease condition and biological context, it is acceptable to use the RNAi agents of the present disclosure to establish a level of Beta-Catenin expression, activity and/or level which is below the normal level, or above the normal level.

Beta-Catenin-Related Diseases

The present disclosure encompasses RNAi agents to Beta-Catenin and administration of the RNAi agents to humans and non-human animals to treat various Beta-Catenin-related diseases.

By "Beta-Catenin-related disease" is meant any disease related to a mutation and/or dysfunction in the level, expression, cellular location, and/or activity of Beta-Catenin, and/or any disease which can be treated, prevented and/or ameliorated by modulating the level, expression, cellular location, and/or activity of Beta-Catenin. In some cases, the "Beta-Catenin-related disease" includes cancers wherein Beta-Catenin is required for tumor growth but is not amplified, over-expressed or mis-localized. A reduction in Beta-Catenin expression, level or activity should thus limit tumor growth. In various embodiments of the present disclosure, a Beta-Catenin-related disease can be treated and/or ameliorated by a RNAi agent to Beta-Catenin.

Beta-Catenin-related diseases are often associated with aberrations in the canonical Wnt/Beta-Catenin pathway. Wnt signaling is involved in virtually every aspect of embryonic development and also controls homeostatic self-renewal in a number of adult tissues. Germline mutations in the Wnt pathway cause several hereditary diseases, and somatic mutations are associated with cancer of the intestine and a variety of other tissues. In the Wnt pathway, when Wnt receptor complexes are not bound by ligand, the serine/threonine kinases, CK1 and GSK3α/β, phosphorylate Beta-Catenin. Phosphorylated Beta-Catenin is recognized by the F box/WD repeat protein β-TrCP, a component of a dedicated E3 ubiquitin ligase complex. Following ubiquitination, Beta-Catenin is targeted for rapid destruction by the proteosome. In the nucleus, the binding of Groucho to TCF (T cell factor) inhibits the transcription of Wnt target genes, including proto-oncogene c-myc. However, Beta-Catenin accumulation in the nucleus can lead to activation of these Wnt target genes. For example, once bound by Wnt, the Frizzled (Fz)/LRP co-receptor complex activates the canonical signaling pathway. Fz interacts with Dsh, a cytoplasmic protein that functions upstream of Beta-Catenin and the kinase GSK3β. Wnt signaling controls phosphorylation of LRP by GSK3β and casein kinase I-γ (CK1γ), thus regulating the docking of Axin. The recruitment of Axin away from the destruction complex leads to the stabilization of beta-catenin in the cytoplasm. Once in the nucleus, Beta-Catenin displaces Groucho from TCF/LEF to promote the transcription of Wnt target genes, including c-myc. Moon et al. 2002 science 296: 1644-1646; Nelson et al. 2004 Science 303: 1483-1487; and Clevers 2006 Cell 127: 469-480; and references cited therein.

Beta-Catenin-related diseases are thus often associated with a mutated form of the protein, and/or an elevated level of mutant or wild-type Beta-Catenin, and/or presence of Beta-Catenin in cytoplasm and/or nucleus. In normal gastric mucosa, Beta-Catenin is localized to the cell membrane. Clements et al. 2002 Cancer Res. 62: 3503-6. As noted above, in the absence of growth or differentiation signals, cytoplasmic Beta-Catenin is rapidly turned over, under the control of the APC (adenomatous polyposis coli) protein and GSK-3β. Beta-Catenin accumulates in the cytoplasm in some cancer cells, chronic wounds and other diseased cells and tissues. Nuclear translocation can also occur. Beta-Catenin accumulation can result in interaction with the T-cell factor 4 or lymphoid-enhancer factor family of transcriptional activators, and can result in the activation of some developmentally-related genes and/or proto-oncogenes, including c-myc. Behrens et al. 1996 Nature 382: 638-642; and He et al. 1998 Science 281: 1509-1512.

As noted above, Beta-Catenin turnover occurs in the proteosome, where Beta-Catenin is degraded after targeted phosphorylation of highly-conserved Ser and Thr residues (Ser33, Ser37, Thr41, and Ser45) and ubiquitination in the $NH_2$ terminus. Mutations in these Ser and Thr residues result in accumulated Beta-Catenin and are associated with various cancers. A Ser37 to Phe37 mutation, at a mutational hotspot, is associated with Beta-Catenin accumulation and increased half-life in the SK23 mel (melanoma) cell line. Rubinfeld et al. 1997 Science 275: 1790-1792. A Ser45 to Tyr45 mutation in the 624 mel cell line also increased the half-life of Beta-Catenin. Rubinfeld et al. 1997. Other deletions and mutations of these residues resulting in Beta-Catenin accumulation are described in Funayama et al. 1995 J. Cell Biol. 128: 959; Munemitsu et al. 1996 Mol. Cell. Biol. 16: 4088; Yost et al. 1996 Genes Dev. 10: 1443; and Ha et al. 2002 Acta Derm. Venereol. 82: 428-431. Altered phosphorylation of Beta-Catenin is also associated with breast cancer. Sommers et al. 1994 Cancer Res. 54: 3544-3552.

Beta-Catenin mutations outside the four Ser and Thr residues have also been associated with disease states. A nearby mutation of Aspartic acid 32 to Tyr was detected in a prostate cancer cell line. Voeller et al. 1998 Cancer Res. 58: 2520-2523. The 321-bp deletion from +82 to +402 was found in the HSC-39 gastric cancer cell line, Kawanishi et al. 1995 Mol. Cell. Biol. 15: 1175-1181. Other mutations at positions 32, 33, 34, 37 and 41 have been associated with pilomatrixomas (skin tumors of unknown origin and aetiology). Chan et al. 1999 Nature Genet. 21: 410-413. Additional mutations associated with gastric cancer were found at positions 8, 11, 13, 21, 24, 25, 28, 29, 32, 37, 39, 47, 48 and 55. Clements et al. 2002 Cancer Res. 62: 3503-3506. Various mutations in colorectal tumors are described in Miyaki et al. 1999 Cancer Res. 59: 4506-4509. All in all, mutations of Beta-Catenin at positions 8, 11, 13, 21, 24, 25, 28, 29, 32, 33, 34, 37, 39, 41, 45, 47, 48 and 55 have been associated with various cancers and other disease states.

In addition, a 321-bp deletion from +82 to +402 occurs in HSC-39 gastric cancer cell line, Kawanishi et al. 1995 Mol. Cell. Biol. 15: 1175-1181. Additional Beta-Catenin mutations (inside and outside the region of the four Ser and Thr residues) have been associated with medulloblastoma, endometroid ovarian carcinoma, uterine endometrial carcinoma, hepatocellular carcinoma, and prostatic adenocarcinoma. Zurawel et al. 1998 Cancer Res. 58: 896-899; Palacios et al. 1998 Cancer Res. 58: 1344-1347; Fukuchi et al. 1998 Cancer Res. 58: 3526-3528; Miyoshi et al. 1998 Cancer Res. 58: 2524-2527; Voeller et al. 1998 Cancer Res. 2520-2523; and Iwao et al. 1998 Cancer Res. 58: 1021-1026; and Garcia-Rostan et al. 1999 Cancer Res. 59: 1811-1815.

Alterations in the genetic or biochemical context can also alter Beta-Catenin level or activity. Excess intracellular Beta-Catenin is expressed in colon and other cancer cells with a defective APC. Munemitsu et al. 1995 Proc. Natl. Acad. Sci. USA 92:3046. A reduced cell-cell adhesion is caused by tyrosine-phosphorylation of Beta-Catenin with v-src gene transfection. Behrens et al. 1993 J. Cell Biol. 120: 757-766; Hamaguchi et al. 1993 EMBO J. 12:307-314; Matsuyoshi et al. 1992 J. Cell Biol. 118: 703-714.

In addition, the term "Beta-Catenin-related disease" includes those diseases in which Beta-Catenin (in normal form, mutant form, and/or in an elevated level of normal or mutant form and/or altered localization within the cell) directly or indirectly causes an increase in expression, level or activity of a factor involved in a disease state; for example, nuclear beta-catenin activates production of c-myc, which is involved in several diseases. In addition, "Beta-Catenin-related disease" includes those diseases related to aberrations in the Wnt/Beta-Catenin pathway. For example, abnormalities of the Wnt/Beta-Catenin pathway are associated with various cancers, osteoporosis, ageing, oligodontia, and degenerative diseases. Clevers et al. 2006 Cell 127: 469-480; Moon et al. 2004 Nat. Rev. Genet. 5: 691-701; He et al. 2004 Develop. 131: 1663-1677; Logan et al. 2004 Ann. Rev. Cell. Dev. Biol. 20: 781-810. In addition, Wilms tumors (a pediatric kidney cancer) are sometimes associated with mutations in the WTX gene, a tumor suppressor gene which has recently been discovered to be involved in the Wnt/Beta-Catenin pathway. Huang et al. 2008. Curr. Opin. Cell Biol. 20: 119-125.

In particular, the term "Beta-Catenin-related disease" includes adenomatous polyposis of the colon, colorectal cancer, basal cell carcinoma, breast cancer, kidney cancer, Wilms tumors, medulloblastoma, ovarian cancer, adrenocortical tumors, gastric cancer, liver cancer, melanoma, pancreatic cancers, prostate cancer, renal cancer, ectopic teeth and taste papillae, skin cancer, pilomatrixoma, anaplastic thyroid carcinoma, and uterine carcinosarcoma, oligodontia, osteoporosis, ageing, degenerative diseases, bedsores, chronic wounds and impaired wound healing. See: Delektorskaya et al. 2008. Bull. Exp. Biol. Med. 146: 616-619; Li et al. 2005 World J. Gastroent. 11: 2117-23; Liu et al. 2010 J. Dental Res. 89: 318-330; Noda et al. 1009 Br. J. Cancer 100: 1647-1658; Saegusa et al. 2009 Am. J. Pathol. 174: 2107-2115; Saldanha et al. Br. J. Dermatol. 151: 157-64; Stojadinovic et al. Am. J. Pathol. 167: 59-69; Thompson et al. 2007 Hepatology 45: 1298-305; Wang et al. 2008 Cancer Epidemiol. Biomarkers Prev. 17: 2101-8.

RNAi agents to Beta-Catenin can be used to treat Beta-Catenin-related diseases, particularly those diseases associated with altered expression, activity, compartmentalization, and/or levels of Beta-Catenin, or wherein Beta-Catenin is required for disease progression (e.g., tumor growth).

RNAi Agents to Beta-Catenin for Treatment of Beta-Catenin-Related Diseases

The RNAi agents to Beta-Catenin described herein can be formulated into pharmaceutical compositions which can be administered to humans or non-human animals. These compositions can comprise one or more RNAi agents, and, optionally, additional treatments useful for treating Beta-Catenin-related diseases. They can be administered as part of an early/preventative treatment, and can be administered in a therapeutically-effective dosage. The pharmaceutical composition can comprise a pharmaceutical carrier and can be administered by any method known in the art. These various aspects of the present disclosure are described in additional detail below.

RNAi agents to Beta-Catenin can be administered to humans and non-human animals for treatment of Beta-Catenin-related diseases.

In one embodiment of the present disclosure, the compositions comprising a Beta-Catenin RNAi agent can be administered to non-human animals. For example, the compositions can be given to chickens, turkeys, livestock animals (such as sheep, pigs, horses, cattle, etc.), companion animals (e.g., cats and dogs) and can have efficacy in treatment of adenomatous polyposis of the colon, colorectal cancer, basal cell carcinoma, breast cancer, kidney cancer, Wilms tumors, medulloblastoma, ovarian cancer, adrenocortical tumors, gastric cancer, liver cancer, melanoma, pancreatic cancers, prostate cancer, renal cancer, ectopic teeth and taste papillae, skin cancer, pilomatrixoma, anaplastic thyroid carcinoma, and uterine carcinosarcoma, oligodontia, osteoporosis, ageing, degenerative diseases, bedsores, chronic wounds and impaired wound healing and similar and related diseases. In each case, the RNAi agent to Beta-Catenin would be selected to match the sequence of the Beta-Catenin of the genome of the animal, and to, particularly, contain at least 1 nt mismatch from all other genes in that animal's genome. The RNAi agents of the present disclosure can thus be used in treatment of Beta-Catenin-related diseases in humans and non-human animals.

As used herein in the context of Beta-Catenin expression, the terms "treat," "treatment," and the like, refer to relief from or alleviation of pathological processes mediated by Beta-Catenin expression. In the context of the present disclosure insofar as it relates to any of the other conditions recited herein below (other than pathological processes mediated by Beta-Catenin expression), the terms "treat," "treatment," and the like mean to relieve or alleviate at least one symptom associated with such condition, or to slow or reverse the progression or anticipated progression of such condition.

By "treatment" is also meant prophylaxis, therapy, cure, or any other change in a patient's condition indicating improvement or absence of degradation of physical condition. By "treatment" is meant treatment of Beta-Catenin-related disease (e.g., adenomatous polyposis of the colon, colorectal cancer, basal cell carcinoma, breast cancer, kidney cancer, Wilms tumors, medulloblastoma, ovarian cancer, adrenocortical tumors, gastric cancer, liver cancer, melanoma, pancreatic cancers, prostate cancer, renal cancer, ectopic teeth and taste papillae, skin cancer, pilomatrixoma, anaplastic thyroid carcinoma, and uterine carcinosarcoma, oligodontia, osteoporosis, ageing, degenerative diseases, bedsores, chronic wounds and impaired wound healing, and similar and related diseases), or any appropriate treatment of any other ailment the patient has. As used herein, the terms "treatment" and "treat" refer to both prophylactic or preventative treatment and curative or disease-modifying treatment, including treatment of patients at risk of contracting a disease or suspected of having a disease, as well as patients already ill or diagnosed as suffering from a condition. The terms "treatment" and "treat" also refer to the maintenance and/or promotion of health in an individual not suffering from a disease but who may be susceptible to developing an unhealthy condition. In one embodiment, "treatment" does not encompass prevention of a disease state. Thus, the present disclosure is useful for suppressing expression of the Beta-Catenin gene and/or treating a Beta-Catenin-related disease in an individual afflicted by a Beta-Catenin-related disease, or an individual susceptible to a Beta-Catenin-related disease. An individual "afflicted" by a Beta-Catenin-related disease has demonstrated detectable symptoms characteristics of the disease, or had otherwise been shown clinically to have been exposed to or to carry Beta-Catenin-related disease pathogens or markers. As non-limiting examples, an individual afflicted by a Beta-Catenin-related disease can show outward symptoms; or can show no outward symptoms but can be shown with a clinical test to carry protein markers associated with a Beta-Catenin-related disease, or proteins or genetic material associated with a pathogen in the blood.

Treatment of some Beta-Catenin-related diseases may be more efficacious if administered early rather than later. Thus, in one particular embodiment, the RNAi agent to Beta-Catenin is administered early, prior to disease manifestation, and/or as a preventative agent, rather than administered after disease establishment.

Additional Treatments Used in Addition to or in Conjunction with RNAi Agents to Beta-Catenin Treatments of Beta-Catenin-related diseases can thus comprises various treatments, comprising a Beta Beta-Catenin RNAi agent, and optionally further comprising an additional treatment, which can be a method (or procedure), and/or an additional composition (e.g., an agent or additional RNAi agent).

Beta-Catenin-related diseases include adenomatous polyposis of the colon, colorectal cancer, basal cell carcinoma, breast cancer, kidney cancer, Wilms tumors, medulloblastoma, ovarian cancer, adrenocortical tumors, gastric cancer, liver cancer, melanoma, pancreatic cancers, prostate cancer, renal cancer, ectopic teeth and taste papillae, skin cancer, pilomatrixoma, anaplastic thyroid carcinoma, and uterine carcinosarcoma, oligodontia, osteoporosis, ageing, degenerative diseases, bedsores, chronic wounds and impaired wound healing, and similar and related diseases. The use of known treatments for any of these diseases is within the capabilities of one of ordinary skill in the art. Any such additional treatment can be used in conjunction with a RNAi agent to Beta-Catenin.

These additional treatments, which can be administered prior to, simultaneously, or after administration of the RNAi agent(s) to Beta-Catenin, include: 5-fluoro-29-deoxyuridine, 7-hydroxystaurosporine, a goserlin implant, antibiotic, bevacizumab, bicalutamide, bleomycin, camptothecin, carboplatin, cetuximab, cisplatin, colcemid, Cycloheximide, cyclophosphamide, cytarabine, cytosine arabinoside (Ara-C), dacarbazine, docetaxel, doxorubicin, edelfosine, ehlorambucil, epipodophyllotoxin, epirubicin, erlotinib, estramustine, etoposide, fenretinide, finasteride, flavopiridol, fludarabine, fluorouracil, gefitinib, gemeitabine, goserelin, hexamethylmelamine, hydroxyurea, ifosfamide, irinotecan, L-asparaginase, leuprolide, meiphalan, mercaptopurine, methotrexate, mitixantrone, mitomycin, mitoxantrone, nitrogen mustard, octreotide, paclitaxel, pirubicin, Puromycin, sargramostim, staurosporine, steroids, tamoxifen, Taxol, tegafur, teniposide, topotecan, trastuzumab, UFT, 1-Hydroxy-2-imidazol-1-yl-phosphonoethyl) phosphonic acid monohydrate (sold under the tradename Zometa® by Novartis), 2-chloro-N-[4-chloro-3-(2-pyridinyl)phenyl]-4-(methylsulfonyl)-benzamide (also known as GDC-0449, and described in PCT Publication No. WO 06/028958), GDC 0941 (PCT Publication Nos. WO 09/036082 and WO 09/055730), BEZ 235 or NVP-BEZ 235 (PCT Publication No. WO 06/122806), ABT-263 (PCT Publication No. WO 09/155386), 5-azacitidine (sold under the tradename Vidaza®), decitabine (sold under the tradename Dacogen®), 6-thioguanine (sold under the tradename Purinethol®), pemetrexed (sold under the tradename Alimta®), Afutuzumab (available from Roche®), pegfilgrastim (sold under the tradename Neulasta® by Amgen), lenalidomide (also known as CC-5013 sold under the tradename Revlimid®), thalidomide (sold under the tradename Thalomid®), Alemtuzumab (sold under the tradename Campath®), Alitretinoin (sold under the tradename Panretin®), tretinoin (all-trans retinoic acid, also known as ATRA sold under the tradename Vesanoid®), Isotretinoin, bexarotene (sold under the tradename Targretin®), Alvocidib (U.S. Pat. No. 5,621,002), Amifostine (sold under the tradename Ethyol®), leucovorin, aminoglutethimide (sold under the tradename Cytadren®), Anagrelide (sold under the tradename Agrylin®), Anti-nausea drugs, Arsenic trioxide (sold under the tradename Trisenox®), asparaginase (also known as L-asparaginase, Erwinia L-asparaginase sold under the tradenames Elspar® and Kidrolase®), axitinib, bacillus calmette-guerin (sold under the tradenames theraCys® and TICE® BCG), denileukin diftitox (sold under the tradename Ontak®), Bortezomib (sold under the tradename Velcade®), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), Cabazitaxel (1-hydroxy-7β,10β-dimethoxy-9-oxo-5β,20-epoxytax-11-ene-2α,4,13α-triyl-4-acetate-13-benzoate-13-[(2R,3S)-3-{[(tert-butoxy)carbonyl]amino}-2-hydroxy-3-phenylpropanoate), larotaxel ((2α,3ξ,4α,5β,7α,10β,13α)-4,10-bis(acetyloxy)-13-({(2R,3S)-3-[(tert-butoxycarbonyl)amino]-2-hydroxy-3-phenylpropanoyl}oxy)-1-hydroxy-9-oxo-5,20-epoxy-7,19-cyclotax-11-en-2-yl benzoate), Capecitabine (sold under the trademark Xeloda® by Roche), Casopitant (sold under the tradenames Rezonic® and Zunrisa® by GlaxoSmithKline), Cervarix® sold by GlaxoSmithKline, Gardasil® sold by Merck, cladribine (also known as 2-chlorodeoxyadenosine (2-CdA) sold under the tradename Leustatin™) Claribine (2-chlorodeoxyadenosine sold under the tradename Leustatin®), Dacetuzumab (also known as SGN-40 or huS2C6, available from Seattle Genetics, Inc), Darbepoetin alfa (sold under the tradename Aranesp® by Amgen), daunorubicin, decitabine (sold under the tradename Dacogen®), Deferasinox (sold under the tradename Exjade® by Novartis), Denosumab (sold under the tradename Prolia® by Amgen), Dulanermin (also known as AMG-951, available from Amgen/Genentech), Elotuzumab (HuLuc63, CAS No. 915296-00-3), Eltrombopag (sold under the tradenames Promacta® and Revolade® by GlaxoSmithKline), etoposide (also known as VP-16 and Etoposide phosphate sold under the tradenames Toposar®, VePesid® and Etopophos®), teniposide (also known as VM-26 sold under the tradename Vumon®), Exemestane (sold under the trademark Aromasin® by Pfizer), letrozole (sold under the tradename Femara® by Novartis), anastrozole (sold under the tradename Arimidex®), Figitumumab (also known as CP-751, 871, available from ACC Corp), robatumumab (CAS No. 934235-44-6), Filgrastim (sold under the tradename Neupogen® by Amgen), floxuridine (sold under the tradename FUDR®), Fluoxymesterone (sold under the tradename Halotestin®), Fulvestrant (sold under the tradename Faslodex®), Gefitnib (sold under the tradename Iressa®), N-[4-[(3-Chloro-4-fluorophenyl)amino]-7-[[(3"S")-tetrahydro-3-furanyl]oxy]-6-quinazolinyl]-4(dimethylamino)-2-butenamide sold under the tradename Tovok® by Boehringer Ingelheim), Gemtuzumab ozogamicin (sold under the tradename Mylotarg® by Pfizer/Wyeth), Hydrocortisone (also known as cortisone, hydrocortisone sodium succinate, hydrocortisone sodium phosphate, and sold under the tradenames Ala-Cort®, Hydrocortisone Phosphate, Solu-Cortef®, Hydrocort Acetate® and Lanacort®), dexamethazone ((8S,9R,10S,11S,13S,14S,16R,17R)-9-fluoro-11,17-dihydroxy-17-(2-hydroxyacetyl)-10,13,16-trimethyl-6,7,8,9,10,11,12,13,14,15,16,17-dodecahydro-3H-cyclopenta[a]phenanthren-3-one), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-Methylprednisolone, Methylprednisolone Acetate, Methylprednisolone Sodium Succinate sold under the tradenames Duralone®, Medralone®, Medrol®, M-Prednisol® and Solu-Medrol®), Ibritumomab tiuxetan (sold under the tradename Zevalin®), idarubicin (sold under the tradenames Idamycin®, Idamycin PFS®), Inotuzumab ozogamicin (also referred to as CMC-544 and WAY-207294, available from Hangzhou Sage Chemical Co., Ltd.), interleukin-2 (also known as aldesleukin and IL-2 sold under the tradename Proleukin®), interleukin-11 (also known as oprevelkin sold under the tradename Neumega®), alpha interferon alfa (also known as IFN-alpha sold under the tradenames Intron® A, and Roferon-A®), Irinotecan (sold under the trademark Camptosar® by Pfizer), topotecan hydrochloride (sold under the tradename Hycamtin® by GlaxoSmithKline), Ixabepilone (sold under the tradename Lxempra® by Bristol-Myers Squibb), lapatinib or lapatinib ditosylate (sold under the trademark Tykerb® by GlaxoSmithKline), Leuprolide or leuprolide acetate (sold under the tradenames Viadure® by Bayer AG, Eligard® by Sanofi-Aventis and Lupron® by Abbott Lab), Linifanib (N-[4-(3-amino-1H-indazol-4-yl)phenyl]-N'-(2-fluoro-5-methylphenyl)urea, also known as ABT 869, available from Genentech), sunitinib malate (sold under the tradename Sutent® by Pfizer), bosutinib (4-[(2,4-dichloro-5-methoxyphenyl)amino]-6-methoxy-7-[3-(4-methylpiperazin-1-yl) propoxy]quinoline-3-carbonitrile, also known as SKI-606, and described in U.S. Pat. No. 6,780,996), dasatinib (sold under the tradename Sprycel® by Bristol-Myers Squibb), armala (also known as pazopanib sold under the tradename Votrient® by GlaxoSmithKline), imatinib and imatinib mesylate (sold under the tradenames Gilvec® and Gleevec® by Novartis), megestrol (also known as megestrol acetate sold under the tradename Megace®), motesanib (N-(2,3-dihydro-3,3-dimethyl-1H-indol-6-yl)-2-[(4-pyridinylmethyl)amino]-3-pyridinecarboxamide, and described in PCT Publication No. WO 02/066470), pasireotide (also known as SOM230, and described in PCT Publication No. WO 02/010192), sorafenib (sold under the tradename Nexavar®), nelarabine ((2R,3S,4R,5R)-2-(2-amino-6-methoxypurin-9-yl)-5-(hydroxymethyl)oxolane-3,4-diol sold under the tradenames Arranon® and Atriance® by GlaxoSmithKline), neratinib (also known as HKI-272, (2E)-N-[4-[[3-chloro-4-[(pyridin-2-yl)methoxy]phenyl]amino]-3-cyano-7-ethoxyquinolin-6-yl]-4-(dimethylamino)but-2-enamide, and described PCT Publication No. WO 05/028443), nilotinib hydrochloride (sold under the tradename Tasigna® by Novartis), Nilutamide (sold under the tradenames Nilandron® and Anandron®), bicalutamide (sold under tradename Casodex®), flutamide (sold under the tradename Fulexin™), N-methyl-2-[[3-[(E)-2-pyridin-2-ylethenyl]-1H-indazol-6-yl]sulfanyl]benzamide, also known as AG013736, and described in PCT Publication No. WO 01/002369, octreotide (also known as octreotide acetate sold under the tradenames Sandostatin® and Sandostatin LAR®). Odanacatib (also know as MK-0822, N-(1-cyanocyclopropyl)-4-fluoro-N²-{(1S)-2,2,2-trifluoro-1-[4'-(methylsulfonyl)biphenyl-4-yl]ethyl}-L-leucinamide, available from Lanzhou Chon Chemicals, ACC Corp., and ChemieTek, and described in PCT Publication no. WO 03/075836), oprelvekin (sold under the tradename Neumega® by Pfizer/Wyeth), oxaliplatin (sold under the tradename Eloxatin® ay Sanofi-Aventis and described in U.S. Pat. No. 4,169,846), Palifermin (sold under the tradename Kepivance® by Amgen), Pamidronate (sold under the tradename Aredia®), zoledronic acid (sold under the tradename Zometa®), panitumumab (sold under the tradename Vectibix® by Amgen), pentostatin (sold under the tradename Nipent®), Pertuzumab (sold under the trademark Omnitarg®, by Genentech), Raloxifene (sold under the tradename Evista®), Rituximab (sold under the trademarks Riuxan® and MabThera® by Genentech/Roche), Romiplostim (sold under the tradename Nplate® by Amgen), tamoxifen (sold under the tradename Novaldex®), Tanespimycin (17-allylamino-17-demethoxygeldanamycin, also known as KOS-953 and 17-AAG, available from SIGMA, and described in U.S. Pat. No. 4,261,989), Temozolomide (sold under the tradenames Temodar® and Temodal® by Schering-Plough/Merck), dactinomycin (also known as actinomycin-D and sold under the tradename Cosmegen®), melphalan (also known as L-PAM, L-sarcolysin, and phenylalanine mustard sold under the tradename Alkeran®), altretamine (also known as hexamethylmelamine (HMM) sold under the tradename Hexalen®), carmustine (sold under the tradename BiCNU®), bendamustine (sold under the tradename Treanda®), busulfan (sold under the tradenames Busulfex® and Myleran®), carboplatin (sold under the tradename Paraplatin®), lomustine (also known as CCNU sold under the tradename CeeNU®), cisplatin (also known as CDDP sold under the tradenames Platinol® and Platinol®-AQ), chlorambucil (sold under the tradename Leukeran®), cyclophosphamide (sold under the tradenames Cytoxan® and Neosar®), dacarbazine (also known as DTIC, DIC and imidazole carboxamide sold under the tradename DTIC-Dome®), altretamine (also known as hexamethylmelamine (HMM) sold under the tradename Hexalen®), ifosfamide (sold under the tradename Ifex®), procarbazine (sold under the tradename Matulane®), mechlorethamine (also known as nitrogen mustard, mustine and mechloroethamine hydrochloride sold under the tradename Mustargen®), streptozocin (sold under the tradename Zanosar®), thiotepa (also known as thiophosphoamide, TESPA and TSPA sold under the tradename Thioplex®, Temsirolimus (sold under the tradename Torisel® by Pfizer), ridaforolimus (formally known as deferolimus, (1R,2R,4S)-4-[(2R)-2 [(1R,9S,12S,15R,16E,18R,19R,21R,23S,24E, 26E,28Z,30S,32S,35R)-1,18-dihydroxy-19,30-dimethoxy-15,17,21,23,29,35-hexamethyl-2,3,10,14,20-pentaoxo-11, 36-dioxa-4-azatricyclo[30.3.1.0$^{4,9}$]hexatriaconta-16,24,26, 28-tetraen-12-yl]propyl]-2-methoxycyclohexyl dimethylphosphinate, also known as AP23573 and MK8669, and described in PCT Publication No. WO 03/064383), everolimus (sold under the tradename Afinitor® by Novartis), Toremifene (sold under the tradename Fareston®), tositumomab (sold under the trademarks Bexxar® by GlaxoSmithKline), ofatumumab (sold under the trademark Arzerra® by GlaxoSmithKline), Tremelimumab (IgG2 monoclonal antibody available from Pfizer, formerly known as ticilimumab, CP-675,206), ipilimumab (CTLA-4 antibody, also known as MDX-010, CAS No. 477202-00-9), vinblastine (also known as vinblastine sulfate, vincaleukoblastine and VLB sold under the tradenames Alkaban-AQ® and Velban®), vincristine (also known as vincristine sulfate, LCR, and VCR sold under the tradenames Oncovin® and Vincasar Pfs®), vinorelbine (sold under the tradename Navelbine®), Voninostat (sold under the tradename Zolinza® by Merck), Xaliproden (also known as SR57746, 1-[2-(2-naphthyl)ethyl]-4-[3-(trifluoromethyl) phenyl]-1,2,3,6-tetrahydropyridine, and described in U.S. Pat. No. 5,266,573), XL-518 (also know as GDC-0973, Cas No. 1029872-29-4, available from ACC Corp.); Selumetinib (5-[(4-bromo-2-chlorophenyl)amino]-4-fluoro-N-(2-hydroxyethoxy)-1-methyl-1H-benzimidazole-6-carboxamide, also known as AZD6244 or ARRY 142886, described in PCT Publication No. WO2003077914); 2-[(2-chloro-4-iodophenyl)amino]-Nyclopropylmethoxy)-3,4-difluoro-benzamide (also known as CI-1040 or PD184352 and described in PCT Publication No. WO2000035436); N-[(2R)-2,3-dihydroxypropoxy]-3,4-difluoro-2-[(2-fluoro-4-iodophenyl)amino]-benzamide (also known as PD0325901 and described in PCT Publication No. WO2002006213); 2,3-bis [amino[(2-aminophenyl)thio]methylene]-butanedinitrile (also known as U0126 and described in U.S. Pat. No. 2,779,780); N-[3,4-difluoro-2-[(2-fluoro-4-iodophenyl) amino]-6-methoxyphenyl]-1-[(2R)-2,3-dihydroxypropyl]-cyclopropanesulfonamide (also known as RDEA119 or BAY869766 and described in PCT Publication No.

WO2007014011); (3S,4R,5Z,8S,9S,11E)-14-(ethylamino)-8,9,16-trihydroxy-3,4-dimethyl-3,4,9,19-tetrahydro-1H-2-benzoxacyclotetradecine-1,7(8H)-dione] (also known as E6201 and described in PCT Publication No. WO2003076424); 2'-Amino-3'-methoxyflavone (also known as PD98059 available from Biaffin GmbH & Co., KG, Germany); AS-703026 (CAS No. 1204531-26-9); AZD-8330 (also known as ARRY-424704 or ARRY-704, CAS No. 1204531-17-8); ARRY-438162 (CAS No. 1073666-70-2); GSK-1120212 (CAS No. 1204531-25-8); RO-4987665 (CAS No. 1204531-24-7); and TAK-733; Antiresorptive agents, Bisphosphonates, Bone anabolic agents, Calcitonin, Calcium, Calcium salts, Estrogen analogs, Raloxifene, RANKL inhibitors, Sodium fluoride, Strontium ranelate, Teriparatide, and Vitamin D.

The dosages of the additional treatments and RNAi agents can be easily determined by one of ordinary skill in the art, and as described herein.

Dosages and Effective Amounts of RNAi Agents

The RNAi agents of the present disclosure are administered in a dosage of a therapeutically effective amount to a patient in need thereof.

An "effective amount" or a "therapeutically effective amount" is an amount that treats a disease or medical condition of an individual, or, more generally, provides a nutritional, physiological or medical benefit to an individual. As used herein, the phrases "therapeutically effective amount" and "prophylactically effective amount" refer to an amount that provides a therapeutic benefit in the treatment, prevention, or management of pathological processes mediated by Beta-Catenin expression or an overt symptom of pathological processes mediated by Beta-Catenin expression. The specific amount that is therapeutically effective can be readily determined by an ordinary medical practitioner, and may vary depending on factors known in the art, such as, for example, the type of pathological processes mediated by Beta-Catenin expression, the patient's history and age, the stage of pathological processes mediated by Beta-Catenin expression, and the administration of other agents that inhibit pathological processes mediated by Beta-Catenin expression.

In various embodiments of the present disclosure, the patient is at least about 1, 3, 6, or 9 months, or 1, 5, 10, 20, 30, 40, 50, 55, 60, 65, 70, or 75 years of age. In various embodiments of the present disclosure, the patient is no more than about 1, 3, 6, or 9 months, or 1, 5, 10, 20, 30, 40, 50, 55, 60, 65, 70, 75, 80, 90, or 100 years of age. In various embodiments the patient has a body weight of at least about 5, 10, 15, 20, 30, 40, 50, 60, 70, 80, 90, 100, 120, 140, 160, 180, 200, 220, 240, 260, 280, 300, 320, 340, 360, 380 or 400 lbs. In various embodiments of the present disclosure, the patient has a body weight of no more than about 5, 10, 15, 20, 30, 40, 50, 60, 70, 80, 90, 100, 120, 140, 160, 180, 200, 220, 240, 260, 280, 300, 320, 340, 360, 380 or 400 lbs.

In various embodiments of the present disclosure, the dosage [measuring only the active ingredient(s)] can be at least about 1, 5, 10, 25, 50, 100, 200, 250, 300, 250, 400, 450, 500, 550, 600, 650, 700, 750, 800, 850, 900, 950 or 1000 ng, 1, 5, 10, 25, 50, 100, 200, 250, 300, 250, 400, 450, 500, 550, 600, 650, 700, 750, 800, 850, 900, 950 or 1000 micrograms, 1, 5, 10, 25, 50, 100, 200, 250, 300, 250, 400, 450, 500, 550, 600, 650, 700, 750, 800, 850, 900, 950 or 1000 mg. In various embodiments of the present disclosure, the dosage can be no more than about 10, 25, 50, 100, 200, 250, 300, 250, 400, 450, 500, 550, 600, 650, 700, 750, 800, 850, 900, 950 or 1000 mg. In various embodiments of the present disclosure, the dosage can be administered at least more than once a day, daily, more than once a weekly, weekly, bi-weekly, monthly, and/or every 2, 3, 4, 5, 6, 7, 8, 9, 10, 11 or 12 months, or a combination thereof.

In various embodiments of the present disclosure, the dosage is correlated to the body weight or body surface area of the individual. The actual dosage level can be varied to obtain an amount of active agent which is effective for a particular patient, composition and mode of administration, without being toxic to the patient. The selected dose will depend on a variety of pharmacokinetic factors, including the activity of the particular RNAi agent employed, the route of administration, the rate of excretion of the RNAi agent, the duration of the treatment, other drugs, compounds and/or materials used in combination with the RNAi agent, the age, sex, weight, condition, general health and prior medical history of the patient, and like factors well known in the medical arts. A physician or veterinarian having ordinary skill in the art can readily determine the effective amount of the RNAi agent required. A suitable dose will be that amount which is the lowest dose effective to produce a therapeutic effect, or a dose low enough to produce a therapeutic effect without causing side effects.

In addition to a therapeutically-effective dosage of one or more RNAi agents to Beta-Catenin, the pharmaceutical compositions of the present disclosure can comprise or be used in conjunction with an additional disease treatment which works synergistically with the RNAi agent. For example, the pharmaceutical composition can comprise an additional antagonist to Beta-Catenin.

Additional Embodiments of RNAi Agents to Beta-Catenin

In a particular embodiment, the present disclosure encompasses a composition comprising one or more Beta-Catenin RNAi agents. In one embodiment, the present disclosure comprises a RNAi agent comprising a sense strand and an anti-sense strand. In one embodiment, the anti-sense strand consists of, consists essentially of, or comprises the sequence of the anti-sense strand of, a RNAi agent listed in Tables 1, 2, 3, 4, 5, 6, 7, 8 and/or 9. In one embodiment, the anti-sense strand consists of, consists essentially of, or comprises a sequence of at least 15 contiguous nt with 0, 1, 2, or 3 mismatches from that of, the anti-sense strand of any RNAi agent listed in Tables 1, 2, 3, 4, 5, 6, 7, 8 and/or 9. In one embodiment, the anti-sense strand consists of the sequence of the anti-sense strand of a RNAi agent listed in Tables 1, 2, 3, 4, 5, 6, 7, 8 and/or 9, and further comprises 0, 1, 2, 3, 4, 5, 6, 7, 8, 9, or 10 nucleotides. In one embodiment, the anti-sense strand consists of a sequence with 0, 1, 2, or 3 mismatches from that of the anti-sense strand of a RNAi agent listed in Tables 1, 2, 3, 4, 5, 6, 7, 8 and/or 9, and further comprises 0, 1, 2, 3, 4, 5, 6, 7, 8, 9, or 10 nucleotides.

In various embodiments of the present disclosure, the composition of the claimed disclosure has the proviso that it does not comprise any particular individual RNAi agent listed in Tables 1, 2 or 3. In various embodiments of the present disclosure, the RNAi agent to Beta-Catenin has the proviso that it does not have the sequence of any Beta-Catenin RNAi agent disclosed in the patent or scientific literature, e.g., WO 2006/086772, US 2007 0207974, US 2007 0042381, US 2005 0255487, US 2007/0275914, US 2007 0039072, US 2006 0193870, or US 2008 0113351.

Additional Embodiments of RNAi Agents

In another particular embodiment, the RNAi agent comprises any of the RNAi agents listed in Table 1, and modified and unmodified variants thereof.

In another particular embodiment, the RNAi agent comprises the sense strand of any of the RNAi agents listed in Tables 1, 2, 3, 4, 5, 6, 7, 8 and/or 9, and modified and unmodified variants thereof.

In another particular embodiment, the RNAi agent comprises the anti-sense strand of any of the RNAi agents listed in Tables 1, 2, 3, 4, 5, 6, 7, 8 and/or 9, and modified and unmodified variants thereof.

In another particular embodiment, the RNAi agent comprises a sense strand with a sequence consisting of that of the sense strand of any of the RNAi agents listed in Tables 1, 2, 3, 4, 5, 6, 7, 8 and/or 9 and modified and unmodified variants thereof.

In another particular embodiment, the RNAi agent comprises an anti-sense strand with a sequence consisting of that of the anti-sense strand any of the RNAi agents listed in Tables 1, 2, 3, 4, 5, 6, 7, 8 and/or 9, and modified and unmodified variants thereof.

In another particular embodiment, the RNAi agent comprises a sense stand with a sequence consisting of that of the sense strand and/or an anti-sense strand with a sequence consisting of that of the anti-sense strand of any RNAi agents listed in Tables 1, 2, 3, 4, 5, 6, 7, 8 and/or 9.

In another particular embodiment, the RNAi agent has a sequence consisting of that of any of the RNAi agents listed in Tables 1, 2, 3, 4, 5, 6, 7, 8 and/or 9, and modified and unmodified variants thereof.

Embodiments Comprising One or More Efficacious RNAi Agents to Beta-Catenin

In various embodiments of the present disclosure, the present disclosure comprises a RNAi agent demonstrating at least about 40, 50, 60, 70, 80, 90 or 95% knockdown (no more than about 60, 50, 40, 30, 20, 10, or 5% residual gene activity, respectively) of the Beta-Catenin gene at an in vitro concentration of 10 or 0.1 nM in HeLa cells.

In various embodiments of the present disclosure, the composition comprises one or more RNAi agents capable of a Fold-Change at 10 nM at 24 hr of ≤0.05, ≤0.10, ≤0.20, ≤0.30, ≤0.40 (indicating a Beta-Catenin gene knock-down of at least 95, 90, 80, 70, or 60%, respectively, at a concentration of 10 nM at 24 hrs in HeLa cells). RNAi agents capable of these levels of activity are disclosed in the Tables herein.

Embodiments Comprising One or More Efficacious RNAi Agents to Beta-Catenin

In various embodiments of the present disclosure, the composition comprises one or more RNAi agents capable of a Fold-Change at 0.1 nM at 120 hr of ≤0.30, ≤0.20, or ≤0.10 (indicating a Beta-Catenin gene knock-down of at least 70, 80, or 90%, respectively, at a concentration of 0.1 nM at 120 hrs in HeLa cells). RNAi agents capable of these levels of activity are disclosed in the Tables herein.

Various Embodiments Comprising One or More RNAi Agents to Beta-Catenin with Low EC50

In various embodiments of the present disclosure, the composition comprises one or more RNAi agents capable of mediating 50% gene knockdown (EC50) of Beta-Catenin at a low concentration in HeLa cells. For many of the RNAi agents listed herein, an estimated EC50 was calculated. Cells were treated at 10 nM, 1 nM, 0.1 nM, 0.01 nM, and 0.001 nM of RNAi agent, and the data fit to a curve. The indicated EC50 is an estimated EC50 calculated from available data that is expected to give 50% gene knock-down of Beta-Catenin in HeLa cells. In various embodiments of the present disclosure, the composition comprises one or more RNAi agents capable of mediating 50% gene knockdown (EC50) at 100, 75, 50, 25, 10, 5, 2.5, 1, 0.75, 0.5, 0.25, 0.2, 0.12, 0.1, 0.09, 0.08, 0.07, 0.06, 0.05, 0.04, 0.03, or 0.02 nM or less in HeLa cells. RNAi agents capable of these levels of activity are disclosed in the Tables herein.

Specific Embodiments of RNAi Agents to Beta-Catenin

In one embodiment, the present disclosure pertains to: a composition comprising any one or more of: a RNAi agent comprising a sense strand and an anti-sense strand, wherein the anti-sense strand comprises at least 15 contiguous nucleotides differing by 0, 1, 2, or 3 nucleotides from the anti-sense strand of: any RNAi agent from Tables 1, 2, 3, 4, 5, 6, 7, 8 and/or 9 and modified or unmodified variants thereof.

In one embodiment, the composition comprises any one or more of: a RNAi agent comprising a sense strand and an anti-sense strand, wherein the anti-sense strand comprises at least 15 contiguous nucleotides differing by 0 nucleotides from the anti-sense strand of any RNAi agent from Tables 1, 2, 3, 4, 5, 6, 7, 8 and/or 9, and modified and unmodified variants thereof.

In one embodiment, the present disclosure pertains to a composition comprising any one or more of: any RNAi agent from Tables 1, 2, 3, 4, 5, 6, 7, 8 and/or 9, and modified and unmodified variants thereof.

In one embodiment, the present disclosure pertains to a composition comprising any one or more of: a RNAi agent comprising an anti-sense strand comprising the sequence of the anti-sense strand of any RNAi agent from Tables 1, 2, 3, 4, 5, 6, 7, 8 and/or 9, and modified and unmodified variants thereof.

In one embodiment, the present disclosure pertains to a composition comprising any one or more of: a RNAi agent comprises an anti-sense strand consisting of the sequence of the anti-sense strand of any RNAi agent from Tables 1, 2, 3, 4, 5, 6, 7, 8 and/or 9, and modified and unmodified variants thereof.

In one embodiment, the present disclosure pertains to a composition comprising any one or more of: a RNAi agent comprising a first strand and a second strand, wherein the sequence of the first strand is the second of the first strand of any RNAi agent from Tables 1, 2, 3, 4, 5, 6, 7, 8 and/or 9, and modified and unmodified variants thereof.

In one embodiment, the present disclosure pertains to a composition comprising any one or more of: a RNAi agent comprising a first and a second strand, wherein the sequences of the first and the second strand are the sequences of the first and second strand of any RNAi agent from Tables 1, 2, 3, 4, 5, 6, 7, 8 and/or 9, and modified and unmodified variants thereof.

In one embodiment, the present disclosure pertains to a composition comprising any one or more of: a RNAi agent comprising a first strand and a second strand, wherein the sequence of the first strand is the second of the first strand of any RNAi agent from Tables 1, 2, 3, 4, 5, 6, 7, 8 and/or 9, and modified and unmodified variants thereof, wherein the first and/or second strand further comprise up to about 20 additional nucleotides.

Additional Embodiments of Specific RNAi Agents to Beta-Catenin

In one embodiment, the present disclosure comprises a RNAi agent comprising a first strand and a second strand, wherein the first strand comprises at least 15 contiguous nucleotides differing by 0, 1, 2, or 3 nt from the sequence of the first strand of any RNAi agent from Tables 1, 2, 3, 4, 5, 6, 7, 8 and/or 9, or modified or unmodified variants thereof.

Thus, in various embodiments, the present disclosure pertains to a composition comprising any one or more of the following:

A RNAi agent comprising: a first strand and a second strand, wherein the first strand comprises at least 15 contiguous nucleotides differing by 0, 1, 2, or 3 nt from the sequence of the first strand of: AD-26104, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26063, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26082, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26034, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26091, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26047, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26651, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26696, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26109, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25941, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26028, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26652, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26742, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26921, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18893, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18983, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25950, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25951, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26042, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26043, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26673, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26704, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26068, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26183, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26700, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26701, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25942, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26076, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26031, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26210, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26664, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26691, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26740, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-19765, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26158, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26180, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26078, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25894, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25964, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26156, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26670, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26743, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25890, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26044, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26685, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26731, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26800, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26066, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26682, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26684, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26757, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26788, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18963, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-19076, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25943, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26052, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26665, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26746, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18974, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25938, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25944, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26178, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26669, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26730, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26825, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25956, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26822, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26108, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26752, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26779, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25891, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26101, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26181, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26218, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26660, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18966, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-19074, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26179, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26722, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26768, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26920, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26020, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26713, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26727, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26808, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25958, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26105, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26674, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26781, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26801, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26813, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26816, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25945, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26203, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26021, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26040, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26069, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26134, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26702, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18933, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26690, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26698, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25910, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26747, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26810, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26083, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26061, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26904, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18903, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18980, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26202, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26679, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26719, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26758, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26783, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26902, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18892, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18897, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25902, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26705, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26782, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-19082, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26176, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26196, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26199, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26678, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26683, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26729, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26804, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26900, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25914, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26060, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26763, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18902, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18914, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26100, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26128, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26193, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26765, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25960, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26018, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25893, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26823, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25940, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26190, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26675, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26797, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26916, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26755, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26901, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-19004, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-19009, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26148, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26186, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26737, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25955, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26029, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26131, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18894, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18939, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26654, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18929, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26135, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26774, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26780, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26819, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26918, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-19050, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18994, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26769, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26666, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26784, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18969, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18986, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25929, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25932, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26095, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26908, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26071, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26912, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-19054, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25918, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26903, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25931, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26146, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26200, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26917, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26794, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26910, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25939, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26032, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26776, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26806, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26748, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26725, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18958, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26672, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26905, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-19056, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-19762, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26919, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18946, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-19066, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-19746, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26057, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26073, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26689, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-19008, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26026, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26761, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-19752, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18981, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18927, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-19753, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25907, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26671, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-19080, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26075, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26681, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18976, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25900, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26126, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26688, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25912, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25930, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18995, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26802, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25892, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25947, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26088, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26098, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26778, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26215, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26739, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18950, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25949, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26141, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18961, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25957, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26826, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25963, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26019, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26035, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25946, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26714, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26022, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26096, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26132, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26062, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18991, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26164, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26209, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25895, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25933, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26017, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-19749, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26653, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26759, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25924, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26153, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25953, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26764, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26790, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-20124, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25919, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18913, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26211, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18936, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25898, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26741, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-19043, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26079, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-19000, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25911, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26786, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-19069, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26037, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26723, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-19067, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25928, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26677, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-19006, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-19758, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26913, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25917, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26189, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26787, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26707, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26094, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26097, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26699, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26756, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26720, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25926, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26212, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26687, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26753, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18982, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18908, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18968, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25948, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26188, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26708, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25961, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26803, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-19741, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26056, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25959, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26059, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26102, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26106, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26744, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26099, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26170, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-19012, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26198, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26766, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18951, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18975, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26749, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18911, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26906, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-19747, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18960, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-25909, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26184, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26077, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26680, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26085, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18926, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18945, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26703, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26911, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26661, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-18905, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: AD-26142, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: Set1_1245, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: Set1_1249, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: Set1_1250, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: Set1_1450, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: Set1_1545, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: Set1_1755, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: Set1_1814, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: Set1_1816, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: Set1_1974, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: Set1_2202, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: Set1_2425, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: Set1_254, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: Set1_3146, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: Set1_3169, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: Set1_3196, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: Set1_3477, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: Set1_703, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: Set1_709, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: Set1_865, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: Set1_889, or modified or unmodified variants thereof.

A RNAi agent comprising: a first strand and a second strand, wherein the first strand comprises at least 15 contiguous nucleotides differing by 0, 1, 2, or 3 nt from the sequence of the first strand of: Set1_895, or modified or unmodified variants thereof.

In various embodiments, the first and second strand can be either the sense and anti-sense strand, or the anti-sense and sense strand.

Additional Embodiments of Specific RNAi Agents to Beta-Catenin

In one embodiment, the present disclosure comprises a RNAi agent comprising an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of any RNAi in Tables 1, 2, 3, 4, 5, 6, 7, 8 and/or 9, and modified and unmodified variants thereof.

Thus, in various embodiments, the present disclosure pertains to a composition comprising any one or more of the following:

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26104, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26063, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26082, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26034, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26091, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26047, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26651, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26696, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26109, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25941, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26028, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26652, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26742, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26921, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18893, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18983, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25950, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25951, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26042, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26043, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26673, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26704, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26068, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26183, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26700, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26701, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25942, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26076, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26031, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26210, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26664, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26691, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26740, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-19765, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26158, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26180, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26078, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25894, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25964, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26156, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26670, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26743, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25890, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26044, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26685, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26731, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26800, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26066, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26682, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26684, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26757, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26788, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18963, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-19076, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25943, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26052, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26665, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26746, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18974, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25938, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25944, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26178, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26669, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26730, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26825, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25956, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26822, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26108, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26752, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26779, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25891, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26101, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26181, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26218, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26660, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18966, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-19074, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26179, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26722, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26768, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26920, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26020, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26713, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26727, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26808, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25958, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26105, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26674, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26781, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26801, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26813, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26816, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25945, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26203, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26021, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26040, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26069, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26134, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26702, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18933, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26690, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26698, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25910, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26747, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26810, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26083, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26061, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26904, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18903, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18980, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26202, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26679, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26719, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26758, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26783, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26902, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18892, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18897, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25902, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26705, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26782, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-19082, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26176, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26196, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26199, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26678, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26683, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26729, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26804, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26900, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25914, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26060, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26763, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18902, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18914, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26100, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26128, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26193, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26765, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25960, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26018, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25893, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26823, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25940, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26190, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26675, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26797, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26916, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26755, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26901, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-19004, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-19009, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26148, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26186, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26737, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25955, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26029, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26131, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18894, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18939, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26654, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18929, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26135, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26774, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26780, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26819, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26918, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-19050, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18994, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26769, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26666, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26784, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18969, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18986, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25929, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25932, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26095, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26908, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26071, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26912, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-19054, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25918, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26903, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25931, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26146, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26200, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26917, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26794, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26910, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25939, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26032, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26776, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26806, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26748, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26725, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18958, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26672, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26905, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-19056, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-19762, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26919, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18946, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-19066, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-19746, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26057, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26073, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26689, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-19008, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26026, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26761, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-19752, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18981, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18927, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-19753, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25907, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26671, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-19080, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26075, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26681, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18976, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25900, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26126, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26688, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25912, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25930, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18995, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26802, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25892, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25947, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26088, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26098, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26778, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26215, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26739, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18950, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25949, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26141, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18961, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25957, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26826, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25963, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26019, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26035, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25946, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26714, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26022, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26096, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26132, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26062, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18991, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26164, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26209, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25895, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25933, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26017, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-19749, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26653, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26759, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25924, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26153, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25953, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26764, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26790, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-20124, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25919, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18913, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26211, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18936, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25898, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26741, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-19043, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26079, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-19000, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25911, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26786, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-19069, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26037, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26723, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-19067, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25928, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26677, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-19006, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-19758, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26913, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25917, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26189, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26787, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26707, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26094, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26097, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26699, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26756, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26720, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25926, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26212, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26687, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26753, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18982, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18908, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18968, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25948, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26188, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26708, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25961, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26803, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-19741, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26056, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25959, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26059, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26102, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26106, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26744, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26099, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26170, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-19012, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26198, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26766, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18951, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18975, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26749, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18911, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26906, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-19747, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18960, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-25909, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26184, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26077, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26680, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26085, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18926, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18945, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26703, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26911, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26661, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-18905, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of AD-26142, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of Set1_1245, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of Set1_1249, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of Set1_1250, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of Set1_1450, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of Set1_1545, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of Set1_1755, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of Set1_1814, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of Set1_1816, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of Set1_1974, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of Set1_2202, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of Set1_2425, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of Set1_254, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of Set1_3146, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of Set1_3169, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of Set1_3196, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of Set1_3477, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of Set1_703, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of Set1_709, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of Set1_865, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of Set1_889, or modified or unmodified variants thereof.

A RNAi agent comprising: an anti-sense strand comprising at least 15 contiguous nucleotides differing by 0, 1, 2, or 3 nt from the sequence of the anti-sense strand, and/or a sense strand comprising at least 15 contiguous nucleotides differing by 0, 1, 2, or 3 nt from the sequence of the sense strand, of Set1_895, or modified or unmodified variants thereof.

Additional Embodiments Encompassing Specific RNAi Agents to Beta-Catenin

In various embodiments, the present disclosure pertains to a composition comprising one or more of the following:

A RNAi agent comprising a sense strand and an anti-sense strand, wherein the sequence of the anti-sense strand is the sequence of the anti-sense strand of AD-26104.

A RNAi agent comprising a sense strand and an anti-sense strand, wherein the sequence of the anti-sense strand is the sequence of the anti-sense strand of AD-26063.

A RNAi agent comprising a sense strand and an anti-sense strand, wherein the sequence of the anti-sense strand is the sequence of the anti-sense strand of AD-26082.

A RNAi agent comprising a sense strand and an anti-sense strand, wherein the sequence of the anti-sense strand is the sequence of the anti-sense strand of AD-26034.

A RNAi agent comprising a sense strand and an anti-sense strand, wherein the sequence of the anti-sense strand is the sequence of the anti-sense strand of AD-26091.

A RNAi agent comprising a sense strand and an anti-sense strand, wherein the sequence of the anti-sense strand is the sequence of the anti-sense strand of AD-26047.

A RNAi agent comprising a sense strand and an anti-sense strand, wherein the sequence of the anti-sense strand is the sequence of the anti-sense strand of AD-26651.

A RNAi agent comprising a sense strand and an anti-sense strand, wherein the sequence of the anti-sense strand is the sequence of the anti-sense strand of AD-26696.

A RNAi agent comprising a sense strand and an anti-sense strand, wherein the sequence of the anti-sense strand is the sequence of the anti-sense strand of AD-26109.

A RNAi agent comprising a sense strand and an anti-sense strand, wherein the sequence of the anti-sense strand is the sequence of the anti-sense strand of AD-25941.

A RNAi agent comprising a sense strand and an anti-sense strand, wherein the sequence of the anti-sense strand is the sequence of the anti-sense strand of AD-26028.

A RNAi agent comprising a sense strand and an anti-sense strand, wherein the sequence of the anti-sense strand is the sequence of the anti-sense strand of AD-26652.

A RNAi agent comprising a sense strand and an anti-sense strand, wherein the sequence of the anti-sense strand is the sequence of the anti-sense strand of AD-26742.

A RNAi agent comprising a sense strand and an anti-sense strand, wherein the sequence of the anti-sense strand is the sequence of the anti-sense strand of AD-26921.

A RNAi agent comprising a sense strand and an anti-sense strand, wherein the sequence of the anti-sense strand is the sequence of the anti-sense strand of AD-18893.

A RNAi agent comprising a sense strand and an anti-sense strand, wherein the sequence of the anti-sense strand is the sequence of the anti-sense strand of AD-18983.

A RNAi agent comprising a sense strand and an anti-sense strand, wherein the sequence of the anti-sense strand is the sequence of the anti-sense strand of AD-25950.

A RNAi agent comprising a sense strand and an anti-sense strand, wherein the sequence of the anti-sense strand is the sequence of the anti-sense strand of AD-25951.

A RNAi agent comprising a sense strand and an anti-sense strand, wherein the sequence of the anti-sense strand is the sequence of the anti-sense strand of AD-26042.

A RNAi agent comprising a sense strand and an anti-sense strand, wherein the sequence of the anti-sense strand is the sequence of the anti-sense strand of AD-26043.

A RNAi agent comprising a sense strand and an anti-sense strand, wherein the sequence of the anti-sense strand is the sequence of the anti-sense strand of AD-26673.

A RNAi agent comprising a sense strand and an anti-sense strand, wherein the sequence of the anti-sense strand is the sequence of the anti-sense strand of AD-26704.

A RNAi agent comprising a sense strand and an anti-sense strand, wherein the sequence of the anti-sense strand is the sequence of the anti-sense strand of AD-26068.

A RNAi agent comprising a sense strand and an anti-sense strand, wherein the sequence of the anti-sense strand is the sequence of the anti-sense strand of AD-26183.

A RNAi agent comprising a sense strand and an anti-sense strand, wherein the sequence of the anti-sense strand is the sequence of the anti-sense strand of AD-26700.

A RNAi agent comprising a sense strand and an anti-sense strand, wherein the sequence of the anti-sense strand is the sequence of the anti-sense strand of AD-26701.

A RNAi agent comprising a sense strand and an anti-sense strand, wherein the sequence of the anti-sense strand is the sequence of the anti-sense strand of AD-25942.

A RNAi agent comprising a sense strand and an anti-sense strand, wherein the sequence of the anti-sense strand is the sequence of the anti-sense strand of AD-26076.

A RNAi agent comprising a sense strand and an anti-sense strand, wherein the sequence of the anti-sense strand is the sequence of the anti-sense strand of AD-26031.

A RNAi agent comprising a sense strand and an anti-sense strand, wherein the sequence of the anti-sense strand is the sequence of the anti-sense strand of AD-26210.

A RNAi agent comprising a sense strand and an anti-sense strand, wherein the sequence of the anti-sense strand is the sequence of the anti-sense strand of AD-26664.

A RNAi agent comprising a sense strand and an anti-sense strand, wherein the sequence of the anti-sense strand is the sequence of the anti-sense strand of AD-26691.

A RNAi agent comprising a sense strand and an anti-sense strand, wherein the sequence of the anti-sense strand is the sequence of the anti-sense strand of AD-26740.

A RNAi agent comprising a sense strand and an anti-sense strand, wherein the sequence of the anti-sense strand is the sequence of the anti-sense strand of AD-19765.

A RNAi agent comprising a sense strand and an anti-sense strand, wherein the sequence of the anti-sense strand is the sequence of the anti-sense strand of AD-26158.

A RNAi agent comprising a sense strand and an anti-sense strand, wherein the sequence of the anti-sense strand is the sequence of the anti-sense strand of AD-26180.

A RNAi agent comprising a sense strand and an anti-sense strand, wherein the sequence of the anti-sense strand is the sequence of the anti-sense strand of AD-26078.

A RNAi agent comprising a sense strand and an anti-sense strand, wherein the sequence of the anti-sense strand is the sequence of the anti-sense strand of AD-25894.

A RNAi agent comprising a sense strand and an anti-sense strand, wherein the sequence of the anti-sense strand is the sequence of the anti-sense strand of AD-25964.

A RNAi agent comprising a sense strand and an anti-sense strand, wherein the sequence of the anti-sense strand is the sequence of the anti-sense strand of AD-26156.

A RNAi agent comprising a sense strand and an anti-sense strand, wherein the sequence of the anti-sense strand is the sequence of the anti-sense strand of AD-26670.

A RNAi agent comprising a sense strand and an anti-sense strand, wherein the sequence of the anti-sense strand is the sequence of the anti-sense strand of AD-26743.

A RNAi agent comprising a sense strand and an anti-sense strand, wherein the sequence of the anti-sense strand is the sequence of the anti-sense strand of AD-25890.

A RNAi agent comprising a sense strand and an anti-sense strand, wherein the sequence of the anti-sense strand is the sequence of the anti-sense strand of AD-26044.

A RNAi agent comprising a sense strand and an anti-sense strand, wherein the sequence of the anti-sense strand is the sequence of the anti-sense strand of AD-26685.

A RNAi agent comprising a sense strand and an anti-sense strand, wherein the sequence of the anti-sense strand is the sequence of the anti-sense strand of AD-26731.

A RNAi agent comprising a sense strand and an anti-sense strand, wherein the sequence of the anti-sense strand is the sequence of the anti-sense strand of AD-26800.

A RNAi agent comprising a sense strand and an anti-sense strand, wherein the sequence of the anti-sense strand is the sequence of the anti-sense strand of AD-26066.

A RNAi agent comprising a sense strand and an anti-sense strand, wherein the sequence of the anti-sense strand is the sequence of the anti-sense strand of AD-26682.

A RNAi agent comprising a sense strand and an anti-sense strand, wherein the sequence of the anti-sense strand is the sequence of the anti-sense strand of AD-26684.

A RNAi agent comprising a sense strand and an anti-sense strand, wherein the sequence of the anti-sense strand is the sequence of the anti-sense strand of AD-26757.

A RNAi agent comprising a sense strand and an anti-sense strand, wherein the sequence of the anti-sense strand is the sequence of the anti-sense strand of AD-26788.

A RNAi agent comprising a sense strand and an anti-sense strand, wherein the sequence of the anti-sense strand is the sequence of the anti-sense strand of AD-18963.

A RNAi agent comprising a sense strand and an anti-sense strand, wherein the sequence of the anti-sense strand is the sequence of the anti-sense strand of AD-19076.

A RNAi agent comprising a sense strand and an anti-sense strand, wherein the sequence of the anti-sense strand is the sequence of the anti-sense strand of AD-25943.

A RNAi agent comprising a sense strand and an anti-sense strand, wherein the sequence of the anti-sense strand is the sequence of the anti-sense strand of AD-26052.

A RNAi agent comprising a sense strand and an anti-sense strand, wherein the sequence of the anti-sense strand is the sequence of the anti-sense strand of AD-26665.

A RNAi agent comprising a sense strand and an anti-sense strand, wherein the sequence of the anti-sense strand is the sequence of the anti-sense strand of AD-26746.

A RNAi agent comprising a sense strand and an anti-sense strand, wherein the sequence of the anti-sense strand is the sequence of the anti-sense strand of AD-18974.

A RNAi agent comprising a sense strand and an anti-sense strand, wherein the sequence of the anti-sense strand is the sequence of the anti-sense strand of AD-25938.

A RNAi agent comprising a sense strand and an anti-sense strand, wherein the sequence of the anti-sense strand is the sequence of the anti-sense strand of AD-25944.

A RNAi agent comprising a sense strand and an anti-sense strand, wherein the sequence of the anti-sense strand is the sequence of the anti-sense strand of AD-26178.

A RNAi agent comprising a sense strand and an anti-sense strand, wherein the sequence of the anti-sense strand is the sequence of the anti-sense strand of AD-26669.

A RNAi agent comprising a sense strand and an anti-sense strand, wherein the sequence of the anti-sense strand is the sequence of the anti-sense strand of AD-26730.

A RNAi agent comprising a sense strand and an anti-sense strand, wherein the sequence of the anti-sense strand is the sequence of the anti-sense strand of AD-26825.

A RNAi agent comprising a sense strand and an anti-sense strand, wherein the sequence of the anti-sense strand is the sequence of the anti-sense strand of AD-25956.

A RNAi agent comprising a sense strand and an anti-sense strand, wherein the sequence of the anti-sense strand is the sequence of the anti-sense strand of AD-26822.

A RNAi agent comprising a sense strand and an anti-sense strand, wherein the sequence of the anti-sense strand is the sequence of the anti-sense strand of AD-26108.

A RNAi agent comprising a sense strand and an anti-sense strand, wherein the sequence of the anti-sense strand is the sequence of the anti-sense strand of AD-26752.

A RNAi agent comprising a sense strand and an anti-sense strand, wherein the sequence of the anti-sense strand is the sequence of the anti-sense strand of AD-26779.

A RNAi agent comprising a sense strand and an anti-sense strand, wherein the sequence of the anti-sense strand is the sequence of the anti-sense strand of AD-25891.

A RNAi agent comprising a sense strand and an anti-sense strand, wherein the sequence of the anti-sense strand is the sequence of the anti-sense strand of AD-26101.

A RNAi agent comprising a sense strand and an anti-sense strand, wherein the sequence of the anti-sense strand is the sequence of the anti-sense strand of AD-26181.

A RNAi agent comprising a sense strand and an anti-sense strand, wherein the sequence of the anti-sense strand is the sequence of the anti-sense strand of AD-26218.

A RNAi agent comprising a sense strand and an anti-sense strand, wherein the sequence of the anti-sense strand is the sequence of the anti-sense strand of AD-26660.

A RNAi agent comprising a sense strand and an anti-sense strand, wherein the sequence of the anti-sense strand is the sequence of the anti-sense strand of AD-18966.

A RNAi agent comprising a sense strand and an anti-sense strand, wherein the sequence of the anti-sense strand is the sequence of the anti-sense strand of AD-19074.

A RNAi agent comprising a sense strand and an anti-sense strand, wherein the sequence of the anti-sense strand is the sequence of the anti-sense strand of AD-26179.

A RNAi agent comprising a sense strand and an anti-sense strand, wherein the sequence of the anti-sense strand is the sequence of the anti-sense strand of AD-26722.

A RNAi agent comprising a sense strand and an anti-sense strand, wherein the sequence of the anti-sense strand is the sequence of the anti-sense strand of AD-26768.

A RNAi agent comprising a sense strand and an anti-sense strand, wherein the sequence of the anti-sense strand is the sequence of the anti-sense strand of AD-26920.

A RNAi agent comprising a sense strand and an anti-sense strand, wherein the sequence of the anti-sense strand is the sequence of the anti-sense strand of AD-26020.

A RNAi agent comprising a sense strand and an anti-sense strand, wherein the sequence of the anti-sense strand is the sequence of the anti-sense strand of AD-26713.

A RNAi agent comprising a sense strand and an anti-sense strand, wherein the sequence of the anti-sense strand is the sequence of the anti-sense strand of AD-26727.

A RNAi agent comprising a sense strand and an anti-sense strand, wherein the sequence of the anti-sense strand is the sequence of the anti-sense strand of AD-26808.

A RNAi agent comprising a sense strand and an anti-sense strand, wherein the sequence of the anti-sense strand is the sequence of the anti-sense strand of AD-25958.

A RNAi agent comprising a sense strand and an anti-sense strand, wherein the sequence of the anti-sense strand is the sequence of the anti-sense strand of AD-26105.

A RNAi agent comprising a sense strand and an anti-sense strand, wherein the sequence of the anti-sense strand is the sequence of the anti-sense strand of AD-26674.

A RNAi agent comprising a sense strand and an anti-sense strand, wherein the sequence of the anti-sense strand is the sequence of the anti-sense strand of AD-26781.

A RNAi agent comprising a sense strand and an anti-sense strand, wherein the sequence of the anti-sense strand is the sequence of the anti-sense strand of AD-26801.

A RNAi agent comprising a sense strand and an anti-sense strand, wherein the sequence of the anti-sense strand is the sequence of the anti-sense strand of AD-26813.

A RNAi agent comprising a sense strand and an anti-sense strand, wherein the sequence of the anti-sense strand is the sequence of the anti-sense strand of AD-26816.

A RNAi agent comprising a sense strand and an anti-sense strand, wherein the sequence of the anti-sense strand is the sequence of the anti-sense strand of AD-25945.

A RNAi agent comprising a sense strand and an anti-sense strand, wherein the sequence of the anti-sense strand is the sequence of the anti-sense strand of AD-26203.

A RNAi agent comprising a sense strand and an anti-sense strand, wherein the sequence of the anti-sense strand is the sequence of the anti-sense strand of AD-26021.

A RNAi agent comprising a sense strand and an anti-sense strand, wherein the sequence of the anti-sense strand is the sequence of the anti-sense strand of AD-26040.

A RNAi agent comprising a sense strand and an anti-sense strand, wherein the sequence of the anti-sense strand is the sequence of the anti-sense strand of AD-26069.

A RNAi agent comprising a sense strand and an anti-sense strand, wherein the sequence of the anti-sense strand is the sequence of the anti-sense strand of AD-26134.

A RNAi agent comprising a sense strand and an anti-sense strand, wherein the sequence of the anti-sense strand is the sequence of the anti-sense strand of AD-26702.

A RNAi agent comprising a sense strand and an anti-sense strand, wherein the sequence of the anti-sense strand is the sequence of the anti-sense strand of AD-18933.

A RNAi agent comprising a sense strand and an anti-sense strand, wherein the sequence of the anti-sense strand is the sequence of the anti-sense strand of AD-26690.

A RNAi agent comprising a sense strand and an anti-sense strand, wherein the sequence of the anti-sense strand is the sequence of the anti-sense strand of AD-26698.

A RNAi agent comprising a sense strand and an anti-sense strand, wherein the sequence of the anti-sense strand is the sequence of the anti-sense strand of AD-25910.

A RNAi agent comprising a sense strand and an anti-sense strand, wherein the sequence of the anti-sense strand is the sequence of the anti-sense strand of AD-26747.

A RNAi agent comprising a sense strand and an anti-sense strand, wherein the sequence of the anti-sense strand is the sequence of the anti-sense strand of AD-26810.

A RNAi agent comprising a sense strand and an anti-sense strand, wherein the sequence of the anti-sense strand is the sequence of the anti-sense strand of AD-26083.

A RNAi agent comprising a sense strand and an anti-sense strand, wherein the sequence of the anti-sense strand is the sequence of the anti-sense strand of AD-26061.

A RNAi agent comprising a sense strand and an anti-sense strand, wherein the sequence of the anti-sense strand is the sequence of the anti-sense strand of AD-26904.

A RNAi agent comprising a sense strand and an anti-sense strand, wherein the sequence of the anti-sense strand is the sequence of the anti-sense strand of AD-18903.

A RNAi agent comprising a sense strand and an anti-sense strand, wherein the sequence of the anti-sense strand is the sequence of the anti-sense strand of AD-18980.

A RNAi agent comprising a sense strand and an anti-sense strand, wherein the sequence of the anti-sense strand is the sequence of the anti-sense strand of AD-26202.

A RNAi agent comprising a sense strand and an anti-sense strand, wherein the sequence of the anti-sense strand is the sequence of the anti-sense strand of AD-26679.

A RNAi agent comprising a sense strand and an anti-sense strand, wherein the sequence of the anti-sense strand is the sequence of the anti-sense strand of AD-26719.

A RNAi agent comprising a sense strand and an anti-sense strand, wherein the sequence of the anti-sense strand is the sequence of the anti-sense strand of AD-26758.

A RNAi agent comprising a sense strand and an anti-sense strand, wherein the sequence of the anti-sense strand is the sequence of the anti-sense strand of AD-26783.

A RNAi agent comprising a sense strand and an anti-sense strand, wherein the sequence of the anti-sense strand is the sequence of the anti-sense strand of AD-26902.

A RNAi agent comprising a sense strand and an anti-sense strand, wherein the sequence of the anti-sense strand is the sequence of the anti-sense strand of AD-18892.

A RNAi agent comprising a sense strand and an anti-sense strand, wherein the sequence of the anti-sense strand is the sequence of the anti-sense strand of AD-18897.

A RNAi agent comprising a sense strand and an anti-sense strand, wherein the sequence of the anti-sense strand is the sequence of the anti-sense strand of AD-25902.

A RNAi agent comprising a sense strand and an anti-sense strand, wherein the sequence of the anti-sense strand is the sequence of the anti-sense strand of AD-26705.

A RNAi agent comprising a sense strand and an anti-sense strand, wherein the sequence of the anti-sense strand is the sequence of the anti-sense strand of AD-26782.

A RNAi agent comprising a sense strand and an anti-sense strand, wherein the sequence of the anti-sense strand is the sequence of the anti-sense strand of AD-19082.

A RNAi agent comprising a sense strand and an anti-sense strand, wherein the sequence of the anti-sense strand is the sequence of the anti-sense strand of AD-26176.

A RNAi agent comprising a sense strand and an anti-sense strand, wherein the sequence of the anti-sense strand is the sequence of the anti-sense strand of AD-26196.

A RNAi agent comprising a sense strand and an anti-sense strand, wherein the sequence of the anti-sense strand is the sequence of the anti-sense strand of AD-26199.

A RNAi agent comprising a sense strand and an anti-sense strand, wherein the sequence of the anti-sense strand is the sequence of the anti-sense strand of AD-26678.

A RNAi agent comprising a sense strand and an anti-sense strand, wherein the sequence of the anti-sense strand is the sequence of the anti-sense strand of AD-26683.

A RNAi agent comprising a sense strand and an anti-sense strand, wherein the sequence of the anti-sense strand is the sequence of the anti-sense strand of AD-26729.

A RNAi agent comprising a sense strand and an anti-sense strand, wherein the sequence of the anti-sense strand is the sequence of the anti-sense strand of AD-26804.

A RNAi agent comprising a sense strand and an anti-sense strand, wherein the sequence of the anti-sense strand is the sequence of the anti-sense strand of AD-26900.

A RNAi agent comprising a sense strand and an anti-sense strand, wherein the sequence of the anti-sense strand is the sequence of the anti-sense strand of AD-25914.

A RNAi agent comprising a sense strand and an anti-sense strand, wherein the sequence of the anti-sense strand is the sequence of the anti-sense strand of AD-26060.

A RNAi agent comprising a sense strand and an anti-sense strand, wherein the sequence of the anti-sense strand is the sequence of the anti-sense strand of AD-26763.

A RNAi agent comprising a sense strand and an anti-sense strand, wherein the sequence of the anti-sense strand is the sequence of the anti-sense strand of AD-18902.

A RNAi agent comprising a sense strand and an anti-sense strand, wherein the sequence of the anti-sense strand is the sequence of the anti-sense strand of AD-18914.

A RNAi agent comprising a sense strand and an anti-sense strand, wherein the sequence of the anti-sense strand is the sequence of the anti-sense strand of AD-26100.

A RNAi agent comprising a sense strand and an anti-sense strand, wherein the sequence of the anti-sense strand is the sequence of the anti-sense strand of AD-26128.

A RNAi agent comprising a sense strand and an anti-sense strand, wherein the sequence of the anti-sense strand is the sequence of the anti-sense strand of AD-26193.

A RNAi agent comprising a sense strand and an anti-sense strand, wherein the sequence of the anti-sense strand is the sequence of the anti-sense strand of AD-26765.

A RNAi agent comprising a sense strand and an anti-sense strand, wherein the sequence of the anti-sense strand is the sequence of the anti-sense strand of AD-25960.

A RNAi agent comprising a sense strand and an anti-sense strand, wherein the sequence of the anti-sense strand is the sequence of the anti-sense strand of AD-26018.

A RNAi agent comprising a sense strand and an anti-sense strand, wherein the sequence of the anti-sense strand is the sequence of the anti-sense strand of AD-25893.

A RNAi agent comprising a sense strand and an anti-sense strand, wherein the sequence of the anti-sense strand is the sequence of the anti-sense strand of AD-26823.

A RNAi agent comprising a sense strand and an anti-sense strand, wherein the sequence of the anti-sense strand is the sequence of the anti-sense strand of AD-25940.

A RNAi agent comprising a sense strand and an anti-sense strand, wherein the sequence of the anti-sense strand is the sequence of the anti-sense strand of AD-26190.

A RNAi agent comprising a sense strand and an anti-sense strand, wherein the sequence of the anti-sense strand is the sequence of the anti-sense strand of AD-26675.

A RNAi agent comprising a sense strand and an anti-sense strand, wherein the sequence of the anti-sense strand is the sequence of the anti-sense strand of AD-26797.

A RNAi agent comprising a sense strand and an anti-sense strand, wherein the sequence of the anti-sense strand is the sequence of the anti-sense strand of AD-26916.

A RNAi agent comprising a sense strand and an anti-sense strand, wherein the sequence of the anti-sense strand is the sequence of the anti-sense strand of AD-26755.

A RNAi agent comprising a sense strand and an anti-sense strand, wherein the sequence of the anti-sense strand is the sequence of the anti-sense strand of AD-26901.

A RNAi agent comprising a sense strand and an anti-sense strand, wherein the sequence of the anti-sense strand is the sequence of the anti-sense strand of AD-19004.

A RNAi agent comprising a sense strand and an anti-sense strand, wherein the sequence of the anti-sense strand is the sequence of the anti-sense strand of AD-19009.

A RNAi agent comprising a sense strand and an anti-sense strand, wherein the sequence of the anti-sense strand is the sequence of the anti-sense strand of AD-26148.

A RNAi agent comprising a sense strand and an anti-sense strand, wherein the sequence of the anti-sense strand is the sequence of the anti-sense strand of AD-26186.

A RNAi agent comprising a sense strand and an anti-sense strand, wherein the sequence of the anti-sense strand is the sequence of the anti-sense strand of AD-26737.

A RNAi agent comprising a sense strand and an anti-sense strand, wherein the sequence of the anti-sense strand is the sequence of the anti-sense strand of AD-25955.

A RNAi agent comprising a sense strand and an anti-sense strand, wherein the sequence of the anti-sense strand is the sequence of the anti-sense strand of AD-26029.

A RNAi agent comprising a sense strand and an anti-sense strand, wherein the sequence of the anti-sense strand is the sequence of the anti-sense strand of AD-26131.

A RNAi agent comprising a sense strand and an anti-sense strand, wherein the sequence of the anti-sense strand is the sequence of the anti-sense strand of AD-18894.

A RNAi agent comprising a sense strand and an anti-sense strand, wherein the sequence of the anti-sense strand is the sequence of the anti-sense strand of AD-18939.

A RNAi agent comprising a sense strand and an anti-sense strand, wherein the sequence of the anti-sense strand is the sequence of the anti-sense strand of AD-26654.

A RNAi agent comprising a sense strand and an anti-sense strand, wherein the sequence of the anti-sense strand is the sequence of the anti-sense strand of AD-18929.

A RNAi agent comprising a sense strand and an anti-sense strand, wherein the sequence of the anti-sense strand is the sequence of the anti-sense strand of AD-26135.

A RNAi agent comprising a sense strand and an anti-sense strand, wherein the sequence of the anti-sense strand is the sequence of the anti-sense strand of AD-26774.

A RNAi agent comprising a sense strand and an anti-sense strand, wherein the sequence of the anti-sense strand is the sequence of the anti-sense strand of AD-26780.

A RNAi agent comprising a sense strand and an anti-sense strand, wherein the sequence of the anti-sense strand is the sequence of the anti-sense strand of AD-26819.

A RNAi agent comprising a sense strand and an anti-sense strand, wherein the sequence of the anti-sense strand is the sequence of the anti-sense strand of AD-26918.

A RNAi agent comprising a sense strand and an anti-sense strand, wherein the sequence of the anti-sense strand is the sequence of the anti-sense strand of AD-19050.

A RNAi agent comprising a sense strand and an anti-sense strand, wherein the sequence of the anti-sense strand is the sequence of the anti-sense strand of AD-18994.

A RNAi agent comprising a sense strand and an anti-sense strand, wherein the sequence of the anti-sense strand is the sequence of the anti-sense strand of AD-26769.

A RNAi agent comprising a sense strand and an anti-sense strand, wherein the sequence of the anti-sense strand is the sequence of the anti-sense strand of AD-26666.

A RNAi agent comprising a sense strand and an anti-sense strand, wherein the sequence of the anti-sense strand is the sequence of the anti-sense strand of AD-26784.

A RNAi agent comprising a sense strand and an anti-sense strand, wherein the sequence of the anti-sense strand is the sequence of the anti-sense strand of AD-18969.

A RNAi agent comprising a sense strand and an anti-sense strand, wherein the sequence of the anti-sense strand is the sequence of the anti-sense strand of AD-18986.

A RNAi agent comprising a sense strand and an anti-sense strand, wherein the sequence of the anti-sense strand is the sequence of the anti-sense strand of AD-25929.

A RNAi agent comprising a sense strand and an anti-sense strand, wherein the sequence of the anti-sense strand is the sequence of the anti-sense strand of AD-25932.

A RNAi agent comprising a sense strand and an anti-sense strand, wherein the sequence of the anti-sense strand is the sequence of the anti-sense strand of AD-26095.

A RNAi agent comprising a sense strand and an anti-sense strand, wherein the sequence of the anti-sense strand is the sequence of the anti-sense strand of AD-26908.

A RNAi agent comprising a sense strand and an anti-sense strand, wherein the sequence of the anti-sense strand is the sequence of the anti-sense strand of AD-26071.

A RNAi agent comprising a sense strand and an anti-sense strand, wherein the sequence of the anti-sense strand is the sequence of the anti-sense strand of AD-26912.

A RNAi agent comprising a sense strand and an anti-sense strand, wherein the sequence of the anti-sense strand is the sequence of the anti-sense strand of AD-19054.

A RNAi agent comprising a sense strand and an anti-sense strand, wherein the sequence of the anti-sense strand is the sequence of the anti-sense strand of AD-25918.

A RNAi agent comprising a sense strand and an anti-sense strand, wherein the sequence of the anti-sense strand is the sequence of the anti-sense strand of AD-26903.

A RNAi agent comprising a sense strand and an anti-sense strand, wherein the sequence of the anti-sense strand is the sequence of the anti-sense strand of AD-25931.

A RNAi agent comprising a sense strand and an anti-sense strand, wherein the sequence of the anti-sense strand is the sequence of the anti-sense strand of AD-26146.

A RNAi agent comprising a sense strand and an anti-sense strand, wherein the sequence of the anti-sense strand is the sequence of the anti-sense strand of AD-26200.

A RNAi agent comprising a sense strand and an anti-sense strand, wherein the sequence of the anti-sense strand is the sequence of the anti-sense strand of AD-26917.

A RNAi agent comprising a sense strand and an anti-sense strand, wherein the sequence of the anti-sense strand is the sequence of the anti-sense strand of AD-26794.

A RNAi agent comprising a sense strand and an anti-sense strand, wherein the sequence of the anti-sense strand is the sequence of the anti-sense strand of AD-26910.

A RNAi agent comprising a sense strand and an anti-sense strand, wherein the sequence of the anti-sense strand is the sequence of the anti-sense strand of AD-25939.

A RNAi agent comprising a sense strand and an anti-sense strand, wherein the sequence of the anti-sense strand is the sequence of the anti-sense strand of AD-26032.

A RNAi agent comprising a sense strand and an anti-sense strand, wherein the sequence of the anti-sense strand is the sequence of the anti-sense strand of AD-26776.

A RNAi agent comprising a sense strand and an anti-sense strand, wherein the sequence of the anti-sense strand is the sequence of the anti-sense strand of AD-26806.

A RNAi agent comprising a sense strand and an anti-sense strand, wherein the sequence of the anti-sense strand is the sequence of the anti-sense strand of AD-26748.

A RNAi agent comprising a sense strand and an anti-sense strand, wherein the sequence of the anti-sense strand is the sequence of the anti-sense strand of AD-26725.

A RNAi agent comprising a sense strand and an anti-sense strand, wherein the sequence of the anti-sense strand is the sequence of the anti-sense strand of AD-18958.

A RNAi agent comprising a sense strand and an anti-sense strand, wherein the sequence of the anti-sense strand is the sequence of the anti-sense strand of AD-26672.

A RNAi agent comprising a sense strand and an anti-sense strand, wherein the sequence of the anti-sense strand is the sequence of the anti-sense strand of AD-26905.

A RNAi agent comprising a sense strand and an anti-sense strand, wherein the sequence of the anti-sense strand is the sequence of the anti-sense strand of AD-19056.

A RNAi agent comprising a sense strand and an anti-sense strand, wherein the sequence of the anti-sense strand is the sequence of the anti-sense strand of AD-19762.

A RNAi agent comprising a sense strand and an anti-sense strand, wherein the sequence of the anti-sense strand is the sequence of the anti-sense strand of AD-26919.

A RNAi agent comprising a sense strand and an anti-sense strand, wherein the sequence of the anti-sense strand is the sequence of the anti-sense strand of AD-18946.

A RNAi agent comprising a sense strand and an anti-sense strand, wherein the sequence of the anti-sense strand is the sequence of the anti-sense strand of AD-19066.

A RNAi agent comprising a sense strand and an anti-sense strand, wherein the sequence of the anti-sense strand is the sequence of the anti-sense strand of AD-19746.

A RNAi agent comprising a sense strand and an anti-sense strand, wherein the sequence of the anti-sense strand is the sequence of the anti-sense strand of AD-26057.

A RNAi agent comprising a sense strand and an anti-sense strand, wherein the sequence of the anti-sense strand is the sequence of the anti-sense strand of AD-26073.

A RNAi agent comprising a sense strand and an anti-sense strand, wherein the sequence of the anti-sense strand is the sequence of the anti-sense strand of AD-26689.

A RNAi agent comprising a sense strand and an anti-sense strand, wherein the sequence of the anti-sense strand is the sequence of the anti-sense strand of AD-19008.

A RNAi agent comprising a sense strand and an anti-sense strand, wherein the sequence of the anti-sense strand is the sequence of the anti-sense strand of AD-26026.

A RNAi agent comprising a sense strand and an anti-sense strand, wherein the sequence of the anti-sense strand is the sequence of the anti-sense strand of AD-26761.

A RNAi agent comprising a sense strand and an anti-sense strand, wherein the sequence of the anti-sense strand is the sequence of the anti-sense strand of AD-19752.

A RNAi agent comprising a sense strand and an anti-sense strand, wherein the sequence of the anti-sense strand is the sequence of the anti-sense strand of AD-18981.

A RNAi agent comprising a sense strand and an anti-sense strand, wherein the sequence of the anti-sense strand is the sequence of the anti-sense strand of AD-18927.

A RNAi agent comprising a sense strand and an anti-sense strand, wherein the sequence of the anti-sense strand is the sequence of the anti-sense strand of AD-19753.

A RNAi agent comprising a sense strand and an anti-sense strand, wherein the sequence of the anti-sense strand is the sequence of the anti-sense strand of AD-25907.

A RNAi agent comprising a sense strand and an anti-sense strand, wherein the sequence of the anti-sense strand is the sequence of the anti-sense strand of AD-26671.

A RNAi agent comprising a sense strand and an anti-sense strand, wherein the sequence of the anti-sense strand is the sequence of the anti-sense strand of AD-19080.

A RNAi agent comprising a sense strand and an anti-sense strand, wherein the sequence of the anti-sense strand is the sequence of the anti-sense strand of AD-26075.

A RNAi agent comprising a sense strand and an anti-sense strand, wherein the sequence of the anti-sense strand is the sequence of the anti-sense strand of AD-26681.

A RNAi agent comprising a sense strand and an anti-sense strand, wherein the sequence of the anti-sense strand is the sequence of the anti-sense strand of AD-18976.

A RNAi agent comprising a sense strand and an anti-sense strand, wherein the sequence of the anti-sense strand is the sequence of the anti-sense strand of AD-25900.

A RNAi agent comprising a sense strand and an anti-sense strand, wherein the sequence of the anti-sense strand is the sequence of the anti-sense strand of AD-26126.

A RNAi agent comprising a sense strand and an anti-sense strand, wherein the sequence of the anti-sense strand is the sequence of the anti-sense strand of AD-26688.

A RNAi agent comprising a sense strand and an anti-sense strand, wherein the sequence of the anti-sense strand is the sequence of the anti-sense strand of AD-25912.

A RNAi agent comprising a sense strand and an anti-sense strand, wherein the sequence of the anti-sense strand is the sequence of the anti-sense strand of AD-25930.

A RNAi agent comprising a sense strand and an anti-sense strand, wherein the sequence of the anti-sense strand is the sequence of the anti-sense strand of AD-18995.

A RNAi agent comprising a sense strand and an anti-sense strand, wherein the sequence of the anti-sense strand is the sequence of the anti-sense strand of AD-26802.

A RNAi agent comprising a sense strand and an anti-sense strand, wherein the sequence of the anti-sense strand is the sequence of the anti-sense strand of AD-25892.

A RNAi agent comprising a sense strand and an anti-sense strand, wherein the sequence of the anti-sense strand is the sequence of the anti-sense strand of AD-25947.

A RNAi agent comprising a sense strand and an anti-sense strand, wherein the sequence of the anti-sense strand is the sequence of the anti-sense strand of AD-26088.

A RNAi agent comprising a sense strand and an anti-sense strand, wherein the sequence of the anti-sense strand is the sequence of the anti-sense strand of AD-26098.

A RNAi agent comprising a sense strand and an anti-sense strand, wherein the sequence of the anti-sense strand is the sequence of the anti-sense strand of AD-26778.

A RNAi agent comprising a sense strand and an anti-sense strand, wherein the sequence of the anti-sense strand is the sequence of the anti-sense strand of AD-26215.

A RNAi agent comprising a sense strand and an anti-sense strand, wherein the sequence of the anti-sense strand is the sequence of the anti-sense strand of AD-26739.

A RNAi agent comprising a sense strand and an anti-sense strand, wherein the sequence of the anti-sense strand is the sequence of the anti-sense strand of AD-18950.

A RNAi agent comprising a sense strand and an anti-sense strand, wherein the sequence of the anti-sense strand is the sequence of the anti-sense strand of AD-25949.

A RNAi agent comprising a sense strand and an anti-sense strand, wherein the sequence of the anti-sense strand is the sequence of the anti-sense strand of AD-26141.

A RNAi agent comprising a sense strand and an anti-sense strand, wherein the sequence of the anti-sense strand is the sequence of the anti-sense strand of AD-18961.

A RNAi agent comprising a sense strand and an anti-sense strand, wherein the sequence of the anti-sense strand is the sequence of the anti-sense strand of AD-25957.

A RNAi agent comprising a sense strand and an anti-sense strand, wherein the sequence of the anti-sense strand is the sequence of the anti-sense strand of AD-26826.

A RNAi agent comprising a sense strand and an anti-sense strand, wherein the sequence of the anti-sense strand is the sequence of the anti-sense strand of AD-25963.

A RNAi agent comprising a sense strand and an anti-sense strand, wherein the sequence of the anti-sense strand is the sequence of the anti-sense strand of AD-26019.

A RNAi agent comprising a sense strand and an anti-sense strand, wherein the sequence of the anti-sense strand is the sequence of the anti-sense strand of AD-26035.

A RNAi agent comprising a sense strand and an anti-sense strand, wherein the sequence of the anti-sense strand is the sequence of the anti-sense strand of AD-25946.

A RNAi agent comprising a sense strand and an anti-sense strand, wherein the sequence of the anti-sense strand is the sequence of the anti-sense strand of AD-26714.

A RNAi agent comprising a sense strand and an anti-sense strand, wherein the sequence of the anti-sense strand is the sequence of the anti-sense strand of AD-26022.

A RNAi agent comprising a sense strand and an anti-sense strand, wherein the sequence of the anti-sense strand is the sequence of the anti-sense strand of AD-26096.

A RNAi agent comprising a sense strand and an anti-sense strand, wherein the sequence of the anti-sense strand is the sequence of the anti-sense strand of AD-26132.

A RNAi agent comprising a sense strand and an anti-sense strand, wherein the sequence of the anti-sense strand is the sequence of the anti-sense strand of AD-26062.

A RNAi agent comprising a sense strand and an anti-sense strand, wherein the sequence of the anti-sense strand is the sequence of the anti-sense strand of AD-18991.

A RNAi agent comprising a sense strand and an anti-sense strand, wherein the sequence of the anti-sense strand is the sequence of the anti-sense strand of AD-26164.

A RNAi agent comprising a sense strand and an anti-sense strand, wherein the sequence of the anti-sense strand is the sequence of the anti-sense strand of AD-26209.

A RNAi agent comprising a sense strand and an anti-sense strand, wherein the sequence of the anti-sense strand is the sequence of the anti-sense strand of AD-25895.

A RNAi agent comprising a sense strand and an anti-sense strand, wherein the sequence of the anti-sense strand is the sequence of the anti-sense strand of AD-25933.

A RNAi agent comprising a sense strand and an anti-sense strand, wherein the sequence of the anti-sense strand is the sequence of the anti-sense strand of AD-26017.

A RNAi agent comprising a sense strand and an anti-sense strand, wherein the sequence of the anti-sense strand is the sequence of the anti-sense strand of AD-19749.

A RNAi agent comprising a sense strand and an anti-sense strand, wherein the sequence of the anti-sense strand is the sequence of the anti-sense strand of AD-26653.

A RNAi agent comprising a sense strand and an anti-sense strand, wherein the sequence of the anti-sense strand is the sequence of the anti-sense strand of AD-26759.

A RNAi agent comprising a sense strand and an anti-sense strand, wherein the sequence of the anti-sense strand is the sequence of the anti-sense strand of AD-25924.

A RNAi agent comprising a sense strand and an anti-sense strand, wherein the sequence of the anti-sense strand is the sequence of the anti-sense strand of AD-26153.

A RNAi agent comprising a sense strand and an anti-sense strand, wherein the sequence of the anti-sense strand is the sequence of the anti-sense strand of AD-25953.

A RNAi agent comprising a sense strand and an anti-sense strand, wherein the sequence of the anti-sense strand is the sequence of the anti-sense strand of AD-26764.

A RNAi agent comprising a sense strand and an anti-sense strand, wherein the sequence of the anti-sense strand is the sequence of the anti-sense strand of AD-26790.

A RNAi agent comprising a sense strand and an anti-sense strand, wherein the sequence of the anti-sense strand is the sequence of the anti-sense strand of AD-20124.

A RNAi agent comprising a sense strand and an anti-sense strand, wherein the sequence of the anti-sense strand is the sequence of the anti-sense strand of AD-25919.

A RNAi agent comprising a sense strand and an anti-sense strand, wherein the sequence of the anti-sense strand is the sequence of the anti-sense strand of AD-18913.

A RNAi agent comprising a sense strand and an anti-sense strand, wherein the sequence of the anti-sense strand is the sequence of the anti-sense strand of AD-26211.

A RNAi agent comprising a sense strand and an anti-sense strand, wherein the sequence of the anti-sense strand is the sequence of the anti-sense strand of AD-18936.

A RNAi agent comprising a sense strand and an anti-sense strand, wherein the sequence of the anti-sense strand is the sequence of the anti-sense strand of AD-25898.

A RNAi agent comprising a sense strand and an anti-sense strand, wherein the sequence of the anti-sense strand is the sequence of the anti-sense strand of AD-26741.

A RNAi agent comprising a sense strand and an anti-sense strand, wherein the sequence of the anti-sense strand is the sequence of the anti-sense strand of AD-19043.

A RNAi agent comprising a sense strand and an anti-sense strand, wherein the sequence of the anti-sense strand is the sequence of the anti-sense strand of AD-26079.

A RNAi agent comprising a sense strand and an anti-sense strand, wherein the sequence of the anti-sense strand is the sequence of the anti-sense strand of AD-19000.

A RNAi agent comprising a sense strand and an anti-sense strand, wherein the sequence of the anti-sense strand is the sequence of the anti-sense strand of AD-25911.

A RNAi agent comprising a sense strand and an anti-sense strand, wherein the sequence of the anti-sense strand is the sequence of the anti-sense strand of AD-26786.

A RNAi agent comprising a sense strand and an anti-sense strand, wherein the sequence of the anti-sense strand is the sequence of the anti-sense strand of AD-19069.

A RNAi agent comprising a sense strand and an anti-sense strand, wherein the sequence of the anti-sense strand is the sequence of the anti-sense strand of AD-26037.

A RNAi agent comprising a sense strand and an anti-sense strand, wherein the sequence of the anti-sense strand is the sequence of the anti-sense strand of AD-26723.

A RNAi agent comprising a sense strand and an anti-sense strand, wherein the sequence of the anti-sense strand is the sequence of the anti-sense strand of AD-19067.

A RNAi agent comprising a sense strand and an anti-sense strand, wherein the sequence of the anti-sense strand is the sequence of the anti-sense strand of AD-25928.

A RNAi agent comprising a sense strand and an anti-sense strand, wherein the sequence of the anti-sense strand is the sequence of the anti-sense strand of AD-26677.

A RNAi agent comprising a sense strand and an anti-sense strand, wherein the sequence of the anti-sense strand is the sequence of the anti-sense strand of AD-19006.

A RNAi agent comprising a sense strand and an anti-sense strand, wherein the sequence of the anti-sense strand is the sequence of the anti-sense strand of AD-19758.

A RNAi agent comprising a sense strand and an anti-sense strand, wherein the sequence of the anti-sense strand is the sequence of the anti-sense strand of AD-26913.

A RNAi agent comprising a sense strand and an anti-sense strand, wherein the sequence of the anti-sense strand is the sequence of the anti-sense strand of AD-25917.

A RNAi agent comprising a sense strand and an anti-sense strand, wherein the sequence of the anti-sense strand is the sequence of the anti-sense strand of AD-26189.

A RNAi agent comprising a sense strand and an anti-sense strand, wherein the sequence of the anti-sense strand is the sequence of the anti-sense strand of AD-26787.

A RNAi agent comprising a sense strand and an anti-sense strand, wherein the sequence of the anti-sense strand is the sequence of the anti-sense strand of AD-26707.

A RNAi agent comprising a sense strand and an anti-sense strand, wherein the sequence of the anti-sense strand is the sequence of the anti-sense strand of AD-26094.

A RNAi agent comprising a sense strand and an anti-sense strand, wherein the sequence of the anti-sense strand is the sequence of the anti-sense strand of AD-26097.

A RNAi agent comprising a sense strand and an anti-sense strand, wherein the sequence of the anti-sense strand is the sequence of the anti-sense strand of AD-26699.

A RNAi agent comprising a sense strand and an anti-sense strand, wherein the sequence of the anti-sense strand is the sequence of the anti-sense strand of AD-26756.

A RNAi agent comprising a sense strand and an anti-sense strand, wherein the sequence of the anti-sense strand is the sequence of the anti-sense strand of AD-26720.

A RNAi agent comprising a sense strand and an anti-sense strand, wherein the sequence of the anti-sense strand is the sequence of the anti-sense strand of AD-25926.

A RNAi agent comprising a sense strand and an anti-sense strand, wherein the sequence of the anti-sense strand is the sequence of the anti-sense strand of AD-26212.

A RNAi agent comprising a sense strand and an anti-sense strand, wherein the sequence of the anti-sense strand is the sequence of the anti-sense strand of AD-26687.

A RNAi agent comprising a sense strand and an anti-sense strand, wherein the sequence of the anti-sense strand is the sequence of the anti-sense strand of AD-26753.

A RNAi agent comprising a sense strand and an anti-sense strand, wherein the sequence of the anti-sense strand is the sequence of the anti-sense strand of AD-18982.

A RNAi agent comprising a sense strand and an anti-sense strand, wherein the sequence of the anti-sense strand is the sequence of the anti-sense strand of AD-18908.

A RNAi agent comprising a sense strand and an anti-sense strand, wherein the sequence of the anti-sense strand is the sequence of the anti-sense strand of AD-18968.

A RNAi agent comprising a sense strand and an anti-sense strand, wherein the sequence of the anti-sense strand is the sequence of the anti-sense strand of AD-25948.

A RNAi agent comprising a sense strand and an anti-sense strand, wherein the sequence of the anti-sense strand is the sequence of the anti-sense strand of AD-26188.

A RNAi agent comprising a sense strand and an anti-sense strand, wherein the sequence of the anti-sense strand is the sequence of the anti-sense strand of AD-26708.

A RNAi agent comprising a sense strand and an anti-sense strand, wherein the sequence of the anti-sense strand is the sequence of the anti-sense strand of AD-25961.

A RNAi agent comprising a sense strand and an anti-sense strand, wherein the sequence of the anti-sense strand is the sequence of the anti-sense strand of AD-26803.

A RNAi agent comprising a sense strand and an anti-sense strand, wherein the sequence of the anti-sense strand is the sequence of the anti-sense strand of AD-19741.

A RNAi agent comprising a sense strand and an anti-sense strand, wherein the sequence of the anti-sense strand is the sequence of the anti-sense strand of AD-26056.

A RNAi agent comprising a sense strand and an anti-sense strand, wherein the sequence of the anti-sense strand is the sequence of the anti-sense strand of AD-25959.

A RNAi agent comprising a sense strand and an anti-sense strand, wherein the sequence of the anti-sense strand is the sequence of the anti-sense strand of AD-26059.

A RNAi agent comprising a sense strand and an anti-sense strand, wherein the sequence of the anti-sense strand is the sequence of the anti-sense strand of AD-26102.

A RNAi agent comprising a sense strand and an anti-sense strand, wherein the sequence of the anti-sense strand is the sequence of the anti-sense strand of AD-26106.

A RNAi agent comprising a sense strand and an anti-sense strand, wherein the sequence of the anti-sense strand is the sequence of the anti-sense strand of AD-26744.

A RNAi agent comprising a sense strand and an anti-sense strand, wherein the sequence of the anti-sense strand is the sequence of the anti-sense strand of AD-26099.

A RNAi agent comprising a sense strand and an anti-sense strand, wherein the sequence of the anti-sense strand is the sequence of the anti-sense strand of AD-26170.

A RNAi agent comprising a sense strand and an anti-sense strand, wherein the sequence of the anti-sense strand is the sequence of the anti-sense strand of AD-19012.

A RNAi agent comprising a sense strand and an anti-sense strand, wherein the sequence of the anti-sense strand is the sequence of the anti-sense strand of AD-26198.

A RNAi agent comprising a sense strand and an anti-sense strand, wherein the sequence of the anti-sense strand is the sequence of the anti-sense strand of AD-26766.

A RNAi agent comprising a sense strand and an anti-sense strand, wherein the sequence of the anti-sense strand is the sequence of the anti-sense strand of AD-18951.

A RNAi agent comprising a sense strand and an anti-sense strand, wherein the sequence of the anti-sense strand is the sequence of the anti-sense strand of AD-18975.

A RNAi agent comprising a sense strand and an anti-sense strand, wherein the sequence of the anti-sense strand is the sequence of the anti-sense strand of AD-26749.

A RNAi agent comprising a sense strand and an anti-sense strand, wherein the sequence of the anti-sense strand is the sequence of the anti-sense strand of AD-18911.

A RNAi agent comprising a sense strand and an anti-sense strand, wherein the sequence of the anti-sense strand is the sequence of the anti-sense strand of AD-26906.

A RNAi agent comprising a sense strand and an anti-sense strand, wherein the sequence of the anti-sense strand is the sequence of the anti-sense strand of AD-19747.

A RNAi agent comprising a sense strand and an anti-sense strand, wherein the sequence of the anti-sense strand is the sequence of the anti-sense strand of AD-18960.

A RNAi agent comprising a sense strand and an anti-sense strand, wherein the sequence of the anti-sense strand is the sequence of the anti-sense strand of AD-25909.

A RNAi agent comprising a sense strand and an anti-sense strand, wherein the sequence of the anti-sense strand is the sequence of the anti-sense strand of AD-26184.

A RNAi agent comprising a sense strand and an anti-sense strand, wherein the sequence of the anti-sense strand is the sequence of the anti-sense strand of AD-26077.

A RNAi agent comprising a sense strand and an anti-sense strand, wherein the sequence of the anti-sense strand is the sequence of the anti-sense strand of AD-26680.

A RNAi agent comprising a sense strand and an anti-sense strand, wherein the sequence of the anti-sense strand is the sequence of the anti-sense strand of AD-26085.

A RNAi agent comprising a sense strand and an anti-sense strand, wherein the sequence of the anti-sense strand is the sequence of the anti-sense strand of AD-18926.

A RNAi agent comprising a sense strand and an anti-sense strand, wherein the sequence of the anti-sense strand is the sequence of the anti-sense strand of AD-18945.

A RNAi agent comprising a sense strand and an anti-sense strand, wherein the sequence of the anti-sense strand is the sequence of the anti-sense strand of AD-26703.

A RNAi agent comprising a sense strand and an anti-sense strand, wherein the sequence of the anti-sense strand is the sequence of the anti-sense strand of AD-26911.

A RNAi agent comprising a sense strand and an anti-sense strand, wherein the sequence of the anti-sense strand is the sequence of the anti-sense strand of AD-26661.

A RNAi agent comprising a sense strand and an anti-sense strand, wherein the sequence of the anti-sense strand is the sequence of the anti-sense strand of AD-18905.

A RNAi agent comprising a sense strand and an anti-sense strand, wherein the sequence of the anti-sense strand is the sequence of the anti-sense strand of AD-26142.

A RNAi agent comprising: a sense strand and an anti-sense strand, wherein the sequence of the anti-sense strand is the sequence of the anti-sense strand of Set1_1245.

A RNAi agent comprising: a sense strand and an anti-sense strand, wherein the sequence of the anti-sense strand is the sequence of the anti-sense strand of Set1_1249.

A RNAi agent comprising: a sense strand and an anti-sense strand, wherein the sequence of the anti-sense strand is the sequence of the anti-sense strand of Set1_1250.

A RNAi agent comprising: a sense strand and an anti-sense strand, wherein the sequence of the anti-sense strand is the sequence of the anti-sense strand of Set1_1450.

A RNAi agent comprising: a sense strand and an anti-sense strand, wherein the sequence of the anti-sense strand is the sequence of the anti-sense strand of Set1_1545.

A RNAi agent comprising: a sense strand and an anti-sense strand, wherein the sequence of the anti-sense strand is the sequence of the anti-sense strand of Set1_1755.

A RNAi agent comprising: a sense strand and an anti-sense strand, wherein the sequence of the anti-sense strand is the sequence of the anti-sense strand of Set1_1814.

A RNAi agent comprising: a sense strand and an anti-sense strand, wherein the sequence of the anti-sense strand is the sequence of the anti-sense strand of Set1_1816.

A RNAi agent comprising: a sense strand and an anti-sense strand, wherein the sequence of the anti-sense strand is the sequence of the anti-sense strand of Set1_1974.

A RNAi agent comprising: a sense strand and an anti-sense strand, wherein the sequence of the anti-sense strand is the sequence of the anti-sense strand of Set1_2202.

A RNAi agent comprising: a sense strand and an anti-sense strand, wherein the sequence of the anti-sense strand is the sequence of the anti-sense strand of Set1_2425.

A RNAi agent comprising: a sense strand and an anti-sense strand, wherein the sequence of the anti-sense strand is the sequence of the anti-sense strand of Set1_254.

A RNAi agent comprising: a sense strand and an anti-sense strand, wherein the sequence of the anti-sense strand is the sequence of the anti-sense strand of Set1_3146.

A RNAi agent comprising: a sense strand and an anti-sense strand, wherein the sequence of the anti-sense strand is the sequence of the anti-sense strand of Set1_3169.

A RNAi agent comprising: a sense strand and an anti-sense strand, wherein the sequence of the anti-sense strand is the sequence of the anti-sense strand of Set1_3196.

A RNAi agent comprising: a sense strand and an anti-sense strand, wherein the sequence of the anti-sense strand is the sequence of the anti-sense strand of Set1_3477.

A RNAi agent comprising: a sense strand and an anti-sense strand, wherein the sequence of the anti-sense strand is the sequence of the anti-sense strand of Set1_703.

A RNAi agent comprising: a sense strand and an anti-sense strand, wherein the sequence of the anti-sense strand is the sequence of the anti-sense strand of Set1_709.

A RNAi agent comprising: a sense strand and an anti-sense strand, wherein the sequence of the anti-sense strand is the sequence of the anti-sense strand of Set1_865.

A RNAi agent comprising: a sense strand and an anti-sense strand, wherein the sequence of the anti-sense strand is the sequence of the anti-sense strand of Set1_889.

A RNAi agent comprising: a sense strand and an anti-sense strand, wherein the sequence of the anti-sense strand is the sequence of the anti-sense strand of Set1_895.

Additional Embodiments Encompassing Specific RNAi Agents to Beta-Catenin

In various embodiments, the present disclosure pertains to a composition comprising one or more of the following:

A RNAi agent comprising a first strand and a second strand, wherein the sequence of the first or second strand is the sequence of the first or second strand of AD-26104, and wherein the first and/or second strand further comprises up to about 20 additional nucleotides.

A RNAi agent comprising a first strand and a second strand, wherein the sequence of the first or second strand is the sequence of the first or second strand of AD-26063, and wherein the first and/or second strand further comprises up to about 20 additional nucleotides.

A RNAi agent comprising a first strand and a second strand, wherein the sequence of the first or second strand is the sequence of the first or second strand of AD-26082, and wherein the first and/or second strand further comprises up to about 20 additional nucleotides.

A RNAi agent comprising a first strand and a second strand, wherein the sequence of the first or second strand is the sequence of the first or second strand of AD-26034, and wherein the first and/or second strand further comprises up to about 20 additional nucleotides.

A RNAi agent comprising a first strand and a second strand, wherein the sequence of the first or second strand is the sequence of the first or second strand of AD-26091, and wherein the first and/or second strand further comprises up to about 20 additional nucleotides.

A RNAi agent comprising a first strand and a second strand, wherein the sequence of the first or second strand is the sequence of the first or second strand of AD-26047, and wherein the first and/or second strand further comprises up to about 20 additional nucleotides.

A RNAi agent comprising a first strand and a second strand, wherein the sequence of the first or second strand is the sequence of the first or second strand of AD-26651, and wherein the first and/or second strand further comprises up to about 20 additional nucleotides.

A RNAi agent comprising a first strand and a second strand, wherein the sequence of the first or second strand is the sequence of the first or second strand of AD-26696, and wherein the first and/or second strand further comprises up to about 20 additional nucleotides.

A RNAi agent comprising a first strand and a second strand, wherein the sequence of the first or second strand is the sequence of the first or second strand of AD-26109, and wherein the first and/or second strand further comprises up to about 20 additional nucleotides.

A RNAi agent comprising a first strand and a second strand, wherein the sequence of the first or second strand is the sequence of the first or second strand of AD-25941, and wherein the first and/or second strand further comprises up to about 20 additional nucleotides.

A RNAi agent comprising a first strand and a second strand, wherein the sequence of the first or second strand is the sequence of the first or second strand of AD-26028, and wherein the first and/or second strand further comprises up to about 20 additional nucleotides.

A RNAi agent comprising a first strand and a second strand, wherein the sequence of the first or second strand is the sequence of the first or second strand of AD-26652, and wherein the first and/or second strand further comprises up to about 20 additional nucleotides.

A RNAi agent comprising a first strand and a second strand, wherein the sequence of the first or second strand is the sequence of the first or second strand of AD-26742, and wherein the first and/or second strand further comprises up to about 20 additional nucleotides.

A RNAi agent comprising a first strand and a second strand, wherein the sequence of the first or second strand is the sequence of the first or second strand of AD-26921, and wherein the first and/or second strand further comprises up to about 20 additional nucleotides.

A RNAi agent comprising a first strand and a second strand, wherein the sequence of the first or second strand is the sequence of the first or second strand of AD-18893, and wherein the first and/or second strand further comprises up to about 20 additional nucleotides.

A RNAi agent comprising a first strand and a second strand, wherein the sequence of the first or second strand is the sequence of the first or second strand of AD-18983, and wherein the first and/or second strand further comprises up to about 20 additional nucleotides.

A RNAi agent comprising a first strand and a second strand, wherein the sequence of the first or second strand is the sequence of the first or second strand of AD-25950, and wherein the first and/or second strand further comprises up to about 20 additional nucleotides.

A RNAi agent comprising a first strand and a second strand, wherein the sequence of the first or second strand is the sequence of the first or second strand of AD-25951, and wherein the first and/or second strand further comprises up to about 20 additional nucleotides.

A RNAi agent comprising a first strand and a second strand, wherein the sequence of the first or second strand is the sequence of the first or second strand of AD-26042, and wherein the first and/or second strand further comprises up to about 20 additional nucleotides.

A RNAi agent comprising a first strand and a second strand, wherein the sequence of the first or second strand is the sequence of the first or second strand of AD-26043, and wherein the first and/or second strand further comprises up to about 20 additional nucleotides.

A RNAi agent comprising a first strand and a second strand, wherein the sequence of the first or second strand is the sequence of the first or second strand of AD-26673, and wherein the first and/or second strand further comprises up to about 20 additional nucleotides.

A RNAi agent comprising a first strand and a second strand, wherein the sequence of the first or second strand is the sequence of the first or second strand of AD-26704, and wherein the first and/or second strand further comprises up to about 20 additional nucleotides.

A RNAi agent comprising a first strand and a second strand, wherein the sequence of the first or second strand is the sequence of the first or second strand of AD-26068, and wherein the first and/or second strand further comprises up to about 20 additional nucleotides.

A RNAi agent comprising a first strand and a second strand, wherein the sequence of the first or second strand is the sequence of the first or second strand of AD-26183, and wherein the first and/or second strand further comprises up to about 20 additional nucleotides.

A RNAi agent comprising a first strand and a second strand, wherein the sequence of the first or second strand is the sequence of the first or second strand of AD-26700, and wherein the first and/or second strand further comprises up to about 20 additional nucleotides.

A RNAi agent comprising a first strand and a second strand, wherein the sequence of the first or second strand is the sequence of the first or second strand of AD-26701, and wherein the first and/or second strand further comprises up to about 20 additional nucleotides.

A RNAi agent comprising a first strand and a second strand, wherein the sequence of the first or second strand is the sequence of the first or second strand of AD-25942, and wherein the first and/or second strand further comprises up to about 20 additional nucleotides.

A RNAi agent comprising a first strand and a second strand, wherein the sequence of the first or second strand is the sequence of the first or second strand of AD-26076, and wherein the first and/or second strand further comprises up to about 20 additional nucleotides.

A RNAi agent comprising a first strand and a second strand, wherein the sequence of the first or second strand is the sequence of the first or second strand of AD-26031, and wherein the first and/or second strand further comprises up to about 20 additional nucleotides.

A RNAi agent comprising a first strand and a second strand, wherein the sequence of the first or second strand is the sequence of the first or second strand of AD-26210, and wherein the first and/or second strand further comprises up to about 20 additional nucleotides.

A RNAi agent comprising a first strand and a second strand, wherein the sequence of the first or second strand is the sequence of the first or second strand of AD-26664, and wherein the first and/or second strand further comprises up to about 20 additional nucleotides.

A RNAi agent comprising a first strand and a second strand, wherein the sequence of the first or second strand is the sequence of the first or second strand of AD-26691, and wherein the first and/or second strand further comprises up to about 20 additional nucleotides.

A RNAi agent comprising a first strand and a second strand, wherein the sequence of the first or second strand is the sequence of the first or second strand of AD-26740, and wherein the first and/or second strand further comprises up to about 20 additional nucleotides.

A RNAi agent comprising a first strand and a second strand, wherein the sequence of the first or second strand is the sequence of the first or second strand of AD-19765, and wherein the first and/or second strand further comprises up to about 20 additional nucleotides.

A RNAi agent comprising a first strand and a second strand, wherein the sequence of the first or second strand is the sequence of the first or second strand of AD-26158, and wherein the first and/or second strand further comprises up to about 20 additional nucleotides.

A RNAi agent comprising a first strand and a second strand, wherein the sequence of the first or second strand is the sequence of the first or second strand of AD-26180, and wherein the first and/or second strand further comprises up to about 20 additional nucleotides.

A RNAi agent comprising a first strand and a second strand, wherein the sequence of the first or second strand is the sequence of the first or second strand of AD-26078, and wherein the first and/or second strand further comprises up to about 20 additional nucleotides.

A RNAi agent comprising a first strand and a second strand, wherein the sequence of the first or second strand is the sequence of the first or second strand of AD-25894, and wherein the first and/or second strand further comprises up to about 20 additional nucleotides.

A RNAi agent comprising a first strand and a second strand, wherein the sequence of the first or second strand is the sequence of the first or second strand of AD-25964, and wherein the first and/or second strand further comprises up to about 20 additional nucleotides.

A RNAi agent comprising a first strand and a second strand, wherein the sequence of the first or second strand is the sequence of the first or second strand of AD-26156, and wherein the first and/or second strand further comprises up to about 20 additional nucleotides.

A RNAi agent comprising a first strand and a second strand, wherein the sequence of the first or second strand is the sequence of the first or second strand of AD-26670, and wherein the first and/or second strand further comprises up to about 20 additional nucleotides.

A RNAi agent comprising a first strand and a second strand, wherein the sequence of the first or second strand is the sequence of the first or second strand of AD-26743, and wherein the first and/or second strand further comprises up to about 20 additional nucleotides.

A RNAi agent comprising a first strand and a second strand, wherein the sequence of the first or second strand is the sequence of the first or second strand of AD-25890, and wherein the first and/or second strand further comprises up to about 20 additional nucleotides.

A RNAi agent comprising a first strand and a second strand, wherein the sequence of the first or second strand is the sequence of the first or second strand of AD-26044, and wherein the first and/or second strand further comprises up to about 20 additional nucleotides.

A RNAi agent comprising a first strand and a second strand, wherein the sequence of the first or second strand is the sequence of the first or second strand of AD-26685, and wherein the first and/or second strand further comprises up to about 20 additional nucleotides.

A RNAi agent comprising a first strand and a second strand, wherein the sequence of the first or second strand is the sequence of the first or second strand of AD-26731, and wherein the first and/or second strand further comprises up to about 20 additional nucleotides.

A RNAi agent comprising a first strand and a second strand, wherein the sequence of the first or second strand is the sequence of the first or second strand of AD-26800, and wherein the first and/or second strand further comprises up to about 20 additional nucleotides.

A RNAi agent comprising a first strand and a second strand, wherein the sequence of the first or second strand is the sequence of the first or second strand of AD-26066, and wherein the first and/or second strand further comprises up to about 20 additional nucleotides.

A RNAi agent comprising a first strand and a second strand, wherein the sequence of the first or second strand is the sequence of the first or second strand of AD-26682, and wherein the first and/or second strand further comprises up to about 20 additional nucleotides.

A RNAi agent comprising a first strand and a second strand, wherein the sequence of the first or second strand is the sequence of the first or second strand of AD-26684, and wherein the first and/or second strand further comprises up to about 20 additional nucleotides.

A RNAi agent comprising a first strand and a second strand, wherein the sequence of the first or second strand is the sequence of the first or second strand of AD-26757, and wherein the first and/or second strand further comprises up to about 20 additional nucleotides.

A RNAi agent comprising a first strand and a second strand, wherein the sequence of the first or second strand is the sequence of the first or second strand of AD-26788, and wherein the first and/or second strand further comprises up to about 20 additional nucleotides.

A RNAi agent comprising a first strand and a second strand, wherein the sequence of the first or second strand is the sequence of the first or second strand of AD-18963, and wherein the first and/or second strand further comprises up to about 20 additional nucleotides.

A RNAi agent comprising a first strand and a second strand, wherein the sequence of the first or second strand is the sequence of the first or second strand of AD-19076, and wherein the first and/or second strand further comprises up to about 20 additional nucleotides.

A RNAi agent comprising a first strand and a second strand, wherein the sequence of the first or second strand is the sequence of the first or second strand of AD-25943, and wherein the first and/or second strand further comprises up to about 20 additional nucleotides.

A RNAi agent comprising a first strand and a second strand, wherein the sequence of the first or second strand is the sequence of the first or second strand of AD-26052, and wherein the first and/or second strand further comprises up to about 20 additional nucleotides.

A RNAi agent comprising a first strand and a second strand, wherein the sequence of the first or second strand is the sequence of the first or second strand of AD-26665, and wherein the first and/or second strand further comprises up to about 20 additional nucleotides.

A RNAi agent comprising a first strand and a second strand, wherein the sequence of the first or second strand is the sequence of the first or second strand of AD-26746, and wherein the first and/or second strand further comprises up to about 20 additional nucleotides.

A RNAi agent comprising a first strand and a second strand, wherein the sequence of the first or second strand is the sequence of the first or second strand of AD-18974, and wherein the first and/or second strand further comprises up to about 20 additional nucleotides.

A RNAi agent comprising a first strand and a second strand, wherein the sequence of the first or second strand is the sequence of the first or second strand of AD-25938, and wherein the first and/or second strand further comprises up to about 20 additional nucleotides.

A RNAi agent comprising a first strand and a second strand, wherein the sequence of the first or second strand is the sequence of the first or second strand of AD-25944, and wherein the first and/or second strand further comprises up to about 20 additional nucleotides.

A RNAi agent comprising a first strand and a second strand, wherein the sequence of the first or second strand is the sequence of the first or second strand of AD-26178, and wherein the first and/or second strand further comprises up to about 20 additional nucleotides.

A RNAi agent comprising a first strand and a second strand, wherein the sequence of the first or second strand is the sequence of the first or second strand of AD-26669, and wherein the first and/or second strand further comprises up to about 20 additional nucleotides.

A RNAi agent comprising a first strand and a second strand, wherein the sequence of the first or second strand is the sequence of the first or second strand of AD-26730, and wherein the first and/or second strand further comprises up to about 20 additional nucleotides.

A RNAi agent comprising a first strand and a second strand, wherein the sequence of the first or second strand is the sequence of the first or second strand of AD-26825, and wherein the first and/or second strand further comprises up to about 20 additional nucleotides.

A RNAi agent comprising a first strand and a second strand, wherein the sequence of the first or second strand is the sequence of the first or second strand of AD-25956, and wherein the first and/or second strand further comprises up to about 20 additional nucleotides.

A RNAi agent comprising a first strand and a second strand, wherein the sequence of the first or second strand is the sequence of the first or second strand of AD-26822, and wherein the first and/or second strand further comprises up to about 20 additional nucleotides.

A RNAi agent comprising a first strand and a second strand, wherein the sequence of the first or second strand is the sequence of the first or second strand of AD-26108, and wherein the first and/or second strand further comprises up to about 20 additional nucleotides.

A RNAi agent comprising a first strand and a second strand, wherein the sequence of the first or second strand is the sequence of the first or second strand of AD-26752, and wherein the first and/or second strand further comprises up to about 20 additional nucleotides.

A RNAi agent comprising a first strand and a second strand, wherein the sequence of the first or second strand is the sequence of the first or second strand of AD-26779, and wherein the first and/or second strand further comprises up to about 20 additional nucleotides.

A RNAi agent comprising a first strand and a second strand, wherein the sequence of the first or second strand is the sequence of the first or second strand of AD-25891, and wherein the first and/or second strand further comprises up to about 20 additional nucleotides.

A RNAi agent comprising a first strand and a second strand, wherein the sequence of the first or second strand is the sequence of the first or second strand of AD-26101, and wherein the first and/or second strand further comprises up to about 20 additional nucleotides.

A RNAi agent comprising a first strand and a second strand, wherein the sequence of the first or second strand is the sequence of the first or second strand of AD-26181, and wherein the first and/or second strand further comprises up to about 20 additional nucleotides.

A RNAi agent comprising a first strand and a second strand, wherein the sequence of the first or second strand is the sequence of the first or second strand of AD-26218, and wherein the first and/or second strand further comprises up to about 20 additional nucleotides.

A RNAi agent comprising a first strand and a second strand, wherein the sequence of the first or second strand is the sequence of the first or second strand of AD-26660, and wherein the first and/or second strand further comprises up to about 20 additional nucleotides.

A RNAi agent comprising a first strand and a second strand, wherein the sequence of the first or second strand is the sequence of the first or second strand of AD-18966, and wherein the first and/or second strand further comprises up to about 20 additional nucleotides.

A RNAi agent comprising a first strand and a second strand, wherein the sequence of the first or second strand is the sequence of the first or second strand of AD-19074, and wherein the first and/or second strand further comprises up to about 20 additional nucleotides.

A RNAi agent comprising a first strand and a second strand, wherein the sequence of the first or second strand is the sequence of the first or second strand of AD-26179, and wherein the first and/or second strand further comprises up to about 20 additional nucleotides.

A RNAi agent comprising a first strand and a second strand, wherein the sequence of the first or second strand is the sequence of the first or second strand of AD-26722, and wherein the first and/or second strand further comprises up to about 20 additional nucleotides.

A RNAi agent comprising a first strand and a second strand, wherein the sequence of the first or second strand is the sequence of the first or second strand of AD-26768, and wherein the first and/or second strand further comprises up to about 20 additional nucleotides.

A RNAi agent comprising a first strand and a second strand, wherein the sequence of the first or second strand is the sequence of the first or second strand of AD-26920, and wherein the first and/or second strand further comprises up to about 20 additional nucleotides.

A RNAi agent comprising a first strand and a second strand, wherein the sequence of the first or second strand is the sequence of the first or second strand of AD-26020, and wherein the first and/or second strand further comprises up to about 20 additional nucleotides.

A RNAi agent comprising a first strand and a second strand, wherein the sequence of the first or second strand is the sequence of the first or second strand of AD-26713, and wherein the first and/or second strand further comprises up to about 20 additional nucleotides.

A RNAi agent comprising a first strand and a second strand, wherein the sequence of the first or second strand is the sequence of the first or second strand of AD-26727, and wherein the first and/or second strand further comprises up to about 20 additional nucleotides.

A RNAi agent comprising a first strand and a second strand, wherein the sequence of the first or second strand is the sequence of the first or second strand of AD-26808, and wherein the first and/or second strand further comprises up to about 20 additional nucleotides.

A RNAi agent comprising a first strand and a second strand, wherein the sequence of the first or second strand is the sequence of the first or second strand of AD-25958, and wherein the first and/or second strand further comprises up to about 20 additional nucleotides.

A RNAi agent comprising a first strand and a second strand, wherein the sequence of the first or second strand is the sequence of the first or second strand of AD-26105, and wherein the first and/or second strand further comprises up to about 20 additional nucleotides.

A RNAi agent comprising a first strand and a second strand, wherein the sequence of the first or second strand is the sequence of the first or second strand of AD-26674, and wherein the first and/or second strand further comprises up to about 20 additional nucleotides.

A RNAi agent comprising a first strand and a second strand, wherein the sequence of the first or second strand is the sequence of the first or second strand of AD-26781, and wherein the first and/or second strand further comprises up to about 20 additional nucleotides.

A RNAi agent comprising a first strand and a second strand, wherein the sequence of the first or second strand is the sequence of the first or second strand of AD-26801, and wherein the first and/or second strand further comprises up to about 20 additional nucleotides.

A RNAi agent comprising a first strand and a second strand, wherein the sequence of the first or second strand is the sequence of the first or second strand of AD-26813, and wherein the first and/or second strand further comprises up to about 20 additional nucleotides.

A RNAi agent comprising a first strand and a second strand, wherein the sequence of the first or second strand is the sequence of the first or second strand of AD-26816, and wherein the first and/or second strand further comprises up to about 20 additional nucleotides.

A RNAi agent comprising a first strand and a second strand, wherein the sequence of the first or second strand is the sequence of the first or second strand of AD-25945, and wherein the first and/or second strand further comprises up to about 20 additional nucleotides.

A RNAi agent comprising a first strand and a second strand, wherein the sequence of the first or second strand is the sequence of the first or second strand of AD-26203, and wherein the first and/or second strand further comprises up to about 20 additional nucleotides.

A RNAi agent comprising a first strand and a second strand, wherein the sequence of the first or second strand is the sequence of the first or second strand of AD-26021, and wherein the first and/or second strand further comprises up to about 20 additional nucleotides.

A RNAi agent comprising a first strand and a second strand, wherein the sequence of the first or second strand is the sequence of the first or second strand of AD-26040, and wherein the first and/or second strand further comprises up to about 20 additional nucleotides.

A RNAi agent comprising a first strand and a second strand, wherein the sequence of the first or second strand is the sequence of the first or second strand of AD-26069, and wherein the first and/or second strand further comprises up to about 20 additional nucleotides.

A RNAi agent comprising a first strand and a second strand, wherein the sequence of the first or second strand is the sequence of the first or second strand of AD-26134, and wherein the first and/or second strand further comprises up to about 20 additional nucleotides.

A RNAi agent comprising a first strand and a second strand, wherein the sequence of the first or second strand is the sequence of the first or second strand of AD-26702, and wherein the first and/or second strand further comprises up to about 20 additional nucleotides.

A RNAi agent comprising a first strand and a second strand, wherein the sequence of the first or second strand is the sequence of the first or second strand of AD-18933, and wherein the first and/or second strand further comprises up to about 20 additional nucleotides.

A RNAi agent comprising a first strand and a second strand, wherein the sequence of the first or second strand is the sequence of the first or second strand of AD-26690, and wherein the first and/or second strand further comprises up to about 20 additional nucleotides.

A RNAi agent comprising a first strand and a second strand, wherein the sequence of the first or second strand is the sequence of the first or second strand of AD-26698, and wherein the first and/or second strand further comprises up to about 20 additional nucleotides.

A RNAi agent comprising a first strand and a second strand, wherein the sequence of the first or second strand is the sequence of the first or second strand of AD-25910, and wherein the first and/or second strand further comprises up to about 20 additional nucleotides.

A RNAi agent comprising a first strand and a second strand, wherein the sequence of the first or second strand is the sequence of the first or second strand of AD-26747, and wherein the first and/or second strand further comprises up to about 20 additional nucleotides.

A RNAi agent comprising a first strand and a second strand, wherein the sequence of the first or second strand is the sequence of the first or second strand of AD-26810, and wherein the first and/or second strand further comprises up to about 20 additional nucleotides.

A RNAi agent comprising a first strand and a second strand, wherein the sequence of the first or second strand is the sequence of the first or second strand of AD-26083, and wherein the first and/or second strand further comprises up to about 20 additional nucleotides.

A RNAi agent comprising a first strand and a second strand, wherein the sequence of the first or second strand is the sequence of the first or second strand of AD-26061, and wherein the first and/or second strand further comprises up to about 20 additional nucleotides.

A RNAi agent comprising a first strand and a second strand, wherein the sequence of the first or second strand is the sequence of the first or second strand of AD-26904, and wherein the first and/or second strand further comprises up to about 20 additional nucleotides.

A RNAi agent comprising a first strand and a second strand, wherein the sequence of the first or second strand is the sequence of the first or second strand of AD-18903, and wherein the first and/or second strand further comprises up to about 20 additional nucleotides.

A RNAi agent comprising a first strand and a second strand, wherein the sequence of the first or second strand is the sequence of the first or second strand of AD-18980, and wherein the first and/or second strand further comprises up to about 20 additional nucleotides.

A RNAi agent comprising a first strand and a second strand, wherein the sequence of the first or second strand is the sequence of the first or second strand of AD-26202, and wherein the first and/or second strand further comprises up to about 20 additional nucleotides.

A RNAi agent comprising a first strand and a second strand, wherein the sequence of the first or second strand is the sequence of the first or second strand of AD-26679, and wherein the first and/or second strand further comprises up to about 20 additional nucleotides.

A RNAi agent comprising a first strand and a second strand, wherein the sequence of the first or second strand is the sequence of the first or second strand of AD-26719, and wherein the first and/or second strand further comprises up to about 20 additional nucleotides.

A RNAi agent comprising a first strand and a second strand, wherein the sequence of the first or second strand is the sequence of the first or second strand of AD-26758, and wherein the first and/or second strand further comprises up to about 20 additional nucleotides.

A RNAi agent comprising a first strand and a second strand, wherein the sequence of the first or second strand is the sequence of the first or second strand of AD-26783, and wherein the first and/or second strand further comprises up to about 20 additional nucleotides.

A RNAi agent comprising a first strand and a second strand, wherein the sequence of the first or second strand is the sequence of the first or second strand of AD-26902, and wherein the first and/or second strand further comprises up to about 20 additional nucleotides.

A RNAi agent comprising a first strand and a second strand, wherein the sequence of the first or second strand is the sequence of the first or second strand of AD-18892, and wherein the first and/or second strand further comprises up to about 20 additional nucleotides.

A RNAi agent comprising a first strand and a second strand, wherein the sequence of the first or second strand is the sequence of the first or second strand of AD-18897, and wherein the first and/or second strand further comprises up to about 20 additional nucleotides.

A RNAi agent comprising a first strand and a second strand, wherein the sequence of the first or second strand is the sequence of the first or second strand of AD-25902, and wherein the first and/or second strand further comprises up to about 20 additional nucleotides.

A RNAi agent comprising a first strand and a second strand, wherein the sequence of the first or second strand is the sequence of the first or second strand of AD-26705, and wherein the first and/or second strand further comprises up to about 20 additional nucleotides.

A RNAi agent comprising a first strand and a second strand, wherein the sequence of the first or second strand is the sequence of the first or second strand of AD-26782, and wherein the first and/or second strand further comprises up to about 20 additional nucleotides.

A RNAi agent comprising a first strand and a second strand, wherein the sequence of the first or second strand is the sequence of the first or second strand of AD-19082, and wherein the first and/or second strand further comprises up to about 20 additional nucleotides.

A RNAi agent comprising a first strand and a second strand, wherein the sequence of the first or second strand is the sequence of the first or second strand of AD-26176, and wherein the first and/or second strand further comprises up to about 20 additional nucleotides.

A RNAi agent comprising a first strand and a second strand, wherein the sequence of the first or second strand is the sequence of the first or second strand of AD-26196, and wherein the first and/or second strand further comprises up to about 20 additional nucleotides.

A RNAi agent comprising a first strand and a second strand, wherein the sequence of the first or second strand is the sequence of the first or second strand of AD-26199, and wherein the first and/or second strand further comprises up to about 20 additional nucleotides.

A RNAi agent comprising a first strand and a second strand, wherein the sequence of the first or second strand is the sequence of the first or second strand of AD-26678, and wherein the first and/or second strand further comprises up to about 20 additional nucleotides.

A RNAi agent comprising a first strand and a second strand, wherein the sequence of the first or second strand is the sequence of the first or second strand of AD-26683, and wherein the first and/or second strand further comprises up to about 20 additional nucleotides.

A RNAi agent comprising a first strand and a second strand, wherein the sequence of the first or second strand is the sequence of the first or second strand of AD-26729, and wherein the first and/or second strand further comprises up to about 20 additional nucleotides.

A RNAi agent comprising a first strand and a second strand, wherein the sequence of the first or second strand is the sequence of the first or second strand of AD-26804, and wherein the first and/or second strand further comprises up to about 20 additional nucleotides.

A RNAi agent comprising a first strand and a second strand, wherein the sequence of the first or second strand is the sequence of the first or second strand of AD-26900, and wherein the first and/or second strand further comprises up to about 20 additional nucleotides.

A RNAi agent comprising a first strand and a second strand, wherein the sequence of the first or second strand is the sequence of the first or second strand of AD-25914, and wherein the first and/or second strand further comprises up to about 20 additional nucleotides.

A RNAi agent comprising a first strand and a second strand, wherein the sequence of the first or second strand is the sequence of the first or second strand of AD-26060, and wherein the first and/or second strand further comprises up to about 20 additional nucleotides.

A RNAi agent comprising a first strand and a second strand, wherein the sequence of the first or second strand is the sequence of the first or second strand of AD-26763, and wherein the first and/or second strand further comprises up to about 20 additional nucleotides.

A RNAi agent comprising a first strand and a second strand, wherein the sequence of the first or second strand is the sequence of the first or second strand of AD-18902, and wherein the first and/or second strand further comprises up to about 20 additional nucleotides.

A RNAi agent comprising a first strand and a second strand, wherein the sequence of the first or second strand is the sequence of the first or second strand of AD-18914, and wherein the first and/or second strand further comprises up to about 20 additional nucleotides.

A RNAi agent comprising a first strand and a second strand, wherein the sequence of the first or second strand is the sequence of the first or second strand of AD-26100, and wherein the first and/or second strand further comprises up to about 20 additional nucleotides.

A RNAi agent comprising a first strand and a second strand, wherein the sequence of the first or second strand is the sequence of the first or second strand of AD-26128, and wherein the first and/or second strand further comprises up to about 20 additional nucleotides.

A RNAi agent comprising a first strand and a second strand, wherein the sequence of the first or second strand is the sequence of the first or second strand of AD-26193, and wherein the first and/or second strand further comprises up to about 20 additional nucleotides.

A RNAi agent comprising a first strand and a second strand, wherein the sequence of the first or second strand is the sequence of the first or second strand of AD-26765, and wherein the first and/or second strand further comprises up to about 20 additional nucleotides.

A RNAi agent comprising a first strand and a second strand, wherein the sequence of the first or second strand is the sequence of the first or second strand of AD-25960, and wherein the first and/or second strand further comprises up to about 20 additional nucleotides.

A RNAi agent comprising a first strand and a second strand, wherein the sequence of the first or second strand is the sequence of the first or second strand of AD-26018, and wherein the first and/or second strand further comprises up to about 20 additional nucleotides.

A RNAi agent comprising a first strand and a second strand, wherein the sequence of the first or second strand is the sequence of the first or second strand of AD-25893, and wherein the first and/or second strand further comprises up to about 20 additional nucleotides.

A RNAi agent comprising a first strand and a second strand, wherein the sequence of the first or second strand is the sequence of the first or second strand of AD-26823, and wherein the first and/or second strand further comprises up to about 20 additional nucleotides.

A RNAi agent comprising a first strand and a second strand, wherein the sequence of the first or second strand is the sequence of the first or second strand of AD-25940, and wherein the first and/or second strand further comprises up to about 20 additional nucleotides.

A RNAi agent comprising a first strand and a second strand, wherein the sequence of the first or second strand is the sequence of the first or second strand of AD-26190, and wherein the first and/or second strand further comprises up to about 20 additional nucleotides.

A RNAi agent comprising a first strand and a second strand, wherein the sequence of the first or second strand is the sequence of the first or second strand of AD-26675, and wherein the first and/or second strand further comprises up to about 20 additional nucleotides.

A RNAi agent comprising a first strand and a second strand, wherein the sequence of the first or second strand is the sequence of the first or second strand of AD-26797, and wherein the first and/or second strand further comprises up to about 20 additional nucleotides.

A RNAi agent comprising a first strand and a second strand, wherein the sequence of the first or second strand is the sequence of the first or second strand of AD-26916, and wherein the first and/or second strand further comprises up to about 20 additional nucleotides.

A RNAi agent comprising a first strand and a second strand, wherein the sequence of the first or second strand is the sequence of the first or second strand of AD-26755, and wherein the first and/or second strand further comprises up to about 20 additional nucleotides.

A RNAi agent comprising a first strand and a second strand, wherein the sequence of the first or second strand is the sequence of the first or second strand of AD-26901, and wherein the first and/or second strand further comprises up to about 20 additional nucleotides.

A RNAi agent comprising a first strand and a second strand, wherein the sequence of the first or second strand is the sequence of the first or second strand of AD-19004, and wherein the first and/or second strand further comprises up to about 20 additional nucleotides.

A RNAi agent comprising a first strand and a second strand, wherein the sequence of the first or second strand is the sequence of the first or second strand of AD-19009, and wherein the first and/or second strand further comprises up to about 20 additional nucleotides.

A RNAi agent comprising a first strand and a second strand, wherein the sequence of the first or second strand is the sequence of the first or second strand of AD-26148, and wherein the first and/or second strand further comprises up to about 20 additional nucleotides.

A RNAi agent comprising a first strand and a second strand, wherein the sequence of the first or second strand is the sequence of the first or second strand of AD-26186, and wherein the first and/or second strand further comprises up to about 20 additional nucleotides.

A RNAi agent comprising a first strand and a second strand, wherein the sequence of the first or second strand is the sequence of the first or second strand of AD-26737, and wherein the first and/or second strand further comprises up to about 20 additional nucleotides.

A RNAi agent comprising a first strand and a second strand, wherein the sequence of the first or second strand is the sequence of the first or second strand of AD-25955, and wherein the first and/or second strand further comprises up to about 20 additional nucleotides.

A RNAi agent comprising a first strand and a second strand, wherein the sequence of the first or second strand is the sequence of the first or second strand of AD-26029, and wherein the first and/or second strand further comprises up to about 20 additional nucleotides.

A RNAi agent comprising a first strand and a second strand, wherein the sequence of the first or second strand is the sequence of the first or second strand of AD-26131, and wherein the first and/or second strand further comprises up to about 20 additional nucleotides.

A RNAi agent comprising a first strand and a second strand, wherein the sequence of the first or second strand is the sequence of the first or second strand of AD-18894, and wherein the first and/or second strand further comprises up to about 20 additional nucleotides.

A RNAi agent comprising a first strand and a second strand, wherein the sequence of the first or second strand is the sequence of the first or second strand of AD-18939, and wherein the first and/or second strand further comprises up to about 20 additional nucleotides.

A RNAi agent comprising a first strand and a second strand, wherein the sequence of the first or second strand is the sequence of the first or second strand of AD-26654, and wherein the first and/or second strand further comprises up to about 20 additional nucleotides.

A RNAi agent comprising a first strand and a second strand, wherein the sequence of the first or second strand is the sequence of the first or second strand of AD-18929, and wherein the first and/or second strand further comprises up to about 20 additional nucleotides.

A RNAi agent comprising a first strand and a second strand, wherein the sequence of the first or second strand is the sequence of the first or second strand of AD-26135, and wherein the first and/or second strand further comprises up to about 20 additional nucleotides.

A RNAi agent comprising a first strand and a second strand, wherein the sequence of the first or second strand is the sequence of the first or second strand of AD-26774, and wherein the first and/or second strand further comprises up to about 20 additional nucleotides.

A RNAi agent comprising a first strand and a second strand, wherein the sequence of the first or second strand is the sequence of the first or second strand of AD-26780, and wherein the first and/or second strand further comprises up to about 20 additional nucleotides.

A RNAi agent comprising a first strand and a second strand, wherein the sequence of the first or second strand is the sequence of the first or second strand of AD-26819, and wherein the first and/or second strand further comprises up to about 20 additional nucleotides.

A RNAi agent comprising a first strand and a second strand, wherein the sequence of the first or second strand is the sequence of the first or second strand of AD-26918, and wherein the first and/or second strand further comprises up to about 20 additional nucleotides.

A RNAi agent comprising a first strand and a second strand, wherein the sequence of the first or second strand is the sequence of the first or second strand of AD-19050, and wherein the first and/or second strand further comprises up to about 20 additional nucleotides.

A RNAi agent comprising a first strand and a second strand, wherein the sequence of the first or second strand is the sequence of the first or second strand of AD-18994, and wherein the first and/or second strand further comprises up to about 20 additional nucleotides.

A RNAi agent comprising a first strand and a second strand, wherein the sequence of the first or second strand is the sequence of the first or second strand of AD-26769, and wherein the first and/or second strand further comprises up to about 20 additional nucleotides.

A RNAi agent comprising a first strand and a second strand, wherein the sequence of the first or second strand is the sequence of the first or second strand of AD-26666, and wherein the first and/or second strand further comprises up to about 20 additional nucleotides.

A RNAi agent comprising a first strand and a second strand, wherein the sequence of the first or second strand is the sequence of the first or second strand of AD-26784, and wherein the first and/or second strand further comprises up to about 20 additional nucleotides.

A RNAi agent comprising a first strand and a second strand, wherein the sequence of the first or second strand is the sequence of the first or second strand of AD-18969, and wherein the first and/or second strand further comprises up to about 20 additional nucleotides.

A RNAi agent comprising a first strand and a second strand, wherein the sequence of the first or second strand is the sequence of the first or second strand of AD-18986, and wherein the first and/or second strand further comprises up to about 20 additional nucleotides.

A RNAi agent comprising a first strand and a second strand, wherein the sequence of the first or second strand is the sequence of the first or second strand of AD-25929, and wherein the first and/or second strand further comprises up to about 20 additional nucleotides.

A RNAi agent comprising a first strand and a second strand, wherein the sequence of the first or second strand is the sequence of the first or second strand of AD-25932, and wherein the first and/or second strand further comprises up to about 20 additional nucleotides.

A RNAi agent comprising a first strand and a second strand, wherein the sequence of the first or second strand is the sequence of the first or second strand of AD-26095, and wherein the first and/or second strand further comprises up to about 20 additional nucleotides.

A RNAi agent comprising a first strand and a second strand, wherein the sequence of the first or second strand is the sequence of the first or second strand of AD-26908, and wherein the first and/or second strand further comprises up to about 20 additional nucleotides.

A RNAi agent comprising a first strand and a second strand, wherein the sequence of the first or second strand is the sequence of the first or second strand of AD-26071, and wherein the first and/or second strand further comprises up to about 20 additional nucleotides.

A RNAi agent comprising a first strand and a second strand, wherein the sequence of the first or second strand is the sequence of the first or second strand of AD-26912, and wherein the first and/or second strand further comprises up to about 20 additional nucleotides.

A RNAi agent comprising a first strand and a second strand, wherein the sequence of the first or second strand is the sequence of the first or second strand of AD-19054, and wherein the first and/or second strand further comprises up to about 20 additional nucleotides.

A RNAi agent comprising a first strand and a second strand, wherein the sequence of the first or second strand is the sequence of the first or second strand of AD-25918, and wherein the first and/or second strand further comprises up to about 20 additional nucleotides.

A RNAi agent comprising a first strand and a second strand, wherein the sequence of the first or second strand is the sequence of the first or second strand of AD-26903, and wherein the first and/or second strand further comprises up to about 20 additional nucleotides.

A RNAi agent comprising a first strand and a second strand, wherein the sequence of the first or second strand is the sequence of the first or second strand of AD-25931, and wherein the first and/or second strand further comprises up to about 20 additional nucleotides.

A RNAi agent comprising a first strand and a second strand, wherein the sequence of the first or second strand is the sequence of the first or second strand of AD-26146, and wherein the first and/or second strand further comprises up to about 20 additional nucleotides.

A RNAi agent comprising a first strand and a second strand, wherein the sequence of the first or second strand is the sequence of the first or second strand of AD-26200, and wherein the first and/or second strand further comprises up to about 20 additional nucleotides.

A RNAi agent comprising a first strand and a second strand, wherein the sequence of the first or second strand is the sequence of the first or second strand of AD-26917, and wherein the first and/or second strand further comprises up to about 20 additional nucleotides.

A RNAi agent comprising a first strand and a second strand, wherein the sequence of the first or second strand is the sequence of the first or second strand of AD-26794, and wherein the first and/or second strand further comprises up to about 20 additional nucleotides.

A RNAi agent comprising a first strand and a second strand, wherein the sequence of the first or second strand is the sequence of the first or second strand of AD-26910, and wherein the first and/or second strand further comprises up to about 20 additional nucleotides.

A RNAi agent comprising a first strand and a second strand, wherein the sequence of the first or second strand is the sequence of the first or second strand of AD-25939, and wherein the first and/or second strand further comprises up to about 20 additional nucleotides.

A RNAi agent comprising a first strand and a second strand, wherein the sequence of the first or second strand is the sequence of the first or second strand of AD-26032, and wherein the first and/or second strand further comprises up to about 20 additional nucleotides.

A RNAi agent comprising a first strand and a second strand, wherein the sequence of the first or second strand is the sequence of the first or second strand of AD-26776, and wherein the first and/or second strand further comprises up to about 20 additional nucleotides.

A RNAi agent comprising a first strand and a second strand, wherein the sequence of the first or second strand is the sequence of the first or second strand of AD-26806, and wherein the first and/or second strand further comprises up to about 20 additional nucleotides.

A RNAi agent comprising a first strand and a second strand, wherein the sequence of the first or second strand is the sequence of the first or second strand of AD-26748, and wherein the first and/or second strand further comprises up to about 20 additional nucleotides.

A RNAi agent comprising a first strand and a second strand, wherein the sequence of the first or second strand is the sequence of the first or second strand of AD-26725, and wherein the first and/or second strand further comprises up to about 20 additional nucleotides.

A RNAi agent comprising a first strand and a second strand, wherein the sequence of the first or second strand is the sequence of the first or second strand of AD-18958, and wherein the first and/or second strand further comprises up to about 20 additional nucleotides.

A RNAi agent comprising a first strand and a second strand, wherein the sequence of the first or second strand is the sequence of the first or second strand of AD-26672, and wherein the first and/or second strand further comprises up to about 20 additional nucleotides.

A RNAi agent comprising a first strand and a second strand, wherein the sequence of the first or second strand is the sequence of the first or second strand of AD-26905, and wherein the first and/or second strand further comprises up to about 20 additional nucleotides.

A RNAi agent comprising a first strand and a second strand, wherein the sequence of the first or second strand is the sequence of the first or second strand of AD-19056, and wherein the first and/or second strand further comprises up to about 20 additional nucleotides.

A RNAi agent comprising a first strand and a second strand, wherein the sequence of the first or second strand is the sequence of the first or second strand of AD-19762, and wherein the first and/or second strand further comprises up to about 20 additional nucleotides.

A RNAi agent comprising a first strand and a second strand, wherein the sequence of the first or second strand is the sequence of the first or second strand of AD-26919, and wherein the first and/or second strand further comprises up to about 20 additional nucleotides.

A RNAi agent comprising a first strand and a second strand, wherein the sequence of the first or second strand is the sequence of the first or second strand of AD-18946, and wherein the first and/or second strand further comprises up to about 20 additional nucleotides.

A RNAi agent comprising a first strand and a second strand, wherein the sequence of the first or second strand is the sequence of the first or second strand of AD-19066, and wherein the first and/or second strand further comprises up to about 20 additional nucleotides.

A RNAi agent comprising a first strand and a second strand, wherein the sequence of the first or second strand is the sequence of the first or second strand of AD-19746, and wherein the first and/or second strand further comprises up to about 20 additional nucleotides.

A RNAi agent comprising a first strand and a second strand, wherein the sequence of the first or second strand is the sequence of the first or second strand of AD-26057, and wherein the first and/or second strand further comprises up to about 20 additional nucleotides.

A RNAi agent comprising a first strand and a second strand, wherein the sequence of the first or second strand is the sequence of the first or second strand of AD-26073, and wherein the first and/or second strand further comprises up to about 20 additional nucleotides.

A RNAi agent comprising a first strand and a second strand, wherein the sequence of the first or second strand is the sequence of the first or second strand of AD-26689, and wherein the first and/or second strand further comprises up to about 20 additional nucleotides.

A RNAi agent comprising a first strand and a second strand, wherein the sequence of the first or second strand is the sequence of the first or second strand of AD-19008, and wherein the first and/or second strand further comprises up to about 20 additional nucleotides.

A RNAi agent comprising a first strand and a second strand, wherein the sequence of the first or second strand is the sequence of the first or second strand of AD-26026, and wherein the first and/or second strand further comprises up to about 20 additional nucleotides.

A RNAi agent comprising a first strand and a second strand, wherein the sequence of the first or second strand is the sequence of the first or second strand of AD-26761, and wherein the first and/or second strand further comprises up to about 20 additional nucleotides.

A RNAi agent comprising a first strand and a second strand, wherein the sequence of the first or second strand is the sequence of the first or second strand of AD-19752, and wherein the first and/or second strand further comprises up to about 20 additional nucleotides.

A RNAi agent comprising a first strand and a second strand, wherein the sequence of the first or second strand is the sequence of the first or second strand of AD-18981, and wherein the first and/or second strand further comprises up to about 20 additional nucleotides.

A RNAi agent comprising a first strand and a second strand, wherein the sequence of the first or second strand is the sequence of the first or second strand of AD-18927, and wherein the first and/or second strand further comprises up to about 20 additional nucleotides.

A RNAi agent comprising a first strand and a second strand, wherein the sequence of the first or second strand is the sequence of the first or second strand of AD-19753, and wherein the first and/or second strand further comprises up to about 20 additional nucleotides.

A RNAi agent comprising a first strand and a second strand, wherein the sequence of the first or second strand is the sequence of the first or second strand of AD-25907, and wherein the first and/or second strand further comprises up to about 20 additional nucleotides.

A RNAi agent comprising a first strand and a second strand, wherein the sequence of the first or second strand is the sequence of the first or second strand of AD-26671, and wherein the first and/or second strand further comprises up to about 20 additional nucleotides.

A RNAi agent comprising a first strand and a second strand, wherein the sequence of the first or second strand is the sequence of the first or second strand of AD-19080, and wherein the first and/or second strand further comprises up to about 20 additional nucleotides.

A RNAi agent comprising a first strand and a second strand, wherein the sequence of the first or second strand is the sequence of the first or second strand of AD-26075, and wherein the first and/or second strand further comprises up to about 20 additional nucleotides.

A RNAi agent comprising a first strand and a second strand, wherein the sequence of the first or second strand is the sequence of the first or second strand of AD-26681, and wherein the first and/or second strand further comprises up to about 20 additional nucleotides.

A RNAi agent comprising a first strand and a second strand, wherein the sequence of the first or second strand is the sequence of the first or second strand of AD-18976, and wherein the first and/or second strand further comprises up to about 20 additional nucleotides.

A RNAi agent comprising a first strand and a second strand, wherein the sequence of the first or second strand is the sequence of the first or second strand of AD-25900, and wherein the first and/or second strand further comprises up to about 20 additional nucleotides.

A RNAi agent comprising a first strand and a second strand, wherein the sequence of the first or second strand is the sequence of the first or second strand of AD-26126, and wherein the first and/or second strand further comprises up to about 20 additional nucleotides.

A RNAi agent comprising a first strand and a second strand, wherein the sequence of the first or second strand is the sequence of the first or second strand of AD-26688, and wherein the first and/or second strand further comprises up to about 20 additional nucleotides.

A RNAi agent comprising a first strand and a second strand, wherein the sequence of the first or second strand is the sequence of the first or second strand of AD-25912, and wherein the first and/or second strand further comprises up to about 20 additional nucleotides.

A RNAi agent comprising a first strand and a second strand, wherein the sequence of the first or second strand is the sequence of the first or second strand of AD-25930, and wherein the first and/or second strand further comprises up to about 20 additional nucleotides.

A RNAi agent comprising a first strand and a second strand, wherein the sequence of the first or second strand is the sequence of the first or second strand of AD-18995, and wherein the first and/or second strand further comprises up to about 20 additional nucleotides.

A RNAi agent comprising a first strand and a second strand, wherein the sequence of the first or second strand is the sequence of the first or second strand of AD-26802, and wherein the first and/or second strand further comprises up to about 20 additional nucleotides.

A RNAi agent comprising a first strand and a second strand, wherein the sequence of the first or second strand is the sequence of the first or second strand of AD-25892, and wherein the first and/or second strand further comprises up to about 20 additional nucleotides.

A RNAi agent comprising a first strand and a second strand, wherein the sequence of the first or second strand is the sequence of the first or second strand of AD-25947, and wherein the first and/or second strand further comprises up to about 20 additional nucleotides.

A RNAi agent comprising a first strand and a second strand, wherein the sequence of the first or second strand is the sequence of the first or second strand of AD-26088, and wherein the first and/or second strand further comprises up to about 20 additional nucleotides.

A RNAi agent comprising a first strand and a second strand, wherein the sequence of the first or second strand is the sequence of the first or second strand of AD-26098, and wherein the first and/or second strand further comprises up to about 20 additional nucleotides.

A RNAi agent comprising a first strand and a second strand, wherein the sequence of the first or second strand is the sequence of the first or second strand of AD-26778, and wherein the first and/or second strand further comprises up to about 20 additional nucleotides.

A RNAi agent comprising a first strand and a second strand, wherein the sequence of the first or second strand is the sequence of the first or second strand of AD-26215, and wherein the first and/or second strand further comprises up to about 20 additional nucleotides.

A RNAi agent comprising a first strand and a second strand, wherein the sequence of the first or second strand is the sequence of the first or second strand of AD-26739, and wherein the first and/or second strand further comprises up to about 20 additional nucleotides.

A RNAi agent comprising a first strand and a second strand, wherein the sequence of the first or second strand is the sequence of the first or second strand of AD-18950, and wherein the first and/or second strand further comprises up to about 20 additional nucleotides.

A RNAi agent comprising a first strand and a second strand, wherein the sequence of the first or second strand is the sequence of the first or second strand of AD-25949, and wherein the first and/or second strand further comprises up to about 20 additional nucleotides.

A RNAi agent comprising a first strand and a second strand, wherein the sequence of the first or second strand is the sequence of the first or second strand of AD-26141, and wherein the first and/or second strand further comprises up to about 20 additional nucleotides.

A RNAi agent comprising a first strand and a second strand, wherein the sequence of the first or second strand is the sequence of the first or second strand of AD-18961, and wherein the first and/or second strand further comprises up to about 20 additional nucleotides.

A RNAi agent comprising a first strand and a second strand, wherein the sequence of the first or second strand is the sequence of the first or second strand of AD-25957, and wherein the first and/or second strand further comprises up to about 20 additional nucleotides.

A RNAi agent comprising a first strand and a second strand, wherein the sequence of the first or second strand is the sequence of the first or second strand of AD-26826, and wherein the first and/or second strand further comprises up to about 20 additional nucleotides.

A RNAi agent comprising a first strand and a second strand, wherein the sequence of the first or second strand is the sequence of the first or second strand of AD-25963, and wherein the first and/or second strand further comprises up to about 20 additional nucleotides.

A RNAi agent comprising a first strand and a second strand, wherein the sequence of the first or second strand is the sequence of the first or second strand of AD-26019, and wherein the first and/or second strand further comprises up to about 20 additional nucleotides.

A RNAi agent comprising a first strand and a second strand, wherein the sequence of the first or second strand is the sequence of the first or second strand of AD-26035, and wherein the first and/or second strand further comprises up to about 20 additional nucleotides.

A RNAi agent comprising a first strand and a second strand, wherein the sequence of the first or second strand is the sequence of the first or second strand of AD-25946, and wherein the first and/or second strand further comprises up to about 20 additional nucleotides.

A RNAi agent comprising a first strand and a second strand, wherein the sequence of the first or second strand is the sequence of the first or second strand of AD-26714, and wherein the first and/or second strand further comprises up to about 20 additional nucleotides.

A RNAi agent comprising a first strand and a second strand, wherein the sequence of the first or second strand is the sequence of the first or second strand of AD-26022, and wherein the first and/or second strand further comprises up to about 20 additional nucleotides.

A RNAi agent comprising a first strand and a second strand, wherein the sequence of the first or second strand is the sequence of the first or second strand of AD-26096, and wherein the first and/or second strand further comprises up to about 20 additional nucleotides.

A RNAi agent comprising a first strand and a second strand, wherein the sequence of the first or second strand is the sequence of the first or second strand of AD-26132, and wherein the first and/or second strand further comprises up to about 20 additional nucleotides.

A RNAi agent comprising a first strand and a second strand, wherein the sequence of the first or second strand is the sequence of the first or second strand of AD-26062, and wherein the first and/or second strand further comprises up to about 20 additional nucleotides.

A RNAi agent comprising a first strand and a second strand, wherein the sequence of the first or second strand is the sequence of the first or second strand of AD-18991, and wherein the first and/or second strand further comprises up to about 20 additional nucleotides.

A RNAi agent comprising a first strand and a second strand, wherein the sequence of the first or second strand is the sequence of the first or second strand of AD-26164, and wherein the first and/or second strand further comprises up to about 20 additional nucleotides.

A RNAi agent comprising a first strand and a second strand, wherein the sequence of the first or second strand is the sequence of the first or second strand of AD-26209, and wherein the first and/or second strand further comprises up to about 20 additional nucleotides.

A RNAi agent comprising a first strand and a second strand, wherein the sequence of the first or second strand is the sequence of the first or second strand of AD-25895, and wherein the first and/or second strand further comprises up to about 20 additional nucleotides.

A RNAi agent comprising a first strand and a second strand, wherein the sequence of the first or second strand is the sequence of the first or second strand of AD-25933, and wherein the first and/or second strand further comprises up to about 20 additional nucleotides.

A RNAi agent comprising a first strand and a second strand, wherein the sequence of the first or second strand is the sequence of the first or second strand of AD-26017, and wherein the first and/or second strand further comprises up to about 20 additional nucleotides.

A RNAi agent comprising a first strand and a second strand, wherein the sequence of the first or second strand is the sequence of the first or second strand of AD-19749, and wherein the first and/or second strand further comprises up to about 20 additional nucleotides.

A RNAi agent comprising a first strand and a second strand, wherein the sequence of the first or second strand is the sequence of the first or second strand of AD-26653, and wherein the first and/or second strand further comprises up to about 20 additional nucleotides.

A RNAi agent comprising a first strand and a second strand, wherein the sequence of the first or second strand is the sequence of the first or second strand of AD-26759, and wherein the first and/or second strand further comprises up to about 20 additional nucleotides.

A RNAi agent comprising a first strand and a second strand, wherein the sequence of the first or second strand is the sequence of the first or second strand of AD-25924, and wherein the first and/or second strand further comprises up to about 20 additional nucleotides.

A RNAi agent comprising a first strand and a second strand, wherein the sequence of the first or second strand is the sequence of the first or second strand of AD-26153, and wherein the first and/or second strand further comprises up to about 20 additional nucleotides.

A RNAi agent comprising a first strand and a second strand, wherein the sequence of the first or second strand is the sequence of the first or second strand of AD-25953, and wherein the first and/or second strand further comprises up to about 20 additional nucleotides.

A RNAi agent comprising a first strand and a second strand, wherein the sequence of the first or second strand is the sequence of the first or second strand of AD-26764, and wherein the first and/or second strand further comprises up to about 20 additional nucleotides.

A RNAi agent comprising a first strand and a second strand, wherein the sequence of the first or second strand is the sequence of the first or second strand of AD-26790, and wherein the first and/or second strand further comprises up to about 20 additional nucleotides.

A RNAi agent comprising a first strand and a second strand, wherein the sequence of the first or second strand is the sequence of the first or second strand of AD-20124, and wherein the first and/or second strand further comprises up to about 20 additional nucleotides.

A RNAi agent comprising a first strand and a second strand, wherein the sequence of the first or second strand is the sequence of the first or second strand of AD-25919, and wherein the first and/or second strand further comprises up to about 20 additional nucleotides.

A RNAi agent comprising a first strand and a second strand, wherein the sequence of the first or second strand is the sequence of the first or second strand of AD-18913, and wherein the first and/or second strand further comprises up to about 20 additional nucleotides.

A RNAi agent comprising a first strand and a second strand, wherein the sequence of the first or second strand is the sequence of the first or second strand of AD-26211, and wherein the first and/or second strand further comprises up to about 20 additional nucleotides.

A RNAi agent comprising a first strand and a second strand, wherein the sequence of the first or second strand is the sequence of the first or second strand of AD-18936, and wherein the first and/or second strand further comprises up to about 20 additional nucleotides.

A RNAi agent comprising a first strand and a second strand, wherein the sequence of the first or second strand is the sequence of the first or second strand of AD-25898, and wherein the first and/or second strand further comprises up to about 20 additional nucleotides.

A RNAi agent comprising a first strand and a second strand, wherein the sequence of the first or second strand is the sequence of the first or second strand of AD-26741, and wherein the first and/or second strand further comprises up to about 20 additional nucleotides.

A RNAi agent comprising a first strand and a second strand, wherein the sequence of the first or second strand is the sequence of the first or second strand of AD-19043, and wherein the first and/or second strand further comprises up to about 20 additional nucleotides.

A RNAi agent comprising a first strand and a second strand, wherein the sequence of the first or second strand is the sequence of the first or second strand of AD-26079, and wherein the first and/or second strand further comprises up to about 20 additional nucleotides.

A RNAi agent comprising a first strand and a second strand, wherein the sequence of the first or second strand is the sequence of the first or second strand of AD-19000, and wherein the first and/or second strand further comprises up to about 20 additional nucleotides.

A RNAi agent comprising a first strand and a second strand, wherein the sequence of the first or second strand is the sequence of the first or second strand of AD-25911, and wherein the first and/or second strand further comprises up to about 20 additional nucleotides.

A RNAi agent comprising a first strand and a second strand, wherein the sequence of the first or second strand is the sequence of the first or second strand of AD-26786, and wherein the first and/or second strand further comprises up to about 20 additional nucleotides.

A RNAi agent comprising a first strand and a second strand, wherein the sequence of the first or second strand is the sequence of the first or second strand of AD-19069, and wherein the first and/or second strand further comprises up to about 20 additional nucleotides.

A RNAi agent comprising a first strand and a second strand, wherein the sequence of the first or second strand is the sequence of the first or second strand of AD-26037, and wherein the first and/or second strand further comprises up to about 20 additional nucleotides.

A RNAi agent comprising a first strand and a second strand, wherein the sequence of the first or second strand is the sequence of the first or second strand of AD-26723, and wherein the first and/or second strand further comprises up to about 20 additional nucleotides.

A RNAi agent comprising a first strand and a second strand, wherein the sequence of the first or second strand is the sequence of the first or second strand of AD-19067, and wherein the first and/or second strand further comprises up to about 20 additional nucleotides.

A RNAi agent comprising a first strand and a second strand, wherein the sequence of the first or second strand is the sequence of the first or second strand of AD-25928, and wherein the first and/or second strand further comprises up to about 20 additional nucleotides.

A RNAi agent comprising a first strand and a second strand, wherein the sequence of the first or second strand is the sequence of the first or second strand of AD-26677, and wherein the first and/or second strand further comprises up to about 20 additional nucleotides.

A RNAi agent comprising a first strand and a second strand, wherein the sequence of the first or second strand is the sequence of the first or second strand of AD-19006, and wherein the first and/or second strand further comprises up to about 20 additional nucleotides.

A RNAi agent comprising a first strand and a second strand, wherein the sequence of the first or second strand is the sequence of the first or second strand of AD-19758, and wherein the first and/or second strand further comprises up to about 20 additional nucleotides.

A RNAi agent comprising a first strand and a second strand, wherein the sequence of the first or second strand is the sequence of the first or second strand of AD-26913, and wherein the first and/or second strand further comprises up to about 20 additional nucleotides.

A RNAi agent comprising a first strand and a second strand, wherein the sequence of the first or second strand is the sequence of the first or second strand of AD-25917, and wherein the first and/or second strand further comprises up to about 20 additional nucleotides.

A RNAi agent comprising a first strand and a second strand, wherein the sequence of the first or second strand is the sequence of the first or second strand of AD-26189, and wherein the first and/or second strand further comprises up to about 20 additional nucleotides.

A RNAi agent comprising a first strand and a second strand, wherein the sequence of the first or second strand is the sequence of the first or second strand of AD-26787, and wherein the first and/or second strand further comprises up to about 20 additional nucleotides.

A RNAi agent comprising a first strand and a second strand, wherein the sequence of the first or second strand is the sequence of the first or second strand of AD-26707, and wherein the first and/or second strand further comprises up to about 20 additional nucleotides.

A RNAi agent comprising a first strand and a second strand, wherein the sequence of the first or second strand is the sequence of the first or second strand of AD-26094, and wherein the first and/or second strand further comprises up to about 20 additional nucleotides.

A RNAi agent comprising a first strand and a second strand, wherein the sequence of the first or second strand is the sequence of the first or second strand of AD-26097, and wherein the first and/or second strand further comprises up to about 20 additional nucleotides.

A RNAi agent comprising a first strand and a second strand, wherein the sequence of the first or second strand is the sequence of the first or second strand of AD-26699, and wherein the first and/or second strand further comprises up to about 20 additional nucleotides.

A RNAi agent comprising a first strand and a second strand, wherein the sequence of the first or second strand is the sequence of the first or second strand of AD-26756, and wherein the first and/or second strand further comprises up to about 20 additional nucleotides.

A RNAi agent comprising a first strand and a second strand, wherein the sequence of the first or second strand is the sequence of the first or second strand of AD-26720, and wherein the first and/or second strand further comprises up to about 20 additional nucleotides.

A RNAi agent comprising a first strand and a second strand, wherein the sequence of the first or second strand is the sequence of the first or second strand of AD-25926, and wherein the first and/or second strand further comprises up to about 20 additional nucleotides.

A RNAi agent comprising a first strand and a second strand, wherein the sequence of the first or second strand is the sequence of the first or second strand of AD-26212, and wherein the first and/or second strand further comprises up to about 20 additional nucleotides.

A RNAi agent comprising a first strand and a second strand, wherein the sequence of the first or second strand is the sequence of the first or second strand of AD-26687, and wherein the first and/or second strand further comprises up to about 20 additional nucleotides.

A RNAi agent comprising a first strand and a second strand, wherein the sequence of the first or second strand is the sequence of the first or second strand of AD-26753, and wherein the first and/or second strand further comprises up to about 20 additional nucleotides.

A RNAi agent comprising a first strand and a second strand, wherein the sequence of the first or second strand is the sequence of the first or second strand of AD-18982, and wherein the first and/or second strand further comprises up to about 20 additional nucleotides.

A RNAi agent comprising a first strand and a second strand, wherein the sequence of the first or second strand is the sequence of the first or second strand of AD-18908, and wherein the first and/or second strand further comprises up to about 20 additional nucleotides.

A RNAi agent comprising a first strand and a second strand, wherein the sequence of the first or second strand is the sequence of the first or second strand of AD-18968, and wherein the first and/or second strand further comprises up to about 20 additional nucleotides.

A RNAi agent comprising a first strand and a second strand, wherein the sequence of the first or second strand is the sequence of the first or second strand of AD-25948, and wherein the first and/or second strand further comprises up to about 20 additional nucleotides.

A RNAi agent comprising a first strand and a second strand, wherein the sequence of the first or second strand is the sequence of the first or second strand of AD-26188, and wherein the first and/or second strand further comprises up to about 20 additional nucleotides.

A RNAi agent comprising a first strand and a second strand, wherein the sequence of the first or second strand is the sequence of the first or second strand of AD-26708, and wherein the first and/or second strand further comprises up to about 20 additional nucleotides.

A RNAi agent comprising a first strand and a second strand, wherein the sequence of the first or second strand is the sequence of the first or second strand of AD-25961, and wherein the first and/or second strand further comprises up to about 20 additional nucleotides.

A RNAi agent comprising a first strand and a second strand, wherein the sequence of the first or second strand is the sequence of the first or second strand of AD-26803, and wherein the first and/or second strand further comprises up to about 20 additional nucleotides.

A RNAi agent comprising a first strand and a second strand, wherein the sequence of the first or second strand is the sequence of the first or second strand of AD-19741, and wherein the first and/or second strand further comprises up to about 20 additional nucleotides.

A RNAi agent comprising a first strand and a second strand, wherein the sequence of the first or second strand is the sequence of the first or second strand of AD-26056, and wherein the first and/or second strand further comprises up to about 20 additional nucleotides.

A RNAi agent comprising a first strand and a second strand, wherein the sequence of the first or second strand is the sequence of the first or second strand of AD-25959, and wherein the first and/or second strand further comprises up to about 20 additional nucleotides.

A RNAi agent comprising a first strand and a second strand, wherein the sequence of the first or second strand is the sequence of the first or second strand of AD-26059, and wherein the first and/or second strand further comprises up to about 20 additional nucleotides.

A RNAi agent comprising a first strand and a second strand, wherein the sequence of the first or second strand is the sequence of the first or second strand of AD-26102, and wherein the first and/or second strand further comprises up to about 20 additional nucleotides.

A RNAi agent comprising a first strand and a second strand, wherein the sequence of the first or second strand is the sequence of the first or second strand of AD-26106, and wherein the first and/or second strand further comprises up to about 20 additional nucleotides.

A RNAi agent comprising a first strand and a second strand, wherein the sequence of the first or second strand is the sequence of the first or second strand of AD-26744, and wherein the first and/or second strand further comprises up to about 20 additional nucleotides.

A RNAi agent comprising a first strand and a second strand, wherein the sequence of the first or second strand is the sequence of the first or second strand of AD-26099, and wherein the first and/or second strand further comprises up to about 20 additional nucleotides.

A RNAi agent comprising a first strand and a second strand, wherein the sequence of the first or second strand is the sequence of the first or second strand of AD-26170, and wherein the first and/or second strand further comprises up to about 20 additional nucleotides.

A RNAi agent comprising a first strand and a second strand, wherein the sequence of the first or second strand is the sequence of the first or second strand of AD-19012, and wherein the first and/or second strand further comprises up to about 20 additional nucleotides.

A RNAi agent comprising a first strand and a second strand, wherein the sequence of the first or second strand is the sequence of the first or second strand of AD-26198, and wherein the first and/or second strand further comprises up to about 20 additional nucleotides.

A RNAi agent comprising a first strand and a second strand, wherein the sequence of the first or second strand is the sequence of the first or second strand of AD-26766, and wherein the first and/or second strand further comprises up to about 20 additional nucleotides.

A RNAi agent comprising a first strand and a second strand, wherein the sequence of the first or second strand is the sequence of the first or second strand of AD-18951, and wherein the first and/or second strand further comprises up to about 20 additional nucleotides.

A RNAi agent comprising a first strand and a second strand, wherein the sequence of the first or second strand is the sequence of the first or second strand of AD-18975, and wherein the first and/or second strand further comprises up to about 20 additional nucleotides.

A RNAi agent comprising a first strand and a second strand, wherein the sequence of the first or second strand is the sequence of the first or second strand of AD-26749, and wherein the first and/or second strand further comprises up to about 20 additional nucleotides.

A RNAi agent comprising a first strand and a second strand, wherein the sequence of the first or second strand is the sequence of the first or second strand of AD-18911, and wherein the first and/or second strand further comprises up to about 20 additional nucleotides.

A RNAi agent comprising a first strand and a second strand, wherein the sequence of the first or second strand is the sequence of the first or second strand of AD-26906, and wherein the first and/or second strand further comprises up to about 20 additional nucleotides.

A RNAi agent comprising a first strand and a second strand, wherein the sequence of the first or second strand is the sequence of the first or second strand of AD-19747, and wherein the first and/or second strand further comprises up to about 20 additional nucleotides.

A RNAi agent comprising a first strand and a second strand, wherein the sequence of the first or second strand is the sequence of the first or second strand of AD-18960, and wherein the first and/or second strand further comprises up to about 20 additional nucleotides.

A RNAi agent comprising a first strand and a second strand, wherein the sequence of the first or second strand is the sequence of the first or second strand of AD-25909, and wherein the first and/or second strand further comprises up to about 20 additional nucleotides.

A RNAi agent comprising a first strand and a second strand, wherein the sequence of the first or second strand is the sequence of the first or second strand of AD-26184, and wherein the first and/or second strand further comprises up to about 20 additional nucleotides.

A RNAi agent comprising a first strand and a second strand, wherein the sequence of the first or second strand is the sequence of the first or second strand of AD-26077, and wherein the first and/or second strand further comprises up to about 20 additional nucleotides.

A RNAi agent comprising a first strand and a second strand, wherein the sequence of the first or second strand is the sequence of the first or second strand of AD-26680, and wherein the first and/or second strand further comprises up to about 20 additional nucleotides.

A RNAi agent comprising a first strand and a second strand, wherein the sequence of the first or second strand is the sequence of the first or second strand of AD-26085, and wherein the first and/or second strand further comprises up to about 20 additional nucleotides.

A RNAi agent comprising a first strand and a second strand, wherein the sequence of the first or second strand is the sequence of the first or second strand of AD-18926, and wherein the first and/or second strand further comprises up to about 20 additional nucleotides.

A RNAi agent comprising a first strand and a second strand, wherein the sequence of the first or second strand is the sequence of the first or second strand of AD-18945, and wherein the first and/or second strand further comprises up to about 20 additional nucleotides.

A RNAi agent comprising a first strand and a second strand, wherein the sequence of the first or second strand is the sequence of the first or second strand of AD-26703, and wherein the first and/or second strand further comprises up to about 20 additional nucleotides.

A RNAi agent comprising a first strand and a second strand, wherein the sequence of the first or second strand is the sequence of the first or second strand of AD-26911, and wherein the first and/or second strand further comprises up to about 20 additional nucleotides.

A RNAi agent comprising a first strand and a second strand, wherein the sequence of the first or second strand is the sequence of the first or second strand of AD-26661, and wherein the first and/or second strand further comprises up to about 20 additional nucleotides.

A RNAi agent comprising a first strand and a second strand, wherein the sequence of the first or second strand is the sequence of the first or second strand of AD-18905, and wherein the first and/or second strand further comprises up to about 20 additional nucleotides.

A RNAi agent comprising a first strand and a second strand, wherein the sequence of the first or second strand is the sequence of the first or second strand of AD-26142, and wherein the first and/or second strand further comprises up to about 20 additional nucleotides.

A RNAi agent comprising: a first strand and a second strand, wherein the sequence of the first or second strand is the sequence of the first or second strand of Set1_1245, and wherein the first and/or second strand further comprises up to about 20 additional nucleotides.

A RNAi agent comprising: a first strand and a second strand, wherein the sequence of the first or second strand is the sequence of the first or second strand of Set1_1249, and wherein the first and/or second strand further comprises up to about 20 additional nucleotides.

A RNAi agent comprising: a first strand and a second strand, wherein the sequence of the first or second strand is the sequence of the first or second strand of Set1_1250, and wherein the first and/or second strand further comprises up to about 20 additional nucleotides.

A RNAi agent comprising: a first strand and a second strand, wherein the sequence of the first or second strand is the sequence of the first or second strand of Set1_1450, and wherein the first and/or second strand further comprises up to about 20 additional nucleotides.

A RNAi agent comprising: a first strand and a second strand, wherein the sequence of the first or second strand is the sequence of the first or second strand of Set1_1545, and wherein the first and/or second strand further comprises up to about 20 additional nucleotides.

A RNAi agent comprising: a first strand and a second strand, wherein the sequence of the first or second strand is the sequence of the first or second strand of Set1_1755, and wherein the first and/or second strand further comprises up to about 20 additional nucleotides.

A RNAi agent comprising: a first strand and a second strand, wherein the sequence of the first or second strand is the sequence of the first or second strand of Set1_1814, and wherein the first and/or second strand further comprises up to about 20 additional nucleotides.

A RNAi agent comprising: a first strand and a second strand, wherein the sequence of the first or second strand is the sequence of the first or second strand of Set1_1816, and wherein the first and/or second strand further comprises up to about 20 additional nucleotides.

A RNAi agent comprising: a first strand and a second strand, wherein the sequence of the first or second strand is the sequence of the first or second strand of Set1_1974, and wherein the first and/or second strand further comprises up to about 20 additional nucleotides.

A RNAi agent comprising: a first strand and a second strand, wherein the sequence of the first or second strand is the sequence of the first or second strand of Set1_2202, and wherein the first and/or second strand further comprises up to about 20 additional nucleotides.

A RNAi agent comprising: a first strand and a second strand, wherein the sequence of the first or second strand is the sequence of the first or second strand of Set1_2425, and wherein the first and/or second strand further comprises up to about 20 additional nucleotides.

A RNAi agent comprising: a first strand and a second strand, wherein the sequence of the first or second strand is the sequence of the first or second strand of Set1_254, and wherein the first and/or second strand further comprises up to about 20 additional nucleotides.

A RNAi agent comprising: a first strand and a second strand, wherein the sequence of the first or second strand is the sequence of the first or second strand of Set1_3146, and wherein the first and/or second strand further comprises up to about 20 additional nucleotides.

A RNAi agent comprising: a first strand and a second strand, wherein the sequence of the first or second strand is the sequence of the first or second strand of Set1_3169, and wherein the first and/or second strand further comprises up to about 20 additional nucleotides.

A RNAi agent comprising: a first strand and a second strand, wherein the sequence of the first or second strand is the sequence of the first or second strand of Set1_3196, and wherein the first and/or second strand further comprises up to about 20 additional nucleotides.

A RNAi agent comprising: a first strand and a second strand, wherein the sequence of the first or second strand is the sequence of the first or second strand of Set1_3477, and wherein the first and/or second strand further comprises up to about 20 additional nucleotides.

A RNAi agent comprising: a first strand and a second strand, wherein the sequence of the first or second strand is the sequence of the first or second strand of Set1_703, and wherein the first and/or second strand further comprises up to about 20 additional nucleotides.

A RNAi agent comprising: a first strand and a second strand, wherein the sequence of the first or second strand is the sequence of the first or second strand of Set1_709, and wherein the first and/or second strand further comprises up to about 20 additional nucleotides.

A RNAi agent comprising: a first strand and a second strand, wherein the sequence of the first or second strand is the sequence of the first or second strand of Set1_865, and wherein the first and/or second strand further comprises up to about 20 additional nucleotides.

A RNAi agent comprising: a first strand and a second strand, wherein the sequence of the first or second strand is the sequence of the first or second strand of Set1_889, and wherein the first and/or second strand further comprises up to about 20 additional nucleotides.

A RNAi agent comprising: a first strand and a second strand, wherein the sequence of the first or second strand is the sequence of the first or second strand of Set1_895, and wherein the first and/or second strand further comprises up to about 20 additional nucleotides.

Additional Embodiments of Specific RNAi Agents to Beta-Catenin.

In various embodiments, the present disclosure pertains to:

A RNAi agent comprising a first strand and a second strand, wherein the sequence of the first strand and/or the second strand, respectively, is or consists of the sequence of SEQ ID NOs: 6096 and/or 6117, or modified or unmodified variants thereof.

A RNAi agent comprising a first strand and a second strand, wherein the sequence of the first strand and/or the second strand, respectively, is or consists of the sequence of SEQ ID NOs: 6097 and/or 6118, or modified or unmodified variants thereof.

A RNAi agent comprising a first strand and a second strand, wherein the sequence of the first strand and/or the second strand, respectively, is or consists of the sequence of SEQ ID NOs: 6098 and/or 6119, or modified or unmodified variants thereof.

A RNAi agent comprising a first strand and a second strand, wherein the sequence of the first strand and/or the second strand, respectively, is or consists of the sequence of SEQ ID NOs: 6100 and/or 6121, or modified or unmodified variants thereof.

A RNAi agent comprising a first strand and a second strand, wherein the sequence of the first strand and/or the second strand, respectively, is or consists of the sequence of SEQ ID NOs: 6101 and/or 6122, or modified or unmodified variants thereof.

A RNAi agent comprising a first strand and a second strand, wherein the sequence of the first strand and/or the second strand, respectively, is or consists of the sequence of SEQ ID NOs: 6103 and/or 6124, or modified or unmodified variants thereof.

A RNAi agent comprising a first strand and a second strand, wherein the sequence of the first strand and/or the second strand, respectively, is or consists of the sequence of SEQ ID NOs: 6105 and/or 6126, or modified or unmodified variants thereof.

A RNAi agent comprising a first strand and a second strand, wherein the sequence of the first strand and/or the second strand, respectively, is or consists of the sequence of SEQ ID NOs: 6106 and/or 6127, or modified or unmodified variants thereof.

A RNAi agent comprising a first strand and a second strand, wherein the sequence of the first strand and/or the second strand, respectively, is or consists of the sequence of SEQ ID NOs: 6107 and/or 6128, or modified or unmodified variants thereof.

A RNAi agent comprising a first strand and a second strand, wherein the sequence of the first strand and/or the second strand, respectively, comprise the sequence of SEQ ID NOs: 6096 and/or 6117, wherein the first and second strand are each no more than about 30 nucleotides in length, or unmodified variants thereof.

A RNAi agent comprising a first strand and a second strand, wherein the sequence of the first strand and/or the second strand, respectively, comprise the sequence of SEQ ID NOs: 6097 and/or 6118, wherein the first and second strand are each no more than about 30 nucleotides in length, or unmodified variants thereof.

A RNAi agent comprising a first strand and a second strand, wherein the sequence of the first strand and/or the second strand, respectively, comprise the sequence of SEQ ID NOs: 6098 and/or 6119, wherein the first and second strand are each no more than about 30 nucleotides in length, or unmodified variants thereof.

A RNAi agent comprising a first strand and a second strand, wherein the sequence of the first strand and/or the second strand, respectively, comprise the sequence of SEQ ID NOs: 6100 and/or 6121, wherein the first and second strand are each no more than about 30 nucleotides in length, or unmodified variants thereof.

A RNAi agent comprising a first strand and a second strand, wherein the sequence of the first strand and/or the second strand, respectively, comprise the sequence of SEQ ID NOs: 6101 and/or 6122, wherein the first and second strand are each no more than about 30 nucleotides in length, or unmodified variants thereof.

A RNAi agent comprising a first strand and a second strand, wherein the sequence of the first strand and/or the second strand, respectively, comprise the sequence of SEQ ID NOs: 6103 and/or 6124, wherein the first and second strand are each no more than about 30 nucleotides in length, or unmodified variants thereof.

A RNAi agent comprising a first strand and a second strand, wherein the sequence of the first strand and/or the second strand, respectively, comprise the sequence of SEQ ID NOs: 6105 and/or 6126, wherein the first and second strand are each no more than about 30 nucleotides in length, or unmodified variants thereof.

A RNAi agent comprising a first strand and a second strand, wherein the sequence of the first strand and/or the second strand, respectively, comprise the sequence of SEQ ID NOs: 6106 and/or 6127, wherein the first and second strand are each no more than about 30 nucleotides in length, or unmodified variants thereof.

A RNAi agent comprising a first strand and a second strand, wherein the sequence of the first strand and/or the second strand, respectively, comprise the sequence of SEQ ID NOs: 6107 and/or 6128, wherein the first and second strand are each no more than about 30 nucleotides in length, or unmodified variants thereof.

A RNAi agent comprising a first strand and a second strand, wherein the sequence of the first strand and/or the second strand, respectively, comprise at least 15 contiguous nucleotides of the sequence of SEQ ID NOs: 6096 and/or 6117, wherein the first and second strand are each no more than about 30 nucleotides in length, or unmodified variants thereof.

A RNAi agent comprising a first strand and a second strand, wherein the sequence of the first strand and/or the second strand, respectively, comprise at least 15 contiguous nucleotides of the sequence of SEQ ID NOs: 6097 and/or 6118, wherein the first and second strand are each no more than about 30 nucleotides in length, or unmodified variants thereof.

A RNAi agent comprising a first strand and a second strand, wherein the sequence of the first strand and/or the second strand, respectively, comprise at least 15 contiguous nucleotides of the sequence of SEQ ID NOs: 6098 and/or 6119, wherein the first and second strand are each no more than about 30 nucleotides in length, or unmodified variants thereof.

A RNAi agent comprising a first strand and a second strand, wherein the sequence of the first strand and/or the second strand, respectively, comprise at least 15 contiguous nucleotides of the sequence of SEQ ID NOs: 6100 and/or 6121, wherein the first and second strand are each no more than about 30 nucleotides in length, or unmodified variants thereof.

A RNAi agent comprising a first strand and a second strand, wherein the sequence of the first strand and/or the second strand, respectively, comprise at least 15 contiguous nucleotides of the sequence of SEQ ID NOs: 6101 and/or 6122, wherein the first and second strand are each no more than about 30 nucleotides in length, or unmodified variants thereof.

A RNAi agent comprising a first strand and a second strand, wherein the sequence of the first strand and/or the second strand, respectively, comprise at least 15 contiguous nucleotides of the sequence of SEQ ID NOs: 6103 and/or 6124, wherein the first and second strand are each no more than about 30 nucleotides in length, or unmodified variants thereof.

A RNAi agent comprising a first strand and a second strand, wherein the sequence of the first strand and/or the second strand, respectively, comprise at least 15 contiguous nucleotides of the sequence of SEQ ID NOs: 6105 and/or 6126, wherein the first and second strand are each no more than about 30 nucleotides in length, or unmodified variants thereof.

A RNAi agent comprising a first strand and a second strand, wherein the sequence of the first strand and/or the second strand, respectively, comprise at least 15 contiguous nucleotides of the sequence of SEQ ID NOs: 6106 and/or 6127, wherein the first and second strand are each no more than about 30 nucleotides in length, or unmodified variants thereof.

A RNAi agent comprising a first strand and a second strand, wherein the sequence of the first strand and/or the second strand, respectively, comprise at least 15 contiguous nucleotides of the sequence of SEQ ID NOs: 6107 and/or 6128, wherein the first and second strand are each no more than about 30 nucleotides in length, or unmodified variants thereof.

A RNAi agent comprising a first strand and a second strand, wherein the sequence of the first strand and/or the second strand, respectively, comprise at least 15 contiguous nucleotides differing by 0, 1, 2 or 3 nucleotides from the sequence of SEQ ID NOs: 6096 and/or 6117, wherein the first and second strand are each no more than about 30 nucleotides in length, or unmodified variants thereof.

A RNAi agent comprising a first strand and a second strand, wherein the sequence of the first strand and/or the second strand, respectively, comprise at least 15 contiguous nucleotides differing by 0, 1, 2 or 3 nucleotides from the sequence of SEQ ID NOs: 6097 and/or 6118, wherein the first and second strand are each no more than about 30 nucleotides in length, or unmodified variants thereof.

A RNAi agent comprising a first strand and a second strand, wherein the sequence of the first strand and/or the second strand, respectively, comprise at least 15 contiguous nucleotides differing by 0, 1, 2 or 3 nucleotides from the sequence of SEQ ID NOs: 6098 and/or 6119, wherein the first and second strand are each no more than about 30 nucleotides in length, or unmodified variants thereof.

A RNAi agent comprising a first strand and a second strand, wherein the sequence of the first strand and/or the second strand, respectively, comprise at least 15 contiguous nucleotides differing by 0, 1, 2 or 3 nucleotides from the sequence of SEQ ID NOs: 6100 and/or 6121, wherein the first and second strand are each no more than about 30 nucleotides in length, or unmodified variants thereof.

A RNAi agent comprising a first strand and a second strand, wherein the sequence of the first strand and/or the second strand, respectively, comprise at least 15 contiguous nucleotides differing by 0, 1, 2 or 3 nucleotides from the sequence of SEQ ID NOs: 6101 and/or 6122, wherein the first and second strand are each no more than about 30 nucleotides in length, or unmodified variants thereof.

A RNAi agent comprising a first strand and a second strand, wherein the sequence of the first strand and/or the second strand, respectively, comprise at least 15 contiguous nucleotides differing by 0, 1, 2 or 3 nucleotides from the sequence of SEQ ID NOs: 6103 and/or 6124, wherein the first and second strand are each no more than about 30 nucleotides in length, or unmodified variants thereof.

A RNAi agent comprising a first strand and a second strand, wherein the sequence of the first strand and/or the second strand, respectively, comprise at least 15 contiguous nucleotides differing by 0, 1, 2 or 3 nucleotides from the sequence of SEQ ID NOs: 6105 and/or 6126, wherein the first and second strand are each no more than about 30 nucleotides in length, or unmodified variants thereof.

A RNAi agent comprising a first strand and a second strand, wherein the sequence of the first strand and/or the second strand, respectively, comprise at least 15 contiguous nucleotides differing by 0, 1, 2 or 3 nucleotides from the sequence of SEQ ID NOs: 6106 and/or 6127, wherein the first and second strand are each no more than about 30 nucleotides in length, or unmodified variants thereof.

A RNAi agent comprising a first strand and a second strand, wherein the sequence of the first strand and/or the second strand, respectively, comprise at least 15 contiguous nucleotides differing by 0, 1, 2 or 3 nucleotides from the sequence of SEQ ID NOs: 6107 and/or 6128, wherein the first and second strand are each no more than about 30 nucleotides in length, or unmodified variants thereof.

In various embodiments, the first and second strand can be either the sense and anti-sense strand, or the anti-sense and sense strand.

Additional Embodiments of Specific RNAi Agents to Beta-Catenin, Further Comprising Additional nt.

In various embodiments of the present disclosure, the RNAi agent comprises an anti-sense strand consisting of a sequence of at least 15 contiguous nucleotides with 0, 1, 2, or 3 mismatches from that of the anti-sense strand of any RNAi agent from Tables 1, 2, 3, 4, 5, 6, 7, 8 and/or 9, or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4, 1-5, 1-6, 1-7, 1-8, 1-9, 1-10, 2-3, 2-4, or 2-5 nt, etc.)

Additional Embodiments Comprising Overlapping Groups of RNAi Agents to Beta-Catenin In various embodiments of the present disclosure, the present disclosure relates to groups of RNAi agents with overlapping sequences. Thus, the present disclosure encompasses groups of RNAi agents wherein each RNAi agent in the group overlaps with each other RNAi agent in the same group by at least 5, 6, 7, 8, 9, 10, 11, 12, 13, 14, 15, 16, 17, 18, 19 or more nucleotides. In one embodiment, the overlap is at least 12 nt. Groups of sequences that overlap are shown in Table 4.

Table 4 shows, for example, that AD-26022 and AD-26204 share the common technical feature of the sequence of CCUGUUCCCUG (SEQ ID NO: 1319) in the sense strand, and the sequence of CAGGGGAACAGG (SEQ ID NO: 2714) in the anti-sense strand. Note of course that only a 12-nt portion of the overlap is shown; many groups of RNAi agents will overlap by more than 12 nt. The position within the gene is also indicated.

The present disclosure thus encompasses various embodiments comprising groups of overlapping RNAi agents, for example (1) RNAi agents comprising the sequences of AD-26022 and AD-26204; (2) RNAi agents consisting of the sequences of AD-26022 and AD-26204; (3) RNAi agents comprising a sense strand and/or a anti-sense strand comprising a sequence of AD-26022 and AD-26204; (4) RNAi agents comprising a sense strand and/or a anti-sense strand comprising 15 contiguous nt with 0 to 3 mismatches from a sequence of AD-26022 and AD-26204; (5) RNAi agents comprising a sense strand comprising 15 contiguous nt with 0 to 3 mismatches from a sequence of AD-26022 and AD-26204; (6) RNAi agents comprising an anti-sense strand comprising 15 contiguous nt with 0 to 3 mismatches from a sequence of AD-26022 and AD-26204; etc. and similar embodiments reflecting all the overlapping groups of RNAi agents.

Thus, in various embodiments, the RNAi agents of the present disclosure comprise a sense strand and an anti-sense (which may optionally be covalently linked, linked via a loop or linker, or contiguous), wherein the sense and/or anti-sense strand consist of, consist essentially of, or comprise sequences of at least 15 contiguous nt with 0, 1, 2, or 3 nt or by mismatches of, the sense and/or anti-sense strand, respectively, of any one or more of the RNAi agents disclosed in Tables 1, 2, 3, 4, 5, 6, 7, 8 and/or 9 (or any member of a group of overlapping RNAi agents from Table 4), optionally further comprising 0-10 nt or bp.

Additional Definitions

The articles "a" and "an" as used herein and in the claims refer to one or more than one (at least one) of the grammatical object of the article.

The terms "RNAi agent," "RNAi agents", "RNAi agent(s)" and the like all refer without limitation to one or more RNAi agents of the present disclosure.

The designations of particular example duplexes of RNAi agents to Beta-Catenin disclosed herein on occasion have the suffix "b" followed by a number. This indicates a batch number. Thus, the suffix "b1" indicates "batch 1." Thus, a RNAi duplex designated, for example, "AD-18892-b1" is specifically from batch 1 and has the same sequence as any RNAi agent designated "AD-18892".

Unless defined otherwise, the technical and scientific terms used herein have the same meaning as that usually understood by a specialist familiar with the field to which the present disclosure belongs.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein.

Claims to the present disclosure are non-limiting and are provided below.

Although particular embodiments and claims have been disclosed herein in detail, this has been done by way of example for purposes of illustration only, and is not intended to be limiting with respect to the scope of the appended claims, or the scope of subject matter of claims of any corresponding future application. In particular, it is contemplated by the inventors that various substitutions, alterations, and modifications may be made to the present disclosure without departing from the spirit and scope of the present disclosure as defined by the claims. The choice of nucleic acid starting material, clone of interest, or library type is believed to be a matter of routine for a person of ordinary skill in the art with knowledge of the embodiments described herein. Other aspects, advantages, and modifications considered to be within the scope of the following claims. Redrafting of claim scope in later-filed corresponding applications may be due to limitations by the patent laws of various countries and should not be interpreted as giving up subject matter of the claims.

Various additional formulations and obvious variants of the described RNAi agents to Beta-Catenin can be devised by those of ordinary skill in the art. Non-limiting example RNAi agents to Beta-Catenin are described in the Examples below, which do not limit the scope of the present disclosure as described in the claims.

Example 1

Bioinformatics and Beta-Catenin RNAi Agent (siRNA) Sequences
Bioinformatics
Transcripts RNAi agent design is carried out to identify RNAi agents targeting the human Beta-Catenin gene (CTNNB1). The design uses the CTNNB1 transcript NM_001098210.1 from the NCBI (National Center for Biotechnology Information) Refseq collection. All RNAi agent duplexes are designed with 100% identity to all three human CTNNB1 transcripts (NM_001098210.1, NM_001098209.1, and NM_001904.3).

siRNA Design and Specificity Prediction

The predicted specificity of all possible 19-mers is predicted from each sequence. The CTNNB1 RNAi agents are used in a comprehensive search against the human transcriptome (defined as the set of NM_ and XM_records within the human NCBI Refseq set) using the FASTA algorithm. The perl script 'parseFasta.pl' is then used to parse the alignments and generate a score based on the position and number of mismatches between the siRNA and any potential 'off-target' transcript. The off-target score is weighted to emphasize differences in the 'seed' region of siRNAs, in positions 2-9 from the 5' end of the molecule. Each oligo-transcript pair from the FASTA search is given a mismatch score by summing the individual mismatch scores; mismatches in the position 2-9 are counted as 2.8, mismatches in the cleavage site positions 10-11 are counted as 1.2, and mismatches in region 12-19 counted as 1.0. An additional off-target prediction is carried out by comparing the frequency of heptamers and octomers derived from 3 distinct, seed-derived hexamers of each oligo. The hexamers from positions 2-7 relative to the 5' start is used to create 2 heptamers and one octomer. The 'heptamer1' is created by adding a 3' A to the hexamer; the heptamer2 is created by adding a 5' A to the hexamer; the octomer is created by adding an A to both 5' and 3' ends of the hexamer. The frequency of octomers and heptamers in the human 3'UTRome (defined as the subsequence of the transcriptome from NCBI's Refseq database where the end of the coding region, the 'CDS', is clearly defined) is pre-calculated. The octomer frequency is normalized to the heptamer frequency using the median value from the range of octomer frequencies. A 'mirSeedScore' is then calculated by calculating the sum of ((3× normalized octomer count)+(2× heptamer2 count)+(1× heptamer1 count)).

Both RNAi agent strands are assigned to a category of specificity according to the calculated scores: a score above 3 qualifies as highly specific, equal to 3 as specific and between 2.2 and 2.8 as moderately specific. RNAi agents are sorted by the specificity of the anti-sense strand. Oligonucleotides with perfect matches to known human microRNA seed regions are excluded.

TABLE 2

RNAi Agents to Beta-Catenin: Unmodified Sequences

| DUPLEX | SENSE SEQUENCE | SENSE SEQ ID NO: | ANTI-SENSE SEQUENCE | Anti-sense SEQ ID NO: | POSITION |
| --- | --- | --- | --- | --- | --- |
| AD-18892 | UGGUGCUGACUAUCCAGUU | 4771 | AACUGGAUAGUCAGCACCA | 5430 | 2500 |
| AD-18893 | CCAUCUGUGCUCUUCGUCA | 4772 | UGACGAAGAGCACAGAUGG | 5431 | 1659 |
| AD-18894 | AUAAGCAGGUGGAUCUAUU | 4773 | AAUAGAUCCACCUGCUUAU | 5432 | 3038 |
| AD-18895 | AUCCAAAGAGUAGCUGCAG | 4774 | CUGCAGCUACUCUUUGGAU | 5433 | 2096 |
| AD-18896 | GACAAUGGCUACUCAAGCU | 4775 | AGCUUGAGUAGCCAUUGUC | 5434 | 265 |
| AD-18897 | CUGUUGGAUUGAUUCGAAA | 4776 | UUUCGAAUCAAUCCAACAG | 5435 | 1797 |
| AD-18898 | GCUGGCCUGGUUUGAUACU | 4777 | AGUAUCAAACCAGGCCAGC | 5436 | 2587 |
| AD-18899 | UCUAACCUCACUUGCAAUA | 4778 | UAUUGCAAGUGAGGUUAGA | 5437 | 1541 |
| AD-18900 | GAUAUCGCCAGGAUGAUCC | 4779 | GGAUCAUCCUGGCGAUAUC | 5438 | 2391 |
| AD-18901 | UGGCCAUCUUUAAGUCUGG | 4780 | CCAGACUUAAAGAUGGCCA | 5439 | 954 |
| AD-18902 | UGUAGAACACUAAUUCAUA | 4781 | UAUGAAUUAGUGUUCUACA | 5440 | 2908 |
| AD-18903 | AUCAGUAAGAGGUGUUAUU | 4782 | AAUAACACCUCUUACUGAU | 5441 | 3104 |
| AD-18904 | GUGCUCUUCGUCAUCUGAC | 4783 | GUCAGAUGACGAAGAGCAC | 5442 | 1665 |
| AD-18905 | UGGUUUGAUACUGACCUGU | 4784 | ACAGGUCAGUAUCAAACCA | 5443 | 2594 |
| AD-18906 | CCAGUUGCCUUUUAUCCCA | 4785 | UGGGAUAAAAGGCAACUGG | 5444 | 3147 |
| AD-18907 | CCUGGUUUGAUACUGACCU | 4786 | AGGUCAGUAUCAAACCAGG | 5445 | 2592 |
| AD-18908 | GACUAUCCAGUUGAUGGGC | 4787 | GCCCAUCAACUGGAUAGUC | 5446 | 2507 |
| AD-18909 | AGCCAAUGGCUUGGAAUGA | 4788 | UCAUUCCAAGCCAUUGGCU | 5447 | 2325 |
| AD-18910 | GCCAAUGGCUUGGAAUGAG | 4789 | CUCAUUCCAAGCCAUUGGC | 5448 | 2326 |
| AD-18911 | AGAUGAGGGCAUGCAGAUC | 4790 | GAUCUGCAUGCCCUCAUCU | 5449 | 577 |
| AD-18912 | GGUCCUCUGUGAACUUGCU | 4791 | AGCAAGUUCACAGAGGACC | 5450 | 2116 |
| AD-18913 | AACCUAGCCUUGCUUGUU | 4792 | AACAAGCAAGGCUAGGGUU | 5451 | 2708 |
| AD-18914 | GAACACUAAUUCAUAAUCA | 4793 | UGAUUAUGAAUUAGUGUUC | 5452 | 2912 |
| AD-18915 | AUCAAACCCUAGCCUUGCU | 4794 | AGCAAGGCUAGGGUUUGAU | 5453 | 2704 |
| AD-18916 | ACCAGUUGCCUUUUAUCCC | 4795 | GGGAUAAAAGGCAACUGGU | 5454 | 3146 |
| AD-18917 | CUAACCUCACUUGCAAUAA | 4796 | UUAUUGCAAGUGAGGUUAG | 5455 | 1542 |
| AD-18918 | AUCCCACUAAUGUCCAGCG | 4797 | CGCUGGACAUUAGUGGGAU | 5456 | 621 |
| AD-18919 | CUGACUAUCCAGUUGAUGG | 4798 | CCAUCAACUGGAUAGUCAG | 5457 | 2505 |

TABLE 2-continued

RNAi Agents to Beta-Catenin: Unmodified Sequences

| DUPLEX | SENSE SEQUENCE | SENSE SEQ ID NO: | ANTI-SENSE SEQUENCE | Anti-sense SEQ ID NO: | POSITION |
|---|---|---|---|---|---|
| AD-18920 | GGCCUGGUUUGAUACUGAC | 4799 | GUCAGUAUCAAACCAGGCC | 5458 | 2590 |
| AD-18921 | GGUAAAUCAGUAAGAGGUG | 4800 | CACCUCUUACUGAUUUACC | 5459 | 3099 |
| AD-18922 | GCCUGGUUUGAUACUGACC | 4801 | GGUCAGUAUCAAACCAGGC | 5460 | 2591 |
| AD-18923 | CAGGGGUCCUCUGUGAACU | 4802 | AGUUCACAGAGGACCCCUG | 5461 | 2112 |
| AD-18925 | CUGGAAUCCAUUCUGGUGC | 4803 | GCACCAGAAUGGAUUCCAG | 5462 | 366 |
| AD-18926 | UGAGAUGGGUGGCCACCAC | 4804 | GUGGUGGCCACCCAUCUCA | 5463 | 2479 |
| AD-18927 | GAUGAUAUAAAUGUGGUCA | 4805 | UGACCACAUUUAUAUCAUC | 5464 | 1502 |
| AD-18928 | UGCUUUAUUCUCCCAUUGA | 4806 | UCAAUGGGAGAAUAAAGCA | 5465 | 2073 |
| AD-18929 | UUAUCAAACCCUAGCCUUG | 4807 | CAAGGCUAGGGUUUGAUAA | 5466 | 2702 |
| AD-18930 | CCACUGGCCUCUGAUAAAG | 4808 | CUUUAUCAGAGGCCAGUGG | 5467 | 1774 |
| AD-18931 | AACUUGCCACACGUGCAAU | 4809 | AUUGCACGUGUGGCAAGUU | 5468 | 708 |
| AD-18932 | GCUCUUCGUCAUCUGACCA | 4810 | UGGUCAGAUGACGAAGAGC | 5469 | 1667 |
| AD-18933 | GUAACAAUACAAAUGGAUU | 4811 | AAUCCAUUUGUAUUGUUAC | 5470 | 2629 |
| AD-18934 | GGGGUCCUCUGUGAACUUG | 4812 | CAAGUUCACAGAGGACCCC | 5471 | 2114 |
| AD-18935 | CAAACCCUAGCCUUGCUUG | 4813 | CAAGCAAGGCUAGGGUUUG | 5472 | 2706 |
| AD-18936 | GAGUAAUGGUGUAGAACAC | 4814 | GUGUUCUACACCAUUACUC | 5473 | 2899 |
| AD-18937 | GGAAGACAUCACUGAGCCU | 4815 | AGGCUCAGUGAUGUCUUCC | 5474 | 1639 |
| AD-18938 | GGGAAGACAUCACUGAGCC | 4816 | GGCUCAGUGAUGUCUUCCC | 5475 | 1638 |
| AD-18939 | GGUGUAGAACACUAAUUCA | 4817 | UGAAUUAGUGUUCUACACC | 5476 | 2906 |
| AD-18940 | UACCAGUUGCCUUUUAUCC | 4818 | GGAUAAAAGGCAACUGGUA | 5477 | 3145 |
| AD-18941 | GGAUAUCGCCAGGAUGAUC | 4819 | GAUCAUCCUGGCGAUAUCC | 5478 | 2390 |
| AD-18942 | AAACCCUAGCCUUGCUUGU | 4820 | ACAAGCAAGGCUAGGGUUU | 5479 | 2707 |
| AD-18943 | CUCUUCGUCAUCUGACCAG | 4821 | CUGGUCAGAUGACGAAGAG | 5480 | 1668 |
| AD-18944 | UGACUAUCCAGUUGAUGGG | 4822 | CCCAUCAACUGGAUAGUCA | 5481 | 2506 |
| AD-18945 | ACAAGCAGAGUGCUGAAGG | 4823 | CCUUCAGCACUCUGCUUGU | 5482 | 1286 |
| AD-18946 | CAUCUGUGCUCUUCGUCAU | 4824 | AUGACGAAGAGCACAGAUG | 5483 | 1660 |
| AD-18947 | CAAUGGCUUGGAAUGAGAC | 4825 | GUCUCAUUCCAAGCCAUUG | 5484 | 2328 |
| AD-18948 | ACUGGCCUCUGAUAAAGGC | 4826 | GCCUUUAUCAGAGGCCAGU | 5485 | 1776 |
| AD-18949 | UCAUCCCACUAAUGUCCAG | 4827 | CUGGACAUUAGUGGGAUGA | 5486 | 619 |
| AD-18950 | AAAAGGAAGCUUCCAGACA | 4828 | UGUCUGGAAGCUUCCUUUU | 5487 | 807 |
| AD-18951 | CGUUCUUUUCACUCUGGUG | 4829 | CACCAGAGUGAAAAGAACG | 5488 | 2417 |
| AD-18952 | AAAGUUGUUGUAACCUGCU | 4830 | AGCAGGUUACAACAACUUU | 5489 | 3165 |
| AD-18953 | ACAAUGGCUACUCAAGCUG | 4831 | CAGCUUGAGUAGCCAUUGU | 5490 | 266 |
| AD-18954 | CUCAUCCCACUAAUGUCCA | 4832 | UGGACAUUAGUGGGAUGAG | 5491 | 618 |
| AD-18955 | AGGGGUCCUCUGUGAACUU | 4833 | AAGUUCACAGAGGACCCCU | 5492 | 2113 |
| AD-18956 | AAGCAGGUGGAUCUAUUUC | 4834 | GAAAUAGAUCCACCUGCUU | 5493 | 3040 |

TABLE 2-continued

RNAi Agents to Beta-Catenin: Unmodified Sequences

| DUPLEX | SENSE SEQUENCE | SENSE SEQ ID NO: | ANTI-SENSE SEQUENCE | Anti-sense SEQ ID NO: | POSITION |
|---|---|---|---|---|---|
| AD-18957 | AAGUUGUUGUAACCUGCUG | 4835 | CAGCAGGUUACAACAACUU | 5494 | 3166 |
| AD-18958 | AGCAGGUGGAUCUAUUUCA | 4836 | UGAAAUAGAUCCACCUGCU | 5495 | 3041 |
| AD-18959 | AGGGCAUGCAGAUCCCAUC | 4837 | GAUGGGAUCUGCAUGCCCU | 5496 | 582 |
| AD-18960 | AAAUGGUUCAGAAUUAAAC | 4838 | GUUUAAUUCUGAACCAUUU | 5497 | 3220 |
| AD-18961 | UGAACUUGCUCAGGACAAG | 4839 | CUUGUCCUGAGCAAGUUCA | 5498 | 2125 |
| AD-18962 | AAGAGUAGCUGCAGGGGUC | 4840 | GACCCCUGCAGCUACUCUU | 5499 | 2101 |
| AD-18963 | CCCACUGGCCUCUGAUAAA | 4841 | UUUAUCAGAGGCCAGUGGG | 5500 | 1773 |
| AD-18964 | CUGGCCUGGUUUGAUACUG | 4842 | CAGUAUCAAACCAGGCCAG | 5501 | 2588 |
| AD-18965 | UUGAUACUGACCUGUAAAU | 4843 | AUUUACAGGUCAGUAUCAA | 5502 | 2598 |
| AD-18966 | GUGUAGAACACUAAUUCAU | 4844 | AUGAAUUAGUGUUCUACAC | 5503 | 2907 |
| AD-18967 | ACUAUCCAGUUGAUGGGCU | 4845 | AGCCCAUCAACUGGAUAGU | 5504 | 2508 |
| AD-18968 | AAAUCAGUAAGAGGUGUUA | 4846 | UAACACCUCUUACUGAUUU | 5505 | 3102 |
| AD-18969 | GCAGGUGGAUCUAUUUCAU | 4847 | AUGAAAUAGAUCCACCUGC | 5506 | 3042 |
| AD-18970 | CUGGUGCUGACUAUCCAGU | 4848 | ACUGGAUAGUCAGCACCAG | 5507 | 2499 |
| AD-18971 | GUGAACUUGCUCAGGACAA | 4849 | UUGUCCUGAGCAAGUUCAC | 5508 | 2124 |
| AD-18972 | UCAGUAAGAGGUGUUAUUU | 4850 | AAAUAACACCUCUUACUGA | 5509 | 3105 |
| AD-18973 | CCUCUGUGAACUUGCUCAG | 4851 | CUGAGCAAGUUCACAGAGG | 5510 | 2119 |
| AD-18974 | UUGGCUGAACCAUCACAGA | 4852 | UCUGUGAUGGUUCAGCCAA | 5511 | 641 |
| AD-18975 | UCAGCUGGCCUGGUUUGAU | 4853 | AUCAAACCAGGCCAGCUGA | 5512 | 2584 |
| AD-18976 | GUAGCUGCAGGGGUCCUCU | 4854 | AGAGGACCCCUGCAGCUAC | 5513 | 2105 |
| AD-18977 | AGGAGCUAAAAUGGCAGUG | 4855 | CACUGCCAUUUUAGCUCCU | 5514 | 1069 |
| AD-18978 | AUGGCUUGGAAUGAGACUG | 4856 | CAGUCUCAUUCCAAGCCAU | 5515 | 2330 |
| AD-18979 | UUGGAUAUCGCCAGGAUGA | 4857 | UCAUCCGGCGAUAUCCAA | 5516 | 2388 |
| AD-18980 | GGUUCAGAAUUAAACUUUU | 4858 | AAAAGUUUAAUUCUGAACC | 5517 | 3224 |
| AD-18981 | GGGUAAAUCAGUAAGAGGU | 4859 | ACCUCUUACUGAUUUACCC | 5518 | 3098 |
| AD-18982 | AUACCAUUCCAUUGUUUGU | 4860 | ACAAACAAUGGAAUGGUAU | 5519 | 2049 |
| AD-18983 | ACUGUUGGAUUGAUUCGAA | 4861 | UUCGAAUCAAUCCAACAGU | 5520 | 1796 |
| AD-18984 | AACUUGCUCAGGACAAGGA | 4862 | UCCUUGUCCUGAGCAAGUU | 5521 | 2127 |
| AD-18985 | AUGCUUAAAAUAAGCAGGU | 4863 | ACCUGCUUAUUUUAAGCAU | 5522 | 3029 |
| AD-18986 | GUUUGAUACUGACCUGUAA | 4864 | UUACAGGUCAGUAUCAAAC | 5523 | 2596 |
| AD-18987 | AAUGGUUCAGAAUUAAACU | 4865 | AGUUUAAUUCUGAACCAUU | 5524 | 3221 |
| AD-18988 | UAUCCCAAAGUUGUUGUAA | 4866 | UUACAACAACUUUGGGAUA | 5525 | 3159 |
| AD-18989 | AUCAGCUGGCCUGGUUUGA | 4867 | UCAAACCAGGCCAGCUGAU | 5526 | 2583 |
| AD-18990 | CCUGCCAUCUGUGCUCUUC | 4868 | GAAGAGCACAGAUGGCAGG | 5527 | 1655 |
| AD-18991 | GCAGAAUACAAAUGAUGUA | 4869 | UACAUCAUUUGUAUUCUGC | 5528 | 874 |
| AD-18992 | UAUGCUUAAAAUAAGCAGG | 4870 | CCUGCUUAUUUUAAGCAUA | 5529 | 3028 |
| AD-18993 | AAUAAGCAGGUGGAUCUAU | 4871 | AUAGAUCCACCUGCUUAUU | 5530 | 3037 |

TABLE 2-continued

RNAi Agents to Beta-Catenin: Unmodified Sequences

| DUPLEX | SENSE SEQUENCE | SENSE SEQ ID NO: | ANTI-SENSE SEQUENCE | Anti-sense SEQ ID NO: | POSITION |
| --- | --- | --- | --- | --- | --- |
| AD-18994 | UGAUAUAAAUGUGGUCACC | 4872 | GGUGACCACAUUUAUAUCA | 5531 | 1504 |
| AD-18995 | GUAGGGUAAAUCAGUAAGA | 4873 | UCUUACUGAUUUACCCUAC | 5532 | 3095 |
| AD-18996 | UAUCAAACCCUAGCCUUGC | 4874 | GCAAGGCUAGGGUUUGAUA | 5533 | 2703 |
| AD-18997 | CCUUUUAUCCCAAAGUUGU | 4875 | ACAACUUUGGGAUAAAAGG | 5534 | 3154 |
| AD-18998 | GGUAGGGUAAAUCAGUAAG | 4876 | CUUACUGAUUUACCCUACC | 5535 | 3094 |
| AD-18999 | UGAUACUGACCUGUAAAUC | 4877 | GAUUUACAGGUCAGUAUCA | 5536 | 2599 |
| AD-19000 | GGCUGAACCAUCACAGAUG | 4878 | CAUCUGUGAUGGUUCAGCC | 5537 | 643 |
| AD-19001 | UGGAUAUCGCCAGGAUGAU | 4879 | AUCAUCCUGGCGAUAUCCA | 5538 | 2389 |
| AD-19002 | UCUUCGUCAUCUGACCAGC | 4880 | GCUGGUCAGAUGACGAAGA | 5539 | 1669 |
| AD-19003 | UAGCUGCAGGGGUCCUCUG | 4881 | CAGAGGACCCCUGCAGCUA | 5540 | 2106 |
| AD-19004 | UGUUGUAACCUGCUGUGAU | 4882 | AUCACAGCAGGUUACAACA | 5541 | 3170 |
| AD-19005 | AAUCAGUAAGAGGUGUUAU | 4883 | AUAACACCUCUUACUGAUU | 5542 | 3103 |
| AD-19006 | UGGCUGAACCAUCACAGAU | 4884 | AUCUGUGAUGGUUCAGCCA | 5543 | 642 |
| AD-19007 | GAAUUAAACUUUUAAUUCA | 4885 | UGAAUUAAAAGUUUAAUUC | 5544 | 3230 |
| AD-19008 | AUGGUUCAGAAUUAAACUU | 4886 | AAGUUUAAUUCUGAACCAU | 5545 | 3222 |
| AD-19009 | UGGUGUAGAACACUAAUUC | 4887 | GAAUUAGUGUUCUACACCA | 5546 | 2905 |
| AD-19010 | AUGGUGUAGAACACUAAUU | 4888 | AAUUAGUGUUCUACACCAU | 5547 | 2904 |
| AD-19011 | AUGAGGGCAUGCAGAUCCC | 4889 | GGGAUCUGCAUGCCCUCAU | 5548 | 579 |
| AD-19012 | GUUGUAACCUGCUGUGAUA | 4890 | UAUCACAGCAGGUUACAAC | 5549 | 3171 |
| AD-19042 | GCUGACUAUCCAGUUGAUG | 4891 | CAUCAACUGGAUAGUCAGC | 5550 | 2504 |
| AD-19043 | UAAGCAGGUGGAUCUAUUU | 4892 | AAAUAGAUCCACCUGCUUA | 5551 | 3039 |
| AD-19044 | UAAAUAAGCAGGUGGAUC | 4893 | GAUCCACCUGCUUAUUUUA | 5552 | 3034 |
| AD-19045 | GAUAUAAAUGUGGUCACCU | 4894 | AGGUGACCACAUUUAUAUC | 5553 | 1505 |
| AD-19046 | AAGCAGAGUGCUGAAGGUG | 4895 | CACCUUCAGCACUCUGCUU | 5554 | 1288 |
| AD-19047 | UGUGAACUUGCUCAGGACA | 4896 | UGUCCUGAGCAAGUUCACA | 5555 | 2123 |
| AD-19048 | CAUCCCACUAAUGUCCAGC | 4897 | GCUGGACAUUAGUGGGAUG | 5556 | 620 |
| AD-19049 | CAAAGUUGUUGUAACCUGC | 4898 | GCAGGUUACAACAACUUUG | 5557 | 3164 |
| AD-19050 | UAAAUCAGUAAGAGGUGUU | 4899 | AACACCUCUUACUGAUUUA | 5558 | 3101 |
| AD-19051 | AAUGGCUUGGAAUGAGACU | 4900 | AGUCUCAUUCCAAGCCAUU | 5559 | 2329 |
| AD-19052 | GGGUCCUCUGUGAACUUGC | 4901 | GCAAGUUCACAGAGGACCC | 5560 | 2115 |
| AD-19053 | GAGUAACAAUACAAAUGGA | 4902 | UCCAUUUGUAUUGUUACUC | 5561 | 2627 |
| AD-19054 | UAAUGGUGUAGAACACUAA | 4903 | UUAGUGUUCUACACCAUUA | 5562 | 2902 |
| AD-19055 | GUGGACAAUGGCUACUCAA | 4904 | UUGAGUAGCCAUUGUCCAC | 5563 | 262 |
| AD-19056 | AACUGUCUUUGGACUCUCA | 4905 | UGAGAGUCCAAAGACAGUU | 5564 | 1406 |
| AD-19057 | CCCUGGUGCUGACUAUCCA | 4906 | UGGAUAGUCAGCACCAGGG | 5565 | 2497 |
| AD-19058 | CAGGUGGAUCUAUUUCAUG | 4907 | CAUGAAAUAGAUCCACCUG | 5566 | 3043 |

TABLE 2-continued

RNAi Agents to Beta-Catenin: Unmodified Sequences

| DUPLEX | SENSE SEQUENCE | SENSE SEQ ID NO: | ANTI-SENSE SEQUENCE | Anti-sense SEQ ID NO: | POSITION |
|---|---|---|---|---|---|
| AD-19059 | UGGCCUGGUUUGAUACUGA | 4908 | UCAGUAUCAAACCAGGCCA | 5567 | 2589 |
| AD-19060 | AGCUGGCCUGGUUUGAUAC | 4909 | GUAUCAAACCAGGCCAGCU | 5568 | 2586 |
| AD-19061 | GCCAUCUGUGCUCUUCGUC | 4910 | GACGAAGAGCACAGAUGGC | 5569 | 1658 |
| AD-19062 | UACCAUUCCAUUGUUUGUG | 4911 | CACAAACAAUGGAAUGGUA | 5570 | 2050 |
| AD-19063 | CCCUUGGAUAUCGCCAGGA | 4912 | UCCUGGCGAUAUCCAAGGG | 5571 | 2385 |
| AD-19064 | AGGGAAGACAUCACUGAGC | 4913 | GCUCAGUGAUGUCUUCCCU | 5572 | 1637 |
| AD-19065 | GAACUUGCCACACGUGCAA | 4914 | UUGCACGUGUGGCAAGUUC | 5573 | 707 |
| AD-19066 | UUUGAUACUGACCUGUAAA | 4915 | UUUACAGGUCAGUAUCAAA | 5574 | 2597 |
| AD-19067 | UCCCAAAGUUGUUGUAACC | 4916 | GGUUACAACAACUUUGGGA | 5575 | 3161 |
| AD-19068 | CAGAAUACAAAUGAUGUAG | 4917 | CUACAUCAUUUGUAUUCUG | 5576 | 875 |
| AD-19069 | AGGUGGAUCUAUUUCAUGU | 4918 | ACAUGAAAUAGAUCCACCU | 5577 | 3044 |
| AD-19070 | GCUCAUCCCACUAAUGUCC | 4919 | GGACAUUAGUGGGAUGAGC | 5578 | 617 |
| AD-19071 | CCUGGUGCUGACUAUCCAG | 4920 | CUGGAUAGUCAGCACCAGG | 5579 | 2498 |
| AD-19072 | UGGAAUCCAUUCUGGUGCC | 4921 | GGCACCAGAAUGGAUUCCA | 5580 | 367 |
| AD-19073 | CCAGGACCUCAUGGAUGGG | 4922 | CCCAUCCAUGAGGUCCUGG | 5581 | 2545 |
| AD-19074 | AACCUCACUUGCAAUAAUU | 4923 | AAUUAUUGCAAGUGAGGUU | 5582 | 1544 |
| AD-19075 | CAGUUGCCUUUUAUCCCAA | 4924 | UUGGGAUAAAAGGCAACUG | 5583 | 3148 |
| AD-19076 | GUAGAACACUAAUUCAUAA | 4925 | UUAUGAAUUAGUGUUCUAC | 5584 | 2909 |
| AD-19077 | CUAUCCAGUUGAUGGGCUG | 4926 | CAGCCCAUCAACUGGAUAG | 5585 | 2509 |
| AD-19078 | CACUGGCCUCUGAUAAAGG | 4927 | CCUUUAUCAGAGGCCAGUG | 5586 | 1775 |
| AD-19079 | ACUGUCUUUGGACUCUCAG | 4928 | CUGAGAGUCCAAAGACAGU | 5587 | 1407 |
| AD-19080 | CCAAUGGCUUGGAAUGAGA | 4929 | UCUCAUUCCAAGCCAUUGG | 5588 | 2327 |
| AD-19081 | GCUUAAAAUAAGCAGGUGG | 4930 | CCACCUGCUUAUUUUAAGC | 5589 | 3031 |
| AD-19082 | AUCUGUGCUCUUCGUCAUC | 4931 | GAUGACGAAGAGCACAGAU | 5590 | 1661 |
| AD-19083 | CCCAAAGUUGUUGUAACCU | 4932 | AGGUUACAACAACUUUGGG | 5591 | 3162 |
| AD-19738 | UACCCAGCGCCGUACGUCC | 4933 | GGACGUACGGCGCUGGGUA | 5592 | 1906 |
| AD-19739 | ACGCUAUCAUGCGUUCUCC | 4934 | GGAGAACGCAUGAUAGCGU | 5593 | 825 |
| AD-19740 | CAUGCACCUUUGCGUGAGC | 4935 | GCUCACGCAAAGGUGCAUG | 5594 | 1838 |
| AD-19741 | GAAUGCAGUUCGCCUUCAC | 4936 | GUGAAGGCGAACUGCAUUC | 5595 | 1714 |
| AD-19742 | GGUGCCAUUCCACGACUAG | 4937 | CUAGUCGUGGAAUGGCACC | 5596 | 1859 |
| AD-19743 | AAGCGGCUGUUAGUCACUG | 4938 | CAGUGACUAACAGCCGCUU | 5597 | 324 |
| AD-19744 | UCGAGCUCAGAGGGUACGA | 4939 | UCGUACCCUCUGAGCUCGA | 5598 | 535 |
| AD-19745 | GACACGCUAUCAUGCGUUC | 4940 | GAACGCAUGAUAGCGUGUC | 5599 | 822 |
| AD-19746 | CGCUAUCAUGCGUUCUCCU | 4941 | AGGAGAACGCAUGAUAGCG | 5600 | 826 |
| AD-19747 | GUGUCUGCUAUUGUACGUA | 4942 | UACGUACAAUAGCAGACAC | 5601 | 851 |
| AD-19748 | GUCUGCUCUAGUAAUAAGC | 4943 | GCUUAUUACUAGAGCAGAC | 5602 | 1313 |
| AD-19749 | GUGCCAUUCCACGACUAGU | 4944 | ACUAGUCGUGGAAUGGCAC | 5603 | 1860 |

TABLE 2-continued

RNAi Agents to Beta-Catenin: Unmodified Sequences

| DUPLEX | SENSE SEQUENCE | SENSE SEQ ID NO: | ANTI-SENSE SEQUENCE | Anti-sense SEQ ID NO: | POSITION |
|---|---|---|---|---|---|
| AD-19750 | AUGUUCACAACCGAAUUGU | 4945 | ACAAUUCGGUUGUGAACAU | 5604 | 2016 |
| AD-19751 | CCACGACUAGUUCAGUUGC | 4946 | GCAACUGAACUAGUCGUGG | 5605 | 1868 |
| AD-19752 | CACGACUAGUUCAGUUGCU | 4947 | AGCAACUGAACUAGUCGUG | 5606 | 1869 |
| AD-19753 | AGUUCAGUUGCUUGUUCGU | 4948 | ACGAACAAGCAACUGAACU | 5607 | 1876 |
| AD-19754 | CCCAGCGCCGUACGUCCAU | 4949 | AUGGACGUACGGCGCUGGG | 5608 | 1908 |
| AD-19755 | GAGUUACUUCACUCUAGGA | 4950 | UCCUAGAGUGAAGUAACUC | 5609 | 2192 |
| AD-19756 | ACAGUAUGCAAUGACUCGA | 4951 | UCGAGUCAUUGCAUACUGU | 5610 | 520 |
| AD-19757 | UAUGCAAUGACUCGAGCUC | 4952 | GAGCUCGAGUCAUUGCAUA | 5611 | 524 |
| AD-19758 | CCCACUAAUGUCCAGCGUU | 4953 | AACGCUGGACAUUAGUGGG | 5612 | 623 |
| AD-19759 | GACCUUGCAUAACCUUUCC | 4954 | GGAAAGGUUAUGCAAGGUC | 5613 | 916 |
| AD-19760 | UAUUACGACAGACUGCCUU | 4955 | AAGGCAGUCUGUCGUAAUA | 5614 | 1153 |
| AD-19761 | AUCUGACCAGCCGACACCA | 4956 | UGGUGUCGGCUGGUCAGAU | 5615 | 1677 |
| AD-19762 | CAUUCCACGACUAGUUCAG | 4957 | CUGAACUAGUCGUGGAAUG | 5616 | 1864 |
| AD-19763 | GUUUUGAAAAUCCAGCGUG | 4958 | CACGCUGGAUUUUCAAAAC | 5617 | 246 |
| AD-19765 | GCGUUUGGCUGAACCAUCA | 4959 | UGAUGGUUCAGCCAAACGC | 5618 | 637 |
| AD-19766 | ACACGCUAUCAUGCGUUCU | 4960 | AGAACGCAUGAUAGCGUGU | 5619 | 823 |
| AD-19767 | UAUGCCAUUACAACUCUCC | 4961 | GGAGAGUUGUAAUGGCAUA | 5620 | 1028 |
| AD-19768 | UCUGCUCUAGUAAUAAGCC | 4962 | GGCUUAUUACUAGAGCAGA | 5621 | 1314 |
| AD-20124 | CGGGAUGUUCACAACCGAA | 4963 | UUCGGUUGUGAACAUCCCG | 5622 | 2012 |
| AD-25889 | ACAAUACAAAUGGAUUUUG | 4964 | CAAAAUCCAUUUGUAUUGU | 5623 | 2632 |
| AD-25890 | ACAAAUGGAUUUUGGGAGU | 4965 | ACUCCCAAAAUCCAUUUGU | 5624 | 2637 |
| AD-25891 | UUGGGAGUGACUCAAGAAG | 4966 | CUUCUUGAGUCACUCCCAA | 5625 | 2648 |
| AD-25892 | UGGGAGUGACUCAAGAAGU | 4967 | ACUUCUUGAGUCACUCCCA | 5626 | 2649 |
| AD-25893 | GAAGUGAAGAAUGCACAAG | 4968 | CUUGUGCAUUCUUCACUUC | 5627 | 2663 |
| AD-25894 | AAGUGAAGAAUGCACAAGA | 4969 | UCUUGUGCAUUCUUCACUU | 5628 | 2664 |
| AD-25895 | GAUGGAAUUUAUCAAACCC | 4970 | GGGUUUGAUAAAUUCCAUC | 5629 | 2694 |
| AD-25896 | AUGGAAUUUAUCAAACCCU | 4971 | AGGGUUUGAUAAAUUCCAU | 5630 | 2695 |
| AD-25897 | GGAAUUUAUCAAACCCUAG | 4972 | CUAGGGUUUGAUAAAUUCC | 5631 | 2697 |
| AD-25898 | GAAUUUAUCAAACCCUAGC | 4973 | GCUAGGGUUUGAUAAAUUC | 5632 | 2698 |
| AD-25899 | AAUUUAUCAAACCCUAGCC | 4974 | GGCUAGGGUUUGAUAAAUU | 5633 | 2699 |
| AD-25900 | GAAUAUCUGUAAUGGUACU | 4975 | AGUACCAUUACAGAUAUUC | 5634 | 2751 |
| AD-25901 | AAUAUCUGUAAUGGUACUG | 4976 | CAGUACCAUUACAGAUAUU | 5635 | 2752 |
| AD-25902 | AUAUCUGUAAUGGUACUGA | 4977 | UCAGUACCAUUACAGAUAU | 5636 | 2753 |
| AD-25903 | UUUUAAGUCUCUCGUAGUG | 4978 | CACUACGAGAGACUUAAAA | 5637 | 2832 |
| AD-25904 | UUUAAGUCUCUCGUAGUGU | 4979 | ACACUACGAGAGACUUAAA | 5638 | 2833 |
| AD-25905 | AGUCUCUCGUAGUGUUAAG | 4980 | CUUAACACUACGAGAGACU | 5639 | 2837 |

TABLE 2-continued

RNAi Agents to Beta-Catenin: Unmodified Sequences

| DUPLEX | SENSE SEQUENCE | SENSE SEQ ID NO: | ANTI-SENSE SEQUENCE | Anti-sense SEQ ID NO: | POSITION |
|---|---|---|---|---|---|
| AD-25906 | UCGUAGUGUUAAGUUAUAG | 4981 | CUAUAACUUAACACUACGA | 5640 | 2843 |
| AD-25907 | CGUAGUGUUAAGUUAUAGU | 4982 | ACUAUAACUUAACACUACG | 5641 | 2844 |
| AD-25908 | GUAGUGUUAAGUUAUAGUG | 4983 | CACUAUAACUUAACACUAC | 5642 | 2845 |
| AD-25909 | UAGUGUUAAGUUAUAGUGA | 4984 | UCACUAUAACUUAACACUA | 5643 | 2846 |
| AD-25910 | UAGUGAAUACUGCUACAGC | 4985 | GCUGUAGCAGUAUUCACUA | 5644 | 2859 |
| AD-25911 | AACACUAAUUCAUAAUCAC | 4986 | GUGAUUAUGAAUUAGUGUU | 5645 | 2913 |
| AD-25912 | ACACUAAUUCAUAAUCACU | 4987 | AGUGAUUAUGAAUUAGUGU | 5646 | 2914 |
| AD-25913 | UAAUUGUAAUCUGAAUAAA | 4988 | UUUAUUCAGAUUACAAUUA | 5647 | 2938 |
| AD-25914 | AUUGUAAUCUGAAUAAAGU | 4989 | ACUUUAUUCAGAUUACAAU | 5648 | 2940 |
| AD-25915 | UUGUAAUCUGAAUAAAGUG | 4990 | CACUUUAUUCAGAUUACAA | 5649 | 2941 |
| AD-25916 | UGUAAUCUGAAUAAAGUGU | 4991 | ACACUUUAUUCAGAUUACA | 5650 | 2942 |
| AD-25917 | GACAAUAGAAAAUGGUCC | 4992 | GGACCAUUUUCUAUUUGUC | 5651 | 2991 |
| AD-25918 | ACAAUAGAAAAUGGUCCA | 4993 | UGGACCAUUUUCUAUUUGU | 5652 | 2992 |
| AD-25919 | UAGAAAAUGGUCCAAUUAG | 4994 | CUAAUUGGACCAUUUUCUA | 5653 | 2997 |
| AD-25920 | AGAAAAUGGUCCAAUUAGU | 4995 | ACUAAUUGGACCAUUUUCU | 5654 | 2998 |
| AD-25921 | UAUUGGGAUAUGUAUGGG | 4996 | CCCAUACAUAUCCCAAAUA | 5655 | 3077 |
| AD-25922 | AUUUGGGAUAUGUAUGGGU | 4997 | ACCCAUACAUAUCCCAAAU | 5656 | 3078 |
| AD-25923 | UUGGGAUAUGUAUGGGUAG | 4998 | CUACCCAUACAUAUCCCAA | 5657 | 3080 |
| AD-25924 | GGAUAUGUAUGGGUAGGGU | 4999 | ACCCUACCCAUACAUAUCC | 5658 | 3083 |
| AD-25925 | AAGAGGUGUUAUUUGGAAC | 5000 | GUUCCAAAUAACACCUCUU | 5659 | 3110 |
| AD-25926 | AGAGGUGUUAUUUGGAACC | 5001 | GGUUCCAAAUAACACCUCU | 5660 | 3111 |
| AD-25927 | GAGGUGUUAUUUGGAACCU | 5002 | AGGUUCCAAAUAACACCUC | 5661 | 3112 |
| AD-25928 | UGGAACCUUGUUUUGGACA | 5003 | UGUCCAAAACAAGGUUCCA | 5662 | 3123 |
| AD-25929 | GGAACCUUGUUUUGGACAG | 5004 | CUGUCCAAAACAAGGUUCC | 5663 | 3124 |
| AD-25930 | GAACCUUGUUUUGGACAGU | 5005 | ACUGUCCAAAACAAGGUUC | 5664 | 3125 |
| AD-25931 | GUUUUGGACAGUUUACCAG | 5006 | CUGGUAAACUGUCCAAAAC | 5665 | 3132 |
| AD-25932 | UUUUGGACAGUUUACCAGU | 5007 | ACUGGUAAACUGUCCAAAA | 5666 | 3133 |
| AD-25933 | UUGGACAGUUUACCAGUUG | 5008 | CAACUGGUAAACUGUCCAA | 5667 | 3135 |
| AD-25934 | GUUGUUGUAACCUGCUGUG | 5009 | CACAGCAGGUUACAACAAC | 5668 | 3168 |
| AD-25935 | UUGUUGUAACCUGCUGUGA | 5010 | UCACAGCAGGUUACAACAA | 5669 | 3169 |
| AD-25936 | UUGUAACCUGCUGUGAUAC | 5011 | GUAUCACAGCAGGUUACAA | 5670 | 3172 |
| AD-25937 | AUGCUUCAAGAGAAAUGC | 5012 | GCAUUUCUCUUGAAGCAU | 5671 | 3192 |
| AD-25938 | AGUGAAGAAUGCACAAGAA | 5013 | UUCUUGUGCAUUCUUCACU | 5672 | 2665 |
| AD-25939 | AAUGGAUCACAAGAUGGAA | 5014 | UUCCAUCUUGUGAUCCAUU | 5673 | 2682 |
| AD-25940 | AUGGAUCACAAGAUGGAAU | 5015 | AUUCCAUCUUGUGAUCCAU | 5674 | 2683 |
| AD-25941 | UGGAUCACAAGAUGGAAUU | 5016 | AAUUCCAUCUUGUGAUCCA | 5675 | 2684 |
| AD-25942 | GGAUCACAAGAUGGAAUUU | 5017 | AAAUUCCAUCUUGUGAUCC | 5676 | 2685 |

TABLE 2-continued

RNAi Agents to Beta-Catenin: Unmodified Sequences

| DUPLEX | SENSE SEQUENCE | SENSE SEQ ID NO: | ANTI-SENSE SEQUENCE | Anti-sense SEQ ID NO: | POSITION |
|---|---|---|---|---|---|
| AD-25943 | GAUCACAAGAUGGAAUUUA | 5018 | UAAAUUCCAUCUUGUGAUC | 5677 | 2686 |
| AD-25944 | AUCACAAGAUGGAAUUUAU | 5019 | AUAAAUUCCAUCUUGUGAU | 5678 | 2687 |
| AD-25945 | UGGAAUUUAUCAAACCCUA | 5020 | UAGGGUUUGAUAAAUUCCA | 5679 | 2696 |
| AD-25946 | ACCCUAGCCUUGCUUGUUA | 5021 | UAACAAGCAAGGCUAGGGU | 5680 | 2709 |
| AD-25947 | CCCUAGCCUUGCUUGUUAA | 5022 | UUACAAGCAAGGCUAGGG | 5681 | 2710 |
| AD-25948 | CCUAGCCUUGCUUGUUAAA | 5023 | UUUACAAGCAAGGCUAGG | 5682 | 2711 |
| AD-25949 | CUAGCCUUGCUUGUUAAAU | 5024 | AUUUAACAAGCAAGGCUAG | 5683 | 2712 |
| AD-25950 | UAGCCUUGCUUGUUAAAUU | 5025 | AAUUUAACAAGCAAGGCUA | 5684 | 2713 |
| AD-25951 | AGCCUUGCUUGUUAAAUUU | 5026 | AAAUUUAACAAGCAAGGCU | 5685 | 2714 |
| AD-25952 | UUAAGUCUCUCGUAGUGUU | 5027 | AACACUACGAGAGACUUAA | 5686 | 2834 |
| AD-25953 | UAAGUCUCUCGUAGUGUUA | 5028 | UAACACUACGAGAGACUUA | 5687 | 2835 |
| AD-25954 | AAGUCUCUCGUAGUGUUAA | 5029 | UUAACACUACGAGAGACUU | 5688 | 2836 |
| AD-25955 | CUCGUAGUGUUAAGUUAUA | 5030 | UAUAACUUAACACUACGAG | 5689 | 2842 |
| AD-25956 | AGUGUUAAGUUAUAGUGAA | 5031 | UUCACUAUAACUUAACACU | 5690 | 2847 |
| AD-25957 | GUGUUAAGUUAUAGUGAAU | 5032 | AUUCACUAUAACUUAACAC | 5691 | 2848 |
| AD-25958 | CUACAGCAAUUUCUAAUUU | 5033 | AAAUUAGAAAUUGCUGUAG | 5692 | 2871 |
| AD-25959 | CAAAUAGAAAAUGGUCCAA | 5034 | UUGGACCAUUUUCUAUUUG | 5693 | 2993 |
| AD-25960 | AUAGAAAAUGGUCCAAUUA | 5035 | UAAUUGGACCAUUUUCUAU | 5694 | 2996 |
| AD-25961 | UUUGGGAUAUGUAUGGGUA | 5036 | UACCCAUACAUAUCCCAAA | 5695 | 3079 |
| AD-25962 | GAUAUGUAUGGGUAGGGUA | 5037 | UACCCUACCCAUACAUAUC | 5696 | 3084 |
| AD-25963 | UGGGUAGGGUAAAUCAGUA | 5038 | UACUGAUUUACCCUACCCA | 5697 | 3092 |
| AD-25964 | UAAGAGGUGUUAUUUGGAA | 5039 | UUCCAAAUAACACCUCUUA | 5698 | 3109 |
| AD-26017 | UGCCUUUUAUCCCAAAGUU | 5040 | AACUUUGGGAUAAAAGGCA | 5699 | 3152 |
| AD-26018 | UGUUGUAACCUGCUGUGAU | 5041 | AUCACAGCAGGUUACAACA | 5700 | 3170 |
| AD-26019 | GUUGUAACCUGCUGUGAUA | 5042 | UAUCACAGCAGGUUACAAC | 5701 | 3171 |
| AD-26020 | CAAGAGAAAAUGCGGUUAU | 5043 | AUAACCGCAUUUUCUCUUG | 5702 | 3198 |
| AD-26021 | AAGAGAAAAUGCGGUUAUA | 5044 | UAUAACCGCAUUUUCUCUU | 5703 | 3199 |
| AD-26022 | CCUGUUCCCUGAGGGUAU | 5045 | AUACCCUCAGGGGAACAGG | 5704 | 207 |
| AD-26023 | CUGUUCCCUGAGGGUAUU | 5046 | AAUACCCUCAGGGGAACAG | 5705 | 208 |
| AD-26024 | CCUGAGGGUAUUUGAAGUA | 5047 | UACUUCAAAUACCCUCAGG | 5706 | 215 |
| AD-26025 | CUGAGGGUAUUUGAAGUAU | 5048 | AUACUUCAAAUACCCUCAG | 5707 | 216 |
| AD-26026 | UGAGGGUAUUUGAAGUAUA | 5049 | UAUACUUCAAAUACCCUCA | 5708 | 217 |
| AD-26027 | GGUAUUUGAAGUAUACCAU | 5050 | AUGGUAUACUUCAAAUACC | 5709 | 221 |
| AD-26028 | GUAUUUGAAGUAUACCAUA | 5051 | UAUGGUAUACUUCAAAUAC | 5710 | 222 |
| AD-26029 | UUUGAAGUAUACCAUACAA | 5052 | UUGUAUGGUAUACUUCAAA | 5711 | 225 |
| AD-26030 | AGUAUACCAUACAACUGUU | 5053 | AACAGUUGUAUGGUAUACU | 5712 | 230 |

TABLE 2-continued

RNAi Agents to Beta-Catenin: Unmodified Sequences

| DUPLEX | SENSE SEQUENCE | SENSE SEQ ID NO: | ANTI-SENSE SEQUENCE | Anti-sense SEQ ID NO: | POSITION |
|---|---|---|---|---|---|
| AD-26031 | GUAUACCAUACAACUGUUU | 5054 | AAACAGUUGUAUGGUAUAC | 5713 | 231 |
| AD-26032 | UAUACCAUACAACUGUUUU | 5055 | AAAACAGUUGUAUGGUAUA | 5714 | 232 |
| AD-26033 | ACCAUACAACUGUUUUGAA | 5056 | UUCAAAACAGUUGUAUGGU | 5715 | 235 |
| AD-26034 | CCAUACAACUGUUUUGAAA | 5057 | UUUCAAAACAGUUGUAUGG | 5716 | 236 |
| AD-26035 | GAAAAUCCAGCGUGGACAA | 5058 | UUGUCCACGCUGGAUUUUC | 5717 | 251 |
| AD-26036 | AAAAUCCAGCGUGGACAAU | 5059 | AUUGUCCACGCUGGAUUUU | 5718 | 252 |
| AD-26037 | CCAGCGUGGACAAUGGCUA | 5060 | UAGCCAUUGUCCACGCUGG | 5719 | 257 |
| AD-26038 | GUGGACAAUGGCUACUCAA | 5061 | UUGAGUAGCCAUUGUCCAC | 5720 | 262 |
| AD-26039 | AAUGGCUACUCAAGCUGAU | 5062 | AUCAGCUUGAGUAGCCAUU | 5721 | 268 |
| AD-26040 | AUGGCUACUCAAGCUGAUU | 5063 | AAUCAGCUUGAGUAGCCAU | 5722 | 269 |
| AD-26041 | UGGCUACUCAAGCUGAUUU | 5064 | AAAUCAGCUUGAGUAGCCA | 5723 | 270 |
| AD-26042 | CUACUCAAGCUGAUUUGAU | 5065 | AUCAAAUCAGCUUGAGUAG | 5724 | 273 |
| AD-26043 | AUUUGAUGGAGUUGGACAU | 5066 | AUGUCCAACUCCAUCAAAU | 5725 | 285 |
| AD-26044 | UGGAGUUGGACAUGGCCAU | 5067 | AUGGCCAUGUCCAACUCCA | 5726 | 291 |
| AD-26045 | GUUGGACAUGGCCAUGGAA | 5068 | UUCCAUGGCCAUGUCCAAC | 5727 | 295 |
| AD-26046 | GCCAUGGAACCAGACAGAA | 5069 | UUCUGUCUGGUUCCAUGGC | 5728 | 305 |
| AD-26047 | CAUGGAACCAGACAGAAAA | 5070 | UUUUCUGUCUGGUUCCAUG | 5729 | 307 |
| AD-26048 | GGAGGCGGAGACGGAGGAA | 5071 | UUCCUCCGUCUCCGCCUCC | 5730 | 111 |
| AD-26049 | AGACAGAAAAGCGGCUGUU | 5072 | AACAGCCGCUUUUCUGUCU | 5731 | 316 |
| AD-26050 | GACAGAAAAGCGGCUGUUA | 5073 | UAACAGCCGCUUUUCUGUC | 5732 | 317 |
| AD-26051 | UGUUAGUCACUGGCAGCAA | 5074 | UUGCUGCCAGUGACUAACA | 5733 | 331 |
| AD-26052 | CACUGGCAGCAACAGUCUU | 5075 | AAGACUGUUGCUGCCAGUG | 5734 | 338 |
| AD-26053 | ACUGGCAGCAACAGUCUUA | 5076 | UAAGACUGUUGCUGCCAGU | 5735 | 339 |
| AD-26054 | UCUUACCUGGACUCUGGAA | 5077 | UUCCAGAGUCCAGGUAAGA | 5736 | 353 |
| AD-26055 | CUUACCUGGACUCUGGAAU | 5078 | AUUCCAGAGUCCAGGUAAG | 5737 | 354 |
| AD-26056 | CCUGGACUCUGGAAUCCAU | 5079 | AUGGAUUCCAGAGUCCAGG | 5738 | 358 |
| AD-26057 | GGCUAGUGGUGGACCCCAA | 5080 | UUGGGGUCCACCACUAGCC | 5739 | 1216 |
| AD-26058 | GCCACUACCACAGCUCCUU | 5081 | AAGGAGCUGUGGUAGUGGC | 5740 | 383 |
| AD-26059 | UCCUUCUCUGAGUGGUAAA | 5082 | UUUACCACUCAGAGAAGGA | 5741 | 397 |
| AD-26060 | CUCUGAGUGGUAAAGGCAA | 5083 | UUGCCUUUACCACUCAGAG | 5742 | 402 |
| AD-26061 | UAAAGGCAAUCCUGAGGAA | 5084 | UUCCUCAGGAUUGCCUUUA | 5743 | 412 |
| AD-26062 | CAAUCCUGAGGAAGAGGAU | 5085 | AUCCUCUUCCUCAGGAUUG | 5744 | 418 |
| AD-26063 | UGAGGAAGAGGAUGUGGAU | 5086 | AUCCACAUCCUCUUCCUCA | 5745 | 424 |
| AD-26064 | AUACCUCCCAAGUCCUGUA | 5087 | UACAGGACUUGGGAGGUAU | 5746 | 441 |
| AD-26065 | UACCUCCCAAGUCCUGUAU | 5088 | AUACAGGACUUGGGAGGUA | 5747 | 442 |
| AD-26066 | AGUCCUGUAUGAGUGGGAA | 5089 | UUCCCACUCAUACAGGACU | 5748 | 451 |
| AD-26067 | UAUGAGUGGGAACAGGGAU | 5090 | AUCCCUGUUCCCACUCAUA | 5749 | 458 |

TABLE 2-continued

RNAi Agents to Beta-Catenin: Unmodified Sequences

| DUPLEX | SENSE SEQUENCE | SENSE SEQ ID NO: | ANTI-SENSE SEQUENCE | Anti-sense SEQ ID NO: | POSITION |
|---|---|---|---|---|---|
| AD-26068 | CAAGCUUUAGUAAAUAUAA | 5091 | UUAUAUUUACUAAAGCUUG | 5750 | 1232 |
| AD-26069 | AAGCUUUAGUAAAUAUAAU | 5092 | AUUAUAUUUACUAAAGCUU | 5751 | 1233 |
| AD-26070 | UGAGUGGGAACAGGGAUUU | 5093 | AAAUCCCUGUUCCCACUCA | 5752 | 460 |
| AD-26071 | GAGUGGGAACAGGGAUUUU | 5094 | AAAAUCCCUGUUCCCACUC | 5753 | 461 |
| AD-26072 | AGGGAUUUUCUCAGUCCUU | 5095 | AAGGACUGAGAAAAUCCCU | 5754 | 471 |
| AD-26073 | UUCUCAGUCCUUCACUCAA | 5096 | UUGAGUGAAGGACUGAGAA | 5755 | 478 |
| AD-26074 | UCAGUCCUUCACUCAAGAA | 5097 | UUCUUGAGUGAAGGACUGA | 5756 | 481 |
| AD-26075 | CUUCACUCAAGAACAAGUA | 5098 | UACUUGUUCUUGAGUGAAG | 5757 | 487 |
| AD-26076 | UCAAGAACAAGUAGCUGAU | 5099 | AUCAGCUACUUGUUCUUGA | 5758 | 493 |
| AD-26077 | CUGAUAUUGAUGGACAGUA | 5100 | UACUGUCCAUCAAUAUCAG | 5759 | 507 |
| AD-26078 | AUUGAUGGACAGUAUGCAA | 5101 | UUGCAUACUGUCCAUCAAU | 5760 | 512 |
| AD-26079 | GACUCGAGCUCAGAGGGUA | 5102 | UACCCUCUGAGCUCGAGUC | 5761 | 532 |
| AD-26080 | CAGAGGGUACGAGCUGCUA | 5103 | UAGCAGCUCGUACCCUCUG | 5762 | 542 |
| AD-26081 | AGAGGGUACGAGCUGCUAU | 5104 | AUAGCAGCUCGUACCCUCU | 5763 | 543 |
| AD-26082 | GGGUACGAGCUGCUAUGUU | 5105 | AACAUAGCAGCUCGUACCC | 5764 | 546 |
| AD-26083 | CUAUGUUCCCUGAGACAUU | 5106 | AAUGUCUCAGGGAACAUAG | 5765 | 558 |
| AD-26084 | UAUGUUCCCUGAGACAUUA | 5107 | UAAUGUCUCAGGGAACAUA | 5766 | 559 |
| AD-26085 | GUUCCCUGAGACAUUAGAU | 5108 | AUCUAAUGUCUCAGGGAAC | 5767 | 562 |
| AD-26086 | UAGAUGAGGGCAUGCAGAU | 5109 | AUCUGCAUGCCCUCAUCUA | 5768 | 576 |
| AD-26087 | GAGGGCAUGCAGAUCCCAU | 5110 | AUGGGAUCUGCAUGCCCUC | 5769 | 581 |
| AD-26088 | GGCAUGCAGAUCCCAUCUA | 5111 | UAGAUGGGAUCUGCAUGCC | 5770 | 584 |
| AD-26089 | AGAUCCCAUCUACACAGUU | 5112 | AACUGUGUAGAUGGGAUCU | 5771 | 591 |
| AD-26090 | CCCAUCUACACAGUUUGAU | 5113 | AUCAAACUGUGUAGAUGGG | 5772 | 595 |
| AD-26091 | ACAGUUUGAUGCUGCUCAU | 5114 | AUGAGCAGCAUCAAACUGU | 5773 | 604 |
| AD-26092 | GAUGCUGCUCAUCCCACUA | 5115 | UAGUGGGAUGAGCAGCAUC | 5774 | 611 |
| AD-26093 | AUGCUGCUCAUCCCACUAA | 5116 | UUAGUGGGAUGAGCAGCAU | 5775 | 612 |
| AD-26094 | UGCUGCUCAUCCCACUAAU | 5117 | AUUAGUGGGAUGAGCAGCA | 5776 | 613 |
| AD-26095 | CCCACUAAUGUCCAGCGUU | 5118 | AACGCUGGACAUUAGUGGG | 5777 | 623 |
| AD-26096 | CAGCGUUUGGCUGAACCAU | 5119 | AUGGUUCAGCCAAACGCUG | 5778 | 635 |
| AD-26097 | UGGCUGAACCAUCACAGAU | 5120 | AUCUGUGAUGGUUCAGCCA | 5779 | 642 |
| AD-26098 | AACCAUCACAGAUGCUGAA | 5121 | UUCAGCAUCUGUGAUGGUU | 5780 | 648 |
| AD-26099 | ACCAUCACAGAUGCUGAAA | 5122 | UUUCAGCAUCUGUGAUGGU | 5781 | 649 |
| AD-26100 | AUCACAGAUGCUGAAACAU | 5123 | AUGUUUCAGCAUCUGUGAU | 5782 | 652 |
| AD-26101 | GAUGCUGAAACAUGCAGUU | 5124 | AACUGCAUGUUUCAGCAUC | 5783 | 658 |
| AD-26102 | CUGAAACAUGCAGUUGUAA | 5125 | UUACAACUGCAUGUUUCAG | 5784 | 662 |
| AD-26103 | AACAUGCAGUUGUAAACUU | 5126 | AAGUUUACAACUGCAUGUU | 5785 | 666 |

TABLE 2-continued

RNAi Agents to Beta-Catenin: Unmodified Sequences

| DUPLEX | SENSE SEQUENCE | SENSE SEQ ID NO: | ANTI-SENSE SEQUENCE | Anti-sense SEQ ID NO: | POSITION |
|---|---|---|---|---|---|
| AD-26104 | AUGCAGUUGUAAACUUGAU | 5127 | AUCAAGUUUACAACUGCAU | 5786 | 669 |
| AD-26105 | UGCAGUUGUAAACUUGAUU | 5128 | AAUCAAGUUUACAACUGCA | 5787 | 670 |
| AD-26106 | CAGUUGUAAACUUGAUUAA | 5129 | UUAAUCAAGUUUACAACUG | 5788 | 672 |
| AD-26107 | CUUGAUUAACUAUCAAGAU | 5130 | AUCUUGAUAGUUAAUCAAG | 5789 | 682 |
| AD-26108 | GAUUAACUAUCAAGAUGAU | 5131 | AUCAUCUUGAUAGUUAAUC | 5790 | 685 |
| AD-26109 | CUAUCAAGAUGAUGCAGAA | 5132 | UUCUGCAUCAUCUUGAUAG | 5791 | 691 |
| AD-26110 | GAACUUGCCACACGUGCAA | 5133 | UUGCACGUGUGGCAAGUUC | 5792 | 707 |
| AD-26111 | AACUUGCCACACGUGCAAU | 5134 | AUUGCACGUGUGGCAAGUU | 5793 | 708 |
| AD-26112 | CACACGUGCAAUCCCUGAA | 5135 | UUCAGGGAUUGCACGUGUG | 5794 | 715 |
| AD-26123 | GCAAUCCCUGAACUGACAA | 5136 | UUGUCAGUUCAGGGAUUGC | 5795 | 722 |
| AD-26124 | CAAUCCCUGAACUGACAAA | 5137 | UUUGUCAGUUCAGGGAUUG | 5796 | 723 |
| AD-26125 | AAUCCCUGAACUGACAAAA | 5138 | UUUUGUCAGUUCAGGGAUU | 5797 | 724 |
| AD-26126 | UGAACUGACAAAACUGCUA | 5139 | UAGCAGUUUUGUCAGUUCA | 5798 | 730 |
| AD-26127 | GAACUGACAAAACUGCUAA | 5140 | UUAGCAGUUUUGUCAGUUC | 5799 | 731 |
| AD-26128 | AACUGACAAAACUGCUAAA | 5141 | UUUAGCAGUUUUGUCAGUU | 5800 | 732 |
| AD-26129 | ACUGACAAAACUGCUAAAU | 5142 | AUUUAGCAGUUUUGUCAGU | 5801 | 733 |
| AD-26130 | GAGGACCAGGUGGUGGUUA | 5143 | UAACCACCACCUGGUCCUC | 5802 | 755 |
| AD-26131 | AGGACCAGGUGGUGGUUAA | 5144 | UUAACCACCACCUGGUCCU | 5803 | 756 |
| AD-26132 | GGACCAGGUGGUGGUUAAU | 5145 | AUUAACCACCACCUGGUCC | 5804 | 757 |
| AD-26133 | GACCAGGUGGUGGUUAAUA | 5146 | UAUUAACCACCACCUGGUC | 5805 | 758 |
| AD-26134 | UCACUUGCAAUAAUUAUAA | 5147 | UUAUAAUUAUUGCAAGUGA | 5806 | 1548 |
| AD-26135 | CUUGCAAUAAUUAUAAGAA | 5148 | UUCUUAUAAUUAUUGCAAG | 5807 | 1551 |
| AD-26136 | ACCAGGUGGUGGUUAAUAA | 5149 | UUAUUAACCACCACCUGGU | 5808 | 759 |
| AD-26137 | GGCUGCAGUUAUGGUCCAU | 5150 | AUGGACCAUAACUGCAGCC | 5809 | 778 |
| AD-26138 | GUUAUGGUCCAUCAGCUUU | 5151 | AAAGCUGAUGGACCAUAAC | 5810 | 785 |
| AD-26139 | AUGGUCCAUCAGCUUUCUA | 5152 | UAGAAAGCUGAUGGACCAU | 5811 | 788 |
| AD-26140 | UGGUCCAUCAGCUUUCUAA | 5153 | UUAGAAAGCUGAUGGACCA | 5812 | 789 |
| AD-26141 | UCGGGCUGGUGACAGGGAA | 5154 | UUCCCUGUCACCAGCCCGA | 5813 | 1624 |
| AD-26142 | GGUCCAUCAGCUUUCUAAA | 5155 | UUUAGAAAGCUGAUGGACC | 5814 | 790 |
| AD-26143 | GUCCAUCAGCUUUCUAAAA | 5156 | UUUUAGAAAGCUGAUGGAC | 5815 | 791 |
| AD-26144 | GAAGCUUCCAGACACGCUA | 5157 | UAGCGUGUCUGGAAGCUUC | 5816 | 812 |
| AD-26145 | AAGCUUCCAGACACGCUAU | 5158 | AUAGCGUGUCUGGAAGCUU | 5817 | 813 |
| AD-26146 | CUUCCAGACACGCUAUCAU | 5159 | AUGAUAGCGUGUCUGGAAG | 5818 | 816 |
| AD-26147 | AGACACGCUAUCAUGCGUU | 5160 | AACGCAUGAUAGCGUGUCU | 5819 | 821 |
| AD-26148 | UCAUGCGUUCUCCUCAGAU | 5161 | AUCUGAGGAGAACGCAUGA | 5820 | 831 |
| AD-26149 | CCUCAGAUGGUGUCUGCUA | 5162 | UAGCAGACACCAUCUGAGG | 5821 | 842 |
| AD-26150 | CUCAGAUGGUGUCUGCUAU | 5163 | AUAGCAGACACCAUCUGAG | 5822 | 843 |

TABLE 2-continued

RNAi Agents to Beta-Catenin: Unmodified Sequences

| DUPLEX | SENSE SEQUENCE | SENSE SEQ ID NO: | ANTI-SENSE SEQUENCE | Anti-sense SEQ ID NO: | POSITION |
|---|---|---|---|---|---|
| AD-26151 | GUGUCUGCUAUUGUACGUA | 5164 | UACGUACAAUAGCAGACAC | 5823 | 851 |
| AD-26152 | CUGCUAUUGUACGUACCAU | 5165 | AUGGUACGUACAAUAGCAG | 5824 | 855 |
| AD-26153 | UUGUACGUACCAUGCAGAA | 5166 | UUCUGCAUGGUACGUACAA | 5825 | 861 |
| AD-26154 | UGUACGUACCAUGCAGAAU | 5167 | AUUCUGCAUGGUACGUACA | 5826 | 862 |
| AD-26155 | CGUACCAUGCAGAAUACAA | 5168 | UUGUAUUCUGCAUGGUACG | 5827 | 866 |
| AD-26156 | CAUGCAGAAUACAAAUGAU | 5169 | AUCAUUUGUAUUCUGCAUG | 5828 | 871 |
| AD-26157 | GCAGAAUACAAAUGAUGUA | 5170 | UACAUCAUUUGUAUUCUGC | 5829 | 874 |
| AD-26158 | GAAUACAAAUGAUGUAGAA | 5171 | UUCUACAUCAUUUGUAUUC | 5830 | 877 |
| AD-26159 | GAUGUAGAAACAGCUCGUU | 5172 | AACGAGCUGUUUCUACAUC | 5831 | 887 |
| AD-26160 | GUUGUACCGCUGGGACCUU | 5173 | AAGGUCCCAGCGGUACAAC | 5832 | 903 |
| AD-26161 | UACCGCUGGGACCUUGCAU | 5174 | AUGCAAGGUCCCAGCGGUA | 5833 | 907 |
| AD-26162 | CCGCUGGGACCUUGCAUAA | 5175 | UUAUGCAAGGUCCCAGCGG | 5834 | 909 |
| AD-26163 | UGGGACCUUGCAUAACCUU | 5176 | AAGGUUAUGCAAGGUCCCA | 5835 | 913 |
| AD-26164 | GGGACCUUGCAUAACCUUU | 5177 | AAAGGUUAUGCAAGGUCCC | 5836 | 914 |
| AD-26165 | CUUGCAUAACCUUUCCCAU | 5178 | AUGGGAAAGGUUAUGCAAG | 5837 | 919 |
| AD-26166 | UCUUAAGUCUGGAGGCAU | 5179 | AUGCCUCCAGACUUAAAGA | 5838 | 960 |
| AD-26167 | GCAUUCCUGCCCUGGUGAA | 5180 | UUCACCAGGGCAGGAAUGC | 5839 | 975 |
| AD-26168 | CAUUCCUGCCCUGGUGAAA | 5181 | UUUCACCAGGGCAGGAAUG | 5840 | 976 |
| AD-26169 | AUUCCUGCCCUGGUGAAAA | 5182 | UUUUCACCAGGGCAGGAAU | 5841 | 977 |
| AD-26170 | UUCCUGCCCUGGUGAAAAU | 5183 | AUUUUCACCAGGGCAGGAA | 5842 | 978 |
| AD-26171 | UGCCCUGGUGAAAAUGCUU | 5184 | AAGCAUUUUCACCAGGGCA | 5843 | 982 |
| AD-26172 | CUGGUGAAAAUGCUUGGUU | 5185 | AACCAAGCAUUUUCACCAG | 5844 | 986 |
| AD-26173 | GCUUGGUUCACCAGUGGAU | 5186 | AUCCACUGGUGAACCAAGC | 5845 | 997 |
| AD-26174 | CUUGGUUCACCAGUGGAUU | 5187 | AAUCCACUGGUGAACCAAG | 5846 | 998 |
| AD-26175 | UGCGUGAGCAGGGUGCCAU | 5188 | AUGGCACCCUGCUCACGCA | 5847 | 1848 |
| AD-26176 | GCGUGAGCAGGGUGCCAUU | 5189 | AAUGGCACCCUGCUCACGC | 5848 | 1849 |
| AD-26177 | CACCAGUGGAUUCUGUGUU | 5190 | AACACAGAAUCCACUGGUG | 5849 | 1005 |
| AD-26178 | CAGUGGAUUCUGUGUUGUU | 5191 | AACAACACAGAAUCCACUG | 5850 | 1008 |
| AD-26179 | AGUGGAUUCUGUGUUGUUU | 5192 | AAACAACACAGAAUCCACU | 5851 | 1009 |
| AD-26180 | GUGGAUUCUGUGUUGUUUU | 5193 | AAAACAACACAGAAUCCAC | 5852 | 1010 |
| AD-26181 | UGGAUUCUGUGUUGUUUUA | 5194 | UAAAACAACACAGAAUCCA | 5853 | 1011 |
| AD-26182 | GGAUUCUGUGUUGUUUUAU | 5195 | AUAAAACAACACAGAAUCC | 5854 | 1012 |
| AD-26183 | UGUGUUGUUUUAUGCCAUU | 5196 | AAUGGCAUAAAACAACACA | 5855 | 1018 |
| AD-26184 | GGGUGGGACACAGCAGCAA | 5197 | UUGCUGCUGUGUCCCACCC | 5856 | 1927 |
| AD-26185 | GUGUUGUUUUAUGCCAUUA | 5198 | UAAUGGCAUAAAACAACAC | 5857 | 1019 |
| AD-26186 | UUGUUUUAUGCCAUUACAA | 5199 | UUGUAAUGGCAUAAAACAA | 5858 | 1022 |

TABLE 2-continued

RNAi Agents to Beta-Catenin: Unmodified Sequences

| DUPLEX | SENSE SEQUENCE | SENSE SEQ ID NO: | ANTI-SENSE SEQUENCE | Anti-sense SEQ ID NO: | POSITION |
|---|---|---|---|---|---|
| AD-26187 | CCAUUACAACUCUCCACAA | 5200 | UUGUGGAGAGUUGUAAUGG | 5859 | 1032 |
| AD-26188 | UACAACUCUCCACAACCUU | 5201 | AAGGUUGUGGAGAGUUGUA | 5860 | 1036 |
| AD-26189 | ACAACUCUCCACAACCUUU | 5202 | AAAGGUUGUGGAGAGUUGU | 5861 | 1037 |
| AD-26190 | CAACUCUCCACAACCUUUU | 5203 | AAAAGGUUGUGGAGAGUUG | 5862 | 1038 |
| AD-26191 | AACUCUCCACAACCUUUUA | 5204 | UAAAAGGUUGUGGAGAGUU | 5863 | 1039 |
| AD-26192 | ACUCUCCACAACCUUUUAU | 5205 | AUAAAAGGUUGUGGAGAGU | 5864 | 1040 |
| AD-26193 | CUCUCCACAACCUUUUAUU | 5206 | AAUAAAAGGUUGUGGAGAG | 5865 | 1041 |
| AD-26194 | UCUCCACAACCUUUUAUUA | 5207 | UAAUAAAAGGUUGUGGAGA | 5866 | 1042 |
| AD-26195 | CAACCUUUUAUUACAUCAA | 5208 | UUGAUGUAAUAAAAGGUUG | 5867 | 1048 |
| AD-26196 | CCUUUUAUUACAUCAAGAA | 5209 | UUCUUGAUGUAAUAAAAGG | 5868 | 1051 |
| AD-26197 | UUACAUCAAGAAGGAGCUA | 5210 | UAGCUCCUUCUUGAUGUAA | 5869 | 1058 |
| AD-26198 | UACAUCAAGAAGGAGCUAA | 5211 | UUAGCUCCUUCUUGAUGUA | 5870 | 1059 |
| AD-26199 | CAUCAAGAAGGAGCUAAAA | 5212 | UUUUAGCUCCUUCUUGAUG | 5871 | 1061 |
| AD-26200 | AUCAAGAAGGAGCUAAAAU | 5213 | AUUUUAGCUCCUUCUUGAU | 5872 | 1062 |
| AD-26201 | GCUAAAAUGGCAGUGCGUU | 5214 | AACGCACUGCCAUUUUAGC | 5873 | 1073 |
| AD-26202 | UAAAAUGGCAGUGCGUUUA | 5215 | UAAACGCACUGCCAUUUUA | 5874 | 1075 |
| AD-26203 | AAAUGGUUGCCUUGCUCAA | 5216 | UUGAGCAAGGCAACCAUUU | 5875 | 1110 |
| AD-26204 | GCCUGUUCCCUGAGGGUA | 5217 | UACCCUCAGGGGAACAGGC | 5876 | 206 |
| AD-26205 | UGGUUGCCUUGCUCAACAA | 5218 | UUGUUGAGCAAGGCAACCA | 5877 | 1113 |
| AD-26206 | GGUUGCCUUGCUCAACAAA | 5219 | UUUGUUGAGCAAGGCAACC | 5878 | 1114 |
| AD-26207 | GUUGCCUUGCUCAACAAAA | 5220 | UUUUGUUGAGCAAGGCAAC | 5879 | 1115 |
| AD-26208 | GCCUUGCUCAACAAAACAA | 5221 | UUGUUUUGUUGAGCAAGGC | 5880 | 1118 |
| AD-26209 | CCUUGCUCAACAAAACAAA | 5222 | UUUGUUUUGUUGAGCAAGG | 5881 | 1119 |
| AD-26210 | GUUAAAUUCUUGGCUAUUA | 5223 | UAAUAGCCAAGAAUUUAAC | 5882 | 1139 |
| AD-26211 | UAUUACGACAGACUGCCUU | 5224 | AAGGCAGUCUGUCGUAAUA | 5883 | 1153 |
| AD-26212 | AUGGCAACCAAGAAAGCAA | 5225 | UUGCUUUCUUGGUUGCCAU | 5884 | 1185 |
| AD-26213 | AGUGGUGGACCCCAAGCUU | 5226 | AAGCUUGGGGUCCACCACU | 5885 | 1220 |
| AD-26214 | GUGGUGGACCCCAAGCUUU | 5227 | AAAGCUUGGGGUCCACCAC | 5886 | 1221 |
| AD-26215 | UGGUGGACCCCAAGCUUUA | 5228 | UAAAGCUUGGGGUCCACCA | 5887 | 1222 |
| AD-26216 | UGGACCCCAAGCUUUAGUA | 5229 | UACUAAAGCUUGGGGUCCA | 5888 | 1225 |
| AD-26217 | GGACCCCAAGCUUUAGUAA | 5230 | UUACUAAAGCUUGGGGUCC | 5889 | 1226 |
| AD-26218 | GACCCCAAGCUUUAGUAAA | 5231 | UUUACUAAAGCUUGGGGUC | 5890 | 1227 |
| AD-26651 | ACCCCAAGCUUUAGUAAAU | 5232 | AUUUACUAAAGCUUGGGGU | 5891 | 1228 |
| AD-26652 | CCCCAAGCUUUAGUAAAUA | 5233 | UAUUUACUAAAGCUUGGGG | 5892 | 1229 |
| AD-26653 | CCCAAGCUUUAGUAAAUAU | 5234 | AUAUUUACUAAAGCUUGGG | 5893 | 1230 |
| AD-26654 | CCAAGCUUUAGUAAAUAUA | 5235 | UAUAUUUACUAAAGCUUGG | 5894 | 1231 |
| AD-26655 | UAAAUAUAAUGAGGACCUA | 5236 | UAGGUCCUCAUUAUAUUUA | 5895 | 1242 |

TABLE 2-continued

RNAi Agents to Beta-Catenin: Unmodified Sequences

| DUPLEX | SENSE SEQUENCE | SENSE SEQ ID NO: | ANTI-SENSE SEQUENCE | Anti-sense SEQ ID NO: | POSITION |
|---|---|---|---|---|---|
| AD-26656 | AAAUAUAAUGAGGACCUAU | 5237 | AUAGGUCCUCAUUAUAUUU | 5896 | 1243 |
| AD-26657 | AAUAUAAUGAGGACCUAUA | 5238 | UAUAGGUCCUCAUUAUAUU | 5897 | 1244 |
| AD-26658 | AUAAUGAGGACCUAUACUU | 5239 | AAGUAUAGGUCCUCAUUAU | 5898 | 1247 |
| AD-26659 | AAACUACUGUGGACCACAA | 5240 | UUGUGGUCCACAGUAGUUU | 5899 | 1271 |
| AD-26660 | CCACAAGCAGAGUGCUGAA | 5241 | UUCAGCACUCUGCUUGUGG | 5900 | 1284 |
| AD-26661 | CAGAGUGCUGAAGGUGCUA | 5242 | UAGCACCUUCAGCACUCUG | 5901 | 1291 |
| AD-26662 | AGAGUGCUGAAGGUGCUAU | 5243 | AUAGCACCUUCAGCACUCU | 5902 | 1292 |
| AD-26663 | AUUGUAGAAGCUGGUGGAA | 5244 | UUCCACCAGCUUCUACAAU | 5903 | 1337 |
| AD-26664 | UUGUAGAAGCUGGUGGAAU | 5245 | AUUCCACCAGCUUCUACAA | 5904 | 1338 |
| AD-26665 | GCUGGUGGAAUGCAAGCUU | 5246 | AAGCUUGCAUUCCACCAGC | 5905 | 1346 |
| AD-26666 | CUGGUGGAAUGCAAGCUUU | 5247 | AAAGCUUGCAUUCCACCAG | 5906 | 1347 |
| AD-26667 | AGGACUUCACCUGACAGAU | 5248 | AUCUGUCAGGUGAAGUCCU | 5907 | 1366 |
| AD-26668 | CUUCACCUGACAGAUCCAA | 5249 | UUGGAUCUGUCAGGUGAAG | 5908 | 1370 |
| AD-26669 | CCUGACAGAUCCAAGUCAA | 5250 | UUGACUUGGAUCUGUCAGG | 5909 | 1375 |
| AD-26670 | AGAUCCAAGUCAACGUCUU | 5251 | AAGACGUUGACUUGGAUCU | 5910 | 1381 |
| AD-26671 | UCCAAGUCAACGUCUUGUU | 5252 | AACAAGACGUUGACUUGGA | 5911 | 1384 |
| AD-26672 | UCUUGUUCAGAACUGUCUU | 5253 | AAGACAGUUCUGAACAAGA | 5912 | 1396 |
| AD-26673 | CUUGUUCAGAACUGUCUUU | 5254 | AAAGACAGUUCUGAACAAG | 5913 | 1397 |
| AD-26674 | GUCUUUGGACUCUCAGGAA | 5255 | UUCCUGAGAGUCCAAAGAC | 5914 | 1410 |
| AD-26675 | UCUUUGGACUCUCAGGAAU | 5256 | AUUCCUGAGAGUCCAAAGA | 5915 | 1411 |
| AD-26676 | UUGGACUCUCAGGAAUCUU | 5257 | AAGAUUCCUGAGAGUCCAA | 5916 | 1414 |
| AD-26677 | UGCCCAGGGAGAACCCCUU | 5258 | AAGGGGUUCUCCCUGGGCA | 5917 | 2371 |
| AD-26678 | UGGACUCUCAGGAAUCUUU | 5259 | AAAGAUUCCUGAGAGUCCA | 5918 | 1415 |
| AD-26679 | UCUCAGGAAUCUUUCAGAU | 5260 | AUCUGAAAGAUUCCUGAGA | 5919 | 1420 |
| AD-26680 | AAUCUUUCAGAUGCUGCAA | 5261 | UUGCAGCAUCUGAAAGAUU | 5920 | 1427 |
| AD-26681 | CUUUCAGAUGCUGCAACUA | 5262 | UAGUUGCAGCAUCUGAAAG | 5921 | 1430 |
| AD-26682 | UUCAGAUGCUGCAACUAAA | 5263 | UUUAGUUGCAGCAUCUGAA | 5922 | 1432 |
| AD-26683 | UGCUGCAACUAAACAGGAA | 5264 | UUCCUGUUUAGUUGCAGCA | 5923 | 1438 |
| AD-26684 | UAAACAGGAAGGGAUGGAA | 5265 | UUCCAUCCCUUCCUGUUUA | 5924 | 1447 |
| AD-26685 | AGGGAUGGAAGGUCUCCUU | 5266 | AAGGAGACCUUCCAUCCCU | 5925 | 1456 |
| AD-26686 | AGGUCUCCUUGGGACUCUU | 5267 | AAGAGUCCCAAGGAGACCU | 5926 | 1465 |
| AD-26687 | UCUCCUUGGGACUCUUGUU | 5268 | AACAAGAGUCCCAAGGAGA | 5927 | 1468 |
| AD-26688 | UGGGACUCUUGUUCAGCUU | 5269 | AAGCUGAACAAGAGUCCCA | 5928 | 1474 |
| AD-26689 | CUUGUUCAGCUUCUGGGUU | 5270 | AACCCAGAAGCUGAACAAG | 5929 | 1481 |
| AD-26690 | UCAGCUUCUGGGUUCAGAU | 5271 | AUCUGAACCCAGAAGCUGA | 5930 | 1486 |
| AD-26691 | GCUUCUGGGUUCAGAUGAU | 5272 | AUCAUCUGAACCCAGAAGC | 5931 | 1489 |

TABLE 2-continued

RNAi Agents to Beta-Catenin: Unmodified Sequences

| DUPLEX | SENSE SEQUENCE | SENSE SEQ ID NO: | ANTI-SENSE SEQUENCE | Anti-sense SEQ ID NO: | POSITION |
|---|---|---|---|---|---|
| AD-26692 | CUUCUGGGUUCAGAUGAUA | 5273 | UAUCAUCUGAACCCAGAAG | 5932 | 1490 |
| AD-26693 | GGCCAGGAUGCCUUGGGUA | 5274 | UACCCAAGGCAUCCUGGCC | 5933 | 2441 |
| AD-26694 | UUCUGGGUUCAGAUGAUAU | 5275 | AUAUCAUCUGAACCCAGAA | 5934 | 1491 |
| AD-26695 | CUGGGUUCAGAUGAUAUAA | 5276 | UUAUAUCAUCUGAACCCAG | 5935 | 1493 |
| AD-26696 | UGGGUUCAGAUGAUAUAAA | 5277 | UUUAUAUCAUCUGAACCCA | 5936 | 1494 |
| AD-26697 | GUCACCUGUGCAGCUGGAA | 5278 | UUCCAGCUGCACAGGUGAC | 5937 | 1517 |
| AD-26698 | UCACCUGUGCAGCUGGAAU | 5279 | AUUCCAGCUGCACAGGUGA | 5938 | 1518 |
| AD-26699 | CACCUGUGCAGCUGGAAUU | 5280 | AAUUCCAGCUGCACAGGUG | 5939 | 1519 |
| AD-26700 | CUGUGCAGCUGGAAUUCUU | 5281 | AAGAAUUCCAGCUGCACAG | 5940 | 1522 |
| AD-26701 | UGUGCAGCUGGAAUUCUUU | 5282 | AAAGAAUUCCAGCUGCACA | 5941 | 1523 |
| AD-26702 | GCAGCUGGAAUUCUUUCUA | 5283 | UAGAAAGAAUUCCAGCUGC | 5942 | 1526 |
| AD-26703 | CAGCUGGAAUUCUUUCUAA | 5284 | UUAGAAAGAAUUCCAGCUG | 5943 | 1527 |
| AD-26704 | UUUCUAACCUCACUUGCAA | 5285 | UUGCAAGUGAGGUUAGAAA | 5944 | 1539 |
| AD-26705 | UUCUAACCUCACUUGCAAU | 5286 | AUUGCAAGUGAGGUUAGAA | 5945 | 1540 |
| AD-26706 | ACCUCACUUGCAAUAAUUA | 5287 | UAAUUAUUGCAAGUGAGGU | 5946 | 1545 |
| AD-26707 | CCUCACUUGCAAUAAUUAU | 5288 | AUAAUUAUUGCAAGUGAGG | 5947 | 1546 |
| AD-26708 | CUCACUUGCAAUAAUUAUA | 5289 | UAUAAUUAUUGCAAGUGAG | 5948 | 1547 |
| AD-26709 | GUCUGCCAAGUGGGUGGUA | 5290 | UACCACCCACUUGGCAGAC | 5949 | 1580 |
| AD-26710 | UCUGCCAAGUGGGUGGUAU | 5291 | AUACCACCCACUUGGCAGA | 5950 | 1581 |
| AD-26711 | GGGUGGUAUAGAGGCUCUU | 5292 | AAGAGCCUCUAUACCACCC | 5951 | 1591 |
| AD-26712 | AUAGAGGCUCUUGUGCGUA | 5293 | UACGCACAAGAGCCUCUAU | 5952 | 1598 |
| AD-26713 | UCUUGUGCGUACUGUCCUU | 5294 | AAGGACAGUACGCACAAGA | 5953 | 1606 |
| AD-26714 | CUGGUGACAGGGAAGACAU | 5295 | AUGUCUUCCCUGUCACCAG | 5954 | 1629 |
| AD-26715 | ACAUCACUGAGCCUGCCAU | 5296 | AUGGCAGGCUCAGUGAUGU | 5955 | 1644 |
| AD-26716 | GCCUGCCAUCUGUGCUCUU | 5297 | AAGAGCACAGAUGGCAGGC | 5956 | 1654 |
| AD-26717 | UCUGACCAGCCGACACCAA | 5298 | UUGGUGUCGGCUGGUCAGA | 5957 | 1678 |
| AD-26718 | GACCAGCCGACACCAAGAA | 5299 | UUCUUGGUGUCGGCUGGUC | 5958 | 1681 |
| AD-26719 | GACACCAAGAAGCAGAGAU | 5300 | AUCUCUGCUUCUUGGUGUC | 5959 | 1689 |
| AD-26720 | AGCAGAGAUGGCCCAGAAU | 5301 | AUUCUGGGCCAUCUCUGCU | 5960 | 1699 |
| AD-26721 | GAUGGCCCAGAAUGCAGUU | 5302 | AACUGCAUUCUGGGCCAUC | 5961 | 1705 |
| AD-26722 | CCAGAAUGCAGUUCGCCUU | 5303 | AAGGCGAACUGCAUUCUGG | 5962 | 1711 |
| AD-26723 | AUGCAGUUCGCCUUCACUA | 5304 | UAGUGAAGGCGAACUGCAU | 5963 | 1716 |
| AD-26724 | UGCAGUUCGCCUUCACUAU | 5305 | AUAGUGAAGGCGAACUGCA | 5964 | 1717 |
| AD-26725 | UCGCCUUCACUAUGGACUA | 5306 | UAGUCCAUAGUGAAGGCGA | 5965 | 1723 |
| AD-26726 | UCACUAUGGACUACCAGUU | 5307 | AACUGGUAGUCCAUAGUGA | 5966 | 1729 |
| AD-26727 | UGGACUACCAGUUGUGGUU | 5308 | AACCACAACUGGUAGUCCA | 5967 | 1735 |
| AD-26728 | GGACUACCAGUUGUGGUUA | 5309 | UAACCACAACUGGUAGUCC | 5968 | 1736 |

TABLE 2-continued

RNAi Agents to Beta-Catenin: Unmodified Sequences

| DUPLEX | SENSE SEQUENCE | SENSE SEQ ID NO: | ANTI-SENSE SEQUENCE | Anti-sense SEQ ID NO: | POSITION |
|---|---|---|---|---|---|
| AD-26729 | GACUACCAGUUGUGGUUAA | 5310 | UUAACCACAACUGGUAGUC | 5969 | 1737 |
| AD-26730 | CAGUUGUGGUUAAGCUCUU | 5311 | AAGAGCUUAACCACAACUG | 5970 | 1743 |
| AD-26731 | AGUUGUGGUUAAGCUCUUA | 5312 | UAAGAGCUUAACCACAACU | 5971 | 1744 |
| AD-26732 | AAGCUCUUACACCCACCAU | 5313 | AUGGUGGGUGUAAGAGCUU | 5972 | 1754 |
| AD-26733 | CAUCCCACUGGCCUCUGAU | 5314 | AUCAGAGGCCAGUGGGAUG | 5973 | 1770 |
| AD-26734 | AUCCCACUGGCCUCUGAUA | 5315 | UAUCAGAGGCCAGUGGGAU | 5974 | 1771 |
| AD-26735 | UCCCACUGGCCUCUGAUAA | 5316 | UUAUCAGAGGCCAGUGGGA | 5975 | 1772 |
| AD-26736 | UGGCCUCUGAUAAAGGCUA | 5317 | UAGCCUUUAUCAGAGGCCA | 5976 | 1778 |
| AD-26737 | UCUGAUAAAGGCUACUGUU | 5318 | AACAGUAGCCUUUAUCAGA | 5977 | 1783 |
| AD-26738 | AUAAAGGCUACUGUUGGAU | 5319 | AUCCAACAGUAGCCUUUAU | 5978 | 1787 |
| AD-26739 | GGCUACUGUUGGAUUGAUU | 5320 | AAUCAAUCCAACAGUAGCC | 5979 | 1792 |
| AD-26740 | UGUUGGAUUGAUUCGAAAU | 5321 | AUUUCGAAUCAAUCCAACA | 5980 | 1798 |
| AD-26741 | UGCCAUUCCACGACUAGUU | 5322 | AACUAGUCGUGGAAUGGCA | 5981 | 1861 |
| AD-26742 | UUCCACGACUAGUUCAGUU | 5323 | AACUGAACUAGUCGUGGAA | 5982 | 1866 |
| AD-26743 | ACGACUAGUUCAGUUGCUU | 5324 | AAGCAACUGAACUAGUCGU | 5983 | 1870 |
| AD-26744 | ACUAGUUCAGUUGCUUGUU | 5325 | AACAAGCAACUGAACUAGU | 5984 | 1873 |
| AD-26745 | GUUGCUUGUUCGUGCACAU | 5326 | AUGUGCACGAACAAGCAAC | 5985 | 1882 |
| AD-26746 | UGUUCGUGCACAUCAGGAU | 5327 | AUCCUGAUGUGCACGAACA | 5986 | 1888 |
| AD-26747 | GUUCGUGCACAUCAGGAUA | 5328 | UAUCCUGAUGUGCACGAAC | 5987 | 1889 |
| AD-26748 | GGUGGGACACAGCAGCAAU | 5329 | AUUGCUGCUGUGUCCCACC | 5988 | 1928 |
| AD-26749 | GUGGGACACAGCAGCAAUU | 5330 | AAUUGCUGCUGUGUCCCAC | 5989 | 1929 |
| AD-26750 | UGGGACACAGCAGCAAUUU | 5331 | AAAUUGCUGCUGUGUCCCA | 5990 | 1930 |
| AD-26751 | GGGGUCCGCAUGGAAGAAA | 5332 | UUUCUUCCAUGCGGACCCC | 5991 | 1955 |
| AD-26752 | GGGUCCGCAUGGAAGAAAU | 5333 | AUUUCUUCCAUGCGGACCC | 5992 | 1956 |
| AD-26753 | UCACAUCCUAGCUCGGGAU | 5334 | AUCCCGAGCUAGGAUGUGA | 5993 | 1999 |
| AD-26754 | CAUCCUAGCUCGGGAUGUU | 5335 | AACAUCCCGAGCUAGGAUG | 5994 | 2002 |
| AD-26755 | UAGCUCGGGAUGUUCACAA | 5336 | UUGUGAACAUCCCGAGCUA | 5995 | 2007 |
| AD-26756 | GGGAUGUUCACAACCGAAU | 5337 | AUUCGGUUGUGAACAUCCC | 5996 | 2013 |
| AD-26757 | GGAUGUUCACAACCGAAUU | 5338 | AAUUCGGUUGUGAACAUCC | 5997 | 2014 |
| AD-26758 | CAGAGGACUAAAUACCAUU | 5339 | AAUGGUAUUUAGUCCUCUG | 5998 | 2038 |
| AD-26759 | GGACUAAAUACCAUUCCAU | 5340 | AUGGAAUGGUAUUUAGUCC | 5999 | 2042 |
| AD-26760 | UAAAUACCAUUCCAUUGUU | 5341 | AACAAUGGAAUGGUAUUUA | 6000 | 2046 |
| AD-26761 | AAAUACCAUUCCAUUGUUU | 5342 | AAACAAUGGAAUGGUAUUU | 6001 | 2047 |
| AD-26762 | AUUGUUUGUGCAGCUGCUU | 5343 | AAGCAGCUGCACAAACAAU | 6002 | 2059 |
| AD-26763 | UUGUUUGUGCAGCUGCUUU | 5344 | AAAGCAGCUGCACAAACAA | 6003 | 2060 |
| AD-26764 | UGUUUGUGCAGCUGCUUUA | 5345 | UAAGCAGCUGCACAAACA | 6004 | 2061 |

TABLE 2-continued

RNAi Agents to Beta-Catenin: Unmodified Sequences

| DUPLEX | SENSE SEQUENCE | SENSE SEQ ID NO: | ANTI-SENSE SEQUENCE | Anti-sense SEQ ID NO: | POSITION |
|---|---|---|---|---|---|
| AD-26765 | GUUUGUGCAGCUGCUUUAU | 5346 | AUAAAGCAGCUGCACAAAC | 6005 | 2062 |
| AD-26766 | UUUGUGCAGCUGCUUUAUU | 5347 | AAUAAAGCAGCUGCACAAA | 6006 | 2063 |
| AD-26767 | AGCUGCUUUAUUCUCCCAU | 5348 | AUGGGAGAAUAAAGCAGCU | 6007 | 2070 |
| AD-26768 | GCUGCUUUAUUCUCCCAUU | 5349 | AAUGGGAGAAUAAAGCAGC | 6008 | 2071 |
| AD-26769 | UUUAUUCUCCCAUUGAAAA | 5350 | UUUUCAAUGGGAGAAUAAA | 6009 | 2076 |
| AD-26770 | AUUCUCCCAUUGAAAACAU | 5351 | AUGUUUUCAAUGGGAGAAU | 6010 | 2079 |
| AD-26771 | UCCCAUUGAAAACAUCCAA | 5352 | UUGGAUGUUUUCAAUGGGA | 6011 | 2083 |
| AD-26772 | UGCAGGGGUCCUCUGUGAA | 5353 | UUCACAGAGGACCCCUGCA | 6012 | 2110 |
| AD-26773 | ACUUGCUCAGGACAAGGAA | 5354 | UUCCUUGUCCUGAGCAAGU | 6013 | 2128 |
| AD-26774 | CAGCUCCUCUGACAGAGUU | 5355 | AACUCUGUCAGAGGAGCUG | 6014 | 2178 |
| AD-26775 | AGCUCCUCUGACAGAGUUA | 5356 | UAACUCUGUCAGAGGAGCU | 6015 | 2179 |
| AD-26776 | UCCUCUGACAGAGUUACUU | 5357 | AAGUAACUCUGUCAGAGGA | 6016 | 2182 |
| AD-26777 | ACAGAGUUACUUCACUCUA | 5358 | UAGAGUGAAGUAACUCUGU | 6017 | 2189 |
| AD-26778 | AGUUACUUCACUCUAGGAA | 5359 | UUCCUAGAGUGAAGUAACU | 6018 | 2193 |
| AD-26779 | GUUACUUCACUCUAGGAAU | 5360 | AUUCCUAGAGUGAAGUAAC | 6019 | 2194 |
| AD-26780 | ACUUCACUCUAGGAAUGAA | 5361 | UUCAUUCCUAGAGUGAAGU | 6020 | 2197 |
| AD-26781 | GCUGCUGUUUUGUUCCGAA | 5362 | UUCGGAACAAAACAGCAGC | 6021 | 2234 |
| AD-26782 | CUGCUGUUUUGUUCCGAAU | 5363 | AUUCGGAACAAAACAGCAG | 6022 | 2235 |
| AD-26783 | GUCUGAGGACAAGCCACAA | 5364 | UUGUGGCUUGUCCUCAGAC | 6023 | 2254 |
| AD-26784 | UGAGGACAAGCCACAAGAU | 5365 | AUCUUGUGGCUUGUCCUCA | 6024 | 2257 |
| AD-26785 | ACAAGCCACAAGAUUACAA | 5366 | UUGUAAUCUUGUGGCUUGU | 6025 | 2262 |
| AD-26786 | AGCCACAAGAUUACAAGAA | 5367 | UUCUUGUAAUCUUGUGGCU | 6026 | 2265 |
| AD-26787 | AGAUUACAAGAAACGGCUU | 5368 | AAGCCGUUUCUUGUAAUCU | 6027 | 2272 |
| AD-26788 | CAAGAAACGGCUUUCAGUU | 5369 | AACUGAAAGCCGUUUCUUG | 6028 | 2278 |
| AD-26789 | AGCUGACCAGCUCUCUCUU | 5370 | AAGAGAGAGCUGGUCAGCU | 6029 | 2298 |
| AD-26790 | ACCAGCUCUCUCUUCAGAA | 5371 | UUCUGAAGAGAGCUGGU | 6030 | 2303 |
| AD-26791 | UAUUGGUGCCCAGGGAGAA | 5372 | UUCUCCCUGGGCACCAAUA | 6031 | 2365 |
| AD-26792 | CAGGGAGAACCCCUUGGAU | 5373 | AUCCAAGGGGUUCUCCCUG | 6032 | 2375 |
| AD-26793 | AGGGAGAACCCCUUGGAUA | 5374 | UAUCCAAGGGGUUCUCCCU | 6033 | 2376 |
| AD-26794 | CCUUGGAUAUCGCCAGGAU | 5375 | AUCCUGGCGAUAUCCAAGG | 6034 | 2386 |
| AD-26795 | UAUCGCCAGGAUGAUCCUA | 5376 | UAGGAUCAUCCUGGCGAUA | 6035 | 2393 |
| AD-26796 | GCCAGGAUGAUCCUAGCUA | 5377 | UAGCUAGGAUCAUCCUGGC | 6036 | 2397 |
| AD-26797 | CCAGGAUGAUCCUAGCUAU | 5378 | AUAGCUAGGAUCAUCCUGG | 6037 | 2398 |
| AD-26798 | GAUGAUCCUAGCUAUCGUU | 5379 | AACGAUAGCUAGGAUCAUC | 6038 | 2402 |
| AD-26799 | AUCCUAGCUAUCGUUCUUU | 5380 | AAAGAACGAUAGCUAGGAU | 6039 | 2406 |
| AD-26800 | UCCUAGCUAUCGUUCUUUU | 5381 | AAAAGAACGAUAGCUAGGA | 6040 | 2407 |
| AD-26801 | UCUUUUCACUCUGGUGGAU | 5382 | AUCCACCAGAGUGAAAAGA | 6041 | 2420 |

TABLE 2-continued

RNAi Agents to Beta-Catenin: Unmodified Sequences

| DUPLEX | SENSE SEQUENCE | SENSE SEQ ID NO: | ANTI-SENSE SEQUENCE | Anti-sense SEQ ID NO: | POSITION |
|---|---|---|---|---|---|
| AD-26802 | CUUUUCACUCUGGUGGAUA | 5383 | UAUCCACCAGAGUGAAAAG | 6042 | 2421 |
| AD-26803 | UUUUCACUCUGGUGGAUAU | 5384 | AUAUCCACCAGAGUGAAAA | 6043 | 2422 |
| AD-26804 | UGGUGGAUAUGGCCAGGAU | 5385 | AUCCUGGCCAUAUCCACCA | 6044 | 2431 |
| AD-26805 | GAUAUGGCCAGGAUGCCUU | 5386 | AAGGCAUCCUGGCCAUAUC | 6045 | 2436 |
| AD-26806 | CCUUGGGUAUGGACCCCAU | 5387 | AUGGGGUCCAUACCCAAGG | 6046 | 2451 |
| AD-26807 | UGGGUAUGGACCCCAUGAU | 5388 | AUCAUGGGGUCCAUACCCA | 6047 | 2454 |
| AD-26808 | UUGUAAACUUGAUUAACUA | 5389 | UAGUUAAUCAAGUUUACAA | 6048 | 675 |
| AD-26809 | UGUAAACUUGAUUAACUAU | 5390 | AUAGUUAAUCAAGUUUACA | 6049 | 676 |
| AD-26810 | AAACUUGAUUAACUAUCAA | 5391 | UUGAUAGUUAAUCAAGUUU | 6050 | 679 |
| AD-26811 | UAUGGACCCCAUGAUGGAA | 5392 | UUCCAUCAUGGGGUCCAUA | 6051 | 2458 |
| AD-26812 | GGACCCCAUGAUGGAACAU | 5393 | AUGUUCCAUCAUGGGGUCC | 6052 | 2461 |
| AD-26813 | CCAUGAUGGAACAUGAGAU | 5394 | AUCUCAUGUUCCAUCAUGG | 6053 | 2466 |
| AD-26814 | ACCACCCUGGUGCUGACUA | 5395 | UAGUCAGCACCAGGGUGGU | 6054 | 2493 |
| AD-26815 | CCACCCUGGUGCUGACUAU | 5396 | AUAGUCAGCACCAGGGUGG | 6055 | 2494 |
| AD-26816 | UGCUGACUAUCCAGUUGAU | 5397 | AUCAACUGGAUAGUCAGCA | 6056 | 2503 |
| AD-26817 | AGUUGAUGGGCUGCCAGAU | 5398 | AUCUGGCAGCCCAUCAACU | 6057 | 2515 |
| AD-26818 | UGCCCAGGACCUCAUGGAU | 5399 | AUCCAUGAGGUCCUGGGCA | 6058 | 2542 |
| AD-26819 | GCAAUCAGCUGGCCUGGUU | 5400 | AACCAGGCCAGCUGAUUGC | 6059 | 2580 |
| AD-26820 | CAAUCAGCUGGCCUGGUUU | 5401 | AAACCAGGCCAGCUGAUUG | 6060 | 2581 |
| AD-26821 | GGUUUGAUACUGACCUGUA | 5402 | UACAGGUCAGUAUCAAACC | 6061 | 2595 |
| AD-26822 | AUACUGACCUGUAAAUCAU | 5403 | AUGAUUUACAGGUCAGUAU | 6062 | 2601 |
| AD-26823 | UGACCUGUAAAUCAUCCUU | 5404 | AAGGAUGAUUUACAGGUCA | 6063 | 2605 |
| AD-26824 | GACCUGUAAAUCAUCCUUU | 5405 | AAAGGAUGAUUUACAGGUC | 6064 | 2606 |
| AD-26825 | ACCUGUAAAUCAUCCUUUA | 5406 | UAAAGGAUGAUUUACAGGU | 6065 | 2607 |
| AD-26826 | AAUACAAAUGAUGUAGAAA | 5407 | UUUCUACAUCAUUUGUAUU | 6066 | 878 |
| AD-26900 | UUUUAAGAAUAUCUGUAAU | 5408 | AUUACAGAUAUUCUUAAAA | 6067 | 2745 |
| AD-26901 | UACAGCAAUUUCUAAUUUU | 5409 | AAAAUUAGAAAUUGCUGUA | 6068 | 2872 |
| AD-26902 | CACUAAUUCAUAAUCACUC | 5410 | GAGUGAUUAUGAAUUAGUG | 6069 | 2915 |
| AD-26903 | ACUAAUUCAUAAUCACUCU | 5411 | AGAGUGAUUAUGAAUUAGU | 6070 | 2916 |
| AD-26904 | UAAUUCAUAAUCACUCUAA | 5412 | UUAGAGUGAUUAUGAAUUA | 6071 | 2918 |
| AD-26905 | AAUUCAUAAUCACUCUAAU | 5413 | AUUAGAGUGAUUAUGAAUU | 6072 | 2919 |
| AD-26906 | AAUUGUAAUCUGAAUAAAG | 5414 | CUUUAUUCAGAUUACAAUU | 6073 | 2939 |
| AD-26907 | UUUGUAUAAAUAGACAAA | 5415 | UUUGUCUAUUUUAUACAAA | 6074 | 2978 |
| AD-26908 | UUGUAUAAAAUAGACAAAU | 5416 | AUUUGUCUAUUUUAUACAA | 6075 | 2979 |
| AD-26909 | UGUAUAAAAUAGACAAAUA | 5417 | UAUUUGUCUAUUUUAUACA | 6076 | 2980 |
| AD-26910 | GUAUAAAAUAGACAAAUAG | 5418 | CUAUUUGUCUAUUUUAUAC | 6077 | 2981 |

TABLE 2-continued

RNAi Agents to Beta-Catenin: Unmodified Sequences

| DUPLEX | SENSE SEQUENCE | SENSE SEQ ID NO: | ANTI-SENSE SEQUENCE | Anti-sense SEQ ID NO: | POSITION |
|---|---|---|---|---|---|
| AD-26911 | AUAAAAUAGACAAAUAGAA | 5419 | UUCUAUUUGUCUAUUUUAU | 6078 | 2983 |
| AD-26912 | UAAAAUAGACAAAUAGAAA | 5420 | UUUCUAUUUGUCUAUUUUA | 6079 | 2984 |
| AD-26913 | AAAUAGACAAAUAGAAAAU | 5421 | AUUUUCUAUUUGUCUAUUU | 6080 | 2986 |
| AD-26914 | UGGGAUAUGUAUGGGUAGG | 5422 | CCUACCCAUACAUAUCCCA | 6081 | 3081 |
| AD-26915 | GGGAUAUGUAUGGGUAGGG | 5423 | CCCUACCCAUACAUAUCCC | 6082 | 3082 |
| AD-26916 | CUAAUUCAUAAUCACUCUA | 5424 | UAGAGUGAUUAUGAAUUAG | 6083 | 2917 |
| AD-26917 | AAAUAGAAAAUGGUCCAAU | 5425 | AUUGGACCAUUUUCUAUUU | 6084 | 2994 |
| AD-26918 | AAUAGAAAAUGGUCCAAUU | 5426 | AAUUGGACCAUUUUCUAUU | 6085 | 2995 |
| AD-26919 | UUUGGACAGUUUACCAGUU | 5427 | AACUGGUAAACUGUCCAAA | 6086 | 3134 |
| AD-26920 | AUUCUUUCUAACCUCACUU | 5428 | AAGUGAGGUUAGAAAGAAU | 6087 | 1535 |
| AD-26921 | UGGAUUGAUUCGAAAUCUU | 5429 | AAGAUUUCGAAUCAAUCCA | 6088 | 1801 |
| SET1_1245 | GACCCCAAGCUUUAGUAAA | 6090 | UUUACUAAAGCUUGGGGUC | 6111 | 1227 |
| SET1_1249 | CCAAGCUUUAGUAAAUAUA | 6091 | UAUAUUUACUAAAGCUUGG | 6112 | 1231 |
| SET1_1250 | CAAGCUUUAGUAAAUAUAA | 6092 | UUAUAUUUACUAAAGCUUG | 6113 | 1232 |
| SET1_1450 | UUCAGAUGCUGCAACUAAA | 6093 | UUUAGUUGCAGCAUCUGAA | 6114 | 1432 |
| SET1_1545 | CAGCUGGAAUUCUUUCUAA | 6094 | UUAGAAAGAAUUCCAGCUG | 6115 | 1527 |
| SET1_1755 | GACUACCAGUUGUGGUUAA | 6095 | UUAACCACAACUGGUAGUC | 6116 | 1737 |
| SET1_1814 | ACUGUUGGAUUGAUUCGAA | 6096 | UUCGAAUCAAUCCAACAGU | 6117 | 1796 |
| SET1_1816 | UGUUGGAUUGAUUCGAAAU | 6097 | AUUUCGAAUCAAUCCAACA | 6118 | 1798 |
| SET1_1974 | GGGUCCGCAUGGAAGAAAU | 6098 | AUUUCUUCCAUGCGGACCC | 6119 | 1956 |
| SET1_2202 | CUCUGACAGAGUUACUUCA | 6099 | UGAAGUAACUCUGUCAGAG | 6120 | 2184 |
| SET1_2425 | UCCUAGCUAUCGUUCUUUU | 6100 | AAAAGAACGAUAGCUAGGA | 6121 | 2407 |
| SET1_254 | CCAUACAACUGUUUUGAAA | 6101 | UUUCAAAACAGUUGUAUGG | 6122 | 236 |
| SET1_3146 | AAGUGAAGAAUGCACAAGA | 6102 | UCUUGUGCAUUCUUCACUU | 6123 | 3128 |
| SET1_3169 | AUCACAAGAUGGAAUUUAU | 6103 | AUAAAUUCCAUCUUGUGAU | 6124 | 3151 |
| SET1_3196 | AGCCUUGCUUGUUAAAUUU | 6104 | AAAUUUAACAAGCAAGGCU | 6125 | 3178 |
| SET1_3477 | AAUAGAAAAUGGUCCAAUU | 6105 | AAUUGGACCAUUUUCUAUU | 6126 | 3459 |
| SET1_703 | GAUUAACUAUCAAGAUGAU | 6106 | AUCAUCUUGAUAGUUAAUC | 6127 | 685 |
| SET1_709 | CUAUCAAGAUGAUGCAGAA | 6107 | UUCUGCAUCAUCUUGAUAG | 6128 | 691 |
| SET1_865 | GAUGGUGUCUGCUAUUGUA | 6108 | UACAAUAGCAGACACCAUC | 6129 | 847 |
| SET1_889 | CAUGCAGAAUACAAAUGAU | 6109 | AUCAUUUGUAUUCUGCAUG | 6130 | 871 |
| SET1_895 | GAAUACAAAUGAUGUAGAA | 6110 | UUCUACAUCAUUUGUAUUC | 6131 | 877 |

Modified sequences are listed in Table 3; the specific modifications are disclosed herein. The sequences in Table 2 correspond to portions of the wild-type Beta-Catenin gene without modifications or dTdT extensions. The positions are also provided. In the sequences in these tables, lower-case letters (e.g., c, u) indicate modified nucleotides while upper case letters (e.g., C, U, A, G) indicate unmodified nucleotides. In Table 3, modified versions of the sequences are shown. However, the present disclosure encompasses unmodified versions of these sequences and other versions which comprise additional or alternative modifications. Thus, for example, AD-18892 can optionally have the unmodified sequence uGGuGcuGAcuAuccAGuu (SEQ ID NO: 429) in the sense strand and AACUGGAuAGUcAGcACcA (SEQ ID NO: 430) in the anti-sense strand. The present disclosure also encompasses alternative modified versions of the duplex comprising uGGuGcuGAcuAuccA-Guu (SEQ ID NO: 429) in the sense strand and AACUG-GAuAGUcAGcACcA (SEQ ID NO: 430) in the anti-sense strand.

In the sequences in Tables 1, 2 and 3, the modified and unmodified sequences can optionally comprise the sequence "dTsdT" or "UU" at the 3' end. In the sequences disclosed herein, the TT and UU dinucleotides were not in the inverted/reverse orientation and "UU" is 2'-OMe-U 2'-OMe-U.

Thus, for example, AD-18892 can optionally have the modified sequence uGGuGcuGAcuAuccAGuudTdT (SEQ ID NO: 6132) or uGGuGcuGAcuAuccAGuudTsdT (SEQ ID NO: 6133) in the sense strand; and AACUGGAuAGUcA-GcACcAdTdT (SEQ ID NO: 6134) or AACUGGAuAGU-cAGcACcAdTsdT (SEQ ID NO: 6135) in the anti-sense strand. As noted in Table 3, below, dT is 2'-deoxy-thymidine-5'-phosphate and sdT is 2'-deoxy Thymidine 5'-phosphorothioate.

In several sequences in this Table, the nickname "Set1_#" can be preceded by the prefix "hsCTNNB1_". Thus "Set1_254" is also designated "hsCTNNB1_Set1_254". The number is derived from one type of calculation of the position on the gene. Thus, the designations Set1_1245, Set1_1249, Set1_1250, Set1_1450, Set1_1545, Set1_1755, Set1_1814, Set1_1816, Set1_1974, Set1_2202, Set1_2425, Set1_254, Set1_3146, Set1_3169, Set1_3196, Set1_3477, Set1_703, Set1_709, Set1_865, Set1_889, Set1_895 indicate duplexes (or modified variants thereof) which correspond to one type of calculation of the positions 1245, 1249, 1250, 1450, 1545, 1755, 1814, 1816, 1974, 2202, 2425, 254, 3146, 3169, 3196, 3477, 703, 709, 865, 889, 895, respectively. However, these positions were calculated using different parameters than other sequences in this Table, resulting in a 18 nt shift. Thus, "Set1_254" pertains to a sequence which corresponds to position 236. Also note that the underscore (_) is sometimes replaced by a space ( ); thus, for example, "Set1_3169" is the same as "Set1 3169"; and "hsCTNNB1_Set2_254_A48_S26" is the same as "hsCTNNB1 Set2 254 A48 S26".

In addition, additional suffixes can be appended to the nickname to designate different variants which have the same sequence (e.g., the same sequence of nucleotides), but different modifications. Thus, assorted variants of duplexes within "hsCTNNB1_Set1_1245" include, inter alia: hsCTNNB1_Set1_254_A22_S26;
hsCTNNB1_Set1_254_A25_S27;
hsCTNNB1_Set1_254_A_LO_V1_S26;
hsCTNNB1_Set1_254_A_LO_V2_S_Lo_V1;
hsCTNNB1_Set2_254_A_LO_V3_S_Lo_V2;
hsCTNNB1_Set2_254_A_LO_V4_S_LO_V1;
hsCTNNB1_Set2_254_A_LO_V5_S_LO_V1; and
hsCTNNB1_Set2_254_A48_S26.

TABLE 3

Beta-Catenin RNAi agents: Example Modified Sequences

| Duplex | Sense Sequence | Sense SEQ ID NO: | Anti-sense Sequence | Anti-sense SEQ ID NO: | Position |
| --- | --- | --- | --- | --- | --- |
| AD-18892 | uGGuGcuGAcuAuccAGuu | 1 | AACUGGAuAGUcAGcACcA | 6497 | 2500 |
| AD-18893 | ccAucuGuGcucuucGucA | 2 | UGACGAAGAGcAcAGAUGG | 661 | 1659 |
| AD-18894 | AuAAGcAGGuGGAucuAuu | 3 | AAuAGAUCcACCUGCUuAU | 662 | 3038 |
| AD-18895 | AuccAAAGAGuAGcuGcAG | 4 | CUGcAGCuACUCUUUGGAU | 663 | 2096 |
| AD-18896 | GAcAAuGGcuAcucAAGcu | 5 | AGCUUGAGuAGCcAUUGUC | 664 | 265 |
| AD-18897 | cuGuuGGAuuGAuucGAAA | 6 | UUUCGAAUcAAUCcAAcAG | 665 | 1797 |
| AD-18898 | GcuGGccuGuuuGAuAcu | 7 | AGuAUcAAACcAGGCcAGC | 666 | 2587 |
| AD-18899 | ucuAAccucAcuuGcAAuA | 8 | uAUUGcAAGUGAGGUuAGA | 667 | 1541 |
| AD-18900 | GAuAucGccAGGAuGAucc | 9 | GGAUcAUCCUGGCGAuAUC | 668 | 2391 |
| AD-18901 | uGGccAucuuuAAGucuGG | 10 | CcAGACUuAAAGAUGGCcA | 669 | 954 |
| AD-18902 | uGuAGAAcAcuAAuucAuA | 11 | uAUGAAUuAGUGUUCuAcA | 670 | 2908 |
| AD-18903 | AucAGuAAGAGGuGuuAuu | 12 | AAuAAcACCUCUuACUGAU | 671 | 3104 |
| AD-18904 | GuGcucuucGucAucuGAc | 13 | GUcAGAUGACGAAGAGcAC | 672 | 1665 |
| AD-18905 | uGGuuuGAuAcuGAccuGu | 14 | AcAGGUcAGuAUcAAAccA | 673 | 2594 |
| AD-18906 | ccAGuuGccuuuuAucccA | 15 | UGGGAuAAAAGGcAACUGG | 674 | 3147 |
| AD-18907 | ccuGGuuuGAuAcuGAccu | 16 | AGGUcAGuAUcAAAccAGG | 675 | 2592 |
| AD-18908 | GAcuAuccAGuuGAuGGGc | 17 | GCCcAUcAACUGGAuAGUC | 676 | 2507 |
| AD-18909 | AGccAAuGGcuuGGAAuGA | 18 | UcAUUCcAAGCcAUUGGCU | 677 | 2325 |
| AD-18910 | GccAAuGGcuuGGAAuGAG | 19 | CUcAUUCcAAGCcAUUGGC | 678 | 2326 |
| AD-18911 | AGAuGAGGGcAuGcAGAuc | 20 | GAUCUGcAUGCCCUcAUCU | 679 | 577 |
| AD-18912 | GGuccucuGuGAAcuuGcu | 21 | AGcAAGUUcAcAGAGGACC | 680 | 2116 |
| AD-18913 | AAcccuAGccuuGcuuGuu | 22 | AAcAAGcAAGGCuAGGGUU | 681 | 2708 |
| AD-18914 | GAAcAcuAAuucAuAAucA | 23 | UGAUuAUGAAUuAGUGUUC | 682 | 2912 |
| AD-18915 | AucAAAcccuAGccuuGcu | 24 | AGcAAGGCuAGGGUUUGAU | 683 | 2704 |
| AD-18916 | AccAGuuGccuuuuAuccc | 25 | GGGAuAAAAGGcAACUGGU | 684 | 3146 |
| AD-18917 | cuAAccucAcuuGcAAuAA | 26 | UuAUUGcAAGUGAGGUuAG | 685 | 1542 |
| AD-18918 | AucccAcuAAuGuccAGcG | 27 | CGCUGGAcAUuAGUGGGAU | 686 | 621 |
| AD-18919 | cuGAcuAuccAGuuGAuGG | 28 | CcAUcAACUGGAuAGUcAG | 687 | 2505 |
| AD-18920 | GGccuGGuuuGAuAcuGAc | 29 | GUcAGuAUcAAACcAGGCC | 688 | 2590 |
| AD-18921 | GGuAAAucAGuAAGAGGuG | 30 | cACCUCUuACUGAUUuACC | 689 | 3099 |
| AD-18922 | GccuGGuuuGAuAcuGAcc | 31 | GGUcAGuAUcAAACcAGGC | 690 | 2591 |
| AD-18923 | cAGGGGuccucuGuGAAcu | 32 | AGUUcAcAGAGGACCCCUG | 691 | 2112 |
| AD-18925 | cuGGAAuccAucuGGuGc | 33 | GcACcAGAAUGGAUUCcAG | 692 | 366 |
| AD-18926 | uGAGuGGGuGGccAccAc | 34 | GUGGUGGCcACCcAUCUcA | 693 | 2479 |
| AD-18927 | GAuGAuAuAAAuGuGGucA | 35 | UGACcAcAUUuAuAUcAUC | 694 | 1502 |
| AD-18928 | uGcuuuAuucucccAuuGA | 36 | UcAAUGGGAGAAuAAAGcA | 695 | 2073 |
| AD-18929 | uuAucAAAcccuAGccuuG | 37 | cAAGGCuAGGGUUUGAuAA | 696 | 2702 |

TABLE 3-continued

Beta-Catenin RNAi agents: Example Modified Sequences

| | | | | | |
|---|---|---|---|---|---|
| AD-18930 | ccAcuGGccucuGAuAAAG | 38 | CUUuAUcAGAGGCcAGUGG | 697 | 1774 |
| AD-18931 | AAcuuGccAcAcGuGcAAu | 39 | AUUGcACGUGUGGcAAGUU | 698 | 708 |
| AD-18932 | GcucuucGucAucuGAccA | 40 | UGGUcAGAUGACGAAGAGC | 699 | 1667 |
| AD-18933 | GuAAcAAuAcAAAuGGAuu | 41 | AAUCcAUUUGuAUUGUuAC | 700 | 2629 |
| AD-18934 | GGGGuccucuGuGAAcuuG | 42 | cAAGUUcAcAGAGGACCCC | 701 | 2114 |
| AD-18935 | cAAAcccuAGccuuGcuuG | 43 | cAAGcAAGGCuAGGGUUUG | 702 | 2706 |
| AD-18936 | GAGuAAuGGuGuAGAAcAc | 44 | GUGUUCuAcACcAUuACUC | 703 | 2899 |
| AD-18937 | GGAAGAcAucAcuGAGccu | 45 | AGGCUcAGUGAUGUCUUCC | 704 | 1639 |
| AD-18938 | GGGAAGAcAucAcuGAGcc | 46 | GGCUcAGUGAUGUCUUCCC | 705 | 1638 |
| AD-18939 | GGuGuAGAAcAcuAAuucA | 47 | UGAAUuAGUGUUCuAcACC | 706 | 2906 |
| AD-18940 | uAccAGuuGccuuuuAucc | 48 | GGAuAAAAGGcAACUGGuA | 707 | 3145 |
| AD-18941 | GGAuAucGccAGGAuGAuc | 49 | GAUcAUCCUGGCGAuAUCC | 708 | 2390 |
| AD-18942 | AAAcccuAGccuuGcuuGu | 50 | AcAAGcAAGGCuAGGGUUU | 709 | 2707 |
| AD-18943 | cucuucGucAucuGAccAG | 51 | CUGGUcAGAUGACGAAGAG | 710 | 1668 |
| AD-18944 | uGAcuAuccAGuuGAuGGG | 52 | CCcAUcAACUGGAuAGUcA | 711 | 2506 |
| AD-18945 | AcAAGcAGAGuGcuGAAGG | 53 | CCUUcAGcACUCUGCUUGU | 712 | 1286 |
| AD-18946 | cAucuGuGcucuucGucAu | 54 | AUGACGAAGcAcAGAUG | 713 | 1660 |
| AD-18947 | cAAuGGcuuGGAAuGAGAc | 55 | GUCUcAUUCcAAGCcAUUG | 714 | 2328 |
| AD-18948 | AcuGGccucuGAuAAAGGc | 56 | GCCUUuAUcAGAGGCcAGU | 715 | 1776 |
| AD-18949 | ucAucccAcuAAuGccAG | 57 | CUGGAcAUuAGUGGGAUGA | 716 | 619 |
| AD-18950 | AAAAGGAAGcuuccAGAcA | 58 | UGUCUGGAAGCUUCCUUUU | 717 | 807 |
| AD-18951 | cGuucuuuucAcucuGGuG | 59 | cACcAGAGUGAAAAGAACG | 718 | 2417 |
| AD-18952 | AAAGuuGuuGuAAccuGcu | 60 | AGcAGGUuAcAAcAACUUU | 719 | 3165 |
| AD-18953 | AcAAuGGcuAcucAAGcuu | 61 | cAGCUUGAGuAGCcAUUGU | 720 | 266 |
| AD-18954 | cucAucccAcuAAuGccA | 62 | UGGAcAUuAGUGGGAUGAG | 721 | 618 |
| AD-18955 | AGGGGuccucuGuGAAcuu | 63 | AAGUUcAcAGAGGACCCCU | 722 | 2113 |
| AD-18956 | AAGcAGGuGGAucuAuuuc | 64 | GAAAuAGAUCcACCUGCUU | 723 | 3040 |
| AD-18957 | AAGuuGuuGuAAccuGcuG | 65 | cAGcAGGUuAcAAcAACUU | 724 | 3166 |
| AD-18958 | AGcAGGuGGAucuAuuucA | 66 | UGAAAuAGAUCcACCUGCU | 725 | 3041 |
| AD-18959 | AGGGcAuGcAGAucccAuc | 67 | GAUGGGAUCUGcAUGCCCU | 726 | 582 |
| AD-18960 | AAAuGGuucAGAAuuAAAc | 68 | GUUuAAUUCUGAACcAUUU | 727 | 3220 |
| AD-18961 | uGAAcuuGcucAGGAcAAG | 69 | CUUGUCCUGAGcAAGUUcA | 728 | 2125 |
| AD-18962 | AAGAGuAGcuGcAGGGGuc | 70 | GACCCCUGcAGCuACUCUU | 729 | 2101 |
| AD-18963 | cccAcuGGccucuGAuAAA | 71 | UUuAUcAGAGGCcAGUGGG | 730 | 1773 |
| AD-18964 | cuGGccuGGuuuGAuAcuG | 72 | cAGuAUcAAAccAGGCcAG | 731 | 2588 |
| AD-18965 | uuGAuAcuGAccuGuAAAu | 73 | AUUuAcAGGUcAGuAUcAA | 732 | 2598 |
| AD-18966 | GuGuAGAAcAcuAAuucAu | 74 | AUGAAUuAGUGUUCuAcAC | 733 | 2907 |
| AD-18967 | AcuAuccAGuuGAuGGGcu | 75 | AGCCcAUcAACUGGAuAGU | 734 | 2508 |
| AD-18968 | AAAucAGuAAGAGGuGuuA | 76 | uAAcACCUCUuACUGAUUU | 735 | 3102 |
| AD-18969 | GcAGGuGGAucuAuuucAu | 77 | AUGAAAuAGAUCcACCUGC | 736 | 3042 |
| AD-18970 | cuGGuGcuGAcuAuccAGu | 78 | ACUGGAuAGUcAGcAccAG | 737 | 2499 |
| AD-18971 | GuGAAcuuGcucAGGAcAA | 79 | UUGUCCUGAGcAAGUUcAC | 738 | 2124 |
| AD-18972 | ucAGuAAGAGGuGuuAuuu | 80 | AAAuAAcACCUCUuACUGA | 739 | 3105 |
| AD-18973 | ccucuGuGAAcuuGcucAG | 81 | CUGAGcAAGUUcAcAGAGG | 740 | 2119 |
| AD-18974 | uuGGcuGAAccAucAcAGA | 82 | UCUGUGAUGGUUcAGCcAA | 741 | 641 |
| AD-18975 | ucAGcuGGccuGGuuuGAu | 83 | AUcAAACcAGGCcAGCUGA | 742 | 2584 |
| AD-18976 | GuAGcuGcAGGGGuccucu | 84 | AGAGGACCCCUGcAGCuAC | 743 | 2105 |
| AD-18977 | AGGAGcuAAAAuGGcAGuG | 85 | cACUGCcAUUUuAGCUCCU | 744 | 1069 |
| AD-18978 | AuGGcuuGGAAuGAGAcuG | 86 | cAGUCUcAUUCcAAGCcAU | 745 | 2330 |
| AD-18979 | uuGGAuAucGccAGGAuGA | 87 | UcAUCCUGGCGAuAUCcAA | 746 | 2388 |
| AD-18980 | GGuucAGAAuuAAAcuuuu | 88 | AAAAGUUuAAUUCUGAACC | 747 | 3224 |
| AD-18981 | GGGuAAucAGuAAGAGGu | 89 | ACCUCUuACUGAUUuACCC | 748 | 3098 |
| AD-18982 | AuAccAuuccAuuGuuuGu | 90 | AcAAAcAAUGGAAUGGuAU | 749 | 2049 |
| AD-18983 | AcuGuuGGAuuGAuucGAA | 91 | UUCGAAUcAAUCcAAcAGU | 750 | 1796 |
| AD-18984 | AAcuuGcucAGGAcAAGGA | 92 | UCCUUGUCCUGAGcAAGUU | 751 | 2127 |
| AD-18985 | AuGcuuAAAAuAAGcAGGu | 93 | ACCUGCUuAUUUuAAGcAU | 752 | 3029 |
| AD-18986 | GuuuGAuAcuGAccuGuAA | 94 | UuAcAGGUcAGuAUcAAAC | 753 | 2596 |
| AD-18987 | AAuGGuucAGAAuuAAAcu | 95 | AGUUuAAUUCUGAACcAUU | 754 | 3221 |
| AD-18988 | uAucccAAAGuuGuuGuAA | 96 | UuAcAAcAACUUUGGGAuA | 755 | 3159 |
| AD-18989 | AucAGcuGGccuGGuuuGA | 97 | UcAAACcAGGCcAGCUGAU | 756 | 2583 |
| AD-18990 | ccuGccAucuGuGcucuuc | 98 | GAAGAGcAcAGAUGGcAGG | 757 | 1655 |
| AD-18991 | GcAGAuAcAAAuGAuGuA | 99 | uAcAUcAUUUGuAUUCUGC | 758 | 874 |
| AD-18992 | uAuGcuuAAAAuAAGcAGG | 100 | CCUGCUuAUUUuAAGcAuA | 759 | 3028 |
| AD-18993 | AAuAAGcAGGuGGAucuAu | 101 | AuAGAUCcACCUGCUuAUU | 760 | 3037 |
| AD-18994 | uGAuAAAAuGuGGucAcc | 102 | GGUGACcAcAUUuAuAUcA | 761 | 1504 |
| AD-18995 | GuAGGGuAAAucAGuAAGA | 103 | UCUuACUGAUuuACCCuAC | 762 | 3095 |
| AD-18996 | uAucAAAcccuAGccuuGc | 104 | GcAAGGCuAGGGUUUGAuA | 763 | 2703 |
| AD-18997 | ccuuuuAucccAAAGuuGu | 105 | AcAACUUUGGGAuAAAAGG | 764 | 3154 |
| AD-18998 | GGuAGGGuAAAucAGuAAG | 106 | CUuACUGAUUuACCCuACC | 765 | 3094 |
| AD-18999 | uGAuAcuGAccuGuAAAuc | 107 | GAUUuAcAGGUcAGuAUcA | 766 | 2599 |
| AD-19000 | GGcuGAAccAucAcAGAuG | 108 | cAUCUGUGAUGGUUcAGCC | 767 | 643 |
| AD-19001 | uGGAuAucGccAGGAuGAu | 109 | AUcAUCCUGGCGAuAUCcA | 768 | 2389 |
| AD-19002 | ucuucGucAucuGAccAGc | 110 | GCUGGUcAGAUGACGAAGA | 769 | 1669 |
| AD-19003 | uAGcuGcAGGGGuccucuG | 111 | cAGAGGACCCCUGcAGCuA | 770 | 2106 |
| AD-19004 | uGuuGuAAccuGcuGuGAu | 112 | AUcAcAGcAGGUuAcAAcA | 771 | 3170 |
| AD-19005 | AAucAGuAAGAGGuGuuAu | 113 | AuAAcACCUCUuACUGAUU | 772 | 3103 |
| AD-19006 | uGGcuGAAccAucAcAGAu | 114 | AUCUGUGAUGGUUcAGCcA | 773 | 642 |
| AD-19007 | GAAuuAAAcuuuuAAuucA | 115 | UGAAUuAAAAGUUuAAUUC | 774 | 3230 |

TABLE 3-continued

Beta-Catenin RNAi agents: Example Modified Sequences

| | | | | | | |
|---|---|---|---|---|---|---|
| AD-19008 | AuGGuucAGAAuuAAAcuu | 116 | AAGUUuAAUUCUGAACcAU | 775 | 3222 |
| AD-19009 | uGGuGuAGAAcAcuAAuuc | 117 | GAAUuAGUGUUCuAcACcA | 776 | 2905 |
| AD-19010 | AuGuGuAGAAcAcuAAuu | 118 | AAUuAGUGUUCuAcACcAU | 777 | 2904 |
| AD-19011 | AuGAGGGcAuGcAGAuccc | 119 | GGGAUCUGcAUGCCCUcAU | 778 | 579 |
| AD-19012 | GuuGuAAccuGcuGAuA | 120 | uAUcAcAGcAGGUuAcAAC | 779 | 3171 |
| AD-19042 | GcuGAcuAuccAGuuGAuG | 121 | cAUcAACUGGAuAGUcAGC | 780 | 2504 |
| AD-19043 | uAAGcAGGuGGAucuAuuu | 122 | AAAAuAGAUCcACCUGCUuA | 781 | 3039 |
| AD-19044 | uAAAAuAAGcAGGuGGAuc | 123 | GAUCcACCUGCUuAUUUuA | 782 | 3034 |
| AD-19045 | GAuAuAAAuGuGGucAccu | 124 | AGGUGACcAcAUUuAuAUC | 783 | 1505 |
| AD-19046 | AAGcAGAGuGcuGAAGGuG | 125 | cACCUUcAGcACUCUGCUU | 784 | 1288 |
| AD-19047 | uGuGAAcuuGcucAGGAcA | 126 | UGUCCUGAGcAAGUUcAcA | 785 | 2123 |
| AD-19048 | cAucccAcuAAuGccAGc | 127 | GCUGGAcAUuAGUGGGAUG | 786 | 620 |
| AD-19049 | cAAAGuuGuuGuAAccuGc | 128 | GcAGGUuAcAAcAACUUUG | 787 | 3164 |
| AD-19050 | uAAAucAGuAAGAGGuGuu | 129 | AAcACCUCUuACUGAUUuA | 788 | 3101 |
| AD-19051 | AAuGGcuuGGAAuGAGAcu | 130 | AGUCUcAUUCcAAGCcAUU | 789 | 2329 |
| AD-19052 | GGGuccucuGuGAAcuuGc | 131 | GcAAGUUcAcAGAGGACCC | 790 | 2115 |
| AD-19053 | GAGuAAcAAuAcAAAuGGA | 132 | UCcAUUUGuAUUGUuACUC | 791 | 2627 |
| AD-19054 | uAAuGGuGuAGAAcAcuAA | 133 | UuAGUGUUCuAcACcAUuA | 792 | 2902 |
| AD-19055 | GuGGAcAAuGGcuAcucAA | 134 | UUGAGuAGCcAUUGUCcAC | 793 | 262 |
| AD-19056 | AAcuGucuuuGGAcucucA | 135 | UGAGAGUCcAAAGAcAGUU | 794 | 1406 |
| AD-19057 | cccuuGuGcuGAcuAuccA | 136 | UGGAuAGUcAGcACcAGGG | 795 | 2497 |
| AD-19058 | cAGGuGGAucuAuuucAuG | 137 | cAUGAAAuAGAUCcACCUG | 796 | 3043 |
| AD-19059 | uGGccuGGuuuGAuAcuGA | 138 | UcAGuAUcAAACcAGGCcA | 797 | 2589 |
| AD-19060 | AGcuGGccuGGuuuGAuAc | 139 | GuAUcAAACcAGGCcAGCU | 798 | 2586 |
| AD-19061 | GccAucuGuGcucuucGuc | 140 | GACGAAGAGcAcAGAUGGC | 799 | 1658 |
| AD-19062 | uAccAuuccAuuGuuuGuG | 141 | cAcAAAcAAUGGAAUGGuA | 800 | 2050 |
| AD-19063 | cccuuGGAuAucGccAGGA | 142 | UCCUGGCGAuAUCcAAGGG | 801 | 2385 |
| AD-19064 | AGGGAAGAcAucAcuGAGc | 143 | GCUcAGUGAUGUCUUCCCU | 802 | 1637 |
| AD-19065 | GAAcuuGccAcAcGuGcAA | 144 | UUGcACGUGUGGcAAGUUC | 803 | 707 |
| AD-19066 | uuuGAuAcuGAccuGuAAA | 145 | UUuAcAGGUcAGuAUcAAA | 804 | 2597 |
| AD-19067 | ucccAAAGuuGuuGuAAcc | 146 | GGUuAcAAcAACUUUGGGA | 805 | 3161 |
| AD-19068 | cAGAAuAcAAAuGAuGuAG | 147 | CuAcAUcAUUUGuAUUCUG | 806 | 875 |
| AD-19069 | AGGuGGAucuAuuucAuGu | 148 | AcAUGAAAuAGAUCcACCU | 807 | 3044 |
| AD-19070 | GcucAucccAcuAAuGucc | 149 | GGAcAUuAGUGGGAUGAGC | 808 | 617 |
| AD-19071 | ccuGGuGcuGAcuAuccAG | 150 | CUGGAuAGUcAGcACcAGG | 809 | 2498 |
| AD-19072 | uGGAAuccAuucuGGuGcc | 151 | GGcACcAGAAUGGAUUCcA | 810 | 367 |
| AD-19073 | ccAGGAccucAuGGAuGGG | 152 | CCcAUCcAUGAGGUCCUGG | 811 | 2545 |
| AD-19074 | AAccucAcuGcAuAAuu | 153 | AAUuAUUGcAAGUGAGGUU | 812 | 1544 |
| AD-19075 | cAGuuGccuuuuAcccAA | 154 | UUGGGAuAAAAGGcAACUG | 813 | 3148 |
| AD-19076 | GuAGAAcAcuAAuucAuAA | 155 | UuAUGAAUuAGUGUUCuAC | 814 | 2909 |
| AD-19077 | cuAuccAGuuGAuGGGcuG | 156 | cAGCCcAUcAACUGGAuAG | 815 | 2509 |
| AD-19078 | cAcuGccucuGAuAAAGG | 157 | CCUUuAUcAGAGGCcAGUG | 816 | 1775 |
| AD-19079 | AcuGucuuuGGAcucucAG | 158 | CUGAGAGUCcAAAGAcAGU | 817 | 1407 |
| AD-19080 | ccAAuGGcuuGGAAuGAGA | 159 | UCUcAUUCcAAGCcAUUGG | 818 | 2327 |
| AD-19081 | GcuuAAAAuAAGcAGGuGG | 160 | CcACCUGCUuAUUUuAAGC | 819 | 3031 |
| AD-19082 | AucuGuGcucuucGucAuc | 161 | GAUGACGAAGAGcAcAGAU | 820 | 1661 |
| AD-19083 | cccAAAGuuGuuGuAAccu | 162 | AGGUuAcAAcAACUUUGGG | 821 | 3162 |
| AD-19738 | uAcccAGcGccAcGucc | 163 | GGACGuACGGCGCUGGGuA | 822 | 1906 |
| AD-19739 | AcGcuAucAuGcGuuccuc | 164 | GGAGAACGcAUGAuAGCGU | 823 | 825 |
| AD-19740 | cAuGcAccuuuGcGuGAGc | 165 | GCUcACGcAAAGGUGcAUG | 824 | 1838 |
| AD-19741 | GAAuGcAGuucGccuucAc | 166 | GUGAAGGCGAACUGcAUUC | 825 | 1714 |
| AD-19742 | GGuGccAuuccAcGAcuAG | 167 | CuAGUCGUGGAUGGcACC | 826 | 1859 |
| AD-19743 | AAGcGGcuGuuAGucAcuG | 168 | cAGUGACuAAcAGCCGCUU | 827 | 324 |
| AD-19744 | ucGAGcucAGAGGGuAcGA | 169 | UCGuACCCUCUGAGCUCGA | 828 | 535 |
| AD-19745 | GAcAcGcuAucAuGcGuuc | 170 | GAACGcAUGAuAGCGUGUC | 829 | 822 |
| AD-19746 | cGcuAucAuGcGuucuccu | 171 | AGGAGAACGcAUGAuAGCG | 830 | 826 |
| AD-19747 | GuGucuGcuAuuGuAcGuA | 172 | uACGuAcAAuAGcAGAcAC | 831 | 851 |
| AD-19748 | GucuGcucuAGuAuAAGc | 173 | GCUuAUuACuAGAGcAGAC | 832 | 1313 |
| AD-19749 | GuGccAuuccAcGAcuAGu | 174 | ACuAGUCGUGGAAUGGcAC | 833 | 1860 |
| AD-19750 | AuGuucAcAAccGAAuuGu | 175 | AcAAUUCGGUUGUGAAcAU | 834 | 2016 |
| AD-19751 | ccAcGAcuAGuucAGuuGc | 176 | GcAACUGAACuAGUCGUGG | 835 | 1868 |
| AD-19752 | cAcGAcuAGuucAGuuGcu | 177 | AGcAACUGAACuAGUCGUG | 836 | 1869 |
| AD-19753 | AGuucAGuuGcuuGuucGu | 178 | ACGAAcAAGcAACUGAACU | 837 | 1876 |
| AD-19754 | cccAGcGccGuAcGuccAu | 179 | AUGGACGuACGGCGCUGGG | 838 | 1908 |
| AD-19755 | GAGuuAcuucAcucuAGGA | 180 | UCCuAGAGUGAAGuAACUC | 839 | 2192 |
| AD-19756 | AcAGuAuGcAAuGAcucGA | 181 | UCGAGUcAUUGcAuACUGU | 840 | 520 |
| AD-19757 | uAuGcAAuGAcucGAGcuc | 182 | GAGCUCGAGUcAUUGcAuA | 841 | 524 |
| AD-19758 | cccAcuAAuGuccAGcGuu | 183 | AACGCUGGAcAUuAGUGGG | 842 | 623 |
| AD-19759 | GAccuuGcAuAAccuuucc | 184 | GGAAAGGUuAUGcAAGGUC | 843 | 916 |
| AD-19760 | uAuuAcGAcAGAcuGccuu | 185 | AAGGcAGUCUGUCGuAAuA | 844 | 1153 |
| AD-19761 | AucuGAccAGccGAcAccA | 186 | UGGUGUCGGCUGGUcAGAU | 845 | 1677 |
| AD-19762 | cAuuccAcGAcuAGuucAG | 187 | CUGAACuAGUCGUGGAAUG | 846 | 1864 |
| AD-19763 | GuuuGAAAAuccAGcGuG | 188 | cACGCUGGAUUUUcAAAAC | 847 | 246 |
| AD-19764 | GcGuuuGGcuGAAccAucA | 189 | UGAUGGUUcAGCcAAACGC | 848 | 637 |
| AD-19765 | AcAcGcuAucAuGcGuucu | 190 | AGAACGcAUGAuAGCGUGU | 849 | 823 |
| AD-19766 | uAuGccAuuAcAAcucucc | 191 | GGAGAGUUGuAAUGGcAuA | 850 | 1028 |
| AD-19767 | ucuGcucuAGuAAuAAGcc | 192 | GGCuAUuACuAGAGcAGA | 851 | 1314 |
| AD-19768 | cGGGAuGuucAcAAccGAA | 193 | UUCGGUUGUGAAcAUCCCG | 852 | 2012 |
| AD-20124 | | | | | |

TABLE 3-continued

Beta-Catenin RNAi agents: Example Modified Sequences

| | | | | | |
|---|---|---|---|---|---|
| AD-25889 | AcAAuAcAAAuGGAuuuuG | 194 | cAAAAUCcAUUUGuAUUGU | 853 | 2632 |
| AD-25890 | AcAAAuGGAuuuuGGGAGu | 195 | ACUCCcAAAAUCcAUUUGU | 854 | 2637 |
| AD-25891 | uuGGGAGuGAcucAAGAAG | 196 | CUUCUUGAGUcACUCCcAA | 855 | 2648 |
| AD-25892 | uGGGAGuGAcucAAGAAGu | 197 | ACUUCUUGAGUcACUCCcA | 856 | 2649 |
| AD-25893 | GAAGuGAAGAAuGcAcAAG | 198 | CUUGUGcAUUCUUcACUUC | 857 | 2663 |
| AD-25894 | AAGuGAAGAAuGcAcAAGA | 199 | UCUUGUGcAUUCUUcACUU | 858 | 2664 |
| AD-25895 | GAuGGAAuuuAucAAAccc | 200 | GGGUUUGAuAAAUUCcAUC | 859 | 2694 |
| AD-25896 | AuGGAAuuuAucAAAcccu | 201 | AGGGUUUGAuAAAUUCcAU | 860 | 2695 |
| AD-25897 | GGAAuuuAucAAAcccuAG | 202 | CuAGGGUUUGAuAAAUUCC | 861 | 2697 |
| AD-25898 | GAAuuuAucAAAcccuAGc | 203 | GCuAGGGUUUGAuAAAUUC | 862 | 2698 |
| AD-25899 | AAuuuAucAAAcccuAGcc | 204 | GGCuAGGGUUUGAuAAAUU | 863 | 2699 |
| AD-25900 | GAAuAucuGuAAuGGuAcu | 205 | AGuACcAUuAcAGAuAUUC | 864 | 2751 |
| AD-25901 | AAuAucuGuAAuGGuAcuG | 206 | cAGuACcAUuAcAGAuAUU | 865 | 2752 |
| AD-25902 | AuAucuGuAAuGGuAcuGA | 207 | UcAGuACcAUuAcAGAuAU | 866 | 2753 |
| AD-25903 | uuuuAAGcucucGuAGuG | 208 | cACuACGAGAGACUuAAAA | 867 | 2832 |
| AD-25904 | uuuuAAGcucucGuAGuGu | 209 | AcACuACGAGAGACUuAAA | 868 | 2833 |
| AD-25905 | AGucucucGuAGuGuuAAG | 210 | CUuAAcACuACGAGAGACU | 869 | 2837 |
| AD-25906 | ucGuAGuGuuAAGuuAuAG | 211 | CuAuAACuuAAcACuACGA | 870 | 2843 |
| AD-25907 | cGuAGuGuuAAGuuAuAGu | 212 | ACuAuAACuuAAcACuACG | 871 | 2844 |
| AD-25908 | GuAGuGuuAAGuuAuAGuG | 213 | cACuAuAACuuAAcACuAC | 872 | 2845 |
| AD-25909 | uAGuGuuAAGuuAuAGuGA | 214 | UcACuAuAACuuAAcACuA | 873 | 2846 |
| AD-25910 | uAGuGAAuAcuGcuAcAGc | 215 | GCUGuAGcAGuAUUcACuA | 874 | 2859 |
| AD-25911 | AAcAcuAAuucAuAAucAc | 216 | GUGAUuAUGAAuuAGUGUU | 875 | 2913 |
| AD-25912 | AcAcuAAuucAuAAucAcu | 217 | AGUGAUuAUGAAuuAGUGU | 876 | 2914 |
| AD-25913 | uAAuuGuAAcuGAAuAAA | 218 | UUuAUUcAGAUuAcAAUuA | 877 | 2938 |
| AD-25914 | AuuGuAAcuGAAuAAAGu | 219 | ACUUuAUUcAGAUuAcAAU | 878 | 2940 |
| AD-25915 | uuGuAAcuGAAuAAAGuG | 220 | cACUUuAUUcAGAUuAcAA | 879 | 2941 |
| AD-25916 | uGuAAucuGAAuAAAGuGu | 221 | AcACUUuAUUcAGAUuAcA | 880 | 2942 |
| AD-25917 | GAcAAAuAGAAAAuGGucc | 222 | GGAccAUUUUcuAUUUGUC | 881 | 2991 |
| AD-25918 | AcAAAuAGAAAAuGGuccA | 223 | UGGACcAUUUUcuAUUUGU | 882 | 2992 |
| AD-25919 | uAGAAAAuGGuccAAuuAG | 224 | CuAAUUGGACcAUUUUcuA | 883 | 2997 |
| AD-25920 | AGAAAAuGGuccAAuuAGu | 225 | ACuAAUUGGACcAUUUUCU | 884 | 2998 |
| AD-25921 | uAuuuGGGAuAuGuAuGGG | 226 | CCcAuAcAuAUCCcAAAuA | 885 | 3077 |
| AD-25922 | AuuuGGGAuAuGuAuGGGu | 227 | ACCcAuAcAuAUCCcAAAU | 886 | 3078 |
| AD-25923 | uuGGGAuAuGuAuGGGuAG | 228 | CuACCcAuAcAuAUCCcAA | 887 | 3080 |
| AD-25924 | GGAuAuGuAuGGGuAGGGu | 229 | ACCCuACCcAuAcAuAUCC | 888 | 3083 |
| AD-25925 | AAGAGGuGuuAuuuGGAAc | 230 | GUUCcAAAuAAcACCUCUU | 889 | 3110 |
| AD-25926 | AGAGGuGuuAuuuGGAAcc | 231 | GGUUCcAAAuAAcACCUCU | 890 | 3111 |
| AD-25927 | GAGGuGuuAuuuGGAACCu | 232 | AGGUUCcAAAuAAcACCUC | 891 | 3112 |
| AD-25928 | uGGAAccuuGuuuuGGAcA | 233 | UGUCcAAAAcAAGGUUCcA | 892 | 3123 |
| AD-25929 | GGAAccuuGuuuuGGAcAG | 234 | CUGUCcAAAAcAAGGUUCC | 893 | 3124 |
| AD-25930 | GAAccuuGuuuuGGAcAGu | 235 | ACUGUCcAAAAcAAGGUUC | 894 | 3125 |
| AD-25931 | GuuuuGGAcAGuuuAccAG | 236 | CUGGuAAACUGUCcAAAAC | 895 | 3132 |
| AD-25932 | uuuuGGAcAGuuuAccAGu | 237 | ACUGGuAAACUGUCcAAAA | 896 | 3133 |
| AD-25933 | uuGGAcAGuuuAccAGuuG | 238 | cAACUGGuAAACUGUCcAA | 897 | 3135 |
| AD-25934 | GuuGuuAAccuGcuGuG | 239 | cAcAGcAGGUuAcAAcAAC | 898 | 3168 |
| AD-25935 | uuGuuGuAAccuGcuGuGA | 240 | UcAcAGcAGGUuAcAAcAA | 899 | 3169 |
| AD-25936 | uuGuAAccuGcuGuGAuc | 241 | GuAUcAcAGcAGGUuAcAA | 900 | 3172 |
| AD-25937 | AuGcuucAAGAGAAAAuGc | 242 | GcAUUUUCUCUUGAAGcAU | 901 | 3192 |
| AD-25938 | AGuGAAGAAuGcAcAAGAA | 243 | UUCUUGUGcAUUCUUcACU | 902 | 2665 |
| AD-25939 | AAuGGAucAcAAGAuGGAA | 244 | UUCcAUCUUGUGAUCcAUU | 903 | 2682 |
| AD-25940 | AuGGAucAcAAGAuGGAAu | 245 | AUUCcAUCUUGUGAUCcAU | 904 | 2683 |
| AD-25941 | uGGAucAcAAGAuGGAAuu | 246 | AAUUCcAUCUUGUGAUCcA | 905 | 2684 |
| AD-25942 | GGAucAcAAGAuGGAAuuu | 247 | AAAUUCcAUCUUGUGAUCC | 906 | 2685 |
| AD-25943 | GAucAcAAGAuGGAAuuuA | 248 | uAAAUUCcAUCUUGUGAUC | 907 | 2686 |
| AD-25944 | AucAcAAGAuGGAAuuuAu | 249 | AuAAAUUCcAUCUUGUGAU | 908 | 2687 |
| AD-25945 | uGGAAuuuAucAAAcccuA | 250 | uAGGGUUUGAuAAAUUCcA | 909 | 2696 |
| AD-25946 | AcccuAGccuuGcuuGuuA | 251 | uAAcAAGcAAGGCuAGGGU | 910 | 2709 |
| AD-25947 | cccuAGccuuGcuuGuuAA | 252 | UuAAcAAGcAAGGCuAGGG | 911 | 2710 |
| AD-25948 | ccuAGccuuGcuuGuuAAA | 253 | UUuAAcAAGcAAGGCuAGG | 912 | 2711 |
| AD-25949 | cuAGccuuGcuuGuuAAAu | 254 | AUUuAAcAAGcAAGGCuAG | 913 | 2712 |
| AD-25950 | uAGccuuGcuuGuuAAAuu | 255 | AAUUuAAcAAGcAAGGCuA | 914 | 2713 |
| AD-25951 | AGccuuGcuuGuuAAAuuu | 256 | AAAUUuAAcAAGcAAGGCU | 915 | 2714 |
| AD-25952 | uuuAAGcucucGuAGuGuu | 257 | AAcACuACGAGAGACUuAA | 916 | 2834 |
| AD-25953 | uAAGcucucGuAGuGuuAA | 258 | UuAAcACuACGAGAGACUu | 917 | 2835 |
| AD-25954 | AAGcucucGuAGuGuuAA | 259 | UuAAcACuACGAGAGACUU | 918 | 2836 |
| AD-25955 | cucGuAGuGuuAAGuuAuA | 260 | uAuAACUuAAcACuACGAG | 919 | 2842 |
| AD-25956 | AGuGuuAAGuuAuAGuGAA | 261 | UUcACuAuAACUuAAcACU | 920 | 2847 |
| AD-25957 | GuGuuAAGuuAuAGuGAAu | 262 | AUUcACuAuAACUuAAcAC | 921 | 2848 |
| AD-25958 | cuAcAGcAAuucuAAuuu | 263 | AAAUuAGAAUUGCUGuAG | 922 | 2871 |
| AD-25959 | cAAuAGAAAAuGGuccAA | 264 | UUGGACcAUUUUcuAUUUG | 923 | 2993 |
| AD-25960 | AuAGAAAAuGGuccAAuuA | 265 | uAAUUGGACcAUUUUcuAU | 924 | 2996 |
| AD-25961 | uuuGGGAuAuGuAuGGGuA | 266 | uACCCuAcAuAUCCcAAA | 925 | 3079 |
| AD-25962 | GAuAuGuAuGGGuAGGGuA | 267 | uACCCuACCcAuAcAuAUC | 926 | 3084 |
| AD-25963 | uGGGuAGGGuAAAucAGuA | 268 | uACUGAUUuACCCuACCCA | 927 | 3092 |
| AD-25964 | uAAGAGGuGuuAuuuGGAA | 269 | UUCcAAAuAAcACCUCUuA | 928 | 3109 |
| AD-26017 | uGccuuuuAucccAAAGuu | 270 | AACUUUGGGAuAAAAGGcA | 929 | 3152 |
| AD-26018 | uGuuGuAAccuGcuGuGAu | 271 | AUcAcAGcAGGUuAcAAcA | 930 | 3170 |

TABLE 3-continued

Beta-Catenin RNAi agents: Example Modified Sequences

| | | | | | | |
|---|---|---|---|---|---|---|
| AD-26019 | GuuGuAAccuGcuGuGAuA | 272 | uAUcAcAGcAGGUuAcAAC | 931 | 3171 |
| AD-26020 | cAAGAGAAAAuGcGGuuAu | 273 | AuAACCGcAUUUUCUCUUG | 932 | 3198 |
| AD-26021 | AAGAGAAAAuGcGGuuAuA | 274 | uAuAACCGcAUUUUCUCUU | 933 | 3199 |
| AD-26022 | ccuGuuccccuGAGGGuAu | 275 | AuACCCUcAGGGGAAcAGG | 934 | 207 |
| AD-26023 | cuGuuccccuGAGGGuAuu | 276 | AAuACCCUcAGGGGAAcAG | 935 | 208 |
| AD-26024 | ccuGAGGGuAuuuGAAGuA | 277 | uACUUcAAAuACCCUcAGG | 936 | 215 |
| AD-26025 | cuGAGGGuAuuuGAAGuAu | 278 | AuACUUcAAAuACCCUcAG | 937 | 216 |
| AD-26026 | uGAGGGuAuuuGAAGuAuA | 279 | uAuACUUcAAAuACCCUcA | 938 | 217 |
| AD-26027 | GGuAuuuGAAGuAuAccAu | 280 | AUGGuAuACUUcAAAuACC | 939 | 221 |
| AD-26028 | GuAuuuGAAGuAuAccAuA | 281 | uAUGGuAuACUUcAAAuAC | 940 | 222 |
| AD-26029 | uuuGAAGuAuAccAuAcAA | 282 | UUGuAUGGuAuACUUcAAA | 941 | 225 |
| AD-26030 | AGuAuAccAuAcAAcuGuu | 283 | AAcAGUUGuAUGGuAuACU | 942 | 230 |
| AD-26031 | GuAuAccAuAcAAcuGuuu | 284 | AAAcAGUUGuAUGGuAuAC | 943 | 231 |
| AD-26032 | uAuAccAuAcAAcuGuuuu | 285 | AAAAcAGUUGuAUGGuAuA | 944 | 232 |
| AD-26033 | AccAuAcAAcuGuuuuGAA | 286 | UUcAAAAcAGUUGuAUGGU | 945 | 235 |
| AD-26034 | ccAuAcAAcuGuuuuGAAA | 287 | UUUcAAAAcAGUUGuAUGG | 946 | 236 |
| AD-26035 | GAAAAuccAGcGuGGAcAA | 288 | UUGUCcACGCUGGAUUUUC | 947 | 251 |
| AD-26036 | AAAAuccAGcGuGGAcAAu | 289 | AUUGUCcACGCUGGAUUUU | 948 | 252 |
| AD-26037 | ccAGcGuGGAcAAuGGcuA | 290 | uAGCcAUUGUCcACGCUGG | 949 | 257 |
| AD-26038 | GuGGAcAAuGGcuAcucAA | 291 | UUGAGuAGCcAUUGUCcAC | 950 | 262 |
| AD-26039 | AAuGGcuAcucAAGcuGAu | 292 | AUcAGCUUGAGuAGCcAUU | 951 | 268 |
| AD-26040 | AuGGcuAcucAAGcuGAuu | 293 | AAUcAGCUUGAGuAGCcAU | 952 | 269 |
| AD-26041 | uGGcuAcucAAGcuGAuuu | 294 | AAAUcAGCUUGAGuAGCcA | 953 | 270 |
| AD-26042 | cuAcucAAGcuGAuuuGAu | 295 | AUcAAAUcAGCUUGAGuAG | 954 | 273 |
| AD-26043 | AuuuGAuGGAGuuGGAcAu | 296 | AUGUCcAACUCcAUcAAAU | 955 | 285 |
| AD-26044 | uGGAGuuGGAcAuGGccAu | 297 | AUGGCcAUGUCcAACUCcA | 956 | 291 |
| AD-26045 | GuuGGAcAuGGccAuGGAA | 298 | UUCcAUGGCcAUGUCcAAC | 957 | 295 |
| AD-26046 | GccAuGGAAccAGAcAGAA | 299 | UUCUGUCUGGUUCcAUGGC | 958 | 305 |
| AD-26047 | cAuGGAAccAGAcAGAAAA | 300 | UUUUCUGUCUGGUUCcAUG | 959 | 307 |
| AD-26048 | GGAGGcGGAGAcGGAGGAA | 301 | UUCCUCCGUCUCCGCCUCC | 960 | 111 |
| AD-26049 | AGAcAGAAAAGcGGcuGuu | 302 | AACAGCCGCUUUUCUGUCU | 961 | 316 |
| AD-26050 | GAcAGAAAAGcGGcuGuuA | 303 | uAAcAGCCGCUUUUCUGUC | 962 | 317 |
| AD-26051 | uGuuAGucAcuGGcAGcAA | 304 | UUGCUGCcAGUGACuAAcA | 963 | 331 |
| AD-26052 | cAcuGGcAGcAAcAGucuu | 305 | AAGACUGUUGCUGCcAGUG | 964 | 338 |
| AD-26053 | AcuGGcAGcAAcAGucuuA | 306 | uAAGACUGUUGCUGCcAGU | 965 | 339 |
| AD-26054 | ucuuAccuGGAcucuGGAA | 307 | UUCcAGAGUCcAGGuAAGA | 966 | 353 |
| AD-26055 | cuuAccuGGAcucuGGAAu | 308 | AUUCcAGAGUCcAGGuAAG | 967 | 354 |
| AD-26056 | ccuGGAcucuGGAAuccAu | 309 | AUGGAUUCcAGAGUCcAGG | 968 | 358 |
| AD-26057 | GGcuAGuGGuGGAccccAA | 310 | UUGGGGUCcACcACuAGCC | 969 | 1216 |
| AD-26058 | GccAcuAccAcAGcuccuu | 311 | AAGGAGCUGUGGuAGUGGC | 970 | 383 |
| AD-26059 | uccuucucuGAGuGuAAAA | 312 | UUuACcACUcAGAGAAGGA | 971 | 397 |
| AD-26060 | cucuGAGuGGuAAAGGcAA | 313 | UUGCCUUuACcACUcAGAG | 972 | 402 |
| AD-26061 | uAAAGGcAAuccuGAGGAA | 314 | UUCCUcAGGAUUGCCUUuA | 973 | 412 |
| AD-26062 | cAAuccuGAGGAAGAGGAA | 315 | AUCCUCUUCCUcAGGAUUG | 974 | 418 |
| AD-26063 | uGAGGAAGAGGAuGuGGAu | 316 | AUCcAcAUCCUCUUCCUcA | 975 | 424 |
| AD-26064 | AuAccucccAAGuccuGuA | 317 | uAcAGGACUUGGGAGGuAU | 976 | 441 |
| AD-26065 | uAccucccAAGuccuGuAu | 318 | AuAcAGGACUUGGGAGGuA | 977 | 442 |
| AD-26066 | AGuccuGuAuGAGuGGGAu | 319 | UUCCcACUcAuAcAGGACU | 978 | 451 |
| AD-26067 | uAuGAGuGGGAAcAGGGAu | 320 | AUCCCUGUUCCcACUcAuA | 979 | 458 |
| AD-26068 | cAAGcuuuAGuAAAuAuAA | 321 | UuAuAUUuACuAAAGCUUG | 980 | 1232 |
| AD-26069 | AAGcuuuAGuAAAuAuAAu | 322 | AUuAuAUUuACuAAAGCUU | 981 | 1233 |
| AD-26070 | uGAGuGGGAACAGGGAuuu | 323 | AAAUCCCUGUUCCcACUcA | 982 | 460 |
| AD-26071 | GAGuGGGAACAGGGAuuuu | 324 | AAAAUCCCUGUUCCcACUC | 983 | 461 |
| AD-26072 | AGGGAuuuucucAGuccuu | 325 | AAGGACUGAGAAAAUCCCU | 984 | 471 |
| AD-26073 | uucucAGuccuucAcucAA | 326 | UUGAGUGAAGGACUGAGAA | 985 | 478 |
| AD-26074 | ucAGuccuucAcucAAGAA | 327 | UUCUUGAGUGAAGGACUGA | 986 | 481 |
| AD-26075 | cuucAcucAAGAAcAAGuA | 328 | uACUUGUUCUUGAGUGAAG | 987 | 487 |
| AD-26076 | ucAAGAAcAAGuAGcuGAu | 329 | AUcAGCuACUUGUUCUUGA | 988 | 493 |
| AD-26077 | cuGAuAuuGAuGGAcAGuA | 330 | uACUGUCcAUcAAuAUcAG | 989 | 507 |
| AD-26078 | AuuGAuGGAcAGuAuGcAA | 331 | UUGcAuACUGUCcAUcAAU | 990 | 512 |
| AD-26079 | GAcucGAGcucAGAGGGuA | 332 | uACCCUCUGAGCUCGAGUC | 991 | 532 |
| AD-26080 | cAGAGGGuAcGAGcuGcuA | 333 | uAGcAGCUCGuACCCUCUG | 992 | 542 |
| AD-26081 | AGAGGGuAcGAGcuGcuAu | 334 | AuAGcAGCUCGuACCCUCU | 993 | 543 |
| AD-26082 | GGGuAcGAGcuGcuAuGuu | 335 | AAcAuAGcAGCUCGuACCC | 994 | 546 |
| AD-26083 | cuAuGuucccuGAGAcAuu | 336 | AAUGUCUcAGGGAAcAuAG | 995 | 558 |
| AD-26084 | uAuGuucccuGAGAcAuuA | 337 | uAAUGUCUcAGGGAAcAuA | 996 | 559 |
| AD-26085 | GuucccuGAGAcAuuAGAu | 338 | AUCuAAUGUCUcAGGGAAC | 997 | 562 |
| AD-26086 | uAGAuGAGGGcAuGcAGAu | 339 | AUCUGcAUGCCCUcAUCuA | 998 | 576 |
| AD-26087 | GAGGGcAuGcAGAucccAu | 340 | AUGGGAUCUGcAUGCCCUC | 999 | 581 |
| AD-26088 | GGcAuGcAGAucccAucuA | 341 | uAGAUGGGAUCUGcAUGCC | 1000 | 584 |
| AD-26089 | AGAucccAucuAcAcAGuu | 342 | AACUGUGuAGAUGGGAUCU | 1001 | 591 |
| AD-26090 | cccAucuAcAcAGuuuGAu | 343 | AUcAAACUGUGuAGAUGGG | 1002 | 595 |
| AD-26091 | AcACuGuuGAUGGcAUcAA | 344 | AUGAGcGAUcAAAcUGU | 1003 | 604 |
| AD-26092 | GAuGcuGcuAucccAcuAA | 345 | uAGUGGGAUGAGcAGcAUC | 1004 | 611 |
| AD-26093 | AuGcuGcuAucccAcuAAu | 346 | UuAGUGGGAUGAGcAGcAU | 1005 | 612 |
| AD-26094 | uGcuGcuAucccAcuAAuu | 347 | AUuAGUGGGAUGAGcAGcA | 1006 | 613 |
| AD-26095 | cccAcuAAuGuccAGcGuu | 348 | AACGCUGGAcAUuAGUGGG | 1007 | 623 |
| AD-26096 | cAGcGuuuGGcuGAAccAu | 349 | AUGGUUcAGCcAAACGCUG | 1008 | 635 |

TABLE 3-continued

Beta-Catenin RNAi agents: Example Modified Sequences

| | | | | | |
|---|---|---|---|---|---|
| AD-26097 | uGGcuGAAccAucAcAGAu | 350 | AUCUGUGAUGGUUcAGCcA | 1009 | 642 |
| AD-26098 | AAccAucAcAGAuGcuGAA | 351 | UUcAGcAUCUGUGAUGGUU | 1010 | 648 |
| AD-26099 | AccAucAcAGAuGcuGAAA | 352 | UUUcAGcAUCUGUGAUGGU | 1011 | 649 |
| AD-26100 | AucAcAGAuGcuGAAAcAu | 353 | AUGUUUcAGcAUCUGUGAU | 1012 | 652 |
| AD-26101 | GAuGcuGAAAcAuGcAGuu | 354 | AACUGcAUGUUUcAGcAUC | 1013 | 658 |
| AD-26102 | cuGAAAcAuGcAGuuGuAA | 355 | UuAcAACUGcAUGUUUcAG | 1014 | 662 |
| AD-26103 | AAcAuGcAGuuGuAAAcuu | 356 | AAGUUuAcAACUGcAUGUU | 1015 | 666 |
| AD-26104 | AuGcAGuuGuAAAcuuGAu | 357 | AUcAAGUUuAcAACUGcAU | 1016 | 669 |
| AD-26105 | uGcAGuuGuAAAcuuGAuu | 358 | AAUcAAGUUuAcAACUGcA | 1017 | 670 |
| AD-26106 | cAGuuGuAAAcuuGAuuAA | 359 | UuAAUcAAGUUuAcAACUG | 1018 | 672 |
| AD-26107 | cuuGAuuAAcuAucAAGAu | 360 | AUCUUGAuAGUuAAUcAAG | 1019 | 682 |
| AD-26108 | GAuuAAcuAucAAGAuGAu | 361 | AUcAUCUUGAuAGUuAAUC | 1020 | 685 |
| AD-26109 | cuAucAAGAuGAuGcAGAA | 362 | UUcUGcAUcAUCUUGAuAG | 1021 | 691 |
| AD-26110 | GAAcuuGccAcAcGuGcAA | 363 | UUGcACGUGUGGcAAGUUC | 1022 | 707 |
| AD-26111 | AAcuuGccAcAcGuGcAAu | 364 | AUUGcACGUGUGGcAAGUU | 1023 | 708 |
| AD-26112 | cAcGuGcAAucccuGAA | 365 | UUcAGGGAUUGcACGUGUG | 1024 | 715 |
| AD-26123 | GcAAucccuGAAcuGAcAA | 366 | UUGUcAGUUcAGGGAUUGC | 1025 | 722 |
| AD-26124 | cAAucccuGAAcuGAcAAA | 367 | UUUGUcAGUUcAGGGAUUG | 1026 | 723 |
| AD-26125 | AAucccuGAAcuGAcAAAA | 368 | UUUUGUcAGUUcAGGGAUU | 1027 | 724 |
| AD-26126 | uGAAcuGAcAAAAcuGcuA | 369 | uAGcAGUUUUGUcAGUUcA | 1028 | 730 |
| AD-26127 | GAAcuGAcAAAAcuGcuAA | 370 | UuAGcAGUUUUGUcAGUUC | 1029 | 731 |
| AD-26128 | AAcuGAcAAAAcuGcuAAA | 371 | UUuAGcAGUUUUGUcAGUU | 1030 | 732 |
| AD-26129 | AcuGAcAAAAcuGcuAAAu | 372 | AUUuAGcAGUUUUGUcAGU | 1031 | 733 |
| AD-26130 | GAGGAccAGGuGGuGGuuA | 373 | uAACcACcACCUGGUCCUC | 1032 | 755 |
| AD-26131 | AGGAccAGGuGGuGGuuAA | 374 | UuAACcACcACCUGGUCCU | 1033 | 756 |
| AD-26132 | GGAccAGGuGGuGGuuAAu | 375 | AUuAACcACcACCUGGUCC | 1034 | 757 |
| AD-26133 | GAccAGGuGGuGGuuAAuA | 376 | uAUuAACcACcACCUGGUC | 1035 | 758 |
| AD-26134 | ucAcuuGcAAuAAuuAuAA | 377 | UuAuAAUuAUUGcAAGUGA | 1036 | 1548 |
| AD-26135 | cuuGcAAuAAuuAuAAGAA | 378 | UUcUuAuAAUuAUUGcAAG | 1037 | 1551 |
| AD-26136 | AccAGGuGGuGGuuAAuAA | 379 | UuAUuAACcACcACCUGGU | 1038 | 759 |
| AD-26137 | GGcuGcAGuuAuGGuccAu | 380 | AUGGAccAuAACUGcAGCC | 1039 | 778 |
| AD-26138 | GuuAuGGuccAucAGcuuu | 381 | AAAGCUGAUGGAccAuAAC | 1040 | 785 |
| AD-26139 | AuGGuccAucAGcuuucA | 382 | uAGAAAGCUGAUGGAccAU | 1041 | 788 |
| AD-26140 | uGGuccAucAGcuuucuAA | 383 | UuAGAAAGCUGAUGGAccA | 1042 | 789 |
| AD-26141 | ucGGGcuGGAcAGGGAA | 384 | UUCCCUGUcAccAGCCCGA | 1043 | 1624 |
| AD-26142 | GGuccAucAGcuuucuAAA | 385 | UUuAGAAAGCUGAUGGACC | 1044 | 790 |
| AD-26143 | GuccAucAGcuuucuAAAA | 386 | UUUuAGAAAGCUGAUGGAC | 1045 | 791 |
| AD-26144 | GAAGcuuccAGAcAcGcuA | 387 | uAGCGUGUCUGGAAGCUUC | 1046 | 812 |
| AD-26145 | AAGcuuccAGAcAcGcuAu | 388 | AuAGCGUGUCUGGAAGCUU | 1047 | 813 |
| AD-26146 | cuuccAGAcAcGcuAucAu | 389 | AUGAuAGCGUGUCUGGAAG | 1048 | 816 |
| AD-26147 | AGAcAcGcuAucAuGcGuu | 390 | AACGcAUGAuAGCGUGUCU | 1049 | 821 |
| AD-26148 | ucAuGcGuucuccucAGAu | 391 | AUCUGAGGAGAACGcAUGA | 1050 | 831 |
| AD-26149 | ccucAGAuGGuGucuGcuA | 392 | uAGcAGAcACcAUCUGAGG | 1051 | 842 |
| AD-26150 | cucAGAuGGuGucuGcuAu | 393 | AuAGcAGAcACcAUCUGAG | 1052 | 843 |
| AD-26151 | GuGucuGcuAuuGuAcGuA | 394 | uACGuAcAAuAGcAGAcAC | 1053 | 851 |
| AD-26152 | cuGcuAuuGuAcGuAccAu | 395 | AUGGuACGuAcAAuAGcAG | 1054 | 855 |
| AD-26153 | uuGuAcGuAccAuGcAGAA | 396 | UUcUGcAUGGuACGuAcAA | 1055 | 861 |
| AD-26154 | uGuAcGuAccAuGcAGAAu | 397 | AUUCUGcAUGGuACGuAcA | 1056 | 862 |
| AD-26155 | cGuAccAuGcAGAAuAcAA | 398 | UUGuAUUCUGcAUGGuACG | 1057 | 866 |
| AD-26156 | cAuGcAGAAuAcAAAuGAu | 399 | AUcAUUUGuAUUCUGcAUG | 1058 | 871 |
| AD-26157 | GcAGAAuAcAAAuGAuGuA | 400 | uAcAUcAUUUGuAUUCUGC | 1059 | 874 |
| AD-26158 | GAAuAcAAAuGAuGuAGAA | 401 | UUCuAcAUcAUUUGuAUUC | 1060 | 877 |
| AD-26159 | GAuGuAGAAAcAGcucGuu | 402 | AACGAGCUGUUUCuAcAUC | 1061 | 887 |
| AD-26160 | GuuGuAccGcuGGGAccuu | 403 | AAGGUCCcAGCGGuAcAAC | 1062 | 903 |
| AD-26161 | uAccGcuGGGAccuuGcAu | 404 | AUGcAAGGUCCcAGCGGuA | 1063 | 907 |
| AD-26162 | ccGcuGGGAccuuGcAuAA | 405 | UuAUGcAAGGUCCcAGCGG | 1064 | 909 |
| AD-26163 | uGGGAccuuGcAuAAccuu | 406 | AAGGUuAUGcAAGGUCCcA | 1065 | 913 |
| AD-26164 | GGGAccuuGcAuAAccuuu | 407 | AAAGGUuAUGcAAGGUCCC | 1066 | 914 |
| AD-26165 | cuuGcAuAAccuuucccAu | 408 | AUGGGAAAGGUuAUGcAAG | 1067 | 919 |
| AD-26166 | ucuuuAAGucuGGAGGcAu | 409 | AUGCCUCcAGACUuAAAGA | 1068 | 960 |
| AD-26167 | GcAuuccuGcccuGGuGAA | 410 | UUcACcAGGGcAGGAAUGC | 1069 | 975 |
| AD-26168 | cAuuccuGcccuGGuGAAA | 411 | UUUcACcAGGGcAGGAAUG | 1070 | 976 |
| AD-26169 | AuuccuGcccuGGuGAAAA | 412 | UUUUcACcAGGGcAGGAAU | 1071 | 977 |
| AD-26170 | uuccuGcccuGGuGAAAAu | 413 | AUUUUcACcAGGGcAGGAA | 1072 | 978 |
| AD-26171 | uGccuGcGuGAAAAuGccu | 414 | AAGcAUUUUcAccAGGGcA | 1073 | 982 |
| AD-26172 | cuGGuGAAAAuGcuuGGuu | 415 | AACcAAGcAUUUUcACcAG | 1074 | 986 |
| AD-26173 | GcuuGGuucAccAGuGGAu | 416 | AUCcACUGGUGAACcAAGC | 1075 | 997 |
| AD-26174 | cuuGGuucAccAGuGGAuu | 417 | AAUCcACUGGUGAACcAAG | 1076 | 998 |
| AD-26175 | uGcGuGAGcAGGGuGccAu | 418 | AUGGcACCCUGCUcACGcA | 1077 | 1848 |
| AD-26176 | GcGuGAGcAGGGuGccAuu | 419 | AAUGGcACCCUGCUcACGC | 1078 | 1849 |
| AD-26177 | cAccAGuGGAuucuGuGuu | 420 | AAcAcAGAAUCcACUGGUG | 1079 | 1005 |
| AD-26178 | cAGuGGAuucuGuGuuGuu | 421 | AAcAAcAcAGAAUCcACUG | 1080 | 1008 |
| AD-26179 | AGuGGAuucuGuGuuGuuu | 422 | AAAcAAcAcAGAAUCcACU | 1081 | 1009 |
| AD-26180 | GuGGAuucuGuGuuGuuuu | 423 | AAAAcAAcAcAGAAUCcAC | 1082 | 1010 |
| AD-26181 | uGGAuucuGuGuuGuuuuA | 424 | uAAAAcAAcAcAGAAUCcA | 1083 | 1011 |
| AD-26182 | GGAuucuGuGuuGuuuuAu | 425 | AuAAAAcAAcAcAGAAUCC | 1084 | 1012 |
| AD-26183 | uGuGuuGuuuuAuGccAuu | 426 | AAUGGcAuAAAAcAAcAcA | 1085 | 1018 |
| AD-26184 | GGGuGGGAcAcAGcAGcAA | 427 | UUGCUGCUGUGUCCcACCC | 1086 | 1927 |

TABLE 3-continued

Beta-Catenin RNAi agents: Example Modified Sequences

| | | | | | | |
|---|---|---|---|---|---|---|
| AD-26185 | GuGuuGuuuuAuGccAuuA | 428 | uAAUGGcAuAAAAcAAcAC | 1087 | 1019 |
| AD-26186 | uuGuuuuAuGccAuuAcAA | 6495 | UUGuAAUGGcAuAAAAcAA | 1088 | 1022 |
| AD-26187 | ccAuuAcAAcucuccAcAA | 6496 | UUGUGGAGAGUUGuAAUGG | 1089 | 1032 |
| AD-26188 | uAcAcucuccAcAAccuu | 431 | AAGGUUGUGGAGAGUUGuA | 1090 | 1036 |
| AD-26189 | AcAAcucuccAcAAccuuu | 432 | AAAGGUUGUGGAGAGUUGU | 1091 | 1037 |
| AD-26190 | cAAcucuccAcAAccuuuu | 433 | AAAAGGUUGUGGAGAGUUG | 1092 | 1038 |
| AD-26191 | AAcucuccAcAAccuuuuA | 434 | uAAAAGGUUGUGGAGAGUU | 1093 | 1039 |
| AD-26192 | AcucuccAcAAccuuuuAu | 435 | AuAAAAGGUUGUGGAGAGU | 1094 | 1040 |
| AD-26193 | cucuccAcAAccuuuuAuu | 436 | AAuAAAAGGUUGUGGAGAG | 1095 | 1041 |
| AD-26194 | ucuccAcAAccuuuuAuuA | 437 | uAAuAAAAGGUUGUGGAGA | 1096 | 1042 |
| AD-26195 | cAAccuuuuAuuAcAucAA | 438 | UUGAUGuAAuAAAAGGUUG | 1097 | 1048 |
| AD-26196 | ccuuuuAuuAcAucAAGAA | 439 | UUCUUGAUGuAAuAAAAGG | 1098 | 1051 |
| AD-26197 | uuAcAucAAGAAGGAGcuA | 440 | uAGCUCCUUCUUGAUGuAA | 1099 | 1058 |
| AD-26198 | uAcAucAAGAAGGAGcuAA | 441 | UuAGCUCCUUCUUGAUGuA | 1100 | 1059 |
| AD-26199 | cAucAAGAAGGAGcuAAAA | 442 | UUUuAGCUCCUUCUUGAUG | 1101 | 1061 |
| AD-26200 | AucAAGAAGGAGcuAAAAu | 443 | AUUUuAGCUCCUUCUUGAU | 1102 | 1062 |
| AD-26201 | GcuAAAAuGGcAGuGcGuu | 444 | AACGcACUGCcAUUUuAGC | 1103 | 1073 |
| AD-26202 | uAAAAuGGcAGuGcGuuuA | 445 | uAAACGcACUGCcAUUUuA | 1104 | 1075 |
| AD-26203 | AAAuGGuuGccuuGcucAA | 446 | UUGAGcAAGGcAACcAUUU | 1105 | 1110 |
| AD-26204 | GccuGuuccccuGAGGGuA | 447 | uACCCUcAGGGGAAcAGGC | 1106 | 206 |
| AD-26205 | uGGuuGccuuGcucAAcAA | 448 | UUGUUGAGcAAGGcAACcA | 1107 | 1113 |
| AD-26206 | GGuuGccuuGcucAAcAAA | 449 | UUUGUUGAGcAAGGcAACC | 1108 | 1114 |
| AD-26207 | GuuGccuuGcucAAcAAAA | 450 | UUUUGUUGAGcAAGGcAAC | 1109 | 1115 |
| AD-26208 | GccuuGcucAAcAAAAcAA | 451 | UUGUUUUGUUGAGcAAGGC | 1110 | 1118 |
| AD-26209 | ccuuGcucAAcAAAAcAAA | 452 | UUUGUUUUGUUGAGcAAGG | 1111 | 1119 |
| AD-26210 | GuuAAAuucuuGGcuAuuA | 453 | uAAuAGCcAAGAAUUuAAC | 1112 | 1139 |
| AD-26211 | uAuuAcGAcAGAcuGccuu | 454 | AAGGcAGUCUGCGuAuuA | 1113 | 1153 |
| AD-26212 | AuGGcAAccAAGAAAGcAA | 455 | UUGCUUUCUUGGUUGCcAU | 1114 | 1185 |
| AD-26213 | AGuGGuGGAccccAAGcuu | 456 | AAGCUUGGGGUCcACcACU | 1115 | 1220 |
| AD-26214 | GuGGuGGAccccAAGcuuu | 457 | AAAGCUUGGGGUCcACcAC | 1116 | 1221 |
| AD-26215 | uGGuGGAccccAAGcuuuA | 458 | uAAAGCUUGGGGUCcACcA | 1117 | 1222 |
| AD-26216 | uGGAccccAAGcuuuAGuA | 459 | uACuAAAGCUUGGGGUCcA | 1118 | 1225 |
| AD-26217 | GGAccccAAGcuuuAGuAA | 460 | UuAcuAAAGCUUGGGGUCC | 1119 | 1226 |
| AD-26218 | GAccccAAGcuuuAGuAAA | 461 | UUuACuAAAGCUUGGGGUC | 1120 | 1227 |
| AD-26651 | AccccAAGcuuuAGuAAAu | 462 | AUUuACuAAAGCUUGGGGU | 1121 | 1228 |
| AD-26652 | ccccAAGcuuuAGuAAAuA | 463 | uAUUuACuAAAGCUUGGGG | 1122 | 1229 |
| AD-26653 | cccAAGcuuuAGuAAAuAu | 464 | AuAUUuACuAAAGCUUGGG | 1123 | 1230 |
| AD-26654 | ccAAGcuuuAGuAAAuAuA | 465 | uAuAUUuACuAAAGCUUGG | 1124 | 1231 |
| AD-26655 | uAAAuAuAAuGAGGAccuA | 466 | uAGGUCCUcAUuAuAUUuA | 1125 | 1242 |
| AD-26656 | AAAuAuAAuGAGGAccuAu | 467 | AuAGGUCCUcAUuAuAUUU | 1126 | 1243 |
| AD-26657 | AAuAuAAuGAGGAccuAuA | 468 | uAAGGUCCUcAUuAuAUU | 1127 | 1244 |
| AD-26658 | AuAuGAGGAccuAuAcuu | 469 | AAGuAuAGGUCCUcAUuAU | 1128 | 1247 |
| AD-26659 | AAAcuAcuGuGGAccAcAA | 470 | UUGUGGUCcAcAGuAGUUU | 1129 | 1271 |
| AD-26660 | ccAcAAGcAGAGuGcuGAA | 471 | UUcAGcACUCUGCUUGUGG | 1130 | 1284 |
| AD-26661 | cAGAGuGcuGAAGGuGcuA | 472 | uAGcACCUUcAGcACUCUG | 1131 | 1291 |
| AD-26662 | AGAGuGcuGAAGGuGcuAu | 473 | AuAGcACCUUcAGcACUCU | 1132 | 1292 |
| AD-26663 | AuuGuAGAAGcuGGuGGAA | 474 | UUCcAccAGCUUCuAcAAU | 1133 | 1337 |
| AD-26664 | uuGuAGAAGcuGGuGGAAu | 475 | AUUCcAccAGCUUCuAcAA | 1134 | 1338 |
| AD-26665 | GcuGGuGGAAuGcAAGcuu | 476 | AAGCUUGcAUUCcAccAGC | 1135 | 1346 |
| AD-26666 | cuGGuGGAAuGcAAGcuuu | 477 | AAAGCUUGcAUUCcAccAG | 1136 | 1347 |
| AD-26667 | AGGAcuucAccuGAcAGAu | 478 | AUCUGUcAGGUGAAGUCCU | 1137 | 1366 |
| AD-26668 | cuucAccuGAcAGAuccAA | 479 | UUGGAUCUGUcAGGUGAAG | 1138 | 1370 |
| AD-26669 | ccuGAcAGAuccAAGucAA | 480 | UUGACUUGGAUCUGUcAGG | 1139 | 1375 |
| AD-26670 | AGAuccAAGucAAcGucuu | 481 | AAGACGUUGACUUGGAUCU | 1140 | 1381 |
| AD-26671 | uccAAGucAAcGucuuGuu | 482 | AAcAAGACGUUGACUUGGA | 1141 | 1384 |
| AD-26672 | ucuuGuucAGAAcuGucuu | 483 | AAGAcAGUUCUGAAcAAGA | 1142 | 1396 |
| AD-26673 | cuuGuucAGAAcuGucuuu | 484 | AAAGAcAGUUCUGAAcAAG | 1143 | 1397 |
| AD-26674 | GucuuuGGAcucucAGGAA | 485 | UUCCUGAGAGUCcAAAGAC | 1144 | 1410 |
| AD-26675 | ucuuuGGAcucucAGGAAu | 486 | AUUCCUGAGAGUCcAAAGA | 1145 | 1411 |
| AD-26676 | uuGGAcucucAGGAAucuu | 487 | AAGAUUCCUGAGAGUCcAA | 1146 | 1414 |
| AD-26677 | uGcccAGGGAGAAcccuu | 488 | AAGGGGUUCUCCCUGGGcA | 1147 | 2371 |
| AD-26678 | uGGAcucucAGGAAucuuu | 489 | AAAGAUUCCUGAGAGUCcA | 1148 | 1415 |
| AD-26679 | ucucAGGAAucuuucAGAu | 490 | AUCUGAAAGAUUCCUGAGA | 1149 | 1420 |
| AD-26680 | AAucuuucAGAuGcuGcAA | 491 | UUGcAGcAUCUGAAAGAUU | 1150 | 1427 |
| AD-26681 | cuuucAGAuGcuGcAAcuu | 492 | uAGUUGcAGcAUCUGAAAG | 1151 | 1430 |
| AD-26682 | uucAGAuGcuGcAAcuAAA | 493 | UUuAGUUGcAGcAUCUGAA | 1152 | 1432 |
| AD-26683 | uGcuGcAcuAAAcAGGAA | 494 | UUCCUGUuAGUUGcAGcA | 1153 | 1438 |
| AD-26684 | uAAAcAGGAAGGGAuGGAA | 495 | UUCcAUCCCUUCCUGUuA | 1154 | 1447 |
| AD-26685 | AGGGAuGGAAGGucuccuu | 496 | AAGGAGACCUUCcAUCCCU | 1155 | 1456 |
| AD-26686 | AGGucuccuuGGGAcucuu | 497 | AAGAGUCCcAAGGAGACCU | 1156 | 1465 |
| AD-26687 | ucuccuuGGGAcucuuGuu | 498 | AAcAAGAGUCCcAAGGAGA | 1157 | 1468 |
| AD-26688 | uGGGAcucuuGuucAGcuu | 499 | AAGCUGAAcAAGAGUCCA | 1158 | 1474 |
| AD-26689 | cuuGuucAGcuucuGGGuu | 500 | AACCcAGAAGCUGAAcAAG | 1159 | 1481 |
| AD-26690 | ucAGcuucuGGGuucAGAu | 501 | AUCUGAACCcAGAAGCUGA | 1160 | 1486 |
| AD-26691 | GcuucuGGGuucAGAuGAu | 502 | AUcAUCUGAACCcAGAAGC | 1161 | 1489 |
| AD-26692 | cuucuGGGuucAGAuGAuA | 503 | uAUcAUCUGAACCcAGAAG | 1162 | 1490 |
| AD-26693 | GGccAGGAuGccuuGGGuA | 504 | uACCcAAGGcAUCCUGGCC | 1163 | 2441 |
| AD-26694 | uucuGGGuucAGAuGAuAu | 505 | AuAUcAUCUGAACCcAGAA | 1164 | 1491 |

TABLE 3-continued

Beta-Catenin RNAi agents: Example Modified Sequences

| | | | | | |
|---|---|---|---|---|---|
| AD-26695 | cuGGGuucAGAuGAuAuAA | 506 | UuAuAUcAUCUGAACCcAG | 1165 | 1493 |
| AD-26696 | uGGGuucAGAuGAuAuAAA | 507 | UUuAuAUcAUCUGAACCcA | 1166 | 1494 |
| AD-26697 | GucAccuGuGcAGcuGgAA | 508 | UUCcAGCUGcAcAGGUGAC | 1167 | 1517 |
| AD-26698 | ucAccuGuGcAGcuGGAAu | 509 | AUUCcAGCUGcAcAGGUGA | 1168 | 1518 |
| AD-26699 | cAccuGuGcAGcuGGAAuu | 510 | AAUUCcAGCUGcAcAGGUG | 1169 | 1519 |
| AD-26700 | cuGuGcAGcuGGAAuucuu | 511 | AAGAAUUCcAGCUGcAcAG | 1170 | 1522 |
| AD-26701 | uGuGcAGcuGGAAuucuuu | 512 | AAAGAAUUCcAGCUGcAcA | 1171 | 1523 |
| AD-26702 | GcAGcuGGAAuucuuucuA | 513 | uAGAAAGAAUUCcAGCUGC | 1172 | 1526 |
| AD-26703 | cAGcuGGAAuucuuucuAA | 514 | UuAGAAAGAAUUCcAGCUG | 1173 | 1527 |
| AD-26704 | uuucuAAccucAcuuGcAA | 515 | UUGcAAGUGAGGUuAGAAA | 1174 | 1539 |
| AD-26705 | uucuAAccucAcuuGcAAu | 516 | AUUGcAAGUGAGGUuAGAA | 1175 | 1540 |
| AD-26706 | AccucAcuuGcAAuAAuuA | 517 | uAAUuAUUGcAAGUGAGGU | 1176 | 1545 |
| AD-26707 | ccucAcuuGcAAuAAuuAu | 518 | AuAAUuAUUGcAAGUGAGG | 1177 | 1546 |
| AD-26708 | cucAcuuGcAAuAAuuAuA | 519 | uAuAAUuAUUGcAAGUGAG | 1178 | 1547 |
| AD-26709 | GucuGccAAGuGGGuGGuA | 520 | uACcACCcACUUGGcAGAC | 1179 | 1580 |
| AD-26710 | ucuGccAAGuGGGuGGuAu | 521 | AuACcACCcACUUGGcAGA | 1180 | 1581 |
| AD-26711 | GGGuGGuAuAGAGGcucuu | 522 | AAGAGCCUCuAuAcCACCC | 1181 | 1591 |
| AD-26712 | AuAGAGGcucuuGuGcGuA | 523 | uACGcAcAAGAGCCUCuAU | 1182 | 1598 |
| AD-26713 | ucuuGuGcGuAcuGuccuu | 524 | AAGGAcAGuACGcAcAAGA | 1183 | 1606 |
| AD-26714 | cuGGuGAcAGGGAAGAcAu | 525 | AUGUCUUCCCUGUcACcAG | 1184 | 1629 |
| AD-26715 | AcAucAcuGAGccuGccAu | 526 | AUGGcAGGCUcAGUGAUGU | 1185 | 1644 |
| AD-26716 | GccuGccAucuGuGcucuu | 527 | AAGAGcAcAGAUGGcAGGC | 1186 | 1654 |
| AD-26717 | ucuGAccAGccGAcAccAA | 528 | UUGGGUGUCGGCUGGUcAGA | 1187 | 1678 |
| AD-26718 | GAccAGccGAcAccAAGAA | 529 | UUCUUGGUGUCGGCUGGUC | 1188 | 1681 |
| AD-26719 | GAcAccAAGAAGcAGAGAu | 530 | AUCUCUGCUUCUUGGUGUC | 1189 | 1689 |
| AD-26720 | AGcAGAGAuGGcccAGAAu | 531 | AUUCUGGGCcAUCUCUGCU | 1190 | 1699 |
| AD-26721 | GAuGGcccAGAAuGcAGuu | 532 | AACUGcAUUCUGGGCcAUC | 1191 | 1705 |
| AD-26722 | ccAGAAuGcAGuucGccuu | 533 | AAGGCGAACUGcAUUCUGG | 1192 | 1711 |
| AD-26723 | AuGcAGuucGccuucAcuA | 534 | uAGUGAAGGCGAACUGcAU | 1193 | 1716 |
| AD-26724 | uGcAGuucGccuucAcuAu | 535 | AuAGUGAAGGCGAACUGcA | 1194 | 1717 |
| AD-26725 | ucGccuucAcuAuGGAcuA | 536 | uAGUCcAuAGUGAAGGCGA | 1195 | 1723 |
| AD-26726 | ucAcuAuGGAcuAccAGuu | 537 | AACUGGuAGUCcAuAGUGA | 1196 | 1729 |
| AD-26727 | uGGAcuAccAGuuGuGGuu | 538 | AACcAcAACUGGuAGUCcA | 1197 | 1735 |
| AD-26728 | GGAcuAccAGuuGuGGuuA | 539 | uAACcAcAACUGGuAGUCC | 1198 | 1736 |
| AD-26729 | GAcuAccAGuuGuGGuuAA | 540 | UuAACcAcAACUGGuAGUC | 1199 | 1737 |
| AD-26730 | cAGuuGuGGuuAAGcucuu | 541 | AAGAGCUuAACcAcAACUG | 1200 | 1743 |
| AD-26731 | AGuuGuGGuuAAGcucuuA | 542 | uAAGAGCUuAACcAcAACU | 1201 | 1744 |
| AD-26732 | AAGcucuuAcAcccAccAu | 543 | AUGGUGGGUGuAAGAGCUU | 1202 | 1754 |
| AD-26733 | cAucccAcuGGccucuGAu | 544 | AUcAGAGGCcAGUGGGAUG | 1203 | 1770 |
| AD-26734 | AucccAcuGGccucuGAuA | 545 | uAUcAGAGGCcAGUGGGAU | 1204 | 1771 |
| AD-26735 | ucccAcuGGccucuGAuAA | 546 | UuAUcAGAGGCcAGUGGGA | 1205 | 1772 |
| AD-26736 | uGGccucuGAuAAAGGcuA | 547 | uAGCCUUuAUcAGAGGCcA | 1206 | 1778 |
| AD-26737 | ucuGAuAAAGGcuAcuGuu | 548 | AAcAGuAGCCUUuAUcAGA | 1207 | 1783 |
| AD-26738 | AuAAAGGcuAcuGuuGGAu | 549 | AUCcAAcAGuAGCCUUuAU | 1208 | 1787 |
| AD-26739 | GGcuAcuGuuGGAuuGAuu | 550 | AAUcAAUCcAAcAGuAGCC | 1209 | 1792 |
| AD-26740 | uGuuGGAuuGAuucGAAAu | 551 | AUUUCGAAUcAAUCcAAcA | 1210 | 1798 |
| AD-26741 | uGccAuuccAcGAcuAGuu | 552 | AACuAGUCGUGGAAUGGcA | 1211 | 1861 |
| AD-26742 | uuccAcGAcuAGuucAGuu | 553 | AACUGAACuAGUCGUGGAA | 1212 | 1866 |
| AD-26743 | AcGAcuAGuucAGuuGcuu | 554 | AAGcAACUGAACuAGUCGU | 1213 | 1870 |
| AD-26744 | AcuAGuucAGuuGcuuGuu | 555 | AAcAAGcAACUGAACuAGU | 1214 | 1873 |
| AD-26745 | GuuGcuuGuuGuGcAcAu | 556 | AUGUGcACGAAcAAGcAAC | 1215 | 1882 |
| AD-26746 | uGuuGcAcAucAGGAu | 557 | AUCCUGAUGUGcACGAAC | 1216 | 1888 |
| AD-26747 | GuucGuGcAcAucAGGAuA | 558 | uAUCCUGAUGUGcACGAAC | 1217 | 1889 |
| AD-26748 | GGuGGGAcAcAGcAGcAAu | 559 | AUUGCUGCUGUGUCCcACC | 1218 | 1928 |
| AD-26749 | GuGGGAcAcAGcAGcAAuu | 560 | AAUUGCUGCUGUGUCCcAC | 1219 | 1929 |
| AD-26750 | uGGGAcAcAGcAGcAAuuu | 561 | AAAUUGCUGCUGUGUCCcA | 1220 | 1930 |
| AD-26751 | GGGGuccGcAuGGAAGAAA | 562 | UUUCUUCcAUGCGGACCCC | 1221 | 1955 |
| AD-26752 | GGGuccGcAuGGAAGAAAu | 563 | AUUUCUUCcAUGCGGACCC | 1222 | 1956 |
| AD-26753 | ucAcAuccuAGcucGGGAu | 564 | AUCCCGAGCuAGGAUGUGA | 1223 | 1999 |
| AD-26754 | cAuccuAGcucGGGAuGcAA | 565 | AAcAUCCCGAGCuAGGAUG | 1224 | 2002 |
| AD-26755 | uAGcucGGGAuGuucAcAA | 566 | UUGUGAAcAUCCCGAGCuA | 1225 | 2007 |
| AD-26756 | GGGAuGuucAcAAccGAAu | 567 | AUUCGGUUGUGAAcAUCCC | 1226 | 2013 |
| AD-26757 | GGAuGuucAcAAccGAAuu | 568 | AAUUCGGUUGUGAAcAUCC | 1227 | 2014 |
| AD-26758 | cAGAGGAcuAAAAuAccAuu | 569 | AAUGGuAUUuAGUCCUCUG | 1228 | 2038 |
| AD-26759 | GGAcuAAAAuAccAuuGuu | 570 | AUGGAAUGGuAUUuAGUCC | 1229 | 2042 |
| AD-26760 | uAAAAuAccAuuccAuuGuu | 571 | AAcAAUGGAAUGGuAUUuA | 1230 | 2046 |
| AD-26761 | AAAAuAccAuuccAuuGuuu | 572 | AAAcAAUGGAAUGGuAUUU | 1231 | 2047 |
| AD-26762 | AuuGuuuGuGcAGcuGcuu | 573 | AAGcAGCUGcAcAAAcAAU | 1232 | 2059 |
| AD-26763 | uuGuuuGuGcAGcuGcuuu | 574 | AAAGcAGCUGcAcAAAcAA | 1233 | 2060 |
| AD-26764 | uGuuuGuGcAGcuGcuuuA | 575 | uAAAGcAGCUGcAcAAAcA | 1234 | 2061 |
| AD-26765 | GuuuGuGcAGcuGcuuuAu | 576 | AuAAAGcAGCUGcAcAAAC | 1235 | 2062 |
| AD-26766 | uuuGuGcAGcuGcuuuAuu | 577 | AAuAAAGcAGCUGcAcAAA | 1236 | 2063 |
| AD-26767 | AGcuGuuuAuucucccAuu | 578 | AUGGGAGAAuAAAcAGCU | 1237 | 2070 |
| AD-26768 | GcuGuuuAuucucccAuuu | 579 | AAUGGGAGAAuAAAGcAGC | 1238 | 2071 |
| AD-26769 | uuuAuucucccAuuGAAAA | 580 | UUUUcAUGGGAGAAuAAA | 1239 | 2076 |
| AD-26770 | AuucucccAuuGAAAAcAu | 581 | AUGUUUUcAUGGGAGAAU | 1240 | 2079 |
| AD-26771 | ucccAuuGAAAAcAuccAA | 582 | UUGGAUGUUUUcAUGGGA | 1241 | 2083 |
| AD-26772 | uGcAGGGGuccucuGuGAA | 583 | UUcAcAGAGGACCCCUGcA | 1242 | 2110 |

TABLE 3-continued

Beta-Catenin RNAi agents: Example Modified Sequences

| | | | | | |
|---|---|---|---|---|---|
| AD-26773 | AcuuGcucAGGAcAAGGAA | 584 | UUCCUUGUCCUGAGcAAGU | 1243 | 2128 |
| AD-26774 | cAGcuccucuGAcAGAGuu | 585 | AACUCUGUcAGAGGAGCUG | 1244 | 2178 |
| AD-26775 | AGcuccucuGAcAGAGuuA | 586 | uAACUCUGUcAGAGGAGCU | 1245 | 2179 |
| AD-26776 | uccucuGAcAGAGuuAcuu | 587 | AAGuAACUCUGUcAGAGGA | 1246 | 2182 |
| AD-26777 | AcAGAGuuAcuuAcucuA | 588 | uAGAGUGAAGuAACUCUGU | 1247 | 2189 |
| AD-26778 | AGuuAcuuAcucuAGGAA | 589 | UUCCuAGAGUGAAGuAACU | 1248 | 2193 |
| AD-26779 | GuuAcuuAcucuAGGAAu | 590 | AUUCCuAGAGUGAAGuAAC | 1249 | 2194 |
| AD-26780 | AcuucAcucuAGGAAuGAA | 591 | UUcAUUCCuAGAGUGAAGU | 1250 | 2197 |
| AD-26781 | GcuGcuGuuuuGuuccGAA | 592 | UUCGGAAcAAAAcAGcAGC | 1251 | 2234 |
| AD-26782 | cuGcuGuuuuGuuccGAAu | 593 | AUUCGGAAcAAAAcAGCAG | 1252 | 2235 |
| AD-26783 | GucuGAGGAcAAGccAcAA | 594 | UUGUGGCUUGUCCUcAGAC | 1253 | 2254 |
| AD-26784 | uGAGGAcAAGccAcAAGAu | 595 | AUCUUGUGGCUUGUCCUcA | 1254 | 2257 |
| AD-26785 | AcAAGccAcAAGAuuAcAA | 596 | UUGuAAUCUUGUGGCUUGU | 1255 | 2262 |
| AD-26786 | AGccAcAAGAuuAcAAGAA | 597 | UUCUUUGuAAUCUUGUGGCU | 1256 | 2265 |
| AD-26787 | AGAuuAcAAGAAAcGGcuu | 598 | AAGCCGUUUCUUGuAAUCU | 1257 | 2272 |
| AD-26788 | cAAGAAAcGGcuuucAGAA | 599 | AACUGAAAGCCGUUUCUUG | 1258 | 2278 |
| AD-26789 | AGcuGAccAGcucucucuu | 600 | AAGAGAGAGCUGGUcAGCU | 1259 | 2298 |
| AD-26790 | AccAGcucucucuucAGAA | 601 | UUCUGAAGAGAGAGCUGGU | 1260 | 2303 |
| AD-26791 | uAuuGGuGcccAGGGAGAA | 602 | UUCUCCCUGGGcAccAAuA | 1261 | 2365 |
| AD-26792 | cAGGGAGAAcccuuGGAu | 603 | AUCcAAGGGGUUCUCCCUG | 1262 | 2375 |
| AD-26793 | AGGGAGAAcccuuGGAuA | 604 | uAUCcAAGGGGUUCUCCCU | 1263 | 2376 |
| AD-26794 | ccuuGGAuAucGccAGGAu | 605 | AUCCUGGCGAuAUCcAAGG | 1264 | 2386 |
| AD-26795 | uAucGccAGGAuGAuccuA | 606 | uAGGAUcAUCCUGGCGAuA | 1265 | 2393 |
| AD-26796 | GccAGGAuGAuccuAGcuA | 607 | uAGCuAGGAUcAUCCUGGC | 1266 | 2397 |
| AD-26797 | ccAGGAuGAuccuAGcuAu | 608 | AuAGCuAGGAUcAUCCUGG | 1267 | 2398 |
| AD-26798 | GAuGAuccuAGcuAucGuu | 609 | AACGAuAGCuAGGAUcAUC | 1268 | 2402 |
| AD-26799 | AuccuAGcuAucGuucuuu | 610 | AAAGAACGAuAGCuAGGAU | 1269 | 2406 |
| AD-26800 | uccuAGcuAucGuucuuuu | 611 | AAAAGAACGAuAGCuAGGA | 1270 | 2407 |
| AD-26801 | ucuuuucAcucuGGuGGAu | 612 | AUCcACcAGAGUGAAAAGA | 1271 | 2420 |
| AD-26802 | cuuuucAcucuGGuGGAuA | 613 | uAUCcACcAGAGUGAAAAG | 1272 | 2421 |
| AD-26803 | uuuucAcucuGGuGGAuAu | 614 | AuAUCcAcAGAGUGAAAA | 1273 | 2422 |
| AD-26804 | uGGuGGAuAuGGccAGGAA | 615 | AUCCUGGCcAuAUCcACcA | 1274 | 2431 |
| AD-26805 | GAuGGccAGGAuGccuu | 616 | AAGGcAUCCUGGCcAuAUC | 1275 | 2436 |
| AD-26806 | ccuuGGGuAuGGAccccAu | 617 | AUGGGGUCcAuACCcAAGG | 1276 | 2451 |
| AD-26807 | uGGGuAuGGAccccAuGAu | 618 | AUcAUGGGGUCcAuACCcA | 1277 | 2454 |
| AD-26808 | uuuGuAAAcuuGAuuAAcuA | 619 | uAGUuAAUcAAGUUuAcAA | 1278 | 675 |
| AD-26809 | uGuAAAcuuGAuuAAcuAu | 620 | AuAGUuAAUcAAGUUuAcA | 1279 | 676 |
| AD-26810 | AAAcuuGAuuAAcuAucAA | 621 | UUGAuAGUuAAUcAAGUUU | 1280 | 679 |
| AD-26811 | uAuGGAccccAuGAuGGAA | 622 | UUCcAUcAUGGGGUCcAuA | 1281 | 2458 |
| AD-26812 | GGAccccAuGAuGGAAcAu | 623 | AUGUUCcAUcAUGGGGUCC | 1282 | 2461 |
| AD-26813 | ccAuGAuGGAAcAuGAGAu | 624 | AUCUcAUGUUCcAUcAUGG | 1283 | 2466 |
| AD-26814 | AccAcccuGGuGcuGAcuA | 625 | uAGUcAGcAccAGGGUGGU | 1284 | 2493 |
| AD-26815 | ccAcccuGGuGcuGAcuAu | 626 | AuAGUcAGcAccAGGGUGG | 1285 | 2494 |
| AD-26816 | uGcuGAcuAuccAGuuGAu | 627 | AUcAACUGGAuAGUcAGcA | 1286 | 2503 |
| AD-26817 | AGuuGAuGGGcuGccAGAu | 628 | AUCUGGcAGCCcAUcAACU | 1287 | 2515 |
| AD-26818 | uGcccAGGAccucAuGGAu | 629 | AUCcAUGAGGUCCUGGGcA | 1288 | 2542 |
| AD-26819 | GcAAucAGcuGGccuGGuu | 630 | AACcAGGCcAGCUGAUUGC | 1289 | 2580 |
| AD-26820 | cAAucAGcuGGccuGGuuu | 631 | AAACcAGGCcAGCUGAUUG | 1290 | 2581 |
| AD-26821 | GGuuuGAuAcuGAccuGuA | 632 | uAcAGGUcAGuAUcAAACC | 1291 | 2595 |
| AD-26822 | AuAcuGAccGuAAAucAu | 633 | AUGAUUuAcAGGUcAGuAU | 1292 | 2601 |
| AD-26823 | uGAccuGuAAAucAuccuu | 634 | AAGGAUGAUUuAcAGGUcA | 1293 | 2605 |
| AD-26824 | GAccuGuAAAucAuccuuu | 635 | AAAGGAUGAUUuAcAGGUC | 1294 | 2606 |
| AD-26825 | AccuGuAAAucAuccuuuA | 636 | uAAAGGAUGAUUuAcAGGU | 1295 | 2607 |
| AD-26826 | AAuAcAAAuGAuGuAGAAA | 637 | UUUCuAcAUcAUUUGuAUU | 1296 | 878 |
| AD-26900 | uuuuAAGAuAucuGuAAu | 638 | AUuAcAGAuAUCUuAAAA | 1297 | 2745 |
| AD-26901 | uAcAGcAuuucuAAuuuu | 639 | AAAAUuAGAAAUUGCUGuA | 1298 | 2872 |
| AD-26902 | cAcuAAuucAuAAucAcuc | 640 | GAGUGAUuAUGAAUuAGUG | 1299 | 2915 |
| AD-26903 | AcuAAuucAuAAucAcucu | 641 | AGAGUGAUuAUGAAuuAGU | 1300 | 2916 |
| AD-26904 | uAAuucAuAAucAcucuAA | 642 | UuAGAGUGAUuAUGAAUuA | 1301 | 2918 |
| AD-26905 | AAuucAuAAucAcucuAAu | 643 | AUuAGAGUGAUuAUGAAUU | 1302 | 2919 |
| AD-26906 | AAuuGAAucuGAAuAAAG | 644 | CUUuAUUcAGAUuAcAAUU | 1303 | 2939 |
| AD-26907 | uuuGuAuAAAAuAGAcAAA | 645 | UUUGUCuAUUUuAuAcAAA | 1304 | 2978 |
| AD-26908 | uuGuAAAAAuAGAcAAAu | 646 | AUUUGUCuAUUUuAuAcAA | 1305 | 2979 |
| AD-26909 | uGuAAAAAuAGAcAAAuA | 647 | uAUUUGUCuAUUUuAuAcA | 1306 | 2980 |
| AD-26910 | GuAuAAAAuAGAcAAAuAG | 648 | CuAUUUGUCuAUUUuAuAC | 1307 | 2981 |
| AD-26911 | AuAAAAuAGAcAAAuAGAA | 649 | UUCuAUUUGUCuAUUUuAU | 1308 | 2983 |
| AD-26912 | uAAAAuAGAcAAAuAGAAA | 650 | UUUCuAUUUGUCuAUUUuA | 1309 | 2984 |
| AD-26913 | AAAAuAGAcAAAuAGAAAu | 651 | AUUUCuAUUUGUCuAUUU | 1310 | 2986 |
| AD-26914 | uGGGAuAuGuAuGGGuAGG | 652 | CCuACCcAuAcAuAUCCcA | 1311 | 3081 |
| AD-26915 | GGGAuAuGuAuGGGuAGGG | 653 | CCCuACCcAuAcAuAUCCC | 1312 | 3082 |
| AD-26916 | cuAuucAuAAucAcucuA | 654 | uAGAGUGAUuAUGAAuuAG | 1313 | 2917 |
| AD-26917 | AAAuAGAAAuGGuccAAu | 655 | AUUGGAccAUUUCuAUUU | 1314 | 2994 |
| AD-26918 | AAuAGAAAAuGGuccAAuu | 656 | AAUUGGACcAUUUCuAUU | 1315 | 2995 |
| AD-26919 | uuuGGAcAGuuuAccAGuu | 657 | AACUGGuAAACUGUCcAAA | 1316 | 3134 |

TABLE 3-continued

Beta-Catenin RNAi agents: Example Modified Sequences

| | | | | | |
|---|---|---|---|---|---|
| AD-26920 | AuucuuucuAAccucAcuu | 658 | AAGUGAGGUuUAGAAAGAAU | 1317 | 1535 |
| AD-26921 | uGGAuuGAuucGAAAucuu | 659 | AAGAUUUCGAAUcAAUCcA | 1318 | 1801 |
| Set1 254 A 22 S26 | ccAtAcAActGttttGAAA | 6141 | TTTcAAAAcAGTTGtATGG | 6309 | 236 |
| Set1 703 A 22 S26 | GAttAActAtcAAGAtGAt | 6142 | ATcATCTTGAtAGTtAATC | 6310 | 685 |
| Set1 709 A 22 S26 | ctAtcAAGAtGAtGcAGAA | 6143 | TTCTGcATCATCTTGAtAG | 6311 | 691 |
| Set1 895 A 22 S26 | GAAtAcAAAtGAtGtAGAA | 6144 | TTCtAcATcATTTGtATTC | 6312 | 877 |
| Set1 1816 A 22 S26 | tGttGGAttGAttcGAAAt | 6145 | ATTTCGAAtcAATCcAAcA | 6313 | 1798 |
| Set1 1974 A 22 S26 | GGGtccGcAtGGAAGAAAt | 6146 | ATTTCTTCcATGCGGACCC | 6314 | 1956 |
| Set1 2425 A 22 S26 | tcctAGctAtcGttcttttt | 6147 | AAAAGAACGAtAGCtAGGA | 6315 | 2407 |
| Set1 3146 A 22 S26 | AAGtGAAGAAtGcAcAAGA | 6148 | TCTTGTGcATTCTTcACTT | 6316 | 3128 |
| Set1 889 A 22 S26 | cAtGcAGAAtAcAAAtGAt | 6149 | ATcATTTGtATTCTGcATG | 6317 | 871 |
| Set1 1814 A 22 S26 | ActGttGGAttGAttcGAA | 6150 | TTCGAAtcAATCcAAcAGT | 6318 | 1796 |
| Set1 1245 A 22 S26 | GAccccAAGctttAGtAAA | 6151 | TTtACtAAAGCTTGGGGTC | 6319 | 1227 |
| Set1 3196 A 22 S26 | AGccttGcttGttAAAttt | 6152 | AAATTtAAcAAGcAAGGCT | 6320 | 3178 |
| Set1 1450 A 22 S26 | ttcAGAtGctGcAActAAA | 6153 | TTtAGTTGcAGcATCTGAA | 6321 | 1432 |
| Set1 3169 A 22 S26 | AtcAcAAGAtGGAAttttAt | 6154 | AtAAATTCcATCTTGTGAT | 6322 | 3151 |
| Set1 3477 A 22 S26 | AAtAGAAAAtGGtccAAtt | 6155 | AATTGGAccATTTTCtATT | 6323 | 3459 |
| Set1 865 A 22 S26 | GAtGGtGtctGctAttGtA | 6156 | tAcAAtAGcAGAcACcATC | 6324 | 847 |
| Set1 1249 A 22 S26 | ccAAGctttAGtAAAtAtA | 6157 | tAtATTtACtAAAGCTTGG | 6325 | 1231 |
| Set1 1250 A 22 S26 | cAAGctttAGtAAAtAtAA | 6158 | TtAtATTtACtAAAGCTTG | 6326 | 1232 |
| Set1 2202 A 22 S26 | ctctGAcAGAGttActtcA | 6159 | TGAAGtAAcTcTGTcAGAG | 6327 | 2184 |
| Set1 1545 A 22 S26 | cAGctGGAAttctttctAA | 6160 | TtAGAAAGAATTCcAGCTG | 6328 | 1527 |
| Set1 1755 A 22 S26 | GActAccAGttGtGGttAA | 6161 | TtAACcAcAACTGGtAGTC | 6329 | 1737 |
| Set1 254 A 25 S27 | CCATACAACTGTTTTGAAA | 6162 | TTTCAAAACAGTTGTATGG | 6330 | 236 |
| Set1 703 A 25 S27 | GATTAACTATCAAGATGAT | 6163 | ATCATCTTGATAGTTAATC | 6331 | 685 |
| Set1 709 A 25 S27 | CTATCAAGATGATGCAGAA | 6164 | TTCTGCATCATCTTGATAG | 6332 | 691 |
| Set1 895 A 25 S27 | GAATACAAATGATGTAGAA | 6165 | TTCTACATCATTTGTATTC | 6333 | 877 |
| Set1 1816 A 25 S27 | TGTTGGATTGATTCGAAAT | 6166 | ATTTCGAATCAATCCAACA | 6334 | 1798 |
| Set1 1974 A 25 S27 | GGGTCCGCATGGAAGAAAT | 6167 | ATTTCTTCCATGCGGACCC | 6335 | 1956 |
| Set1 2425 A 25 S27 | TCCTAGCTATCGTTCTTTT | 6168 | AAAAGAACGATAGCTAGGA | 6336 | 2407 |

TABLE 3-continued

Beta-Catenin RNAi agents: Example Modified Sequences

| | | | | | |
|---|---|---|---|---|---|
| Set1 3146 A 25 S27 | AAGTGAAGAATGCACAAGA | 6169 | TCTTGTGCATTCTTCACTT | 6337 | 3128 |
| Set1 889 A 25 S27 | CATGCAGAATACAAATGAT | 6170 | ATCATTTGTATTCTGCATG | 6338 | 871 |
| Set1 1814 A 25 S27 | ACTGTTGGATTGATTCGAA | 6171 | TTCGAATCAATCCAACAGT | 6339 | 1796 |
| Set1 1245 A 25 S27 | GACCCCAAGCTTTAGTAAA | 6172 | TTTACTAAAGCTTGGGGTC | 6340 | 1227 |
| Set1 3196 A 25 S27 | AGCCTTGCTTGTTAAATTT | 6173 | AAATTTAACAAGCAAGGCT | 6341 | 3178 |
| Set1 1450 A 25 S27 | TTCAGATGCTGCAACTAAA | 6174 | TTTAGTTGCAGCATCTGAA | 6342 | 1432 |
| Set1 3169 A 25 S27 | ATCACAAGATGGAATTTAT | 6175 | ATAAATTCCATCTTGTGAT | 6343 | 3151 |
| Set1 3477 A 25 S27 | AATAGAAAATGGTCCAATT | 6176 | AATTGGACCATTTTCTATT | 6344 | 3459 |
| Set1 865 A 25 S27 | GATGGTGTCTGCTATTGTA | 6177 | TACAATAGCAGACACCATC | 6345 | 847 |
| Set1 1249 A 25 S27 | CCAAGCTTTAGTAAATATA | 6178 | TATATTTACTAAAGCTTGG | 6346 | 1231 |
| Set1 1250 A 25 S27 | CAAGCTTTAGTAAATATAA | 6179 | TTATATTTACTAAAGCTTG | 6347 | 1232 |
| Set1 2202 A 25 S27 | CTCTGACAGAGTTACTTCA | 6180 | TGAAGTAACTCTGTCAGAG | 6348 | 2184 |
| Set1 1545 A 25 S27 | CAGCTGGAATTCTTTCTAA | 6181 | TTAGAAAGAATTCCAGCTG | 6349 | 1527 |
| Set1 1755 A 25 S27 | GACTACCAGTTGTGGTTAA | 6182 | TTAACCACAACTGGTAGTC | 6350 | 1737 |
| Set1 254 A L0 V1 S26 | ccAtAcAActGttttGAAA | 6183 | TTtcAAAAcAGttGtAtGG | 6351 | 236 |
| Set1 703 A L0 V1 S26 | GAttAActAtcAAGAtGAt | 6184 | ATcAtcttGAtAGTtAAtc | 6352 | 685 |
| Set1 709 A L0 V1 S26 | ctAtcAAGAtGAtGcAGAA | 6185 | TTctGcAtcAtctTGAtAG | 6353 | 691 |
| Set1 895 A L0 V1 S26 | GAAtAcAAAtGAtGtAGAA | 6186 | TTctAcAtcAtttGtAttc | 6354 | 877 |
| Set1 1816 A L0 V1 S26 | tGttGGAttGAttcGAAAt | 6187 | ATttcGAAtcAAtCcAAcA | 6355 | 1798 |
| Set1 1974 A L0 V1 S26 | GGGtccGcAtGGAAGAAAt | 6188 | ATttcttccAtGcGGAccc | 6356 | 1956 |
| Set1 2425 A L0 V1 S26 | tcctAGctAtcGttcttt | 6189 | AAAAGAAcGAtAGCtAGGA | 6357 | 2407 |
| Set1 3146 A L0 V1 S26 | AAGtGAAGAAtGcAcAAGA | 6190 | TCttGtGcAttctTcActt | 6358 | 3128 |
| Set1 889 A L0 V1 S26 | cAtGcAGAAtAcAAAtGAt | 6191 | ATcAtttGtAttcTGcAtG | 6359 | 871 |
| Set1 1814 A L0 V1 S26 | ActGttGGAttGAttcGAA | 6192 | TTcGAAtcAAtccAAcAGt | 6360 | 1796 |

TABLE 3-continued

Beta-Catenin RNAi agents: Example Modified Sequences

| | | | | | |
|---|---|---|---|---|---|
| Set1 1245 A LO V1 S26 | GAccccAAGctttAGtAAA | 6193 | TTtActAAAGcttGGGGtc | 6361 | 1227 |
| Set1 3196 A LO V1 S26 | AGccttGcttGttAAAttt | 6194 | AAAtttAAcAAGcAAGGct | 6362 | 3178 |
| Set1 1450 A LO V1 S26 | ttcAGAtGctGcAActAAA | 6195 | TTtAGttGcAGcATctGAA | 6363 | 1432 |
| Set1 3169 A LO V1 S26 | AtcAcAAGAtGGAAtttAt | 6196 | ATAAAttccAtctTGtGAt | 6364 | 3151 |
| Set1 3477 A LO V1 S26 | AAtAGAAAAtGGtccAAtt | 6197 | AAttGGAccAtttTctAtt | 6365 | 3459 |
| Set1 865 A LO V1 S26 | GAtGGtGtctGctAttGtA | 6198 | TAcAAtAGcAGAcAccAtc | 6366 | 847 |
| Set1 1249 A LO V1 S26 | ccAAGctttAGtAAAtAtA | 6199 | TAtAtttActAAAGcttGG | 6367 | 1231 |
| Set1 1250 A LO V1 S26 | cAAGctttAGtAAAtAtAA | 6200 | TTAtAtttActAAAGcttG | 6368 | 1232 |
| Set1 2202 A LO V1 S26 | ctctGAcAGAGttActtcA | 6201 | TGAAGtAActctGTcAGAG | 6369 | 2184 |
| Set1 1545 A LO V1 S26 | cAGctGGAAttctttctAA | 6202 | TTAGAAAGAAttcCAGctG | 6370 | 1527 |
| Set1 1755 A LO V1 S26 | GActAccAGttGtGGttAA | 6203 | TTAAccAcAActGGtAGtc | 6371 | 1737 |
| Set1 254 A LO V2 S LO V1 | ccAtACAaCTGtTTtGAaa | 6204 | TTtCAAaCaGTtGTATgg | 6372 | 236 |
| Set1 703 A LO V2 S LO V1 | gaTtAACtATCaAGaTGat | 6205 | ATcATCtTGaTAgTTAAtc | 6373 | 685 |
| Set1 709 A LO V2 S LO V1 | ctAtCAAgATGaTGcAGaa | 6206 | TTcTGCaTCaTCtTGATag | 6374 | 691 |
| Set1 895 A LO V2 S LO V1 | gaAtACAaATGaTGtAGaa | 6207 | TTcTACaTCaTTtGTATtc | 6375 | 877 |
| Set1 1816 A LO V2 S LO V1 | tgTtGGAtTGaTCgAAat | 6208 | ATtTCGaATCaATCCAAca | 6376 | 1798 |
| Set1 1974 A LO V2 S LO V1 | ggGtCCGcATGgAAgAAat | 6209 | ATtTCTtCCaTGcGGACcc | 6377 | 1956 |
| Set1 2425 A LO V2 S LO V1 | tcCtAGCtATCgTTcTTtt | 6210 | AAaAGAaCGaTAgCTAGga | 6378 | 2407 |
| Set1 3146 A LO V2 S LO V1 | aaGtGAAgAATgCAcAAga | 6211 | TCtTGTgCAtTCtTCACtt | 6379 | 3128 |
| Set1 889 A LO V2 S LO V1 | caTgCAGaATAcAAaTGat | 6212 | ATcATTtGTaTTcTGCAtg | 6380 | 871 |
| Set1 1814 A LO V2 S LO V1 | acTgTTGgATTgATtCGaa | 6213 | TTcGAAtCAaTCcAACAgt | 6381 | 1796 |

TABLE 3-continued

Beta-Catenin RNAi agents: Example Modified Sequences

| | | | | | |
|---|---|---|---|---|---|
| Set1 1245 A LO V2 S LO V1 | gaCcCCAaGCTtTAgTAaa | 6214 | TTtACTaAAgCTtGGGGtc | 6382 | 1227 |
| Set1 3196 A LO V2 S LO V1 | agCcTTGcTTGtTAaATtt | 6215 | AAaTTTaACaAGcAAGGct | 6383 | 3178 |
| Set1 1450 A LO V2 S LO V1 | ttCaGATgCTGcAAcTAaa | 6216 | TTtAGTtGCaGCaTCTGaa | 6384 | 1432 |
| Set1 3169 A LO V2 S LO V1 | atCaCAAgATGgAAtTTat | 6217 | ATaAATtCCaTCtTGTGat | 6385 | 3151 |
| Set1 3477 A LO V2 S LO V1 | aaTaGAAaATGgTCcAAtt | 6218 | AAtGGaCCaTTtTCTAtt | 6386 | 3459 |
| Set1 865 A LO V2 S LO V1 | gaTgGTGtCTGcTAtTGta | 6219 | TAcAATaGCaGAcACCAtc | 6387 | 847 |
| Set1 1249 A LO V2 S LO V1 | ccAaGCTtTAGtAAaTAta | 6220 | TAtATTtACtAAaGCTTgg | 6388 | 1231 |
| Set1 1250 A LO V2 S LO V1 | caAgCTTtAGTaAAtATaa | 6221 | TTaTATtTAcTAaAGCTtg | 6389 | 1232 |
| Set1 2202 A LO V2 S LO V1 | ctCtGACaGAGtTAcTTca | 6222 | TGaAGTaACtCTgTCAGag | 6390 | 2184 |
| Set1 1545 A LO V2 S LO V1 | caGcTGGaATTcTTtCTaa | 6223 | TTaGAAaGAaTTcCAGCtg | 6391 | 1527 |
| Set1 1755 A LO V2 S LO V1 | gaCtACCaGTTgTGgTTaa | 6224 | TTaACCaCAaCTgGTAGtc | 6392 | 1737 |
| Set2 254 A LO V3 S LO V2 | ccAtACAaCTGtTTtGAaa | 6225 | TTtCAAaACaGTtGTATgg | 6393 | 236 |
| Set2 703 A LO V3 S LO V2 | gaTtAACtATCaAGaTGat | 6226 | ATcATCtTGaTAgTTAAtc | 6394 | 685 |
| Set2 709 A LO V3 S LO V2 | ctAtCAAgATGaTGcAGaa | 6227 | TTcTGCaTCaTCtTGATag | 6395 | 691 |
| Set2 895 A LO V3 S LO V2 | gaAtACAaATGaTGtAGaa | 6228 | TTcTACaTCaTTtGTATtc | 6396 | 877 |
| Set2 1816 A LO V3 S LO V2 | tgTtGGAtTGAtTCgAAat | 6229 | ATtTCGaATcAAtCCAAca | 6397 | 1798 |
| Set2 1974 A LO V3 S LO V2 | ggGtCCGcATGgAAgAAat | 6230 | ATtTCTtCCaTGcGGACcc | 6398 | 1956 |
| Set2 2425 A LO V3 S LO V2 | tcCtAGCtATCgTTcTTtt | 6231 | AAaAGAaCGaTAgCTAGga | 6399 | 2407 |
| Set2 3146 A LO V3 S LO V2 | aaGtGAAgAATgCAcAAga | 6232 | TCtTGTgCAtTCtTCACtt | 6400 | 3128 |
| Set2 889 A LO V3 S LO V2 | caTgCAGaATAcAAaTGat | 6233 | ATcATTtGTaTTcTGCAtg | 6401 | 871 |
| Set2 1814 A LO V3 S LO V2 | acTgTTGgATTgATtCGaa | 6234 | TTcGAAtCAaTCcAACAgt | 6402 | 1796 |

TABLE 3-continued

Beta-Catenin RNAi agents: Example Modified Sequences

| | | | | | |
|---|---|---|---|---|---|
| Set2 1245 A LO V3 S LO V2 | gaCcCCAaGCTtTAgTAaa | 6235 | TTtACTaAAgCTtGGGGtc | 6403 | 1227 |
| Set2 3196 A LO V3 S LO V2 | agCcTTGcTTGtTAaATtt | 6236 | AAaTTTaACaAGcAAGGct | 6404 | 3178 |
| Set2 1450 A LO V3 S LO V2 | ttCaGATgCTGcAAcTAaa | 6237 | TTtAGTtGCaGCaTCTGaa | 6405 | 1432 |
| Set2 3169 A LO V3 S LO V2 | atCaCAAgATGgAAtTTat | 6238 | ATaAATtCCaTCtTGTGat | 6406 | 3151 |
| Set2 3477 A LO V3 S LO V2 | aaTaGAAaATGgTCcAAtt | 6239 | AAtGGaCCaTTtTCTAtt | 6407 | 3459 |
| Set2 865 A LO V3 S LO V2 | gaTgGTGtCTGcTAtTGta | 6240 | TAcAATaGCaGAcACCAtc | 6408 | 847 |
| Set2 1249 A LO V3 S LO V2 | ccAaGCTtTAGtAAaTAta | 6241 | TAtATTtACtAAaGCTTgg | 6409 | 1231 |
| Set2 1250 A LO V3 S LO V2 | caAgCTTtAGTaAaTATaa | 6242 | TTaTATtTAcTAaAGCTtg | 6410 | 1232 |
| Set2 2202 A LO V3 S LO V2 | ctCtGACAGAGTTAcTTca | 6243 | TGaAGTaACtCTgTCAGag | 6411 | 2184 |
| Set2 1545 A LO V3 S LO V2 | caGcTGGaATTcTTtCTaa | 6244 | TTaGAAaGAaTTcCAGCtg | 6412 | 1527 |
| Set2 1755 A LO V3 S LO V2 | gaCtACCaGTTgTGgTTaa | 6245 | TTaACCaCAaCTgGTAGtc | 6413 | 1737 |
| Set2 254 A LO V4 S LO V1 | ccAtACAaCTGtTTtGAaa | 6246 | tTtCAAaACaGTtGTATgg | 6414 | 236 |
| Set2 703 A LO V4 S LO V1 | gaTtAACtATCaAGaTGat | 6247 | aTcATCtTGaTAgTTAAtc | 6415 | 685 |
| Set2 709 A LO V4 S LO V1 | ctAtCAAgATGaTGcAGaa | 6248 | tTcTGCaTCaTCtTGATag | 6416 | 691 |
| Set2 895 A LO V4 S LO V1 | gaAtACAaATGaTGtAGaa | 6249 | tTcTACaTCaTTtGTATtc | 6417 | 877 |
| Set2 1816 A LO V4 S LO V1 | tgTtGGAtTGaTtCgAAat | 6250 | aTtTCGaATCaAtCCAAca | 6418 | 1798 |
| Set2 1974 A LO V4 S LO V1 | ggGtCCGcATGgAAgAAat | 6251 | aTtTCTtCCaTGcGGACcc | 6419 | 1956 |
| Set2 2425 A LO V4 S LO V1 | tcCtAGCtATCgTTcTTtt | 6252 | aAaAGAaCGaTAgCTAGga | 6420 | 2407 |
| Set2 3146 A LO V4 S LO V1 | aaGtGAAgAATgCAcAAga | 6253 | tCtTGTgCAtTCtTCACtt | 6421 | 3128 |
| Set2 889 A LO V4 S LO V1 | caTgCAGaATAcAAaTGat | 6254 | aTcATTtGTaTTcTGCAtg | 6422 | 871 |
| Set2 1814 A LO V4 S LO V1 | acTgTTGgATTgATtCGaa | 6255 | tTcGAAtCAaTCcAACAgt | 6423 | 1796 |

TABLE 3-continued

Beta-Catenin RNAi agents: Example Modified Sequences

| | | | | | |
|---|---|---|---|---|---|
| Set2 1245 A LO V4 S LO V1 | gaCcCCAaGCTtTAgTAaa | 6256 | tTtACTaAAgCTtGGGGtc | 6424 | 1227 |
| Set2 3196 A LO V4 S LO V1 | agCcTTGcTTGtTAaATtt | 6257 | aAaTTTaACaAGcAAGGct | 6425 | 3178 |
| Set2 1450 A LO V4 S LO V1 | ttCaGATgCTGcAAcTAaa | 6258 | tTtAGTtGCaGCaTCTGaa | 6426 | 1432 |
| Set2 3169 A LO V4 S LO V1 | atCaCAAgATGgAAtTTat | 6259 | aTaAATtCCaTCtTGTGat | 6427 | 3151 |
| Set2 3477 A LO V4 S LO V1 | aaTaGAAaATGgTCcAAtt | 6260 | aAtGGaCCaTTtTCTAtt | 6428 | 3459 |
| Set2 865 A LO V4 S LO V1 | gaTgGTGtCTGcTAtTGta | 6261 | tAcAATaGCaGAcACCAtc | 6429 | 847 |
| Set2 1249 A LO V4 S LO V1 | ccAaGCTtTAGtAAaTAta | 6262 | tAtATTtACtAAaGCTTgg | 6430 | 1231 |
| Set2 1250 A LO V4 S LO V1 | caAgCTTtAGTaAAtATaa | 6263 | tTaTATtTAcTAaAGCTtg | 6431 | 1232 |
| Set2 2202 A LO V4 S LO V1 | ctCtGACaGAGtTAcTTca | 6264 | tGaAGTaACtCTgTCAGag | 6432 | 2184 |
| Set2 1545 A LO V4 S LO V1 | caGcTGGaATTcTTtCTaa | 6265 | tTaGAAaGAaTTcCAGCtg | 6433 | 1527 |
| Set2 1755 A LO V4 S LO V1 | gaCtACCaGTTgTGgTTaa | 6266 | tTaACCaCAaCTgGTAGtc | 6434 | 1737 |
| Set2 254 A LO V5 S LO V1 | ccAtACAaCTGtTTtGAaa | 6267 | tTtCAAaACaGTtGTATgg | 6435 | 236 |
| Set2 703 A LO V5 S LO V1 | gaTtAACtATCaAGaTGat | 6268 | aTcATCtTGaTAgTTAAtc | 6436 | 685 |
| Set2 709 A LO V5 S LO V1 | ctAtCAAgATGaTGcAGaa | 6269 | tTcTGCaTCaTCtTGATag | 6437 | 691 |
| Set2 895 A LO V5 S LO V1 | gaAtACAaATGaTGtAGaa | 6270 | tTcTACaTCaTTtGTATtc | 6438 | 877 |
| Set2 1816 A LO V5 S LO V1 | tgTtGGAtTGAtTCgAAat | 6271 | aTtTCGaATcAAtCCAAca | 6439 | 1798 |
| Set2 1974 A LO V5 S LO V1 | ggGtCCGcATGgAAgAAat | 6272 | aTtTCTtCCaTGcGGACcc | 6440 | 1956 |
| Set2 2425 A LO V5 S LO V1 | tcCtAGCtATCgTTcTTtt | 6273 | aAaAGAaCGaTAgCTAGga | 6441 | 2407 |
| Set2 3146 A LO V5 S LO V1 | aaGtGAAgAATgCAcAAga | 6274 | tCtTGTgCAtTCtTCACtt | 6442 | 3128 |
| Set2 889 A LO V5 S LO V1 | caTgCAGaAATAcAAaTGat | 6275 | aTcATTtGTaTTcTGCAtg | 6443 | 871 |
| Set2 1814 A LO V5 S LO V1 | acTgTTGgATTgATtCGaa | 6276 | tTcGAAtCAaTCcAACAgt | 6444 | 1796 |

TABLE 3-continued

Beta-Catenin RNAi agents: Example Modified Sequences

| Set2 1245 A LO V5 S LO V1 | gaCcCCAaGCTtTAgTAaa | 6277 | tTtACTaAAgCTtGGGGtc | 6445 | 1227 |
|---|---|---|---|---|---|
| Set2 3196 A LO V5 S LO V1 | agCcTTGcTTGtTAaATtt | 6278 | aAaTTTaACaAGcAAGGct | 6446 | 3178 |
| Set2 1450 A LO V5 S LO V1 | ttCaGATgCTGcAAcTAaa | 6279 | tTtAGTtGCaGCaTCTGaa | 6447 | 1432 |
| Set2 3169 A LO V5 S LO V1 | atCaCAAgATGgAAtTTat | 6280 | aTaAATtCCaTCtTGTGat | 6448 | 3151 |
| Set2 3477 A LO V5 S LO V1 | aaTaGAAaATGgTCcAAtt | 6281 | aAtTGGaCCaTTtTCTAtt | 6449 | 3459 |
| Set2 865 A LO V5 S LO V1 | gaTgGTGtCTGcTAtTGta | 6282 | tAcAATaGCaGAcACCAtc | 6450 | 847 |
| Set2 1249 A LO V5 S LO V1 | ccAaGCTtTAGtAAaTAta | 6283 | tAtATTtACtAAaGCTTgg | 6451 | 1231 |
| Set2 1250 A LO V5 S LO V1 | caAgCTTtAGTaAAtATaa | 6284 | tTaTATtTAcTAaAGCTtg | 6452 | 1232 |
| Set2 2202 A LO V5 S LO V1 | ctCtGACaGAGtTAcTTca | 6285 | tGaAGTaACtCTgTCAGag | 6453 | 2184 |
| Set2 1545 A LO V5 S LO V1 | caGcTGGaATTcTTtCTaa | 6286 | tTaGAAaGAaTTcCAGCtg | 6454 | 1527 |
| Set2 1755 A LO V5 S LO V1 | gaCtACCaGTTgTGgTTaa | 6287 | tTaACCaCAaCTgGTAGtc | 6455 | 1737 |
| Set2 254 A 48 S26 | ccAtAcAAActGttttGAAA | 6288 | tTTcAAAAcAGTTGtATGG | 6456 | 236 |
| Set2 703 A 48 S26 | GAttAAcTAtcAAGAtGAt | 6289 | aTcATCTTGAtAGTtAATC | 6457 | 685 |
| Set2 709 A 48 S26 | ctAtcAAGAtGAtGcAGAA | 6290 | tTCTGcATcATCTTGAtAG | 6458 | 691 |
| Set2 895 A 48 S26 | GAAtAcAAAtGAtGtAGAA | 6291 | tTCtAcATcATTTGtATTC | 6459 | 877 |
| Set2 1816 A 48 S26 | tGttGGAttGAttcGAAAt | 6292 | aTTTCGAATcAATCcAAcA | 6460 | 1798 |
| Set2 1974 A 48 S26 | GGGtccGcAtGGAAGAAAt | 6293 | aTTTCTTCcATGCGGACCC | 6461 | 1956 |
| Set2 2425 A 48 S26 | tcctAGctAtcGttctttt | 6294 | aAAAGAACGAtAGCtAGGA | 6462 | 2407 |
| Set2 3146 A 48 S26 | AAGtGAAGAAtGcAcAAGA | 6295 | tCTTGTGcATTCTTcACTT | 6463 | 3128 |
| Set2 889 A 48 S26 | cAtGcAGAAtAcAAAtGAt | 6296 | aTcATTTGtATTCTGcATG | 6464 | 871 |
| Set2 1814 A 48 S26 | ActGttGGAttGAttcGAA | 6297 | tTCGAATcAATCcAAcAGT | 6465 | 1796 |
| Set2 1245 A 48 S26 | GAccccAAGctttAGtAAA | 6298 | tTtACtAAAGCTTGGGGTC | 6466 | 1227 |
| Set2 3196 A 48 S26 | AGccttGcttGttAAAttt | 6299 | aAATTtAAcAAGcAAGGCT | 6467 | 3178 |
| Set2 1450 A 48 S26 | ttcAGAtGctGcAActAAA | 6300 | tTtAGTTGcAGcATCTGAA | 6468 | 1432 |

TABLE 3-continued

Beta-Catenin RNAi agents: Example Modified Sequences

| Set2 3169 A 48 S26 | AtcAcAAGAtGGAAtttAt | 6301 | atAAATTCcATCTTGTGAT | 6469 | 3151 |
|---|---|---|---|---|---|
| Set2 3477 A 48 S26 | AAtAGAAAAtGGtccAAtt | 6302 | aATTGGACcATTTTCtATT | 6470 | 3459 |
| Set2 865 A 48 S26 | GAtGGtGtctGctAttGtA | 6303 | tAcAAtAGcAGAcACcATC | 6471 | 847 |
| Set2 1249 A 48 S26 | ccAAGctttAGtAAAtAtA | 6304 | tAtATTtACtAAAGCTTGG | 6472 | 1231 |
| Set2 1250 A 48 S26 | cAAGctttAGtAAAtAtAA | 6305 | ttAtATTtACtAAAGCTTG | 6473 | 1232 |
| Set2 2202 A 48 S26 | ctctGAcAGAGttActtcA | 6306 | tGAAGtAAcTcTGTcAGAG | 6474 | 2184 |
| Set2 1545 A 48 S26 | cAGctGGAAttctttctAA | 6307 | ttAGAAAGAATTCcAGCTG | 6475 | 1527 |
| Set2 1755 A 48 S26 | GActAccAGttGtGGttAA | 6308 | ttAACcAcAACTGGtAGTC | 6476 | 1737 |

| Nickname | First Strand Sequence | SEQ ID NO: | Second Strand Sequence | SEQ ID NO: |
|---|---|---|---|---|
| hs_CTNNB1_1816_AD26740_A22S26 | uGuuGGAuuGAuucGAAAuuu | 6477 | AUUUCGAAUcAAUCcAAcAuu | 6486 |
| hs_CTNNB1_3477_AD-26918-A22S26 | AAuAGAAAAuGGuccAAuuuu | 6478 | AAUUGGACcAUUUUCuAUUuu | 6487 |
| hs_CTNNB1_1814_AD18983_A22S26 | AcuGuuGGAuuGAuucGAAuu | 6479 | UUCGAAUcAAUCcAAcAGUuu | 6488 |
| hs_CTNNB1_709_AD26109_A22S26 | cuAucAAGAuGAuGcAGAAuu | 6480 | UUCUGcAUcAUCUUGAuAGuu | 6489 |
| hs_CTNNB1_254_AD-26034-A22S26 | ccAuAcAAcuGuuuuGAAAuu | 6481 | UUUcAAAAcAGUUGuAUGGuu | 6490 |
| hs_CTNNB1_3169_AD-25944-A22S26 | AucAcAAGAuGGAAuuuAuuu | 6482 | AuAAAUUCcAUCUUGUGAUuu | 6491 |
| hs_CTNNB1_703_AD-26108-A22S26 | AUcAUCUUGAuAGUuAAUCuu | 6483 | uccuAGcuAucGuucuuuuuu | 6492 |
| hs_CTNNB1_2425_AD-26800-A22S26 | uccuAGcuAucGuucuuuuuu | 6484 | AAAAGAACGAuAGCuAGGAuu | 6493 |
| hs_CTNNB1_1974_AD-26752-A22S26 | GGGuccGcAuGGAAGAAAuuu | 6485 | AUUUCUUCcAUGCGGACCCuu | 6494 |

"Position" indicates the position of the RNAi agent in the human Beta-Catenin sequence NM_001098210.1.

The sequences in Table 3 are represented by the abbreviations in Table 3A:

TABLE 3A

| ABBREVIATIONS | |
|---|---|
| Abbreviation[a] | Nucleotide(s) |
| A | adenosine-5'-phosphate |
| C | cytidine-5'-phosphate |
| G | guanosine-5'-phosphate |
| dT | 2'-deoxy-thymidine-5'-phosphate |
| U | uridine-5'-phosphate |
| c | 2'-O-methylcytidine-5'-phosphate |
| u | 2'-O-methyluridine-5'-phosphate |
| sdT | 2'-deoxy Thymidine 5'-phosphorothioate |

Modified and unmodified variants of the RNAi agents of Tables 1, 2 and 3 are easily conceived by one of skill in the art. Unmodified variants include those which do not comprise a modification of the base (such as provided in Table 3). In several cases, a pyrimidine in the sense strand is modified; and/or a pyrimidine preceding a "A" base in the anti-sense strand is modified. Modifications involving other positions (or the absence of a modification at a particular base) are easily conceived.

In general, the sense strand is heavily modified, and the anti-sense strand lightly modified. Some modifications are placed at sites predicted to be sensitive to endonucleases. Some modifications are designed to eliminate an immune response to the RNAi agent while preserving activity. Some modifications serve more than one purpose.

RNAi agents are also on occasion referenced by a "ND" prefix rather than "AD"; thus RNAi agents designated AD-18892 and ND-18892, for example, are identical and comprise the same sequence.

Of the RNAi agents listed herein, many were synthesized, as described in Example 2, and tested in vitro, as described in Example 3.

Example 1A

Overlapping siRNAs

Some of the siRNAs listed above overlap each other in sequence. The following table presents a compilation of groups of RNAi agents, wherein each member of a group overlaps with each other member of the same group by at least 12 nt. A 12-nt portion of the overlap of the sense strands and a 12-nt portion of the overlap of the anti-sense strand are presented. Thus, for example, AD-26022 and AD-26204 share the common technical feature of the sequence of CCUGUUCCCUG (SEQ ID NO: 1319) in the sense strand, and the sequence of CAGGGGAACAGG (SEQ ID NO: 2714) in the anti-sense strand. Note of course that only a 12-nt portion of the overlap is shown; many groups of RNAi agents will overlap by more than 12 nt. The position within the gene is also indicated.

The disclosure also encompasses subgroups of the disclosed groups of overlapping RNAi agents. For example, the disclosure contemplates the group of AD-26027, AD-26024, AD-26028, AD-26026, AD-26025, which all share the sequences of SEQ ID NOs: 1334 and 2729. However, the disclosure also contemplates all subgroups or partial groups within this group, e.g., AD-26027 and AD-26024; AD-26027, AD-26024, AD-26028, and AD-26026; AD-26028, AD-26026, and AD-26025; AD-26027 and AD-26028; AD-26028 and AD-26025; etc. The disclosure thus encompasses any subgroup within a disclosed group of overlapping RNAi agents. The sequences of members of these subgroups can be combined with any other element disclosed herein (e.g., modification, sets of modification, 5' and/or 3' end cap(s), blunt end(s), overhang(s), ligand(s), additional treatment(s) or method(s), pharmaceutical carrier(s), additional RNAi agent(s), etc.), provided that such combinations are not mutually exclusive (e.g., a RNAi agent comprising two strands cannot by definition have both two blunt ends and two overhangs).

TABLE 4

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 206 | CCUGUUCCCUG | 1319 | CAGGGGAACAGG | 2714 | AD-26022, AD-26204 |
| 207 | CUGUUCCCUGA | 1320 | UCAGGGGAACAG | 2715 | AD-26022, AD-26204 |
| 208 | UGUUCCCUGAG | 1321 | CUCAGGGGAACA | 2716 | AD-26022, AD-26023 |
| 209 | GUUCCCUGAGG | 1322 | CCUCAGGGGAAC | 2717 | AD-26022, AD-26023, AD-26204 |
| 210 | UUCCCUGAGGG | 1323 | CCCUCAGGGGAA | 2718 | AD-26022, AD-26023, AD-26204 |
| 211 | UCCCUGAGGGU | 1324 | ACCCUCAGGGGA | 2719 | AD-26022, AD-26023, AD-26204 |
| 212 | CCCUGAGGGUA | 1325 | UACCCUCAGGGG | 2720 | AD-26022, AD-26023, AD-26204 |
| 213 | CCCUGAGGGUAU | 1326 | AUACCCUCAGGG | 2721 | AD-26022, AD-26023 |
| 214 | CCUGAGGGUAUU | 1327 | AAUACCCUCAGG | 2722 | AD-26024, AD-26023 |
| 215 | CUGAGGGUAUUU | 1328 | AAAUACCCUCAG | 2723 | AD-26024, AD-26025 |
| 216 | UGAGGGUAUUUG | 1329 | CAAAUACCCUCA | 2724 | AD-26024, AD-26026 |
| 217 | GAGGGUAUUUGA | 1330 | UCAAAUACCCUC | 2725 | AD-26024, AD-26025 |
| 218 | AGGGUAUUUGAA | 1331 | UUCAAAUACCCU | 2726 | AD-26024, AD-26026, AD-26025 |
| 219 | GGGUAUUUGAAG | 1332 | CUUCAAAUACCC | 2727 | AD-26024, AD-26026, AD-26025 |
| 220 | GGUAUUUGAAGU | 1333 | ACUUCAAAUACC | 2728 | AD-26027, AD-26024, AD-26026, AD-26025 |
| 221 | GUAUUUGAAGUA | 1334 | UACUUCAAAUAC | 2729 | AD-26027, AD-26024, AD-26028, AD-26026, AD-26025 |
| 222 | UAUUUGAAGUAU | 1335 | AUACUUCAAAUA | 2730 | AD-26027, AD-26028, AD-26026, AD-26025 |
| 223 | AUUUGAAGUAUA | 1336 | UAUACUUCAAAU | 2731 | AD-26027, AD-26028 |
| 224 | UUUGAAGUAUAC | 1337 | GUAUACUUCAAA | 2732 | AD-26027, AD-26029 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 225 | UUGAAGUAUACC | 1338 | GGUAUACUUCAA | 2733 | AD-26029, AD-26028 |
| 226 | UGAAGUAUACCA | 1339 | UGGUAUACUUCA | 2734 | AD-26027, AD-26029, AD-26028 |
| 227 | GAAGUAUACCAU | 1340 | AUGGUAUACUUC | 2735 | AD-26027, AD-26029, AD-26028 |
| 228 | AAGUAUACCAUA | 1341 | UAUGGUAUACUU | 2736 | AD-26029, AD-26028 |
| 229 | AGUAUACCAUAC | 1342 | GUAUGGUAUACU | 2737 | AD-26029, AD-26030 |
| 230 | GUAUACCAUACA | 1343 | UGUAUGGUAUAC | 2738 | AD-26031, AD-26029, AD-26030 |
| 231 | UAUACCAUACAA | 1344 | UUGUAUGGUAUA | 2739 | AD-26032, AD-26031, AD-26029, AD-26030 |
| 232 | AUACCAUACAAC | 1345 | GUUGUAUGGUAU | 2740 | AD-26032, AD-26031 |
| 233 | UACCAUACAACU | 1346 | AGUUGUAUGGUA | 2741 | AD-26032, AD-26031, AD-26030 |
| 234 | ACCAUACAACUG | 1347 | CAGUUGUAUGGU | 2742 | AD-26032, AD-26031, AD-26033, AD-26030 |
| 235 | CCAUACAACUGU | 1348 | ACAGUUGUAUGG | 2743 | AD-26032, AD-26034, AD-26031, AD-26033, AD-26030 |
| 236 | CAUACAACUGUU | 1349 | AACAGUUGUAUG | 2744 | AD-26032, AD-26034, AD-26031, AD-26033, AD-26030 |
| 237 | AUACAACUGUUU | 1350 | AAACAGUUGUAU | 2745 | AD-26032, AD-26034, AD-26031, AD-26033 |
| 238 | UACAACUGUUUU | 1351 | AAAACAGUUGUA | 2746 | AD-26032, AD-26034, AD-26033 |
| 239 | ACAACUGUUUUG | 1352 | CAAAACAGUUGU | 2747 | AD-26034, AD-26033 |
| 240 | CAACUGUUUUGA | 1353 | UCAAAACAGUUG | 2748 | AD-26034, AD-26033 |
| 241 | AACUGUUUUGAA | 1354 | UUCAAAACAGUU | 2749 | AD-26034, AD-26033 |
| 250 | GAAAUCCAGCG | 1355 | CGCUGGAUUUUC | 2750 | AD-19763, AD-26035 |
| 251 | AAAUCCAGCGU | 1356 | ACGCUGGAUUUU | 2751 | AD-26036, AD-19763, AD-26035 |
| 252 | AAAUCCAGCGUG | 1357 | CACGCUGGAUUU | 2752 | AD-26036, AD-19763, AD-26035 |
| 253 | AAUCCAGCGUGG | 1358 | CCACGCUGGAUU | 2753 | AD-26036, AD-26035 |
| 254 | AUCCAGCGUGGA | 1359 | UCCACGCUGGAU | 2754 | AD-26036, AD-26035 |
| 255 | UCCAGCGUGGAC | 1360 | GUCCACGCUGGA | 2755 | AD-26036, AD-26035 |
| 256 | CCAGCGUGGACA | 1361 | UGUCCACGCUGG | 2756 | AD-26036, AD-26035, AD-26037 |
| 257 | CAGCGUGGACAA | 1362 | UUGUCCACGCUG | 2757 | AD-26036, AD-26035, AD-26037 |
| 258 | AGCGUGGACAAU | 1363 | AUUGUCCACGCU | 2758 | AD-26036, AD-26037 |
| 261 | GUGGACAAUGGC | 1364 | GCCAUUGUCCAC | 2759 | AD-26038, AD-26037 |
| 262 | UGGACAAUGGCU | 1365 | AGCCAUUGUCCA | 2760 | AD-26038, AD-26037 |
| 263 | GGACAAUGGCUA | 1366 | UAGCCAUUGUCC | 2761 | AD-26038, AD-26037 |

TABLE 4-continued

Groups of overlapping RNAi agents to Beta-Catenin

| Position | Sense overlap | SEQ ID NO: Anti-sense overlap | | SEQ ID NO: | Overlapping groups of RNAi agents |
|---|---|---|---|---|---|
| 264 | GACAAUGGCUAC | 1367 | GUAGCCAUUGUC | 2762 | AD-18896, AD-26038 |
| 265 | ACAAUGGCUACU | 1368 | AGUAGCCAUUGU | 2763 | AD-18896, AD-26038, AD-18953 |
| 266 | CAAUGGCUACUC | 1369 | GAGUAGCCAUUG | 2764 | AD-18896, AD-26038, AD-18953 |
| 267 | AAUGGCUACUCA | 1370 | UGAGUAGCCAUU | 2765 | AD-18896, AD-26038, AD-18953 |
| 268 | AUGGCUACUCAA | 1371 | UUGAGUAGCCAU | 2766 | AD-18896, AD-26038, AD-18953, AD-26040 |
| 269 | UGGCUACUCAAG | 1372 | CUUGAGUAGCCA | 2767 | AD-18896, AD-26041, AD-18953, AD-26040 |
| 270 | GGCUACUCAAGC | 1373 | GCUUGAGUAGCC | 2768 | AD-18896, AD-26041, AD-26039, AD-18953, AD-26040 |
| 271 | GCUACUCAAGCU | 1374 | AGCUUGAGUAGC | 2769 | AD-18896, AD-26041, AD-18953, AD-26040 |
| 272 | CUACUCAAGCUG | 1375 | CAGCUUGAGUAG | 2770 | AD-26041, AD-26042, AD-18953, AD-26040 |
| 273 | UACUCAAGCUGA | 1376 | UCAGCUUGAGUA | 2771 | AD-26041, AD-26042, AD-26040 |
| 274 | ACUCAAGCUGAU | 1377 | AUCAGCUUGAGU | 2772 | AD-26041, AD-26042, AD-26039, AD-26040 |
| 275 | CUCAAGCUGAUU | 1378 | AAUCAGCUUGAG | 2773 | AD-26041, AD-26042, AD-26040 |
| 276 | UCAAGCUGAUUU | 1379 | AAAUCAGCUUGA | 2774 | AD-26041, AD-26042 |
| 290 | UGGAGUUGGACA | 1380 | UGUCCAACUCCA | 2775 | AD-26043, AD-26044 |
| 291 | GGAGUUGGACAU | 1381 | AUGUCCAACUCC | 2776 | AD-26043, AD-26044 |
| 294 | GUUGGACAUGGC | 1382 | GCCAUGUCCAAC | 2777 | AD-26045, AD-26044 |
| 295 | UUGGACAUGGCC | 1383 | GGCCAUGUCCAA | 2778 | AD-26045, AD-26044 |
| 296 | UGGACAUGGCCA | 1384 | UGGCCAUGUCCA | 2779 | AD-26045, AD-26044 |
| 297 | GGACAUGGCCAU | 1385 | AUGGCCAUGUCC | 2780 | AD-26045, AD-26044 |
| 306 | CAUGGAACCAGA | 1386 | UCUGGUUCCAUG | 2781 | AD-26047, AD-26046 |
| 307 | AUGGAACCAGAC | 1387 | GUCUGGUUCCAU | 2782 | AD-26047, AD-26046 |
| 308 | UGGAACCAGACA | 1388 | UGUCUGGUUCCA | 2783 | AD-26047, AD-26046 |
| 309 | GGAACCAGACAG | 1389 | CUGUCUGGUUCC | 2784 | AD-26047, AD-26046 |
| 310 | GAACCAGACAGA | 1390 | UCUGUCUGGUUC | 2785 | AD-26047, AD-26046 |
| 311 | AACCAGACAGAA | 1391 | UUCUGUCUGGUU | 2786 | AD-26047, AD-26046 |
| 316 | GACAGAAAAGCG | 1392 | CGCUUUUCUGUC | 2787 | AD-26050, AD-26049 |
| 317 | ACAGAAAAGCGG | 1393 | CCGCUUUUCUGU | 2788 | AD-26050, AD-26049 |
| 318 | CAGAAAAGCGGC | 1394 | GCCGCUUUUCUG | 2789 | AD-26050, AD-26049 |
| 319 | AGAAAAGCGGCU | 1395 | AGCCGCUUUUCU | 2790 | AD-26050, AD-26049 |
| 320 | GAAAAGCGGCUG | 1396 | CAGCCGCUUUUC | 2791 | AD-26050, AD-26049 |
| 321 | AAAAGCGGCUGU | 1397 | ACAGCCGCUUUU | 2792 | AD-26050, AD-26049 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 322 | AAAGCGGCUGUU | 1398 | AACAGCCGCUUU | 2793 | AD-26050, AD-26049 |
| 323 | AAGCGGCUGUUA | 1399 | UAACAGCCGCUU | 2794 | AD-26050, AD-19743 |
| 330 | UGUUAGUCACUG | 1400 | CAGUGACUAACA | 2795 | AD-26051, AD-19743 |
| 337 | CACUGGCAGCAA | 1401 | UUGCUGCCAGUG | 2796 | AD-26051, AD-26052 |
| 338 | ACUGGCAGCAAC | 1402 | GUUGCUGCCAGU | 2797 | AD-26053, AD-26052 |
| 339 | CUGGCAGCAACA | 1403 | UGUUGCUGCCAG | 2798 | AD-26053, AD-26052 |
| 340 | UGGCAGCAACAG | 1404 | CUGUUGCUGCCA | 2799 | AD-26053, AD-26052 |
| 341 | GGCAGCAACAGU | 1405 | ACUGUUGCUGCC | 2800 | AD-26053, AD-26052 |
| 342 | GCAGCAACAGUC | 1406 | GACUGUUGCUGC | 2801 | AD-26053, AD-26052 |
| 343 | CAGCAACAGUCU | 1407 | AGACUGUUGCUG | 2802 | AD-26053, AD-26052 |
| 344 | AGCAACAGUCUU | 1408 | AAGACUGUUGCU | 2803 | AD-26053, AD-26052 |
| 353 | CUUACCUGGACU | 1409 | AGUCCAGGUAAG | 2804 | AD-26054, AD-26055 |
| 354 | UUACCUGGACUC | 1410 | GAGUCCAGGUAA | 2805 | AD-26054, AD-26055 |
| 355 | UACCUGGACUCU | 1411 | AGAGUCCAGGUA | 2806 | AD-26054, AD-26055 |
| 356 | ACCUGGACUCUG | 1412 | CAGAGUCCAGGU | 2807 | AD-26054, AD-26055 |
| 357 | CCUGGACUCUGG | 1413 | CCAGAGUCCAGG | 2808 | AD-26056, AD-26055 |
| 358 | CUGGACUCUGGA | 1414 | UCCAGAGUCCAG | 2809 | AD-26054, AD-26056, AD-26055 |
| 359 | UGGACUCUGGAA | 1415 | UUCCAGAGUCCA | 2810 | AD-26054, AD-26056, AD-26055 |
| 360 | GGACUCUGGAAU | 1416 | AUUCCAGAGUCC | 2811 | AD-26056, AD-26055 |
| 366 | UGGAAUCCAUUC | 1417 | GAAUGGAUUCCA | 2812 | AD-19072, AD-18925 |
| 367 | GGAAUCCAUUCU | 1418 | AGAAUGGAUUCC | 2813 | AD-19072, AD-18925 |
| 368 | GAAUCCAUUCUG | 1419 | CAGAAUGGAUUC | 2814 | AD-19072, AD-18925 |
| 369 | AAUCCAUUCUGG | 1420 | CCAGAAUGGAUU | 2815 | AD-19072, AD-18925 |
| 370 | AUCCAUUCUGGU | 1421 | ACCAGAAUGGAU | 2816 | AD-19072, AD-18925 |
| 371 | UCCAUUCUGGUG | 1422 | CACCAGAAUGGA | 2817 | AD-19072, AD-18925 |
| 372 | CCAUUCUGGUGC | 1423 | GCACCAGAAUGG | 2818 | AD-19072, AD-18925 |
| 401 | CUCUGAGUGGUA | 1424 | UACCACUCAGAG | 2819 | AD-26060, AD-26059 |
| 402 | UCUGAGUGGUAA | 1425 | UUACCACUCAGA | 2820 | AD-26060, AD-26059 |
| 403 | CUGAGUGGUAAA | 1426 | UUUACCACUCAG | 2821 | AD-26060, AD-26059 |
| 417 | CAAUCCUGAGGA | 1427 | UCCUCAGGAUUG | 2822 | AD-26062, AD-26061 |
| 418 | AAUCCUGAGGAA | 1428 | UUCCUCAGGAUU | 2823 | AD-26062, AD-26061 |
| 423 | UGAGGAAGAGGA | 1429 | UCCUCUUCCUCA | 2824 | AD-26062, AD-26063 |
| 424 | GAGGAAGAGGAU | 1430 | AUCCUCUUCCUC | 2825 | AD-26062, AD-26063 |
| 441 | UACCUCCCAAGU | 1431 | ACUUGGGAGGUA | 2826 | AD-26065, AD-26064 |
| 442 | ACCUCCCAAGUC | 1432 | GACUUGGGAGGU | 2827 | AD-26065, AD-26064 |
| 443 | CCUCCCAAGUCC | 1433 | GGACUUGGGAGG | 2828 | AD-26065, AD-26064 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 444 | CUCCCAAGUCCU | 1434 | AGGACUUGGGAG | 2829 | AD-26065, AD-26064 |
| 445 | UCCCAAGUCCUG | 1435 | CAGGACUUGGGA | 2830 | AD-26065, AD-26064 |
| 446 | CCCAAGUCCUGU | 1436 | ACAGGACUUGGG | 2831 | AD-26065, AD-26064 |
| 447 | CCAAGUCCUGUA | 1437 | UACAGGACUUGG | 2832 | AD-26065, AD-26064 |
| 457 | UAUGAGUGGGAA | 1438 | UUCCCACUCAUA | 2833 | AD-26066, AD-26067 |
| 459 | UGAGUGGGAACA | 1439 | UGUUCCCACUCA | 2834 | AD-26070, AD-26067 |
| 460 | GAGUGGGAACAG | 1440 | CUGUUCCCACUC | 2835 | AD-26071, AD-26070, AD-26067 |
| 461 | AGUGGGAACAGG | 1441 | CCUGUUCCCACU | 2836 | AD-26071, AD-26070, AD-26067 |
| 462 | GUGGGAACAGGG | 1442 | CCCUGUUCCCAC | 2837 | AD-26071, AD-26070, AD-26067 |
| 463 | UGGGAACAGGGA | 1443 | UCCCUGUUCCCA | 2838 | AD-26071, AD-26070, AD-26067 |
| 464 | GGGAACAGGGAU | 1444 | AUCCCUGUUCCC | 2839 | AD-26071, AD-26070, AD-26067 |
| 465 | GGAACAGGGAUU | 1445 | AAUCCCUGUUCC | 2840 | AD-26071, AD-26070 |
| 466 | GAACAGGGAUUU | 1446 | AAAUCCCUGUUC | 2841 | AD-26071, AD-26070 |
| 477 | UUCUCAGUCCUU | 1447 | AAGGACUGAGAA | 2842 | AD-26073, AD-26072 |
| 480 | UCAGUCCUUCAC | 1448 | GUGAAGGACUGA | 2843 | AD-26074, AD-26073 |
| 481 | CAGUCCUUCACU | 1449 | AGUGAAGGACUG | 2844 | AD-26074, AD-26073 |
| 482 | AGUCCUUCACUC | 1450 | GAGUGAAGGACU | 2845 | AD-26074, AD-26073 |
| 483 | GUCCUUCACUCA | 1451 | UGAGUGAAGGAC | 2846 | AD-26074, AD-26073 |
| 484 | UCCUUCACUCAA | 1452 | UUGAGUGAAGGA | 2847 | AD-26074, AD-26073 |
| 486 | CUUCACUCAAGA | 1453 | UCUUGAGUGAAG | 2848 | AD-26074, AD-26075 |
| 487 | UUCACUCAAGAA | 1454 | UUCUUGAGUGAA | 2849 | AD-26074, AD-26075 |
| 492 | UCAAGAACAAGU | 1455 | ACUUGUUCUUGA | 2850 | AD-26076, AD-26075 |
| 493 | CAAGAACAAGUA | 1456 | UACUUGUUCUUG | 2851 | AD-26076, AD-26075 |
| 511 | AUUGAUGGACAG | 1457 | CUGUCCAUCAAU | 2852 | AD-26077, AD-26078 |
| 512 | UUGAUGGACAGU | 1458 | ACUGUCCAUCAA | 2853 | AD-26077, AD-26078 |
| 513 | UGAUGGACAGUA | 1459 | UACUGUCCAUCA | 2854 | AD-26077, AD-26078 |
| 523 | UAUGCAAUGACU | 1460 | AGUCAUUGCAUA | 2855 | AD-19757, AD-19756 |
| 524 | AUGCAAUGACUC | 1461 | GAGUCAUUGCAU | 2856 | AD-19757, AD-19756 |
| 525 | UGCAAUGACUCG | 1462 | CGAGUCAUUGCA | 2857 | AD-19757, AD-19756 |
| 526 | GCAAUGACUCGA | 1463 | UCGAGUCAUUGC | 2858 | AD-19757, AD-19756 |
| 534 | UCGAGCUCAGAG | 1464 | CUCUGAGCUCGA | 2859 | AD-19744, AD-26079 |
| 535 | CGAGCUCAGAGG | 1465 | CCUCUGAGCUCG | 2860 | AD-19744, AD-26079 |
| 536 | GAGCUCAGAGGG | 1466 | CCCUCUGAGCUC | 2861 | AD-19744, AD-26079 |
| 537 | AGCUCAGAGGGU | 1467 | ACCCUCUGAGCU | 2862 | AD-19744, AD-26079 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 538 | GCUCAGAGGGUA | 1468 | UACCCUCUGAGC | 2863 | AD-19744, AD-26079 |
| 541 | CAGAGGGUACGA | 1469 | UCGUACCCUCUG | 2864 | AD-26080, AD-19744 |
| 542 | AGAGGGUACGAG | 1470 | CUCGUACCCUCU | 2865 | AD-26080, AD-26081 |
| 543 | GAGGGUACGAGC | 1471 | GCUCGUACCCUC | 2866 | AD-26080, AD-26081 |
| 544 | AGGGUACGAGCU | 1472 | AGCUCGUACCCU | 2867 | AD-26080, AD-26081 |
| 545 | GGGUACGAGCUG | 1473 | CAGCUCGUACCC | 2868 | AD-26080, AD-26081 |
| 546 | GGUACGAGCUGC | 1474 | GCAGCUCGUACC | 2869 | AD-26080, AD-26082 |
| 547 | GUACGAGCUGCU | 1475 | AGCAGCUCGUAC | 2870 | AD-26080, AD-26081, AD-26082 |
| 548 | UACGAGCUGCUA | 1476 | UAGCAGCUCGUA | 2871 | AD-26080, AD-26081, AD-26082 |
| 549 | ACGAGCUGCUAU | 1477 | AUAGCAGCUCGU | 2872 | AD-26081, AD-26082 |
| 558 | UAUGUUCCCUGA | 1478 | UCAGGGAACAUA | 2873 | AD-26084, AD-26083 |
| 559 | AUGUUCCCUGAG | 1479 | CUCAGGGAACAU | 2874 | AD-26084, AD-26083 |
| 560 | UGUUCCCUGAGA | 1480 | UCUCAGGGAACA | 2875 | AD-26084, AD-26083 |
| 561 | GUUCCCUGAGAC | 1481 | GUCUCAGGGAAC | 2876 | AD-26084, AD-26085, AD-26083 |
| 562 | UUCCCUGAGACA | 1482 | UGUCUCAGGGAA | 2877 | AD-26084, AD-26085, AD-26083 |
| 563 | UCCCUGAGACAU | 1483 | AUGUCUCAGGGA | 2878 | AD-26084, AD-26085, AD-26083 |
| 564 | CCCUGAGACAUU | 1484 | AAUGUCUCAGGG | 2879 | AD-26084, AD-26085, AD-26083 |
| 565 | CCUGAGACAUUA | 1485 | UAAUGUCUCAGG | 2880 | AD-26084, AD-26085 |
| 576 | AGAUGAGGGCAU | 1486 | AUGCCCUCAUCU | 2881 | AD-26086, AD-18911 |
| 577 | GAUGAGGGCAUG | 1487 | CAUGCCCUCAUC | 2882 | AD-26086, AD-18911 |
| 578 | AUGAGGGCAUGC | 1488 | GCAUGCCCUCAU | 2883 | AD-19011, AD-18911 |
| 579 | UGAGGGCAUGCA | 1489 | UGCAUGCCCUCA | 2884 | AD-26086, AD-19011, AD-18911 |
| 580 | GAGGGCAUGCAG | 1490 | CUGCAUGCCCUC | 2885 | AD-18911, AD-26087 |
| 581 | AGGGCAUGCAGA | 1491 | UCUGCAUGCCCU | 2886 | AD-18959, AD-26086, AD-18911, AD-26087 |
| 582 | GGGCAUGCAGAU | 1492 | AUCUGCAUGCCC | 2887 | AD-18911, AD-26087 |
| 583 | GGCAUGCAGAUC | 1493 | GAUCUGCAUGCC | 2888 | AD-26088, AD-18911, AD-26087 |
| 584 | GCAUGCAGAUCC | 1494 | GGAUCUGCAUGC | 2889 | AD-26088, AD-26087 |
| 585 | CAUGCAGAUCCC | 1495 | GGGAUCUGCAUG | 2890 | AD-26088, AD-18959, AD-19011, AD-26087 |
| 586 | AUGCAGAUCCCA | 1496 | UGGGAUCUGCAU | 2891 | AD-26088, AD-26087 |
| 587 | UGCAGAUCCCAU | 1497 | AUGGGAUCUGCA | 2892 | AD-26088, AD-18959 |
| 588 | GCAGAUCCCAUC | 1498 | GAUGGGAUCUGC | 2893 | AD-26088, AD-18959 |
| 590 | AGAUCCCAUCUA | 1499 | UAGAUGGGAUCU | 2894 | AD-26088, AD-26089 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 594 | CCCAUCUACACA | 1500 | UGUGUAGAUGGG | 2895 | AD-26089, AD-26090 |
| 595 | CCAUCUACACAG | 1501 | CUGUGUAGAUGG | 2896 | AD-26089, AD-26090 |
| 596 | CAUCUACACAGU | 1502 | ACUGUGUAGAUG | 2897 | AD-26089, AD-26090 |
| 597 | AUCUACACAGUU | 1503 | AACUGUGUAGAU | 2898 | AD-26089, AD-26090 |
| 610 | GAUGCUGCUCAU | 1504 | AUGAGCAGCAUC | 2899 | AD-26091, AD-26092 |
| 611 | AUGCUGCUCAUC | 1505 | GAUGAGCAGCAU | 2900 | AD-26092, AD-26093 |
| 612 | UGCUGCUCAUCC | 1506 | GGAUGAGCAGCA | 2901 | AD-26092, AD-26094 |
| 613 | GCUGCUCAUCCC | 1507 | GGGAUGAGCAGC | 2902 | AD-26092, AD-26093 |
| 614 | CUGCUCAUCCCA | 1508 | UGGGAUGAGCAG | 2903 | AD-26092, AD-26093, AD-26094 |
| 615 | UGCUCAUCCCAC | 1509 | GUGGGAUGAGCA | 2904 | AD-26092, AD-26093, AD-26094 |
| 616 | GCUCAUCCCACU | 1510 | AGUGGGAUGAGC | 2905 | AD-26092, AD-26093, AD-26094 |
| 617 | CUCAUCCCACUA | 1511 | UAGUGGGAUGAG | 2906 | AD-26092, AD-26094 |
| 618 | UCAUCCCACUAA | 1512 | UUAGUGGGAUGA | 2907 | AD-19070, AD-18949, AD-26093, AD-26094 |
| 619 | CAUCCCACUAAU | 1513 | AUUAGUGGGAUG | 2908 | AD-18949, AD-19048, AD-18954, AD-26094 |
| 620 | AUCCCACUAAUG | 1514 | CAUUAGUGGGAU | 2909 | AD-19070, AD-18918, AD-19048, AD-18954 |
| 621 | UCCCACUAAUGU | 1515 | ACAUUAGUGGGA | 2910 | AD-19070, AD-18949, AD-18918, AD-19048, AD-18954 |
| 622 | CCCACUAAUGUC | 1516 | GACAUUAGUGGG | 2911 | AD-26095, AD-19070, AD-18918, AD-19048, AD-18954 |
| 623 | CCACUAAUGUCC | 1517 | GGACAUUAGUGG | 2912 | AD-26095, AD-18949, AD-18918, AD-19048, AD-18954 |
| 624 | CACUAAUGUCCA | 1518 | UGGACAUUAGUG | 2913 | AD-26095, AD-18949, AD-18918, AD-19048, AD-18954 |
| 625 | ACUAAUGUCCAG | 1519 | CUGGACAUUAGU | 2914 | AD-26095, AD-18918, AD-19048 |
| 626 | CUAAUGUCCAGC | 1520 | GCUGGACAUUAG | 2915 | AD-26095, AD-18918, AD-19048 |
| 627 | UAAUGUCCAGCG | 1521 | CGCUGGACAUUA | 2916 | AD-26095, AD-18918 |
| 636 | GCGUUUGGCUGA | 1522 | UCAGCCAAACGC | 2917 | AD-26096, AD-19765 |
| 637 | CGUUUGGCUGAA | 1523 | UUCAGCCAAACG | 2918 | AD-26096, AD-19765 |
| 638 | GUUUGGCUGAAC | 1524 | GUUCAGCCAAAC | 2919 | AD-26096, AD-19765 |
| 639 | UUUGGCUGAACC | 1525 | GGUUCAGCCAAA | 2920 | AD-26096, AD-19765 |
| 640 | UUGGCUGAACCA | 1526 | UGGUUCAGCCAA | 2921 | AD-26096, AD-18974, AD-19765 |
| 641 | UGGCUGAACCAU | 1527 | AUGGUUCAGCCA | 2922 | AD-26096, AD-19765, AD-26097 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 642 | GGCUGAACCAUC | 1528 | GAUGGUUCAGCC | 2923 | AD-18974, AD-19000, AD-19765, AD-26097 |
| 643 | GCUGAACCAUCA | 1529 | UGAUGGUUCAGC | 2924 | AD-18974, AD-19765, AD-26097 |
| 644 | CUGAACCAUCAC | 1530 | GUGAUGGUUCAG | 2925 | AD-18974, AD-19000 |
| 645 | UGAACCAUCACA | 1531 | UGUGAUGGUUCA | 2926 | AD-18974, AD-26097 |
| 646 | GAACCAUCACAG | 1532 | CUGUGAUGGUUC | 2927 | AD-18974, AD-19000, AD-26097 |
| 647 | AACCAUCACAGA | 1533 | UCUGUGAUGGUU | 2928 | AD-18974, AD-19000, AD-26098, AD-26097 |
| 648 | ACCAUCACAGAU | 1534 | AUCUGUGAUGGU | 2929 | AD-19000, AD-26098, AD-26099, AD-26097 |
| 649 | CCAUCACAGAUG | 1535 | CAUCUGUGAUGG | 2930 | AD-19000, AD-26098, AD-26099 |
| 650 | CAUCACAGAUGC | 1536 | GCAUCUGUGAUG | 2931 | AD-26098, AD-26099 |
| 651 | AUCACAGAUGCU | 1537 | AGCAUCUGUGAU | 2932 | AD-26100, AD-26098 |
| 652 | UCACAGAUGCUG | 1538 | CAGCAUCUGUGA | 2933 | AD-26100, AD-26099 |
| 653 | CACAGAUGCUGA | 1539 | UCAGCAUCUGUG | 2934 | AD-26100, AD-26098, AD-26099 |
| 654 | ACAGAUGCUGAA | 1540 | UUCAGCAUCUGU | 2935 | AD-26100, AD-26099 |
| 655 | CAGAUGCUGAAA | 1541 | UUUCAGCAUCUG | 2936 | AD-26100, AD-26099 |
| 657 | GAUGCUGAAACA | 1542 | UGUUUCAGCAUC | 2937 | AD-26100, AD-26101 |
| 658 | AUGCUGAAACAU | 1543 | AUGUUUCAGCAU | 2938 | AD-26100, AD-26101 |
| 661 | CUGAAACAUGCA | 1544 | UGCAUGUUUCAG | 2939 | AD-26101, AD-26102 |
| 662 | UGAAACAUGCAG | 1545 | CUGCAUGUUUCA | 2940 | AD-26101, AD-26102 |
| 663 | GAAACAUGCAGU | 1546 | ACUGCAUGUUUC | 2941 | AD-26101, AD-26102 |
| 664 | AAACAUGCAGUU | 1547 | AACUGCAUGUUU | 2942 | AD-26101, AD-26102 |
| 665 | AACAUGCAGUUG | 1548 | CAACUGCAUGUU | 2943 | AD-26103, AD-26102 |
| 666 | ACAUGCAGUUGU | 1549 | ACAACUGCAUGU | 2944 | AD-26103, AD-26102 |
| 667 | CAUGCAGUUGUA | 1550 | UACAACUGCAUG | 2945 | AD-26103, AD-26102 |
| 668 | AUGCAGUUGUAA | 1551 | UUACAACUGCAU | 2946 | AD-26104, AD-26103, AD-26102 |
| 669 | UGCAGUUGUAAA | 1552 | UUUACAACUGCA | 2947 | AD-26105, AD-26103 |
| 670 | GCAGUUGUAAAC | 1553 | GUUUACAACUGC | 2948 | AD-26105, AD-26104, AD-26103 |
| 671 | CAGUUGUAAACU | 1554 | AGUUUACAACUG | 2949 | AD-26105, AD-26104, AD-26103, AD-26106 |
| 672 | AGUUGUAAACUU | 1555 | AAGUUUACAACU | 2950 | AD-26105, AD-26103, AD-26106 |
| 673 | GUUGUAAACUUG | 1556 | CAAGUUUACAAC | 2951 | AD-26105, AD-26104, AD-26106 |
| 674 | UUGUAAACUUGA | 1557 | UCAAGUUUACAA | 2952 | AD-26105, AD-26808, AD-26104, AD-26106 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 675 | UGUAAACUUGAU | 1558 | AUCAAGUUUACA | 2953 | AD-26105, AD-26808, AD-26104, AD-26106, AD-26809 |
| 676 | GUAAACUUGAUU | 1559 | AAUCAAGUUUAC | 2954 | AD-26105, AD-26808, AD-26106, AD-26809 |
| 677 | UAAACUUGAUUA | 1560 | UAAUCAAGUUUA | 2955 | AD-26808, AD-26106, AD-26809 |
| 678 | AAACUUGAUUAA | 1561 | UUAAUCAAGUUU | 2956 | AD-26808, AD-26810, AD-26106, AD-26809 |
| 679 | AACUUGAUUAAC | 1562 | GUUAAUCAAGUU | 2957 | AD-26808, AD-26810, AD-26809 |
| 680 | ACUUGAUUAACU | 1563 | AGUUAAUCAAGU | 2958 | AD-26808, AD-26809 |
| 681 | CUUGAUUAACUA | 1564 | UAGUUAAUCAAG | 2959 | AD-26107, AD-26808, AD-26810, AD-26809 |
| 682 | UUGAUUAACUAU | 1565 | AUAGUUAAUCAA | 2960 | AD-26107, AD-26810, AD-26809 |
| 683 | UGAUUAACUAUC | 1566 | GAUAGUUAAUCA | 2961 | AD-26107, AD-26810 |
| 684 | GAUUAACUAUCA | 1567 | UGAUAGUUAAUC | 2962 | AD-26107, AD-26810, AD-26108 |
| 685 | AUUAACUAUCAA | 1568 | UUGAUAGUUAAU | 2963 | AD-26107, AD-26108 |
| 686 | UUAACUAUCAAG | 1569 | CUUGAUAGUUAA | 2964 | AD-26107, AD-26108 |
| 687 | UAACUAUCAAGA | 1570 | UCUUGAUAGUUA | 2965 | AD-26107, AD-26108 |
| 688 | AACUAUCAAGAU | 1571 | AUCUUGAUAGUU | 2966 | AD-26107, AD-26108 |
| 690 | CUAUCAAGAUGA | 1572 | UCAUCUUGAUAG | 2967 | AD-26109, AD-26108 |
| 691 | UAUCAAGAUGAU | 1573 | AUCAUCUUGAUA | 2968 | AD-26109, AD-26108 |
| 707 | AACUUGCCACAC | 1574 | GUGUGGCAAGUU | 2969 | AD-26110, AD-26111 |
| 708 | ACUUGCCACACG | 1575 | CGUGUGGCAAGU | 2970 | AD-26110, AD-26111 |
| 709 | CUUGCCACACGU | 1576 | ACGUGUGGCAAG | 2971 | AD-26110, AD-26111 |
| 710 | UUGCCACACGUG | 1577 | CACGUGUGGCAA | 2972 | AD-26110, AD-26111 |
| 711 | UGCCACACGUGC | 1578 | GCACGUGUGGCA | 2973 | AD-26110, AD-26111 |
| 712 | GCCACACGUGCA | 1579 | UGCACGUGUGGC | 2974 | AD-26110, AD-26111 |
| 713 | CCACACGUGCAA | 1580 | UUGCACGUGUGG | 2975 | AD-26110, AD-26111 |
| 714 | CACACGUGCAAU | 1581 | AUUGCACGUGUG | 2976 | AD-26112, AD-26111 |
| 721 | GCAAUCCCUGAA | 1582 | UUCAGGGAUUGC | 2977 | AD-26112, AD-26123 |
| 722 | CAAUCCCUGAAC | 1583 | GUUCAGGGAUUG | 2978 | AD-26124, AD-26123 |
| 723 | AAUCCCUGAACU | 1584 | AGUUCAGGGAUU | 2979 | AD-26124, AD-26125 |
| 724 | AUCCCUGAACUG | 1585 | CAGUUCAGGGAU | 2980 | AD-26124, AD-26123 |
| 725 | UCCCUGAACUGA | 1586 | UCAGUUCAGGGA | 2981 | AD-26124, AD-26125 |
| 726 | CCCUGAACUGAC | 1587 | GUCAGUUCAGGG | 2982 | AD-26124, AD-26123 |
| 727 | CCUGAACUGACA | 1588 | UGUCAGUUCAGG | 2983 | AD-26124, AD-26123, AD-26125 |

TABLE 4-continued

Groups of overlapping RNAi agents to Beta-Catenin

| Position | Sense overlap | SEQ ID NO: Anti-sense overlap | SEQ ID NO: Overlapping groups of RNAi agents |
|---|---|---|---|
| 728 | CUGAACUGACAA | 1589 UUGUCAGUUCAG | 2984 AD-26124, AD-26123, AD-26125 |
| 729 | UGAACUGACAAA | 1590 UUUGUCAGUUCA | 2985 AD-26124, AD-26125, AD-26126 |
| 730 | GAACUGACAAAA | 1591 UUUUGUCAGUUC | 2986 AD-26125, AD-26126 |
| 731 | AACUGACAAAAC | 1592 GUUUUGUCAGUU | 2987 AD-26128, AD-26126, AD-26127 |
| 732 | ACUGACAAAACU | 1593 AGUUUUGUCAGU | 2988 AD-26128, AD-26126, AD-26129 |
| 733 | CUGACAAAACUG | 1594 CAGUUUUGUCAG | 2989 AD-26128, AD-26126, AD-26129 |
| 734 | UGACAAAACUGC | 1595 GCAGUUUUGUCA | 2990 AD-26128, AD-26127, AD-26129 |
| 735 | GACAAAACUGCU | 1596 AGCAGUUUUGUC | 2991 AD-26128, AD-26126, AD-26129 |
| 736 | ACAAAACUGCUA | 1597 UAGCAGUUUUGU | 2992 AD-26128, AD-26126, AD-26127, AD-26129 |
| 737 | CAAAACUGCUAA | 1598 UUAGCAGUUUUG | 2993 AD-26128, AD-26127, AD-26129 |
| 738 | AAAACUGCUAAA | 1599 UUUAGCAGUUUU | 2994 AD-26128, AD-26129 |
| 755 | AGGACCAGGUGG | 1600 CCACCUGGUCCU | 2995 AD-26131, AD-26130 |
| 756 | GGACCAGGUGGU | 1601 ACCACCUGGUCC | 2996 AD-26132, AD-26131, AD-26130 |
| 757 | GACCAGGUGGUG | 1602 CACCACCUGGUC | 2997 AD-26132, AD-26133, AD-26131, AD-26130 |
| 758 | ACCAGGUGGUGG | 1603 CCACCACCUGGU | 2998 AD-26132, AD-26133, AD-26131, AD-26130, AD-26136 |
| 759 | CCAGGUGGUGGU | 1604 ACCACCACCUGG | 2999 AD-26132, AD-26131, AD-26136 |
| 760 | CAGGUGGUGGUU | 1605 AACCACCACCUG | 3000 AD-26132, AD-26133, AD-26131, AD-26136 |
| 761 | AGGUGGUGGUUA | 1606 UAACCACCACCU | 3001 AD-26132, AD-26131, AD-26130, AD-26136 |
| 762 | GGUGGUGGUUAA | 1607 UUAACCACCACC | 3002 AD-26132, AD-26131 |
| 763 | GUGGUGGUUAAU | 1608 AUUAACCACCAC | 3003 AD-26132, AD-26133, AD-26136 |
| 764 | UGGUGGUUAAUA | 1609 UAUUAACCACCA | 3004 AD-26133, AD-26136 |
| 784 | GUUAUGGUCCAU | 1610 AUGGACCAUAAC | 3005 AD-26138, AD-26137 |
| 787 | AUGGUCCAUCAG | 1611 CUGAUGGACCAU | 3006 AD-26138, AD-26139 |
| 788 | UGGUCCAUCAGC | 1612 GCUGAUGGACCA | 3007 AD-26138, AD-26139, AD-26140 |
| 789 | GGUCCAUCAGCU | 1613 AGCUGAUGGACC | 3008 AD-26142, AD-26140 |
| 790 | GUCCAUCAGCUU | 1614 AAGCUGAUGGAC | 3009 AD-26143, AD-26142, AD-26140 |
| 791 | UCCAUCAGCUUU | 1615 AAAGCUGAUGGA | 3010 AD-26139, AD-26143, AD-26142, AD-26140 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 792 | CCAUCAGCUUUC | 1616 | GAAAGCUGAUGG | 3011 | AD-26143, AD-26142, AD-26140 |
| 793 | CAUCAGCUUUCU | 1617 | AGAAAGCUGAUG | 3012 | AD-26139, AD-26143, AD-26142, AD-26140 |
| 794 | AUCAGCUUUCUA | 1618 | UAGAAAGCUGAU | 3013 | AD-26143, AD-26142, AD-26140 |
| 795 | UCAGCUUUCUAA | 1619 | UUAGAAAGCUGA | 3014 | AD-26143, AD-26142 |
| 796 | CAGCUUUCUAAA | 1620 | UUUAGAAAGCUG | 3015 | AD-26143, AD-26142 |
| 811 | GAAGCUUCCAGA | 1621 | UCUGGAAGCUUC | 3016 | AD-26144, AD-18950 |
| 812 | AAGCUUCCAGAC | 1622 | GUCUGGAAGCUU | 3017 | AD-26144, AD-18950 |
| 813 | AGCUUCCAGACA | 1623 | UGUCUGGAAGCU | 3018 | AD-26145, AD-26144, AD-18950 |
| 814 | GCUUCCAGACAC | 1624 | GUGUCUGGAAGC | 3019 | AD-26145, AD-26144 |
| 815 | CUUCCAGACACG | 1625 | CGUGUCUGGAAG | 3020 | AD-26145, AD-26144 |
| 816 | UUCCAGACACGC | 1626 | GCGUGUCUGGAA | 3021 | AD-26146, AD-26144 |
| 817 | UCCAGACACGCU | 1627 | AGCGUGUCUGGA | 3022 | AD-26145, AD-26146, AD-26144 |
| 818 | CCAGACACGCUA | 1628 | UAGCGUGUCUGG | 3023 | AD-26145, AD-26146 |
| 819 | CAGACACGCUAU | 1629 | AUAGCGUGUCUG | 3024 | AD-26145, AD-26146 |
| 820 | AGACACGCUAUC | 1630 | GAUAGCGUGUCU | 3025 | AD-26146, AD-26147 |
| 821 | GACACGCUAUCA | 1631 | UGAUAGCGUGUC | 3026 | AD-19745, AD-26146 |
| 822 | ACACGCUAUCAU | 1632 | AUGAUAGCGUGU | 3027 | AD-19745, AD-26146, AD-26147 |
| 823 | CACGCUAUCAUG | 1633 | CAUGAUAGCGUG | 3028 | AD-19745, AD-26147 |
| 824 | ACGCUAUCAUGC | 1634 | GCAUGAUAGCGU | 3029 | AD-19745, AD-19739, AD-26147 |
| 825 | CGCUAUCAUGCG | 1635 | CGCAUGAUAGCG | 3030 | AD-19745, AD-19746, AD-19739 |
| 826 | GCUAUCAUGCGU | 1636 | ACGCAUGAUAGC | 3031 | AD-19766, AD-19739, AD-26147 |
| 827 | CUAUCAUGCGUU | 1637 | AACGCAUGAUAG | 3032 | AD-19766, AD-19745, AD-19739, AD-26147 |
| 828 | UAUCAUGCGUUC | 1638 | GAACGCAUGAUA | 3033 | AD-19766, AD-19745, AD-19739 |
| 829 | AUCAUGCGUUCU | 1639 | AGAACGCAUGAU | 3034 | AD-19766, AD-19746, AD-19739 |
| 830 | UCAUGCGUUCUC | 1640 | GAGAACGCAUGA | 3035 | AD-19739, AD-26148 |
| 831 | CAUGCGUUCUCC | 1641 | GGAGAACGCAUG | 3036 | AD-19739, AD-26148 |
| 832 | AUGCGUUCUCCU | 1642 | AGGAGAACGCAU | 3037 | AD-19746, AD-26148 |
| 842 | CUCAGAUGGUGU | 1643 | ACACCAUCUGAG | 3038 | AD-26150, AD-26149 |
| 843 | UCAGAUGGUGUC | 1644 | GACACCAUCUGA | 3039 | AD-26150, AD-26149 |
| 844 | CAGAUGGUGUCU | 1645 | AGACACCAUCUG | 3040 | AD-26150, AD-26149 |
| 845 | AGAUGGUGUCUG | 1646 | CAGACACCAUCU | 3041 | AD-26150, AD-26149 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 846 | GAUGGUGUCUGC | 1647 | GCAGACACCAUC | 3042 | AD-26150, AD-26149 |
| 847 | AUGGUGUCUGCU | 1648 | AGCAGACACCAU | 3043 | AD-26150, AD-26149 |
| 848 | UGGUGUCUGCUA | 1649 | UAGCAGACACCA | 3044 | AD-26150, AD-26149 |
| 854 | CUGCUAUUGUAC | 1650 | GUACAAUAGCAG | 3045 | AD-26151, AD-26152 |
| 855 | UGCUAUUGUACG | 1651 | CGUACAAUAGCA | 3046 | AD-26151, AD-26152 |
| 856 | GCUAUUGUACGU | 1652 | ACGUACAAUAGC | 3047 | AD-26151, AD-26152 |
| 857 | CUAUUGUACGUA | 1653 | UACGUACAAUAG | 3048 | AD-26151, AD-26152 |
| 860 | UUGUACGUACCA | 1654 | UGGUACGUACAA | 3049 | AD-26153, AD-26152 |
| 861 | UGUACGUACCAU | 1655 | AUGGUACGUACA | 3050 | AD-26154, AD-26153, AD-26152 |
| 862 | GUACGUACCAUG | 1656 | CAUGGUACGUAC | 3051 | AD-26154, AD-26153 |
| 863 | UACGUACCAUGC | 1657 | GCAUGGUACGUA | 3052 | AD-26154, AD-26153 |
| 864 | ACGUACCAUGCA | 1658 | UGCAUGGUACGU | 3053 | AD-26154, AD-26153 |
| 865 | CGUACCAUGCAG | 1659 | CUGCAUGGUACG | 3054 | AD-26154, AD-26153 |
| 866 | GUACCAUGCAGA | 1660 | UCUGCAUGGUAC | 3055 | AD-26154, AD-26155 |
| 867 | UACCAUGCAGAA | 1661 | UUCUGCAUGGUA | 3056 | AD-26154, AD-26155, AD-26153 |
| 868 | ACCAUGCAGAAU | 1662 | AUUCUGCAUGGU | 3057 | AD-26154, AD-26155 |
| 870 | CAUGCAGAAUAC | 1663 | GUAUUCUGCAUG | 3058 | AD-26155, AD-26156 |
| 871 | AUGCAGAAUACA | 1664 | UGUAUUCUGCAU | 3059 | AD-26155, AD-26156 |
| 872 | UGCAGAAUACAA | 1665 | UUGUAUUCUGCA | 3060 | AD-26155, AD-26156 |
| 873 | GCAGAAUACAAA | 1666 | UUUGUAUUCUGC | 3061 | AD-26156, AD-26157 |
| 874 | CAGAAUACAAAU | 1667 | AUUUGUAUUCUG | 3062 | AD-19068, AD-26157 |
| 875 | AGAAUACAAAUG | 1668 | CAUUUGUAUUCU | 3063 | AD-19068, AD-26156 |
| 876 | GAAUACAAAUGA | 1669 | UCAUUUGUAUUC | 3064 | AD-19068, AD-26156, AD-26157 |
| 877 | AAUACAAAUGAU | 1670 | AUCAUUUGUAUU | 3065 | AD-19068, AD-26158, AD-26826, AD-26157 |
| 878 | AUACAAAUGAUG | 1671 | CAUCAUUUGUAU | 3066 | AD-19068, AD-26158, AD-26157 |
| 879 | UACAAAUGAUGU | 1672 | ACAUCAUUUGUA | 3067 | AD-26158, AD-26826, AD-26157 |
| 880 | ACAAAUGAUGUA | 1673 | UACAUCAUUUGU | 3068 | AD-19068, AD-26158, AD-26826, AD-26157 |
| 881 | CAAAUGAUGUAG | 1674 | CUACAUCAUUUG | 3069 | AD-19068, AD-26158, AD-26826 |
| 882 | AAAUGAUGUAGA | 1675 | UCUACAUCAUUU | 3070 | AD-26158, AD-26826 |
| 883 | AAUGAUGUAGAA | 1676 | UUCUACAUCAUU | 3071 | AD-26158, AD-26826 |
| 906 | UACCGCUGGGAC | 1677 | GUCCCAGCGGUA | 3072 | AD-26161, AD-26160 |
| 907 | ACCGCUGGGACC | 1678 | GGUCCCAGCGGU | 3073 | AD-26161, AD-26160 |
| 908 | CCGCUGGGACCU | 1679 | AGGUCCCAGCGG | 3074 | AD-26161, AD-26162 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 909 | CGCUGGGACCUU | 1680 | AAGGUCCCAGCG | 3075 | AD-26162, AD-26160 |
| 910 | GCUGGGACCUUG | 1681 | CAAGGUCCCAGC | 3076 | AD-26161, AD-26162 |
| 911 | CUGGGACCUUGC | 1682 | GCAAGGUCCCAG | 3077 | AD-26161, AD-26162 |
| 912 | UGGGACCUUGCA | 1683 | UGCAAGGUCCCA | 3078 | AD-26161, AD-26162, AD-26163 |
| 913 | GGGACCUUGCAU | 1684 | AUGCAAGGUCCC | 3079 | AD-26161, AD-26162, AD-26163, AD-26164 |
| 914 | GGACCUUGCAUA | 1685 | UAUGCAAGGUCC | 3080 | AD-26162, AD-26163, AD-26164 |
| 915 | GACCUUGCAUAA | 1686 | UUAUGCAAGGUC | 3081 | AD-19759, AD-26162, AD-26163, AD-26164 |
| 916 | ACCUUGCAUAAC | 1687 | GUUAUGCAAGGU | 3082 | AD-19759, AD-26163, AD-26164 |
| 917 | CCUUGCAUAACC | 1688 | GGUUAUGCAAGG | 3083 | AD-19759, AD-26164 |
| 918 | CUUGCAUAACCU | 1689 | AGGUUAUGCAAG | 3084 | AD-19759, AD-26163, AD-26164, AD-26165 |
| 919 | UUGCAUAACCUU | 1690 | AAGGUUAUGCAA | 3085 | AD-19759, AD-26163, AD-26164, AD-26165 |
| 920 | UGCAUAACCUUU | 1691 | AAAGGUUAUGCA | 3086 | AD-19759, AD-26164, AD-26165 |
| 921 | GCAUAACCUUUC | 1692 | GAAAGGUUAUGC | 3087 | AD-19759, AD-26165 |
| 922 | CAUAACCUUUCC | 1693 | GGAAAGGUUAUG | 3088 | AD-19759, AD-26165 |
| 959 | UCUUUAAGUCUG | 1694 | CAGACUUAAAGA | 3089 | AD-26166, AD-18901 |
| 960 | CUUUAAGUCUGG | 1695 | CCAGACUUAAAG | 3090 | AD-26166, AD-18901 |
| 975 | CAUUCCUGCCCU | 1696 | AGGGCAGGAAUG | 3091 | AD-26167, AD-26168 |
| 976 | AUUCCUGCCCUG | 1697 | CAGGGCAGGAAU | 3092 | AD-26167, AD-26168, AD-26169 |
| 977 | UUCCUGCCCUGG | 1698 | CCAGGGCAGGAA | 3093 | AD-26170, AD-26167, AD-26168, AD-26169 |
| 978 | UCCUGCCCUGGU | 1699 | ACCAGGGCAGGA | 3094 | AD-26170, AD-26168, AD-26169 |
| 979 | CCUGCCCUGGUG | 1700 | CACCAGGGCAGG | 3095 | AD-26170, AD-26168 |
| 980 | CUGCCCUGGUGA | 1701 | UCACCAGGGCAG | 3096 | AD-26170, AD-26167, AD-26169 |
| 981 | UGCCCUGGUGAA | 1702 | UUCACCAGGGCA | 3097 | AD-26170, AD-26167, AD-26171, AD-26168, AD-26169 |
| 982 | GCCCUGGUGAAA | 1703 | UUUCACCAGGGC | 3098 | AD-26170, AD-26171, AD-26168, AD-26169 |
| 983 | CCCUGGUGAAAA | 1704 | UUUUCACCAGGG | 3099 | AD-26170, AD-26171, AD-26169 |
| 984 | CCUGGUGAAAAU | 1705 | AUUUUCACCAGG | 3100 | AD-26170, AD-26171 |
| 985 | CUGGUGAAAAUG | 1706 | CAUUUUCACCAG | 3101 | AD-26172, AD-26171 |
| 986 | UGGUGAAAAUGC | 1707 | GCAUUUUCACCA | 3102 | AD-26172, AD-26171 |
| 987 | GGUGAAAAUGCU | 1708 | AGCAUUUUCACC | 3103 | AD-26172, AD-26171 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 988 | GUGAAAAUGCUU | 1709 | AAGCAUUUUCAC | 3104 | AD-26172, AD-26171 |
| 997 | CUUGGUUCACCA | 1710 | UGGUGAACCAAG | 3105 | AD-26173, AD-26174 |
| 998 | UUGGUUCACCAG | 1711 | CUGGUGAACCAA | 3106 | AD-26173, AD-26174 |
| 999 | UGGUUCACCAGU | 1712 | ACUGGUGAACCA | 3107 | AD-26173, AD-26174 |
| 1000 | GGUUCACCAGUG | 1713 | CACUGGUGAACC | 3108 | AD-26173, AD-26174 |
| 1001 | GUUCACCAGUGG | 1714 | CCACUGGUGAAC | 3109 | AD-26173, AD-26174 |
| 1002 | UUCACCAGUGGA | 1715 | UCCACUGGUGAA | 3110 | AD-26173, AD-26174 |
| 1003 | UCACCAGUGGAU | 1716 | AUCCACUGGUGA | 3111 | AD-26173, AD-26174 |
| 1004 | CACCAGUGGAUU | 1717 | AAUCCACUGGUG | 3112 | AD-26177, AD-26174 |
| 1007 | CAGUGGAUUCUG | 1718 | CAGAAUCCACUG | 3113 | AD-26177, AD-26178 |
| 1008 | AGUGGAUUCUGU | 1719 | ACAGAAUCCACU | 3114 | AD-26177, AD-26178, AD-26179 |
| 1009 | GUGGAUUCUGUG | 1720 | CACAGAAUCCAC | 3115 | AD-26177, AD-26178, AD-26179, AD-26180 |
| 1010 | UGGAUUCUGUGU | 1721 | ACACAGAAUCCA | 3116 | AD-26177, AD-26181, AD-26178, AD-26179, AD-26180 |
| 1011 | GGAUUCUGUGUU | 1722 | AACACAGAAUCC | 3117 | AD-26177, AD-26181, AD-26178, AD-26179, AD-26182, AD-26180 |
| 1012 | GAUUCUGUGUUG | 1723 | CAACACAGAAUC | 3118 | AD-26181, AD-26178, AD-26179, AD-26182, AD-26180 |
| 1013 | AUUCUGUGUUGU | 1724 | ACAACACAGAAU | 3119 | AD-26181, AD-26178, AD-26179, AD-26182 |
| 1014 | UUCUGUGUUGUU | 1725 | AACAACACAGAA | 3120 | AD-26181, AD-26179, AD-26182, AD-26180 |
| 1015 | UCUGUGUUGUUU | 1726 | AAACAACACAGA | 3121 | AD-26181, AD-26179, AD-26182, AD-26180 |
| 1016 | CUGUGUUGUUUU | 1727 | AAAACAACACAG | 3122 | AD-26181, AD-26182, AD-26180 |
| 1017 | UGUGUUGUUUUA | 1728 | UAAAACAACACA | 3123 | AD-26183, AD-26181, AD-26182 |
| 1018 | GUGUUGUUUUAU | 1729 | AUAAAACAACAC | 3124 | AD-26183, AD-26182, AD-26185 |
| 1019 | UGUUGUUUUAUG | 1730 | CAUAAAACAACA | 3125 | AD-26183, AD-26185 |
| 1020 | GUUGUUUUAUGC | 1731 | GCAUAAAACAAC | 3126 | AD-26183, AD-26185 |
| 1021 | UUGUUUUAUGCC | 1732 | GGCAUAAAACAA | 3127 | AD-26183, AD-26186 |
| 1022 | UGUUUUAUGCCA | 1733 | UGGCAUAAAACA | 3128 | AD-26183, AD-26185 |
| 1023 | GUUUUAUGCCAU | 1734 | AUGGCAUAAAAC | 3129 | AD-26183, AD-26185, AD-26186 |
| 1024 | UUUUAUGCCAUU | 1735 | AAUGGCAUAAAA | 3130 | AD-26183, AD-26185, AD-26186 |
| 1025 | UUUAUGCCAUUA | 1736 | UAAUGGCAUAAA | 3131 | AD-26185, AD-26186 |
| 1027 | UAUGCCAUUACA | 1737 | UGUAAUGGCAUA | 3132 | AD-26186, AD-19767 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 1028 | AUGCCAUUACAA | 1738 | UUGUAAUGGCAU | 3133 | AD-26186, AD-19767 |
| 1031 | CCAUUACAACUC | 1739 | GAGUUGUAAUGG | 3134 | AD-26187, AD-19767 |
| 1032 | CAUUACAACUCU | 1740 | AGAGUUGUAAUG | 3135 | AD-26187, AD-19767 |
| 1033 | AUUACAACUCUC | 1741 | GAGAGUUGUAAU | 3136 | AD-26187, AD-19767 |
| 1034 | UUACAACUCUCC | 1742 | GGAGAGUUGUAA | 3137 | AD-26187, AD-19767 |
| 1035 | UACAACUCUCCA | 1743 | UGGAGAGUUGUA | 3138 | AD-26188, AD-26187 |
| 1036 | ACAACUCUCCAC | 1744 | GUGGAGAGUUGU | 3139 | AD-26188, AD-26189, AD-26187 |
| 1037 | CAACUCUCCACA | 1745 | UGUGGAGAGUUG | 3140 | AD-26190, AD-26188, AD-26189, AD-26187 |
| 1038 | AACUCUCCACAA | 1746 | UUGUGGAGAGUU | 3141 | AD-26190, AD-26191, AD-26188, AD-26189, AD-26187 |
| 1039 | ACUCUCCACAAC | 1747 | GUUGUGGAGAGU | 3142 | AD-26190, AD-26192, AD-26191, AD-26188, AD-26189 |
| 1040 | CUCUCCACAACC | 1748 | GGUUGUGGAGAG | 3143 | AD-26190, AD-26192, AD-26193, AD-26191, AD-26188, AD-26189 |
| 1041 | UCUCCACAACCU | 1749 | AGGUUGUGGAGA | 3144 | AD-26190, AD-26192, AD-26193, AD-26194, AD-26191, AD-26188, AD-26189 |
| 1042 | CUCCACAACCUU | 1750 | AAGGUUGUGGAG | 3145 | AD-26190, AD-26192, AD-26193, AD-26194, AD-26191, AD-26189 |
| 1043 | UCCACAACCUUU | 1751 | AAAGGUUGUGGA | 3146 | AD-26190, AD-26192, AD-26193, AD-26194, AD-26189 |
| 1044 | CCACAACCUUUU | 1752 | AAAAGGUUGUGG | 3147 | AD-26190, AD-26192, AD-26193, AD-26194, AD-26191 |
| 1045 | CACAACCUUUUA | 1753 | UAAAAGGUUGUG | 3148 | AD-26192, AD-26193, AD-26194, AD-26191 |
| 1046 | ACAACCUUUUAU | 1754 | AUAAAAGGUUGU | 3149 | AD-26192, AD-26193, AD-26194 |
| 1047 | CAACCUUUUAUU | 1755 | AAUAAAAGGUUG | 3150 | AD-26193, AD-26194, AD-26195 |
| 1048 | AACCUUUUAUUA | 1756 | UAAUAAAAGGUU | 3151 | AD-26194, AD-26195 |
| 1050 | CCUUUUAUUACA | 1757 | UGUAAUAAAAGG | 3152 | AD-26196, AD-26195 |
| 1051 | CUUUUAUUACAU | 1758 | AUGUAAUAAAAG | 3153 | AD-26196, AD-26195 |
| 1052 | UUUUAUUACAUC | 1759 | GAUGUAAUAAAA | 3154 | AD-26196, AD-26195 |
| 1053 | UUUAUUACAUCA | 1760 | UGAUGUAAUAAA | 3155 | AD-26196, AD-26195 |
| 1054 | UUAUUACAUCAA | 1761 | UUGAUGUAAUAA | 3156 | AD-26196, AD-26195 |
| 1057 | UUACAUCAAGAA | 1762 | UUCUUGAUGUAA | 3157 | AD-26197, AD-26196 |
| 1058 | UACAUCAAGAAG | 1763 | CUUCUUGAUGUA | 3158 | AD-26198, AD-26197 |
| 1059 | ACAUCAAGAAGG | 1764 | CCUUCUUGAUGU | 3159 | AD-26198, AD-26197 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 1060 | CAUCAAGAAGGA | 1765 | UCCUUCUUGAUG | 3160 | AD-26198, AD-26199, AD-26197 |
| 1061 | AUCAAGAAGGAG | 1766 | CUCCUUCUUGAU | 3161 | AD-26198, AD-26199, AD-26197, AD-26200 |
| 1062 | UCAAGAAGGAGC | 1767 | GCUCCUUCUUGA | 3162 | AD-26198, AD-26199, AD-26200 |
| 1063 | CAAGAAGGAGCU | 1768 | AGCUCCUUCUUG | 3163 | AD-26198, AD-26197, AD-26200 |
| 1064 | AAGAAGGAGCUA | 1769 | UAGCUCCUUCUU | 3164 | AD-26198, AD-26199, AD-26197, AD-26200 |
| 1065 | AGAAGGAGCUAA | 1770 | UUAGCUCCUUCU | 3165 | AD-26198, AD-26199, AD-26200 |
| 1066 | GAAGGAGCUAAA | 1771 | UUUAGCUCCUUC | 3166 | AD-26199, AD-26200 |
| 1067 | AAGGAGCUAAAA | 1772 | UUUUAGCUCCUU | 3167 | AD-26199, AD-26200 |
| 1068 | AGGAGCUAAAAU | 1773 | AUUUUAGCUCCU | 3168 | AD-26200, AD-18977 |
| 1072 | GCUAAAAUGGCA | 1774 | UGCCAUUUUAGC | 3169 | AD-26201, AD-18977 |
| 1073 | CUAAAAUGGCAG | 1775 | CUGCCAUUUUAG | 3170 | AD-26201, AD-18977 |
| 1074 | UAAAAUGGCAGU | 1776 | ACUGCCAUUUUA | 3171 | AD-26201, AD-26202, AD-18977 |
| 1075 | AAAAUGGCAGUG | 1777 | CACUGCCAUUUU | 3172 | AD-26201, AD-18977 |
| 1076 | AAAUGGCAGUGC | 1778 | GCACUGCCAUUU | 3173 | AD-26201, AD-26202 |
| 1077 | AAUGGCAGUGCG | 1779 | CGCACUGCCAUU | 3174 | AD-26201, AD-26202 |
| 1078 | AUGGCAGUGCGU | 1780 | ACGCACUGCCAU | 3175 | AD-26201, AD-26202 |
| 1079 | UGGCAGUGCGUU | 1781 | AACGCACUGCCA | 3176 | AD-26201, AD-26202 |
| 1112 | UGGUUGCCUUGC | 1782 | GCAAGGCAACCA | 3177 | AD-26205, AD-26203 |
| 1113 | GGUUGCCUUGCU | 1783 | AGCAAGGCAACC | 3178 | AD-26206, AD-26205, AD-26203 |
| 1114 | GUUGCCUUGCUC | 1784 | GAGCAAGGCAAC | 3179 | AD-26206, AD-26205, AD-26203, AD-26207 |
| 1115 | UUGCCUUGCUCA | 1785 | UGAGCAAGGCAA | 3180 | AD-26206, AD-26205, AD-26203 |
| 1116 | UGCCUUGCUCAA | 1786 | UUGAGCAAGGCA | 3181 | AD-26206, AD-26203, AD-26207 |
| 1117 | GCCUUGCUCAAC | 1787 | GUUGAGCAAGGC | 3182 | AD-26205, AD-26208, AD-26207 |
| 1118 | CCUUGCUCAACA | 1788 | UGUUGAGCAAGG | 3183 | AD-26206, AD-26205, AD-26208, AD-26207, AD-26209 |
| 1119 | CUUGCUCAACAA | 1789 | UUGUUGAGCAAG | 3184 | AD-26206, AD-26205, AD-26208, AD-26207, AD-26209 |
| 1120 | UUGCUCAACAAA | 1790 | UUUGUUGAGCAA | 3185 | AD-26206, AD-26208, AD-26207, AD-26209 |
| 1121 | UGCUCAACAAAA | 1791 | UUUUGUUGAGCA | 3186 | AD-26208, AD-26207, AD-26209 |
| 1122 | GCUCAACAAAAC | 1792 | GUUUUGUUGAGC | 3187 | AD-26208, AD-26209 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 1123 | CUCAACAAAACA | 1793 | UGUUUUGUUGAG | 3188 | AD-26208, AD-26209 |
| 1124 | UCAACAAAACAA | 1794 | UUGUUUUGUUGA | 3189 | AD-26208, AD-26209 |
| 1219 | AGUGGUGGACCC | 1795 | GGGUCCACCACU | 3190 | AD-26057, AD-26213 |
| 1220 | GUGGUGGACCCC | 1796 | GGGGUCCACCAC | 3191 | AD-26057, AD-26213, AD-26214 |
| 1221 | UGGUGGACCCCA | 1797 | UGGGGUCCACCA | 3192 | AD-26215, AD-26057, AD-26213, AD-26214 |
| 1222 | GGUGGACCCCAA | 1798 | UUGGGGUCCACC | 3193 | AD-26215, AD-26057, AD-26213 |
| 1223 | GUGGACCCCAAG | 1799 | CUUGGGGUCCAC | 3194 | AD-26215, AD-26213, AD-26214 |
| 1224 | UGGACCCCAAGC | 1800 | GCUUGGGGUCCA | 3195 | AD-26215, AD-26216, AD-26213, AD-26214 |
| 1225 | GGACCCCAAGCU | 1801 | AGCUUGGGGUCC | 3196 | AD-26215, AD-26217, AD-26216, AD-26213, AD-26214 |
| 1226 | GACCCCAAGCUU | 1802 | AAGCUUGGGGUC | 3197 | AD-26215, AD-26217, AD-26216, AD-26213, AD-26214, AD-26218 |
| 1227 | ACCCCAAGCUUU | 1803 | AAAGCUUGGGGU | 3198 | AD-26215, AD-26651, AD-26217, AD-26216, AD-26218 |
| 1228 | CCCCAAGCUUUA | 1804 | UAAAGCUUGGGG | 3199 | AD-26215, AD-26652, AD-26217, AD-26216, AD-26218 |
| 1229 | CCCAAGCUUUAG | 1805 | CUAAAGCUUGGG | 3200 | AD-26651, AD-26652, AD-26217, AD-26216, AD-26653, AD-26218 |
| 1230 | CCAAGCUUUAGU | 1806 | ACUAAAGCUUGG | 3201 | AD-26654, AD-26651, AD-26652, AD-26217, AD-26216, AD-26653, AD-26218 |
| 1231 | CAAGCUUUAGUA | 1807 | UACUAAAGCUUG | 3202 | AD-26654, AD-26651, AD-26652, AD-26217, AD-26068, AD-26216, AD-26653, AD-26218 |
| 1232 | AAGCUUUAGUAA | 1808 | UUACUAAAGCUU | 3203 | AD-26654, AD-26651, AD-26652, AD-26217, AD-26068, AD-26653, AD-26069, AD-26218 |
| 1233 | AGCUUUAGUAAA | 1809 | UUUACUAAAGCU | 3204 | AD-26654, AD-26651, AD-26652, AD-26068, AD-26653, AD-26069, AD-26218 |
| 1234 | GCUUUAGUAAAU | 1810 | AUUUACUAAAGC | 3205 | AD-26654, AD-26651, AD-26652, AD-26068, AD-26653, AD-26069 |
| 1235 | CUUUAGUAAAUA | 1811 | UAUUUACUAAAG | 3206 | AD-26654, AD-26652, AD-26068, AD-26653, AD-26069 |
| 1236 | UUUAGUAAAUAU | 1812 | AUAUUUACUAAA | 3207 | AD-26654, AD-26068, AD-26653, AD-26069 |

TABLE 4-continued

Groups of overlapping RNAi agents to Beta-Catenin

| Position | Sense overlap | SEQ ID NO: Anti-sense overlap | SEQ ID NO: | Overlapping groups of RNAi agents |
|---|---|---|---|---|
| 1237 | UUAGUAAUAUA | 1813 UAUAUUUACUAA | 3208 | AD-26654, AD-26068, AD-26069 |
| 1238 | UAGUAAAUAUAA | 1814 UUAUAUUUACUA | 3209 | AD-26068, AD-26069 |
| 1242 | AAAUAUAAUGAG | 1815 CUCAUUAUAUUU | 3210 | AD-26655, AD-26656 |
| 1243 | AAUAUAAUGAGG | 1816 CCUCAUUAUAUU | 3211 | AD-26655, AD-26657 |
| 1244 | AUAUAAUGAGGA | 1817 UCCUCAUUAUAU | 3212 | AD-26655, AD-26656, AD-26657 |
| 1245 | UAUAAUGAGGAC | 1818 GUCCUCAUUAUA | 3213 | AD-26655, AD-26656, AD-26657 |
| 1246 | AUAAUGAGGACC | 1819 GGUCCUCAUUAU | 3214 | AD-26655, AD-26656, AD-26657 |
| 1247 | UAAUGAGGACCU | 1820 AGGUCCUCAUUA | 3215 | AD-26658, AD-26655, AD-26656, AD-26657 |
| 1248 | AAUGAGGACCUA | 1821 UAGGUCCUCAUU | 3216 | AD-26658, AD-26655, AD-26657 |
| 1249 | AUGAGGACCUAU | 1822 AUAGGUCCUCAU | 3217 | AD-26658, AD-26656, AD-26657 |
| 1250 | UGAGGACCUAUA | 1823 UAUAGGUCCUCA | 3218 | AD-26658, AD-26657 |
| 1285 | ACAAGCAGAGUG | 1824 CACUCUGCUUGU | 3219 | AD-18945, AD-26660 |
| 1286 | CAAGCAGAGUGC | 1825 GCACUCUGCUUG | 3220 | AD-18945, AD-26660 |
| 1287 | AAGCAGAGUGCU | 1826 AGCACUCUGCUU | 3221 | AD-18945, AD-26660 |
| 1288 | AGCAGAGUGCUG | 1827 CAGCACUCUGCU | 3222 | AD-18945, AD-19046 |
| 1289 | GCAGAGUGCUGA | 1828 UCAGCACUCUGC | 3223 | AD-18945, AD-26660, AD-19046 |
| 1290 | CAGAGUGCUGAA | 1829 UUCAGCACUCUG | 3224 | AD-18945, AD-26660, AD-19046, AD-26661 |
| 1291 | AGAGUGCUGAAG | 1830 CUUCAGCACUCU | 3225 | AD-18945, AD-19046, AD-26661, AD-26662 |
| 1292 | GAGUGCUGAAGG | 1831 CCUUCAGCACUC | 3226 | AD-18945, AD-19046, AD-26662 |
| 1293 | AGUGCUGAAGGU | 1832 ACCUUCAGCACU | 3227 | AD-19046, AD-26661, AD-26662 |
| 1294 | GUGCUGAAGGUG | 1833 CACCUUCAGCAC | 3228 | AD-19046, AD-26662 |
| 1295 | UGCUGAAGGUGC | 1834 GCACCUUCAGCA | 3229 | AD-26661, AD-26662 |
| 1296 | GCUGAAGGUGCU | 1835 AGCACCUUCAGC | 3230 | AD-26661, AD-26662 |
| 1297 | CUGAAGGUGCUA | 1836 UAGCACCUUCAG | 3231 | AD-26661, AD-26662 |
| 1313 | UCUGCUCUAGUA | 1837 UACUAGAGCAGA | 3232 | AD-19768, AD-19748 |
| 1314 | CUGCUCUAGUAA | 1838 UUACUAGAGCAG | 3233 | AD-19768, AD-19748 |
| 1315 | UGCUCUAGUAAU | 1839 AUUACUAGAGCA | 3234 | AD-19768, AD-19748 |
| 1316 | GCUCUAGUAAUA | 1840 UAUUACUAGAGC | 3235 | AD-19768, AD-19748 |
| 1317 | CUCUAGUAAUAA | 1841 UUAUUACUAGAG | 3236 | AD-19768, AD-19748 |
| 1318 | UCUAGUAAUAAG | 1842 CUUAUUACUAGA | 3237 | AD-19768, AD-19748 |
| 1319 | CUAGUAAUAAGC | 1843 GCUUAUUACUAG | 3238 | AD-19768, AD-19748 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 1337 | UUGUAGAAGCUG | 1844 | CAGCUUCUACAA | 3239 | AD-26664, AD-26663 |
| 1338 | UGUAGAAGCUGG | 1845 | CCAGCUUCUACA | 3240 | AD-26664, AD-26663 |
| 1339 | GUAGAAGCUGGU | 1846 | ACCAGCUUCUAC | 3241 | AD-26664, AD-26663 |
| 1340 | UAGAAGCUGGUG | 1847 | CACCAGCUUCUA | 3242 | AD-26664, AD-26663 |
| 1341 | AGAAGCUGGUGG | 1848 | CCACCAGCUUCU | 3243 | AD-26664, AD-26663 |
| 1342 | GAAGCUGGUGGA | 1849 | UCCACCAGCUUC | 3244 | AD-26664, AD-26663 |
| 1343 | AAGCUGGUGGAA | 1850 | UUCCACCAGCUU | 3245 | AD-26664, AD-26663 |
| 1346 | CUGGUGGAAUGC | 1851 | GCAUUCCACCAG | 3246 | AD-26665, AD-26666 |
| 1347 | UGGUGGAAUGCA | 1852 | UGCAUUCCACCA | 3247 | AD-26665, AD-26666 |
| 1348 | GGUGGAAUGCAA | 1853 | UUGCAUUCCACC | 3248 | AD-26665, AD-26666 |
| 1349 | GUGGAAUGCAAG | 1854 | CUUGCAUUCCAC | 3249 | AD-26665, AD-26666 |
| 1350 | UGGAAUGCAAGC | 1855 | GCUUGCAUUCCA | 3250 | AD-26665, AD-26666 |
| 1351 | GGAAUGCAAGCU | 1856 | AGCUUGCAUUCC | 3251 | AD-26665, AD-26666 |
| 1352 | GAAUGCAAGCUU | 1857 | AAGCUUGCAUUC | 3252 | AD-26665, AD-26666 |
| 1369 | CUUCACCUGACA | 1858 | UGUCAGGUGAAG | 3253 | AD-26667, AD-26668 |
| 1370 | UUCACCUGACAG | 1859 | CUGUCAGGUGAA | 3254 | AD-26667, AD-26668 |
| 1371 | UCACCUGACAGA | 1860 | UCUGUCAGGUGA | 3255 | AD-26667, AD-26668 |
| 1372 | CACCUGACAGAU | 1861 | AUCUGUCAGGUG | 3256 | AD-26667, AD-26668 |
| 1374 | CCUGACAGAUCC | 1862 | GGAUCUGUCAGG | 3257 | AD-26669, AD-26668 |
| 1375 | CUGACAGAUCCA | 1863 | UGGAUCUGUCAG | 3258 | AD-26669, AD-26668 |
| 1376 | UGACAGAUCCAA | 1864 | UUGGAUCUGUCA | 3259 | AD-26669, AD-26668 |
| 1380 | AGAUCCAAGUCA | 1865 | UGACUUGGAUCU | 3260 | AD-26669, AD-26670 |
| 1381 | GAUCCAAGUCAA | 1866 | UUGACUUGGAUC | 3261 | AD-26669, AD-26670 |
| 1383 | UCCAAGUCAACG | 1867 | CGUUGACUUGGA | 3262 | AD-26671, AD-26670 |
| 1384 | CCAAGUCAACGU | 1868 | ACGUUGACUUGG | 3263 | AD-26671, AD-26670 |
| 1385 | CAAGUCAACGUC | 1869 | GACGUUGACUUG | 3264 | AD-26671, AD-26670 |
| 1386 | AAGUCAACGUCU | 1870 | AGACGUUGACUU | 3265 | AD-26671, AD-26670 |
| 1387 | AGUCAACGUCUU | 1871 | AAGACGUUGACU | 3266 | AD-26671, AD-26670 |
| 1396 | CUUGUUCAGAAC | 1872 | GUUCUGAACAAG | 3267 | AD-26672, AD-26673 |
| 1397 | UUGUUCAGAACU | 1873 | AGUUCUGAACAA | 3268 | AD-26672, AD-26673 |
| 1398 | UGUUCAGAACUG | 1874 | CAGUUCUGAACA | 3269 | AD-26672, AD-26673 |
| 1399 | GUUCAGAACUGU | 1875 | ACAGUUCUGAAC | 3270 | AD-26672, AD-26673 |
| 1400 | UUCAGAACUGUC | 1876 | GACAGUUCUGAA | 3271 | AD-26672, AD-26673 |
| 1401 | UCAGAACUGUCU | 1877 | AGACAGUUCUGA | 3272 | AD-26672, AD-26673 |
| 1402 | CAGAACUGUCUU | 1878 | AAGACAGUUCUG | 3273 | AD-26672, AD-26673 |
| 1406 | ACUGUCUUUGGA | 1879 | UCCAAAGACAGU | 3274 | AD-19056, AD-19079 |
| 1407 | CUGUCUUUGGAC | 1880 | GUCCAAAGACAG | 3275 | AD-19056, AD-19079 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 1408 | UGUCUUUGGACU | 1881 | AGUCCAAAGACA | 3276 | AD-19056, AD-19079 |
| 1409 | GUCUUUGGACUC | 1882 | GAGUCCAAAGAC | 3277 | AD-26674, AD-19056, AD-19079 |
| 1410 | UCUUUGGACUCU | 1883 | AGAGUCCAAAGA | 3278 | AD-26674, AD-26675, AD-19056, AD-19079 |
| 1411 | CUUUGGACUCUC | 1884 | GAGAGUCCAAAG | 3279 | AD-26674, AD-19056, AD-19079 |
| 1412 | UUUGGACUCUCA | 1885 | UGAGAGUCCAAA | 3280 | AD-26674, AD-26675, AD-19079 |
| 1413 | UUGGACUCUCAG | 1886 | CUGAGAGUCCAA | 3281 | AD-26675, AD-26676, AD-19079 |
| 1414 | UGGACUCUCAGG | 1887 | CCUGAGAGUCCA | 3282 | AD-26674, AD-26675, AD-26676, AD-26678 |
| 1415 | GGACUCUCAGGA | 1888 | UCCUGAGAGUCC | 3283 | AD-26674, AD-26676, AD-26678 |
| 1416 | GACUCUCAGGAA | 1889 | UUCCUGAGAGUC | 3284 | AD-26674, AD-26675, AD-26676, AD-26678 |
| 1417 | ACUCUCAGGAAU | 1890 | AUUCCUGAGAGU | 3285 | AD-26675, AD-26676, AD-26678 |
| 1418 | CUCUCAGGAAUC | 1891 | GAUUCCUGAGAG | 3286 | AD-26676, AD-26678 |
| 1419 | UCUCAGGAAUCU | 1892 | AGAUUCCUGAGA | 3287 | AD-26679, AD-26676, AD-26678 |
| 1420 | CUCAGGAAUCUU | 1893 | AAGAUUCCUGAG | 3288 | AD-26679, AD-26678 |
| 1421 | UCAGGAAUCUUU | 1894 | AAAGAUUCCUGA | 3289 | AD-26679, AD-26678 |
| 1426 | AAUCUUUCAGAU | 1895 | AUCUGAAAGAUU | 3290 | AD-26679, AD-26680 |
| 1429 | CUUUCAGAUGCU | 1896 | AGCAUCUGAAAG | 3291 | AD-26681, AD-26680 |
| 1430 | UUUCAGAUGCUG | 1897 | CAGCAUCUGAAA | 3292 | AD-26681, AD-26680 |
| 1431 | UUCAGAUGCUGC | 1898 | GCAGCAUCUGAA | 3293 | AD-26682, AD-26680 |
| 1432 | UCAGAUGCUGCA | 1899 | UGCAGCAUCUGA | 3294 | AD-26682, AD-26681 |
| 1433 | CAGAUGCUGCAA | 1900 | UUGCAGCAUCUG | 3295 | AD-26682, AD-26681, AD-26680 |
| 1434 | AGAUGCUGCAAC | 1901 | GUUGCAGCAUCU | 3296 | AD-26682, AD-26681 |
| 1435 | GAUGCUGCAACU | 1902 | AGUUGCAGCAUC | 3297 | AD-26682, AD-26681 |
| 1436 | AUGCUGCAACUA | 1903 | UAGUUGCAGCAU | 3298 | AD-26682, AD-26681 |
| 1437 | UGCUGCAACUAA | 1904 | UUAGUUGCAGCA | 3299 | AD-26682, AD-26683 |
| 1438 | GCUGCAACUAAA | 1905 | UUUAGUUGCAGC | 3300 | AD-26682, AD-26683 |
| 1467 | UCUCCUUGGGAC | 1906 | GUCCCAAGGAGA | 3301 | AD-26687, AD-26686 |
| 1468 | CUCCUUGGGACU | 1907 | AGUCCCAAGGAG | 3302 | AD-26687, AD-26686 |
| 1469 | UCCUUGGGACUC | 1908 | GAGUCCCAAGGA | 3303 | AD-26687, AD-26686 |
| 1470 | CCUUGGGACUCU | 1909 | AGAGUCCCAAGG | 3304 | AD-26687, AD-26686 |
| 1471 | CUUGGGACUCUU | 1910 | AAGAGUCCCAAG | 3305 | AD-26687, AD-26686 |
| 1473 | UGGGACUCUUGU | 1911 | ACAAGAGUCCCA | 3306 | AD-26688, AD-26687 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 1474 | GGGACUCUUGUU | 1912 | AACAAGAGUCCC | 3307 | AD-26688, AD-26687 |
| 1480 | CUUGUUCAGCUU | 1913 | AAGCUGAACAAG | 3308 | AD-26689, AD-26688 |
| 1485 | UCAGCUUCUGGG | 1914 | CCCAGAAGCUGA | 3309 | AD-26689, AD-26690 |
| 1486 | CAGCUUCUGGGU | 1915 | ACCCAGAAGCUG | 3310 | AD-26689, AD-26690 |
| 1487 | AGCUUCUGGGUU | 1916 | AACCCAGAAGCU | 3311 | AD-26689, AD-26690 |
| 1488 | GCUUCUGGGUUC | 1917 | GAACCCAGAAGC | 3312 | AD-26691, AD-26690 |
| 1489 | CUUCUGGGUUCA | 1918 | UGAACCCAGAAG | 3313 | AD-26692, AD-26691, AD-26690 |
| 1490 | UUCUGGGUUCAG | 1919 | CUGAACCCAGAA | 3314 | AD-26692, AD-26691, AD-26694, AD-26690 |
| 1491 | UCUGGGUUCAGA | 1920 | UCUGAACCCAGA | 3315 | AD-26692, AD-26694, AD-26690 |
| 1492 | CUGGGUUCAGAU | 1921 | AUCUGAACCCAG | 3316 | AD-26692, AD-26691, AD-26694, AD-26695, AD-26690 |
| 1493 | UGGGUUCAGAUG | 1922 | CAUCUGAACCCA | 3317 | AD-26692, AD-26691, AD-26696, AD-26694, AD-26695 |
| 1494 | GGGUUCAGAUGA | 1923 | UCAUCUGAACCC | 3318 | AD-26692, AD-26691, AD-26696, AD-26694 |
| 1495 | GGUUCAGAUGAU | 1924 | AUCAUCUGAACC | 3319 | AD-26692, AD-26691, AD-26694, AD-26695 |
| 1496 | GUUCAGAUGAUA | 1925 | UAUCAUCUGAAC | 3320 | AD-26696, AD-26694, AD-26695 |
| 1497 | UUCAGAUGAUAU | 1926 | AUAUCAUCUGAA | 3321 | AD-26696, AD-26694, AD-26695 |
| 1498 | UCAGAUGAUAUA | 1927 | UAUAUCAUCUGA | 3322 | AD-26696, AD-26695 |
| 1499 | CAGAUGAUAUAA | 1928 | UUAUAUCAUCUG | 3323 | AD-26696, AD-26695 |
| 1503 | UGAUAUAAAUGU | 1929 | ACAUUUAUAUCA | 3324 | AD-18994, AD-18927 |
| 1504 | GAUAUAAAUGUG | 1930 | CACAUUUAUAUC | 3325 | AD-19045, AD-18994 |
| 1505 | AUAUAAAUGUGG | 1931 | CCACAUUUAUAU | 3326 | AD-19045, AD-18927 |
| 1506 | UAUAAAUGUGGU | 1932 | ACCACAUUUAUA | 3327 | AD-18994, AD-18927 |
| 1507 | AUAAAUGUGGUC | 1933 | GACCACAUUUAU | 3328 | AD-19045, AD-18994, AD-18927 |
| 1508 | UAAAUGUGGUCA | 1934 | UGACCACAUUUA | 3329 | AD-19045, AD-18994, AD-18927 |
| 1509 | AAAUGUGGUCAC | 1935 | GUGACCACAUUU | 3330 | AD-19045, AD-18994 |
| 1510 | AAUGUGGUCACC | 1936 | GGUGACCACAUU | 3331 | AD-19045, AD-18994 |
| 1517 | UCACCUGUGCAG | 1937 | CUGCACAGGUGA | 3332 | AD-26697, AD-26698 |
| 1518 | CACCUGUGCAGC | 1938 | GCUGCACAGGUG | 3333 | AD-26697, AD-26698 |
| 1519 | ACCUGUGCAGCU | 1939 | AGCUGCACAGGU | 3334 | AD-26697, AD-26699 |
| 1520 | CCUGUGCAGCUG | 1940 | CAGCUGCACAGG | 3335 | AD-26697, AD-26699, AD-26698 |
| 1521 | CUGUGCAGCUGG | 1941 | CCAGCUGCACAG | 3336 | AD-26700, AD-26697, AD-26699, AD-26698 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 1522 | UGUGCAGCUGGA | 1942 | UCCAGCUGCACA | 3337 | AD-26700, AD-26697, AD-26699, AD-26701, AD-26698 |
| 1523 | GUGCAGCUGGAA | 1943 | UUCCAGCUGCAC | 3338 | AD-26700, AD-26699, AD-26701, AD-26698 |
| 1524 | UGCAGCUGGAAU | 1944 | AUUCCAGCUGCA | 3339 | AD-26700, AD-26699, AD-26701, AD-26698 |
| 1525 | GCAGCUGGAAUU | 1945 | AAUUCCAGCUGC | 3340 | AD-26700, AD-26699, AD-26701, AD-26702 |
| 1526 | CAGCUGGAAUUC | 1946 | GAAUUCCAGCUG | 3341 | AD-26700, AD-26701, AD-26702 |
| 1527 | AGCUGGAAUUCU | 1947 | AGAAUUCCAGCU | 3342 | AD-26700, AD-26703, AD-26702 |
| 1528 | GCUGGAAUUCUU | 1948 | AAGAAUUCCAGC | 3343 | AD-26700, AD-26703, AD-26701, AD-26702 |
| 1529 | CUGGAAUUCUUU | 1949 | AAAGAAUUCCAG | 3344 | AD-26703, AD-26701, AD-26702 |
| 1530 | UGGAAUUCUUUC | 1950 | GAAAGAAUUCCA | 3345 | AD-26703, AD-26702 |
| 1531 | GGAAUUCUUUCU | 1951 | AGAAAGAAUUCC | 3346 | AD-26703, AD-26702 |
| 1532 | GAAUUCUUUCUA | 1952 | UAGAAAGAAUUC | 3347 | AD-26703, AD-26702 |
| 1538 | UUUCUAACCUCA | 1953 | UGAGGUUAGAAA | 3348 | AD-26704, AD-26920 |
| 1539 | UUCUAACCUCAC | 1954 | GUGAGGUUAGAA | 3349 | AD-26704, AD-26920, AD-26705 |
| 1540 | UCUAACCUCACU | 1955 | AGUGAGGUUAGA | 3350 | AD-26704, AD-26920, AD-26705, AD-18899 |
| 1541 | CUAACCUCACUU | 1956 | AAGUGAGGUUAG | 3351 | AD-26704, AD-26920, AD-26705, AD-18899, AD-18917 |
| 1542 | UAACCUCACUUG | 1957 | CAAGUGAGGUUA | 3352 | AD-26704, AD-26705, AD-18899, AD-18917 |
| 1543 | AACCUCACUUGC | 1958 | GCAAGUGAGGUU | 3353 | AD-26704, AD-19074, AD-26705, AD-18899, AD-18917 |
| 1544 | ACCUCACUUGCA | 1959 | UGCAAGUGAGGU | 3354 | AD-26704, AD-26706, AD-19074, AD-26705, AD-18899, AD-18917 |
| 1545 | CCUCACUUGCAA | 1960 | UUGCAAGUGAGG | 3355 | AD-26704, AD-26706, AD-26707, AD-19074, AD-26705, AD-18899, AD-18917 |
| 1546 | CUCACUUGCAAU | 1961 | AUUGCAAGUGAG | 3356 | AD-26706, AD-26707, AD-19074, AD-26708, AD-26705, AD-18899, AD-18917 |
| 1547 | UCACUUGCAAUA | 1962 | UAUUGCAAGUGA | 3357 | AD-26706, AD-26134, AD-26707, AD-19074, AD-26708, AD-18899, AD-18917 |
| 1548 | CACUUGCAAUAA | 1963 | UUAUUGCAAGUG | 3358 | AD-26706, AD-26134, AD-26707, AD-19074, AD-26708, AD-18917 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 1549 | ACUUGCAAUAAU | 1964 | AUUAUUGCAAGU | 3359 | AD-26706, AD-26134, AD-26707, AD-19074, AD-26708 |
| 1550 | CUUGCAAUAAUU | 1965 | AAUUAUUGCAAG | 3360 | AD-26706, AD-26134, AD-26707, AD-19074, AD-26708, AD-26135 |
| 1551 | UUGCAAUAAUUA | 1966 | UAAUUAUUGCAA | 3361 | AD-26706, AD-26134, AD-26707, AD-26708, AD-26135 |
| 1552 | UGCAAUAAUUAU | 1967 | AUAAUUAUUGCA | 3362 | AD-26134, AD-26707, AD-26708, AD-26135 |
| 1553 | GCAAUAAUUAUA | 1968 | UAUAAUUAUUGC | 3363 | AD-26134, AD-26708, AD-26135 |
| 1554 | CAAUAAUUAUAA | 1969 | UUAUAAUUAUUG | 3364 | AD-26134, AD-26135 |
| 1580 | UCUGCCAAGUGG | 1970 | CCACUUGGCAGA | 3365 | AD-26710, AD-26709 |
| 1581 | CUGCCAAGUGGG | 1971 | CCCACUUGGCAG | 3366 | AD-26710, AD-26709 |
| 1582 | UGCCAAGUGGGU | 1972 | ACCCACUUGGCA | 3367 | AD-26710, AD-26709 |
| 1583 | GCCAAGUGGGUG | 1973 | CACCCACUUGGC | 3368 | AD-26710, AD-26709 |
| 1584 | CCAAGUGGGUGG | 1974 | CCACCCACUUGG | 3369 | AD-26710, AD-26709 |
| 1585 | CAAGUGGGUGGU | 1975 | ACCACCCACUUG | 3370 | AD-26710, AD-26709 |
| 1586 | AAGUGGGUGGUA | 1976 | UACCACCCACUU | 3371 | AD-26710, AD-26709 |
| 1597 | AUAGAGGCUCUU | 1977 | AAGAGCCUCUAU | 3372 | AD-26712, AD-26711 |
| 1628 | CUGGUGACAGGG | 1978 | CCCUGUCACCAG | 3373 | AD-26714, AD-26141 |
| 1629 | UGGUGACAGGGA | 1979 | UCCCUGUCACCA | 3374 | AD-26714, AD-26141 |
| 1630 | GGUGACAGGGAA | 1980 | UUCCCUGUCACC | 3375 | AD-26714, AD-26141 |
| 1637 | GGGAAGACAUCA | 1981 | UGAUGUCUUCCC | 3376 | AD-18938, AD-19064 |
| 1638 | GGAAGACAUCAC | 1982 | GUGAUGUCUUCC | 3377 | AD-18938, AD-18937 |
| 1639 | GAAGACAUCACU | 1983 | AGUGAUGUCUUC | 3378 | AD-18938, AD-19064 |
| 1640 | AAGACAUCACUG | 1984 | CAGUGAUGUCUU | 3379 | AD-19064, AD-18937 |
| 1641 | AGACAUCACUGA | 1985 | UCAGUGAUGUCU | 3380 | AD-18938, AD-19064, AD-18937 |
| 1642 | GACAUCACUGAG | 1986 | CUCAGUGAUGUC | 3381 | AD-18938, AD-19064, AD-18937 |
| 1643 | ACAUCACUGAGC | 1987 | GCUCAGUGAUGU | 3382 | AD-18938, AD-19064, AD-18937, AD-26715 |
| 1644 | CAUCACUGAGCC | 1988 | GGCUCAGUGAUG | 3383 | AD-18938, AD-18937, AD-26715 |
| 1645 | AUCACUGAGCCU | 1989 | AGGCUCAGUGAU | 3384 | AD-18937, AD-26715 |
| 1654 | CCUGCCAUCUGU | 1990 | ACAGAUGGCAGG | 3385 | AD-26716, AD-18990 |
| 1655 | CUGCCAUCUGUG | 1991 | CACAGAUGGCAG | 3386 | AD-26716, AD-18990 |
| 1656 | UGCCAUCUGUGC | 1992 | GCACAGAUGGCA | 3387 | AD-26716, AD-18990 |
| 1657 | GCCAUCUGUGCU | 1993 | AGCACAGAUGGC | 3388 | AD-26716, AD-18990, AD-19061 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 1658 | CCAUCUGUGCUC | 1994 | GAGCACAGAUGG | 3389 | AD-26716, AD-18990, AD-18893, AD-19061 |
| 1659 | CAUCUGUGCUCU | 1995 | AGAGCACAGAUG | 3390 | AD-26716, AD-18946, AD-18990, AD-18893, AD-19061 |
| 1660 | AUCUGUGCUCUU | 1996 | AAGAGCACAGAU | 3391 | AD-26716, AD-18946, AD-18990, AD-19082, AD-18893, AD-19061 |
| 1661 | UCUGUGCUCUUC | 1997 | GAAGAGCACAGA | 3392 | AD-18946, AD-18990, AD-19082, AD-18893, AD-19061 |
| 1662 | CUGUGCUCUUCG | 1998 | CGAAGAGCACAG | 3393 | AD-18946, AD-19082, AD-19061 |
| 1663 | UGUGCUCUUCGU | 1999 | ACGAAGAGCACA | 3394 | AD-18946, AD-19082, AD-18893, AD-19061 |
| 1664 | GUGCUCUUCGUC | 2000 | GACGAAGAGCAC | 3395 | AD-18946, AD-18904, AD-19082, AD-18893, AD-19061 |
| 1665 | UGCUCUUCGUCA | 2001 | UGACGAAGAGCA | 3396 | AD-18946, AD-18904, AD-19082, AD-18893 |
| 1666 | GCUCUUCGUCAU | 2002 | AUGACGAAGAGC | 3397 | AD-18946, AD-18932, AD-18904, AD-19082 |
| 1667 | CUCUUCGUCAUC | 2003 | GAUGACGAAGAG | 3398 | AD-18932, AD-19082, AD-18943 |
| 1668 | UCUUCGUCAUCU | 2004 | AGAUGACGAAGA | 3399 | AD-18932, AD-18904, AD-18943 |
| 1669 | CUUCGUCAUCUG | 2005 | CAGAUGACGAAG | 3400 | AD-18904, AD-19002, AD-18943 |
| 1670 | UUCGUCAUCUGA | 2006 | UCAGAUGACGAA | 3401 | AD-18932, AD-18904, AD-19002, AD-18943 |
| 1671 | UCGUCAUCUGAC | 2007 | GUCAGAUGACGA | 3402 | AD-18904, AD-18943 |
| 1672 | CGUCAUCUGACC | 2008 | GGUCAGAUGACG | 3403 | AD-18932, AD-19002, AD-18943 |
| 1673 | GUCAUCUGACCA | 2009 | UGGUCAGAUGAC | 3404 | AD-18932, AD-18943 |
| 1674 | UCAUCUGACCAG | 2010 | CUGGUCAGAUGA | 3405 | AD-19002, AD-18943 |
| 1677 | UCUGACCAGCCG | 2011 | CGGCUGGUCAGA | 3406 | AD-26717, AD-19761 |
| 1678 | CUGACCAGCCGA | 2012 | UCGGCUGGUCAG | 3407 | AD-26717, AD-19761 |
| 1679 | UGACCAGCCGAC | 2013 | GUCGGCUGGUCA | 3408 | AD-26717, AD-19761 |
| 1680 | GACCAGCCGACA | 2014 | UGUCGGCUGGUC | 3409 | AD-26717, AD-19761 |
| 1681 | ACCAGCCGACAC | 2015 | GUGUCGGCUGGU | 3410 | AD-26717, AD-26718 |
| 1682 | CCAGCCGACACC | 2016 | GGUGUCGGCUGG | 3411 | AD-26717, AD-26718, AD-19761 |
| 1683 | CAGCCGACACCA | 2017 | UGGUGUCGGCUG | 3412 | AD-26717, AD-26718, AD-19761 |
| 1684 | AGCCGACACCAA | 2018 | UUGGUGUCGGCU | 3413 | AD-26717, AD-26718 |
| 1704 | GAUGGCCCAGAA | 2019 | UUCUGGGCCAUC | 3414 | AD-26721, AD-26720 |
| 1705 | AUGGCCCAGAAU | 2020 | AUUCUGGGCCAU | 3415 | AD-26721, AD-26720 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 1710 | CCAGAAUGCAGU | 2021 | ACUGCAUUCUGG | 3416 | AD-26721, AD-26722 |
| 1711 | CAGAAUGCAGUU | 2022 | AACUGCAUUCUG | 3417 | AD-26721, AD-26722 |
| 1713 | GAAUGCAGUUCG | 2023 | CGAACUGCAUUC | 3418 | AD-26722, AD-19741 |
| 1714 | AAUGCAGUUCGC | 2024 | GCGAACUGCAUU | 3419 | AD-26722, AD-19741 |
| 1715 | AUGCAGUUCGCC | 2025 | GGCGAACUGCAU | 3420 | AD-26722, AD-19741, AD-26723 |
| 1716 | UGCAGUUCGCCU | 2026 | AGGCGAACUGCA | 3421 | AD-26724, AD-26722, AD-19741, AD-26723 |
| 1717 | GCAGUUCGCCUU | 2027 | AAGGCGAACUGC | 3422 | AD-26724, AD-19741, AD-26723 |
| 1718 | CAGUUCGCCUUC | 2028 | GAAGGCGAACUG | 3423 | AD-26724, AD-26723 |
| 1719 | AGUUCGCCUUCA | 2029 | UGAAGGCGAACU | 3424 | AD-26724, AD-19741 |
| 1720 | GUUCGCCUUCAC | 2030 | GUGAAGGCGAAC | 3425 | AD-19741, AD-26723 |
| 1721 | UUCGCCUUCACU | 2031 | AGUGAAGGCGAA | 3426 | AD-26724, AD-26723 |
| 1722 | UCGCCUUCACUA | 2032 | UAGUGAAGGCGA | 3427 | AD-26724, AD-26725, AD-26723 |
| 1723 | CGCCUUCACUAU | 2033 | AUAGUGAAGGCG | 3428 | AD-26724, AD-26725 |
| 1728 | UCACUAUGGACU | 2034 | AGUCCAUAGUGA | 3429 | AD-26725, AD-26726 |
| 1729 | CACUAUGGACUA | 2035 | UAGUCCAUAGUG | 3430 | AD-26725, AD-26726 |
| 1734 | UGGACUACCAGU | 2036 | ACUGGUAGUCCA | 3431 | AD-26727, AD-26726 |
| 1735 | GGACUACCAGUU | 2037 | AACUGGUAGUCC | 3432 | AD-26727, AD-26728 |
| 1736 | GACUACCAGUUG | 2038 | CAACUGGUAGUC | 3433 | AD-26728, AD-26729 |
| 1737 | ACUACCAGUUGU | 2039 | ACAACUGGUAGU | 3434 | AD-26727, AD-26729 |
| 1738 | CUACCAGUUGUG | 2040 | CACAACUGGUAG | 3435 | AD-26727, AD-26728, AD-26729 |
| 1739 | UACCAGUUGUGG | 2041 | CCACAACUGGUA | 3436 | AD-26727, AD-26728, AD-26729 |
| 1740 | ACCAGUUGUGGU | 2042 | ACCACAACUGGU | 3437 | AD-26727, AD-26728, AD-26729 |
| 1741 | CCAGUUGUGGUU | 2043 | AACCACAACUGG | 3438 | AD-26727, AD-26728, AD-26729 |
| 1742 | CAGUUGUGGUUA | 2044 | UAACCACAACUG | 3439 | AD-26728, AD-26730, AD-26729 |
| 1743 | AGUUGUGGUUAA | 2045 | UUAACCACAACU | 3440 | AD-26731, AD-26730, AD-26729 |
| 1744 | GUUGUGGUUAAG | 2046 | CUUAACCACAAC | 3441 | AD-26731, AD-26730 |
| 1745 | UUGUGGUUAAGC | 2047 | GCUUAACCACAA | 3442 | AD-26731, AD-26730 |
| 1746 | UGUGGUUAAGCU | 2048 | AGCUUAACCACA | 3443 | AD-26731, AD-26730 |
| 1747 | GUGGUUAAGCUC | 2049 | GAGCUUAACCAC | 3444 | AD-26731, AD-26730 |
| 1748 | UGGUUAAGCUCU | 2050 | AGAGCUUAACCA | 3445 | AD-26731, AD-26730 |
| 1749 | GGUUAAGCUCUU | 2051 | AAGAGCUUAACC | 3446 | AD-26731, AD-26730 |
| 1770 | AUCCCACUGGCC | 2052 | GGCCAGUGGGAU | 3447 | AD-26734, AD-26733 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 1771 | UCCCACUGGCCU | 2053 | AGGCCAGUGGGA | 3448 | AD-26734, AD-26733, AD-26735 |
| 1772 | CCCACUGGCCUC | 2054 | GAGGCCAGUGGG | 3449 | AD-26734, AD-18963, AD-26733, AD-26735 |
| 1773 | CCACUGGCCUCU | 2055 | AGAGGCCAGUGG | 3450 | AD-26734, AD-18930, AD-18963, AD-26733, AD-26735 |
| 1774 | CACUGGCCUCUG | 2056 | CAGAGGCCAGUG | 3451 | AD-26734, AD-18930, AD-18963, AD-26733, AD-26735, AD-19078 |
| 1775 | ACUGGCCUCUGA | 2057 | UCAGAGGCCAGU | 3452 | AD-26734, AD-18930, AD-18963, AD-26733, AD-18948, AD-19078 |
| 1776 | CUGGCCUCUGAU | 2058 | AUCAGAGGCCAG | 3453 | AD-26734, AD-18963, AD-26733, AD-26735, AD-18948, AD-19078 |
| 1777 | UGGCCUCUGAUA | 2059 | UAUCAGAGGCCA | 3454 | AD-26734, AD-18930, AD-26736, AD-18963, AD-26735, AD-18948, AD-19078 |
| 1778 | GGCCUCUGAUAA | 2060 | UUAUCAGAGGCC | 3455 | AD-18930, AD-26736, AD-18963, AD-26735, AD-18948, AD-19078 |
| 1779 | GCCUCUGAUAAA | 2061 | UUUAUCAGAGGC | 3456 | AD-18930, AD-26736, AD-18963, AD-18948, AD-19078 |
| 1780 | CCUCUGAUAAAG | 2062 | CUUUAUCAGAGG | 3457 | AD-18930, AD-26736, AD-18948, AD-19078 |
| 1781 | CUCUGAUAAAGG | 2063 | CCUUUAUCAGAG | 3458 | AD-26736, AD-18948, AD-19078 |
| 1782 | UCUGAUAAAGGC | 2064 | GCCUUUAUCAGA | 3459 | AD-26736, AD-18948, AD-26737 |
| 1783 | CUGAUAAAGGCU | 2065 | AGCCUUUAUCAG | 3460 | AD-26736, AD-26737 |
| 1784 | UGAUAAAGGCUA | 2066 | UAGCCUUUAUCA | 3461 | AD-26736, AD-26737 |
| 1786 | AUAAAGGCUACU | 2067 | AGUAGCCUUUAU | 3462 | AD-26738, AD-26737 |
| 1787 | UAAAGGCUACUG | 2068 | CAGUAGCCUUUA | 3463 | AD-26738, AD-26737 |
| 1788 | AAAGGCUACUGU | 2069 | ACAGUAGCCUUU | 3464 | AD-26738, AD-26737 |
| 1789 | AAGGCUACUGUU | 2070 | AACAGUAGCCUU | 3465 | AD-26738, AD-26737 |
| 1791 | GGCUACUGUUGG | 2071 | CCAACAGUAGCC | 3466 | AD-26738, AD-26739 |
| 1792 | GCUACUGUUGGA | 2072 | UCCAACAGUAGC | 3467 | AD-26738, AD-26739 |
| 1793 | CUACUGUUGGAU | 2073 | AUCCAACAGUAG | 3468 | AD-26738, AD-26739 |
| 1795 | ACUGUUGGAUUG | 2074 | CAAUCCAACAGU | 3469 | AD-18983, AD-26739 |
| 1796 | CUGUUGGAUUGA | 2075 | UCAAUCCAACAG | 3470 | AD-18983, AD-26739, AD-18897 |
| 1797 | UGUUGGAUUGAU | 2076 | AUCAAUCCAACA | 3471 | AD-26740, AD-18983, AD-26739, AD-18897 |
| 1798 | GUUGGAUUGAUU | 2077 | AAUCAAUCCAAC | 3472 | AD-26740, AD-26739, AD-18897 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 1799 | UUGGAUUGAUUC | 2078 | GAAUCAAUCCAA | 3473 | AD-26740, AD-18983, AD-18897 |
| 1800 | UGGAUUGAUUCG | 2079 | CGAAUCAAUCCA | 3474 | AD-26740, AD-18897, AD-26921 |
| 1801 | GGAUUGAUUCGA | 2080 | UCGAAUCAAUCC | 3475 | AD-26740, AD-18983, AD-18897, AD-26921 |
| 1802 | GAUUGAUUCGAA | 2081 | UUCGAAUCAAUC | 3476 | AD-18983, AD-18897, AD-26921 |
| 1803 | AUUGAUUCGAAA | 2082 | UUUCGAAUCAAU | 3477 | AD-26740, AD-18897, AD-26921 |
| 1804 | UUGAUUCGAAAU | 2083 | AUUUCGAAUCAA | 3478 | AD-26740, AD-26921 |
| 1848 | GCGUGAGCAGGG | 2084 | CCCUGCUCACGC | 3479 | AD-26175, AD-26176 |
| 1849 | CGUGAGCAGGGU | 2085 | ACCCUGCUCACG | 3480 | AD-26175, AD-26176 |
| 1850 | GUGAGCAGGGUG | 2086 | CACCCUGCUCAC | 3481 | AD-26175, AD-26176 |
| 1851 | UGAGCAGGGUGC | 2087 | GCACCCUGCUCA | 3482 | AD-26175, AD-26176 |
| 1852 | GAGCAGGGUGCC | 2088 | GGCACCCUGCUC | 3483 | AD-26175, AD-26176 |
| 1853 | AGCAGGGUGCCA | 2089 | UGGCACCCUGCU | 3484 | AD-26175, AD-26176 |
| 1854 | GCAGGGUGCCAU | 2090 | AUGGCACCCUGC | 3485 | AD-26175, AD-26176 |
| 1859 | GUGCCAUUCCAC | 2091 | GUGGAAUGGCAC | 3486 | AD-19742, AD-19749 |
| 1860 | UGCCAUUCCACG | 2092 | CGUGGAAUGGCA | 3487 | AD-26741, AD-19749 |
| 1861 | GCCAUUCCACGA | 2093 | UCGUGGAAUGGC | 3488 | AD-26741, AD-19742 |
| 1862 | CCAUUCCACGAC | 2094 | GUCGUGGAAUGG | 3489 | AD-26741, AD-19742, AD-19749 |
| 1863 | CAUUCCACGACU | 2095 | AGUCGUGGAAUG | 3490 | AD-26741, AD-19742, AD-19749, AD-19762 |
| 1864 | AUUCCACGACUA | 2096 | UAGUCGUGGAAU | 3491 | AD-26741, AD-19742, AD-19749 |
| 1865 | UUCCACGACUAG | 2097 | CUAGUCGUGGAA | 3492 | AD-26742, AD-26741, AD-19742, AD-19749, AD-19762 |
| 1866 | UCCACGACUAGU | 2098 | ACUAGUCGUGGA | 3493 | AD-26742, AD-26741, AD-19749, AD-19762 |
| 1867 | CCACGACUAGUU | 2099 | AACUAGUCGUGG | 3494 | AD-26742, AD-26741, AD-19751, AD-19762 |
| 1868 | CACGACUAGUUC | 2100 | GAACUAGUCGUG | 3495 | AD-26742, AD-19751, AD-19762, AD-19752 |
| 1869 | ACGACUAGUUCA | 2101 | UGAACUAGUCGU | 3496 | AD-26742, AD-26743, AD-19751, AD-19762 |
| 1870 | CGACUAGUUCAG | 2102 | CUGAACUAGUCG | 3497 | AD-26742, AD-26743, AD-19751, AD-19762, AD-19752 |
| 1871 | GACUAGUUCAGU | 2103 | ACUGAACUAGUC | 3498 | AD-26742, AD-26743, AD-19751, AD-19752 |
| 1872 | ACUAGUUCAGUU | 2104 | AACUGAACUAGU | 3499 | AD-26742, AD-26743, AD-19751, AD-19752, AD-26744 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 1873 | CUAGUUCAGUUG | 2105 | CAACUGAACUAG | 3500 | AD-26743, AD-19752, AD-26744 |
| 1874 | UAGUUCAGUUGC | 2106 | GCAACUGAACUA | 3501 | AD-26743, AD-19751, AD-19752, AD-26744 |
| 1875 | AGUUCAGUUGCU | 2107 | AGCAACUGAACU | 3502 | AD-26743, AD-19753, AD-26744 |
| 1876 | GUUCAGUUGCUU | 2108 | AAGCAACUGAAC | 3503 | AD-26743, AD-19753, AD-26744 |
| 1877 | UUCAGUUGCUUG | 2109 | CAAGCAACUGAA | 3504 | AD-19753, AD-26744 |
| 1878 | UCAGUUGCUUGU | 2110 | ACAAGCAACUGA | 3505 | AD-19753, AD-26744 |
| 1879 | CAGUUGCUUGUU | 2111 | AACAAGCAACUG | 3506 | AD-19753, AD-26744 |
| 1881 | GUUGCUUGUUCG | 2112 | CGAACAAGCAAC | 3507 | AD-19753, AD-26745 |
| 1882 | UUGCUUGUUCGU | 2113 | ACGAACAAGCAA | 3508 | AD-19753, AD-26745 |
| 1887 | UGUUCGUGCACA | 2114 | UGUGCACGAACA | 3509 | AD-26746, AD-26745 |
| 1888 | GUUCGUGCACAU | 2115 | AUGUGCACGAAC | 3510 | AD-26746, AD-26747, AD-26745 |
| 1889 | UUCGUGCACAUC | 2116 | GAUGUGCACGAA | 3511 | AD-26746, AD-26747 |
| 1890 | UCGUGCACAUCA | 2117 | UGAUGUGCACGA | 3512 | AD-26746, AD-26747 |
| 1891 | CGUGCACAUCAG | 2118 | CUGAUGUGCACG | 3513 | AD-26746, AD-26747 |
| 1892 | GUGCACAUCAGG | 2119 | CCUGAUGUGCAC | 3514 | AD-26746, AD-26747 |
| 1893 | UGCACAUCAGGA | 2120 | UCCUGAUGUGCA | 3515 | AD-26746, AD-26747 |
| 1894 | GCACAUCAGGAU | 2121 | AUCCUGAUGUGC | 3516 | AD-26746, AD-26747 |
| 1907 | CCCAGCGCCGUA | 2122 | UACGGCGCUGGG | 3517 | AD-19738, AD-19754 |
| 1908 | CCAGCGCCGUAC | 2123 | GUACGGCGCUGG | 3518 | AD-19738, AD-19754 |
| 1909 | CAGCGCCGUACG | 2124 | CGUACGGCGCUG | 3519 | AD-19738, AD-19754 |
| 1910 | AGCGCCGUACGU | 2125 | ACGUACGGCGCU | 3520 | AD-19738, AD-19754 |
| 1911 | GCGCCGUACGUC | 2126 | GACGUACGGCGC | 3521 | AD-19738, AD-19754 |
| 1912 | CGCCGUACGUCC | 2127 | GGACGUACGGCG | 3522 | AD-19738, AD-19754 |
| 1927 | GGUGGGACACAG | 2128 | CUGUGUCCCACC | 3523 | AD-26184, AD-26748 |
| 1928 | GUGGGACACAGC | 2129 | GCUGUGUCCCAC | 3524 | AD-26749, AD-26184, AD-26748 |
| 1929 | UGGGACACAGCA | 2130 | UGCUGUGUCCCA | 3525 | AD-26749, AD-26750, AD-26184, AD-26748 |
| 1930 | GGGACACAGCAG | 2131 | CUGCUGUGUCCC | 3526 | AD-26749, AD-26750, AD-26184 |
| 1931 | GGACACAGCAGC | 2132 | GCUGCUGUGUCC | 3527 | AD-26749, AD-26184, AD-26748 |
| 1932 | GACACAGCAGCA | 2133 | UGCUGCUGUGUC | 3528 | AD-26749, AD-26750, AD-26184, AD-26748 |
| 1933 | ACACAGCAGCAA | 2134 | UUGCUGCUGUGU | 3529 | AD-26750, AD-26184, AD-26748 |
| 1934 | CACAGCAGCAAU | 2135 | AUUGCUGCUGUG | 3530 | AD-26749, AD-26750, AD-26748 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 1935 | ACAGCAGCAAUU | 2136 | AAUUGCUGCUGU | 3531 | AD-26749, AD-26750 |
| 1955 | GGGUCCGCAUGG | 2137 | CCAUGCGGACCC | 3532 | AD-26751, AD-26752 |
| 1956 | GGUCCGCAUGGA | 2138 | UCCAUGCGGACC | 3533 | AD-26751, AD-26752 |
| 1957 | GUCCGCAUGGAA | 2139 | UUCCAUGCGGAC | 3534 | AD-26751, AD-26752 |
| 1958 | UCCGCAUGGAAG | 2140 | CUUCCAUGCGGA | 3535 | AD-26751, AD-26752 |
| 1959 | CCGCAUGGAAGA | 2141 | UCUUCCAUGCGG | 3536 | AD-26751, AD-26752 |
| 1960 | CGCAUGGAAGAA | 2142 | UUCUUCCAUGCG | 3537 | AD-26751, AD-26752 |
| 1961 | GCAUGGAAGAAA | 2143 | UUUCUUCCAUGC | 3538 | AD-26751, AD-26752 |
| 2001 | CAUCCUAGCUCG | 2144 | CGAGCUAGGAUG | 3539 | AD-26753, AD-26754 |
| 2002 | AUCCUAGCUCGG | 2145 | CCGAGCUAGGAU | 3540 | AD-26753, AD-26754 |
| 2003 | UCCUAGCUCGGG | 2146 | CCCGAGCUAGGA | 3541 | AD-26753, AD-26754 |
| 2004 | CCUAGCUCGGGA | 2147 | UCCCGAGCUAGG | 3542 | AD-26753, AD-26754 |
| 2005 | CUAGCUCGGGAU | 2148 | AUCCCGAGCUAG | 3543 | AD-26753, AD-26754 |
| 2006 | UAGCUCGGGAUG | 2149 | CAUCCCGAGCUA | 3544 | AD-26755, AD-26754 |
| 2007 | AGCUCGGGAUGU | 2150 | ACAUCCCGAGCU | 3545 | AD-26755, AD-26754 |
| 2008 | GCUCGGGAUGUU | 2151 | AACAUCCCGAGC | 3546 | AD-26755, AD-26754 |
| 2011 | CGGGAUGUUCAC | 2152 | GUGAACAUCCCG | 3547 | AD-26755, AD-20124 |
| 2012 | GGGAUGUUCACA | 2153 | UGUGAACAUCCC | 3548 | AD-26756, AD-26755, AD-20124 |
| 2013 | GGAUGUUCACAA | 2154 | UUGUGAACAUCC | 3549 | AD-26756, AD-26755, AD-26757, AD-20124 |
| 2014 | GAUGUUCACAAC | 2155 | GUUGUGAACAUC | 3550 | AD-26756, AD-26757, AD-20124 |
| 2015 | AUGUUCACAACC | 2156 | GGUUGUGAACAU | 3551 | AD-26756, AD-26757, AD-20124 |
| 2016 | UGUUCACAACCG | 2157 | CGGUUGUGAACA | 3552 | AD-26756, AD-19750, AD-20124 |
| 2017 | GUUCACAACCGA | 2158 | UCGGUUGUGAAC | 3553 | AD-19750, AD-26757, AD-20124 |
| 2018 | UUCACAACCGAA | 2159 | UUCGGUUGUGAA | 3554 | AD-26756, AD-19750, AD-26757, AD-20124 |
| 2019 | UCACAACCGAAU | 2160 | AUUCGGUUGUGA | 3555 | AD-26756, AD-19750, AD-26757 |
| 2020 | CACAACCGAAUU | 2161 | AAUUCGGUUGUG | 3556 | AD-19750, AD-26757 |
| 2041 | GGACUAAAUACC | 2162 | GGUAUUUAGUCC | 3557 | AD-26758, AD-26759 |
| 2042 | GACUAAAUACCA | 2163 | UGGUAUUUAGUC | 3558 | AD-26758, AD-26759 |
| 2043 | ACUAAAUACCAU | 2164 | AUGGUAUUUAGU | 3559 | AD-26758, AD-26759 |
| 2044 | CUAAAUACCAUU | 2165 | AAUGGUAUUUAG | 3560 | AD-26758, AD-26759 |
| 2045 | UAAAUACCAUUC | 2166 | GAAUGGUAUUUA | 3561 | AD-26760, AD-26759 |
| 2046 | AAAUACCAUUCC | 2167 | GGAAUGGUAUUU | 3562 | AD-26760, AD-26761, AD-26759 |

TABLE 4-continued

Groups of overlapping RNAi agents to Beta-Catenin

| Position | Sense overlap | SEQ ID NO: Anti-sense overlap | SEQ ID NO: | Overlapping groups of RNAi agents |
|---|---|---|---|---|
| 2047 | AAUACCAUUCCA | 2168 UGGAAUGGUAUU | 3563 | AD-26760, AD-26759 |
| 2048 | AUACCAUUCCAU | 2169 AUGGAAUGGUAU | 3564 | AD-26760, AD-26761, AD-26759, AD-18982 |
| 2049 | UACCAUUCCAUU | 2170 AAUGGAAUGGUA | 3565 | AD-26760, AD-19062, AD-18982 |
| 2050 | ACCAUUCCAUUG | 2171 CAAUGGAAUGGU | 3566 | AD-26760, AD-26761, AD-19062, AD-18982 |
| 2051 | CCAUUCCAUUGU | 2172 ACAAUGGAAUGG | 3567 | AD-26761, AD-19062, AD-18982 |
| 2052 | CAUUCCAUUGUU | 2173 AACAAUGGAAUG | 3568 | AD-26760, AD-26761, AD-19062 |
| 2053 | AUUCCAUUGUUU | 2174 AAACAAUGGAAU | 3569 | AD-26761, AD-19062, AD-18982 |
| 2054 | UUCCAUUGUUUG | 2175 CAAACAAUGGAA | 3570 | AD-19062, AD-18982 |
| 2055 | UCCAUUGUUUGU | 2176 ACAAACAAUGGA | 3571 | AD-19062, AD-18982 |
| 2059 | UUGUUUGUGCAG | 2177 CUGCACAAACAA | 3572 | AD-26763, AD-26762 |
| 2060 | UGUUUGUGCAGC | 2178 GCUGCACAAACA | 3573 | AD-26764, AD-26763, AD-26762 |
| 2061 | GUUUGUGCAGCU | 2179 AGCUGCACAAAC | 3574 | AD-26764, AD-26765, AD-26763, AD-26762 |
| 2062 | UUUGUGCAGCUG | 2180 CAGCUGCACAAA | 3575 | AD-26764, AD-26765, AD-26766, AD-26763, AD-26762 |
| 2063 | UUGUGCAGCUGC | 2181 GCAGCUGCACAA | 3576 | AD-26764, AD-26765, AD-26766, AD-26763 |
| 2064 | UGUGCAGCUGCU | 2182 AGCAGCUGCACA | 3577 | AD-26764, AD-26766, AD-26763, AD-26762 |
| 2065 | GUGCAGCUGCUU | 2183 AAGCAGCUGCAC | 3578 | AD-26765, AD-26766, AD-26763, AD-26762 |
| 2066 | UGCAGCUGCUUU | 2184 AAAGCAGCUGCA | 3579 | AD-26764, AD-26765, AD-26766, AD-26763 |
| 2067 | GCAGCUGCUUUA | 2185 UAAAGCAGCUGC | 3580 | AD-26764, AD-26765, AD-26766 |
| 2068 | CAGCUGCUUUAU | 2186 AUAAAGCAGCUG | 3581 | AD-26765, AD-26766 |
| 2069 | AGCUGCUUUAUU | 2187 AAUAAAGCAGCU | 3582 | AD-26766, AD-26767 |
| 2070 | GCUGCUUUAUUC | 2188 GAAUAAAGCAGC | 3583 | AD-26768, AD-26767 |
| 2071 | CUGCUUUAUUCU | 2189 AGAAUAAAGCAG | 3584 | AD-26768, AD-26767 |
| 2072 | UGCUUUAUUCUC | 2190 GAGAAUAAAGCA | 3585 | AD-26768, AD-26767 |
| 2073 | GCUUUAUUCUCC | 2191 GGAGAAUAAAGC | 3586 | AD-26768, AD-18928 |
| 2074 | CUUUAUUCUCCC | 2192 GGGAGAAUAAAG | 3587 | AD-26768, AD-18928, AD-26767 |
| 2075 | UUUAUUCUCCCA | 2193 UGGGAGAAUAAA | 3588 | AD-26769, AD-18928, AD-26767 |
| 2076 | UUAUUCUCCCAU | 2194 AUGGGAGAAUAA | 3589 | AD-26769, AD-26768, AD-18928, AD-26767 |
| 2077 | UAUUCUCCCAUU | 2195 AAUGGGAGAAUA | 3590 | AD-26769, AD-26768, AD-18928 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 2078 | AUUCUCCCAUUG | 2196 | CAAUGGGAGAAU | 3591 | AD-26770, AD-18928 |
| 2079 | UUCUCCCAUUGA | 2197 | UCAAUGGGAGAA | 3592 | AD-26769, AD-26770 |
| 2080 | UCUCCCAUUGAA | 2198 | UUCAAUGGGAGA | 3593 | AD-26769, AD-26770 |
| 2081 | CUCCCAUUGAAA | 2199 | UUUCAAUGGGAG | 3594 | AD-26769, AD-26770 |
| 2082 | UCCCAUUGAAAA | 2200 | UUUUCAAUGGGA | 3595 | AD-26771, AD-26769, AD-26770 |
| 2083 | CCCAUUGAAAAC | 2201 | GUUUUCAAUGGG | 3596 | AD-26771, AD-26770 |
| 2084 | CCAUUGAAAACA | 2202 | UGUUUUCAAUGG | 3597 | AD-26771, AD-26770 |
| 2085 | CAUUGAAAACAU | 2203 | AUGUUUUCAAUG | 3598 | AD-26771, AD-26770 |
| 2100 | AAGAGUAGCUGC | 2204 | GCAGCUACUCUU | 3599 | AD-18962, AD-18895 |
| 2101 | AGAGUAGCUGCA | 2205 | UGCAGCUACUCU | 3600 | AD-18962, AD-18895 |
| 2102 | GAGUAGCUGCAG | 2206 | CUGCAGCUACUC | 3601 | AD-18962, AD-18895 |
| 2104 | GUAGCUGCAGGG | 2207 | CCCUGCAGCUAC | 3602 | AD-18962, AD-18976 |
| 2105 | UAGCUGCAGGGG | 2208 | CCCCUGCAGCUA | 3603 | AD-19003, AD-18962 |
| 2106 | AGCUGCAGGGGU | 2209 | ACCCCUGCAGCU | 3604 | AD-19003, AD-18962, AD-18976 |
| 2107 | GCUGCAGGGGUC | 2210 | GACCCCUGCAGC | 3605 | AD-18962, AD-18976 |
| 2108 | CUGCAGGGGUCC | 2211 | GGACCCCUGCAG | 3606 | AD-19003, AD-18976 |
| 2109 | UGCAGGGGUCCU | 2212 | AGGACCCCUGCA | 3607 | AD-19003, AD-26772, AD-18976 |
| 2110 | GCAGGGGUCCUC | 2213 | GAGGACCCCUGC | 3608 | AD-19003, AD-26772, AD-18976 |
| 2111 | CAGGGGUCCUCU | 2214 | AGAGGACCCCUG | 3609 | AD-18923, AD-19003, AD-26772, AD-18976 |
| 2112 | AGGGGUCCUCUG | 2215 | CAGAGGACCCCU | 3610 | AD-18923, AD-19003, AD-18955, AD-26772 |
| 2113 | GGGGUCCUCUGU | 2216 | ACAGAGGACCCC | 3611 | AD-18923, AD-18955, AD-26772 |
| 2114 | GGGUCCUCUGUG | 2217 | CACAGAGGACCC | 3612 | AD-18923, AD-18934, AD-18955, AD-26772 |
| 2115 | GGUCCUCUGUGA | 2218 | UCACAGAGGACC | 3613 | AD-18923, AD-18934, AD-19052, AD-18912, AD-18955 |
| 2116 | GUCCUCUGUGAA | 2219 | UUCACAGAGGAC | 3614 | AD-18923, AD-19052, AD-18912, AD-18955, AD-26772 |
| 2117 | UCCUCUGUGAAC | 2220 | GUUCACAGAGGA | 3615 | AD-18923, AD-18934, AD-19052, AD-18912, AD-18955 |
| 2118 | CCUCUGUGAACU | 2221 | AGUUCACAGAGG | 3616 | AD-18923, AD-18934, AD-18973, AD-19052, AD-18912, AD-18955 |
| 2119 | CUCUGUGAACUU | 2222 | AAGUUCACAGAG | 3617 | AD-18934, AD-18973, AD-19052, AD-18912, AD-18955 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 2120 | UCUGUGAACUUG | 2223 | CAAGUUCACAGA | 3618 | AD-18934, AD-18973, AD-19052, AD-18912 |
| 2121 | CUGUGAACUUGC | 2224 | GCAAGUUCACAG | 3619 | AD-18973, AD-19052, AD-18912 |
| 2122 | UGUGAACUUGCU | 2225 | AGCAAGUUCACA | 3620 | AD-18973, AD-19047 |
| 2123 | GUGAACUUGCUC | 2226 | GAGCAAGUUCAC | 3621 | AD-18973, AD-19047, AD-18971 |
| 2124 | UGAACUUGCUCA | 2227 | UGAGCAAGUUCA | 3622 | AD-18973, AD-19047, AD-18971, AD-18961 |
| 2125 | GAACUUGCUCAG | 2228 | CUGAGCAAGUUC | 3623 | AD-18973, AD-19047, AD-18971, AD-18961 |
| 2126 | AACUUGCUCAGG | 2229 | CCUGAGCAAGUU | 3624 | AD-19047, AD-18984, AD-18971, AD-18961 |
| 2127 | ACUUGCUCAGGA | 2230 | UCCUGAGCAAGU | 3625 | AD-19047, AD-18984, AD-26773, AD-18971, AD-18961 |
| 2128 | CUUGCUCAGGAC | 2231 | GUCCUGAGCAAG | 3626 | AD-19047, AD-18984, AD-26773, AD-18971 |
| 2129 | UUGCUCAGGACA | 2232 | UGUCCUGAGCAA | 3627 | AD-19047, AD-18984, AD-26773, AD-18971, AD-18961 |
| 2130 | UGCUCAGGACAA | 2233 | UUGUCCUGAGCA | 3628 | AD-18984, AD-26773, AD-18971, AD-18961 |
| 2131 | GCUCAGGACAAG | 2234 | CUUGUCCUGAGC | 3629 | AD-18984, AD-26773, AD-18961 |
| 2132 | CUCAGGACAAGG | 2235 | CCUUGUCCUGAG | 3630 | AD-18984, AD-26773 |
| 2133 | UCAGGACAAGGA | 2236 | UCCUUGUCCUGA | 3631 | AD-18984, AD-26773 |
| 2178 | AGCUCCUCUGAC | 2237 | GUCAGAGGAGCU | 3632 | AD-26775, AD-26774 |
| 2179 | GCUCCUCUGACA | 2238 | UGUCAGAGGAGC | 3633 | AD-26775, AD-26774 |
| 2180 | CUCCUCUGACAG | 2239 | CUGUCAGAGGAG | 3634 | AD-26775, AD-26774 |
| 2181 | UCCUCUGACAGA | 2240 | UCUGUCAGAGGA | 3635 | AD-26775, AD-26774 |
| 2182 | CCUCUGACAGAG | 2241 | CUCUGUCAGAGG | 3636 | AD-26775, AD-26776 |
| 2183 | CUCUGACAGAGU | 2242 | ACUCUGUCAGAG | 3637 | AD-26776, AD-26774 |
| 2184 | UCUGACAGAGUU | 2243 | AACUCUGUCAGA | 3638 | AD-26775, AD-26776, AD-26774 |
| 2185 | CUGACAGAGUUA | 2244 | UAACUCUGUCAG | 3639 | AD-26775, AD-26776 |
| 2188 | ACAGAGUUACUU | 2245 | AAGUAACUCUGU | 3640 | AD-26777, AD-26776 |
| 2191 | GAGUUACUUCAC | 2246 | GUGAAGUAACUC | 3641 | AD-26777, AD-19755 |
| 2192 | AGUUACUUCACU | 2247 | AGUGAAGUAACU | 3642 | AD-26777, AD-26778, AD-19755 |
| 2193 | GUUACUUCACUC | 2248 | GAGUGAAGUAAC | 3643 | AD-26777, AD-26779, AD-26778, AD-19755 |
| 2194 | UUACUUCACUCU | 2249 | AGAGUGAAGUAA | 3644 | AD-26777, AD-26779, AD-19755 |
| 2195 | UACUUCACUCUA | 2250 | UAGAGUGAAGUA | 3645 | AD-26777, AD-26778, AD-19755 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 2196 | ACUUCACUCUAG | 2251 | CUAGAGUGAAGU | 3646 | AD-26780, AD-26778, AD-19755 |
| 2197 | CUUCACUCUAGG | 2252 | CCUAGAGUGAAG | 3647 | AD-26779, AD-26780, AD-26778, AD-19755 |
| 2198 | UUCACUCUAGGA | 2253 | UCCUAGAGUGAA | 3648 | AD-26779, AD-26780, AD-26778, AD-19755 |
| 2199 | UCACUCUAGGAA | 2254 | UUCCUAGAGUGA | 3649 | AD-26779, AD-26780, AD-26778 |
| 2200 | CACUCUAGGAAU | 2255 | AUUCCUAGAGUG | 3650 | AD-26779, AD-26780 |
| 2234 | CUGCUGUUUUGU | 2256 | ACAAAACAGCAG | 3651 | AD-26782, AD-26781 |
| 2235 | UGCUGUUUUGUU | 2257 | AACAAAACAGCA | 3652 | AD-26782, AD-26781 |
| 2236 | GCUGUUUUGUUC | 2258 | GAACAAAACAGC | 3653 | AD-26782, AD-26781 |
| 2237 | CUGUUUUGUUCC | 2259 | GGAACAAAACAG | 3654 | AD-26782, AD-26781 |
| 2238 | UGUUUUGUUCCG | 2260 | CGGAACAAAACA | 3655 | AD-26782, AD-26781 |
| 2239 | GUUUUGUUCCGA | 2261 | UCGGAACAAAAC | 3656 | AD-26782, AD-26781 |
| 2240 | UUUUGUUCCGAA | 2262 | UUCGGAACAAAA | 3657 | AD-26782, AD-26781 |
| 2256 | UGAGGACAAGCC | 2263 | GGCUUGUCCUCA | 3658 | AD-26783, AD-26784 |
| 2257 | GAGGACAAGCCA | 2264 | UGGCUUGUCCUC | 3659 | AD-26783, AD-26784 |
| 2258 | AGGACAAGCCAC | 2265 | GUGGCUUGUCCU | 3660 | AD-26783, AD-26784 |
| 2259 | GGACAAGCCACA | 2266 | UGUGGCUUGUCC | 3661 | AD-26783, AD-26784 |
| 2260 | GACAAGCCACAA | 2267 | UUGUGGCUUGUC | 3662 | AD-26783, AD-26784 |
| 2261 | ACAAGCCACAAG | 2268 | CUUGUGGCUUGU | 3663 | AD-26784, AD-26785 |
| 2262 | CAAGCCACAAGA | 2269 | UCUUGUGGCUUG | 3664 | AD-26784, AD-26785 |
| 2263 | AAGCCACAAGAU | 2270 | AUCUUGUGGCUU | 3665 | AD-26784, AD-26785 |
| 2264 | AGCCACAAGAUU | 2271 | AAUCUUGUGGCU | 3666 | AD-26786, AD-26785 |
| 2265 | GCCACAAGAUUA | 2272 | UAAUCUUGUGGC | 3667 | AD-26786, AD-26785 |
| 2266 | CCACAAGAUUAC | 2273 | GUAAUCUUGUGG | 3668 | AD-26786, AD-26785 |
| 2267 | CACAAGAUUACA | 2274 | UGUAAUCUUGUG | 3669 | AD-26786, AD-26785 |
| 2268 | ACAAGAUUACAA | 2275 | UUGUAAUCUUGU | 3670 | AD-26786, AD-26785 |
| 2271 | AGAUUACAAGAA | 2276 | UUCUUGUAAUCU | 3671 | AD-26786, AD-26787 |
| 2277 | CAAGAAACGGCU | 2277 | AGCCGUUUCUUG | 3672 | AD-26788, AD-26787 |
| 2278 | AAGAAACGGCUU | 2278 | AAGCCGUUUCUU | 3673 | AD-26788, AD-26787 |
| 2302 | ACCAGCUCUCUC | 2279 | GAGAGAGCUGGU | 3674 | AD-26790, AD-26789 |
| 2303 | CCAGCUCUCUCU | 2280 | AGAGAGAGCUGG | 3675 | AD-26790, AD-26789 |
| 2304 | CAGCUCUCUCUU | 2281 | AAGAGAGAGCUG | 3676 | AD-26790, AD-26789 |
| 2325 | GCCAAUGGCUUG | 2282 | CAAGCCAUUGGC | 3677 | AD-18909, AD-18910 |
| 2326 | CCAAUGGCUUGG | 2283 | CCAAGCCAUUGG | 3678 | AD-18909, AD-18910, AD-19080 |
| 2327 | CAAUGGCUUGGA | 2284 | UCCAAGCCAUUG | 3679 | AD-18909, AD-18947, AD-18910, AD-19080 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 2328 | AAUGGCUUGGAA | 2285 | UUCCAAGCCAUU | 3680 | AD-18909, AD-19051, AD-18947, AD-18910, AD-19080 |
| 2329 | AUGGCUUGGAAU | 2286 | AUUCCAAGCCAU | 3681 | AD-18909, AD-19051, AD-18947, AD-18978, AD-18910 |
| 2330 | UGGCUUGGAAUG | 2287 | CAUUCCAAGCCA | 3682 | AD-18909, AD-19051, AD-18947, AD-18978, AD-19080 |
| 2331 | GGCUUGGAAUGA | 2288 | UCAUUCCAAGCC | 3683 | AD-18909, AD-19051, AD-18947, AD-18978, AD-18910, AD-19080 |
| 2332 | GCUUGGAAUGAG | 2289 | CUCAUUCCAAGC | 3684 | AD-19051, AD-18947, AD-18978, AD-18910, AD-19080 |
| 2333 | CUUGGAAUGAGA | 2290 | UCUCAUUCCAAG | 3685 | AD-19051, AD-18947, AD-18978, AD-19080 |
| 2334 | UUGGAAUGAGAC | 2291 | GUCUCAUUCCAA | 3686 | AD-19051, AD-18947, AD-18978 |
| 2335 | UGGAAUGAGACU | 2292 | AGUCUCAUUCCA | 3687 | AD-19051, AD-18978 |
| 2370 | UGCCCAGGGAGA | 2293 | UCUCCCUGGGCA | 3688 | AD-26677, AD-26791 |
| 2371 | GCCCAGGGAGAA | 2294 | UUCUCCCUGGGC | 3689 | AD-26677, AD-26791 |
| 2374 | CAGGGAGAACCC | 2295 | GGGUUCUCCCUG | 3690 | AD-26792, AD-26677 |
| 2375 | AGGGAGAACCCC | 2296 | GGGGUUCUCCCU | 3691 | AD-26793, AD-26677 |
| 2376 | GGGAGAACCCCU | 2297 | AGGGGUUCUCCC | 3692 | AD-26793, AD-26792 |
| 2377 | GGAGAACCCCUU | 2298 | AAGGGGUUCUCC | 3693 | AD-26793, AD-26792, AD-26677 |
| 2378 | GAGAACCCCUUG | 2299 | CAAGGGGUUCUC | 3694 | AD-26793, AD-26792 |
| 2379 | AGAACCCCUUGG | 2300 | CCAAGGGGUUCU | 3695 | AD-26793, AD-26792 |
| 2380 | GAACCCCUUGGA | 2301 | UCCAAGGGGUUC | 3696 | AD-26793, AD-26792 |
| 2381 | AACCCCUUGGAU | 2302 | AUCCAAGGGGUU | 3697 | AD-26793, AD-26792 |
| 2385 | CCUUGGAUAUCG | 2303 | CGAUAUCCAAGG | 3698 | AD-26794, AD-19063 |
| 2386 | CUUGGAUAUCGC | 2304 | GCGAUAUCCAAG | 3699 | AD-26794, AD-19063 |
| 2387 | UUGGAUAUCGCC | 2305 | GGCGAUAUCCAA | 3700 | AD-18979, AD-26794, AD-19063 |
| 2388 | UGGAUAUCGCCA | 2306 | UGGCGAUAUCCA | 3701 | AD-18979, AD-19001, AD-26794, AD-19063 |
| 2389 | GGAUAUCGCCAG | 2307 | CUGGCGAUAUCC | 3702 | AD-18979, AD-18941, AD-19001, AD-26794, AD-19063 |
| 2390 | GAUAUCGCCAGG | 2308 | CCUGGCGAUAUC | 3703 | AD-18979, AD-18941, AD-19001, AD-18900, AD-26794, AD-19063 |
| 2391 | AUAUCGCCAGGA | 2309 | UCCUGGCGAUAU | 3704 | AD-18979, AD-18941, AD-19001, AD-18900, AD-26794 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 2392 | UAUCGCCAGGAU | 2310 | AUCCUGGCGAUA | 3705 | AD-18979, AD-18941, AD-19001, AD-18900, AD-26794, AD-26795 |
| 2393 | AUCGCCAGGAUG | 2311 | CAUCCUGGCGAU | 3706 | AD-18979, AD-18941, AD-19001, AD-26795 |
| 2394 | UCGCCAGGAUGA | 2312 | UCAUCCUGGCGA | 3707 | AD-18979, AD-18941, AD-19001, AD-18900, AD-26795 |
| 2395 | CGCCAGGAUGAU | 2313 | AUCAUCCUGGCG | 3708 | AD-18941, AD-19001, AD-18900, AD-26795 |
| 2396 | GCCAGGAUGAUC | 2314 | GAUCAUCCUGGC | 3709 | AD-18941, AD-26796, AD-26795 |
| 2397 | CCAGGAUGAUCC | 2315 | GGAUCAUCCUGG | 3710 | AD-26796, AD-18900, AD-26795, AD-26797 |
| 2398 | CAGGAUGAUCCU | 2316 | AGGAUCAUCCUG | 3711 | AD-26796, AD-26795, AD-26797 |
| 2399 | AGGAUGAUCCUA | 2317 | UAGGAUCAUCCU | 3712 | AD-26796, AD-26795 |
| 2400 | GGAUGAUCCUAG | 2318 | CUAGGAUCAUCC | 3713 | AD-26796, AD-26797 |
| 2401 | GAUGAUCCUAGC | 2319 | GCUAGGAUCAUC | 3714 | AD-26796, AD-26798, AD-26797 |
| 2402 | AUGAUCCUAGCU | 2320 | AGCUAGGAUCAU | 3715 | AD-26796, AD-26797 |
| 2403 | UGAUCCUAGCUA | 2321 | UAGCUAGGAUCA | 3716 | AD-26796, AD-26798, AD-26797 |
| 2404 | GAUCCUAGCUAU | 2322 | AUAGCUAGGAUC | 3717 | AD-26798, AD-26797 |
| 2405 | AUCCUAGCUAUC | 2323 | GAUAGCUAGGAU | 3718 | AD-26799, AD-26798 |
| 2406 | UCCUAGCUAUCG | 2324 | CGAUAGCUAGGA | 3719 | AD-26799, AD-26800 |
| 2407 | CCUAGCUAUCGU | 2325 | ACGAUAGCUAGG | 3720 | AD-26799, AD-26798 |
| 2408 | CUAGCUAUCGUU | 2326 | AACGAUAGCUAG | 3721 | AD-26799, AD-26798, AD-26800 |
| 2409 | UAGCUAUCGUUC | 2327 | GAACGAUAGCUA | 3722 | AD-26799, AD-26800 |
| 2410 | AGCUAUCGUUCU | 2328 | AGAACGAUAGCU | 3723 | AD-26799, AD-26800 |
| 2411 | GCUAUCGUUCUU | 2329 | AAGAACGAUAGC | 3724 | AD-26799, AD-26800 |
| 2412 | CUAUCGUUCUUU | 2330 | AAAGAACGAUAG | 3725 | AD-26799, AD-26800 |
| 2419 | UCUUUUCACUCU | 2331 | AGAGUGAAAAGA | 3726 | AD-18951, AD-26801 |
| 2420 | CUUUUCACUCUG | 2332 | CAGAGUGAAAAG | 3727 | AD-18951, AD-26802, AD-26801 |
| 2421 | UUUUCACUCUGG | 2333 | CCAGAGUGAAAA | 3728 | AD-18951, AD-26803, AD-26802, AD-26801 |
| 2422 | UUUCACUCUGGU | 2334 | ACCAGAGUGAAA | 3729 | AD-18951, AD-26802, AD-26801 |
| 2423 | UUCACUCUGGUG | 2335 | CACCAGAGUGAA | 3730 | AD-18951, AD-26803, AD-26801 |
| 2424 | UCACUCUGGUGG | 2336 | CCACCAGAGUGA | 3731 | AD-26803, AD-26802 |
| 2425 | CACUCUGGUGGA | 2337 | UCCACCAGAGUG | 3732 | AD-26803, AD-26801 |

TABLE 4-continued

Groups of overlapping RNAi agents to Beta-Catenin

| Position | Sense overlap | SEQ ID NO: Anti-sense overlap | SEQ ID NO: | Overlapping groups of RNAi agents |
|---|---|---|---|---|
| 2426 | ACUCUGGUGGAU | 2338 AUCCACCAGAGU | 3733 | AD-26803, AD-26802, AD-26801 |
| 2427 | CUCUGGUGGAUA | 2339 UAUCCACCAGAG | 3734 | AD-26803, AD-26802 |
| 2435 | GAUAUGGCCAGG | 2340 CCUGGCCAUAUC | 3735 | AD-26805, AD-26804 |
| 2436 | AUAUGGCCAGGA | 2341 UCCUGGCCAUAU | 3736 | AD-26805, AD-26804 |
| 2437 | UAUGGCCAGGAU | 2342 AUCCUGGCCAUA | 3737 | AD-26805, AD-26804 |
| 2440 | GGCCAGGAUGCC | 2343 GGCAUCCUGGCC | 3738 | AD-26693, AD-26805 |
| 2441 | GCCAGGAUGCCU | 2344 AGGCAUCCUGGC | 3739 | AD-26693, AD-26805 |
| 2442 | CCAGGAUGCCUU | 2345 AAGGCAUCCUGG | 3740 | AD-26693, AD-26805 |
| 2453 | UGGGUAUGGACC | 2346 GGUCCAUACCCA | 3741 | AD-26806, AD-26807 |
| 2454 | GGGUAUGGACCC | 2347 GGGUCCAUACCC | 3742 | AD-26806, AD-26807 |
| 2455 | GGUAUGGACCCC | 2348 GGGGUCCAUACC | 3743 | AD-26806, AD-26807 |
| 2456 | GUAUGGACCCCA | 2349 UGGGGUCCAUAC | 3744 | AD-26806, AD-26807 |
| 2457 | UAUGGACCCCAU | 2350 AUGGGGUCCAUA | 3745 | AD-26806, AD-26811, AD-26807 |
| 2458 | AUGGACCCCAUG | 2351 CAUGGGGUCCAU | 3746 | AD-26811, AD-26807 |
| 2459 | UGGACCCCAUGA | 2352 UCAUGGGGUCCA | 3747 | AD-26811, AD-26807 |
| 2460 | GGACCCCAUGAU | 2353 AUCAUGGGGUCC | 3748 | AD-26811, AD-26807, AD-26812 |
| 2461 | GACCCCAUGAUG | 2354 CAUCAUGGGGUC | 3749 | AD-26811, AD-26812 |
| 2462 | ACCCCAUGAUGG | 2355 CCAUCAUGGGGU | 3750 | AD-26811, AD-26812 |
| 2463 | CCCCAUGAUGGA | 2356 UCCAUCAUGGGG | 3751 | AD-26811, AD-26812 |
| 2464 | CCCAUGAUGGAA | 2357 UUCCAUCAUGGG | 3752 | AD-26811, AD-26812 |
| 2465 | CCAUGAUGGAAC | 2358 GUUCCAUCAUGG | 3753 | AD-26813, AD-26812 |
| 2466 | CAUGAUGGAACA | 2359 UGUUCCAUCAUG | 3754 | AD-26813, AD-26812 |
| 2467 | AUGAUGGAACAU | 2360 AUGUUCCAUCAU | 3755 | AD-26813, AD-26812 |
| 2493 | CCACCCUGGUGC | 2361 GCACCAGGGUGG | 3756 | AD-26814, AD-26815 |
| 2494 | CACCCUGGUGCU | 2362 AGCACCAGGGUG | 3757 | AD-26814, AD-26815 |
| 2495 | ACCCUGGUGCUG | 2363 CAGCACCAGGGU | 3758 | AD-26814, AD-26815 |
| 2496 | CCCUGGUGCUGA | 2364 UCAGCACCAGGG | 3759 | AD-26814, AD-26815, AD-19057 |
| 2497 | CCUGGUGCUGAC | 2365 GUCAGCACCAGG | 3760 | AD-19071, AD-26814, AD-26815, AD-19057 |
| 2498 | CUGGUGCUGACU | 2366 AGUCAGCACCAG | 3761 | AD-19071, AD-26814, AD-26815, AD-18970, AD-19057 |
| 2499 | UGGUGCUGACUA | 2367 UAGUCAGCACCA | 3762 | AD-19071, AD-26814, AD-26815, AD-18970, AD-19057, AD-18892 |
| 2500 | GGUGCUGACUAU | 2368 AUAGUCAGCACC | 3763 | AD-19071, AD-26815, AD-18970, AD-19057, AD-18892 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 2501 | GUGCUGACUAUC | 2369 | GAUAGUCAGCAC | 3764 | AD-19071, AD-18970, AD-19057, AD-18892 |
| 2502 | UGCUGACUAUCC | 2370 | GGAUAGUCAGCA | 3765 | AD-19071, AD-26816, AD-18970, AD-19057, AD-18892 |
| 2503 | GCUGACUAUCCA | 2371 | UGGAUAGUCAGC | 3766 | AD-19071, AD-19042, AD-26816, AD-18970, AD-19057 |
| 2504 | CUGACUAUCCAG | 2372 | CUGGAUAGUCAG | 3767 | AD-19071, AD-19042, AD-26816, AD-18970, AD-18919, AD-18892 |
| 2505 | UGACUAUCCAGU | 2373 | ACUGGAUAGUCA | 3768 | AD-19042, AD-18944, AD-18970, AD-18919, AD-18892 |
| 2506 | GACUAUCCAGUU | 2374 | AACUGGAUAGUC | 3769 | AD-19042, AD-26816, AD-18944, AD-18908, AD-18919, AD-18892 |
| 2507 | ACUAUCCAGUUG | 2375 | CAACUGGAUAGU | 3770 | AD-19042, AD-26816, AD-18967, AD-18944, AD-18908, AD-18919 |
| 2508 | CUAUCCAGUUGA | 2376 | UCAACUGGAUAG | 3771 | AD-19042, AD-26816, AD-18967, AD-18944, AD-18908, AD-19077, AD-18919 |
| 2509 | UAUCCAGUUGAU | 2377 | AUCAACUGGAUA | 3772 | AD-19042, AD-26816, AD-18967, AD-18944, AD-18908, AD-19077, AD-18919 |
| 2510 | AUCCAGUUGAUG | 2378 | CAUCAACUGGAU | 3773 | AD-19042, AD-18967, AD-18944, AD-18908, AD-19077, AD-18919 |
| 2511 | UCCAGUUGAUGG | 2379 | CCAUCAACUGGA | 3774 | AD-18967, AD-18944, AD-18908, AD-19077, AD-18919 |
| 2512 | CCAGUUGAUGGG | 2380 | CCCAUCAACUGG | 3775 | AD-18967, AD-18944, AD-18908, AD-19077 |
| 2513 | CAGUUGAUGGGC | 2381 | GCCCAUCAACUG | 3776 | AD-18967, AD-18908, AD-19077 |
| 2514 | AGUUGAUGGGCU | 2382 | AGCCCAUCAACU | 3777 | AD-26817, AD-18967, AD-19077 |
| 2515 | GUUGAUGGGCUG | 2383 | CAGCCCAUCAAC | 3778 | AD-26817, AD-19077 |
| 2544 | CCAGGACCUCAU | 2384 | AUGAGGUCCUGG | 3779 | AD-19073, AD-26818 |
| 2545 | CAGGACCUCAUG | 2385 | CAUGAGGUCCUG | 3780 | AD-19073, AD-26818 |
| 2546 | AGGACCUCAUGG | 2386 | CCAUGAGGUCCU | 3781 | AD-19073, AD-26818 |
| 2547 | GGACCUCAUGGA | 2387 | UCCAUGAGGUCC | 3782 | AD-19073, AD-26818 |
| 2548 | GACCUCAUGGAU | 2388 | AUCCAUGAGGUC | 3783 | AD-19073, AD-26818 |
| 2580 | CAAUCAGCUGGC | 2389 | GCCAGCUGAUUG | 3784 | AD-26819, AD-26820 |
| 2581 | AAUCAGCUGGCC | 2390 | GGCCAGCUGAUU | 3785 | AD-26819, AD-26820 |
| 2582 | AUCAGCUGGCCU | 2391 | AGGCCAGCUGAU | 3786 | AD-26819, AD-18989, AD-26820 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 2583 | UCAGCUGGCCUG | 2392 | CAGGCCAGCUGA | 3787 | AD-18975, AD-26819, AD-18989, AD-26820 |
| 2584 | CAGCUGGCCUGG | 2393 | CCAGGCCAGCUG | 3788 | AD-18975, AD-26819, AD-18989, AD-26820 |
| 2585 | AGCUGGCCUGGU | 2394 | ACCAGGCCAGCU | 3789 | AD-18975, AD-19060, AD-26819, AD-18989, AD-26820 |
| 2586 | GCUGGCCUGGUU | 2395 | AACCAGGCCAGC | 3790 | AD-18975, AD-18898, AD-26819, AD-18989, AD-26820 |
| 2587 | CUGGCCUGGUUU | 2396 | AAACCAGGCCAG | 3791 | AD-18975, AD-19060, AD-18898, AD-18989, AD-26820 |
| 2588 | UGGCCUGGUUUG | 2397 | CAAACCAGGCCA | 3792 | AD-18975, AD-19059, AD-19060, AD-18964, AD-18898, AD-18989 |
| 2589 | GGCCUGGUUUGA | 2398 | UCAAACCAGGCC | 3793 | AD-18920, AD-19059, AD-19060, AD-18964, AD-18898, AD-18989 |
| 2590 | GCCUGGUUUGAU | 2399 | AUCAAACCAGGC | 3794 | AD-18975, AD-18920, AD-19059, AD-19060, AD-18964, AD-18898 |
| 2591 | CCUGGUUUGAUA | 2400 | UAUCAAACCAGG | 3795 | AD-18922, AD-19059, AD-19060, AD-18907, AD-18964, AD-18898 |
| 2592 | CUGGUUUGAUAC | 2401 | GUAUCAAACCAG | 3796 | AD-18922, AD-18920, AD-19060, AD-18907, AD-18964, AD-18898 |
| 2593 | UGGUUUGAUACU | 2402 | AGUAUCAAACCA | 3797 | AD-18905, AD-18922, AD-18920, AD-18907, AD-18964 |
| 2594 | GGUUUGAUACUG | 2403 | CAGUAUCAAACC | 3798 | AD-18905, AD-18920, AD-26821, AD-18907, AD-18964 |
| 2595 | GUUUGAUACUGA | 2404 | UCAGUAUCAAAC | 3799 | AD-18922, AD-18920, AD-19059, AD-26821, AD-18986 |
| 2596 | UUUGAUACUGAC | 2405 | GUCAGUAUCAAA | 3800 | AD-18905, AD-18922, AD-18920, AD-26821, AD-18907, AD-19066, AD-18986 |
| 2597 | UUGAUACUGACC | 2406 | GGUCAGUAUCAA | 3801 | AD-18905, AD-26821, AD-18907, AD-18986 |
| 2598 | UGAUACUGACCU | 2407 | AGGUCAGUAUCA | 3802 | AD-18905, AD-18999, AD-18907, AD-18965, AD-19066 |
| 2599 | GAUACUGACCUG | 2408 | CAGGUCAGUAUC | 3803 | AD-18905, AD-26821, AD-18999, AD-18965, AD-19066, AD-18986 |
| 2600 | AUACUGACCUGU | 2409 | ACAGGUCAGUAU | 3804 | AD-26822, AD-18905, AD-18965, AD-19066, AD-18986 |
| 2601 | UACUGACCUGUA | 2410 | UACAGGUCAGUA | 3805 | AD-26822, AD-26821, AD-18999, AD-18965, AD-19066, AD-18986 |

TABLE 4-continued

Groups of overlapping RNAi agents to Beta-Catenin

| Position | Sense overlap | SEQ ID NO: Anti-sense overlap | SEQ ID NO: | Overlapping groups of RNAi agents |
|---|---|---|---|---|
| 2602 | ACUGACCUGUAA | 2411 UUACAGGUCAGU | 3806 | AD-26822, AD-18999, AD-18965, AD-19066, AD-18986 |
| 2603 | CUGACCUGUAAA | 2412 UUUACAGGUCAG | 3807 | AD-26822, AD-18999, AD-18965, AD-19066 |
| 2604 | UGACCUGUAAAU | 2413 AUUUACAGGUCA | 3808 | AD-26822, AD-18999, AD-18965, AD-26823 |
| 2605 | GACCUGUAAAUC | 2414 GAUUUACAGGUC | 3809 | AD-26822, AD-26824, AD-18999, AD-26823 |
| 2606 | ACCUGUAAAUCA | 2415 UGAUUUACAGGU | 3810 | AD-26822, AD-26824, AD-26825, AD-26823 |
| 2607 | CCUGUAAAUCAU | 2416 AUGAUUUACAGG | 3811 | AD-26822, AD-26824, AD-26825, AD-26823 |
| 2608 | CUGUAAAUCAUC | 2417 GAUGAUUUACAG | 3812 | AD-26824, AD-26825, AD-26823 |
| 2609 | UGUAAAUCAUCC | 2418 GGAUGAUUUACA | 3813 | AD-26824, AD-26823 |
| 2610 | GUAAAUCAUCCU | 2419 AGGAUGAUUUAC | 3814 | AD-26825, AD-26823 |
| 2611 | UAAAUCAUCCUU | 2420 AAGGAUGAUUUA | 3815 | AD-26824, AD-26825, AD-26823 |
| 2612 | AAAUCAUCCUUU | 2421 AAAGGAUGAUUU | 3816 | AD-26824, AD-26825 |
| 2628 | GUAACAAUACAA | 2422 UUGUAUUGUUAC | 3817 | AD-18933, AD-19053 |
| 2629 | UAACAAUACAAA | 2423 UUUGUAUUGUUA | 3818 | AD-18933, AD-19053 |
| 2630 | AACAAUACAAAU | 2424 AUUUGUAUUGUU | 3819 | AD-18933, AD-19053 |
| 2631 | ACAAUACAAAUG | 2425 CAUUUGUAUUGU | 3820 | AD-18933, AD-19053 |
| 2632 | CAAUACAAAUGG | 2426 CCAUUUGUAUUG | 3821 | AD-18933, AD-19053, AD-25889 |
| 2633 | AAUACAAAUGGA | 2427 UCCAUUUGUAUU | 3822 | AD-18933, AD-25889 |
| 2634 | AUACAAAUGGAU | 2428 AUCCAUUUGUAU | 3823 | AD-18933, AD-25889 |
| 2635 | UACAAAUGGAUU | 2429 AAUCCAUUUGUA | 3824 | AD-18933, AD-25889 |
| 2636 | ACAAAUGGAUUU | 2430 AAAUCCAUUUGU | 3825 | AD-25890, AD-25889 |
| 2637 | CAAAUGGAUUUU | 2431 AAAAUCCAUUUG | 3826 | AD-25890, AD-25889 |
| 2638 | AAAUGGAUUUUG | 2432 CAAAAUCCAUUU | 3827 | AD-25890, AD-25889 |
| 2648 | UGGGAGUGACUC | 2433 GAGUCACUCCCA | 3828 | AD-25892, AD-25891 |
| 2649 | GGGAGUGACUCA | 2434 UGAGUCACUCCC | 3829 | AD-25892, AD-25891 |
| 2650 | GGAGUGACUCAA | 2435 UUGAGUCACUCC | 3830 | AD-25892, AD-25891 |
| 2651 | GAGUGACUCAAG | 2436 CUUGAGUCACUC | 3831 | AD-25892, AD-25891 |
| 2652 | AGUGACUCAAGA | 2437 UCUUGAGUCACU | 3832 | AD-25892, AD-25891 |
| 2653 | GUGACUCAAGAA | 2438 UUCUUGAGUCAC | 3833 | AD-25892, AD-25891 |
| 2654 | UGACUCAAGAAG | 2439 CUUCUUGAGUCA | 3834 | AD-25892, AD-25891 |
| 2663 | AAGUGAAGAAUG | 2440 CAUUCUUCACUU | 3835 | AD-25894, AD-25893 |
| 2664 | AGUGAAGAAUGC | 2441 GCAUUCUUCACU | 3836 | AD-25894, AD-25938 |
| 2665 | GUGAAGAAUGCA | 2442 UGCAUUCUUCAC | 3837 | AD-25893, AD-25938 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 2666 | UGAAGAAUGCAC | 2443 | GUGCAUUCUUCA | 3838 | AD-25894, AD-25893 |
| 2667 | GAAGAAUGCACA | 2444 | UGUGCAUUCUUC | 3839 | AD-25894, AD-25893, AD-25938 |
| 2668 | AAGAAUGCACAA | 2445 | UUGUGCAUUCUU | 3840 | AD-25894, AD-25893, AD-25938 |
| 2669 | AGAAUGCACAAG | 2446 | CUUGUGCAUUCU | 3841 | AD-25894, AD-25893, AD-25938 |
| 2670 | GAAUGCACAAGA | 2447 | UCUUGUGCAUUC | 3842 | AD-25894, AD-25938 |
| 2682 | AUGGAUCACAAG | 2448 | CUUGUGAUCCAU | 3843 | AD-25940, AD-25939 |
| 2683 | UGGAUCACAAGA | 2449 | UCUUGUGAUCCA | 3844 | AD-25941, AD-25940, AD-25939 |
| 2684 | GGAUCACAAGAU | 2450 | AUCUUGUGAUCC | 3845 | AD-25941, AD-25940, AD-25942, AD-25939 |
| 2685 | GAUCACAAGAUG | 2451 | CAUCUUGUGAUC | 3846 | AD-25941, AD-25940, AD-25942, AD-25939, AD-25943 |
| 2686 | AUCACAAGAUGG | 2452 | CCAUCUUGUGAU | 3847 | AD-25941, AD-25940, AD-25944, AD-25942, AD-25939, AD-25943 |
| 2687 | UCACAAGAUGGA | 2453 | UCCAUCUUGUGA | 3848 | AD-25941, AD-25940, AD-25944, AD-25942, AD-25943 |
| 2688 | CACAAGAUGGAA | 2454 | UUCCAUCUUGUG | 3849 | AD-25941, AD-25944, AD-25942, AD-25939, AD-25943 |
| 2689 | ACAAGAUGGAAU | 2455 | AUUCCAUCUUGU | 3850 | AD-25941, AD-25940, AD-25944, AD-25942, AD-25943 |
| 2690 | CAAGAUGGAAUU | 2456 | AAUUCCAUCUUG | 3851 | AD-25941, AD-25944, AD-25942, AD-25943 |
| 2691 | AAGAUGGAAUUU | 2457 | AAAUUCCAUCUU | 3852 | AD-25944, AD-25942, AD-25943 |
| 2692 | AGAUGGAAUUUA | 2458 | UAAAUUCCAUCU | 3853 | AD-25944, AD-25943 |
| 2693 | GAUGGAAUUUAU | 2459 | AUAAAUUCCAUC | 3854 | AD-25944, AD-25895 |
| 2694 | AUGGAAUUUAUC | 2460 | GAUAAAUUCCAU | 3855 | AD-25895, AD-25896 |
| 2695 | UGGAAUUUAUCA | 2461 | UGAUAAAUUCCA | 3856 | AD-25895, AD-25896, AD-25945 |
| 2696 | GGAAUUUAUCAA | 2462 | UUGAUAAAUUCC | 3857 | AD-25895, AD-25896, AD-25897, AD-25945 |
| 2697 | GAAUUUAUCAAA | 2463 | UUUGAUAAAUUC | 3858 | AD-25895, AD-25896, AD-25898, AD-25897, AD-25945 |
| 2698 | AAUUUAUCAAAC | 2464 | GUUUGAUAAAUU | 3859 | AD-25895, AD-25899, AD-25896, AD-25898, AD-25945 |
| 2699 | AUUUAUCAAACC | 2465 | GGUUUGAUAAAU | 3860 | AD-25895, AD-25896, AD-25898, AD-25897, AD-25945 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 2700 | UUUAUCAAACCC | 2466 | GGGUUUGAUAAA | 3861 | AD-25895, AD-25899, AD-25896, AD-25898, AD-25897, AD-25945 |
| 2701 | UUAUCAAACCCU | 2467 | AGGGUUUGAUAA | 3862 | AD-25899, AD-25896, AD-25897, AD-18929, AD-25945 |
| 2702 | UAUCAAACCCUA | 2468 | UAGGGUUUGAUA | 3863 | AD-25899, AD-25898, AD-25897, AD-18929, AD-25945 |
| 2703 | AUCAAACCCUAG | 2469 | CUAGGGUUUGAU | 3864 | AD-18996, AD-25899, AD-18915, AD-25898, AD-25897, AD-18929 |
| 2704 | UCAAACCCUAGC | 2470 | GCUAGGGUUUGA | 3865 | AD-18996, AD-25899, AD-18915, AD-25898, AD-18929 |
| 2705 | CAAACCCUAGCC | 2471 | GGCUAGGGUUUG | 3866 | AD-18935, AD-18996, AD-25899, AD-18915 |
| 2706 | AAACCCUAGCCU | 2472 | AGGCUAGGGUUU | 3867 | AD-18915, AD-18942, AD-18929 |
| 2707 | AACCCUAGCCUU | 2473 | AAGGCUAGGGUU | 3868 | AD-18913, AD-18935, AD-18996, AD-18915 |
| 2708 | ACCCUAGCCUUG | 2474 | CAAGGCUAGGGU | 3869 | AD-18913, AD-18996, AD-18915, AD-18942, AD-18929, AD-25946 |
| 2709 | CCCUAGCCUUGC | 2475 | GCAAGGCUAGGG | 3870 | AD-18913, AD-18935, AD-18996, AD-25947, AD-18915, AD-25946 |
| 2710 | CCUAGCCUUGCU | 2476 | AGCAAGGCUAGG | 3871 | AD-18913, AD-25948, AD-18935, AD-25947, AD-18915, AD-18942, AD-25946 |
| 2711 | CUAGCCUUGCUU | 2477 | AAGCAAGGCUAG | 3872 | AD-18913, AD-25948, AD-18935, AD-25949, AD-25947, AD-18942, AD-25946 |
| 2712 | UAGCCUUGCUUG | 2478 | CAAGCAAGGCUA | 3873 | AD-18913, AD-25948, AD-18935, AD-25950, AD-25947, AD-18942, AD-25946 |
| 2713 | AGCCUUGCUUGU | 2479 | ACAAGCAAGGCU | 3874 | AD-18913, AD-25948, AD-25951, AD-25949, AD-25947, AD-18942, AD-25946 |
| 2714 | GCCUUGCUUGUU | 2480 | AACAAGCAAGGC | 3875 | AD-18913, AD-25948, AD-25951, AD-25950, AD-25949, AD-25947, AD-25946 |
| 2715 | CCUUGCUUGUUA | 2481 | UAACAAGCAAGG | 3876 | AD-25948, AD-25951, AD-25950, AD-25949, AD-25947, AD-25946 |
| 2716 | CUUGCUUGUUAA | 2482 | UUAACAAGCAAG | 3877 | AD-25948, AD-25951, AD-25950, AD-25949, AD-25947 |
| 2717 | UUGCUUGUUAAA | 2483 | UUUAACAAGCAA | 3878 | AD-25948, AD-25951, AD-25950, AD-25949 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 2718 | UGCUUGUUAAAU | 2484 | AUUUAACAAGCA | 3879 | AD-25951, AD-25950, AD-25949 |
| 2719 | GCUUGUUAAAUU | 2485 | AAUUUAACAAGC | 3880 | AD-25951, AD-25950 |
| 2750 | GAAUAUCUGUAA | 2486 | UUACAGAUAUUC | 3881 | AD-25900, AD-26900 |
| 2751 | AAUAUCUGUAAU | 2487 | AUUACAGAUAUU | 3882 | AD-25900, AD-26900, AD-25901 |
| 2752 | AUAUCUGUAAUG | 2488 | CAUUACAGAUAU | 3883 | AD-25900, AD-25902, AD-25901 |
| 2753 | UAUCUGUAAUGG | 2489 | CCAUUACAGAUA | 3884 | AD-25900, AD-25902, AD-25901 |
| 2754 | AUCUGUAAUGGU | 2490 | ACCAUUACAGAU | 3885 | AD-25900, AD-25901 |
| 2755 | UCUGUAAUGGUA | 2491 | UACCAUUACAGA | 3886 | AD-25902, AD-25901 |
| 2756 | CUGUAAUGGUAC | 2492 | GUACCAUUACAG | 3887 | AD-25900, AD-25902, AD-25901 |
| 2757 | UGUAAUGGUACU | 2493 | AGUACCAUUACA | 3888 | AD-25900, AD-25902 |
| 2758 | GUAAUGGUACUG | 2494 | CAGUACCAUUAC | 3889 | AD-25902, AD-25901 |
| 2832 | UUUAAGUCUCUC | 2495 | GAGAGACUUAAA | 3890 | AD-25903, AD-25904 |
| 2833 | UUAAGUCUCUCG | 2496 | CGAGAGACUUAA | 3891 | AD-25903, AD-25952, AD-25904 |
| 2834 | UAAGUCUCUCGU | 2497 | ACGAGAGACUUA | 3892 | AD-25903, AD-25952, AD-25904, AD-25953 |
| 2835 | AAGUCUCUCGUA | 2498 | UACGAGAGACUU | 3893 | AD-25954, AD-25903, AD-25952, AD-25904, AD-25953 |
| 2836 | AGUCUCUCGUAG | 2499 | CUACGAGAGACU | 3894 | AD-25954, AD-25903, AD-25952, AD-25904, AD-25953, AD-25905 |
| 2837 | GUCUCUCGUAGU | 2500 | ACUACGAGAGAC | 3895 | AD-25954, AD-25903, AD-25952, AD-25904, AD-25953 |
| 2838 | UCUCUCGUAGUG | 2501 | CACUACGAGAGA | 3896 | AD-25954, AD-25952, AD-25904, AD-25953, AD-25905 |
| 2839 | CUCUCGUAGUGU | 2502 | ACACUACGAGAG | 3897 | AD-25954, AD-25952, AD-25904, AD-25953, AD-25905 |
| 2840 | UCUCGUAGUGUU | 2503 | AACACUACGAGA | 3898 | AD-25954, AD-25952, AD-25953, AD-25905 |
| 2841 | CUCGUAGUGUUA | 2504 | UAACACUACGAG | 3899 | AD-25954, AD-25955, AD-25953, AD-25905 |
| 2842 | UCGUAGUGUUAA | 2505 | UUAACACUACGA | 3900 | AD-25954, AD-25906, AD-25955, AD-25905 |
| 2843 | CGUAGUGUUAAG | 2506 | CUUAACACUACG | 3901 | AD-25907, AD-25906, AD-25955 |
| 2844 | GUAGUGUUAAGU | 2507 | ACUUAACACUAC | 3902 | AD-25907, AD-25906, AD-25955 |
| 2845 | UAGUGUUAAGUU | 2508 | AACUUAACACUA | 3903 | AD-25907, AD-25908, AD-25906, AD-25955, AD-25909 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 2846 | AGUGUUAAGUUA | 2509 | UAACUUAACACU | 3904 | AD-25907, AD-25908, AD-25956, AD-25906, AD-25955, AD-25909 |
| 2847 | GUGUUAAGUUAU | 2510 | AUAACUUAACAC | 3905 | AD-25907, AD-25908, AD-25956, AD-25957, AD-25906, AD-25955, AD-25909 |
| 2848 | UGUUAAGUUAUA | 2511 | UAUAACUUAACA | 3906 | AD-25907, AD-25908, AD-25956, AD-25957, AD-25906, AD-25909 |
| 2849 | GUUAAGUUAUAG | 2512 | CUAUAACUUAAC | 3907 | AD-25907, AD-25908, AD-25956, AD-25957, AD-25906, AD-25909 |
| 2850 | UUAAGUUAUAGU | 2513 | ACUAUAACUUAA | 3908 | AD-25907, AD-25956, AD-25957, AD-25909 |
| 2851 | UAAGUUAUAGUG | 2514 | CACUAUAACUUA | 3909 | AD-25908, AD-25956, AD-25957, AD-25909 |
| 2852 | AAGUUAUAGUGA | 2515 | UCACUAUAACUU | 3910 | AD-25956, AD-25957, AD-25909 |
| 2853 | AGUUAUAGUGAA | 2516 | UUCACUAUAACU | 3911 | AD-25956, AD-25957 |
| 2871 | UACAGCAAUUUC | 2517 | GAAAUUGCUGUA | 3912 | AD-26901, AD-25958 |
| 2872 | ACAGCAAUUUCU | 2518 | AGAAAUUGCUGU | 3913 | AD-26901, AD-25958 |
| 2873 | CAGCAAUUUCUA | 2519 | UAGAAAUUGCUG | 3914 | AD-26901, AD-25958 |
| 2874 | AGCAAUUUCUAA | 2520 | UUAGAAAUUGCU | 3915 | AD-26901, AD-25958 |
| 2875 | GCAAUUUCUAAU | 2521 | AUUAGAAAUUGC | 3916 | AD-26901, AD-25958 |
| 2876 | CAAUUUCUAAUU | 2522 | AAUUAGAAAUUG | 3917 | AD-26901, AD-25958 |
| 2877 | AAUUUCUAAUUU | 2523 | AAAUUAGAAAUU | 3918 | AD-26901, AD-25958 |
| 2901 | UAAUGGUGUAGA | 2524 | UCUACACCAUUA | 3919 | AD-18936, AD-19054 |
| 2902 | AAUGGUGUAGAA | 2525 | UUCUACACCAUU | 3920 | AD-18936, AD-19054 |
| 2903 | AUGGUGUAGAAC | 2526 | GUUCUACACCAU | 3921 | AD-18936, AD-19010, AD-19054 |
| 2904 | UGGUGUAGAACA | 2527 | UGUUCUACACCA | 3922 | AD-18936, AD-19009, AD-19010, AD-19054 |
| 2905 | GGUGUAGAACAC | 2528 | GUGUUCUACACC | 3923 | AD-18936, AD-19009, AD-18939, AD-19054 |
| 2906 | GUGUAGAACACU | 2529 | AGUGUUCUACAC | 3924 | AD-18966, AD-19009, AD-19010, AD-18939, AD-19054 |
| 2907 | UGUAGAACACUA | 2530 | UAGUGUUCUACA | 3925 | AD-18966, AD-19009, AD-18902, AD-19010, AD-18939, AD-19054 |
| 2908 | GUAGAACACUAA | 2531 | UUAGUGUUCUAC | 3926 | AD-18966, AD-19009, AD-18902, AD-19010, AD-18939, AD-19054, AD-19076 |
| 2909 | UAGAACACUAAU | 2532 | AUUAGUGUUCUA | 3927 | AD-18966, AD-19009, AD-18902, AD-19010, AD-18939, AD-19076 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 2910 | AGAACACUAAUU | 2533 | AAUUAGUGUUCU | 3928 | AD-18966, AD-19009, AD-19010, AD-18939, AD-19076 |
| 2911 | GAACACUAAUUC | 2534 | GAAUUAGUGUUC | 3929 | AD-18966, AD-18902, AD-18914, AD-18939, AD-19076 |
| 2912 | AACACUAAUUCA | 2535 | UGAAUUAGUGUU | 3930 | AD-18966, AD-18902, AD-18914, AD-25911, AD-19076 |
| 2913 | ACACUAAUUCAU | 2536 | AUGAAUUAGUGU | 3931 | AD-18966, AD-18902, AD-18914, AD-25912, AD-19076 |
| 2914 | CACUAAUUCAUA | 2537 | UAUGAAUUAGUG | 3932 | AD-18902, AD-18914, AD-25912, AD-25911, AD-26902 |
| 2915 | ACUAAUUCAUAA | 2538 | UUAUGAAUUAGU | 3933 | AD-18914, AD-25912, AD-25911, AD-26903, AD-26902, AD-19076 |
| 2916 | CUAAUUCAUAAU | 2539 | AUUAUGAAUUAG | 3934 | AD-18914, AD-25912, AD-25911, AD-26903, AD-26902 |
| 2917 | UAAUUCAUAAUC | 2540 | GAUUAUGAAUUA | 3935 | AD-26916, AD-25911, AD-26903, AD-26902, AD-26904 |
| 2918 | AAUUCAUAAUCA | 2541 | UGAUUAUGAAUU | 3936 | AD-26905, AD-26916, AD-18914, AD-25912, AD-25911, AD-26903, AD-26902, AD-26904 |
| 2919 | AUUCAUAAUCAC | 2542 | GUGAUUAUGAAU | 3937 | AD-26905, AD-26916, AD-25912, AD-25911, AD-26903, AD-26902, AD-26904 |
| 2920 | UUCAUAAUCACU | 2543 | AGUGAUUAUGAA | 3938 | AD-26905, AD-26916, AD-25912, AD-26903, AD-26902, AD-26904 |
| 2921 | UCAUAAUCACUC | 2544 | GAGUGAUUAUGA | 3939 | AD-26905, AD-26916, AD-26903, AD-26902, AD-26904 |
| 2922 | CAUAAUCACUCU | 2545 | AGAGUGAUUAUG | 3940 | AD-26905, AD-26916, AD-26903, AD-26904 |
| 2923 | AUAAUCACUCUA | 2546 | UAGAGUGAUUAU | 3941 | AD-26905, AD-26916, AD-26904 |
| 2924 | UAAUCACUCUAA | 2547 | UUAGAGUGAUUA | 3942 | AD-26905, AD-26904 |
| 2938 | AAUUGUAAUCUG | 2548 | CAGAUUACAAUU | 3943 | AD-25913, AD-26906 |
| 2939 | AUUGUAAUCUGA | 2549 | UCAGAUUACAAU | 3944 | AD-25913, AD-26906, AD-25914 |
| 2940 | UUGUAAUCUGAA | 2550 | UUCAGAUUACAA | 3945 | AD-25913, AD-26906, AD-25915, AD-25914 |
| 2941 | UGUAAUCUGAAU | 2551 | AUUCAGAUUACA | 3946 | AD-25916, AD-25913, AD-26906, AD-25915, AD-25914 |
| 2942 | GUAAUCUGAAUA | 2552 | UAUUCAGAUUAC | 3947 | AD-25916, AD-25913, AD-26906, AD-25914 |

TABLE 4-continued

Groups of overlapping RNAi agents to Beta-Catenin

| Position | Sense overlap | SEQ ID NO: Anti-sense overlap | SEQ ID NO: | Overlapping groups of RNAi agents |
|---|---|---|---|---|
| 2943 | UAAUCUGAAUAA | 2553 UUAUUCAGAUUA | 3948 | AD-26906, AD-25915, AD-25914 |
| 2944 | AAUCUGAAUAAA | 2554 UUUAUUCAGAUU | 3949 | AD-25916, AD-25913, AD-26906, AD-25915, AD-25914 |
| 2945 | AUCUGAAUAAAG | 2555 CUUUAUUCAGAU | 3950 | AD-25916, AD-26906, AD-25915, AD-25914 |
| 2946 | UCUGAAUAAAGU | 2556 ACUUUAUUCAGA | 3951 | AD-25916, AD-25915, AD-25914 |
| 2947 | CUGAAUAAAGUG | 2557 CACUUUAUUCAG | 3952 | AD-25916, AD-25915 |
| 2978 | UUGUAUAAAAUA | 2558 UAUUUUAUACAA | 3953 | AD-26908, AD-26907 |
| 2979 | UGUAUAAAAUAG | 2559 CUAUUUUAUACA | 3954 | AD-26908, AD-26907, AD-26909 |
| 2980 | GUAUAAAAUAGA | 2560 UCUAUUUUAUAC | 3955 | AD-26908, AD-26909 |
| 2981 | UAUAAAAUAGAC | 2561 GUCUAUUUUAUA | 3956 | AD-26908, AD-26910, AD-26907, AD-26909 |
| 2982 | AUAAAAUAGACA | 2562 UGUCUAUUUUAU | 3957 | AD-26910, AD-26911, AD-26907, AD-26909 |
| 2983 | UAAAAUAGACAA | 2563 UUGUCUAUUUUA | 3958 | AD-26908, AD-26910, AD-26911, AD-26907, AD-26909 |
| 2984 | AAAAUAGACAAA | 2564 UUUGUCUAUUUU | 3959 | AD-26908, AD-26910, AD-26912, AD-26911, AD-26907, AD-26909 |
| 2985 | AAAUAGACAAAU | 2565 AUUUGUCUAUUU | 3960 | AD-26908, AD-26912, AD-26911, AD-26913, AD-26909 |
| 2986 | AAUAGACAAAUA | 2566 UAUUUGUCUAUU | 3961 | AD-26910, AD-26912, AD-26911, AD-26913, AD-26909 |
| 2987 | AUAGACAAAUAG | 2567 CUAUUUGUCUAU | 3962 | AD-26910, AD-26912, AD-26911, AD-26913 |
| 2988 | UAGACAAAUAGA | 2568 UCUAUUUGUCUA | 3963 | AD-26912, AD-26911 |
| 2989 | AGACAAAUAGAA | 2569 UUCUAUUUGUCU | 3964 | AD-26912, AD-26911, AD-26913 |
| 2990 | GACAAAUAGAAA | 2570 UUUCUAUUUGUC | 3965 | AD-25917, AD-26913 |
| 2991 | ACAAAUAGAAAA | 2571 UUUUCUAUUUGU | 3966 | AD-26913, AD-25918 |
| 2992 | CAAAUAGAAAAU | 2572 AUUUUCUAUUUG | 3967 | AD-25917, AD-25959, AD-25918 |
| 2993 | AAAUAGAAAAUG | 2573 CAUUUUCUAUUU | 3968 | AD-25917, AD-25959, AD-26917, AD-25918 |
| 2994 | AAUAGAAAAUGG | 2574 CCAUUUUCUAUU | 3969 | AD-25917, AD-26918, AD-25959, AD-26917 |
| 2995 | AUAGAAAAUGGU | 2575 ACCAUUUUCUAU | 3970 | AD-25917, AD-26918, AD-25959, AD-26917, AD-25918, AD-25960 |
| 2996 | UAGAAAAUGGUC | 2576 GACCAUUUUCUA | 3971 | AD-25917, AD-26918, AD-25959, AD-26917, AD-25919, AD-25918, AD-25960 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 2997 | AGAAAAUGGUCC | 2577 | GGACCAUUUUCU | 3972 | AD-25917, AD-26918, AD-25920, AD-25959, AD-26917, AD-25919, AD-25918, AD-25960 |
| 2998 | GAAAAUGGUCCA | 2578 | UGGACCAUUUUC | 3973 | AD-26918, AD-25920, AD-25959, AD-26917, AD-25919, AD-25918, AD-25960 |
| 2999 | AAAAUGGUCCAA | 2579 | UUGGACCAUUUU | 3974 | AD-26918, AD-25920, AD-25959, AD-26917, AD-25919, AD-25960 |
| 3000 | AAAUGGUCCAAU | 2580 | AUUGGACCAUUU | 3975 | AD-26918, AD-25920, AD-26917, AD-25919, AD-25960 |
| 3001 | AAUGGUCCAAUU | 2581 | AAUUGGACCAUU | 3976 | AD-26918, AD-25920, AD-25919, AD-25960 |
| 3002 | AUGGUCCAAUUA | 2582 | UAAUUGGACCAU | 3977 | AD-25920, AD-25919, AD-25960 |
| 3003 | UGGUCCAAUUAG | 2583 | CUAAUUGGACCA | 3978 | AD-25920, AD-25919 |
| 3028 | AUGCUUAAAAUA | 2584 | UAUUUUAAGCAU | 3979 | AD-18985, AD-18992 |
| 3029 | UGCUUAAAAUAA | 2585 | UUAUUUUAAGCA | 3980 | AD-18985, AD-18992 |
| 3030 | GCUUAAAAUAAG | 2586 | CUUAUUUUAAGC | 3981 | AD-18985, AD-18992 |
| 3031 | CUUAAAAUAAGC | 2587 | GCUUAUUUUAAG | 3982 | AD-18985, AD-18992, AD-19081 |
| 3032 | UUAAAAUAAGCA | 2588 | UGCUUAUUUUAA | 3983 | AD-18985, AD-19081 |
| 3033 | UAAAAUAAGCAG | 2589 | CUGCUUAUUUUA | 3984 | AD-18985, AD-18992, AD-19081, AD-19044 |
| 3034 | AAAAUAAGCAGG | 2590 | CCUGCUUAUUUU | 3985 | AD-18985, AD-18992, AD-19081 |
| 3035 | AAAUAAGCAGGU | 2591 | ACCUGCUUAUUU | 3986 | AD-18985, AD-19044 |
| 3036 | AAUAAGCAGGUG | 2592 | CACCUGCUUAUU | 3987 | AD-18993, AD-19081, AD-19044 |
| 3037 | AUAAGCAGGUGG | 2593 | CCACCUGCUUAU | 3988 | AD-18993, AD-18894, AD-19081, AD-19044 |
| 3038 | UAAGCAGGUGGA | 2594 | UCCACCUGCUUA | 3989 | AD-19043, AD-18993, AD-18894, AD-19044 |
| 3039 | AAGCAGGUGGAU | 2595 | AUCCACCUGCUU | 3990 | AD-19043, AD-18956, AD-18993, AD-18894 |
| 3040 | AGCAGGUGGAUC | 2596 | GAUCCACCUGCU | 3991 | AD-19043, AD-18956, AD-18993, AD-18894, AD-19044, AD-18958 |
| 3041 | GCAGGUGGAUCU | 2597 | AGAUCCACCUGC | 3992 | AD-19043, AD-18956, AD-18993, AD-18894, AD-18958 |
| 3042 | CAGGUGGAUCUA | 2598 | UAGAUCCACCUG | 3993 | AD-19043, AD-18956, AD-18894, AD-18969, AD-18958, AD-19058 |
| 3043 | AGGUGGAUCUAU | 2599 | AUAGAUCCACCU | 3994 | AD-19069, AD-19043, AD-18956, AD-18993, AD-18894, AD-18969, AD-18958, AD-19058 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 3044 | GGUGGAUCUAUU | 2600 | AAUAGAUCCACC | 3995 | AD-19069, AD-19043, AD-18956, AD-18894, AD-18969, AD-18958, AD-19058 |
| 3045 | GUGGAUCUAUUU | 2601 | AAAUAGAUCCAC | 3996 | AD-19069, AD-19043, AD-18956, AD-18969, AD-18958, AD-19058 |
| 3046 | UGGAUCUAUUUC | 2602 | GAAAUAGAUCCA | 3997 | AD-19069, AD-18956, AD-18969, AD-18958, AD-19058 |
| 3047 | GGAUCUAUUUCA | 2603 | UGAAAUAGAUCC | 3998 | AD-19069, AD-18969, AD-18958, AD-19058 |
| 3048 | GAUCUAUUUCAU | 2604 | AUGAAAUAGAUC | 3999 | AD-19069, AD-18969, AD-19058 |
| 3049 | AUCUAUUUCAUG | 2605 | CAUGAAAUAGAU | 4000 | AD-19069, AD-19058 |
| 3077 | AUUUGGGAUAUG | 2606 | CAUAUCCCAAAU | 4001 | AD-25921, AD-25922 |
| 3078 | UUUGGGAUAUGU | 2607 | ACAUAUCCCAAA | 4002 | AD-25961, AD-25921, AD-25922 |
| 3079 | UUGGGAUAUGUA | 2608 | UACAUAUCCCAA | 4003 | AD-25961, AD-25923, AD-25921, AD-25922 |
| 3080 | UGGGAUAUGUAU | 2609 | AUACAUAUCCCA | 4004 | AD-25961, AD-25923, AD-26914, AD-25921, AD-25922 |
| 3081 | GGGAUAUGUAUG | 2610 | CAUACAUAUCCC | 4005 | AD-25961, AD-25923, AD-26915, AD-26914, AD-25921, AD-25922 |
| 3082 | GGAUAUGUAUGG | 2611 | CCAUACAUAUCC | 4006 | AD-25961, AD-25923, AD-25924, AD-26915, AD-26914, AD-25921, AD-25922 |
| 3083 | GAUAUGUAUGGG | 2612 | CCCAUACAUAUC | 4007 | AD-25961, AD-25923, AD-25924, AD-26915, AD-25962, AD-26914, AD-25921, AD-25922 |
| 3084 | AUAUGUAUGGGU | 2613 | ACCCAUACAUAU | 4008 | AD-25961, AD-25923, AD-25924, AD-26915, AD-25962, AD-26914, AD-25922 |
| 3085 | UAUGUAUGGGUA | 2614 | UACCCAUACAUA | 4009 | AD-25961, AD-25923, AD-25924, AD-26915, AD-25962, AD-26914 |
| 3086 | AUGUAUGGGUAG | 2615 | CUACCCAUACAU | 4010 | AD-25923, AD-25924, AD-26915, AD-25962, AD-26914 |
| 3087 | UGUAUGGGUAGG | 2616 | CCUACCCAUACA | 4011 | AD-25924, AD-26915, AD-25962, AD-26914 |
| 3088 | GUAUGGGUAGGG | 2617 | CCCUACCCAUAC | 4012 | AD-25924, AD-26915, AD-25962 |
| 3089 | UAUGGGUAGGGU | 2618 | ACCCUACCCAUA | 4013 | AD-25924, AD-25962 |
| 3093 | GGUAGGGUAAAU | 2619 | AUUUACCCUACC | 4014 | AD-18998, AD-25963 |
| 3094 | GUAGGGUAAAUC | 2620 | GAUUUACCCUAC | 4015 | AD-18998, AD-25963, AD-18995 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 3095 | UAGGGUAAAUCA | 2621 | UGAUUUACCCUA | 4016 | AD-18998, AD-25963, AD-18995 |
| 3096 | AGGGUAAAUCAG | 2622 | CUGAUUUACCCU | 4017 | AD-18998, AD-25963, AD-18995 |
| 3097 | GGGUAAAUCAGU | 2623 | ACUGAUUUACCC | 4018 | AD-18998, AD-25963, AD-18981, AD-18995 |
| 3098 | GGUAAAUCAGUA | 2624 | UACUGAUUUACC | 4019 | AD-18921, AD-18998, AD-25963, AD-18981, AD-18995 |
| 3099 | GUAAAUCAGUAA | 2625 | UUACUGAUUUAC | 4020 | AD-18921, AD-18998, AD-18981, AD-18995 |
| 3100 | UAAAUCAGUAAG | 2626 | CUUACUGAUUUA | 4021 | AD-18921, AD-18998, AD-18981, AD-19050, AD-18995 |
| 3101 | AAAUCAGUAAGA | 2627 | UCUUACUGAUUU | 4022 | AD-18921, AD-18968, AD-18981, AD-19050 |
| 3102 | AAUCAGUAAGAG | 2628 | CUCUUACUGAUU | 4023 | AD-18921, AD-18968, AD-18981, AD-19050, AD-19005 |
| 3103 | AUCAGUAAGAGG | 2629 | CCUCUUACUGAU | 4024 | AD-18921, AD-18968, AD-18981, AD-19050, AD-18903, AD-19005 |
| 3104 | UCAGUAAGAGGU | 2630 | ACCUCUUACUGA | 4025 | AD-18921, AD-18968, AD-18972, AD-18981, AD-19050, AD-18903, AD-19005 |
| 3105 | CAGUAAGAGGUG | 2631 | CACCUCUUACUG | 4026 | AD-18921, AD-18968, AD-18972, AD-19050, AD-18903, AD-19005 |
| 3106 | AGUAAGAGGUGU | 2632 | ACACCUCUUACU | 4027 | AD-18968, AD-19050, AD-18903, AD-19005 |
| 3107 | GUAAGAGGUGUU | 2633 | AACACCUCUUAC | 4028 | AD-18972, AD-19050, AD-18903, AD-19005 |
| 3108 | UAAGAGGUGUUA | 2634 | UAACACCUCUUA | 4029 | AD-18968, AD-18972, AD-18903, AD-25964, AD-19005 |
| 3109 | AAGAGGUGUUAU | 2635 | AUAACACCUCUU | 4030 | AD-18972, AD-18903, AD-25964, AD-19005 |
| 3110 | AGAGGUGUUAUU | 2636 | AAUAACACCUCU | 4031 | AD-18972, AD-18903, AD-25925, AD-25926, AD-25964 |
| 3111 | GAGGUGUUAUUU | 2637 | AAAUAACACCUC | 4032 | AD-25925, AD-25926, AD-25964 |
| 3112 | AGGUGUUAUUUG | 2638 | CAAAUAACACCU | 4033 | AD-25927, AD-25925, AD-25926, AD-25964 |
| 3113 | GGUGUUAUUUGG | 2639 | CCAAAUAACACC | 4034 | AD-25927, AD-25926, AD-25964 |
| 3114 | GUGUUAUUUGGA | 2640 | UCCAAAUAACAC | 4035 | AD-25927, AD-25925, AD-25926, AD-25964 |
| 3115 | UGUUAUUUGGAA | 2641 | UUCCAAAUAACA | 4036 | AD-25925, AD-25926, AD-25964 |

TABLE 4-continued

Groups of overlapping RNAi agents to Beta-Catenin

| Position | Sense overlap | SEQ ID NO: Anti-sense overlap | SEQ ID NO: | Overlapping groups of RNAi agents |
|---|---|---|---|---|
| 3116 | GUUAUUUGGAAC | 2642 GUUCCAAAUAAC | 4037 | AD-25927, AD-25925, AD-25926 |
| 3117 | UUAUUUGGAACC | 2643 GGUUCCAAAUAA | 4038 | AD-25927, AD-25926 |
| 3123 | GGAACCUUGUUU | 2644 AAACAAGGUUCC | 4039 | AD-25929, AD-25928 |
| 3124 | GAACCUUGUUUU | 2645 AAAACAAGGUUC | 4040 | AD-25930, AD-25928 |
| 3125 | AACCUUGUUUUG | 2646 CAAAACAAGGUU | 4041 | AD-25930, AD-25929, AD-25928 |
| 3126 | ACCUUGUUUUGG | 2647 CCAAAACAAGGU | 4042 | AD-25930, AD-25929 |
| 3127 | CCUUGUUUUGGA | 2648 UCCAAAACAAGG | 4043 | AD-25930, AD-25929, AD-25928 |
| 3128 | CUUGUUUUGGAC | 2649 GUCCAAAACAAG | 4044 | AD-25930, AD-25929, AD-25928 |
| 3129 | UUGUUUUGGACA | 2650 UGUCCAAAACAA | 4045 | AD-25929, AD-25928 |
| 3130 | UGUUUUGGACAG | 2651 CUGUCCAAAACA | 4046 | AD-25930, AD-25929 |
| 3131 | GUUUUGGACAGU | 2652 ACUGUCCAAAAC | 4047 | AD-25930, AD-25931 |
| 3132 | UUUUGGACAGUU | 2653 AACUGUCCAAAA | 4048 | AD-25932, AD-25931 |
| 3133 | UUUGGACAGUUU | 2654 AAACUGUCCAAA | 4049 | AD-25932, AD-26919, AD-25931 |
| 3134 | UUGGACAGUUUA | 2655 UAAACUGUCCAA | 4050 | AD-25933, AD-26919, AD-25931 |
| 3135 | UGGACAGUUUAC | 2656 GUAAACUGUCCA | 4051 | AD-25933, AD-25932, AD-26919, AD-25931 |
| 3136 | GGACAGUUUACC | 2657 GGUAAACUGUCC | 4052 | AD-25933, AD-25932, AD-25931 |
| 3137 | GACAGUUUACCA | 2658 UGGUAAACUGUC | 4053 | AD-25932, AD-26919, AD-25931 |
| 3138 | ACAGUUUACCAG | 2659 CUGGUAAACUGU | 4054 | AD-25933, AD-25932, AD-26919, AD-25931 |
| 3139 | CAGUUUACCAGU | 2660 ACUGGUAAACUG | 4055 | AD-25933, AD-25932, AD-26919 |
| 3140 | AGUUUACCAGUU | 2661 AACUGGUAAACU | 4056 | AD-25933, AD-26919 |
| 3145 | ACCAGUUGCCUU | 2662 AAGGCAACUGGU | 4057 | AD-18940, AD-18916 |
| 3146 | CCAGUUGCCUUU | 2663 AAAGGCAACUGG | 4058 | AD-18940, AD-18906, AD-18916 |
| 3147 | CAGUUGCCUUUU | 2664 AAAAGGCAACUG | 4059 | AD-18940, AD-18906, AD-18916 |
| 3148 | AGUUGCCUUUUA | 2665 UAAAAGGCAACU | 4060 | AD-18940, AD-19075, AD-18916 |
| 3149 | GUUGCCUUUUAU | 2666 AUAAAAGGCAAC | 4061 | AD-19075, AD-18906, AD-18916 |
| 3150 | UUGCCUUUUAUC | 2667 GAUAAAAGGCAA | 4062 | AD-18940, AD-19075, AD-18906, AD-18916 |
| 3151 | UGCCUUUUAUCC | 2668 GGAUAAAAGGCA | 4063 | AD-18940, AD-19075, AD-18906, AD-18916 |
| 3152 | GCCUUUUAUCCC | 2669 GGGAUAAAAGGC | 4064 | AD-18906, AD-18916 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 3153 | CCUUUUAUCCCA | 2670 | UGGGAUAAAAGG | 4065 | AD-26017, AD-19075, AD-18906, AD-18997 |
| 3154 | CUUUUAUCCCAA | 2671 | UUGGGAUAAAAG | 4066 | AD-26017, AD-19075, AD-18997 |
| 3155 | UUUUAUCCCAAA | 2672 | UUUGGGAUAAAA | 4067 | AD-26017, AD-18997 |
| 3156 | UUUAUCCCAAAG | 2673 | CUUUGGGAUAAA | 4068 | AD-26017, AD-18997 |
| 3157 | UUAUCCCAAAGU | 2674 | ACUUUGGGAUAA | 4069 | AD-26017, AD-18997 |
| 3158 | UAUCCCAAAGUU | 2675 | AACUUUGGGAUA | 4070 | AD-26017, AD-18997, AD-18988 |
| 3159 | AUCCCAAAGUUG | 2676 | CAACUUUGGGAU | 4071 | AD-18997, AD-18988 |
| 3160 | UCCCAAAGUUGU | 2677 | ACAACUUUGGGA | 4072 | AD-19067, AD-18997, AD-18988 |
| 3161 | CCCAAAGUUGUU | 2678 | AACAACUUUGGG | 4073 | AD-19067, AD-19083 |
| 3162 | CCAAAGUUGUUG | 2679 | CAACAACUUUGG | 4074 | AD-19083, AD-18988 |
| 3163 | CAAAGUUGUUGU | 2680 | ACAACAACUUUG | 4075 | AD-19067, AD-19083, AD-19049, AD-18988 |
| 3164 | AAAGUUGUUGUA | 2681 | UACAACAACUUU | 4076 | AD-19067, AD-19083, AD-18952, AD-19049, AD-18988 |
| 3165 | AAGUUGUUGUAA | 2682 | UUACAACAACUU | 4077 | AD-19067, AD-19083, AD-18957, AD-18952, AD-19049, AD-18988 |
| 3166 | AGUUGUUGUAAC | 2683 | GUUACAACAACU | 4078 | AD-19067, AD-19083, AD-18957, AD-18952, AD-19049 |
| 3167 | GUUGUUGUAACC | 2684 | GGUUACAACAAC | 4079 | AD-19067, AD-19083, AD-18957, AD-25934, AD-18952, AD-19049 |
| 3168 | UUGUUGUAACCU | 2685 | AGGUUACAACAA | 4080 | AD-19083, AD-18957, AD-25934, AD-18952, AD-25935, AD-19049 |
| 3169 | UGUUGUAACCUG | 2686 | CAGGUUACAACA | 4081 | AD-18957, AD-25934, AD-18952, AD-26018, AD-25935, AD-19049 |
| 3170 | GUUGUAACCUGC | 2687 | GCAGGUUACAAC | 4082 | AD-26019, AD-18957, AD-25934, AD-18952, AD-26018, AD-25935, AD-19049 |
| 3171 | UUGUAACCUGCU | 2688 | AGCAGGUUACAA | 4083 | AD-26019, AD-18957, AD-25936, AD-25934, AD-18952, AD-26018, AD-25935 |
| 3172 | UGUAACCUGCUG | 2689 | CAGCAGGUUACA | 4084 | AD-26019, AD-18957, AD-25936, AD-25934, AD-26018, AD-25935 |
| 3173 | GUAACCUGCUGU | 2690 | ACAGCAGGUUAC | 4085 | AD-26019, AD-25936, AD-25934, AD-26018 |
| 3174 | UAACCUGCUGUG | 2691 | CACAGCAGGUUA | 4086 | AD-26019, AD-25936, AD-25934, AD-26018, AD-25935 |
| 3175 | AACCUGCUGUGA | 2692 | UCACAGCAGGUU | 4087 | AD-26019, AD-25936, AD-26018, AD-25935 |

TABLE 4-continued

Groups of overlapping RNAi agents to Beta-Catenin

| Position | Sense overlap | SEQ ID NO: | Anti-sense overlap | SEQ ID NO: | Overlapping groups of RNAi agents |
|---|---|---|---|---|---|
| 3176 | ACCUGCUGUGAU | 2693 | AUCACAGCAGGU | 4088 | AD-26019, AD-25936, AD-26018 |
| 3177 | CCUGCUGUGAUA | 2694 | UAUCACAGCAGG | 4089 | AD-26019, AD-25936 |
| 3197 | CAAGAGAAAAUG | 2695 | CAUUUUCUCUUG | 4090 | AD-26020, AD-25937 |
| 3198 | AAGAGAAAAUGC | 2696 | GCAUUUUCUCUU | 4091 | AD-26020, AD-26021, AD-25937 |
| 3199 | AGAGAAAAUGCG | 2697 | CGCAUUUUCUCU | 4092 | AD-26020, AD-26021 |
| 3200 | GAGAAAAUGCGG | 2698 | CCGCAUUUUCUC | 4093 | AD-26020, AD-26021 |
| 3201 | AGAAAAUGCGGU | 2699 | ACCGCAUUUUCU | 4094 | AD-26020, AD-26021 |
| 3202 | GAAAAUGCGGUU | 2700 | AACCGCAUUUUC | 4095 | AD-26020, AD-26021 |
| 3203 | AAAAUGCGGUUA | 2701 | UAACCGCAUUUU | 4096 | AD-26020, AD-26021 |
| 3204 | AAAUGCGGUUAU | 2702 | AUAACCGCAUUU | 4097 | AD-26020, AD-26021 |
| 3220 | AAUGGUUCAGAA | 2703 | UUCUGAACCAUU | 4098 | AD-18960, AD-18987 |
| 3221 | AUGGUUCAGAAU | 2704 | AUUCUGAACCAU | 4099 | AD-18960, AD-18987, AD-19008 |
| 3222 | UGGUUCAGAAUU | 2705 | AAUUCUGAACCA | 4100 | AD-18960, AD-18987, AD-19008 |
| 3223 | GGUUCAGAAUUA | 2706 | UAAUUCUGAACC | 4101 | AD-18980, AD-18987, AD-19008 |
| 3224 | GUUCAGAAUUAA | 2707 | UUAAUUCUGAAC | 4102 | AD-18960, AD-18987, AD-19008 |
| 3225 | UUCAGAAUUAAA | 2708 | UUUAAUUCUGAA | 4103 | AD-18960, AD-18980, AD-19008 |
| 3226 | UCAGAAUUAAAC | 2709 | GUUUAAUUCUGA | 4104 | AD-18960, AD-18980, AD-18987, AD-19008 |
| 3227 | CAGAAUUAAACU | 2710 | AGUUUAAUUCUG | 4105 | AD-18980, AD-18987, AD-19008 |
| 3228 | AGAAUUAAACUU | 2711 | AAGUUUAAUUCU | 4106 | AD-18980, AD-19008 |
| 3229 | GAAUUAAACUUU | 2712 | AAAGUUUAAUUC | 4107 | AD-18980, AD-19007 |
| 3230 | AAUUAAACUUUU | 2713 | AAAAGUUUAAUU | 4108 | AD-18980, AD-19007 |

Example 2

Synthesis of Beta-Catenin RNAi Agent Sequences
Beta-Catenin RNAi Agent Sequence Selection
479 sense and 479 anti-sense CTNNB1-derived RNAi agent oligos listed herein are synthesized and formed into duplexes.
Synthesis of Beta-Catenin Sequences
Synthesis:
Beta-Catenin sequences are synthesized on MerMade 192 synthesizer at 1 µmol scale.
958 single strand sequences (corresponding to 479 RNAi agent duplexes) are synthesized for the human Beta-Catenin gene. For all the sequences, 'endolight' chemistry is applied as detailed below.
All pyrimidines (cytosine and uridine) in the sense strand are replaced with corresponding 2'-O-Methyl bases (2' O-Methyl C and 2'-O-Methyl U)

In the anti-sense strand, pyrimidines (C and U) adjacent to (towards 5' position) ribo A nucleoside are replaced with their corresponding 2-O-Methyl nucleosides
A two base dTdT extension at 3' end of both sense and anti-sense sequences is introduced. This two base overhang has a phosphodiester linkage
The sequence file is converted to a text file to make it compatible for loading in the MerMade 192 synthesis software
The synthesis of Beta-Catenin sequences uses solid supported oligonucleotide synthesis using phosphoramidite chemistry
The synthesis of the above sequences is performed at 1 µm scale in 96-well plates and 192 sequences are made per run. The amidite solutions are prepared at 0.1M concentration and ethyl thio tetrazole (0.6M in acetonitrile) is used as activator.

Cleavage and De-Protection:

The synthesized sequences are cleaved and de-protected in 96-well plates, using methylamine in the first step and triethylamine $^3$HF in the second step. The crude sequences thus obtained are precipitated using acetone: ethanol mix and the pellet is re-suspended in 0.02M sodium acetate buffer. Samples from each sequence are analyzed by LC-MS and the resulting mass data confirms the identity of the sequences. A selected set of samples are also analyzed by IEX chromatography.

Purification:

Next step in the process is purification. All sequences are purified on AKTA explorer purification system using Source 15Q column. Purification is performed using a column and in-line buffer heater set at 60° C. A single peak corresponding to the full length sequence is collected in the eluent and is subsequently analyzed for purity by ion exchange chromatography.

The purified sequences are desalted on a Sephadex G25 column using AKTA purifier. The desalted Beta-Catenin sequences are analyzed for concentration and purity. The single strands are then annealed to form RNAi agent duplexes. Each duplex is made at a concentration of 10 μM in 1×PBS.

A detailed list of Beta-Catenin single strands and duplexes are shown herein, in Example 1, above. The duplexes are used in in vitro screening to test their ability to knock down Beta-Catenin gene level, Example 3, below.

Example 3

In Vitro Screening of Beta-Catenin RNAi Agents
In Vitro Screening:

RNAi agents listed herein (Example 1) and synthesized as described in Example 2, are tested for activity in vitro.

Cell Culture and Transfections:

HeLa cells (ATCC, Manassas, Va.) are grown to near confluence at 37° C. in an atmosphere of 5% $CO_2$ in Eagle's Minimum Essential Medium (EMEM, ATCC) supplemented with 10% FBS, streptomycin, and glutamine (ATCC) before being released from the plate by trypsinization. Reverse transfection is carried out by adding 5 μl of Opti-MEM to 5 μl of RNAi agent duplexes per well into a 96-well plate along with 10 μl of Opti-MEM plus 0.2 μl of Lipofectamine RNAiMax per well (Invitrogen, Carlsbad, Calif. cat #13778-150) and incubated at room temperature for 15 minutes. For assays performed at 24 hours, 80 μl of complete growth media without antibiotic containing ~2×10$^4$ HeLa cells are then added to the RNAi agent mixture. For assays performed at 120 hours, 80 μl of complete growth media without antibiotic containing ~2×10$^4$ HeLa cells are then added to the RNAi agent mixture. Cells are incubated for either 24 or 48 hours prior to RNA purification. Single dose experiments are performed at 10 nM and in some cases 0.1 nM final duplex concentration and dose response experiments are done at 10, 1, 0.5, 0.1, 0.05, 0.01, 0.005, 0.001, 0.0005, 0.0001, 0.00005, 0.00001 nM final duplex concentration.

Total RNA Isolation Using MagMAX-96 Total RNA Isolation Kit (Applied Biosystem, Foster City Calif., Part #: AM1830):

Cells are harvested and lysed in 140 μl of Lysis/Binding Solution then mixed for 1 minute at 850 rpm using and Eppendorf Thermomixer (the mixing speed is the same throughout the process). Twenty micro liters of magnetic beads and Lysis/Binding Enhancer mixture are added into cell-lysate and mixed for 5 minutes. Magnetic beads are captured using magnetic stand and the supernatant is removed without disturbing the beads. After removing supernatant, magnetic beads are washed with Wash Solution 1 (isopropanol added) and mixed for 1 minute. Beads are captured again and supernatant removed. Beads are then washed with 150 μl Wash Solution 2 (Ethanol added), captured and supernatant is removed. 50 μl of DNase mixture (MagMax turbo DNase Buffer and Turbo DNase) is then added to the beads and they are mixed for 10 to 15 minutes. After mixing, 100 μl of RNA Rebinding Solution is added and mixed for 3 minutes. Supernatant is removed and magnetic beads are washed again with 150 μl Wash Solution 2 and mixed for 1 minute and supernatant is removed completely. The magnetic beads are mixed for 2 minutes to dry before RNA is eluted with 50 μl of water.

cDNA Synthesis Using ABI High Capacity cDNA Reverse Transcription Kit (Applied Biosystems, Foster City, Calif., Cat #4368813):

A master mix of 2 μl 10× Buffer, 0.8 μl 25× dNTPs, 2 μl Random primers, 1 μl Reverse Transcriptase, 1 μl RNase inhibitor and 3.2 μl of $H_2O$ per reaction are added into 10 μl total RNA. cDNA is generated using a Bio-Rad C-1000 or S-1000 thermal cycler (Hercules, Calif.) through the following steps: 25° C. 10 min, 37° C. 120 min, 85° C. 5 sec, 4° C. hold.

Real Time PCR:

2 μl of cDNA are added to a master mix containing 1 μl 18S TaqMan Probe (Applied Biosystems Cat #4319413E), 1 ul β-catenin TaqMan probe (Applied Biosystems cat # HS00170025_m1) and 10 μl TaqMan Universal PCR Master Mix (Applied Biosystems Cat #4324018) per well in a MicroAmp Optical 96 well plate (Applied Biosystems cat #4326659). Real time PCR is done in an ABI 7900HT Real Time PCR system (Applied Biosystems) using the ΔΔCt (RQ) assay. Each duplex is tested in two independent transfections and each transfections is assayed in duplicate, unless otherwise noted in the summary tables.

Real time data are analyzed using the ΔΔCt method and normalized to assays performed with cells transfected with 10 nM AD-1955 (a control RNAi agent that does not bind to Beta-Catenin) to calculate relative fold-change.

The results are shown below. Table 5 shows the results of experiments performed at 0.1 or 10 nM final duplex concentration for single dose screens with each of the Beta-Catenin duplexes. The "Residual Gene Activity" (Fold-Change) indicates the residual gene level, at 10 nm or 0.1 nM. Thus, for AD-18892, a "Residual Gene Activity" at 10 nM at 24 hr of 0.054 indicates 5.4% remaining gene activity, or 94.6% gene knock-down. The Avg. EC50 (nM) indicates the estimated EC50 (concentration estimated to give 50% gene knock-down in HeLa cells), as calculated from available data collected at 10 nM, 1 nM, 0.1 nM, 0.01 nM, and 0.001 nM. "NA" indicates data is not available.

TABLE 5

Analysis of RNAi agents to Beta-Catenin

| Duplex | Sense SEQ ID NO: | Anti-sense SEQ ID NO: | Residual Gene Activity 10 nM 24 hr | Residual Gene Activity 0.1 nM 120 hr | Avg. EC50 (nM) |
|---|---|---|---|---|---|
| AD-18892 | 1 | 6497 | 0.054 | 0.47 | NA |
| AD-18893 | 2 | 661 | 0.026 | NA | 0.008 |
| AD-18894 | 3 | 662 | 0.068 | NA | 0.005 |
| AD-18895 | 4 | 663 | 0.466 | NA | NA |
| AD-18896 | 5 | 664 | 0.244 | NA | NA |
| AD-18897 | 6 | 665 | 0.054 | NA | 0.028 |
| AD-18898 | 7 | 666 | 0.903 | NA | NA |
| AD-18899 | 8 | 667 | 0.301 | NA | NA |

TABLE 5-continued

Analysis of RNAi agents to Beta-Catenin

| Duplex | Sense SEQ ID NO: | Anti-sense SEQ ID NO: | Residual Gene Activity 10 nM 24 hr | Residual Gene Activity 0.1 nM 120 hr | Avg. EC50 (nM) |
|---|---|---|---|---|---|
| AD-18900 | 9 | 668 | 1.157 | NA | NA |
| AD-18901 | 10 | 669 | 0.359 | NA | NA |
| AD-18902 | 11 | 670 | 0.058 | NA | 0.005 |
| AD-18903 | 12 | 671 | 0.052 | NA | 0.002 |
| AD-18904 | 13 | 672 | 0.690 | NA | NA |
| AD-18905 | 14 | 673 | 0.198 | NA | 1.260 |
| AD-18906 | 15 | 674 | 0.248 | NA | NA |
| AD-18907 | 16 | 675 | 0.379 | NA | NA |
| AD-18908 | 17 | 676 | 0.157 | NA | NA |
| AD-18909 | 18 | 677 | 0.441 | NA | NA |
| AD-18910 | 19 | 678 | 0.385 | NA | NA |
| AD-18911 | 20 | 679 | 0.186 | NA | 1.664 |
| AD-18912 | 21 | 680 | 0.221 | NA | NA |
| AD-18913 | 22 | 681 | 0.124 | NA | 0.018 |
| AD-18914 | 23 | 682 | 0.058 | NA | 0.002 |
| AD-18915 | 24 | 683 | 0.242 | NA | NA |
| AD-18916 | 25 | 684 | 0.530 | NA | NA |
| AD-18917 | 26 | 685 | 0.527 | 0.66 | NA |
| AD-18918 | 27 | 686 | 1.161 | NA | NA |
| AD-18919 | 28 | 687 | 0.387 | NA | NA |
| AD-18920 | 29 | 688 | 1.124 | NA | NA |
| AD-18921 | 30 | 689 | 0.752 | NA | NA |
| AD-18922 | 31 | 690 | 0.587 | NA | NA |
| AD-18923 | 32 | 691 | 0.773 | NA | NA |
| AD-18925 | 33 | 692 | 0.738 | NA | NA |
| AD-18926 | 34 | 693 | 0.193 | NA | 0.033 |
| AD-18927 | 35 | 694 | 0.091 | NA | 0.764 |
| AD-18928 | 36 | 695 | 0.228 | NA | NA |
| AD-18929 | 37 | 696 | 0.069 | NA | NA |
| AD-18930 | 38 | 697 | 0.428 | NA | NA |
| AD-18931 | 39 | 698 | 1.195 | NA | NA |
| AD-18932 | 40 | 699 | 0.876 | NA | NA |
| AD-18933 | 41 | 700 | 0.047 | NA | 0.001 |
| AD-18934 | 42 | 701 | 0.651 | NA | NA |
| AD-18935 | 43 | 702 | 0.419 | NA | NA |
| AD-18936 | 44 | 703 | 0.125 | NA | 0.158 |
| AD-18937 | 45 | 704 | 0.839 | NA | NA |
| AD-18938 | 46 | 705 | 0.436 | NA | NA |
| AD-18939 | 47 | 706 | 0.068 | NA | 0.011 |
| AD-18940 | 48 | 707 | 0.515 | NA | NA |
| AD-18941 | 49 | 708 | 0.421 | NA | NA |
| AD-18942 | 50 | 709 | 1.397 | NA | NA |
| AD-18943 | 51 | 710 | 0.990 | NA | NA |
| AD-18944 | 52 | 711 | 0.550 | NA | NA |
| AD-18945 | 53 | 712 | 0.193 | NA | 0.780 |
| AD-18946 | 54 | 713 | 0.086 | 0.47 | NA |
| AD-18947 | 55 | 714 | 0.397 | NA | NA |
| AD-18948 | 56 | 715 | 0.885 | NA | NA |
| AD-18949 | 57 | 716 | 0.863 | NA | NA |
| AD-18950 | 58 | 717 | 0.103 | NA | 0.145 |
| AD-18951 | 59 | 718 | 0.184 | NA | 0.519 |
| AD-18952 | 60 | 719 | 0.382 | NA | NA |
| AD-18953 | 61 | 720 | 1.349 | NA | NA |
| AD-18954 | 62 | 721 | 0.766 | NA | NA |
| AD-18955 | 63 | 722 | 0.649 | 0.64 | NA |
| AD-18956 | 64 | 723 | 0.240 | NA | NA |
| AD-18957 | 65 | 724 | 1.198 | NA | NA |
| AD-18958 | 66 | 725 | 0.083 | NA | 0.012 |
| AD-18959 | 67 | 726 | 0.713 | NA | NA |
| AD-18960 | 68 | 727 | 0.188 | NA | 0.310 |
| AD-18961 | 69 | 728 | 0.105 | NA | 0.209 |
| AD-18962 | 70 | 729 | 0.942 | NA | NA |
| AD-18963 | 71 | 730 | 0.037 | 0.37 | 0.049 |
| AD-18964 | 72 | 731 | 0.907 | NA | NA |
| AD-18965 | 73 | 732 | 0.440 | 0.48 | NA |
| AD-18966 | 74 | 733 | 0.042 | NA | 0.000 |
| AD-18967 | 75 | 734 | 0.695 | NA | NA |
| AD-18968 | 76 | 735 | 0.158 | NA | 0.134 |
| AD-18969 | 77 | 736 | 0.073 | NA | 0.004 |
| AD-18970 | 78 | 737 | 0.810 | NA | NA |
| AD-18971 | 79 | 738 | 0.336 | NA | NA |
| AD-18972 | 80 | 739 | 0.332 | NA | NA |
| AD-18973 | 81 | 740 | 0.707 | NA | NA |
| AD-18974 | 82 | 741 | 0.038 | NA | 0.007 |
| AD-18975 | 83 | 742 | 0.184 | 0.73 | NA |
| AD-18976 | 84 | 743 | 0.094 | NA | 0.118 |
| AD-18977 | 85 | 744 | 0.965 | NA | NA |
| AD-18978 | 86 | 745 | 0.848 | NA | NA |
| AD-18979 | 87 | 746 | 0.375 | NA | NA |
| AD-18980 | 88 | 747 | 0.052 | NA | NA |
| AD-18981 | 89 | 748 | 0.090 | NA | 0.004 |
| AD-18982 | 90 | 749 | 0.156 | NA | 0.156 |
| AD-18983 | 91 | 750 | 0.026 | 0.23 | 0.070 |
| AD-18984 | 92 | 751 | 0.913 | NA | NA |
| AD-18985 | 93 | 752 | 0.578 | NA | NA |
| AD-18986 | 94 | 753 | 0.073 | NA | 0.003 |
| AD-18987 | 95 | 754 | 0.626 | NA | NA |
| AD-18988 | 96 | 755 | 0.379 | NA | NA |
| AD-18989 | 97 | 756 | 0.879 | NA | NA |
| AD-18990 | 98 | 757 | 0.299 | NA | NA |
| AD-18991 | 99 | 758 | 0.112 | NA | 0.454 |
| AD-18992 | 100 | 759 | 1.171 | NA | NA |
| AD-18993 | 101 | 760 | 0.802 | NA | NA |
| AD-18994 | 102 | 761 | 0.071 | NA | 0.313 |
| AD-18995 | 103 | 762 | 0.096 | NA | 0.006 |
| AD-18996 | 104 | 763 | 0.450 | NA | NA |
| AD-18997 | 105 | 764 | 0.226 | NA | NA |
| AD-18998 | 106 | 765 | 0.279 | NA | NA |
| AD-18999 | 107 | 766 | 0.337 | NA | NA |
| AD-19000 | 108 | 767 | 0.134 | NA | 0.347 |
| AD-19001 | 109 | 768 | 0.470 | 0.71 | NA |
| AD-19002 | 110 | 769 | 0.619 | NA | NA |
| AD-19003 | 111 | 770 | 0.610 | NA | NA |
| AD-19004 | 112 | 771 | 0.066 | NA | 0.007 |
| AD-19005 | 113 | 772 | 0.274 | NA | NA |
| AD-19006 | 114 | 773 | 0.139 | NA | 0.994 |
| AD-19007 | 115 | 774 | 0.655 | NA | NA |
| AD-19008 | 116 | 775 | 0.088 | NA | 0.001 |
| AD-19009 | 117 | 776 | 0.066 | NA | 0.000 |
| AD-19010 | 118 | 111 | 0.227 | NA | NA |
| AD-19011 | 119 | 778 | 0.721 | NA | NA |
| AD-19012 | 120 | 779 | 0.175 | NA | 0.181 |
| AD-19042 | 121 | 780 | 0.283 | NA | NA |
| AD-19043 | 122 | 781 | 0.131 | NA | 0.006 |
| AD-19044 | 123 | 782 | 0.333 | NA | NA |
| AD-19045 | 124 | 783 | 0.553 | NA | NA |
| AD-19046 | 125 | 784 | 0.947 | NA | NA |
| AD-19047 | 126 | 785 | 0.774 | NA | NA |
| AD-19048 | 127 | 786 | 0.838 | NA | NA |
| AD-19049 | 128 | 787 | 0.938 | NA | NA |
| AD-19050 | 129 | 788 | 0.070 | NA | 0.001 |
| AD-19051 | 130 | 789 | 0.551 | NA | NA |
| AD-19052 | 131 | 790 | 0.818 | NA | NA |
| AD-19053 | 132 | 791 | 0.364 | NA | NA |
| AD-19054 | 133 | 792 | 0.075 | NA | 0.002 |
| AD-19055 | 134 | 793 | 0.210 | NA | NA |
| AD-19056 | 135 | 794 | 0.085 | NA | 0.019 |
| AD-19057 | 136 | 795 | 0.599 | NA | NA |
| AD-19058 | 137 | 796 | 0.577 | NA | NA |
| AD-19059 | 138 | 797 | 0.728 | NA | NA |
| AD-19060 | 139 | 798 | 1.072 | NA | NA |
| AD-19061 | 140 | 799 | 0.885 | NA | NA |
| AD-19062 | 141 | 800 | 0.810 | NA | NA |
| AD-19063 | 142 | 801 | 0.741 | NA | NA |
| AD-19064 | 143 | 802 | 0.591 | NA | NA |
| AD-19065 | 144 | 803 | 0.323 | NA | NA |
| AD-19066 | 145 | 804 | 0.086 | 0.48 | NA |
| AD-19067 | 146 | 805 | 0.138 | NA | NA |
| AD-19068 | 147 | 806 | 0.321 | NA | NA |
| AD-19069 | 148 | 807 | 0.135 | NA | 1.403 |
| AD-19070 | 149 | 808 | 0.892 | NA | NA |
| AD-19071 | 150 | 809 | 0.658 | NA | NA |
| AD-19072 | 151 | 810 | 0.704 | NA | NA |
| AD-19073 | 152 | 811 | 0.838 | NA | NA |
| AD-19074 | 153 | 812 | 0.042 | NA | 0.008 |
| AD-19075 | 154 | 813 | 0.841 | NA | NA |
| AD-19076 | 155 | 814 | 0.037 | NA | 0.002 |
| AD-19077 | 156 | 815 | 0.226 | NA | NA |

TABLE 5-continued

Analysis of RNAi agents to Beta-Catenin

| Duplex | Sense SEQ ID NO: | Anti-sense SEQ ID NO: | Residual Gene Activity 10 nM 24 hr | Residual Gene Activity 0.1 nM 120 hr | Avg. EC50 (nM) |
|---|---|---|---|---|---|
| AD-19078 | 157 | 816 | 0.719 | NA | NA |
| AD-19079 | 158 | 817 | 0.545 | NA | NA |
| AD-19080 | 159 | 818 | 0.092 | NA | 0.172 |
| AD-19081 | 160 | 819 | 0.203 | NA | 8.936 |
| AD-19082 | 161 | 820 | 0.055 | NA | 0.090 |
| AD-19083 | 162 | 821 | 0.404 | NA | NA |
| AD-19738 | 163 | 822 | 1.361 | NA | NA |
| AD-19739 | 164 | 823 | 0.970 | NA | NA |
| AD-19740 | 165 | 824 | 0.679 | NA | NA |
| AD-19741 | 166 | 825 | 0.168 | NA | NA |
| AD-19742 | 167 | 826 | 0.958 | NA | NA |
| AD-19743 | 168 | 827 | 0.839 | NA | NA |
| AD-19744 | 169 | 828 | 0.978 | NA | NA |
| AD-19745 | 170 | 829 | 0.852 | NA | NA |
| AD-19746 | 171 | 830 | 0.086 | NA | NA |
| AD-19747 | 172 | 831 | 0.187 | NA | NA |
| AD-19748 | 173 | 832 | 0.794 | NA | NA |
| AD-19749 | 174 | 833 | 0.115 | NA | NA |
| AD-19750 | 175 | 834 | 0.317 | NA | NA |
| AD-19751 | 176 | 835 | 0.591 | NA | NA |
| AD-19752 | 177 | 836 | 0.089 | NA | NA |
| AD-19753 | 178 | 837 | 0.091 | NA | NA |
| AD-19754 | 179 | 838 | 0.756 | NA | NA |
| AD-19755 | 180 | 839 | 0.443 | NA | NA |
| AD-19756 | 181 | 840 | 0.529 | NA | NA |
| AD-19757 | 182 | 841 | 0.265 | NA | NA |
| AD-19758 | 183 | 842 | 0.139 | NA | NA |
| AD-19759 | 184 | 843 | 0.465 | NA | NA |
| AD-19760 | 185 | 844 | 0.213 | NA | NA |
| AD-19761 | 186 | 845 | 1.234 | NA | NA |
| AD-19762 | 187 | 846 | 0.085 | NA | NA |
| AD-19763 | 188 | 847 | 0.593 | NA | NA |
| AD-19765 | 189 | 848 | 0.031 | NA | NA |
| AD-19766 | 190 | 849 | 0.469 | NA | NA |
| AD-19767 | 191 | 850 | 0.587 | NA | NA |
| AD-19768 | 192 | 851 | 0.780 | NA | NA |
| AD-20124 | 193 | 852 | 0.123 | 0.44 | NA |
| AD-25889 | 194 | 853 | 0.605 | 0.73 | NA |
| AD-25890 | 195 | 854 | 0.034 | 0.49 | 0.050 |
| AD-25891 | 196 | 855 | 0.041 | 0.16 | 0.050 |
| AD-25892 | 197 | 856 | 0.099 | 0.34 | NA |
| AD-25893 | 198 | 857 | 0.062 | 0.23 | 0.040 |
| AD-25894 | 199 | 858 | 0.033 | 0.13 | 0.004 |
| AD-25895 | 200 | 859 | 0.113 | 0.60 | NA |
| AD-25896 | 201 | 860 | 0.276 | 0.74 | NA |
| AD-25897 | 202 | 861 | 0.213 | 0.82 | NA |
| AD-25898 | 203 | 862 | 0.127 | 0.79 | NA |
| AD-25899 | 204 | 863 | 0.729 | 0.61 | NA |
| AD-25900 | 205 | 864 | 0.094 | 0.64 | NA |
| AD-25901 | 206 | 865 | 0.842 | 0.91 | NA |
| AD-25902 | 207 | 866 | 0.054 | 0.24 | NA |
| AD-25903 | 208 | 867 | 0.646 | 0.96 | NA |
| AD-25904 | 209 | 868 | 0.681 | 0.83 | NA |
| AD-25905 | 210 | 869 | 0.680 | 1.61 | NA |
| AD-25906 | 211 | 870 | 0.413 | 0.96 | NA |
| AD-25907 | 212 | 871 | 0.091 | 0.90 | NA |
| AD-25908 | 213 | 872 | 0.355 | 0.72 | NA |
| AD-25909 | 214 | 873 | 0.189 | 0.76 | NA |
| AD-25910 | 215 | 874 | 0.048 | 0.48 | 0.070 |
| AD-25911 | 216 | 875 | 0.134 | 0.81 | NA |
| AD-25912 | 217 | 876 | 0.095 | 0.66 | NA |
| AD-25913 | 218 | 877 | 0.291 | 0.94 | NA |
| AD-25914 | 219 | 878 | 0.057 | 0.47 | 0.054 |
| AD-25915 | 220 | 879 | 0.453 | 0.79 | NA |
| AD-25916 | 221 | 880 | 0.219 | 0.79 | NA |
| AD-25917 | 222 | 881 | 0.143 | 0.73 | NA |
| AD-25918 | 223 | 882 | 0.075 | 0.29 | 0.013 |
| AD-25919 | 224 | 883 | 0.123 | 0.68 | NA |
| AD-25920 | 225 | 884 | 0.255 | 0.69 | NA |
| AD-25921 | 226 | 885 | 0.637 | 0.81 | NA |
| AD-25922 | 227 | 886 | 0.283 | 0.83 | NA |
| AD-25923 | 228 | 887 | 0.575 | 0.64 | NA |
| AD-25924 | 229 | 888 | 0.118 | 0.52 | NA |
| AD-25925 | 230 | 889 | 0.242 | 0.96 | NA |
| AD-25926 | 231 | 890 | 0.150 | 0.67 | NA |
| AD-25927 | 232 | 891 | 0.394 | 0.72 | NA |
| AD-25928 | 233 | 892 | 0.138 | 0.62 | NA |
| AD-25929 | 234 | 893 | 0.073 | 0.50 | NA |
| AD-25930 | 235 | 894 | 0.095 | 0.71 | NA |
| AD-25931 | 236 | 895 | 0.076 | 0.77 | NA |
| AD-25932 | 237 | 896 | 0.073 | 0.61 | NA |
| AD-25933 | 238 | 897 | 0.113 | 0.79 | NA |
| AD-25934 | 239 | 898 | 0.223 | 0.46 | NA |
| AD-25935 | 240 | 899 | 0.288 | 0.78 | NA |
| AD-25936 | 241 | 900 | 0.413 | 0.78 | NA |
| AD-25937 | 242 | 901 | 0.838 | 0.77 | NA |
| AD-25938 | 243 | 902 | 0.038 | 0.08 | 0.006 |
| AD-25939 | 244 | 903 | 0.078 | 0.21 | NA |
| AD-25940 | 245 | 904 | 0.063 | 0.31 | NA |
| AD-25941 | 246 | 905 | 0.025 | 0.19 | 0.008 |
| AD-25942 | 247 | 906 | 0.029 | 0.20 | 0.016 |
| AD-25943 | 248 | 907 | 0.037 | 0.44 | 0.080 |
| AD-25944 | 249 | 908 | 0.038 | 0.23 | 0.007 |
| AD-25945 | 250 | 909 | 0.045 | 0.26 | NA |
| AD-25946 | 251 | 910 | 0.107 | 0.46 | NA |
| AD-25947 | 252 | 911 | 0.100 | 0.72 | NA |
| AD-25948 | 253 | 912 | 0.159 | 0.33 | NA |
| AD-25949 | 254 | 913 | 0.104 | 0.39 | NA |
| AD-25950 | 255 | 914 | 0.026 | 0.26 | 0.010 |
| AD-25951 | 256 | 915 | 0.026 | 0.28 | 0.007 |
| AD-25952 | 257 | 916 | 0.349 | 0.80 | NA |
| AD-25953 | 258 | 917 | 0.120 | 0.65 | NA |
| AD-25954 | 259 | 918 | 0.550 | 0.92 | NA |
| AD-25955 | 260 | 919 | 0.067 | 0.53 | NA |
| AD-25956 | 261 | 920 | 0.039 | 0.40 | 0.042 |
| AD-25957 | 262 | 921 | 0.105 | 0.64 | NA |
| AD-25958 | 263 | 922 | 0.044 | 0.38 | 0.024 |
| AD-25959 | 264 | 923 | 0.169 | 0.59 | NA |
| AD-25960 | 265 | 924 | 0.060 | 0.37 | 0.044 |
| AD-25961 | 266 | 925 | 0.162 | 0.67 | NA |
| AD-25962 | 267 | 926 | 0.684 | 0.76 | NA |
| AD-25963 | 268 | 927 | 0.106 | 0.48 | 0.275 |
| AD-25964 | 269 | 928 | 0.033 | 0.47 | 0.050 |
| AD-26017 | 270 | 929 | 0.113 | 0.87 | NA |
| AD-26018 | 271 | 930 | 0.060 | 0.37 | NA |
| AD-26019 | 272 | 931 | 0.106 | 0.42 | NA |
| AD-26020 | 273 | 932 | 0.043 | 0.50 | NA |
| AD-26021 | 274 | 933 | 0.046 | 0.69 | NA |
| AD-26022 | 275 | 934 | 0.109 | 0.83 | NA |
| AD-26023 | 276 | 935 | 0.637 | 0.80 | NA |
| AD-26024 | 277 | 936 | 0.226 | 0.73 | NA |
| AD-26025 | 278 | 937 | 0.252 | 0.96 | NA |
| AD-26026 | 279 | 938 | 0.088 | 0.58 | NA |
| AD-26027 | 280 | 939 | 0.228 | 0.96 | NA |
| AD-26028 | 281 | 940 | 0.025 | 0.28 | 0.050 |
| AD-26029 | 282 | 941 | 0.067 | 0.76 | NA |
| AD-26030 | 283 | 942 | 0.275 | 0.52 | NA |
| AD-26031 | 284 | 943 | 0.030 | 0.25 | 0.012 |
| AD-26032 | 285 | 944 | 0.078 | 0.50 | NA |
| AD-26033 | 286 | 945 | 0.353 | 0.69 | NA |
| AD-26034 | 287 | 946 | 0.022 | 0.16 | 0.009 |
| AD-26035 | 288 | 947 | 0.106 | 0.36 | NA |
| AD-26036 | 289 | 948 | 0.336 | 0.63 | NA |
| AD-26037 | 290 | 949 | 0.136 | 0.45 | NA |
| AD-26038 | 291 | 950 | 0.215 | 0.46 | NA |
| AD-26039 | 292 | 951 | 0.591 | 0.69 | NA |
| AD-26040 | 293 | 952 | 0.046 | 0.15 | 0.099 |
| AD-26041 | 294 | 953 | 0.324 | 0.67 | NA |
| AD-26042 | 295 | 954 | 0.026 | 0.38 | 0.010 |
| AD-26043 | 296 | 955 | 0.026 | 0.09 | 0.075 |
| AD-26044 | 297 | 956 | 0.034 | 0.37 | NA |
| AD-26045 | 298 | 957 | 0.531 | 0.77 | NA |
| AD-26046 | 299 | 958 | 0.531 | 0.58 | NA |
| AD-26047 | 300 | 959 | 0.023 | 0.47 | 0.058 |
| AD-26048 | 301 | 960 | 0.397 | 0.95 | NA |
| AD-26049 | 302 | 961 | 0.212 | 0.65 | NA |
| AD-26050 | 303 | 962 | 0.204 | 0.95 | NA |
| AD-26051 | 304 | 963 | 0.619 | 0.57 | NA |

TABLE 5-continued

Analysis of RNAi agents to Beta-Catenin

| Duplex | Sense SEQ ID NO: | Anti-sense SEQ ID NO: | Residual Gene Activity 10 nM 24 hr | Residual Gene Activity 0.1 nM 120 hr | Avg. EC50 (nM) |
|---|---|---|---|---|---|
| AD-26052 | 305 | 964 | 0.037 | 0.55 | NA |
| AD-26053 | 306 | 965 | 0.369 | 0.71 | NA |
| AD-26054 | 307 | 966 | 0.616 | 0.78 | NA |
| AD-26055 | 308 | 967 | 0.424 | 0.64 | NA |
| AD-26056 | 309 | 968 | 0.168 | 0.81 | NA |
| AD-26057 | 310 | 969 | 0.086 | 0.28 | NA |
| AD-26058 | 311 | 970 | 0.456 | 0.67 | NA |
| AD-26059 | 312 | 971 | 0.169 | 0.47 | NA |
| AD-26060 | 313 | 972 | 0.057 | 0.19 | 0.139 |
| AD-26061 | 314 | 973 | 0.050 | 0.42 | NA |
| AD-26062 | 315 | 974 | 0.110 | 0.64 | NA |
| AD-26063 | 316 | 975 | 0.021 | 0.74 | NA |
| AD-26064 | 317 | 976 | 0.785 | 0.62 | NA |
| AD-26065 | 318 | 977 | 0.678 | 0.84 | NA |
| AD-26066 | 319 | 978 | 0.035 | 0.44 | NA |
| AD-26067 | 320 | 979 | 0.305 | 0.51 | NA |
| AD-26068 | 321 | 980 | 0.028 | 0.50 | 0.102 |
| AD-26069 | 322 | 981 | 0.046 | 0.50 | NA |
| AD-26070 | 323 | 982 | 0.446 | 0.64 | NA |
| AD-26071 | 324 | 983 | 0.074 | 0.48 | NA |
| AD-26072 | 325 | 984 | 0.742 | 0.84 | NA |
| AD-26073 | 326 | 985 | 0.086 | 0.33 | NA |
| AD-26074 | 327 | 986 | 0.227 | 0.55 | NA |
| AD-26075 | 328 | 987 | 0.092 | 0.74 | NA |
| AD-26076 | 329 | 988 | 0.029 | 0.24 | 0.159 |
| AD-26077 | 330 | 989 | 0.191 | 0.70 | NA |
| AD-26078 | 331 | 990 | 0.032 | 0.32 | 0.106 |
| AD-26079 | 332 | 991 | 0.131 | 0.55 | NA |
| AD-26080 | 333 | 992 | 0.589 | 0.86 | NA |
| AD-26081 | 334 | 993 | 0.538 | 0.66 | NA |
| AD-26082 | 335 | 994 | 0.021 | 0.42 | 0.039 |
| AD-26083 | 336 | 995 | 0.049 | 0.25 | NA |
| AD-26084 | 337 | 996 | 0.334 | 0.75 | NA |
| AD-26085 | 338 | 997 | 0.192 | 0.69 | NA |
| AD-26086 | 339 | 998 | 0.524 | 0.62 | NA |
| AD-26087 | 340 | 999 | 0.276 | 0.71 | NA |
| AD-26088 | 341 | 1000 | 0.101 | 0.83 | NA |
| AD-26089 | 342 | 1001 | 0.821 | 0.93 | NA |
| AD-26090 | 343 | 1002 | 0.367 | 0.77 | NA |
| AD-26091 | 344 | 1003 | 0.022 | 0.32 | 0.057 |
| AD-26092 | 345 | 1004 | 0.246 | 0.75 | NA |
| AD-26093 | 346 | 1005 | 0.570 | 0.70 | NA |
| AD-26094 | 347 | 1006 | 0.145 | 0.57 | NA |
| AD-26095 | 348 | 1007 | 0.073 | 0.58 | NA |
| AD-26096 | 349 | 1008 | 0.109 | 0.51 | NA |
| AD-26097 | 350 | 1009 | 0.145 | 0.57 | NA |
| AD-26098 | 351 | 1010 | 0.101 | 0.43 | NA |
| AD-26099 | 352 | 1011 | 0.171 | 0.68 | NA |
| AD-26100 | 353 | 1012 | 0.058 | 0.21 | NA |
| AD-26101 | 354 | 1013 | 0.041 | 0.30 | 0.030 |
| AD-26102 | 355 | 1014 | 0.169 | 0.93 | NA |
| AD-26103 | 356 | 1015 | 0.209 | 0.61 | NA |
| AD-26104 | 357 | 1016 | 0.016 | 0.22 | 0.058 |
| AD-26105 | 358 | 1017 | 0.044 | 0.49 | NA |
| AD-26106 | 359 | 1018 | 0.169 | 0.75 | NA |
| AD-26107 | 360 | 1019 | 0.290 | 0.90 | NA |
| AD-26108 | 361 | 1020 | 0.040 | 0.50 | 0.030 |
| AD-26109 | 362 | 1021 | 0.024 | 0.22 | 0.025 |
| AD-26110 | 363 | 1022 | 0.326 | 0.79 | NA |
| AD-26111 | 364 | 1023 | 0.798 | 0.77 | NA |
| AD-26112 | 365 | 1024 | 0.301 | 0.51 | NA |
| AD-26123 | 366 | 1025 | 0.652 | 0.84 | NA |
| AD-26124 | 367 | 1026 | 0.277 | 0.48 | NA |
| AD-26125 | 368 | 1027 | 0.342 | 0.64 | NA |
| AD-26126 | 369 | 1028 | 0.094 | 0.46 | NA |
| AD-26127 | 370 | 1029 | 0.455 | 0.80 | NA |
| AD-26128 | 371 | 1030 | 0.058 | 0.24 | 0.066 |
| AD-26129 | 372 | 1031 | 0.409 | 0.57 | NA |
| AD-26130 | 373 | 1032 | 0.892 | 0.80 | NA |
| AD-26131 | 374 | 1033 | 0.067 | 0.41 | 0.104 |
| AD-26132 | 375 | 1034 | 0.109 | 0.19 | 0.060 |
| AD-26133 | 376 | 1035 | 0.790 | 0.85 | NA |
| AD-26134 | 377 | 1036 | 0.046 | 0.27 | 0.103 |
| AD-26135 | 378 | 1037 | 0.069 | 0.38 | NA |
| AD-26136 | 379 | 1038 | 0.451 | 0.78 | NA |
| AD-26137 | 380 | 1039 | 0.685 | 0.64 | NA |
| AD-26138 | 381 | 1040 | 0.579 | 0.63 | NA |
| AD-26139 | 382 | 1041 | 0.857 | 0.59 | NA |
| AD-26140 | 383 | 1042 | 0.384 | 0.71 | NA |
| AD-26141 | 384 | 1043 | 0.104 | 0.49 | NA |
| AD-26142 | 385 | 1044 | 0.199 | 0.59 | NA |
| AD-26143 | 386 | 1045 | 0.205 | 0.61 | NA |
| AD-26144 | 387 | 1046 | 0.821 | 1.04 | NA |
| AD-26145 | 388 | 1047 | 0.860 | 0.86 | NA |
| AD-26146 | 389 | 1048 | 0.076 | 0.34 | NA |
| AD-26147 | 390 | 1049 | 0.559 | 0.65 | NA |
| AD-26148 | 391 | 1050 | 0.066 | 0.48 | NA |
| AD-26149 | 392 | 1051 | 0.326 | 0.50 | NA |
| AD-26150 | 393 | 1052 | 0.396 | 0.66 | NA |
| AD-26151 | 394 | 1053 | 0.249 | 0.54 | NA |
| AD-26152 | 395 | 1054 | 0.837 | 0.74 | NA |
| AD-26153 | 396 | 1055 | 0.119 | 0.39 | NA |
| AD-26154 | 397 | 1056 | 0.600 | 0.64 | NA |
| AD-26155 | 398 | 1057 | 0.693 | 0.69 | NA |
| AD-26156 | 399 | 1058 | 0.033 | 0.35 | 0.020 |
| AD-26157 | 400 | 1059 | 0.220 | 0.74 | NA |
| AD-26158 | 401 | 1060 | 0.031 | 0.40 | 0.033 |
| AD-26159 | 402 | 1061 | 0.387 | 0.49 | NA |
| AD-26160 | 403 | 1062 | 0.836 | 0.73 | NA |
| AD-26161 | 404 | 1063 | 0.831 | 0.76 | NA |
| AD-26162 | 405 | 1064 | 0.358 | 0.50 | NA |
| AD-26163 | 406 | 1065 | 0.817 | 0.66 | NA |
| AD-26164 | 407 | 1066 | 0.112 | 0.59 | NA |
| AD-26165 | 408 | 1067 | 0.272 | 0.67 | NA |
| AD-26166 | 409 | 1068 | 0.300 | 0.63 | NA |
| AD-26167 | 410 | 1069 | 0.664 | 0.77 | NA |
| AD-26168 | 411 | 1070 | 0.771 | 0.78 | NA |
| AD-26169 | 412 | 1071 | 0.480 | 0.67 | NA |
| AD-26170 | 413 | 1072 | 0.174 | 0.47 | NA |
| AD-26171 | 414 | 1073 | 0.410 | 0.75 | NA |
| AD-26172 | 415 | 1074 | 0.294 | 0.74 | NA |
| AD-26173 | 416 | 1075 | 0.384 | 0.71 | NA |
| AD-26174 | 417 | 1076 | 0.388 | 0.79 | NA |
| AD-26175 | 418 | 1077 | 0.611 | 0.72 | NA |
| AD-26176 | 419 | 1078 | 0.055 | 0.44 | NA |
| AD-26177 | 420 | 1079 | 0.310 | 0.67 | NA |
| AD-26178 | 421 | 1080 | 0.038 | 0.20 | 0.094 |
| AD-26179 | 422 | 1081 | 0.042 | 0.33 | 0.108 |
| AD-26180 | 423 | 1082 | 0.031 | 0.21 | 0.036 |
| AD-26181 | 424 | 1083 | 0.041 | 0.08 | 0.034 |
| AD-26182 | 425 | 1084 | 0.237 | 0.79 | NA |
| AD-26183 | 426 | 1085 | 0.028 | 0.37 | 0.070 |
| AD-26184 | 427 | 1086 | 0.189 | 0.54 | NA |
| AD-26185 | 428 | 1087 | 0.357 | 0.76 | NA |
| AD-26186 | 6495 | 1088 | 0.066 | 0.60 | NA |
| AD-26187 | 6496 | 1089 | 0.298 | 0.60 | NA |
| AD-26188 | 431 | 1090 | 0.159 | 0.51 | NA |
| AD-26189 | 432 | 1091 | 0.143 | 0.51 | NA |
| AD-26190 | 433 | 1092 | 0.063 | 0.34 | NA |
| AD-26191 | 434 | 1093 | 0.674 | 0.82 | NA |
| AD-26192 | 435 | 1094 | 0.446 | 0.75 | NA |
| AD-26193 | 436 | 1095 | 0.058 | 0.36 | 0.055 |
| AD-26194 | 437 | 1096 | 0.289 | 0.84 | NA |
| AD-26195 | 438 | 1097 | 0.353 | 0.81 | NA |
| AD-26196 | 439 | 1098 | 0.055 | 0.35 | NA |
| AD-26197 | 440 | 1099 | 0.440 | 0.68 | NA |
| AD-26198 | 441 | 1100 | 0.175 | 0.53 | NA |
| AD-26199 | 442 | 1101 | 0.055 | 0.58 | NA |
| AD-26200 | 443 | 1102 | 0.076 | 0.46 | NA |
| AD-26201 | 444 | 1103 | 0.283 | 0.48 | NA |
| AD-26202 | 445 | 1104 | 0.052 | 0.70 | NA |
| AD-26203 | 446 | 1105 | 0.045 | 0.22 | 0.162 |
| AD-26204 | 447 | 1106 | 0.660 | 0.73 | NA |
| AD-26205 | 448 | 1107 | 0.324 | 0.76 | NA |
| AD-26206 | 449 | 1108 | 0.520 | 1.12 | NA |
| AD-26207 | 450 | 1109 | 0.367 | 0.75 | NA |
| AD-26208 | 451 | 1110 | 0.795 | 0.73 | NA |
| AD-26209 | 452 | 1111 | 0.112 | 0.54 | NA |

TABLE 5-continued

Analysis of RNAi agents to Beta-Catenin

| Duplex | Sense SEQ ID NO: | Anti-sense SEQ ID NO: | Residual Gene Activity 10 nM 24 hr | Residual Gene Activity 0.1 nM 120 hr | Avg. EC50 (nM) |
|---|---|---|---|---|---|
| AD-26210 | 453 | 1112 | 0.030 | 0.39 | NA |
| AD-26211 | 454 | 1113 | 0.124 | 0.25 | NA |
| AD-26212 | 455 | 1114 | 0.151 | 0.45 | NA |
| AD-26213 | 456 | 1115 | 0.223 | 0.63 | NA |
| AD-26214 | 457 | 1116 | 0.513 | 0.66 | NA |
| AD-26215 | 458 | 1117 | 0.102 | 0.29 | NA |
| AD-26216 | 459 | 1118 | 0.496 | 0.58 | NA |
| AD-26217 | 460 | 1119 | 0.410 | 0.77 | NA |
| AD-26218 | 461 | 1120 | 0.041 | 0.15 | 0.026 |
| AD-26651 | 462 | 1121 | 0.023 | 0.21 | 0.041 |
| AD-26652 | 463 | 1122 | 0.025 | 0.21 | 0.026 |
| AD-26653 | 464 | 1123 | 0.115 | 0.76 | NA |
| AD-26654 | 465 | 1124 | 0.068 | 0.88 | NA |
| AD-26655 | 466 | 1125 | 0.682 | 0.86 | NA |
| AD-26656 | 467 | 1126 | 0.684 | 0.91 | NA |
| AD-26657 | 468 | 1127 | 0.468 | 0.89 | NA |
| AD-26658 | 469 | 1128 | 0.305 | 0.50 | NA |
| AD-26659 | 470 | 1129 | 0.481 | 0.50 | NA |
| AD-26660 | 471 | 1130 | 0.041 | 0.20 | 0.010 |
| AD-26661 | 472 | 1131 | 0.194 | 0.77 | NA |
| AD-26662 | 473 | 1132 | 0.717 | 1.00 | NA |
| AD-26663 | 474 | 1133 | 0.546 | 1.02 | NA |
| AD-26664 | 475 | 1134 | 0.030 | 0.36 | NA |
| AD-26665 | 476 | 1135 | 0.037 | 0.25 | 0.008 |
| AD-26666 | 477 | 1136 | 0.072 | 0.57 | NA |
| AD-26667 | 478 | 1137 | 0.587 | 0.65 | NA |
| AD-26668 | 479 | 1138 | 0.760 | 0.70 | NA |
| AD-26669 | 480 | 1139 | 0.038 | 0.64 | NA |
| AD-26670 | 481 | 1140 | 0.033 | 0.32 | 0.005 |
| AD-26671 | 482 | 1141 | 0.091 | 0.71 | NA |
| AD-26672 | 483 | 1142 | 0.084 | 0.56 | NA |
| AD-26673 | 484 | 1143 | 0.027 | 0.18 | 0.012 |
| AD-26674 | 485 | 1144 | 0.044 | 0.32 | 0.021 |
| AD-26675 | 486 | 1145 | 0.063 | 0.67 | NA |
| AD-26676 | 487 | 1146 | 0.617 | 0.81 | NA |
| AD-26677 | 488 | 1147 | 0.138 | 0.50 | NA |
| AD-26678 | 489 | 1148 | 0.055 | 0.34 | NA |
| AD-26679 | 490 | 1149 | 0.052 | 0.44 | NA |
| AD-26680 | 491 | 1150 | 0.191 | 0.42 | NA |
| AD-26681 | 492 | 1151 | 0.092 | 0.57 | NA |
| AD-26682 | 493 | 1152 | 0.035 | 0.11 | 0.007 |
| AD-26683 | 494 | 1153 | 0.055 | 0.87 | NA |
| AD-26684 | 495 | 1154 | 0.035 | 0.16 | 0.009 |
| AD-26685 | 496 | 1155 | 0.034 | 0.37 | NA |
| AD-26686 | 497 | 1156 | 0.821 | 0.77 | NA |
| AD-26687 | 498 | 1157 | 0.151 | 0.29 | NA |
| AD-26688 | 499 | 1158 | 0.094 | 0.69 | NA |
| AD-26689 | 500 | 1159 | 0.086 | 0.61 | NA |
| AD-26690 | 501 | 1160 | 0.047 | 0.36 | NA |
| AD-26691 | 502 | 1161 | 0.030 | 0.24 | 0.020 |
| AD-26692 | 503 | 1162 | 0.222 | 0.62 | NA |
| AD-26693 | 504 | 1163 | 0.739 | 0.76 | NA |
| AD-26694 | 505 | 1164 | 0.331 | 0.63 | NA |
| AD-26695 | 506 | 1165 | 0.371 | 0.66 | NA |
| AD-26696 | 507 | 1166 | 0.023 | 0.37 | 0.027 |
| AD-26697 | 508 | 1167 | 1.024 | 0.80 | NA |
| AD-26698 | 509 | 1168 | 0.047 | 0.22 | NA |
| AD-26699 | 510 | 1169 | 0.145 | 0.71 | NA |
| AD-26700 | 511 | 1170 | 0.028 | 0.08 | 0.005 |
| AD-26701 | 512 | 1171 | 0.028 | 0.21 | 0.006 |
| AD-26702 | 513 | 1172 | 0.046 | 0.43 | NA |
| AD-26703 | 514 | 1173 | 0.193 | 0.65 | NA |
| AD-26704 | 515 | 1174 | 0.027 | 0.36 | 0.010 |
| AD-26705 | 516 | 1175 | 0.054 | 0.40 | NA |
| AD-26706 | 517 | 1176 | 0.223 | 0.52 | NA |
| AD-26707 | 518 | 1177 | 0.144 | 0.70 | NA |
| AD-26708 | 519 | 1178 | 0.160 | 0.59 | NA |
| AD-26709 | 520 | 1179 | 0.818 | 0.80 | NA |
| AD-26710 | 521 | 1180 | 0.307 | 0.84 | NA |
| AD-26711 | 522 | 1181 | 0.209 | 0.46 | NA |
| AD-26712 | 523 | 1182 | 0.276 | 0.76 | NA |
| AD-26713 | 524 | 1183 | 0.043 | 0.23 | 0.014 |
| AD-26714 | 525 | 1184 | 0.108 | 0.65 | NA |
| AD-26715 | 526 | 1185 | 0.777 | 0.67 | NA |
| AD-26716 | 527 | 1186 | 0.551 | 0.69 | NA |
| AD-26717 | 528 | 1187 | 0.643 | 0.80 | NA |
| AD-26718 | 529 | 1188 | 0.821 | 0.70 | NA |
| AD-26719 | 530 | 1189 | 0.053 | 0.35 | NA |
| AD-26720 | 531 | 1190 | 0.148 | 0.62 | NA |
| AD-26721 | 532 | 1191 | 0.906 | 0.92 | NA |
| AD-26722 | 533 | 1192 | 0.042 | 0.38 | 0.033 |
| AD-26723 | 534 | 1193 | 0.136 | 0.69 | NA |
| AD-26724 | 535 | 1194 | 0.472 | 1.00 | NA |
| AD-26725 | 536 | 1195 | 0.082 | 0.39 | NA |
| AD-26726 | 537 | 1196 | 0.258 | 0.70 | NA |
| AD-26727 | 538 | 1197 | 0.043 | 0.33 | NA |
| AD-26728 | 539 | 1198 | 0.612 | 0.80 | NA |
| AD-26729 | 540 | 1199 | 0.056 | 0.15 | 0.007 |
| AD-26730 | 541 | 1200 | 0.038 | 0.13 | 0.007 |
| AD-26731 | 542 | 1201 | 0.034 | 0.10 | 0.035 |
| AD-26732 | 543 | 1202 | 0.853 | 0.74 | NA |
| AD-26733 | 544 | 1203 | 0.805 | 0.77 | NA |
| AD-26734 | 545 | 1204 | 0.580 | 0.77 | NA |
| AD-26735 | 546 | 1205 | 0.457 | 1.02 | NA |
| AD-26736 | 547 | 1206 | 0.701 | 0.75 | NA |
| AD-26737 | 548 | 1207 | 0.066 | 0.33 | NA |
| AD-26738 | 549 | 1208 | 0.327 | 0.79 | NA |
| AD-26739 | 550 | 1209 | 0.102 | 0.44 | NA |
| AD-26740 | 551 | 1210 | 0.030 | 0.08 | 0.006 |
| AD-26741 | 552 | 1211 | 0.128 | 0.50 | NA |
| AD-26742 | 553 | 1212 | 0.025 | 0.34 | 0.057 |
| AD-26743 | 554 | 1213 | 0.033 | 0.38 | 0.061 |
| AD-26744 | 555 | 1214 | 0.170 | 0.74 | NA |
| AD-26745 | 556 | 1215 | 0.304 | 0.55 | NA |
| AD-26746 | 557 | 1216 | 0.037 | 0.33 | NA |
| AD-26747 | 558 | 1217 | 0.048 | 0.43 | NA |
| AD-26748 | 559 | 1218 | 0.081 | 0.51 | NA |
| AD-26749 | 560 | 1219 | 0.184 | 0.70 | NA |
| AD-26750 | 561 | 1220 | 0.209 | 0.64 | NA |
| AD-26751 | 562 | 1221 | 0.570 | 0.71 | NA |
| AD-26752 | 563 | 1222 | 0.040 | 0.45 | 0.042 |
| AD-26753 | 564 | 1223 | 0.153 | 0.61 | NA |
| AD-26754 | 565 | 1224 | 0.518 | 0.79 | NA |
| AD-26755 | 566 | 1225 | 0.064 | 0.27 | NA |
| AD-26756 | 567 | 1226 | 0.146 | 0.48 | NA |
| AD-26757 | 568 | 1227 | 0.035 | 0.22 | 0.047 |
| AD-26758 | 569 | 1228 | 0.053 | 0.46 | NA |
| AD-26759 | 570 | 1229 | 0.116 | 0.59 | NA |
| AD-26760 | 571 | 1230 | 0.435 | 0.60 | NA |
| AD-26761 | 572 | 1231 | 0.088 | 0.44 | NA |
| AD-26762 | 573 | 1232 | 0.385 | 0.57 | NA |
| AD-26763 | 574 | 1233 | 0.057 | 0.22 | 0.015 |
| AD-26764 | 575 | 1234 | 0.120 | 0.47 | NA |
| AD-26765 | 576 | 1235 | 0.058 | 0.43 | NA |
| AD-26766 | 577 | 1236 | 0.183 | 0.72 | NA |
| AD-26767 | 578 | 1237 | 0.582 | 0.57 | NA |
| AD-26768 | 579 | 1238 | 0.042 | 0.39 | NA |
| AD-26769 | 580 | 1239 | 0.071 | 0.52 | NA |
| AD-26770 | 581 | 1240 | 0.398 | 0.58 | NA |
| AD-26771 | 582 | 1241 | 0.576 | 0.71 | NA |
| AD-26772 | 583 | 1242 | 0.784 | 0.64 | NA |
| AD-26773 | 584 | 1243 | 0.353 | 0.58 | NA |
| AD-26774 | 585 | 1244 | 0.069 | 0.55 | NA |
| AD-26775 | 586 | 1245 | 0.506 | 0.86 | NA |
| AD-26776 | 587 | 1246 | 0.079 | 0.26 | NA |
| AD-26777 | 588 | 1247 | 0.363 | 0.73 | NA |
| AD-26778 | 589 | 1248 | 0.101 | 0.40 | NA |
| AD-26779 | 590 | 1249 | 0.040 | 0.34 | 0.109 |
| AD-26780 | 591 | 1250 | 0.069 | 0.25 | NA |
| AD-26781 | 592 | 1251 | 0.044 | 0.24 | NA |
| AD-26782 | 593 | 1252 | 0.054 | 0.53 | NA |
| AD-26783 | 594 | 1253 | 0.053 | 0.51 | NA |
| AD-26784 | 595 | 1254 | 0.072 | 0.53 | NA |
| AD-26785 | 596 | 1255 | 0.201 | 0.51 | NA |
| AD-26786 | 597 | 1256 | 0.134 | 0.81 | NA |
| AD-26787 | 598 | 1257 | 0.143 | 0.60 | NA |
| AD-26788 | 599 | 1258 | 0.036 | 0.57 | 0.053 |
| AD-26789 | 600 | 1259 | 0.418 | 0.74 | NA |

TABLE 5-continued

Analysis of RNAi agents to Beta-Catenin

| Duplex | Sense SEQ ID NO: | Anti-sense SEQ ID NO: | Residual Gene Activity 10 nM 24 hr | Residual Gene Activity 0.1 nM 120 hr | Avg. EC50 (nM) |
|---|---|---|---|---|---|
| AD-26790 | 601 | 1260 | 0.122 | 0.62 | NA |
| AD-26791 | 602 | 1261 | 0.305 | 0.73 | NA |
| AD-26792 | 603 | 1262 | 0.346 | 0.76 | NA |
| AD-26793 | 604 | 1263 | 0.391 | 0.63 | NA |
| AD-26794 | 605 | 1264 | 0.077 | 0.40 | NA |
| AD-26795 | 606 | 1265 | 0.586 | 0.65 | NA |
| AD-26796 | 607 | 1266 | 0.392 | 0.70 | NA |
| AD-26797 | 608 | 1267 | 0.063 | 0.73 | NA |
| AD-26798 | 609 | 1268 | 0.249 | 0.62 | NA |
| AD-26799 | 610 | 1269 | 0.345 | 0.66 | NA |
| AD-26800 | 611 | 1270 | 0.034 | 0.20 | 0.025 |
| AD-26801 | 612 | 1271 | 0.044 | 0.46 | NA |
| AD-26802 | 613 | 1272 | 0.096 | 0.57 | NA |
| AD-26803 | 614 | 1273 | 0.162 | 0.57 | NA |
| AD-26804 | 615 | 1274 | 0.056 | 0.35 | NA |
| AD-26805 | 616 | 1275 | 0.742 | 0.66 | NA |
| AD-26806 | 617 | 1276 | 0.080 | 0.69 | NA |
| AD-26807 | 618 | 1277 | 0.517 | 0.62 | NA |
| AD-26808 | 619 | 1278 | 0.043 | 0.51 | NA |
| AD-26809 | 620 | 1279 | 0.227 | 0.61 | NA |
| AD-26810 | 621 | 1280 | 0.048 | 0.22 | 0.039 |
| AD-26811 | 622 | 1281 | 0.333 | 0.85 | NA |
| AD-26812 | 623 | 1282 | 0.522 | 0.84 | NA |
| AD-26813 | 624 | 1283 | 0.044 | 0.33 | 0.076 |
| AD-26814 | 625 | 1284 | 0.545 | 0.72 | NA |
| AD-26815 | 626 | 1285 | 0.594 | 0.63 | NA |
| AD-26816 | 627 | 1286 | 0.044 | 0.37 | NA |
| AD-26817 | 628 | 1287 | 0.523 | 0.68 | NA |
| AD-26818 | 629 | 1288 | 0.575 | 1.80 | NA |
| AD-26819 | 630 | 1289 | 0.069 | 0.41 | NA |
| AD-26820 | 631 | 1290 | 0.484 | 0.76 | NA |
| AD-26821 | 632 | 1291 | 0.245 | 0.70 | NA |
| AD-26822 | 633 | 1292 | 0.039 | 0.23 | 0.037 |
| AD-26823 | 634 | 1293 | 0.062 | 0.09 | 0.033 |
| AD-26824 | 635 | 1294 | 0.304 | 0.60 | NA |
| AD-26825 | 636 | 1295 | 0.038 | 0.36 | NA |
| AD-26826 | 637 | 1296 | 0.105 | 0.57 | NA |
| AD-26900 | 638 | 1297 | 0.056 | 0.73 | 0.033 |
| AD-26901 | 639 | 1298 | 0.065 | 0.68 | NA |
| AD-26902 | 640 | 1299 | 0.053 | 0.42 | NA |
| AD-26903 | 641 | 1300 | 0.075 | 0.59 | NA |
| AD-26904 | 642 | 1301 | 0.051 | 0.38 | NA |
| AD-26905 | 643 | 1302 | 0.084 | 0.45 | NA |
| AD-26906 | 644 | 1303 | 0.186 | 0.76 | NA |
| AD-26907 | 645 | 1304 | 0.610 | 0.82 | NA |
| AD-26908 | 646 | 1305 | 0.073 | 0.78 | NA |
| AD-26909 | 647 | 1306 | 0.235 | 0.99 | NA |
| AD-26910 | 648 | 1307 | 0.077 | 0.78 | NA |
| AD-26911 | 649 | 1308 | 0.193 | 0.96 | NA |
| AD-26912 | 650 | 1309 | 0.074 | 0.73 | NA |
| AD-26913 | 651 | 1310 | 0.141 | 0.88 | NA |
| AD-26914 | 652 | 1311 | 0.519 | 0.64 | NA |
| AD-26915 | 653 | 1312 | 0.587 | 0.71 | NA |
| AD-26916 | 654 | 1313 | 0.063 | 0.62 | NA |
| AD-26917 | 655 | 1314 | 0.076 | 0.55 | NA |
| AD-26918 | 656 | 1315 | 0.069 | 0.28 | 0.029 |
| AD-26919 | 657 | 1316 | 0.085 | 0.55 | NA |
| AD-26920 | 658 | 1317 | 0.042 | 0.31 | NA |
| AD-26921 | 659 | 1318 | 0.025 | 0.09 | 0.014 |

NA: data not available or not determined.

"Fold-Change" represents the residual level (in HeLa cells) at a particular time and concentration, relative to control. Thus, a "Fold-Change 10 nM 24 hr" for AD-18892 of "0.054" indicates that, at a concentration of 10 nM, there was 5.4% residual Beta-Catenin level, or 94.6% gene knock-down, in HeLa cells at 24 hr after treating the cells with the RNAi agent.

"Fold-Change 0.1 nM 120 hr" indicates the residual Beta-Catenin level at a concentration of 0.1 nM, measured at 120 hr.

"Avg. EC50 (nM)" indicates a concentration estimated, based on available data, to allow 50% gene knock-down in HeLa cells. Thus, for AD-18893, a concentration of 0.008 nM is estimated to knock down Beta-Catenin by 50%. To calculate estimated average EC50 figures, HeLa cells were treated with RNAi agents at concentrations of 10 nM, 1 nM, 0.1 nM, 0.01 nM, and 0.001 nM of RNAi agent, and the data fit to a curve. The indicated EC50 is an estimated EC50 calculated from available data that is expected to give 50% gene knock-down of Beta-Catenin in HeLa cells.

Tables 1 to 8 thus disclose various RNAi agents capable of mediating gene knock-down of Beta-Catenin.

TABLE 6

Analysis of RNAi agents to Beta-Catenin
Additional duplexes targeting Beta-Catenin (listed in Table 3) were tested in vitro against HeLa cells. 48 hour results were measured; duplex concentration was 6 nM, 3 nM and 1.5 nM. Data in this table represents residual gene activity; thus Set1 254 A22 S26 showed 4.9% residual gene activity (e.g., 95.1% gene knockdown) at 48 hours at 6 nM in HeLa cells.

| Nickname | AV HeLa set1-2 d3-6 nM | AV HeLa set1-2 3 nM | AV HeLa set1-2 1.5 nM | SD HeLa set1-2 d3-6 nM | SD HeLa set1-2 3 nM | SD HeLa set1-2 1.5 nM |
|---|---|---|---|---|---|---|
| Set1 254 A22 S26 | 4.9 | 11.1 | 22.5 | 1.6 | 2.1 | 1.6 |
| Set1 703 A22 S26 | 4.8 | 12.4 | 29.0 | 1.5 | 2.4 | 7.3 |
| Set1 709 A22 S26 | 6.5 | 13.9 | 30.7 | 1.1 | 2.0 | 7.1 |
| Set1 895 A22 S26 | 5.9 | 13.1 | 48.0 | 0.8 | 3.9 | 25.6 |
| Set1 1816 A22 S26 | 4.9 | 12.3 | 28.6 | 0.5 | 2.8 | 4.3 |
| Set1 1974 A22 S26 | 6.6 | 12.5 | 36.9 | 1.0 | 0.9 | 0.6 |
| Set1 2425 A22 S26 | 5.6 | 13.6 | 27.3 | 0.4 | 1.7 | 9.7 |
| Set1 3146 A22 S26 | 4.5 | 9.3 | 21.0 | 1.1 | 1.2 | 2.9 |
| Set1 889 A22 S26 | 8.6 | 14.2 | 37.9 | 3.4 | 3.7 | 17.1 |
| Set1 1814 A22 S26 | 6.0 | 11.8 | 21.3 | 2.2 | 3.8 | 4.6 |
| Set1 1245 A22 S26 | 6.7 | 12.0 | 28.2 | 2.6 | 2.5 | 8.7 |
| Set1 3196 A22 S26 | 4.5 | 9.1 | 17.1 | 0.5 | 0.0 | 5.3 |
| Set1 1450 A22 S26 | 4.4 | 12.5 | 25.4 | 0.3 | 3.6 | 2.7 |
| Set1 3169 A22 S26 | 6.3 | 13.1 | 29.7 | 0.9 | 2.2 | 9.8 |

TABLE 6-continued

Analysis of RNAi agents to Beta-Catenin
Additional duplexes targeting Beta-Catenin (listed in Table 3) were tested in vitro against
HeLa cells. 48 hour results were measured; duplex concentration was 6 nM, 3 nM and 1.5 nM.
Data in this table represents residual gene activity; thus Set1 254 A22 S26 showed 4.9%
residual gene activity (e.g., 95.1% gene knockdown) at 48 hours at 6 nM in HeLa cells.

| Nickname | AV HeLa set1-2 d3-6 nM | AV HeLa set1-2 3 nM | AV HeLa set1-2 1.5 nM | SD HeLa set1-2 d3-6 nM | SD HeLa set1-2 3 nM | SD HeLa set1-2 1.5 nM |
|---|---|---|---|---|---|---|
| Set1 3477 A22 S26 | 9.6 | 19.8 | 40.9 | 2.0 | 2.6 | 10.9 |
| Set1 865 A22 S26 | 12.0 | 24.5 | 57.3 | 3.3 | 7.5 | 14.2 |
| Set1 1249 A22 S26 | 34.4 | 71.2 | 73.3 | 7.9 | 24.7 | 12.3 |
| Set1 1250 A22 S26 | 12.0 | 30.6 | 61.6 | 2.0 | 8.4 | 4.2 |
| Set1 2202 A22 S26 | 8.3 | 14.0 | 45.8 | 3.1 | 1.8 | 12.2 |
| Set1 1545 A22 S26 | 34.4 | 62.0 | 81.5 | 11.6 | 4.1 | 12.5 |
| Set1 1755 A22 S26 | 8.7 | 21.9 | 64.9 | 1.0 | 6.4 | 8.0 |
| Set1 254 A25 S27 | 6.3 | 12.3 | 17.6 | 1.2 | 3.4 | 1.7 |
| Set1 703 A25 S27 | 7.0 | 13.7 | 32.8 | 1.2 | 2.9 | 8.0 |
| Set1 709 A25 S27 | 5.6 | 11.4 | 23.4 | 1.8 | 0.5 | 7.7 |
| Set1 895 A25 S27 | 6.6 | 13.5 | 35.7 | 1.9 | 2.5 | 6.8 |
| Set1 1816 A25 S27 | 7.8 | 15.6 | 26.4 | 1.3 | 1.2 | 4.8 |
| Set1 1974 A25 S27 | 8.1 | 16.2 | 34.7 | 2.6 | 1.3 | 3.8 |
| Set1 2425 A25 S27 | 7.8 | 16.5 | 35.3 | 1.0 | 2.2 | 2.5 |
| Set1 3146 A25 S27 | 4.9 | 11.9 | 31.0 | 0.3 | 1.3 | 4.2 |
| Set1 889 A25 S27 | 9.3 | 15.0 | 37.2 | 1.3 | 1.9 | 4.1 |
| Set1 1814 A25 S27 | 6.2 | 13.7 | 43.2 | 1.1 | 0.9 | 6.1 |
| Set1 1245 A25 S27 | 7.2 | 15.2 | 36.2 | 0.3 | 2.4 | 11.7 |
| Set1 3196 A25 S27 | 5.5 | 10.3 | 24.2 | 1.4 | 0.8 | 2.1 |
| Set1 1450 A25 S27 | 4.3 | 10.4 | 29.9 | 1.1 | 1.1 | 6.4 |
| Set1 3169 A25 S27 | 4.3 | 11.5 | 22.0 | 0.4 | 2.3 | 2.7 |
| Set1 3477 A25 S27 | 7.5 | 12.8 | 22.8 | 1.1 | 1.3 | 2.1 |
| Set1 865 A25 S27 | 5.1 | 10.9 | 18.1 | 0.7 | 1.2 | 2.9 |
| Set1 1249 A25 S27 | 8.0 | 22.9 | 37.2 | 1.8 | 5.1 | 6.7 |
| Set1 1250 A25 S27 | 16.6 | 28.2 | 49.1 | 3.1 | 2.7 | 8.9 |
| Set1 2202 A25 S27 | 6.1 | 10.0 | 29.2 | 2.3 | 3.6 | 4.8 |
| Set1 1545 A25 S27 | 9.0 | 16.6 | 41.9 | 1.3 | 2.2 | 2.2 |
| Set1 1755 A25 S27 | 5.8 | 15.1 | 33.8 | 1.2 | 2.2 | 6.1 |
| Set1 254 A LO V1 S26 | 6.0 | 16.4 | 32.9 | 0.3 | 3.8 | 5.1 |
| Set1 703 A LO V1 S26 | 8.1 | 22.7 | 50.3 | 2.8 | 3.4 | 16.2 |
| Set1 709 A LO V1 S26 | 6.2 | 14.8 | 37.1 | 1.2 | 1.7 | 5.1 |
| Set1 895 A LO V1 S26 | 42.7 | 63.9 | 82.3 | 7.8 | 15.5 | 10.2 |
| Set1 1816 A LO V1 S26 | 6.9 | 16.9 | 43.4 | 0.9 | 1.4 | 15.1 |
| Set1 1974 A LO V1 S26 | 9.0 | 18.5 | 36.8 | 1.4 | 3.6 | 6.8 |
| Set1 2425 A LO V1 S26 | 5.5 | 13.9 | 30.0 | 0.4 | 1.6 | 7.5 |
| Set1 3146 A LO V1 S26 | 12.1 | 27.7 | 61.2 | 1.5 | 2.7 | 3.8 |
| Set1 889 A LO V1 S26 | 24.5 | 37.8 | 60.3 | 3.2 | 3.2 | 9.1 |
| Set1 1814 A LO V1 S26 | 8.6 | 20.7 | 46.5 | 1.5 | 2.6 | 11.1 |
| Set1 1245 A LO V1 S26 | 42.0 | 61.4 | 85.9 | 5.8 | 8.4 | 10.4 |
| Set1 3196 A LO V1 S26 | 6.1 | 14.0 | 31.0 | 0.6 | 1.2 | 5.4 |
| Set1 1450 A LO V1 S26 | 9.4 | 21.1 | 47.6 | 1.4 | 1.3 | 8.0 |
| Set1 3169 A LO V1 S26 | 5.3 | 15.5 | 30.5 | 1.3 | 3.7 | 1.9 |
| Set1 3477 A LO V1 S26 | 8.6 | 16.9 | 39.8 | 1.0 | 1.0 | 2.3 |
| Set1 865 A LO V1 S26 | 5.5 | 18.1 | 34.5 | 0.9 | 3.1 | 11.0 |
| Set1 1249 A LO V1 S26 | 61.0 | 90.3 | 82.0 | 5.6 | 29.0 | 6.6 |
| Set1 1250 A LO V1 S26 | 11.3 | 23.1 | 58.2 | 0.9 | 3.0 | 5.1 |
| Set1 2202 A LO V1 S26 | 5.7 | 14.5 | 45.2 | 1.0 | 1.4 | 1.5 |
| Set1 1545 A LO V1 S26 | 5.6 | 13.1 | 38.6 | 0.4 | 0.9 | 3.2 |
| Set1 1755 A LO V1 S26 | 39.5 | 53.6 | 77.5 | 3.8 | 3.3 | 5.0 |
| Set1 254 A LO V2 S LO V1 | 8.7 | 18.6 | 44.9 | 2.5 | 1.4 | 6.6 |
| Set1 703 A LO V2 S LO V1 | 39.9 | 51.7 | 75.8 | 3.9 | 3.2 | 9.9 |
| Set1 709 A LO V2 S LO V1 | 9.2 | 20.3 | 45.0 | 1.2 | 0.7 | 8.7 |
| Set1 895 A LO V2 S LO V1 | 33.3 | 64.9 | 84.8 | 1.8 | 6.5 | 5.8 |
| Set1 1816 A LO V2 S LO V1 | 14.4 | 33.1 | 61.2 | 2.2 | 2.9 | 9.3 |
| Set1 1974 A LO V2 S LO V1 | 56.7 | 65.4 | 91.8 | 15.4 | 5.6 | 6.7 |
| Set1 2425 A LO V2 S LO V1 | 13.3 | 21.4 | 54.2 | 1.5 | 3.6 | 6.0 |
| Set1 3146 A LO V2 S LO V1 | 9.7 | 16.7 | 32.7 | 2.0 | 1.7 | 5.0 |
| Set1 889 A LO V2 S LO V1 | 18.0 | 34.6 | 58.8 | 1.4 | 4.2 | 7.0 |
| Set1 1814 A LO V2 S LO V1 | 8.9 | 18.5 | 44.1 | 3.3 | 5.0 | 1.0 |
| Set1 1245 A LO V2 S LO V1 | 52.2 | 43.1 | 93.4 | 13.1 | 4.1 | 6.2 |
| Set1 3196 A LO V2 S LO V1 | 7.8 | 15.1 | 28.0 | 2.7 | 3.1 | 2.5 |
| Set1 1450 A LO V2 S LO V1 | 6.6 | 14.4 | 35.0 | 0.4 | 2.0 | 4.0 |
| Set1 3169 A LO V2 S LO V1 | 5.3 | 14.5 | 26.4 | 0.5 | 2.8 | 2.2 |
| Set1 3477 A LO V2 S LO V1 | 9.4 | 22.0 | 35.2 | 1.5 | 0.8 | 1.6 |
| Set1 865 A LO V2 S LO V1 | 11.2 | 18.5 | 45.9 | 5.4 | 4.2 | 18.2 |
| Set1 1249 A LO V2 S LO V1 | 65.5 | 97.0 | 82.0 | 19.2 | 22.0 | 10.3 |
| Set1 1250 A LO V2 S LO V1 | 49.4 | 62.9 | 92.4 | 6.3 | 19.6 | 22.4 |
| Set1 2202 A LO V2 S LO V1 | 6.7 | 17.3 | 34.9 | 0.8 | 3.6 | 1.6 |
| Set1 1545 A LO V2 S LO V1 | 17.9 | 32.6 | 58.3 | 1.2 | 5.0 | 8.2 |

TABLE 6-continued

Analysis of RNAi agents to Beta-Catenin
Additional duplexes targeting Beta-Catenin (listed in Table 3) were tested in vitro against
HeLa cells. 48 hour results were measured; duplex concentration was 6 nM, 3 nM and 1.5 nM.
Data in this table represents residual gene activity; thus Set1 254 A22 S26 showed 4.9%
residual gene activity (e.g., 95.1% gene knockdown) at 48 hours at 6 nM in HeLa cells.

| Nickname | AV HeLa set1-2 d3-6 nM | AV HeLa set1-2 3 nM | AV HeLa set1-2 1.5 nM | SD HeLa set1-2 d3-6 nM | SD HeLa set1-2 3 nM | SD HeLa set1-2 1.5 nM |
|---|---|---|---|---|---|---|
| Set1 1755 A LO V2 S LO V1 | 10.5 | 23.3 | 43.1 | 1.0 | 3.3 | 7.3 |
| Set2 254 A LO V3 S LO V2 | 15.0 | 88.6 | 75.0 | 3.4 | 21.7 | 4.4 |
| Set2 703 A LO V3 S LO V2 | 112.0 | 235.3 | 135.2 | 25.2 | 30.1 | 22.4 |
| Set2 709 A LO V3 S LO V2 | 36.7 | 93.6 | 98.4 | 2.6 | 7.6 | 4.8 |
| Set2 895 A LO V3 S LO V2 | 80.2 | 163.3 | 117.7 | 9.1 | 62.4 | 10.6 |
| Set2 1816 A LO V3 S LO V2 | 66.3 | 113.1 | 116.6 | 10.0 | 22.2 | 12.6 |
| Set2 1974 A LO V3 S LO V2 | 110.7 | 142.7 | 134.5 | 13.1 | 19.0 | 12.8 |
| Set2 2425 A LO V3 S LO V2 | 50.9 | 119.3 | 151.5 | 13.1 | 20.2 | 7.0 |
| Set2 3146 A LO V3 S LO V2 | 30.8 | 73.2 | 99.6 | 5.0 | 13.5 | 14.3 |
| Set2 889 A LO V3 S LO V2 | 72.5 | 135.6 | 112.8 | 12.0 | 37.8 | 9.4 |
| Set2 1814 A LO V3 S LO V2 | 80.7 | 129.6 | 133.9 | 23.6 | 13.9 | 15.2 |
| Set2 1245 A LO V3 S LO V2 | 94.9 | 128.9 | 129.1 | 13.2 | 18.1 | 13.8 |
| Set2 3196 A LO V3 S LO V2 | 20.5 | 69.2 | 89.8 | 1.4 | 8.7 | 15.8 |
| Set2 1450 A LO V3 S LO V2 | 35.3 | 95.3 | 109.0 | 1.6 | 15.1 | 16.1 |
| Set2 3169 A LO V3 S LO V2 | 26.2 | 90.9 | 85.7 | 8.9 | 26.1 | 7.7 |
| Set2 3477 A LO V3 S LO V2 | 16.3 | 71.8 | 68.0 | 3.7 | 20.3 | 2.2 |
| Set2 865 A LO V3 S LO V2 | 99.3 | 122.9 | 115.4 | 9.0 | 29.0 | 14.5 |
| Set2 1249 A LO V3 S LO V2 | 62.7 | 114.9 | 113.5 | 7.5 | 19.6 | 3.4 |
| Set2 1250 A LO V3 S LO V2 | 101.9 | 112.5 | 116.1 | 8.7 | 12.1 | 11.1 |
| Set2 2202 A LO V3 S LO V2 | 72.2 | 118.5 | 129.7 | 7.1 | 22.3 | 7.5 |
| Set2 1545 A LO V3 S LO V2 | 65.6 | 109.5 | 120.7 | 12.9 | 6.5 | 9.3 |
| Set2 1755 A LO V3 S LO V2 | 84.7 | 140.6 | 146.9 | 11.1 | 52.2 | 13.5 |
| Set2 254 A LO V4 S LO V1 | 11.2 | 50.5 | 59.8 | 1.4 | 4.6 | 4.5 |
| Set2 703 A LO V4 S LO V1 | 29.1 | 94.0 | 100.5 | 3.4 | 10.3 | 6.1 |
| Set2 709 A LO V4 S LO V1 | 6.3 | 25.9 | 32.9 | 0.2 | 2.6 | 2.2 |
| Set2 895 A LO V4 S LO V1 | 26.4 | 86.4 | 108.5 | 1.2 | 6.5 | 30.8 |
| Set2 1816 A LO V4 S LO V1 | 15.0 | 94.1 | 88.1 | 1.5 | 13.2 | 25.2 |
| Set2 1974 A LO V4 S LO V1 | 47.3 | 100.2 | 126.0 | 9.1 | 4.5 | 21.6 |
| Set2 2425 A LO V4 S LO V1 | 13.0 | 44.3 | 61.8 | 3.7 | 1.7 | 6.9 |
| Set2 3146 A LO V4 S LO V1 | 11.8 | 36.2 | 34.8 | 2.5 | 2.4 | 3.6 |
| Set2 889 A LO V4 S LO V1 | 28.9 | 79.6 | 79.8 | 9.2 | 13.4 | 10.7 |
| Set2 1814 A LO V4 S LO V1 | 10.4 | 50.1 | 62.9 | 0.9 | 17.3 | 9.2 |
| Set2 1245 A LO V4 S LO V1 | 31.7 | 88.0 | 105.1 | 5.3 | 18.8 | 14.2 |
| Set2 3196 A LO V4 S LO V1 | 9.8 | 27.2 | 39.2 | 1.1 | 1.4 | 4.9 |
| Set2 1450 A LO V4 S LO V1 | 8.9 | 27.8 | 44.0 | 2.1 | 7.6 | 10.9 |
| Set2 3169 A LO V4 S LO V1 | 8.1 | 26.3 | 29.7 | 1.4 | 7.1 | 6.6 |
| Set2 3477 A LO V4 S LO V1 | 7.9 | 19.2 | 29.1 | 0.6 | 2.5 | 9.5 |
| Set2 865 A LO V4 S LO V1 | 6.2 | 23.8 | 33.4 | 0.6 | 0.7 | 5.6 |
| Set2 1249 A LO V4 S LO V1 | 69.5 | 103.4 | 103.4 | 19.1 | 17.3 | 11.8 |
| Set2 1250 A LO V4 S LO V1 | 61.4 | 90.3 | 94.6 | 15.3 | 12.4 | 11.7 |
| Set2 2202 A LO V4 S LO V1 | 9.3 | 35.7 | 42.8 | 2.9 | 6.9 | 5.5 |
| Set2 1545 A LO V4 S LO V1 | 32.8 | 68.0 | 92.2 | 6.1 | 17.1 | 23.2 |
| Set2 1755 A LO V4 S LO V1 | 13.9 | 50.4 | 62.0 | 3.6 | 4.6 | 12.5 |
| Set2 254 A LO V5 S LO V1 | 11.4 | 28.3 | 52.5 | 1.8 | 8.2 | 4.8 |
| Set2 703 A LO V5 S LO V1 | 31.1 | 88.4 | 97.0 | 1.4 | 14.7 | 6.3 |
| Set2 709 A LO V5 S LO V1 | 13.0 | 34.2 | 37.9 | 3.4 | 8.8 | 5.7 |
| Set2 895 A LO V5 S LO V1 | 25.9 | 81.1 | 109.1 | 3.0 | 8.2 | 20.0 |
| Set2 1816 A LO V5 S LO V1 | 12.9 | 42.3 | 53.7 | 2.5 | 7.0 | 12.1 |
| Set2 1974 A LO V5 S LO V1 | 39.5 | 80.3 | 93.6 | 11.6 | 5.5 | 10.4 |
| Set2 2425 A LO V5 S LO V1 | 11.5 | 38.8 | 59.9 | 1.4 | 5.4 | 3.3 |
| Set2 3146 A LO V5 S LO V1 | 9.3 | 32.1 | 41.6 | 0.7 | 5.6 | 4.3 |
| Set2 889 A LO V5 S LO V1 | 26.9 | 64.9 | 89.5 | 5.2 | 23.5 | 17.5 |
| Set2 1814 A LO V5 S LO V1 | 11.0 | 47.9 | 79.5 | 1.5 | 9.1 | 11.6 |
| Set2 1245 A LO V5 S LO V1 | 29.5 | 78.6 | 127.3 | 2.2 | 5.1 | 16.7 |
| Set2 3196 A LO V5 S LO V1 | 8.1 | 28.6 | 55.6 | 0.7 | 9.8 | 9.7 |
| Set2 1450 A LO V5 S LO V1 | 6.6 | 27.8 | 46.3 | 1.6 | 12.7 | 12.4 |
| Set2 3169 A LO V5 S LO V1 | 7.8 | 24.2 | 32.6 | 1.5 | 0.8 | 5.5 |
| Set2 3477 A LO V5 S LO V1 | 11.5 | 46.6 | 57.9 | 2.3 | 25.4 | 7.1 |
| Set2 865 A LO V5 S LO V1 | 11.4 | 35.2 | 40.9 | 1.6 | 8.6 | 6.7 |
| Set2 1249 A LO V5 S LO V1 | 52.0 | 82.3 | 89.6 | 3.2 | 3.0 | 12.9 |
| Set2 1250 A LO V5 S LO V1 | 45.0 | 75.2 | 97.3 | 6.1 | 4.2 | 13.0 |
| Set2 2202 A LO V5 S LO V1 | 5.8 | 26.1 | 35.7 | 0.8 | 5.2 | 4.2 |
| Set2 1545 A LO V5 S LO V1 | 23.8 | 59.7 | 73.5 | 3.5 | 18.3 | 11.0 |
| Set2 1755 A LO V5 S LO V1 | 10.8 | 40.5 | 73.9 | 0.8 | 10.6 | 4.8 |
| Set2 254 A48 S26 | 7.3 | 20.0 | 36.8 | 0.8 | 1.5 | 1.7 |
| Set2 703 A48 S26 | 7.4 | 27.7 | 48.1 | 0.7 | 2.6 | 5.7 |
| Set2 709 A48 S26 | 10.3 | 35.4 | 42.0 | 0.3 | 12.1 | 1.3 |
| Set2 895 A48 S26 | 8.7 | 30.7 | 64.5 | 0.7 | 6.6 | 8.0 |
| Set2 1816 A48 S26 | 10.0 | 29.4 | 36.0 | 1.8 | 6.7 | 7.5 |

TABLE 6-continued

Analysis of RNAi agents to Beta-Catenin
Additional duplexes targeting Beta-Catenin (listed in Table 3) were tested in vitro against HeLa cells. 48 hour results were measured; duplex concentration was 6 nM, 3 nM and 1.5 nM. Data in this table represents residual gene activity; thus Set1 254 A22 S26 showed 4.9% residual gene activity (e.g., 95.1% gene knockdown) at 48 hours at 6 nM in HeLa cells.

| Nickname | AV HeLa set1-2 d3-6 nM | AV HeLa set1-2 3 nM | AV HeLa set1-2 1.5 nM | SD HeLa set1-2 d3-6 nM | SD HeLa set1-2 3 nM | SD HeLa set1-2 1.5 nM |
|---|---|---|---|---|---|---|
| Set2 1974 A48 S26 | 9.3 | 27.7 | 45.1 | 1.3 | 7.5 | 2.3 |
| Set2 2425 A48 S26 | 8.2 | 38.6 | 40.5 | 1.8 | 2.5 | 6.6 |
| Set2 3146 A48 S26 | 5.8 | 22.4 | 28.5 | 0.5 | 2.2 | 5.6 |
| Set2 889 A48 S26 | 7.2 | 21.9 | 30.6 | 0.9 | 5.9 | 2.8 |
| Set2 1814 A48 S26 | 7.3 | 19.3 | 25.2 | 2.6 | 7.8 | 7.6 |
| Set2 1245 A48 S26 | 8.3 | 47.7 | 58.2 | 2.0 | 19.3 | 10.5 |
| Set2 3196 A48 S26 | 8.0 | 20.2 | 27.0 | 0.4 | 6.9 | 7.2 |
| Set2 1450 A48 S26 | 7.5 | 27.4 | 40.4 | 1.8 | 9.7 | 6.6 |
| Set2 3169 A48 S26 | 8.4 | 18.2 | 30.5 | 0.8 | 3.1 | 7.4 |
| Set2 3477 A48 S26 | 12.5 | 44.1 | 59.8 | 2.2 | 10.3 | 5.5 |
| Set2 865 A48 S26 | 13.0 | 38.2 | 42.5 | 2.4 | 5.3 | 8.4 |
| Set2 1249 A48 S26 | 47.7 | 74.5 | 88.6 | 9.0 | 13.3 | 12.3 |
| Set2 1250 A48 S26 | 11.5 | 56.4 | 66.0 | 2.4 | 7.2 | 7.4 |
| Set2 2202 A48 S26 | 6.7 | 28.1 | 33.2 | 0.8 | 5.4 | 4.9 |
| Set2 1545 A48 S26 | 37.0 | 72.7 | 61.7 | 10.9 | 13.6 | 24.3 |
| Set2 1755 A48 S26 | 8.4 | 25.9 | 39.7 | 2.4 | 4.7 | 6.4 |

Example 4

Screening in Insensitive Cells

In various embodiments, preferred RNAi agents to Beta-Catenin are those which are specific to Beta-Catenin and, in effect, do not exhibit off-target effects. Thus, in order to continue lead selection, various RNAi agents to Beta-Catenin are tested against cell lines which produce little or no Beta-Catenin. The Beta-Catenin RNAi agents which do not greatly reduce viability of these so-called "insensitive cell lines" are thought to have little or not off-target effects. The "insensitive" cell lines used are NCI-H28 and RKO. NCI-H28 is a mesothelioma cell line in which the Beta-Catenin gene has been deleted; RKO is a colorectal cell line which has low or no Beta-Catenin expression.

105 RNAi agents to Beta-Catenin found had been found to be effective in the dose-response analysis. These are tested against "insensitive" cell lines used are NCI-H28 and RKO at doses of 50 nM, 10 nM, 1 nM, 0.1 nM, and 0.0001 nM, and cell viability is determined at the time points of 3, 5 and 7 days.

The following RNAi agents demonstrate at least 80% viability (no more than 20% growth inhibition) of RKO cells and at least 80% viability of NCI-H28 cells on day 5, at 50 or 10 nM.

TABLE 7

| RNAi agent | IC50 |
|---|---|
| AD-18963-b2 | 0.049 |
| AD-25894-b1 | 0.004 |
| AD-25914-b1 | 0.054 |
| AD-25956-b1 | 0.042 |
| AD-26028-b1 | 0.050 |
| AD-26034-b1 | 0.009 |
| AD-26108-b1 | 0.030 |
| AD-26131-b1 | 0.104 |
| AD-26134-b1 | 0.103 |
| AD-26158-b1 | 0.033 |
| AD-26193-b1 | 0.055 |
| AD-26218-b1 | 0.026 |
| AD-26652-b1 | 0.026 |

TABLE 7-continued

| RNAi agent | IC50 |
|---|---|
| AD-26704-b1 | 0.010 |
| AD-26900-b1 | 0.033 |
| AD-26918-b1 | 0.029 |

The following RNAi agents demonstrate at least 80% viability (no more than 20% growth inhibition) of RKO cells and about 60 to 80% viability of NCI-H28 cells on day 5, at 50 or 10 nM.

TABLE 8

| RNAi Agent | IC50 |
|---|---|
| AD-18983-b2 | 0.070 |
| AD-25893-b1 | 0.040 |
| AD-25918-b1 | 0.013 |
| AD-25943-b1 | 0.080 |
| AD-25944-b1 | 0.007 |
| AD-25951-b1 | 0.007 |
| AD-25958-b1 | 0.024 |
| AD-26068-b1 | 0.102 |
| AD-26109-b1 | 0.025 |
| AD-26156-b1 | 0.020 |
| AD-26673-b1 | 0.012 |
| AD-26682-b1 | 0.007 |
| AD-26696-b1 | 0.027 |
| AD-26740-b1 | 0.006 |
| AD-26752-b1 | 0.042 |
| AD-26757-b1 | 0.047 |
| AD-26779-b1 | 0.109 |
| AD-26788-b1 | 0.053 |
| AD-26800-b1 | 0.025 |

Thus, 35 RNAi agents to Beta-Catenin did not greatly reduce viability of cell lines which do not depend on Beta-Catenin; these 35 RNAi agents to Beta-Catenin are: AD-18963-b2, AD-18983-b2, AD-25893-b1, AD-25894-b1, AD-25914-b1, AD-25918-b1, AD-25943-b1, AD-25944-b1, AD-25951-b1, AD-25956-b1, AD-25958-b1, AD-26028-b1, AD-26034-b1, AD-26068-b1, AD-26108-b1, AD-26109-b1, AD-26131-b1, AD-26134-b1, AD-26156-b1, AD-26158-b1, AD-26193-b1, AD-26218-b1, AD-26652-b1, AD-26673-b1, AD-26682-b1, AD-26696-b1, AD-26704-b1, AD-26740-b1, AD-26752-b1, AD-26757-b1, AD-26779-b1, AD-26788-b1, AD-26800-b1, AD-26900-b1, and AD-26918-b1 (wherein "b1" indicates "batch 1").

Example 5

Screening in Sensitive Cell Lines

Further screening is performed on the 35 RNAi agents to Beta-Catenin which were able to reduce Beta-Catenin expression in vitro, and did which did not greatly reduce viability of cell lines which do not depend on Beta-Catenin, as shown in the previous Examples.

These 35 RNAi agents were tested on four colorectal cell lines with an APC mutation (LoVo, DLD-1, LS411N and SW403). In the wild-type Wnt pathway, Beta-Catenin protein is phosphorylated by GSK-3, and then degraded by APC; thus, Beta-Catenin protein levels do not accumulate. However, in the case of the APC mutation, the Beta-Catenin is not degraded and thus the protein accumulates. These four cell lines are, in fact, dependent on Beta-Catenin and stop growing if Beta-Catenin expression is down-regulated.

The cell lines are each treated with each of the 35 RNAi agents to Beta-Catenin at doses of 50 nM, 10 nM, 1 nM, 0.1 nM, and 0.0001 nM, and tested at 3, 5 and 7 days. The data used are from DLD-1 treated at 1 nM, LoVo at 1 nM, and LS411N at 0.1 nM, and data collected at 7 days. SW403 data is not used, as these data did not distinguish among the various siRNAs even at 0.1 nM.

The screening data for RNAi agents to Beta-Catenin in sensitive cell lines is presented below.

TABLE 9

SCREENING DATA

| siRNA | Pos | Species | 24 hr Average IC50 (nM) | DLD1 1 nM Day 7 | LoVo 1 nM Day 7 | LS411N 0.1 nM Day 7 | PBMC |
| --- | --- | --- | --- | --- | --- | --- | --- |
| AD-18983 | CDS | Hu, Cy, Mo | 0.07 | 0.258 | 0.150 | 0.054 | Neg |
| AD-26156 | CDS | Hu, Cy, Mo | 0.02 | 0.458 | 0.194 | 0.187 | Neg |
| AD-25951 | 3'UTR | Hu, Cy | 0.007 | 0.659 | 0.188 | 0.465 | Neg |
| AD-26109 | CDS | Hu, Cy | 0.025 | 0.156 | 0.172 | 0.410 | Neg |
| AD-26218 | CDS | Hu, Cy | 0.026 | 0.376 | 0.243 | 0.566 | Neg |
| AD-25894 | 3'UTR | Hu, Cy | 0.004 | 0.378 | 0.293 | 0.307 | Neg |
| AD-26740 | CDS | Hu, Cy | 0.006 | 0.511 | 0.227 | 0.330 | Neg |
| AD-26158 | CDS | Hu, Cy | 0.033 | 0.347 | 0.227 | 0.398 | Neg |
| AD-26682 | CDS | Hu, Cy | 0.007 | 0.484 | 0.297 | 0.923 | Neg |
| AD-26034 | CDS | Hu, Cy | 0.009 | 0.673 | 0.267 | 0.656 | Neg |
| AD-25944 | 3'UTR | Hu, Cy | 0.007 | 0.633 | 0.264 | 0.589 | Neg |
| AD-26800 | CDS | Hu, Cy | 0.025 | 0.449 | 0.240 | 0.815 | Neg |
| AD-26108 | CDS | Hu, Cy | 0.03 | 0.437 | 0.305 | 0.880 | Neg |
| AD-26752 | CDS | Hu, Cy | 0.042 | 0.518 | 0.396 | 0.500 | Neg |
| AD-26918 | 3'UTR | Hu, Cy | 0.029 | 0.371 | 0.345 | 0.965 | Neg |

In this table, the position is shown, wherein CDS indicates the coding segment (or open reading frame), and 3'UTR indicates the 3' untranslated region. The species forms of Beta-Catenin to which the RNAi agents match is also shown. Thus, AD-18983 matches each of the hman (Hu), cynomolgus (Cy), and Mouse (Mo) forms of Beta-Catenin. The estimated 24-hr average IC50 is shown (in nM). The cell viability in DLD1, LoVo, and LS411N cells is shown. For AD-18983, "0.258" indicates that at 1 nM at day 7, there was 25.8% cell viability of DLD1 cells, or 74.2% viability reduction. Similarly, there was 15.0% cell viability of LoVo cells (85.5% viability reduction) at 1 nM, and 5.4% cell viability (94.6% viability reduction) of LS411N cells (at 0.1 nM). PBMC indicates the peripheral blood mononuclear cell assay used as a test to measure potential immunogenicity of RNAi agents; "Neg" indicates that the RNAi agents did not illicit an immune response, as indicated by an increase in INF-α and TNF-α.

Thus, the following RNAi agents to Beta-Catenin demonstrated a significant reduction of cell viability in at least one colorectal cell line that depends on Beta-Catenin for growth: AD-18963-b2, AD-25894-b1, AD-25944-b1, AD-25951-b1, AD-26034-b1, AD-26108-b1, AD-26109-b1, AD-26156-b1, AD-26158-b1, AD-26218-b1, AD-26682-b1, AD-26740-b1, AD-26752-b1, AD-26800-b1, and AD-26918-b1.

EQUIVALENTS

A composition of embodiment 1 is a composition comprising a RNAi agent comprising a sense strand and an antisense strand, wherein the antisense strand comprises at least 15 contiguous nucleotides differing by 0, 1, 2, or 3 nucleotides from the antisense strand of a RNAi agent specific to Beta-Catenin provided in Table 1.

The composition of embodiment 1, wherein the composition further comprises a second RNAi agent to Beta-Catenin.

The composition of embodiment 1, wherein the antisense strand is 30 or fewer nucleotides in length.

The composition of embodiment 1, wherein the sense strand and the antisense strand form a duplex region 15 to 30 nucleotide pairs in length.

The composition of embodiment 1, wherein the antisense strand and the sense strand are independently 19 to 23 nucleotides in length.

The composition of embodiment 1, wherein the RNAi agent comprises a modification that causes the RNAi agent to have increased stability in a biological sample or environment.

The composition of embodiment 1, wherein the RNAi agent comprises at least one modified backbone and/or at least one 2'-modified nucleotide.

The composition of embodiment 1, wherein the RNAi agent comprises:
  a) at least one 5'-uridine-adenine-3' (5'-ua-3') dinucleotide, wherein the uridine is a 2'-modified nucleotide; and/or
  b) at least one 5'-uridine-guanine-3' (5'-ug-3') dinucleotide, wherein the 5'-uridine is a 2'-modified nucleotide; and/or c) at least one 5'-cytidine-adenine-3' (5'-ca-3') dinucleotide, wherein the 5'-cytidine is a 2'-modified nucleotide; and/or d) at least one 5'-uridine-uridine-3' (5'-uu-3') dinucleotide, wherein the 5'-uridine is a 2'-modified nucleotide.

The composition of embodiment 1, wherein the RNAi agent comprises a 2'-modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA).

The composition of embodiment 1, wherein the RNAi agent comprises a blunt end.

The composition of embodiment 1, wherein the RNAi agent comprises an overhang having 1 to 4 unpaired nucleotides.

The composition of embodiment 1, wherein the RNAi agent comprises an overhang at the 3'-end of the antisense strand of the RNAi agent.

The composition of embodiment 1, wherein the RNAi agent is ligated to one or more agent selected from: one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

The composition of embodiment 1, wherein the RNAi agent is capable of inhibiting expression of the Beta-Catenin gene by at least about 60% at a concentration of 10 nM in HeLa, GTL-16, or SK-BR-3 cells in vitro.

The composition of embodiment 1, wherein the RNAi agent is capable of inhibiting expression of the Beta-Catenin gene by at least about 70% at a concentration of 10 nM in HeLa, GTL-16, or SK-BR-3 cells in vitro.

The composition of embodiment 1, wherein the RNAi agent is capable of inhibiting expression of the Beta-Catenin gene by at least about 80% at a concentration of 10 nM in HeLa, GTL-16, or SK-BR-3 cells in vitro.

The composition of embodiment 1, wherein the RNAi agent is capable of inhibiting expression of the Beta-Catenin gene by at least about 90% at a concentration of 10 nM in HeLa, GTL-16, or SK-BR-3 cells in vitro.

The composition of embodiment 1, wherein the RNAi has an EC50 of no more than about 0.1 nM.

The composition of embodiment 1, wherein the RNAi has an EC50 of no more than about 0.01 nM.

The composition of embodiment 1, wherein the RNAi has an EC50 of no more than about 0.001 nM.

A composition of embodiment 2 is a composition comprising a RNAi agent comprising a first strand and a second strand, wherein the first strand and second strand comprise at least 15 contiguous nucleotides differing by 0, 1, 2, or 3 nucleotides from the first and second strand, respectively, of a RNAi agent specific to Beta-Catenin provided in Table 1.

The composition of embodiment 2, wherein the composition comprises a second RNAi agent to Beta-Catenin.

The composition of embodiment 2, wherein the second strand is 30 or fewer nucleotides in length.

The composition of embodiment 2, wherein the first strand and the second strand form a duplex region 15 to 30 nucleotide pairs in length.

The composition of embodiment 2, wherein the first strand and the second strand are independently 19 to 23 nucleotides in length.

The composition of embodiment 2, wherein the RNAi agent comprises a modification that causes the RNAi agent to have increased stability in a biological sample or environment.

The composition of embodiment 2, wherein the RNAi agent comprises a phosphorothioate and/or a 2'-modified nucleotide.

The composition of embodiment 2, wherein the RNAi agent comprises:

at least one 5'-uridine-adenine-3' (5'-ua-3') dinucleotide, wherein the uridine is a 2'-modified nucleotide; and/or at least one 5'-uridine-guanine-3' (5'-ug-3') dinucleotide, wherein the 5'-uridine is a 2'-modified nucleotide;

and/or at least one 5'-cytidine-adenine-3' (5'-ca-3') dinucleotide, wherein the 5'-cytidine is a 2'-modified nucleotide;

and/or at least one 5'-uridine-uridine-3' (5'-uu-3') dinucleotide, wherein the 5'-uridine is a 2'-modified nucleotide.

The composition of embodiment 2, wherein the RNAi agent comprises one or more 2'-modifications selected from the group consisting of:

2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-0-DMAP), 2'-O-dimethylaminoethyloxyethyl (2'-O-DMAEOE), and 2'-O—N-methylacetamido (2'-O-NMA).

The composition of embodiment 2, wherein the RNAi agent comprises a blunt end.

The composition of embodiment 2, wherein the RNAi agent comprises an overhang having 1 to 4 unpaired nucleotides.

The composition of embodiment 2, wherein the RNAi agent comprises an overhang at the 3'-end of the antisense strand.

The composition of embodiment 2, wherein the RNAi agent is ligated to one or more agents, the agent selected from a: one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

The composition of embodiment 2, wherein the RNAi agent is capable of inhibiting expression of the Beta-Catenin gene by at least about 60% at a concentration of 10 nM in HeLa, GTL-16, or SK-BR-3 cells in vitro.

The composition of embodiment 2, wherein the RNAi agent is capable of inhibiting expression of the Beta-Catenin gene by at least about 70% at a concentration of 10 nM in HeLa, GTL-16, or SK-BR-3 cells in vitro.

The composition of embodiment 2, wherein the RNAi agent is capable of inhibiting expression of the Beta-Catenin gene by at least about 80% at a concentration of 10 nM in HeLa, GTL-16, or SK-BR-3 cells in vitro.

The composition of embodiment 2, wherein the RNAi agent is capable of inhibiting expression of the Beta-Catenin gene by at least about 90% at a concentration of 10 nM in HeLa, GTL-16, or SK-BR-3 cells in vitro.

The composition of embodiment 2, wherein the RNAi has an EC50 of no more than about 0.1 nM.

The composition of embodiment 2, wherein the RNAi has an EC50 of no more than about 0.01 nM.

The composition of embodiment 2, wherein the RNAi has an EC50 of no more than about 0.001 nM.

A method of embodiment 3 is a method comprising a method of treating a Beta-Catenin-related disease in an individual, comprising the step of administering to the individual a therapeutically effective amount of a composition comprising a RNAi agent comprising a sense strand and an antisense strand, wherein the antisense strand comprises at least 15 contiguous nucleotides differing by 0, 1, 2, or 3 nucleotides from the antisense strand of a RNAi agent specific to Beta-Catenin provided in Table 1.

The method of embodiment 3, wherein the Beta-Catenin-related disease is cancer, autoimmune, or a viral disease.

The method of embodiment 3, wherein the Beta-Catenin-related disease is cancer.

The method of embodiment 3, wherein the method further comprises the step of administering an additional treatment for cancer, autoimmune, or a viral disease.

The method of embodiment 3, wherein the composition comprises a second RNAi agent to Beta-Catenin.

The method of embodiment 3, wherein the method further comprises the step of administering an additional RNAi agent to Beta-Catenin.

The method of embodiment 3, further comprising the administration of an additional treatment.

The method of embodiment 3, wherein the additional treatment is a composition.

The method of embodiment 3, wherein the additional treatment is a method.

The method of embodiment 3, wherein the additional treatment and the RNAi agent can be administered in any order.

A method of embodiment 4 is a method comprising a method of inhibiting the expression of the Beta-Catenin gene in an individual, comprising the step of administering to the individual a therapeutically effective amount of a composition comprising a RNAi agent comprising a sense strand and an antisense strand, wherein the antisense strand comprises at least 15 contiguous nucleotides differing by 0, 1, 2, or 3 nucleotides from the antisense strand of a RNAi agent specific to Beta-Catenin provided in Table 1.

The method of embodiment 4, wherein the individual is afflicted with or susceptible to a Beta-Catenin-related disease.

The method of embodiment 4, wherein the Beta-Catenin-related disease is cancer, autoimmune, or a viral disease.

The method of embodiment 4, wherein the Beta-Catenin-related disease is cancer.

The method of embodiment 4, further comprising the administration of an additional treatment.

The method of embodiment 4, wherein the additional treatment is a composition.

The method of embodiment 4, wherein the additional treatment is a method.

The method of embodiment 4, wherein the additional treatment and the RNAi agent can be administered in any order.

A composition of embodiment 5 is a composition comprising a medicament for use in an RNAi formulation comprising a RNAi agent comprising a sense strand and an antisense strand, wherein the antisense strand comprises at least 15 contiguous nucleotides differing by 0, 1, 2, or 3 nucleotides from the antisense strand of a RNAi agent specific to Beta-Catenin provided in Table 1.

Any composition above in a pharmaceutically effective formulation.

The composition according to embodiment 5, for use in a method of treating a Beta-Catenin-related disease in an individual, the method comprising the step of administering to the individual a therapeutically effective amount of a composition according to embodiment 1.

The use of a composition according to embodiment 5, in the manufacture of a medicament for the treatment of a Beta-Catenin-related disease.

The use of embodiment 5, wherein the Beta-Catenin-related disease is cancer, autoimmune, or a viral disease.

The composition of embodiment 5, wherein all the pyrimidines are 2' O-methyl-modified nucleotides.

The composition of embodiment 5, wherein all the pyrimidines are 2' O-methyl-modified nucleotides.

ADDITIONAL EQUIVALENTS

A composition of embodiment 6 is a composition comprising a RNAi agent comprising a sense strand and an antisense strand, wherein the antisense strand comprises at least 15 contiguous nucleotides differing by 0, 1, 2, or 3 nucleotides from the antisense strand of a RNAi agent specific to Beta-ENaC provided in Table 1.

The composition of embodiment 6, wherein the composition further comprises a second RNAi agent to Beta-ENaC.

The composition of embodiment 6, wherein the antisense strand is 30 or fewer nucleotides in length.

The composition of embodiment 6, wherein the sense strand and the antisense strand form a duplex region 15 to 30 nucleotide pairs in length.

The composition of embodiment 6, wherein the antisense strand and the sense strand are independently 19 to 23 nucleotides in length.

The composition of embodiment 6, wherein the RNAi agent comprises a modification that causes the RNAi agent to have increased stability in a biological sample or environment.

The composition of embodiment 6, wherein the RNAi agent comprises at least one modified backbone and/or at least one 2'-modified nucleotide.

The composition of embodiment 6, wherein the RNAi agent comprises:

a) at least one 5'-uridine-adenine-3' (5'-ua-3') dinucleotide, wherein the uridine is a 2'-modified nucleotide; and/or b) at least one 5'-uridine-guanine-3' (5'-ug-3') dinucleotide, wherein the 5'-uridine is a 2'-modified nucleotide; and/or c) at least one 5'-cytidine-adenine-3' (5'-ca-3') dinucleotide, wherein the 5'-cytidine is a 2'-modified nucleotide; and/or d) at least one 5'-uridine-uridine-3' (5'-uu-3') dinucleotide, wherein the 5'-uridine is a 2'-modified nucleotide.

The composition of embodiment 6, wherein the RNAi agent comprises a 2'-modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA).

The composition of cla embodiment 6, wherein the RNAi agent comprises a blunt end.

The composition of embodiment 6, wherein the RNAi agent comprises an overhang having 1 to 4 unpaired nucleotides.

The composition of embodiment 6, wherein the RNAi agent comprises an overhang at the 3'-end of the antisense strand of the RNAi agent.

The composition of embodiment 6, wherein the RNAi agent is ligated to one or more agent selected from: diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

The composition of embodiment 6, wherein the RNAi agent is capable of inhibiting expression of the Beta-ENaC gene by at least about 60% at a concentration of 10 nM in H441 cells in vitro.

The composition of embodiment 6, wherein the RNAi agent is capable of inhibiting expression of the Beta-ENaC gene by at least about 70% at a concentration of 10 nM in H441 cells in vitro.

The composition of embodiment 6, wherein the RNAi agent is capable of inhibiting expression of the Beta-ENaC gene by at least about 80% at a concentration of 10 nM in H441 cells in vitro.

The composition of embodiment 6, wherein the RNAi agent is capable of inhibiting expression of the Beta-ENaC gene by at least about 90% at a concentration of 10 nM in H441 cells in vitro.

The composition of embodiment 6, wherein the RNAi has an EC50 of no more than about 0.1 nM.

The composition of embodiment 6, wherein the RNAi has an EC50 of no more than about 0.01 nM.

The composition of embodiment 6, wherein the RNAi has an EC50 of no more than about 0.001 nM.

A composition of embodiment 7 is a composition comprising a RNAi agent comprising a first strand and a second strand, wherein the first strand and second strand comprise at least 15 contiguous nucleotides differing by 0, 1, 2, or 3 nucleotides from the first and second strand, respectively, of a RNAi agent specific to Beta-ENaC provided in Table 1.

The composition of embodiment 7, wherein the composition comprises a second RNAi agent to Beta-ENaC.

The composition of embodiment 7, wherein the second strand is 30 or fewer nucleotides in length.

The composition of embodiment 7, wherein the first strand and the second strand form a duplex region 15 to 30 nucleotide pairs in length.

The composition of embodiment 7, wherein the first strand and the second strand are independently 19 to 23 nucleotides in length.

The composition of embodiment 7, wherein the RNAi agent comprises a modification that causes the RNAi agent to have increased stability in a biological sample or environment.

The composition of embodiment 7, wherein the RNAi agent comprises a phosphorothioate and/or a 2'-modified nucleotide.

The composition of embodiment 7, wherein the RNAi agent comprises:

at least one 5'-uridine-adenine-3' (5'-ua-3') dinucleotide, wherein the uridine is a 2'-modified nucleotide; and/or at least one 5'-uridine-guanine-3' (5'-ug-3') dinucleotide, wherein the 5'-uridine is a 2'-modified nucleotide;

and/or at least one 5'-cytidine-adenine-3' (5'-ca-3') dinucleotide, wherein the 5'-cytidine is a 2'-modified nucleotide;

and/or at least one 5'-uridine-uridine-3' (5'-uu-3') dinucleotide, wherein the 5'-uridine is a 2'-modified nucleotide.

The composition of embodiment 7, wherein the RNAi agent comprises one or more 2'-modifications selected from the group consisting of:

2'-deoxy, 2'-deoxy-2'-fluoro, 2'-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-0-DMAP), 2'-O-dimethylaminoethyloxyethyl (2'-O-DMAEOE), and 2'-O—N-methylacetamido (2'-O-NMA).

The composition of embodiment 7, wherein the RNAi agent comprises a blunt end.

The composition of embodiment 7, wherein the RNAi agent comprises an overhang having 1 to 4 unpaired nucleotides.

The composition of embodiment 7, wherein the RNAi agent comprises an overhang at the 3'-end of the antisense strand.

The composition of embodiment 7, wherein the RNAi agent is ligated to one or more agents, the agent selected from a: diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

The composition of embodiment 7, wherein the RNAi agent is capable of inhibiting expression of the Beta-ENaC gene by at least about 60% at a concentration of 10 nM in H441 cells in vitro.

The composition of embodiment 7, wherein the RNAi agent is capable of inhibiting expression of the Beta-ENaC gene by at least about 70% at a concentration of 10 nM in H441 cells in vitro.

The composition of embodiment 7, wherein the RNAi agent is capable of inhibiting expression of the Beta-ENaC gene by at least about 80% at a concentration of 10 nM in H441 cells in vitro.

The composition of embodiment 7, wherein the RNAi agent is capable of inhibiting expression of the Beta-ENaC gene by at least about 90% at a concentration of 10 nM in H441 cells in vitro.

The composition of embodiment 7, wherein the RNAi has an EC50 of no more than about 0.1 nM.

The composition of embodiment 7, wherein the RNAi has an EC50 of no more than about 0.01 nM.

The composition of embodiment 7, wherein the RNAi has an EC50 of no more than about 0.001 nM.

A method of embodiment 8 is a method of treating a Beta-ENaC-related disease in an individual, comprising the step of administering to the individual a therapeutically effective amount of a composition comprising a RNAi agent comprising a sense strand and an antisense strand, wherein the antisense strand comprises at least 15 contiguous nucleotides differing by 0, 1, 2, or 3 nucleotides from the antisense strand of a RNAi agent specific to Beta-ENaC provided in Table 1.

The method of embodiment 8, wherein the Beta-ENaC-related disease is cystic fibrosis, pseudohypoaldosteronism type 1 (PHA1), Liddle's syndrome, hypertension, alkalosis, hypokalemia, and/or obesity-associated hypertension.

The method of embodiment 8, wherein the Beta-ENaC-related disease is cystic fibrosis.

The method of embodiment 8, wherein the method further comprises the step of administering an additional treatment for cystic fibrosis, pseudohypoaldosteronism type 1 (PHA1), Liddle's syndrome, hypertension, alkalosis, hypokalemia, and/or obesity-associated hypertension.

The method of embodiment 8, wherein the composition comprises a second RNAi agent to Beta-ENaC.

The method of embodiment 8, wherein the method further comprises the step of administering an additional RNAi agent to Beta-ENaC.

The method of embodiment 8, further comprising the administration of an additional treatment.

The method of embodiment 8, wherein the additional treatment is a composition.

The method of embodiment 8, wherein the additional treatment is a method.

The method of embodiment 8, wherein the additional treatment and the RNAi agent can be administered in any order.

A method of embodiment 9 is a method of inhibiting the expression of the Beta-ENaC gene in an individual, comprising the step of administering to the individual a therapeutically effective amount of a composition comprising a RNAi agent comprising a sense strand and an antisense strand, wherein the antisense strand comprises at least 15 contiguous nucleotides differing by 0, 1, 2, or 3 nucleotides from the antisense strand of a RNAi agent specific to Beta-ENaC provided in Table 1.

The method of embodiment 9, wherein the individual is afflicted with or susceptible to a Beta-ENaC-related disease.

The method of embodiment 9, wherein the Beta-ENaC-related disease is cystic fibrosis, pseudohypoaldosteronism type 1 (PHA1), Liddle's syndrome, hypertension, alkalosis, hypokalemia, and/or obesity-associated hypertension.

The method of embodiment 9, wherein the Beta-ENaC-related disease is cystic fibrosis.

The method of embodiment 9, further comprising the administration of an additional treatment.

The method of embodiment 9, wherein the additional treatment is a composition.

The method of embodiment 9, wherein the additional treatment is a method.

The method of embodiment 9, wherein the additional treatment and the RNAi agent can be administered in any order.

A medicament for use in an RNAi formulation comprising a RNAi agent comprising a sense strand and an antisense strand, wherein the antisense strand comprises at least 15 contiguous nucleotides differing by 0, 1, 2, or 3 nucleotides from the antisense strand of a RNAi agent specific to Beta-ENaC provided in Table 1.

A composition of embodiment 10 is a composition comprising a RNAi agent comprising a first strand and a second strand, wherein the sequence of the first strand comprises the sequence of the first strand of a RNAi agent specific to Beta-ENaC provided in Table 1.

The composition of embodiment 10, wherein the composition comprises a second RNAi agent to Beta-ENaC.

The composition of embodiment 10, wherein the second strand is 30 or fewer nucleotides in length.

The composition of embodiment 10, wherein the first strand and the second strand form a duplex region 15 to 30 nucleotide pairs in length.

The composition of embodiment 10, wherein the first strand and the second strand are independently 19 to 23 nucleotides in length.

The composition of embodiment 10, wherein the RNAi agent comprises a modification that causes the RNAi agent to have increased stability in a biological sample or environment.

The composition of embodiment 10, wherein the RNAi agent comprises a phosphorothioate and/or a 2'-modified nucleotide.

The composition of embodiment 10, wherein the RNAi agent comprises:
at least one 5'-uridine-adenine-3' (5'-ua-3') dinucleotide, wherein the uridine is a 2'-modified nucleotide; and/or at least one 5'-uridine-guanine-3' (5'-ug-3') dinucleotide, wherein the 5'-uridine is a 2'-modified nucleotide;
and/or at least one 5'-cytidine-adenine-3' (5'-ca-3') dinucleotide, wherein the 5'-cytidine is a 2'-modified nucleotide;
and/or at least one 5'-uridine-uridine-3' (5'-uu-3') dinucleotide, wherein the 5'-uridine is a 2'-modified nucleotide.

The composition of embodiment 10, wherein the RNAi agent comprises one or more 2'-modifications selected from the group consisting of:
2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-0-DMAP), 2'-O-dimethylaminoethyloxyethyl (2'-O-DMAEOE), and 2'-O—N-methylacetamido (2'-O-NMA).

The composition of embodiment 10, wherein the RNAi agent comprises a blunt end.

The composition of embodiment 10, wherein the RNAi agent comprises an overhang having 1 to 4 unpaired nucleotides.

The composition of embodiment 10, wherein the RNAi agent comprises an overhang at the 3'-end of the antisense strand.

The composition of embodiment 10, wherein the RNAi agent is ligated to one or more agents, the agent selected from a: diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

The composition of embodiment 10, wherein the RNAi agent is capable of inhibiting expression of the Beta-ENaC gene by at least about 60% at a concentration of 10 nM in H441 cells in vitro.

The composition of embodiment 10, wherein the RNAi agent is capable of inhibiting expression of the Beta-ENaC gene by at least about 70% at a concentration of 10 nM in H441 cells in vitro.

The composition of embodiment 10, wherein the RNAi agent is capable of inhibiting expression of the Beta-ENaC gene by at least about 80% at a concentration of 10 nM in H441 cells in vitro.

The composition of embodiment 10, wherein the RNAi agent is capable of inhibiting expression of the Beta-ENaC gene by at least about 90% at a concentration of 10 nM in H441 cells in vitro.

The composition of embodiment 10, wherein the RNAi has an EC50 of no more than about 0.1 nM.

The composition of embodiment 10, wherein the RNAi has an EC50 of no more than about 0.01 nM.

The composition of embodiment 10, wherein the RNAi has an EC50 of no more than about 0.001 nM.

A composition of embodiment 11 is a composition comprising a RNAi agent comprising a first strand and a second strand, wherein the sequence of the first strand is the sequence of the first strand of a RNAi agent specific to Beta-ENaC provided in Table 1.

The composition of embodiment 11, wherein the composition comprises a second RNAi agent to Beta-ENaC.

The composition of embodiment 11, wherein the second strand is 30 or fewer nucleotides in length.

The composition of embodiment 11, wherein the first strand and the second strand form a duplex region 15 to 30 nucleotide pairs in length.

The composition of embodiment 11, wherein the first strand and the second strand are independently 19 to 23 nucleotides in length.

The composition of embodiment 11, wherein the RNAi agent comprises a modification that causes the RNAi agent to have increased stability in a biological sample or environment.

The composition of embodiment 11, wherein the RNAi agent comprises a phosphorothioate and/or a 2'-modified nucleotide.

The composition of embodiment 11, wherein the RNAi agent comprises:

at least one 5'-uridine-adenine-3' (5'-ua-3') dinucleotide, wherein the uridine is a 2'-modified nucleotide; and/or at least one 5'-uridine-guanine-3' (5'-ug-3') dinucleotide, wherein the 5'-uridine is a 2'-modified nucleotide;

and/or at least one 5'-cytidine-adenine-3' (5'-ca-3') dinucleotide, wherein the 5'-cytidine is a 2'-modified nucleotide;

and/or at least one 5'-uridine-uridine-3' (5'-uu-3') dinucleotide, wherein the 5'-uridine is a 2'-modified nucleotide.

The composition of embodiment 11, wherein the RNAi agent comprises one or more 2'-modifications selected from the group consisting of:

2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-0-DMAP), 2'-O-dimethylaminoethyloxyethyl (2'-O-DMAEOE), and 2'-O—N-methylacetamido (2'-O-NMA).

The composition of embodiment 11, wherein the RNAi agent comprises a blunt end.

The composition of embodiment 11, wherein the RNAi agent comprises an overhang having 1 to 4 unpaired nucleotides.

The composition of embodiment 11, wherein the RNAi agent comprises an overhang at the 3'-end of the antisense strand.

The composition of embodiment 11, wherein the RNAi agent is ligated to one or more agents, the agent selected from a: diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

The composition of embodiment 11, wherein the RNAi agent is capable of inhibiting expression of the Beta-ENaC gene by at least about 60% at a concentration of 10 nM in H441 cells in vitro.

The composition of embodiment 11, wherein the RNAi agent is capable of inhibiting expression of the Beta-ENaC gene by at least about 70% at a concentration of 10 nM in H441 cells in vitro.

The composition of embodiment 11, wherein the RNAi agent is capable of inhibiting expression of the Beta-ENaC gene by at least about 80% at a concentration of 10 nM in H441 cells in vitro.

The composition of embodiment 11, wherein the RNAi agent is capable of inhibiting expression of the Beta-ENaC gene by at least about 90% at a concentration of 10 nM in H441 cells in vitro.

The composition of embodiment 11, wherein the RNAi has an EC50 of no more than about 0.1 nM.

The composition of embodiment 11, wherein the RNAi has an EC50 of no more than about 0.01 nM.

The composition of embodiment 11, wherein the RNAi has an EC50 of no more than about 0.001 nM.

A composition of embodiment 12 is any composition above in a pharmaceutically effective formulation.

The composition according to embodiment 12, for use in a method of treating a Beta-ENaC-related disease in an individual, the method comprising the step of administering to the individual a therapeutically effective amount of a composition comprising a RNAi agent comprising a sense strand and an antisense strand, wherein the antisense strand comprises at least 15 contiguous nucleotides differing by 0, 1, 2, or 3 nucleotides from the antisense strand of a RNAi agent specific to Beta-ENaC provided in Table 1.

The use of a composition according to embodiment 12, in the manufacture of a medicament for the treatment of a Beta-ENaC-related disease.

The use of a composition according to embodiment 12, wherein the Beta-ENaC-related disease is cystic fibrosis, pseudohypoaldosteronism type 1 (PHA1), Liddle's syndrome, hypertension, alkalosis, hypokalemia, and/or obesity-associated hypertension.

The composition of embodiment 12, wherein all the pyrimidines are 2' O-methyl-modified nucleotides.

The composition of embodiment 12, wherein all the pyrimidines are 2' O-methyl-modified nucleotides.

Unless defined otherwise, the technical and scientific terms used herein have the same meaning as that usually understood by a specialist familiar with the field to which the disclosure belongs.

Unless indicated otherwise, all methods, steps, techniques and manipulations that are not specifically described in detail can be performed and have been performed in a manner known per se, as will be clear to the skilled person.

Reference is for example again made to the standard handbooks and the general background art mentioned herein and to the further references cited therein. Unless indicated otherwise, each of the references cited herein is incorporated in its entirety by reference.

Claims to the invention are non-limiting and are provided below.

Although particular embodiments and claims have been disclosed herein in detail, this has been done by way of example for purposes of illustration only, and is not intended to be limiting with respect to the scope of the appended claims, or the scope of subject matter of claims of any corresponding future application. In particular, it is contemplated by the inventors that various substitutions, alterations, and modifications may be made to the disclosure without departing from the spirit and scope of the disclosure as defined by the claims. The choice of nucleic acid starting material, clone of interest, or library type is believed to be a matter of routine for a person of ordinary skill in the art with knowledge of the embodiments described herein. Other aspects, advantages, and modifications considered to be within the scope of the following claims. Those skilled in the art will recognize or be able to ascertain, using no more than routine experimentation, many equivalents of the specific embodiments of the invention described herein. Such equivalents are intended to be encompassed by the following claims. Redrafting of claim scope in later filed corresponding applications may be due to limitations by the patent laws of various countries and should not be interpreted as giving up subject matter of the claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10023862B2). An electronic copy of the "Sequence Listing" will also be available from the USPTO upon request and payment of the fee set forth in 37 CFR 1.19(b)(3).

We claim:

1. A composition comprising a RNAi agent comprising a sense strand and an antisense strand, wherein the antisense strand is 19-40 nucleotides in length and comprises the sequence AAAAGAACGAUAGCUAGGA (SEQ ID NO: 6121) (5'→3'), wherein SEQ ID NO: 6121 is nucleotides 1-19 from the 5' terminal end of the antisense strand, and wherein SEQ ID NO: 6121 comprises at least one modified backbone and/or at least one 2'-modified nucleotide.

2. The composition of claim 1, wherein the composition further comprises a second RNAi agent to Beta-Catenin.

3. The composition of claim 1, wherein the sense strand of the RNAi agent comprises at least one modified backbone and/or at least one 2'-modified nucleotide.

4. The composition of claim 1, wherein the RNAi agent is ligated to one or more agent selected from: diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

5. The composition of claim 1, wherein the RNAi agent comprises a phosphorothioate linkage and/or a 2'-O-methyl modified nucleotide.

6. The composition of claim 4, wherein the RNAi agent is ligated to one or more agents, the agent selected from cholesterol, carbohydrate, synthetic carbohydrate, natural polymer, low- or medium-molecular weight polymer, integrin-targeting molecule, peptide, polyamine, peptide mimic, and/or transferrin.

7. The composition of claim 1, further comprising a pharmaceutically effective excipient.

8. The composition of claim 1, wherein all the pyrimidines are 2' O-methyl-modified nucleotides.

9. The composition of claim 4, wherein all the pyrimidines are 2' O-methyl-modified nucleotides.

* * * * *